US012642851B2

(12) United States Patent
Lynn et al.

(10) Patent No.: US 12,642,851 B2
(45) Date of Patent: Jun. 2, 2026

(54) SELF-ASSEMBLING NANOPARTICLES

(71) Applicants: Barinthus Biotherapeutics North America, Inc., Germantown, MD (US); The United States of America, as represented by the Secretary, Department of Health and Human Servic, Bethesda, MD (US)

(72) Inventors: Geoffrey Martin Lynn, Baltimore, MD (US); Christopher Martin O'Brien Garliss, Baltimore, MD (US); Andrew Scott Ishizuka, Washington, DC (US); Hugh Clarke Welles, Baltimore, MD (US)

(73) Assignees: Barinthus Biotherapeutics North America, Inc., Germantown, MD (US); The United States of America, as represented by the Secretary, Department of Health and Human Services, Bethesda, MD (US)

( * ) Notice: Subject to any disclaimer, the term of this patent is extended or adjusted under 35 U.S.C. 154(b) by 0 days.

(21) Appl. No.: 19/067,426

(22) Filed: Feb. 28, 2025

(65) Prior Publication Data

US 2025/0242015 A1 Jul. 31, 2025

Related U.S. Application Data

(63) Continuation of application No. 18/494,491, filed on Oct. 25, 2023.

(60) Provisional application No. 63/380,931, filed on Oct. 25, 2022.

(51) Int. Cl.

| | |
|---|---|
| ***A61K 39/385*** | (2006.01) |
| ***A61K 39/35*** | (2006.01) |
| ***A61K 47/54*** | (2017.01) |
| ***A61K 47/64*** | (2017.01) |
| ***A61K 47/69*** | (2017.01) |
| ***A61P 3/10*** | (2006.01) |
| ***A61P 37/06*** | (2006.01) |
| *A61K 39/00* | (2006.01) |

(52) U.S. Cl.

CPC ............ *A61K 39/385* (2013.01); *A61K 39/35* (2013.01); *A61K 47/545* (2017.08); *A61K 47/549* (2017.08); *A61K 47/646* (2017.08); *A61K 47/6935* (2017.08); *A61P 3/10* (2018.01); *A61P 37/06* (2018.01); *A61K 2039/54* (2013.01); *A61K 2039/577* (2013.01); *A61K 2039/6093* (2013.01)

(58) Field of Classification Search

CPC .. A61K 39/385; A61K 39/35; A61K 47/6929; A61K 47/646; A61K 2039/6093

See application file for complete search history.

(56) References Cited

U.S. PATENT DOCUMENTS

| | | | | |
|---|---|---|---|---|
| 5,312,620 | A | 5/1994 | Ribi | |
| 6,573,245 | B1 | 6/2003 | Marciani | |
| 6,747,137 | B1 | 6/2004 | Weinstock et al. | |
| 6,858,396 | B2 | 2/2005 | Dix | |
| 9,115,402 | B2 | 8/2015 | Hacohen et al. | |
| 9,120,841 | B2 | 9/2015 | Hauser et al. | |
| 9,682,934 | B2 | 6/2017 | Stafford et al. | |
| 9,962,453 | B2 | 5/2018 | Georges | |
| 11,191,821 | B2 | 12/2021 | Seder et al. | |
| 11,723,950 | B2 * | 8/2023 | Pakyari ................ | C12N 15/102 424/134.1 |
| 2004/0057958 | A1 | 3/2004 | Waggoner et al. | |
| 2006/0216702 | A1 | 9/2006 | Compans et al. | |
| 2008/0139481 | A1 | 6/2008 | Dix | |
| 2008/0160089 | A1 | 7/2008 | Vitiello et al. | |
| 2009/0048410 | A1 | 2/2009 | Wakefield et al. | |
| 2010/0028381 | A1 | 2/2010 | Gorski et al. | |
| 2010/0129439 | A1 | 5/2010 | Alexis et al. | |
| 2011/0150978 | A1 | 6/2011 | Lee et al. | |

(Continued)

FOREIGN PATENT DOCUMENTS

| | | | |
|---|---|---|---|
| CA | 2627903 | A1 | 9/2009 |
| CN | 101684174 | B | 4/2012 |

(Continued)

OTHER PUBLICATIONS

Accardo et al. Self-assembled or mixed peptide amphiphile micelles from Herpes simplex virus glycoproteins as potential immunomodulatory treatment. Int J Nanomedicine. 2014;9:2137-2148.

(Continued)

*Primary Examiner* — Gyan Chandra
(74) *Attorney, Agent, or Firm* — Goodwin Procter LLP

(57) ABSTRACT

The present disclosure relates to a vaccine comprising at least one peptide antigen conjugate having the formula selected from PEG-[E1]-A-[E2]-[U]-H and H-[U]-[E1]-A-[E2]-PEG, wherein E1 is an N terminal extension, E2 is a C terminal extension, A is peptide antigen, H is hydrobhobic block, wherein one or more drug molecules (D) are optionally attached to each H directly or via a suitable linker X1; U is a linker, [ ] denotes the group is optional and - denotes that the two adjacent groups are directly attached to one another by a covalent bond or indirectly to one another via a suitable linker X. The vaccine is useful in treating or preventing a cancer, an autoimmune disease, an allergy, or an infectious disease.

25 Claims, 28 Drawing Sheets

Specification includes a Sequence Listing.

(56) References Cited

U.S. PATENT DOCUMENTS

2012/0114699 A1 5/2012 Mistrello et al.
2012/0141409 A1 6/2012 Seymour et al.
2013/0144023 A1 6/2013 Kim et al.
2013/0237561 A1 9/2013 Leoni et al.
2013/0287857 A1 10/2013 von Andrian et al.
2013/0330367 A1 12/2013 Song et al.
2013/0336996 A1 12/2013 Vernejoul et al.
2014/0037747 A1 2/2014 Hong et al.
2016/0310584 A1 10/2016 Fritsch et al.
2017/0112923 A1 4/2017 Seymour et al.
2017/0224803 A1 8/2017 Berti et al.
2017/0304420 A1 10/2017 Fisher et al.
2017/0348430 A1 12/2017 Amir et al.
2018/0221277 A1 8/2018 Hong et al.
2019/0060435 A1 2/2019 Seder et al.
2019/0070233 A1 3/2019 Yeung et al.
2020/0009069 A1 1/2020 Luo et al.
2020/0054741 A1 2/2020 Lynn et al.
2021/0000934 A1 1/2021 Fisher et al.
2021/0113705 A1 4/2021 Lynn et al.
2021/0393523 A1 12/2021 Lynn et al.
2022/0152170 A1 5/2022 Seder et al.
2022/0305099 A1 9/2022 Stojdl et al.
2023/0381112 A1 11/2023 Lynn et al.
2024/0269269 A1 8/2024 Lynn et al.
2024/0382614 A1 11/2024 Lynn et al.
2025/0090658 A1 3/2025 Fisher et al.

FOREIGN PATENT DOCUMENTS

CN 113214171 A 8/2021
EP 0324455 A2 7/1989
EP 2958994 B1 5/2019
JP 2001294636 A 10/2001
JP 2014139139 A 7/2014
KR 20090002946 A 1/2009
WO WO-1993022338 A1 11/1993
WO WO-1996015249 A1 5/1996
WO WO-1998001558 A2 1/1998
WO WO-1998019710 A2 5/1998
WO WO-2000016746 A2 3/2000
WO WO-2000074722 A2 12/2000
WO WO-2001018035 A2 3/2001
WO WO-2001052614 A2 7/2001
WO WO-2002070006 A2 9/2002
WO WO-2002094994 A2 11/2002
WO WO-2003075956 A2 9/2003
WO WO-2004007525 A3 3/2004
WO WO-2005007789 A2 1/2005
WO WO-2005099752 A2 10/2005
WO WO-2006083874 A2 8/2006
WO WO-2006084319 A1 8/2006
WO WO-2007075502 A2 7/2007
WO WO-2004071457 A3 10/2007
WO WO-2007149802 A2 12/2007
WO WO-2009043165 A1 4/2009
WO WO-2009051837 A2 4/2009
WO WO-2009104001 A2 8/2009
WO WO-2010067041 A1 6/2010
WO WO-2010128303 A1 11/2010
WO WO-2011101332 A1 8/2011
WO WO-2011150240 A1 12/2011
WO WO-2012041669 A1 4/2012
WO WO-2012049317 A3 6/2012
WO WO-2012090002 A1 7/2012
WO WO-2012139094 A3 11/2012
WO WO-2013006050 A9 2/2013
WO WO-2013019669 A2 2/2013
WO WO-2013080187 A1 6/2013
WO WO-2013051936 A9 9/2013
WO WO-2013151771 A1 10/2013
WO WO-2013154774 A1 10/2013
WO WO-2014142653 A1 9/2014
WO WO-2015033140 A1 3/2015
WO WO-2015082905 A1 6/2015
WO WO-2015085233 A1 6/2015
WO WO-2016043620 A1 3/2016
WO WO-2016055812 A1 4/2016
WO WO-2016146143 A1 9/2016
WO WO-2016146260 A1 9/2016
WO WO-2017044803 A1 3/2017
WO WO-2017083963 A1 5/2017
WO WO-2017147597 A1 8/2017
WO WO-2017157964 A1 9/2017
WO WO-2017173321 A1 10/2017
WO WO-2018055060 A1 3/2018
WO WO-2018059896 A1 4/2018
WO WO-2018148671 A1 8/2018
WO WO-2018187356 A2 10/2018
WO WO-2018187515 A1 10/2018
WO WO-2019094642 A1 5/2019
WO WO-2019126186 A1 6/2019
WO WO-2019126371 A1 6/2019
WO WO-2019134049 A1 7/2019
WO WO-2019195626 A1 10/2019
WO WO-2019204663 A1 10/2019
WO WO-2019226828 A2 11/2019
WO WO-2019241306 A2 12/2019
WO WO-2019246315 A1 12/2019
WO WO-2020072681 A1 4/2020
WO WO-2020190762 A1 9/2020
WO WO-2020191305 A3 10/2020
WO WO-2020231274 A1 11/2020
WO WO-2021041518 A2 3/2021
WO WO-2021156404 A3 9/2021
WO WO-2022066635 A1 3/2022
WO WO-2022086853 A1 4/2022
WO WO-2022177993 A1 8/2022
WO WO-2022266340 A1 12/2022
WO WO-2024092030 A1 5/2024
WO WO-2024092028 A3 7/2024

OTHER PUBLICATIONS

Acrylamide, retrieved from <https://en.wikipedia.org/wiki/Acrylamide> on Jun. 4, 2016.

Adjuvant Therapy, retrieved from <http://en.wikipedia.org/wiki/Adjuvant_therapy> on May 28, 2012.

Adjuvant, retrieved from <http://en.wikipedia.org/wiki/Adjuvant> on May 9, 2012.

Amino Acid Structures, Codes, and Reference Information, retrieved from <www.promega.com/resources/tools/amino-acid-chart-amino-acid-structure> on Apr. 21, 2022.

Amino Acids Molecular Weights, retrieved from <http://fortiusbio.com/Aa_MW.html> on Dec. 22, 2021.

Arnon et al. Antiviral response elicited by a completely synthetic antigen with built-in adjuvanticity. Proc Natl Acad Sci U S A. 1980;77(11):6769-6772.

Atherton et al. Preclinical development of peptide vaccination combined with oncolytic MG1-E6E7 for HPV-associated cancer. Vaccine. 2018;36(16):2181-2192.

Audibert et al. Successful immunization with a totally synthetic diphtheria vaccine. Proc Natl Acad Sci U S A. 1982;79(16):5042-5046.

Bachmann MF, Jennings GT. Vaccine delivery: a matter of size, geometry, kinetics and molecular patterns. Nat Rev Immunol. 2010;10(11):787-796.

Baharom et al. Intravenous nanoparticle vaccination generates stem-like TCF1+ neoantigen-specific CD8+ T cells. Nat Immunol. 2021;22(1):41-52.

Barrios & Celis. TriVax-HPV: an improved peptide-based therapeutic vaccination strategy against human papillomavirus-induced cancers. Cancer Immunol Immunother. 2012;61(8):1307-1317.

Başalp et al. Immune response to 17beta-estradiol involved in polymer gels: antigen specificity and affinity of hybridoma clones. Hybridoma. 2000;19(6):495-499.

Belnoue et al. Enhancing Antitumor Immune Responses by Optimized Combinations of Cell-penetrating Peptide-based Vaccines and Adjuvants. Mol Ther. 2016;24(9):1675-1685.

(56) References Cited

OTHER PUBLICATIONS

Belnoue et al. Targeting self and neo-epitopes with a modular self-adjuvanting cancer vaccine. JCI Insight. 2019;5(11):e127305.
Bissett et al. Phase I and pharmacokinetic (PK) study of MAG-CPT (PNU 166148): a polymeric derivative of camptothecin (CPT). Br J Cancer. 2004;91(1):50-55.
Black et al. Self-assembled peptide amphiphile micelles containing a cytotoxic T-cell epitope promote a protective immune response in vivo. Adv Mater. 2012;24(28):3845-3849.
Bogyo et al. Substrate binding and sequence preference of the proteasome revealed by active-site-directed affinity probes. Chem Biol. 1998;5(6):307-320.
Brito & O'Hagan. Designing and building the next generation of improved vaccine adjuvants. J Control Release. 2014;190:563-579.
Cabral et al. Optimization of (1,2-diamino-cyclohexane)platinum(II)-loaded polymeric micelles directed to improved tumor targeting and enhanced antitumor activity. J Control Release. 2007;121(3):146-155.
Carr et al. Complexation Hydrogels for the Oral Delivery of Growth Hormone and Salmon Calcitonin. Ind Eng Chem Res. 2010;49(23):11991-11995.
CD40 (Protein), retrieved at <https://en.wikipedia.org/w/index.php?title=CD40_(protein)&oldid=742991040>.
Chan et al. Synthesis and immunological characterization of toll-like receptor 7 agonistic conjugates. Bioconjug Chem. 2009;20(6):1194-1200.
Chaudhuri et al. High-throughput biophysical analysis of protein therapeutics to examine interrelationships between aggregate formation and conformational stability. AAPS J. 2014;16(1):48-64.
Chedid et al. Enhancement of certain biological activities of muramyl dipeptide derivatives after conjugation to a multi-poly(DL-alanine)—poly(L-lysine) carrier. Proc Natl Acad Sci U S A. 1979;76(12):6557-6561.
Chemistry of Crosslinking, retrieved at <www.thermofisher.com/us/en/home/life-science/protein-biology/protein-biology-learning-center/protein-biology-resource-library/pierce-protein-methods/chemistry-crosslinking.html> (first available 2015).
ChitoClear—A Natural and Functional Ingredient for Personal Care Products & LipoSan—The Natural Way of Weight Loss, retrieved at <http://www.primex.is/Products> (2013).
Chitosan, retrieved at <http://en.wikipedia.org/wiki/Chitosan> on Aug. 29, 2014.
Cho et al. BiVax: a peptide/poly-IC subunit vaccine that mimics an acute infection elicits vast and effective anti-tumor CD8 T-cell responses. Cancer Immunol Immunother. 2013;62(4):787-799.
Choe Y et al. Substrate profiling of cysteine proteases using a combinatorial peptide library identifies functionally unique specificities. J Biol Chem. 2006;281(18):12824-12832.
Chruszcz et al. Serum albumins-unusual allergens. Biochim Biophys Acta. 2013;1830(12):5375-5381.
Collins et al. Self-assembly of peptides into spherical nanoparticles for delivery of hydrophilic moieties to the cytosol. ACS Nano. 2010;4(5):2856-2864.
Co-pending U.S. Appl. No. 18/277,220, filed Aug. 14, 2023.
Cristofaro & Opal. The Toll-like receptors and their role in septic shock. Expert Opin Ther Targets. 2003;7(5):603-612.
Dane et al. Big thinking for adjuvants. Nat Biotechnol. 2015;33(11):1146-1148.
Dehsorkhi et al. Self-assembling amphiphilic peptides. J Pept Sci. 2014;20(7):453-467.
Dintzis et al. Molecular determinants of immunogenicity: the immunon model of immune response. Proc Natl Acad Sci U S A. 1976;73(10):3671-3675.
DNA methyltransferase [Brachyspira hyodysenteriae]—NCBI Reference Sequence: WP_047111413.1, NCBI Protein Database <https://www.ncbi.nlm.nih.gov>, earliest reference of 1986, accessed Oct. 12, 2023.
Du et al. Paclitaxel-loaded micelles composed of folate-poly(ethylene glycol) and poly(gamma-benzyl l-glutamate) diblock copolymer. Colloid Surf A. 2010;353:140-148.
Duncan & Vicent MJ. Do HPMA copolymer conjugates have a future as clinically useful nanomedicines? A critical overview of current status and future opportunities. Adv Drug Deliv Rev. 2010;62(2):272-282.
Duncan et al. Anticancer agents coupled to N-(2-hydroxypropyl)methacrylamide copolymers. II. Evaluation of daunomycin conjugates in vivo against L1210 leukaemia. Br J Cancer. 1988;57(2):147-156.
Duong et al. Pronounced peptide selectivity for melanoma through tryptophan end-tagging. Sci Rep. 2016;6:24952.
Ekladious et al. Polymer-drug conjugate therapeutics: advances, insights and prospects. Nat Rev Drug Discov. 2019;18(4):273-294.
Etrych et al. Synthesis of HPMA Copolymers Containing Doxorubicin Bound via a Hydrazone Linkage. Effect of Spacer on Drug Release and in vitro Cytotoxicity. Macromol. Biosci. 2002;2(1):43-52.
Feng et al. Polymeric Conjugates for Anti-Cancer Drug Delivery. Literature Seminar. 2010.
Fexby & Bülow. Hydrophobic peptide tags as tools in bioseparation. Trends Biotechnol. 2004;22(10):511-516.
Francica et al. Thermoresponsive Polymer Nanoparticles Co-deliver RSV F Trimers with a TLR-7/8 Adjuvant. Bioconjug Chem. 2016;27(10):2372-2385.
Fujita et al. 6-(4-Amino-2-butyl-imidazoquinolyl)-norleucine: Toll-like receptor 7 and 8 agonist amino acid for self-adjuvanting peptide vaccine. Amino Acids. 2016;48(5):1319-1329.
Fuks et al. Biohybrid block copolymers: towards functional micelles and vesicles. Chem Soc Rev. 2011;40(5):2475-2493.
Gerster et al. Synthesis and structure-activity-relationships of 1H-imidazo[4,5-c]quinolines that induce interferon production. J Med Chem. 2005;48(10):3481-3491.
Ghendon et al. Chitosan as an adjuvant for parenterally administered inactivated influenza vaccines. Arch Virol. 2008;153(5):831-837.
Golovanov et al. A simple method for improving protein solubility and long-term stability. J Am Chem Soc. 2004;126(29):8933-8939.
Greco & Vicent. Combination therapy: opportunities and challenges for polymer-drug conjugates as anticancer nanomedicines. Adv Drug Deliv Rev. 2009;61(13):1203-1213.
Grela et al. The TLR7 agonist R848 alleviates allergic inflammation by targeting invariant NKT cells to produce IFN-gamma. J Immunol. 2011; 186(1):284-290.).
Guidelines on Adjuvants in Vaccines for Human Use, EMEA Adjuvants Guidance, The European Medicines Agency Evaluation of Medicines for Human Use (2005).
Guo et al. Cell-penetrating peptides: Possible transduction mechanisms and therapeutic applications. Biomed Rep. 2016;4(5):528-534.
Gutjahr et al. Triggering Intracellular Receptors for Vaccine Adjuvantation [published correction appears in Trends Immunol. Oct. 2016;37(10):716.
Hamaguchi et al. NK105, a paclitaxel-incorporating micellar nanoparticle formulation, can extend in vivo antitumour activity and reduce the neurotoxicity of paclitaxel. Br J Cancer. 2005;92(7):1240-1246.
Harris et al. Rapid and general profiling of protease specificity by using combinatorial fluorogenic substrate libraries. Proc Natl Acad Sci U S A. 2000;97(14):7754-7759.
Harris et al. Substrate specificity of the human proteasome. Chem Biol. 2001;8(12):1131-1141.
Hein et al. Click Chemistry, A Powerful Tool for Pharmaceutical Sciences. Pharmaceutical Research. 2008; 25(10):2216-2230.
Heuking & Borchard. Toll-like receptor-7 agonist decoration enhances the adjuvanticity of chitosan-DNA nanoparticles. J Pharm Sci. 2012;101(3):1166-1177.
Heuking et al. Stimulation of human macrophages (THP-1) using Toll-like receptor-2 (TLR-2) agonist decorated nanocarriers. J Drug Target. 2009;17(8):662-670.
Heuking et al. Toll-like receptor-2 agonist functionalized biopolymer for mucosal vaccination. Int J Pharm. 2009;381(2):97-105.
How to Enhance the Solubility of L-Tyrosine in Cell Culture Media Applications, retrieved from <https://healthcare.evonik.com/en/biopharma/cell-culture/common-challenges/performance-improvement> on Dec. 1, 2022.

(56) References Cited

OTHER PUBLICATIONS

Huber et al. Immuno- and constitutive proteasome crystal structures reveal differences in substrate and inhibitor specificity. Cell. 2012;148(4):727-738.

Seder et al., U.S. Appl. No. 16/079,972, filed Aug. 24, 2018.

International Preliminary Examination Report dated Sep. 13, 2011 and received in PCT/GB2010/000915, 19 pages.

International Search Report and Written Opinion dated Aug. 19, 2010and received in PCT/GB2010/000915, 14 pages.

International Search Report and Written Opinion dated Dec. 14, 2015 and received in PCT/GB2015/052974, 13 pages.

International Search Report and Written Opinion dated Dec. 5, 2019 and received in PCT/US2019/033612, 23 pages.

International Search Report and Written Opinion dated Feb. 20, 2024 and received in PCT/US2023/077767, 19 pages.

International Search Report and Written Opinion dated Jan. 25, 2022 and received in PCT/US2021/051298, 15 pages.

International Search Report and Written Opinion dated Jan. 6, 2020 and received in PCT/US2019/054343, 13 pages.

International Search Report and Written Opinion dated Jun. 17, 2024 and received in PCT/US2023/077765, 11 pages.

International Search Report and Written Opinion dated Mar. 1, 2021 and received in PCT/US2020/047962, 16 pages.

International Search Report and Written Opinion dated May 8, 2022 and received in PCT/US2022/016600, 26 pages.

International Search Report and Written Opinion dated Sep. 24, 2018 and received in PCT/US2018/026145, 13 pages.

International Search Report and Written Opinion of International Application No. PCT/US2022/033819, dated Sep. 13, 2022.

Iurovskiĭ et al. [Artificial peptide and carbohydrate antigens. Immobilization of haptens and adjuvant (MDP) on polyacrylamide]. Abstract. Bioorg Khim. 1986;12(1):100-105.

Jackson DC, Lau YF, Le T, et al. A totally synthetic vaccine of generic structure that targets Toll-like receptor 2 on dendritic cells and promotes antibody or cytotoxic T cell responses. Proc Natl Acad Sci U S A. 2004;101(43):15440-15445.

Ji & Feng. Solubility of amino acids in water and aqueous solutions by the statistical associating fluid theory. Ind. Eng. Chem. Res. 2008;47(16):6275-6279.

Joshi et al. Inflammation directs memory precursor and short-lived effector CD8+ T cell fates via the graded expression of T-bet transcription factor. Immunity. 2007;27(2):281-295.

Kim et al. Phase I and pharmacokinetic study of Genexol-PM, a cremophor-free, polymeric micelle-formulated paclitaxel, in patients with advanced malignancies. Clin Cancer Res. 2004;10(11):3708-3716.

Klein et al. Design and characterization of structured protein linkers with differing flexibilities. Prot. Eng. Des. Selection. 2014; 27:325-330.

Kleine et al. Lipopeptide-polyoxyethylene conjugates as mitogens and adjuvants. Immunobiology. 1994;190(1-2):53-66.

Levina et al. Synthesis of polyamine-containing oligonucleotides. Russ. J. Bioorg. Chem. 2008;34(1):89-95.

Liras et al. Thermo-responsive allyl-f2-(2-methoxyethoxy)ethyl methacrylate-based polymers as versatile precursors for smart polymer conjugates and conetworks. Macromolecules. 2011;44(10):3739-3745.

Liu et al. Structure-based programming of lymph-node targeting in molecular vaccines. Nature. 2014;507(7493):519-522; Supplementary Information pp. 1-9.

Luo et al. Synthetic nanovaccines for immunotherapy. J Control Release. 2017;263:200-210.

Lynn et al. In vivo characterization of the physicochemical properties of polymer-linked TLR agonists that enhance vaccine immunogenicity. Nat Biotechnol. 2015;33(11):1201-1210; Supplementary Figures 1-15; Supplementary Materials and Methods pp. 1-17.

Lynn et al. Induction of anti-cancer T cell immunity by in situ vaccination using systemically administered nanomedicines. Cancer Lett. 2019;459:192-203.

Lynn et al. Peptide-TLR-7/8a conjugate vaccines chemically programmed for nanoparticle self-assembly enhance CD8 T-cell immunity to tumor antigens. Nat Biotechnol. 2020;38(3):320-332.

Lynn t al. In vivo characterization of the physicochemical properties of polymer-linked TLR agonists that enhance vaccine immunogenicity. Nat Biotechnol. 2015;33(11):1201-1210.

MacKay et al. Self-assembling chimeric polypeptide-doxorubicin conjugate nanoparticles that abolish tumours after a single injection. Nat Mater. 2009;8(12):993-999.

Maurer et al. CpG-DNA aided cross-presentation of soluble antigens by dendritic cells. Eur J Immunol. 2002;32(8):2356-2364.

McGray et al. Oncolytic Maraba virus armed with tumor antigen boosts vaccine priming and reveals diverse therapeutic response patterns when combined with checkpoint blockade in ovarian cancer. J Immunother Cancer. 2019;7(1):189.

Meerum Terwogt et al. Phase I clinical and pharmacokinetic study of PNU166945, a novel water-soluble polymer-conjugated prodrug of paclitaxel. Anticancer Drugs. 2001;12(4):315-323.

Methacrylamide, retrieved from <https://en.wikipedia.org/wiki/Methacrylamide> on Jun. 4, 2016.

Mitsui et al. Polyarginine-mediated protein delivery to dendritic cells presents antigen more efficiently onto MHC class I and class II and elicits superior antitumor immunity. J Invest Dermatol. 2006;126(8):1804-1812.

Morgan et al. Evaluation of N-(2-hydroxypropyl)methacrylamide copolymer-peptide conjugates as potential oral vaccines. Studies on their degradation by isolated rat small intestinal peptidases and their uptake by adult rat small intestinal tissue in vitro. Int. J. Pharm. 1996; 128(1-2):99-111.

Moyle & Toth. Self-adjuvanting lipopeptide vaccines. Curr Med Chem. 2008;15(5):506-516.

Moynihan et al. Eradication of large established tumors in mice by combination immunotherapy that engages innate and adaptive immune responses. Nat Med. 2016;22(12):1402-1410.

Oh, et al., “pH-sensitive properties of surface charge-switched multifunctional polymeric micelle”, Int J Pharm, Jul. 2009, vol. 376(1-2): pp. 134-140. Epub Apr. 24, 2009. doi: 10.1016/j.ijpharm.2009.04.021.

Orädd et al. Effects of peptide hydrophobicity on its incorporation in phospholipid membranes—an NMR and ellipsometry study. Biochim Biophys Acta. 2011;1808(1):244-252.

P04141—CSF2_Human—Granulocyte-Macrophage Colony-Stimulating Factor Precursor—CSF2, retrieved at <http://www.uniprot.org/uniprot/P04141>.

P23510—TNFL4_Human—Tumor Necrosis Factor Ligand Superfamily Member 4 - TNFSF4, retrieved from <http://www.uniprot.org/uniprot/P23510>.

P25942—TNR5_Human—Tumor necrosis factor receptor superfamily member 5—CD40, retrieved at <http://www.uniprot.org/uniprot/P25942>.

Particulate Contamination—Risk Prevention in Infusion Therapy, B. Braun Melsungen AG, No. 6069091, Edition: 03, 2011.

Pelin, Bio-engineering vaccinia viruses for increased oncolytic potential, University of Ottawa, Dec. 2, 2019, retrieved from <http://hdl.handle.net/10393/39909> on Jun. 28, 2022.

Pentadecane, retrieved at <https://pubchem.ncbi.nlm.nih.gov/compound/Pentadecane> on Oct. 12, 2023.

Peptide Mimetics, retrieved at <www.biosyn.com/tew/peptide-mimetics.aspx> (2012).

Perrie et al. Vaccine adjuvant systems: enhancing the efficacy of sub-unit protein antigens. Int J Pharm. 2008;364(2):272-280.

Petho et al. Amphiphilic drug-peptide-polymer conjugates based on poly(ethylene glycol) and hyperbranched polyglycerol for epidermal growth factor receptor targeting: the effect of conjugate aggregation on in vitro activity. Soft Matter. 2020;16(24):5759-5769.

Pina et al. Tryptophan tags and de novo designed complementary affinity ligands for the expression and purification of recombinant proteins. J Chromatogr A. 2016;1472:55-65.

Pol et al. Development and applications of oncolytic Maraba virus vaccines. Oncolytic Virother. 2018;7:117-128.

Pola et al. Click chemistry as a powerful and chemoselective tool for the attachment of targeting ligands to polymer drug carriers. Polym. Chem. 2014;5(4):1340-1350.

(56) References Cited

OTHER PUBLICATIONS

Polyacrylamide, retrieved at <https://en.wikipedia.org/wiki/Polyacrylamide> on Jun. 4, 2016.
Raissi et al. Enhanced potency of the metalloprotease inhibitor TAPI-2 by multivalent display. Bioorg Med Chem Lett. 2014;24(8):2002-2007.
Ríhová et al. HPMA-based biodegradable hydrogels containing different forms of doxorubicin. Antitumor effects and biocompatibility. Ann N Y Acad Sci. 1997;831:57-71.
Rowe, Validating transgenic Farmington viruses for the treatment of glioblastoma multiforme, University of Ottawa, Jan. 1, 2015, retrieved from <http://hdl.handle.net/10393/33354> on Nov. 19, 2019.
Ryu et al. Stimulation of innate immune cells by light-activated TLR7/8 agonists. J Am Chem Soc. 2014;136(31):10823-10825.
Sainz et al. Alpha-Galactosylceramide and peptide-based nanovaccine synergistically induced a strong tumor suppressive effect in melanoma. Acta Biomater. 2018;76:193-207.
Segura & Hubbell. Synthesis and in vitro characterization of an ABC triblock copolymer for siRNA delivery. Bioconjug Chem. 2007;18(3):736-745.
Seymour et al. Hepatic drug targeting: phase I evaluation of polymer-bound doxorubicin. J Clin Oncol. 2002;20(6):1668-1676.
Seymour et al. Phase II studies of polymer-doxorubicin (PK1, FCE28068) in the treatment of breast, lung and colorectal cancer. Int J Oncol. 2009;34(6):1629-1636.
Shakya et al. Characterization of chemically defined poly-N-isopropylacrylamide based copolymeric adjuvants. Vaccine. 2013;31(35):3519-3527.
Shi et al. Novel vaccine adjuvant LPS-Hydrogel for truncated basic fibroblast growth factor to induce antitumor immunity. Carbohydr Polym. 2012;89(4):1101-1109.
Shukla et al. Toward self-adjuvanting subunit vaccines: model peptide and protein antigens incorporating covalently bound toll-like receptor-7 agonistic imidazoquinolines. Bioorg Med Chem Lett. 2011;21(11):3232-3236.
Speir et al. Glycolipid-peptide conjugate vaccines enhance CD8+ T cell responses against human viral proteins. Sci Rep. 2017;7(1):14273.
Subr et al. Coating of adenovirus type 5 with polymers containing quaternary amines prevents binding to blood components. J Control Release. 2009;135(2):152-158.
Tanji et al. Structural reorganization of the Toll-like receptor 8 dimer induced by agonistic ligands. Science. 2013;339(6126):1426-1429.
TentaGel® PAP TentaGel resins for the synthesis of PEG attached peptides, Rapp Polymere, retrieved from http://www.rapp-polymere.com/index.php?id=936.
Toll-Like Receptor, retrieved from <http://en.wikipedia.org/wiki/Toll-like_receptor> on May 28, 2012.
Tom et al. Applications of Immunomodulatory Immune Synergies to Adjuvant Discovery and Vaccine Development. Trends Biotechnol. 2019;37(4):373-388.
Trent et al. Peptide amphiphile micelles self-adjuvant group A streptococcal vaccination. AAPS J. 2015;17(2):380-388.
Trzcinska et al. Bioactive mesoglobules of poly(di(ethylene glycol) monomethyl ether methacrylate)-peptide conjugate. Polym. Chem. 2012;50(15):3104-3115.
Tyrosine Y (Tyr), retrieved from http://www.biology.arizona.edu/biochemistry/problem_sets/aa/tyrosine.html (2003).
Tyrosine, retrieved from <www.russelllab.org/aas/Tyr.html#:-:text=Substitutions%3A%20As%20Tyrosine%20is%20an,position%20on%20the%20benzene%20ring> on Apr. 21, 2022.
Wagner & Musso. New naturally occurring amino acids. Angew. Chem. Int. 1983;22:816-828.
Wang & Roberts (Ed.). Aggregation of therapeutic proteins passage. 5.3.6 Turbidimetry and Nephelometry (pp. 235-237), p. 236, second and third paragraphs (2010).
Water Absorption (How Much Water Gets Soaked Up)—The Percentage Increase in Weight of a Plastic Article When Immersed in Water for a Specified Time and at a Specified Temperature, Properties—Water Absorption, www. curbellplastics.com.
Weterings et al. Synthesis of 2-alkoxy-8-hydroxyadenylpeptides: towards synthetic epitope-based vaccines. Bioorg Med Chem Lett. 2006;16(12):3258-3261.
Wille-Reece et al. HIV Gag protein conjugated to a Toll-like receptor 7/8 agonist improves the magnitude and quality of Th1 and CD8+ T cell responses in nonhuman primates. Proc Natl Acad Sci U S A. 2005;102(42):15190-15194.
Wille-Reece et al. Immunization with HIV-1 Gag protein conjugated to a TLR7/8 agonist results in the generation of HIV-1 Gag-specific Th1 and CD8+ T cell responses. J Immunol. 2005;174(12):7676-7683.
Wille-Reece et al. Toll-like receptor agonists influence the magnitude and quality of memory T cell responses after prime-boost immunization in nonhuman primates. J Exp Med. 2006;203(5):1249-1258.
Wilson et al. pH-Responsive nanoparticle vaccines for dual-delivery of antigens and immunostimulatory oligonucleotides. ACS Nano. 2013;7(5):3912-3925.
Wu et al. Immunotherapeutic activity of a conjugate of a Toll-like receptor 7 ligand. Proc Natl Acad Sci U S A. 2007;104(10):3990-3995.
Wu. Strategies for designing synthetic immune agonists. Immunology. 2016;148(4):315-325.
Yadav et al. Predicting immunogenic tumour mutations by combining mass spectrometry and exome sequencing. Nature. 2014;515(7528):572-576.
Zeng et al. A modular approach to assembly of totally synthetic self-adjuvanting lipopeptide-based vaccines allows conformational epitope building. J Biol Chem. 2011;286(15):12944-12951.
Zhang et al. Tunable diblock copolypeptide hydrogel depots for local delivery of hydrophobic molecules in healthy and injured central nervous system. Biomaterials. 2014;35(6):1989-2000.
Zhu et al. Albumin/vaccine nanocomplexes that assemble in vivo for combination cancer immunotherapy. Nat Commun. 2017;8(1):1954.
Zom et al. Efficient induction of antitumor immunity by synthetic toll-like receptor ligand-peptide conjugates. Cancer Immunol Res. 2014;2(8):756-764.
U.S. Appl. No. 13/318,844, filed Feb. 21, 2012, Multi-Valent Adjuvant Display, Abandoned.
U.S. Appl. No. 15/299,936, filed Oct. 21, 2016, Multi-Valent Adjuvant Display, Abandoned.
U.S. Appl. No. 15/517,121, filed Apr. 5, 2017, Polymer Adjuvant, Abandoned.
U.S. Appl. No. 16/907,912, filed Jun. 22, 2020, Polymer Adjuvant, Abandoned.
U.S. Appl. No. 18/970,451, filed Dec. 5, 2024, Polymer Adjuvant, Pending.
U.S. Appl. No. 16/500,762, filed Oct. 3, 2019, Peptide-Based Vaccines, Methods of Manufacturing, and Uses Thereof for Inducing an Immune Response, Published as US 2020-0054741 A1.
U.S. Appl. No. 17/057,658, filed Nov. 21, 2020, Improved Methods of Manufacturing Peptide-Based Vaccines, Published as US 2021/0113705 A1.
U.S. Appl. No. 17/282,447, filed Apr. 2, 2021, Aromatic Ring Substituted Amphiphilic Polymers as Drug Delivery Systems, Published as US 2021/0393523 A1.
U.S. Appl. No. 17/604,227, filed Oct. 15, 2021, Compositions and Methods of Manufacturing Star Polymers for Ligand Display and/or Drug Delivery, Pulished as US 2023/0026627 A1.
U.S. Appl. No. 18/277,220, filed Aug. 14, 2023, Self-Assembling Nanoparticles Based on Amphiphilic Peptides, Pending.
U.S. Appl. No. 18/570,579, filed Dec. 14, 2023, Self-Assembling Nanoparticles Based on Amphiphilic Peptides for Drug Delivery Applications, Published as US 2024/0382614 A1.
U.S. Appl. No. 18/027,346, filed Mar. 20, 2023, Compositions and Methods of Manufacturing Amphiphilic Block Copolymers that Form Nanoparticles in Situ, Published as US 2023/0381112 A1.
U.S. Appl. No. 18/032,538, filed Apr. 18, 2023, Star Polymer Drug Conjugates, Published as US 2023/0390406 A1.
U.S. Appl. No. 17/638,576, filed Feb. 25, 2022, Methods for Inducing An Immune Response Against Neoantigens, Published as US 202210305099 A1.

(56) References Cited

OTHER PUBLICATIONS

U.S. Appl. No. 18/494,491, filed Oct. 25, 2023, Self-Assembling Nanoparticles, Published as US 2024/0269269 A1.
Fuks et al., Biohybrid block copolymers: towards functional micelles and vesicles, Chem. Soc. Rev., 40:2475-2493 (2011).
Komatsu et al., Facile preparation of degradable thermoresponsive polymers as biomaterials, Polymer 130:68-73 (2017).
Co-Pending U.S. Appl. No. 19/242,746, filed Jun. 18, 2025.
Co-Pending U.S. Appl. No. 19/246,539, filed Jun. 23, 2025.
Co-Pending U.S. Appl. No. 19/183,635, filed Apr. 18, 2025.

* cited by examiner

C57BL/6
*n* = 10 / group

▼ EAE Induction (day 0)
● Treatment (day 0, 7, 14)
○ Euthanize (day 28)

Dose: 2.5 nmol

[1]
[2]
[3]
[4]
[11]

--•-- [1] Vehicle IM

--■-- [2] Vehicle SC

--◦-- [5] MOG + Rapamycin IM; 8 nmol x3

--▲-- [8] MOG + Rapamycin SC; 8 nmol x3

--★-- [12] MOG + Rapamycin IM; 8 nmol x1

--◦-- [13] MOG + Rapamycin SC; 8 nmol x1

SELF-ASSEMBLING NANOPARTICLES

CROSS-REFERENCE TO RELATED APPLICATIONS

This application is a continuation of U.S. application Ser. No. 18/494,491, filed on Oct. 25, 2023, which claims the benefit of, and priority to, U.S. Provisional Application No. 63/380,931, filed on Oct. 25, 2022, the contents of each of which are hereby incorporated by reference in their entirety for all purposes.

GOVERNMENT RIGHTS

This invention was created in the performance of a Cooperative Research and Development Agreement with the National Institutes of Health, an Agency of the Department of Health and Human Services. The Government of the United States has certain rights in this invention.

FIELD OF THE DISCLOSURE

The present disclosure relates to novel PEGylated peptide antigen conjugate compositions, that can be used to form nanoparticles, including micelle structures or polymersomes, methods of manufacturing the pegylated peptide antigen conjugate compositions, processes for formulating drug molecules with the pegylated peptide antigen conjugate compositions that form nanoparticles, and therapeutic uses of the nanoparticles for drug delivery.

REFERENCE TO SEQUENCE LISTING

The instant application contains a Sequence Listing which has been submitted electronically in XML format and is hereby incorporated by reference in its entirety. Said XML file, created on Feb. 9, 2025, is named BARI-102USC1_SL.xml and is 638.4 kilobytes in size.

BACKGROUND OF THE DISCLOSURE

Various peptide-based vaccine technologies are known and have been developed for delivering peptide antigen to induce an immune response. U.S. Pat. Appl. No 2020/0054741 relates to novel peptide-based vaccines, methods of manufacturing the novel peptide-based vaccines and uses thereof for delivering peptide antigens to induce an immune response. U.S. Pat. Appl. No 2021/0113705 discloses improved methods of manufacturing peptide-based vaccines.

PEGylation has been widely deployed as a means for shielding molecules from the immune system. Numerous PEGylated recombinant proteins (Ramos-de-la-Peña, A M, et al. International Journal of Peptide Research and Therapeutics, 2020, 26:333-348) have been approved by the FDA on the basis of improved pharmacokinetics, which has been attributed to improved ability to evade the immune system. PEGylated liposomal carriers, including DOXIL have also been developed based on a similar principle that PEGylation reduces immune recognition. Our prior results with PEGylated peptide antigen conjugates as disclosed in U.S. Pat. Appl. No 2020/0054741 indicated that such PEGylation was likely deleterious to immune responses generated with peptide antigens.

Recently, there has been increasing interest in use of peptide-based vaccines, for inducing tolerance for treating autoimmunity. WO 2022/177993 relates to a vaccine comprising novel amphiphile compositions and at least one peptide antigen conjugate having charged block, wherein the amphiphile and/or at least one peptide antigen conjugate comprises a dendron amplifier. A potential challenge was that peptide antigen conjugate having charged block were found to cause dose-dependent red blood cell hemolysis. Though amphiphilic carrier was introduced to overcome the problem, there was still an associated decrease in hydrodynamic stability. Therefore, there is currently a need for improved peptide antigen conjugate compositions that have reduced hemolytic activity while maintaining hydrodynamic stability and improved methods of delivering multiple immunomodulators and peptide antigens in particles for inducing tolerance. It is an object of present disclosure to provide improved compositions, methods of manufacturing vaccines that address the aforementioned challenges and use of the same for inducing immune response.

SUMMARY OF THE DISCLOSURE

The present disclosure provides novel PEGylated peptide antigen conjugate compositions, that can be used to form nanoparticles, including micelle structures or polymersomes, methods of manufacturing the pegylated peptide antigen conjugate compositions, processes for formulating drug molecules with the pegylated peptide antigen conjugate compositions that form nanoparticles, and therapeutic uses of the nanoparticles for drug delivery.

In a first aspect of the present disclosure, a vaccine is provided comprising at least one peptide antigen conjugate having the formula selected from PEG-[E1]-A-[E2]-[U]-H and H-[U]-[E1]-A-[E2]-PEG wherein A is a peptide antigen;

E1 is an N-terminal extension;

E2 is a C terminal extension;

H, independently for each occurrence is a hydrophobic block, wherein one or more drug molecules (D) are optionally attached to each H directly or via a suitable linker X1;

U, independently for each occurrence, is a linker;

[ ] denotes that the group is optional, and

- denotes that the two adjacent groups are directly attached to one another by a covalent bond or indirectly to one another via a suitable linker X.

In a second aspect of the present disclosure, a vaccine is provided comprising at least one peptide antigen conjugate having the formula selected from PEG-[E1]-A-[E2]-[U]-H and H-[U]-[E1]-A-[E2]-PEG, and an amphiphile having the formula S-[B]-[U]-H, wherein A is a peptide antigen;

E1 is an N-terminal extension;

E2 is a C terminal extension;

H, independently for each occurrence is a hydrophobic block, wherein one or more drug molecules (D) are optionally attached to each H directly or via a suitable linker X1;

S is a solubilizing block;

B is a spacer;

U, independently for each occurrence, is a linker;

[ ] denotes that the group is optional, and

- denotes that the two adjacent groups are directly attached to one another by a covalent bond or indirectly to one another via a suitable linker X.

In one embodiment of the vaccine, the S of the amphiphile comprises a dendron amplifier.

In a third aspect of the present disclosure, a vaccine for inducing tolerance is provided comprising at least one peptide antigen conjugate having the formula selected from PEG-[E1]-A-[E2]-[U]-H and H-[U]-[E1]-A-[E2]-PEG, and an amphiphile having the formula S-[B]-[U]-H, wherein A is a peptide antigen;

E1 is an N-terminal extension;

E2 is a C terminal extension;

H, independently for each occurrence is a hydrophobic block, wherein one or more drug molecules (D) are optionally attached to each H directly or via a suitable linker X1;

S is a solubilizing block;

B is a spacer;

U, independently for each occurrence, is a linker;

[ ] denotes that the group is optional,

- denotes that the two adjacent groups are directly attached to one another by a covalent bond or indirectly to one another via a suitable linker X;

wherein the amphiphile comprises a dendron amplifier; and at least one peptide antigen A is selected from an autoantigen, alloantigen and allergen.

In a fourth aspect of the present disclosure, provided herein is a vaccine comprising at least one peptide antigen conjugate having the formula selected from PEG-[E1]-A-[E2]-[U]-H and H-[U]-[E1]-A-[E2]-PEG, and an amphiphile having the formula S-[B]-[U]-H, wherein A is peptide antigen;

E1 is an N-terminal extension;

E2 is a C terminal extension;

H, independently for each occurrence is a hydrophobic block, wherein one or more drug molecules (D) are optionally attached to each H directly or via a suitable linker X1;

S is a solubilizing block;

B is a spacer;

U, independently for each occurrence, is a linker;

[ ] denotes that the group is optional,

- denotes that the two adjacent groups are directly attached to one another by a covalent bond or indirectly to one another via a suitable linker X;

wherein the amphiphile comprises a dendron amplifier; and wherein at least one A comprises a sequence wherein one or more cysteine residues have been replaced with alpha amino-butyric acid and/or one or more methionine residues have been replaced with norleucine.

In a fifth aspect of the present disclosure, a vaccine is provided comprising at least one peptide antigen (A), wherein at least one A comprises a sequence wherein one or more cysteine residues have been replaced with alpha amino-butyric acid and/or one or more methionine residues have been replaced with norleucine.

In one embodiment of the present disclosure, a vaccine is provided wherein at least one peptide antigen (A) comprises alpha amino-butyric acid and/or norleucine.

In a sixth aspect of the present disclosure, a vaccine for inducing tolerance is provided comprising at least one peptide antigen conjugate having the formula selected from PEG-[E1]-A-[E2]-[U]-H and H-[U]-[E1]-A-[E2]-PEG, and an amphiphile having the formula S-[B]-[U]-H, wherein A is a peptide antigen;

E1 is an N-terminal extension;

E2 is a C terminal extension;

H, independently for each occurrence is a hydrophobic block, wherein one or more drug molecules (D) are optionally attached to each H directly or via a suitable linker X1;

S is a solubilizing block;

B is a spacer;

U, independently for each occurrence, is a linker;

[ ] denotes that the group is optional,

- denotes that the two adjacent groups are directly attached to one another by a covalent bond or indirectly to one another via a suitable linker X;

wherein the amphiphile comprises a dendron amplifier; and at least one A is selected from an autoantigen, alloantigen and allergen and at least one D is present.

In one embodiment of the vaccine for inducing tolerance, the at least one D is selected from inhibitors of mTOR, RORγt, CDK8/19, and HDAC and agonists of AHR, RAR and $A_{2a}$.

In another embodiment of the vaccine for inducing tolerance, the at least one D is selected from ATP-competitive mTOR inhibitors.

In some embodiments of the vaccine for inducing tolerance, the at least one D is selected from AZD-8055, AZD-2016, KU-0063794, CC223, Torin-1, Torin-2, INK-128, WYE354, WYE132, OSI-027, OXA-01, PI-103, NVP-BEZ235, GNE-493, GSK2126458, rapamycin, tacrolimus, everolimus, RAD001, CCI-779 and AP23573.

In a seventh aspect of the present disclosure, a peptide antigen conjugate is provided having formula selected from PEG-[E1]-A-[E2]-[U]-H and H-[U]-[E1]-A-[E2]-PEG, wherein A is a peptide antigen;

E1 is an N-terminal extension;

E2 is a C terminal extension;

H, independently for each occurrence is a hydrophobic block, wherein one or more drug molecules (D) are optionally attached to each H directly or via a suitable linker X1;

U, independently for each occurrence, is a linker;

[ ] denotes that the group is optional, and

- denotes that the two adjacent groups are directly attached to one another by a covalent bond or indirectly to one another via a suitable linker.

In an eighth aspect of the present disclosure, provided herein is a method of treating or preventing an inflammatory disease in a subject in need thereof comprising administering to the subject a vaccine comprising at least one peptide antigen conjugate having the formula selected from PEG-[E1]-A-[E2]-[U]-H and H-[U]-[E1]-A-[E2]-PEG, and an amphiphile having the formula S-[B]-[U]-H, wherein A is a peptide antigen;

E1 is an N-terminal extension;

E2 is a C terminal extension;

H, independently for each occurrence is a hydrophobic block, wherein one or more drug molecules (D) are optionally attached to each H directly or via a suitable linker X1;

S is a solubilizing block;

B is a spacer;

U, independently for each occurrence, is a linker;

[ ] denotes that the group is optional,

- denotes that the two adjacent groups are directly attached to one another by a covalent bond or indirectly to one another via a suitable linker; and
  wherein the amphiphile comprises a dendron amplifier and at least one peptide antigen is selected from an autoantigen and foreign antigen.

In one embodiment of the method of treating autoimmune disease, the vaccine is administered intravenously, subcutaneously or intramuscularly.

In a ninth aspect of the present disclosure, provided herein is a method for enhancing the efficacy and/or tolerability of a vaccine said method comprising administering to the subject a vaccine comprising at least one peptide antigen conjugate having the formula selected from PEG-[E1]-A-[E2]-[U]-H and H-[U]-[E1]-A-[E2]-PEG, and an amphiphile having the formula S-[B]-[U]-H, wherein E1 is an N-terminal extension;

E2 is a C terminal extension;

H, independently for each occurrence is a hydrophobic block, wherein one or more drug molecules (D) are optionally attached to each H directly or via a suitable linker X1;

S is a solubilizing block;

B is a spacer;

U, independently for each occurrence, is a linker;

[ ] denotes that the group is optional,

- denotes that the two adjacent groups are directly attached to one another by a covalent bond or indirectly to one another via a suitable linker; and
  wherein the amphiphile comprises a dendron amplifier and at least one peptide antigen is selected from an autoantigen and foreign antigen.

In a tenth aspect of the present disclosure, provided herein is a method for preparing a peptide antigen conjugate having formula PEG-[E1]-A-[E2]-[U]-H and H-[U]-[E1]-A-[E2]-PEG.

In an eleventh aspect of the present disclosure, provided herein is a method of preparing vaccine comprising peptide antigen conjugate of formula PEG-[E1]-A-[E2]-[U]-H, and an amphiphile having the formula S-[B]-[U]-H, wherein A is a peptide antigen;

E1 is an N-terminal extension;

E2 is a C terminal extension;

H, independently for each occurrence is a hydrophobic block, wherein one or more drug molecules (D) are optionally attached to each H directly or via a suitable linker X1;

S is a solubilizing block;

B is a spacer;

U, independently for each occurrence, is a linker;

[ ] denotes that the group is optional, and

- denotes that the two adjacent groups are directly attached to one another by a covalent bond or indirectly to one another via a suitable linker X.

In a twelfth aspect of the present disclosure, provided herein is a vaccine for inducing tolerance comprising at least one peptide antigen conjugate having the formula selected from PEG-[E1]-A-[E2]-[U]-H-[D] and [D]-H-[U]-[E1]-A-[E2]-PEG, wherein A is a peptide antigen; E1 is an N-terminal extension; E2 is a C terminal extension;

H, independently for each occurrence is a hydrophobic block, wherein at least one drug molecule (D) are optionally attached to each H directly or via a suitable linker X1;

U, independently for each occurrence, is a linker;

[ ] denotes that the group is optional, and

- denotes that the two adjacent groups are directly attached to one another by a covalent bond or indirectly to one another via a suitable linker X.

In some embodiments of the vaccine for inducing tolerance, when the at least one peptide antigen has a grand average of hydropathy value >0 and/or the average peptide antigen solubility in aqueous solution at pH between 5.5 to 8.5 is <1 mg/mL, the vaccine further comprise an amphiphile having the formula S-[B]-[U]-H, wherein S is a solubilizing block;

B is a spacer;

H is a hydrophobic block;

U is a linker;

[ ] denotes that the group is optional; and

- denotes that the two adjacent groups are directly attached to one another by a covalent bond or indirectly to one another via a suitable linker X, wherein the S of the amphiphile comprises a dendron amplifier.

In some embodiments of the vaccine for inducing tolerance, the vaccine does not contain an amphiphile having the formula S-[B]-[U]-H.

In some embodiment of the vaccine for inducing tolerance, wherein when the at least one peptide antigen has a grand average of hydropathy value ≤0 and/or the average peptide antigen solubility in aqueous solution at pH between 5.5 to 8.5 is ≥1 mg/mL, the vaccine does not contain an amphiphile having the formula S-[B]-[U]-H.

In some embodiments of the vaccine for inducing tolerance, the vaccine comprises at least one D selected from ATP-competitive mTOR inhibitors; preferably wherein the at least one D is selected from AZD-8055, AZD-2016, KU-0063794, CC223, Torin-1, Torin-2, INK-128, WYE354, WYE132, OSI-027, OXA-01, PI-103, NVP-BEZ235, GNE-493, GSK2126458, rapamycin, tacrolimus, everolimus, RAD001, CCI-779 and AP23573.

In some embodiments of the vaccine for inducing tolerance, the at least one D is covalently linked to the hydrophobic block (H) directly or indirectly through a linker X1.

In some embodiments of the vaccine for inducing tolerance, the linker X1 comprises an amide, carbamate, hydrazone, ketal or silyl ether moiety.

In some specific embodiments of the vaccine for inducing tolerance, the linker X1 comprises degradable peptide comprising 2 to 6 amino acids.

In some embodiments of the vaccine for inducing tolerance, the linker X1 comprising enzyme degradable peptide comprises an amino acid residue P1 selected from arginine, lysine, acetyl lysine, boc protected lysine, citrulline, glutamine, threonine, leucine, norleucine, alpha-aminobutyric acid, and methionine; and an amino acid residue a P2 selected from beta-alanine, glycine, serine, leucine, valine, and isoleucine.

In a thirteenth aspect of the present disclosure, provided herein is a vaccine comprising at least one peptide antigen conjugate having the formula selected from PEG-[E1]-A-[E2]-[U]-H and H-[U]-[E1]-A-[E2]-PEG, wherein E1 is an N-terminal extension;

E2 is a C terminal extension;

H, independently for each occurrence is a hydrophobic block, wherein one or more drug molecules (D) are optionally attached to each H directly or via a suitable linker X1; U, independently for each occurrence, is a linker;

[ ] denotes that the group is optional, and

- denotes that the two adjacent groups are directly attached to one another by a covalent bond or indirectly to one another via a suitable linker X; and A is a peptide antigen selected from group consisting of

QLQPFPQPELPYPQPQLPYPQPQPFR, (SEQ ID NO: 486)

PQLPYPQPELPYPQPQPFRPEQPYPQPQP, (SEQ ID NO: 487)

QGIIQPEQPAQLEVI, (SEQ ID NO: 464)

PQPQQPEQPFPQPEQEFPQPQQPQQSFPEQQPPL, (SEQ ID NO: 488)

PQQPFPQPEQPFCQQPQ, (SEQ ID NO: 489)

QQFLQPEQPFPQQPEQPYPQQPEQPFPQPQQ, (SEQ ID NO: 490)

QQFSQPEQEFPQPQQPQQSFPEQQPPF, (SEQ ID NO: 491)

PTPLQPEQPFPQQPQQPQQPFPQPEQPFPWQPQ, (SEQ ID NO: 492)

SSPLQPEQPFPQQPQQPFPEQPQQPQ, (SEQ ID NO: 493)

QSIPQPEQPFPQPEQPFPQSQE, (SEQ ID NO: 494)

PQQPFPQQPQQIIPQ, (SEQ ID NO: 495)

PQQPIPEQPQPYPEQPQPYPQQ, (SEQ ID NO: 496)

QQPPFSEQEQPVLPQ, (SEQ ID NO: 484)

QPPFSQQQESPFSQQ (SEQ ID NO: 485)
and

PQQPFPQPEQPFBQQPQ. (SEQ ID NO: 497)

In one embodiment of the vaccine of the present disclosure, the peptide antigen conjugates having the formula selected from PEG-[E1]-A-[E2]-[U]-H and H-[U]-[E1]-A-[E2]-PEG self assembles into nanoparticle micelles when the peptide antigen conjugate comprises peptide antigen (A) that are water soluble to at least 1 mg/mL or wherein the peptide antigen conjugates exhibits a tendency to aggregate after 24 h at room temperature when the total peptide antigen conjugate concentrations are ≥0.5 mM in an aqueous formulation buffer with no more than 20% organic solvent.

In some embodiments of the vaccine of the present disclosure, the micelles are between about 5 nm to about 50 nm in diameter, or between about 10 nm and about 30 nm in diameter.

In one embodiment of the vaccine of the present disclosure, at least one drug molecule (D) is noncovalently associated with the micelles.

In a fourteenth aspect of the present disclosure, provided herein is vaccine formulation comprising compositions of at least one peptide antigen conjugate having the formula selected from PEG-[E1]-A-[E2]-[U]-H and H-[U]-[E1]-A-[E2]-PEG, wherein A is a peptide antigen;

E1 is an N-terminal extension;

E2 is a C terminal extension;

H, independently for each occurrence is a hydrophobic block, wherein one or more drug molecules (D) are optionally attached to each H directly or via a suitable linker X1;

U, independently for each occurrence, is a linker;

[ ] denotes that the group is optional, and

- denotes that the two adjacent groups are directly attached to one another by a covalent bond or indirectly to one another via a suitable linker X and formulation buffer, said formulation buffer comprising 10% DMSO (v/v) in phosphate buffered saline at pH 7.4 or tris(hydroxymethyl)aminomethane in saline (0.9% NaCl) at a pH 6.5-8.5.

In one embodiment of the vaccine formulation, further a non-ionic surfactant is included.

In some embodiments of the vaccine formulation, the non-ionic surfactant is selected from Polysorbate-20 and sodium dodecyl sulfate.

BRIEF DESCRIPTION OF DRAWINGS

FIG. 3A shows the experimental plan and vaccination schedule. FIG. 3B shows body weight kinetics with body weight normalized to day 0. FIG. 3C shows survival in a Kaplan-Meier curve. See Table 3B and experimental section for a description of the materials and methods.

FIG. 4A shows experimental plan for EAE induction and treatment dates. FIG. 4B-C show disability score kinetics for groups by intravenous and subcutaneous routes.

FIG. 6A shows the experimental plan including multiple EAE inductions and treatment days. FIG. 6B-C show disability score kinetics for groups receiving treatment by the intravenous (IV) or intramuscular route (IM). FIG. 6D shows the disability score kinetics of IM treated mice after a second induction with EAE. The data show that treatments with vaccine compositions comprising peptide antigen conjugates of PEG-E1-A-E2-U-H or C-E1-A-E2-U-H reverse disease but that peptide antigen conjugates of formula PEG-E1-A-E2-U-H provide superior efficacy compared with C-E1-A-E2-U-H, and that PEG-E1-A-E2-U-H shows comparable efficacy by both the IM and IV routes.

FIG. 8B shows filtration recovery for representative vaccines (Table 8) with varying storage temperature and concentration of peptide antigen conjugate. Filtration recovery was assessed at 24 hours (hr) after formulation and storage by filtering each vaccine composition through a 0.2 μm filter and then assessing area under the curve at 220 nm by HPLC and dividing pre-filtration AUC by post-filtration AUC.

FIG. 13A shows the experimental plan including EAE induction and treatment days. FIG. 13B-D show disability score kinetics for groups receiving treatment by the intramuscular route (IM). FIG. 13B shows that inclusion of irrelevant peptide antigen (CPNE1) does not impact efficacy. FIG. 13C shows the inclusion of Torin-1 or Rapamycin improves efficacy. FIG. 13D shows that inclusion of Rapamycin at a 1:1 molar ratio of the drug molecule to peptide antigen conjugate demonstrated highest efficacy compared to no Rapamycin inclusion or 0.5:1 mole ratio of Rapamycin to peptide antigen conjugate. The data show that treatments with vaccine compositions comprising peptide antigen conjugates of PEG-E1-A-E2-U-H provide protection from developing EAE disease but that peptide antigen conjugates of formula PEG-E1-A-E2-U-H+D provide superior efficacy compared the same formulation lacking mTOR inhibitor drug.

FIG. 14A shows the experimental plan including EAE induction and treatment days. FIG. 14B-D show disability score kinetics for groups receiving treatment by the intramuscular route (IM) at doses of 2.5, 10 or 40 nmol of peptide antigen respectively. At equivalent doses, the four formulations tested demonstrated effectively equal efficacy. The data show that a formulation comprised of PEG-E1-A-E2-U-H is equivalent or superior in efficacy to formulations comprised of either (i) E1-A-E2-U-H+S-B-[U]-H, (ii) PEG-E1-A-E2-U-H+S-B-[U]-H+surfactant or (iii) PEG-E1-A-E2-U-H+S-B-[U]-H. FIG. 14E shows a comparison of the EAE disease score efficacy of PEG-E1-A-E2-U-H formulation at doses of 2.5, 10 or 40 nmol respectively. FIG. 14F shows an assessment of the EAE disease score area under the curve for days 7-28 with statistical assessment between groups (one-way ANOVA with Tukey corrected multiple comparisons with asterisk denotes p-value ≤0.0001). The data demonstrate that there is a strong relationship between dose of peptide antigen construct administered and EAE disease score.

FIG. 15A shows the experimental plan including EAE induction and treatment days. Groups and only received treatment on day 0. FIG. 15B shows a comparison of the EAE disease score efficacy IM or SC dosed mice with treatment administered either three times or only a single time on day 0. FIG. 15C shows an assessment of the EAE disease score area under the curve for days 7-21.

FIG. 16A shows experimental plan including gliadin and gluten peptide sensitization on days −14 and −7 followed by peptide antigen conjugate treatment on days 0, 7, 14, 21, and 28. FIG. 16B shows anti-gliadin antibody titer on study day 35 in both gliadin sensitized and non-sensitized (naïve) rats. FIG. 16C shows an assessment of phospho-S6 activation levels in antigen presenting cells (RT1B+, CD3−) isolated from blood four hours after treatment on study day 0. FIG. 16D shows the frequency (%) of IFN-γ+ cells among the CD4+ cell population isolated from blood on day 35. FIG. 16E shows the frequency (%) of IL-17+ cells among the CD4+ cell population isolated from blood on day 35. FIG. 16F shows the frequency (%) of IFN-γ+ cells among the CD8+ cell population isolated from blood on day 35. FIG. 16G shows the frequency (%) of IL-17+ cells among the CD8+ cell population isolated from blood on day 35.

FIG. 17A shows mTOR inhibition as measured by pS6 assay using small molecule drug analogs of Everolimus with conjugatable handles. FIG. 17B shows mTOR inhibition as measured by pS6 assay using peptide antigen conjugates with Everolimus derivatives conjugated to the H-block. These two examples demonstrate that Everolimus or Rapamycin are capable of being modified to conjugate to other molecules and that the conjugated version of the mTOR inhibitor remains active when conjugated either via an amide linkage (group [7]) or cleavable linkage (group [8]). FIG. 17C shows mTOR inhibition as measured by pS6 assay using small molecule analogs of Torin-1.

DETAILED DESCRIPTION OF THE DISCLOSURE

Figure 1A:
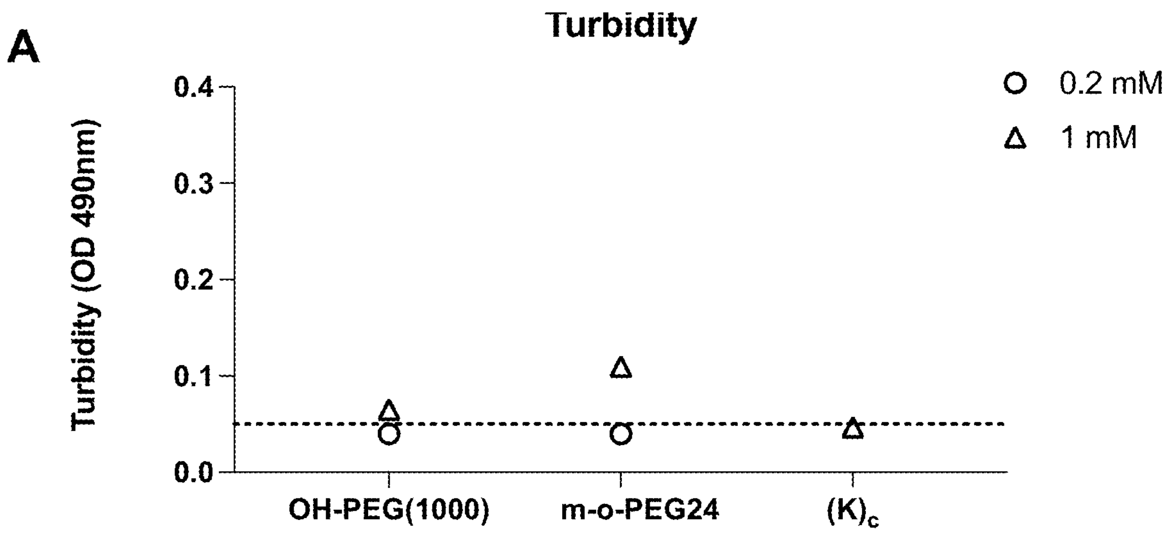
FIG. 1A-1B shows the turbidity (FIG. 1A) and particle size (FIG. 1B) of vaccine formulations comprising peptide antigen conjugates with different N-terminal groups, i.e., charged block (C) or PEG. See Table 1C and experimental section for a description of the materials and methods.

The above-mentioned aspects, as well as other aspects, features, and advantages of the present disclosure are described below in connection with various embodiments, with reference made to the accompanying figures.

Definitions

Details of terms and methods are given below to provide greater clarity concerning compounds, compositions, methods and the use(s) thereof for the purpose of guiding those of ordinary skill in the art in the practice of the present disclosure. The terminology in this disclosure is understood to be useful for the purpose of providing a better description of particular embodiments and should not be considered limiting.

About: In the context of the present disclosure, "about" when referring to a measurable value such as an amount, a temporal duration, and the like, is meant to encompass variations of ±20%, ±10%, ±5%, ±1%, or ±0.1% from the specified value, as such variations are appropriate to perform the disclosed methods. For example, "about 10" refers to 9.5 to 10.5. A ratio of "about 5:1" refers to a ratio from 4.75:1 to 5.25:1.

Administration: To provide or give to a subject an agent, for example, an immunogenic composition comprising amphiphilic block copolymers and drug(s) as described herein, by any effective route. Exemplary routes of administration include, but are not limited to, oral, injection (such as subcutaneous, intramuscular, intradermal, intraperitoneal, and intravenous), transdermal, topical, intranasal, vaginal, and inhalation routes.

"Administration of" and "administering a" compound should be understood to mean providing a compound, a prodrug of a compound, or a pharmaceutical composition as described herein. The compound or composition can be administered by another person to the subject or it can be self-administered by the subject.

Antigen: Any molecule that contains an epitope that binds to a T cell or B cell receptor and can stimulate an immune response, in particular, a B cell response and/or a T cell response in a subject. The epitopes may comprise peptides, glycopeptides, lipids or any suitable molecules that contain an epitope that can interact with components of specific B cell or T cell receptors. Such interactions may generate a response by the immune cell. "Epitope" refers to the region of a peptide antigen to which B and/or T cell proteins, i.e., B-cell receptors and T-cell receptors, interact. Antigens used in embodiments of the present disclosure may be selected from pathogens, cancerous cells, autoantigens, alloantigens or allergens. Many such antigens may be used according to embodiments of the inventions of the present disclosure and are discussed in greater detail throughout this specification.

Antigen-presenting cell (APC): Any cell that presents antigen bound to MHC class I or class II molecules to T cells, including but not limited to monocytes, macrophages, dendritic cells, B cells, T cells and Langerhans cells.

Amphiphilic: The term "amphiphilic" is used herein to mean a substance containing both hydrophilic or polar and hydrophobic groups.

CD4: Cluster of differentiation 4, a surface glycoprotein that interacts with MHC Class II molecules present on the surface of other cells. A subset of T cells express CD4 and these cells are commonly referred to as helper T cells or CD4 T cells.

CD8: Cluster of differentiation 8, a surface glycoprotein that interacts with MHC Class I molecules present on the surface of other cells. A subset of T cells express CD8 and these cells are commonly referred to as cytotoxic T cells (CTLs), killer T cells or CD8 T cells.

Charge: A physical property of matter that affects its interactions with other atoms and molecules, including solutes and solvents. Charged matter experiences electrostatic force from other types of charged matter as well as molecules that do not hold a full integer value of charge, such as polar molecules. Two charged molecules of like charge repel each other, whereas two charged molecules of different charge attract each other. Charge is often described in positive or negative integer units. The charge of a molecule can be readily estimated based on the molecule's Lewis structure and accepted methods known to those skilled in the art. Charge may result from inductive effects, e.g., atoms bonded together with differences in electron affinity may result in a polar covalent bond resulting in a partially negatively charged atom and a partially positively charged atom. For example, nitrogen bonded to hydrogen results in partial negative charge on nitrogen and a partial positive charge on the hydrogen atom. Alternatively, an atom in a molecule may be considered to have a full integer value of charge when the number of electrons assigned to that atom is less than or equal to the atomic number of the atom. The charge of the molecule is determined by summing the charge of each atom comprising the molecule. Those skilled in the art are familiar with the process of estimating charge of a molecule by summing the formal charge of each atom in a molecule. "Charged functional groups refer to functional groups that may be permanently charged or have charge depending on the pH. Charged functional groups may be partial or full integer values of charge, which may be positive or negative, are referred to as positively charged functional groups or negatively charged functional groups, respectively. The portion of a molecule that comprises one or more charged functional groups, which may be positive or negative, is referred to as a "charged group," e.g., positively charged group or negatively charged group. Charged groups may comprise positive functional groups, negative functional groups or both positive and negative functional groups. The net charge of the charged group may be positive, negative or neutral. Charged monomers refer to monomers that comprise charged groups. Charged amino acids are a type of charged monomer. Note: the net charge of a particle comprising amphiphiles and/or peptide antigen conjugates further comprising charged groups, e.g., charged monomers, such as charged amino acids, can be estimated by summing the charge of each functional group within the amphiphiles and/or peptide antigen conjugates. Charged blocks (C) are a type of solubilizing block.

Click chemistry reaction: A bio-orthogonal reaction that joins two compounds together under mild conditions in a high yield reaction that generates minimal, biocompatible and/or inoffensive byproducts. An exemplary click chemistry reaction used in the present disclosure is the reaction of an azide group with an alkyne to form a triazole linker through strain-promoted [3+2] azide-alkyne cyclo-addition.

Copolymer: A polymer derived from two (or more) different monomers, as opposed to a homopolymer where only one monomer is used. Since a copolymer includes at least two types of constituent units (also structural units), copolymers may be classified based on how these units are arranged along the chain. A copolymer may be a statistical (or random) copolymer wherein the two or monomer units are distributed randomly; the copolymer may be an alternating copolymer wherein the two or more monomer units are distributed in an alternating sequence; or, e.g., the copolymer, e.g., a poly(amino acid) may be produced by solid-phase peptide synthesis (SPPS) and have a specific order of monomer units. The term "block copolymer" refers generically to a polymer composed of two or more contiguous blocks of different constituent monomers or comonomers (if a block comprises two or more different monomers). Block copolymer may be used herein to refer to a copolymer that comprises two or more homopolymer subunits, two or more copolymer subunits or one or more homopolymer subunits and one or more copolymer subunits, wherein the subunits may be linked directly by covalent bonds or the subunits may be linked indirectly via an intermediate non-repeating subunit, such as a junction block or linker. Blocks may be based on linear and/or brush architectures. Block copolymers with two or three distinct blocks are referred to herein as "diblock copolymers" and "triblock copolymers," respectively. Copolymers may be referred to generically as polymers, e.g., a statistical copolymer may be referred to as a polymer or copolymer. Similarly, a block copolymer may be referred to generically as a polymer. While a copolymer used in herein means a polymer comprising two or more types of monomers, terpolymer is a copolymer with three monomer units.

Critical micelle concentration (CMC): Refers to the concentration of a material above which micelles spontaneously form to satisfy thermodynamic equilibrium.

Drug: refers to any pharmaceutically active molecule—including, without limitation, proteins, peptides, sugars, saccharides, nucleosides, inorganic compounds, lipids, nucleic acids, small synthetic chemical compounds, macrocycles, etc.—that has a physiological effect when ingested or otherwise introduced into the body. Pharmaceutically active compounds can be selected from a variety of known classes of compounds, including, for example, analgesics, anesthetics, anti-inflammatory agents, anthelmintics, anti-arrhythmic agents, antiasthma agents, antibiotics (including penicillins), anticancer agents, anticoagulants, antidepressants, antidiabetic agents, antiepileptics, antihistamines, antitussives, antihypertensive agents, antimuscarinic agents, antimycobacterial agents, antineoplastic agents, antioxidant agents, antipyretics, immunosuppressants, immunostimulants, antithyroid agents, antiviral agents, anxiolytic sedatives (hypnotics and neuroleptics), astringents, bacteriostatic agents, beta-adrenoceptor blocking agents, blood products and substitutes, bronchodilators, buffering agents, cardiac inotropic agents, chemotherapeutics, contrast media, corticosteroids, cough suppressants (expectorants and mucolytics), diagnostic agents, diagnostic imaging agents, diuretics, dopaminergics (antiparkinsonian agents), free radical scavenging agents, growth factors, haemostatics, immunological agents, lipid regulating agents, muscle relaxants, proteins, such as therapeutic antibodies and antibody fragments, MHC-peptide complexes, cytokines and growth factors, glycoproteins, peptides and polypeptides, parasympathomimetics, parathyroid calcitonin, biphosphonates, prostaglandins, radio-pharmaceuticals, hormones, sex hormones (including steroids), anti-allergic agents, stimulants and anoretics, steroids, sympathomimetics, thyroid agents, vaccines, vasodilators, and xanthines. Drugs may also be referred to as pharmaceutically active agents, pharmaceutically active substances or biologically active compounds or bioactive molecules. Any drug molecules in the formulae described herein are abbreviated "D."

Drug delivery: A method or process of administering a pharmaceutical compound to achieve a therapeutic effect in humans or animals.

Effective amount: The amount of a compound, material, or composition effective to achieve a particular biological result such as, but not limited to, biological results disclosed, described, or exemplified herein. Such results may include, but are not limited to, the effective reduction of symptoms associated with any of the disease states mentioned herein, as determined by any means suitable in the art.

Hydropathy index/GRAVY value: Is a number representing the hydrophobic or hydrophilic characteristics of an amino acid or sequence of amino acids. There are a variety of scales that can be used to describe the relative hydrophobic and hydrophilic characteristics of amino acids comprising peptides. In the present disclosure, the Hydropathy scale of Kyte and Doolittle (Kyte J, Doolittle R F, J. *Mol. Biol* 157:105-32, 1983) is used to calculate the grand average of hydropathy (GRAVY) value, sometimes referred to as the GRAVY score. The GRAVY value of a peptide is the sum of the Hydropathy values of all amino acids comprising the peptide divided by the length (i.e., number of amino acids) of the peptide. The GRAVY value is a relative value. The larger the GRAVY value, the more hydrophobic a peptide sequence is considered, whereas the lower the GRAVY value, the more hydrophilic a peptide sequence is considered.

Hydrophilic: Refers to the tendency of a material to disperse freely or be solubilized in aqueous solutions (sometimes referred to as aqueous media). A material is considered hydrophilic if it prefers interacting with other hydrophilic material and avoids interacting with hydrophobic material. In some cases, hydrophilicity may be used as a relative term, e.g., the same molecule could be described as hydrophilic or not depending on what it is being compared to. Hydrophilic molecules are often polar and/or charged and have good water solubility, e.g., are soluble at concentrations of at least 1.0 mg/mL or more. Hydrophilic group refers to the portion of a molecule that is polar and/or charged and has good water solubility.

Hydrophobic: Refers to the tendency of a material to avoid contact with water. A material is considered hydrophobic if it prefers interacting with other hydrophobic material and avoids interacting with hydrophilic material. Hydrophobicity is a relative term; the same molecule could be described as hydrophobic or not depending on what it is being compared to. Hydrophobic molecules are often non-polar and non-charged and have poor water solubility, e.g., are insoluble in water, or are soluble in water only at concentrations of less than 1 mg/mL, typically 0.1 mg/mL or less or more preferably 0.01 mg/mL or less. Hydrophobic monomers are monomers, e.g., hydrophobic amino acids, that comprise hydrophobic groups and form polymers that are insoluble in water or insoluble in water at certain temperatures, pH and salt concentration. Hydrophobic group refers to a portion of a molecule that is hydrophobic. For example, a styrene monomer may be referred to as a hydrophobic monomer because poly(styrene) is a water insoluble polymer. Hydrophobic drugs refer to drug molecules that are insoluble or soluble only at concentrations of about 1.0 mg/mL or less in aqueous solutions at pH of about pH 7.4. Amphiphilic drugs are drug molecules that have the tendency to assemble into supramolecular structures, e.g., micelles, in aqueous solutions and/or have limited solubility in aqueous solutions at pH of about pH 7.4.

Immune response: A change in the activity of a cell of the immune system, such as a B cell, T cell, or monocyte, as a result of a stimulus, either directly or indirectly, such as through a cellular or cytokine intermediary. In certain embodiments, the response is specific for a particular antigen (an "antigen-specific response"). An immune response may comprise a T cell response, such as a CD4 T cell response or a CD8 T cell response. Such an immune response may result in the production of additional T cell progeny and/or in the movement of T cells. In other embodiments, the response is a B cell response, and results in the production of specific antibodies or the production of additional B cell progeny. In yet other embodiments, the response is an antigen-presenting cell response. An antigen may be used to stimulate an immune response leading to the activation of cytotoxic T cells that kills virally infected cells or cancerous cells. In other embodiments, an antigen may be used to induce tolerance or immune suppression. A tolerogenic response may result from the unresponsiveness of a T cell or B cell to an antigen. A suppressive immune response may result from the priming and/or activation of regulatory cells, such as regulatory T cells, or the trans-differentiation of effectors cells to regulatory cells that downregulate the immune response, i.e., dampen the immune response.

Immunogenic composition: A formulation of materials comprising an antigen and optionally an immunomodulator that induces a measurable immune response against the antigen. For examples, vaccines are a type of immunogenic composition.

Immunomodulators: refers to a type of drug that modulates the activity of cells of the immune system, which includes immunostimulants and immunosuppressants.

Immunostimulants: refers to any synthetic or naturally occurring drugs that promote proinflammatory and/or cytotoxic activity by immune cells. Exemplary immunostimulants include pattern recognition receptor (PRR) agonists, such as synthetic or naturally occurring agonists of Toll-like receptors (TLRs), stimulator of interferon gene agonists (STINGa), nucleotide-binding oligomerization domain-like receptor (NLR) agonists, retinoic acid-inducible gene-I-like receptors (RLR) agonists and certain C-type lectin receptor (CLR), as well as certain cytokines (e.g., certain interleukins), such as IL-2; certain chemokines or small molecules that bind chemokine receptors; certain antibodies, antibody fragments or synthetic peptides that activate immune cells, e.g., through binding to stimulatory receptors, e.g., anti-CD40, or, e.g., by blocking inhibitory receptors, e.g., anti-CTLA4, anti-PD1, etc. Various immunostimulants suitable for the practice of the present disclosure are described throughout the specification. For clarity, certain pharmaceutically active compounds that stimulate the immune system may be referred to as immunostimulants or more generally as drug molecules (abbreviated "D" in formulae).

Immunosuppressants: refers to any synthetic or naturally occurring drugs that suppress proinflammatory and/or cytotoxic activity by immune cells or the humoral immune system, e.g., antibodies and complement proteins. Immunosuppressants may mediate effects through one or more of the following mechanisms of action: by priming suppressor cells, e.g., regulatory T cells; killing, inhibiting or deactivating proinflammatory cells, cytotoxic cells and/or B cells; trans-differentiating proinflammatory and/or cytotoxic T cells to suppressor cells; and/or sequestering and/or limiting the mobility of proinflammatory cells, cytotoxic cells and/or B cells. Exemplary immunosuppressants include synthetic or naturally occurring agonists of the aryl hydrocarbon receptor (AHR); certain steroids, including glucocorticoids; certain histone deacetylase inhibitors (HDACS), such as inhibitors of HDAC9; retinoic acid receptor agonists; mammalian target of rapamycin (mTOR) inhibitors, such as rapamycin; certain cyclin dependent kinase (CDK) inhibitors; certain adenosine receptor agonists; agonists of PD1; and other molecules that suppress proinflammatory or cytotoxic activity by immune cells or antibodies. Various immunosuppressants suitable for the practice of the present disclosure are described throughout the specification and include Treg promoting immunomodulators. For clarity, immunosuppressants may be referred to more generally as drug molecules (abbreviated "D" in formulae).

In vivo delivery: Administration of a composition, such as a composition comprising amphiphilic block copolymers and drug(s), by topical, transdermal, suppository (rectal, vaginal), pessary (vaginal), intravenous, oral, subcutaneous, intraperitoneal, intrathecal, intramuscular, intracranial, inhalational, oral, or any other suitable route to a subject.

Linked or coupled: The terms "linked" and "coupled" mean joined together, either directly or indirectly. A first moiety may be covalently or noncovalently linked to a second moiety. In some embodiments, a first molecule is linked by a covalent bond to another molecule. In some embodiments, a first molecule is linked by electrostatic attraction to another molecule. In some embodiments, a first molecule is linked by dipole-dipole forces (for example, hydrogen bonding) to another molecule. In some embodiments, a first molecule is linked by van der Waals forces (also known as London forces) to another molecule. A first molecule may be linked by any and all combinations of such couplings to another molecule. The molecules may be linked indirectly, such as by using a linker (sometimes referred to as linker molecule). The molecules may be linked indirectly by interposition of a component that binds non-covalently to both molecules independently. The term "Linker," sometimes abbreviated "X," used in chemical formulae herein means any suitable linker molecule. Specific, preferred linkers may be indicated by other symbols, such as X1, X2, X3, X4, X5 and U. Various linkers are described throughout the specification.

A "bilayer membrane" or "bilayer(s)" is a self-assembled membrane of amphiphiles or super-amphiphiles in aqueous solutions.

Micelles: Spherical receptacles having a single monolayer defining a closed compartment. Generally, amphiphilic molecules spontaneously form micellar structures in polar solvents. In contrast to bilayers, e.g., liposomal bilayers, micelles are "sided" in that they project a hydrophilic, polar outer surface and display a hydrophobic interior surface.

Mol %: Refers to the percentage of a particular type of monomeric unit (or "monomer") that is present in a polymer. For example, a polymer having 100 monomeric units of A and B with a density (or "mol %") of monomer A equal to 10 mol % would have 10 monomeric units of A, and the remaining 90 monomeric units (or "monomers") may be monomer B or another monomer unless otherwise specified.

Monomeric unit: The term "monomeric unit" or "monomer unit" is used herein to mean a unit of polymer molecule containing the same or similar number of atoms as one of the monomers. Monomeric units, as used in this specification, may be of a single type (homogeneous) or a variety of types (heterogeneous). For example, poly(amino acids) comprise amino acid monomeric units. Monomeric units may also be referred to as monomers or monomer units or the like.

Net charge: The sum of electrostatic charges carried by a molecule or, if specified, a portion or section of a molecule.

Particle: A nano- or micro-sized supramolecular structure composed of an assembly of molecules. For example, amphiphiles and peptide antigen conjugates of the present disclosure form particles in aqueous solution. In some embodiments, particle formation by the amphiphiles and/or peptide antigen conjugates is dependent on pH or temperature. In some embodiments, the nanoparticles composed of amphiphiles and/or peptide antigen conjugates have an average diameter between 5 nanometers (nm) to 500 nm. In some embodiments, the nanoparticles composed of amphiphiles and/or peptide antigen conjugates form micelles and have an average diameter between 5 nanometers (nm) to 50 nm, such as between 10 and 30 nm. In some embodiments, the nanoparticles composed of amphiphiles and/or peptide antigen conjugates may be larger than 100 nm.

Pattern recognition receptors (PRRs): Receptors expressed by various cell populations, particularly innate immune cells that bind to a diverse group of synthetic and naturally occurring molecules. There are several classes of PRRs. Non-limiting examples of PRRs include Toll-like receptors (TLRs), RIG-I-like receptors (RLRs), NOD-like receptors (NLRs), Stimulator of Interferon Genes receptor (STING), and C-type lectin receptors (CLRs). Agonists of such PRRs are referred to as immunostimulant drugs and can be used to enhance and/or modify an immune response to an antigen. For more information on pattern recognition receptors, see Wales et al., Biochem Soc Trans., 35:1501-1503, 2007.

Peptide or polypeptide: Two or more natural or non-natural amino acid residues that are joined together in a series through one or more amide bonds. The amino acid residues may contain post-translational modification(s) (e.g., glycosylation, citrullination, homocitrullination, oxidation and/or phosphorylation). Such modifications may mimic post-translational modifications that occur naturally in vivo or may be non-natural. Any one or more of the components of the amphiphiles and/or peptide antigen conjugates may comprise peptides.

Peptide Modifications: Peptides may be altered or otherwise synthesized with one or more of several modifications as set forth below. In addition, analogs (non-peptide organic molecules), derivatives (chemically functionalized peptide molecules obtained starting from a peptide) and variants (homologs) of these peptides can be utilized in the methods described herein. The peptides described herein comprise a sequence of amino acids, analogs, derivatives, and variants, which may be either L- and/or D-versions. Unless otherwise specified, any peptide sequences referenced herein comprise L amino acids, preferably exclusively L amino acids. Such peptides may contain peptides, analogs, derivatives, and variants that are naturally occurring and otherwise.

Peptides can be modified through any of a variety of chemical techniques to produce derivatives having similar activity as the unmodified peptides, and optionally having other desirable properties. For example, carboxylic acid groups of the peptide, whether at the carboxyl terminus or at a side chain, can be provided in the form of a salt of a pharmaceutically-acceptable cation or esterified to form a CC1-CC16 ester, wherein CC refers to a carbon chain (and thus, CC1 refers to a single carbon and CC16 refers to 16 carbons), or converted to an amide. Amino groups of the peptide, whether at the amino terminus or at a side chain, can be in the form of a pharmaceutically-acceptable acid addition salt, such as the HCl, HBr, acetic, trifluoroacetic, formic, benzoic, toluene sulfonic, maleic, tartaric and other organic salts, or can be modified or converted to an amide, e.g., by acetylation.

Peptides may be modified to contain substituent groups that contain a positive or negative charge or both. The positive and/or negative charge may be affected by the pH at which the peptide is present.

Hydroxyl groups of the peptide side chains may be converted to $C_1$-$C_{16}$ alkoxy or to a $C_1$-$C_{16}$ ester using well-recognized techniques, or the hydroxyl groups may be converted (e.g., sulfated or phosphorylated) to introduce negative charge. Phenyl and phenolic rings of the peptide side chains may be substituted with one or more halogen atoms, such as fluorine, chlorine, bromine or iodine, or with $C_1$-$C_{16}$ alkyl, $C_1$-$C_{16}$ alkoxy, carboxylic acids and esters thereof, or amides of such carboxylic acids. Methylene groups of the peptide side chains can be extended to homologous $C_2$-$C_4$ alkylenes. Thiols can be used to form disulfide bonds or thioethers, for example through reaction with a maleimide. Thiols may be protected with any of a number of well-recognized protecting groups, such as acetamide groups. Those skilled in the art will also recognize methods for introducing cyclic structures into the peptides of this invention to select and provide conformational constraints to the structure that result in enhanced stability. Reference may be made to Greene et al., "Greene's Protective Groups in Organic Synthesis" Fourth Edition, John Wiley & Sons, Inc. 2006 for details of additional modifications that can be made to functional groups.

Cysteine residues of naturally occurring peptide antigens can be replaced with alpha aminobutyric acid or serine, and methionine residues can be replaced with norleucine, to yield nonnatural peptide antigens that induce immune responses that are cross-reactive with the naturally occurring peptide antigens. Preferred methods for preparing and using peptide antigens with nonnatural sequences are described throughout the specification as well as in WO 2022/177993, which is incorporated by reference herein.

Pharmaceutically acceptable vehicles: The pharmaceutically acceptable vehicles (or carriers) useful in this disclosure include conventional carriers, excipients, and diluents. Remington's Pharmaceutical Sciences, by E. W. Martin, Mack Publishing Co., Easton, PA, 15th Edition (1975), describes compositions and formulations suitable for pharmaceutical delivery of one or more therapeutic compositions, such as one or more therapeutic cancer vaccines, and additional pharmaceutical agents.

Pharmaceutically acceptable carriers are well known in the art and include, for example, aqueous solutions such as water or physiologically buffered saline or other solvents or vehicles such as glycols, glycerol, oils such as olive oil, or injectable organic esters. In preferred embodiments, when such pharmaceutical compositions are for human administration, particularly for invasive routes of administration (i.e., routes, such as injection or implantation, that circumvent transport or diffusion through an epithelial barrier), the aqueous solution is pyrogen-free, or substantially pyrogen-free. The excipients can be chosen, for example, to effect delayed release of an agent or to selectively target one or more cells, tissues or organs. The pharmaceutical composition can be in dosage unit form such as tablet, capsule (including sprinkle capsule and gelatin capsule), granule, lyophile for reconstitution, powder, solution, syrup, suppository, injection, or the like. The composition can also be present in a transdermal delivery system, e.g., a skin patch. The composition can also be present in a solution suitable for topical administration, such as an ointment or cream.

A pharmaceutically acceptable carrier can contain physiologically acceptable agents that act, for example, to stabilize, increase solubility or to increase the absorption of a compound such as a compound of the invention. Such physiologically acceptable agents include, for example, carbohydrates, such as glucose, sucrose or dextrans, antioxidants, such as ascorbic acid or glutathione, chelating agents, low molecular weight proteins or other stabilizers or excipients. The choice of a pharmaceutically acceptable carrier, including a physiologically acceptable agent, depends, for example, on the route of administration of the composition. The preparation of pharmaceutical composition can be a self-emulsifying drug delivery system or a self-microemulsifying drug delivery system. The pharmaceutical composition (preparation) also can be a liposome or other polymer matrix, which can have incorporated therein, for example, a compound of the invention. Liposomes, for example, which comprise phospholipids or other lipids, are nontoxic, physiologically acceptable and metabolizable carriers that are relatively simple to make and administer.

Polar: A description of the properties of matter. Polar is a relative term and may describe a molecule or a portion of a molecule that has partial charge that arises from differences in electronegativity between atoms bonded together in a molecule, such as the bond between nitrogen and hydrogen. Polar molecules prefer interacting with other polar molecules and typically do not associate with non-polar molecules. In specific, non-limiting cases, a polar group may contain a hydroxyl group, or an amino group, or a carboxyl group, or a charged group. In specific, non-limiting cases, a polar group may prefer interacting with a polar solvent such as water. In specific, non-limiting cases, introduction of additional polar groups may increase the solubility of a portion of a molecule.

Polymer: A molecule containing repeating structural units (monomers). As described in greater detail throughout the disclosure, polymers may be used for any number of components of amphiphiles, peptide antigens conjugates and drug molecule conjugates and may be natural or synthetic. Various compositions of polymers useful for the practice of the invention are discussed in greater detail elsewhere. Note: polymer is used throughout the specification to broadly encompass molecules with as few as three or more monomers, which may sometimes be referred to as oligomers.

Polymerization: A chemical reaction, usually carried out with a catalyst, heat or light, in which monomers combine to form a chainlike, branched or cross-linked macromolecule (a polymer). The chains, branches or cross-linked macromolecules can be further modified by additional chemical synthesis using the appropriate substituent groups and chemical reactions. Polymerization commonly occurs by addition or condensation. Addition polymerization occurs when an initiator, usually a free radical, reacts with a double bond in the monomer. The free radical adds to one side of the double bond, producing a free electron on the other side. This free electron then reacts with another monomer, and the chain becomes self-propagating, thus adding one monomer unit at a time to the end of a growing chain. Condensation polymerization involves the reaction of two monomer units resulting in the splitting out of a water molecule. In other forms of polymerization, a monomer is added one at a time to a growing chain through the staged introduction of activated monomers, such as during solid phase peptide synthesis (SPPS).

Polymersome: Vesicle, which is assembled from synthetic multi-block polymers in aqueous solutions. Unlike liposomes, a polymersome does not include lipids or phospholipids as its majority component. Consequently, polymersomes can be thermally, mechanically, and chemically distinct and, in particular, more durable and resilient than the most stable of lipid vesicles. The polymersomes assemble during processes of lamellar swelling, e.g., by film or bulk rehydration or through an additional phoresis step, as described below, or by other known methods. Like liposomes, polymersomes form by "self-assembly," a spontaneous, entropy-driven process of preparing a closed semi-permeable membrane.

Purified: A substance or composition that is relatively free of impurities or substances that adulterate or contaminate the substance or composition. The term purified is a relative term and does not require absolute purity. Substantial purification denotes purification from impurities. A substantially purified substance or composition is at typically at least 60%, 70%, 80%, 90%, 95%, 98%, or 99% pure.

Soluble: Capable of becoming molecularly or ionically dispersed in a solvent to form a homogeneous solution. When referring to an amphiphile, peptide antigen conjugate, drug molecule conjugate and/or drug molecule, soluble is understood to be a single molecule in solution that does not assemble into multimers or other supramolecular structures through hydrophobic or other non-covalent interactions. A soluble molecule is understood to be freely dispersed as single molecules in solution. Hydrophobic blocks (H)

described herein are insoluble or soluble only to concentrations of about 0.1 mg/mL or less. Solubility can be determined by visual inspection, turbidity measurements or dynamic light scattering.

Subject and patient: These terms may be used interchangeably herein to refer to both human and non-human animals, including birds and non-human mammals, such as rodents (for example, mice and rats), non-human primates (for example, rhesus macaques), companion animals (for example domesticated dogs and cats), livestock (for example pigs, sheep, cows, llamas, and camels), as well as non-domesticated animals (for example big cats).

Targeting molecules: Are broadly defined as molecules that direct drug molecules to a specific tissue or cell population. Targeting molecules are defined by their intended use and therefore include structurally diverse molecules including without limitation antibodies, Fabs, peptides, aptamers, saccharides (e.g., saccharides that bind to lectin receptors and/or are recognized by cellular transporters), amino acids, neurotransmitters, etc. As targeting molecules are often selected from molecules that bind cellular receptors that can activate downstream signaling cascades and/or impact the activity of other linked molecules, targeting molecules are often classified as drug molecules (D) in the present disclosure. Additionally, targeting molecules can also have solubilizing effects, and may be considered either or both drug molecules (D) and/or solubilizing (SG) groups.

T Cell: A type of white blood cell that is part of the immune system and may participate in an immune response. T cells include, but are not limited to, CD4 T cells and CD8 T cells. A CD4 T cell displays the CD4 glycoprotein on its surface and these cells are often referred to as helper T cells. These cells often coordinate immune responses, including antibody responses and cytotoxic T cell responses, however, CD4 T cells (e.g., regulatory T cells) can also suppress immune responses or CD4 T cells may act as cytotoxic T cells. A CD8 T cell displays the CD8 glycoprotein on its surface and these cells are often referred to as cytotoxic or killer T cells, however, CD8 T cells can also suppress immune responses.

Treating, preventing, or ameliorating a disease: "Treating" refers to an intervention that reduces a sign or symptom or marker of a disease or pathological condition after it has begun to develop. For example, treating a disease may result in a reduction in tumor burden, meaning a decrease in the number or size of tumors and/or metastases, or treating a disease may result in immune tolerance that reduces systems associated with autoimmunity. "Preventing" a disease refers to inhibiting the full development of a disease. A disease may be prevented from developing at all. A disease may be prevented from developing in severity or extent or kind. "Ameliorating" refers to the reduction in the number or severity of signs or symptoms or marker of a disease, such as cancer.

Reducing a sign or symptom or marker of a disease or pathological condition related to a disease, refers to any observable beneficial effect of the treatment and/or any observable effect on a proximal, surrogate endpoint, for example, tumor volume, whether symptomatic or not. Reducing a sign or symptom associated with a tumor or viral infection can be evidenced, for example, by a delayed onset of clinical symptoms of the disease in a susceptible subject (such as a subject having a tumor which has not yet metastasized, or a subject that may be exposed to a viral infection), a reduction in severity of some or all clinical symptoms of the disease, a slower progression of the disease (for example by prolonging the life of a subject having a tumor or viral infection), a reduction in the number of relapses of the disease, an improvement in the overall health or well-being of the subject, or by other parameters well known in the art (e.g., that are specific to a particular tumor or viral infection). A "prophylactic" treatment is a treatment administered to a subject who does not exhibit signs of a disease or exhibits only early signs for the purpose of decreasing the risk or severity of developing pathology.

Tumor or cancer or neoplasm: An abnormal growth of cells, which can be benign or malignant, often but not always causing clinical symptoms. "Neoplastic" cell growth refers to cell growth that is not responsive to physiologic cues, such as growth and inhibitory factors.

A "tumor" is a collection of neoplastic cells. In most cases, tumor refers to a collection of neoplastic cells that forms a solid mass. Such tumors may be referred to as solid tumors. In some cases, neoplastic cells may not form a solid mass, such as the case with some leukemias. In such cases, the collection of neoplastic cells may be referred to as a liquid cancer.

Cancer refers to a malignant growth of neoplastic cells, being either solid or liquid. Features of a cancer that define it as malignant include metastasis, interference with the normal functioning of neighboring cells, release of cytokines or other secretory products at abnormal levels and suppression or aggravation of inflammatory or immunological response(s), invasion of surrounding or distant tissues or organs, such as lymph nodes, etc.

A tumor that does not present substantial adverse clinical symptoms and/or is slow growing is referred to as "benign."

"Malignant" means causing, or likely to cause in the future, significant clinical symptoms. A tumor that invades the surrounding tissue and/or metastasizes and/or produces substantial clinical symptoms through production and secretion of chemical mediators having an effect on nearby or distant body systems is referred to as "malignant."

"Metastatic disease" refers to cancer cells that have left the original tumor site and migrated to other parts of the body, for example via the bloodstream, via the lymphatic system, or via body cavities, such as the peritoneal cavity or thoracic cavity.

The amount of a tumor in an individual is the "tumor burden". The tumor burden can be measured as the number, volume, or mass of the tumor, and is often assessed by physical examination, radiological imaging, or pathological examination.

An "established" or "existing" tumor is a tumor that exists at the time a therapy is initiated. Often, an established tumor can be discerned by diagnostic tests. In some embodiments, an established tumor can be palpated. In some embodiments, an established tumor is at least 500 $mm^3$, such as at least 600 $mm^3$, at least 700 $mm^3$, or at least 800 $mm^3$ in size. In other embodiments, the tumor is at least 1 cm long. With regard to a solid tumor, an established tumor generally has a newly established and robust blood supply and may have induced the regulatory T cells (Tregs) and myeloid derived suppressor cells (MDSC).

Unit dose: A discrete amount of the pharmaceutical composition comprising a predetermined amount of the active ingredient.

Vesicle: A fluid filled sac. In some embodiments the vesicle is a sac comprising an amphiphilic substance. In some embodiments, the sac is a nanoparticle-based vesicle, which refers to a vesicle with a size or dimensions in the nanometer range. In some embodiments, a polymer vesicle is a vesicle that is formed from one or more polymers.

Definitions

As used herein, the terms "optional" or "optionally" mean that the subsequently described event or circumstance may occur or may not occur, and that the description includes instances where the event or circumstance occurs as well as instances in which it does not. For example, "optionally substituted alkyl" refers to an alkyl which may be substituted or not substituted.

It is understood that substituents and substitution patterns on the compounds of the present invention can be selected by one of ordinary skilled person in the art to result chemically stable compounds which can be readily synthesized by techniques known in the art, as well as those methods set forth below, from readily available starting materials. If a substituent is itself substituted with more than one group, it is understood that these multiple groups may be on the same carbon or on different carbons, so long as a stable structure results.

As used herein, the term "optionally substituted" refers to the replacement of one to six hydrogen radicals in a given structure with the radical of a specified substituent including, but not limited to: hydroxyl, hydroxyalkyl, alkoxy, halogen, alkyl, nitro, silyl, acyl, acyloxy, aryl, cycloalkyl, heterocyclyl, amino, aminoalkyl, cyano, haloalkyl, haloalkoxy, —OCO—$CH_2$—O-alkyl, —OP(O)(O-alkyl)$_2$ or —$CH_2$—OP(O)(O-alkyl)$_2$. Preferably, "optionally substituted" refers to the replacement of one to four hydrogen radicals in a given structure with the substituents mentioned above. More preferably, one to three hydrogen radicals are replaced by the substituents as mentioned above. It is understood that the substituent can be further substituted.

As used herein, the term "alkyl" refers to saturated aliphatic groups, including but not limited to $C_1$-$C_{10}$ straight-chain alkyl groups or $C_1$-$C_{10}$ branched-chain alkyl groups. Preferably, the "alkyl" group refers to $C_1$-$C_6$ straight-chain alkyl groups or $C_1$-$C_6$ branched-chain alkyl groups. Most preferably, the "alkyl" group refers to $C_1$-$C_4$ straight-chain alkyl groups or $C_1$-$C_4$ branched-chain alkyl groups. Examples of "alkyl" include, but are not limited to, methyl, ethyl, 1-propyl, 2-propyl, n-butyl, sec-butyl, tert-butyl, 1-pentyl, 2-pentyl, 3-pentyl, neo-pentyl, 1-hexyl, 2-hexyl, 3-hexyl, 1-heptyl, 2-heptyl, 3-heptyl, 4-heptyl, 1-octyl, 2-octyl, 3-octyl or 4-octyl and the like. The "alkyl" group may be optionally substituted.

The term "acyl" is art-recognized and refers to a group represented by the general formula hydrocarbylC(O)—, preferably alkylC(O)—.

The term "acylamino" is art-recognized and refers to an amino group substituted with an acyl group and may be represented, for example, by the formula hydrocarbylC(O)NH—.

The term "acyloxy" is art-recognized and refers to a group represented by the general formula hydrocarbylC(O)O—, preferably alkylC(O)O—.

The term "alkoxy" refers to an alkyl group having an oxygen attached thereto. Representative alkoxy groups include methoxy, ethoxy, propoxy, tert-butoxy and the like.

The term "alkoxyalkyl" refers to an alkyl group substituted with an alkoxy group and may be represented by the general formula alkyl-O-alkyl.

The term "alkyl" refers to saturated aliphatic groups, including straight-chain alkyl groups, branched-chain alkyl groups, cycloalkyl (alicyclic) groups, alkyl-substituted cycloalkyl groups, and cycloalkyl-substituted alkyl groups. In preferred embodiments, a straight chain or branched chain alkyl has 30 or fewer carbon atoms in its backbone (e.g., $C_{1-30}$ for straight chains, $C_{3-30}$ for branched chains), and more preferably 20 or fewer.

Moreover, the term "alkyl" as used throughout the specification, examples, and claims is intended to include both unsubstituted and substituted alkyl groups, the latter of which refers to alkyl moieties having substituents replacing a hydrogen on one or more carbons of the hydrocarbon backbone, including haloalkyl groups such as trifluoromethyl and 2,2,2-trifluoroethyl, etc.

The term "$C_{x-y}$" or "$C_x$-$C_y$", when used in conjunction with a chemical moiety, such as, acyl, acyloxy, alkyl, alkenyl, alkynyl, or alkoxy is meant to include groups that contain from x to y carbons in the chain. $C_0$alkyl indicates a hydrogen where the group is in a terminal position, a bond if internal. A $C_{1-6}$alkyl group, for example, contains from one to six carbon atoms in the chain.

The term "alkylamino", as used herein, refers to an amino group substituted with at least one alkyl group.

The term "alkylthio", as used herein, refers to a thiol group substituted with an alkyl group and may be represented by the general formula alkylS—.

The term "amide", as used herein, refers to a group

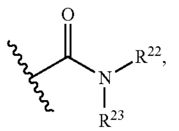

wherein $R^{22}$ and $R^{23}$ each independently represent a hydrogen or hydrocarbyl group, or $R^{22}$ and $R^{23}$ taken together with the N atom to which they are attached complete a heterocycle having from 4 to 8 atoms in the ring structure.

The terms "amine" and "amino" are art-recognized and refer to both unsubstituted and substituted amines and salts thereof, e.g., a moiety that can be represented by

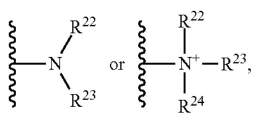

wherein $R^{22}$, $R^{23}$, and $R^{24}$ each independently represent a hydrogen or a hydrocarbyl group, or $R^{22}$ and $R^{23}$ taken together with the N atom to which they are attached complete a heterocycle having from 4 to 8 atoms in the ring structure.

The term "aminoalkyl", as used herein, refers to an alkyl group substituted with an amino group.

The term "aralkyl", as used herein, refers to an alkyl group substituted with an aryl group.

The term "aryl" as used herein includes substituted or unsubstituted aromatic carbocycles as well as heteroaryls. The term "aryl" is used interchangeably with the term "aromatic group" herein. Unless specifically stated otherwise specifically in the specification, an aryl moiety is optionally substituted by one or more substituents which are independently alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, trimethylsilanyl, —$OR^a$, —$SR^a$, —OC (O)—$R^a$, —$N(R^a)_2$, —$C(O)R^a$, —$C(O)OR^a$, —$OC(O)N(R^a)_2$, —$C(O)N(R^a)_2$, —$N(R^a)C(O)OR^a$, —$N(R^a)C(O)R^a$, —$N(R^a)C(O)N(R^a)_2$, —$N(R^a)C(NR^a)N(R^a)_2$, —$N(R^a)S(O)_tR^a$ (where t is 1 or 2), —$S(O)_tOR^a$ (where t is 1 or 2), —$S(O)_tN(R^a)_2$ (where t is 1 or 2), or $PO_3(R^a)_2$, where each $R^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl. Aromatic carbocycles include single-ring aromatic groups in which each atom of the ring is carbon. Preferably the ring is a 5- to 7-membered ring, more preferably a 6-membered ring. The term "aryl" also includes polycyclic ring systems having two or more cyclic rings in which two or more carbons are common to two adjoining rings wherein at least one of the rings is aromatic, e.g., the other cyclic rings can be cycloalkyls, cycloalkenyls, cycloalkynyls, aryls, heteroaryls, and/or heterocyclyls. Aryl groups include benzene, naphthalene, phenanthrene, phenol, aniline, and the like.

The term "carbamate" is art-recognized and refers to a group

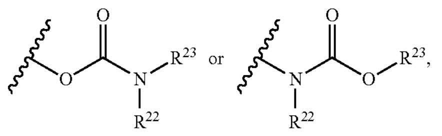

wherein $R^{22}$ and $R^{23}$ independently represent hydrogen or a hydrocarbyl group.

The term "carbocyclylalkyl", as used herein, refers to an alkyl group substituted with a carbocycle group.

The term "carbocycle" includes 5-7 membered monocyclic and 8-12 membered bicyclic rings. Each ring of a bicyclic carbocycle may be selected from saturated, unsaturated and aromatic rings. Carbocycle includes bicyclic molecules in which one, two or three or more atoms are shared between the two rings. The term "fused carbocycle" refers to a bicyclic carbocycle in which each of the rings shares two adjacent atoms with the other ring. Each ring of a fused carbocycle may be selected from saturated, unsaturated and aromatic rings. For example, an aromatic ring, e.g., phenyl, may be fused to a saturated or unsaturated ring, e.g., cyclohexane, cyclopentane, or cyclohexene. Any combination of saturated, unsaturated and aromatic bicyclic rings, as valence permits, is included in the definition of carbocyclic. Exemplary "carbocycles" include cyclopentane, cyclohexane, bicyclo[2.2.1]heptane, 1,5-cyclooctadiene, 1,2,3,4-tetrahydronaphthalene, bicyclo[4.2.0]oct-3-ene, naphthalene and adamantane. Exemplary fused carbocycles include decalin, naphthalene, 1,2,3,4-tetrahydronaphthalene, bicyclo[4.2.0]octane, 4,5,6,7-tetrahydro-1H-indene and bicyclo[4.1.0]hept-3-ene. "Carbocycles" may be substituted at any one or more positions capable of bearing a hydrogen atom.

The term "carbocyclylalkyl", as used herein, refers to an alkyl group substituted with a carbocycle group.

The term "carbonate" is art-recognized and refers to a group —$OCO_2$—.

The term "carboxy", as used herein, refers to a group represented by the formula —$CO_2H$. The term "ester", as used herein, refers to a group —$C(O)OR^{22}$ wherein $R^{22}$ represents a hydrocarbyl group.

The term "ether", as used herein, refers to a hydrocarbyl group linked through an oxygen to another hydrocarbyl group. Accordingly, an ether substituent of a hydrocarbyl group may be hydrocarbyl-O—. Ethers may be either symmetrical or unsymmetrical. Examples of ethers include, but are not limited to, heterocycle-O-heterocycle and aryl-O-heterocycle. Ethers include "alkoxyalkyl" groups, which may be represented by the general formula alkyl-O-alkyl.

The terms "halo" and "halogen" as used herein means halogen and includes chloro, fluoro, bromo, and iodo.

The terms "hetaralkyl" and "heteroaralkyl", as used herein, refers to an alkyl group substituted with a hetaryl group.

The terms "heteroaryl" and "hetaryl" include substituted or unsubstituted aromatic single ring structures, preferably 5- to 7-membered rings, more preferably 5- to 6-membered rings, whose ring structures include at least one heteroatom, preferably one to four heteroatoms, more preferably one or two heteroatoms. The terms "heteroaryl" and "hetaryl" also include polycyclic ring systems having two or more cyclic rings in which two or more carbons are common to two adjoining rings wherein at least one of the rings is heteroaromatic, e.g., the other cyclic rings can be cycloalkyls, cycloalkenyls, cycloalkynyls, aryls, heteroaryls, and/or heterocyclyls. Heteroaryl groups include, for example, pyrrole, furan, thiophene, imidazole, oxazole, thiazole, pyrazole, pyridine, pyrazine, pyridazine, and pyrimidine, and the like.

The term "heteroatom" as used herein means an atom of any element other than carbon or hydrogen. Preferred heteroatoms are nitrogen, oxygen, and sulfur.

The term "heterocyclylalkyl", as used herein, refers to an alkyl group substituted with a heterocycle group.

The terms "heterocyclyl", "heterocycle", and "heterocyclic" refer to substituted or unsubstituted non-aromatic ring structures, preferably 3- to 10-membered rings, more preferably 3- to 7-membered rings, whose ring structures include at least one heteroatom, preferably one to four heteroatoms, more preferably one or two heteroatoms. The terms "heterocyclyl" and "heterocyclic" also include polycyclic ring systems having two or more cyclic rings in which two or more carbons are common to two adjoining rings wherein at least one of the rings is heterocyclic, e.g., the other cyclic rings can be cycloalkyls, cycloalkenyls, cycloalkynyls, aryls, heteroaryls, and/or heterocyclyls. Heterocyclyl groups include, for example, piperidine, piperazine, pyrrolidine, morpholine, lactones, lactams, and the like.

The term "hydrocarbyl", as used herein, refers to a group that is bonded through a carbon atom that does not have a =O or =S substituent, and typically has at least one carbon-hydrogen bond and a primarily carbon backbone, but may optionally include heteroatoms. Thus, groups like methyl, ethoxyethyl, 2-pyridyl, and even trifluoromethyl are considered to be hydrocarbyl for the purposes of this application, but substituents such as acetyl (which has a =O substituent on the linking carbon) and ethoxy (which is linked through oxygen, not carbon) are not. Hydrocarbyl groups include, but are not limited to aryl, heteroaryl, carbocycle, heterocycle, alkyl, alkenyl, alkynyl, and combinations thereof.

The term "hydroxyalkyl", as used herein, refers to an alkyl group substituted with a hydroxy group.

The term "lower" when used in conjunction with a chemical moiety, such as, acyl, acyloxy, alkyl, alkenyl, alkynyl, or alkoxy is meant to include groups where there are ten or fewer atoms in the substituent, preferably six or fewer. A "lower alkyl", for example, refers to an alkyl group that contains ten or fewer carbon atoms, preferably six or fewer. In certain embodiments, acyl, acyloxy, alkyl, alkenyl, alkynyl, or alkoxy substituents defined herein are respectively lower acyl, lower acyloxy, lower alkyl, lower alkenyl, lower alkynyl, or lower alkoxy, whether they appear alone or in combination with other substituents, such as in the recitations hydroxyalkyl and aralkyl (in which case, for example, the atoms within the aryl group are not counted when counting the carbon atoms in the alkyl substituent).

The terms "polycyclyl", "polycycle", and "polycyclic" refer to two or more rings (e.g., cycloalkyls, cycloalkenyls, cycloalkynyls, aryls, heteroaryls, and/or heterocyclyls) in which two or more atoms are common to two adjoining rings, e.g., the rings are "fused rings". Each of the rings of the polycycle can be substituted or unsubstituted. In certain embodiments, each ring of the polycycle contains from 3 to 10 atoms in the ring, preferably from 5 to 7.

The term "sulfate" is art-recognized and refers to the group $-OSO_3H$, or a pharmaceutically acceptable salt thereof.

The term "sulfonamide" is art-recognized and refers to the group represented by the general formulae

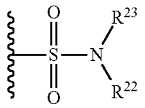

or

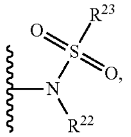

wherein $R^{22}$ and $R^{23}$ independently represents hydrogen or hydrocarbyl.

The term "sulfoxide" is art-recognized and refers to the group $-S(O)-$.

The term "sulfonate" is art-recognized and refers to the group $SO_3H$, or a pharmaceutically acceptable salt thereof.

The term "sulfone" is art-recognized and refers to the group $-S(O)_2-$.

The term "substituted" refers to moieties having substituents replacing a hydrogen on one or more carbons of the backbone. It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. The permissible substituents can be one or more and the same or different for appropriate organic compounds. For purposes of this invention, the heteroatoms such as nitrogen may have hydrogen substituents and/or any permissible substituents of organic compounds described herein which satisfy the valences of the heteroatoms. Substituents can include any substituents described herein, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that the moieties substituted on the hydrocarbon chain can themselves be substituted, if appropriate.

The term "thioalkyl", as used herein, refers to an alkyl group substituted with a thiol group.

The term "thioester", as used herein, refers to a group $-C(O)SR^{22}$ or $-SC(O)R^{22}$ wherein $R^{22}$ represents a hydrocarbyl.

The term "thioether", as used herein, is equivalent to an ether, wherein the oxygen is replaced with a sulfur.

The term "urea" is art-recognized and may be represented by the general formula

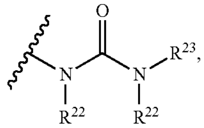

wherein $R^{22}$ and $R^{23}$ independently represent hydrogen or a hydrocarbyl.

The term "aromatic amino acid" includes amino acids with a side chain comprising an aromatic group, such as phenylalanine, tyrosine, or tryptophan. Aromatic group refers to the portion of a molecule that comprises an aromatic ring. For example, phenylalanine is an aromatic amino acid that comprises an aromatic group, i.e., benzyl group. Phenylalanine (Phe) and Tryptophan (Trp) are prototypical aromatic amino acids.

A person of ordinary skill in the art would recognize that the definitions provided above are not intended to include impermissible substitution patterns (e.g., methyl substituted with 5 different groups, and the like). Such impermissible substitution patterns are easily recognized by a person of ordinary skill in the art. Any functional group disclosed herein and/or defined above can be substituted or unsubstituted, unless otherwise indicated herein. Unless otherwise explained, all technical and scientific terms used herein have the same meaning as commonly understood by one of ordinary skill in the art to which this disclosure belongs. The term "comprises" means "includes." Therefore, comprising "A" or "B" refers to including A, including B, or including both A and B. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of the present disclosure, suitable methods and materials are described herein. In case of conflict, the present specification, including explanations of terms, will control. In addition, the materials, methods, and examples are illustrative only and not intended to be limiting.

DESCRIPTION OF EMBODIMENTS

Provided herein are compositions of particles comprising amphiphiles and drug molecules useful for the treatment or prevention of a disease, e.g., cancer(s), autoimmune disease (s), allergy(ies) and/or infectious disease(s). Particles comprising certain compositions of amphiphiles and peptide antigen conjugates have particular utility for use as vaccines for treating or preventing disease, such as preventing or treating cancer(s), autoimmune disease(s), allergy(ies) and/or infectious disease(s).

The present disclosure relates to a vaccine comprising at least one peptide antigen conjugate having the formula selected from PEG-[E1]-A-[E2]-[U]-H and H-[U]-[E1]-A-[E2]-PEG wherein A is a peptide antigen;

E1 is an N-terminal extension;

E2 is a C terminal extension;

H, independently for each occurrence is a hydrophobic block, wherein one or more drug molecules (D) are optionally attached to each H directly or via a suitable linker X1;

U, independently for each occurrence, is a linker;

[ ] denotes that the group is optional, and

- denotes that the two adjacent groups are directly attached to one another by a covalent bond or indirectly to one another via a suitable linker X.

In embodiments of the vaccines, wherein either (i) the average aqueous solubility of the peptide antigens (A) of the one or more peptide antigen conjugates is less than 1 mg/mL or (ii) the average GRAVY score of the peptide antigens (A) of the one or more peptide antigen conjugates is >0, the amphiphile is present.

The present disclosure relates to a vaccine comprising at least one peptide antigen conjugate having the formula selected from PEG-[E1]-A-[E2]-[U]-H and H-[U]-[E1]-A-[E2]-PEG, and an amphiphile having the formula S-[B]-[U]-H, wherein A is a peptide antigen;

E1 is an N-terminal extension;

E2 is a C terminal extension;

H, independently for each occurrence is a hydrophobic block, wherein one or more drug molecules (D) are optionally attached to each H directly or via a suitable linker X1;

S is a solubilizing block;

B is a spacer;

U, independently for each occurrence, is a linker;

[ ] denotes that the group is optional, and

- denotes that the two adjacent groups are directly attached to one another by a covalent bond or indirectly to one another via a suitable linker X.

In one embodiment of the vaccine, the PEG group of the peptide antigen conjugate includes a terminal functional group selected from OH, MeO— and $NH_2$.

In a particular embodiment of the vaccine, the PEG group of the peptide antigen conjugate is polyethylene glycol.

In some embodiments of the vaccines, the PEG group of the peptide antigen conjugate comprises between 4 and 36 monomeric units.

In a particular embodiment of the vaccine, the PEG group of the peptide antigen conjugate comprises between 4 and 12 monomeric units, or between 12 and 36 monomeric units, preferably 24 monomeric units.

In some embodiments of the vaccine, when the amphiphile is present, the amphiphile comprises a dendron amplifier.

In some embodiments of the vaccine, the S of the amphiphile comprises a dendron amplifier. In other embodiments, the S of the amphiphile has a dendritic architecture.

In some embodiments of the vaccine, the S of the amphiphile comprises two or more solubilizing groups (SGs). In other embodiments, the two or more SGs are connected to the remaining portion of the S by a dendron amplifier, e.g., 4 to 8 SGs are connected to the S.

In some embodiments of the vaccine, the SGs are independently selected from amines, hydroxyls, carboxylic acids and/or sugar molecules, wherein the sugar molecules are independently selected from mannose, glucose, glucosamine, N-acetyl glucose, galactose, galactosamine, N-acetyl galactosamine, N-acetyl glucosamine, phosphoserine and any derivatives thereof, agonists of CD22a, sialyl lewis x, and combinations thereof.

In some embodiments of the vaccine, the dendron amplifier comprises repeating monomer units of 1 to 10 generations having between 2 to 6 branches per generation. In other embodiments, the dendron amplifier comprises repeating monomer units of 2 to 3 generations having between 2 to 3 branches per generation. In some embodiments of the vaccine, the repeating monomer units are selected from FG1-$(CH_2)_{y2}CH(R^1)_2$, FG1-$(CH_2)_{y2}C(R^1)_3$, FG1-$(CH_2CH_2O)_{y2}CH(R^1)_2$, FG1-$(CH_2CH_2O)_{y2}C(R^1)_3$, and FG1-$CH(R^1)_2$, FG1-$C(R^1)_3$, wherein $R^1$, independently for each occurrence, is selected from $(CH_2)_{y3}$-FG2, $(OCH_2CH_2)_{y3}$-FG2, and $CH_2$ $(OCH_2CH_2)_{y3}$-FG2); y2 and y3, independently for each occurrence, are each an integer of repeating units from 1 to 6; FG1 is a first functional group; and FG2 is a second functional group. In some embodiments, FG1 is —$NH_2$; and FG2, independently for each occurrence, is —$CO_2$— or —$CO_2H$. In some embodiments, FG1, independently for each occurrence, is —$CO_2$— or —$CO_2H$; and FG2 is —$NH_2$.

In some embodiments of the vaccine, the SGs are linked to S via a suitable linker X5. In some embodiments of the vaccine, the suitable linker X5 that links the SGs to S is selected from lower alkyl and PEG groups. In some embodiments of the vaccine, two or more SGs are connected to the remaining portion of the S by a dendron amplifier through a suitable linker X5, which links the two or more SGs to a terminal functional (FGt) group of the dendron amplifier through an amide bond. In some embodiments, the linker X5 joining the SGs to the dendron amplifier is selected from —NH—$R^{19}$, —NH—C(O)—$R^{19}$, —C(O)—NH—$R^{19}$— or —C(O)—$R^{19}$, wherein $R^{19}$ may be selected from but is not limited to —$(CH_2)_t$—, —$(CH_2CH_2O)$—$CH_2CH_2$—, —$(CH_2)$t-C(O)—NH—$(CH_2)_u$—, —$(CH_2CH_2O)_t$ $CH_2CH_2C(O)$—NH—$(CH_2)_u$—, —$(CH_2)_t$—NH—C(O)—NH—$(CH_2)_u$—, or —$(CH_2CH_2O)_tCH_2CH_2NH$—C(O)—$(CH_2)_u$— where t and u are each independently an integer typically selected from between 1 to 6, such as 1, 2, 3, 4, 5 or 6.

In some embodiments of the vaccine, the dendron amplifier comprises a polyethylene oxide (PEG) group.

In some embodiments of the vaccine, the H of the amphiphile comprises a higher alkane, an aromatic group, a fatty acid, a sterol, a polyunsaturated hydrocarbon, squalene, saponins, and/or a polymer.

In some embodiments of the vaccine, the H of the peptide antigen conjugate comprises a higher alkane, an aromatic group, fatty acid, a sterol, a polyunsaturated hydrocarbon, and/or a polymer.

In some embodiments of the vaccine, each H independently comprises a poly(amino acid) comprising monomers selected from hydrophobic amino acids (M), reactive amino acids (N), spacer amino acids (O), charged amino acids (P) and combinations thereof provided that at least one of M or N is present.

In some embodiments of the vaccine, each H independently comprises a poly(amino acid) having the formula:

$$-(M)_m-(N)_n-(O)_o-(P)_p-R^3,$$

wherein M, N, O and P are each independently present or absent, provided that at least one of M or Nis present;

m, n, o and p each independently denote an integer of 1 to 100 with the sum of m, n, o and p less than or equal to 100;

$R^3$ is selected from hydrogen, $NH_2$, NH—$CH_3$, NH—$(CH_2)_{y5}CH_3$, OH or a drug molecule (D) either connected directly or through a suitable linker X1; and y5 is an integer selected from 1 to 6.

In some embodiments of the vaccine, P is absent. In other embodiments, N, O, and P are each absent.

In some embodiments of the vaccine, P is

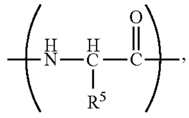

wherein each $R^5$, independently, is a group that comprises 1 to 2 charged functional groups.

In some embodiments of the vaccine, O is

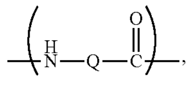

wherein each Q, independently, is selected from $(CH_2)_{y6}$ and $(CH_2CH_2O)_{y7}CH_2CH_2$; each y6 is independently selected from an integer from 1 to 6; and each y7 is independently selected from an integer from 1 to 4.

In some embodiments of the vaccine, N is

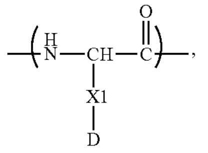

wherein each X1, independently, is a suitable linker; and each D, independently, is a drug molecule. In some embodiments of the vaccine, X1 is absent. In other embodiments, X1 is present and is selected from lower alkyl and PEG groups. In other embodiments, X1 is present and is selected from an enzyme cleavable linker and a pH sensitive linker. In some embodiments of the vaccine, X1 is present and comprise as enzyme degradable peptide and/or a self-immolative linker.

In some embodiments X1 is present and selected from —$(CH_2)_{y10}$—W and —$(CH_2)_{y10}$—$R^6$, wherein y10 is an integer selected from 1 to 6, and $R^6$ is selected from any one or more of —C(O)—NH—$R^7$, —NH—C(O)—$R^7$, —NH—C(O)—O—$R^7$, —O—C(O)—NH—$R^7$, —O—C(O)—$R^7$, —C(O)—O—$R^7$, —O—$R^7$, O—C(O)—W, or —C(O)—W, wherein $R^7$ is selected from any one or more of —$(CH_2)_{y11}$—W, —$(CH_2)_{y11}$—$(OCH_2CH_2)_{y12}$—W, —$(CH_2)_{y11}$—$(OCH_2CH_2)_{y12}$—$(CH_2)_{y13}$—W, —$CHR^8$—C(O)—W, —$CHR^8$—C(O)—(NH—$CHR^8$—C(O))$_j$—W, —$(CH_2)_{y11}$—C(O)—NH—$CHR^8$—C(O)—W, —$(CH_2)_{y11}$—C(O)—NH—$CHR^8$—C(O)—(NH—$CHR^8$—C(O))$_j$—W, —$(CH_2)_{y11}$—$(OCH_2CH_2)_{y12}$—C(O)—NH—$CHR^8$—C(O)—W, —$(CH_2)_{y11}$—$(OCH_2CH_2)_{y12}$—$(CH_2)_{y13}$C(O)—NH—$CHR^8$—C(O)—W, —$(CH_2)_{y11}$—$(OCH_2CH_2)_{y12}$—C(O)—NH—$CHR^8$—C(O)—(NH—$CHR^8$—C(O))$_j$—W, —$(CH_2)_{y11}$—$(OCH_2CH_2)_{y12}$—$(CH_2)_{y13}$—C(O)—NH—$CHR^8$—C(O)—(NH—$CHR^8$—C(O))$_j$—W, —$CHR^8$—C(O)—NH—$C_6H_4$—$CH_2$—O—C(O)—W, —$CHR^8$—C(O)—NH$(CH_3)(CH_2)_2$—O—C(O)—W, —$CHR^8$—C(O)—(NH—$CHR^8$—C(O))$_j$—NH—$C_6H_4$—$CH_2$—O—C(O)—W, —$CHR^8$—C(O)—(NH—$CHR^8$—C(O))$_j$—NH$(CH_3)(CH_2)_2$—O—C(O)—W, —$(CH_2)_{y11}$—C(O)—(NH—$CHR^8$—C(O))$_j$—NH—$C_6H_4$—$CH_2$—O—C(O)—W, —$(CH_2)_{y11}$—C(O)—(NH—$CHR^8$—C(O))$_j$—NH$(CH_3)(CH_2)_2$—O—C(O)—W, —$(CH_2)_{y11}$—$(OCH_2CH_2)_{y12}$—C(O)—(NH—$CHR^8$—C(O))$_j$—NH—$C_6H_4$—$CH_2$—O—C(O)—W, —$(CH_2)_{y11}$—$(OCH_2CH_2)_{y12}$—C(O)—(NH—$CHR^8$—C(O))$_j$—NH$(CH_3)(CH_2)_2$—O—C(O)—W, —$(CH_2)_{y11}$—$(OCH_2CH_2)_{y12}$—$(CH_2)_{y13}$C(O)—(NH—$CHR^8$—C(O))$_j$—NH—$C_6H_4$—$CH_2$—O—C(O)—W, —$(CH_2)_{y11}$—$(OCH_2CH_2)_{y12}$—$(CH_2)_{y13}$C(O)—(NH—$CHR^8$—C(O))$_j$—NH$(CH_3)(CH_2)_2$—O—C(O)—W, —$(CH_2)_{y11}$—$(OCH_2CH_2)_{y12}$—$(CH_2)_{y13}$—C(O)—NH—$(CH_2)_{y14}$—C(O)—(NH—$CHR^8$—C(O))$_j$—NH—$C_6H_4$—$CH_2$—O—C(O)—W, $(CH_2)_{y11}$—$(OCH_2CH_2)_{y12}$—$(CH_2)_{y13}$C(O)—NH—$(CH_2)_{y14}$—C(O)—(NH—$CHR^8$—C(O))$_j$—NH$(CH_3)(CH_2)_2$—O—C(O)—W, —$(CH_2)_{y11}$—$(OCH_2CH_2)_{y12}$—C(O)—NH—$(CH_2)_{y14}$—C(O)—(NH—$CHR^8$—C(O))$_j$—NH—$C_6H_4$—$CH_2$—O—C(O)—W, —$(CH_2)_{y11}$—$(OCH_2CH_2)_{y12}$—C(O)—NH—$(CH_2)_{y14}$—C(O)—(NH—$CHR^8$—C(O))$_j$—NH$(CH_3)(CH_2)_2$—O—C(O)—W, —$CHR^8$—C(O)—NH—$(CH_2)_{y15}$—W, —$CHR^8$—NH—C(O)—$(CH_2)_{y15}$—W, —$CHR^8$—C(O)—(NH—$CHR^8$—C(O))$_j$—NH—$(CH_2)_{y15}$—W, —$CHR^8$—NH—(C(O)—$CHR^8$—NH)$_j$—C(O)—$(CH_2)_{y15}$—W, where y11, y12, y13, y14, y15 and j are each independently selected from an integer selected from 1 to 6, $R^8$ is any amino acid side group, and W can be independently selected from H (hydrogen), FG3, LG and w; wherein FG3 is any suitable functional group for attachment to a functional group ("FG4") present on a drug molecule, which may be selected from, but not limited to, carboxylic acid, activated carboxylic acids (e.g., carbonylthiazolidine-2-thione ("TT"), NHS or nitrophenol esters), carboxylic acid anhydrides, amine and protected amines (e.g., tert-butyloxycarbonyl protected amine), $OSi(CH_3)$, alkene, azide, alkyne, stained-alkyne, halogen (e.g., fluoride, chloride), olefins and endo cyclic olefins (e.g., allyl), CN, OH, and epoxy, hydrazines (including hydrazides), carbohydrazides, aldehydes, ketones, carbamates and activated carbamates, LG is any suitable leaving group, which may be selected from any suitable leaving group (e.g., NHS, TT, nitrophenol, etc.); and w is a group that results from the reaction of either FG4 with FG3 or the displacement of LG with FG4, and is typically selected from NH—, C(O)—, NH—C(O)—, C(O)—NH—, O—C(O)—NH—, C(O)—NH—N═$C(CH_3)$—, NH—N═$C(CH_3)$— or —$C(CH_3)$═N—NH—C(O)—, wherein w is always linked to D either directly (i.e. w-D) or indirectly via X3 (i.e., w-X3-D).

In some embodiments of the vaccine, M is

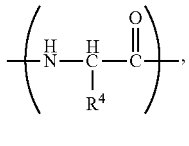

wherein each $R^4$ is, independently, a hydrophobic group.

In some embodiments of the vaccine, $R^4$ is,

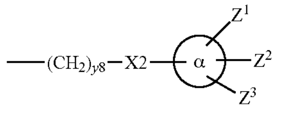

wherein

α is aryl or heteroaryl;

X2 is present or absent and when present is a suitable linker;

y8 is selected from an integer from 0 and 6; and $Z^1$, $Z^2$, and $Z^3$ are each independently selected from H, F, hydroxy, amino, alkyl, and fluoroalkyl.

In some embodiments of the vaccine, a is an aryl, e.g., phenyl or naphthyl. In other embodiments, α is a heteroaryl, e.g., pyridinyl, quinolinyl, isoquinolinyl, indolyl, or benzimidazolyl.

In some embodiments of the vaccine, X2 is absent. In other embodiments, X2 is present and is selected from C(O), $CO_2$ $(CH_2)_{y9}$, $CO_2$, C(O) $NH(CH_2)_{y9}$, NHC(O) and NHC $(O)(CH_2)_{y9}$, wherein y9 is an integer typically selected from 1 to 6. In other embodiments, X2 is present and is selected from lower alkyl and PEG groups.

In some embodiments of the vaccine, each $R^4$ is independently selected from:

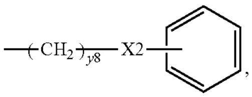
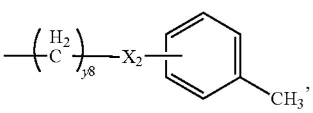
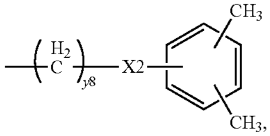
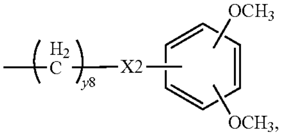
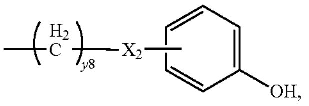
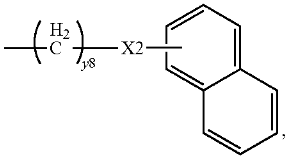
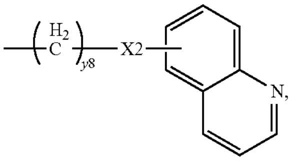
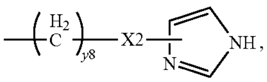
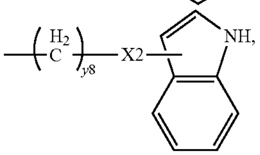
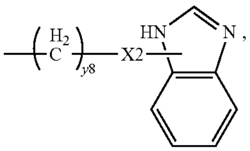
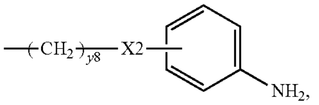
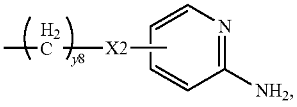
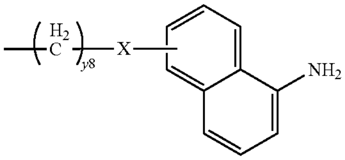
and -continued

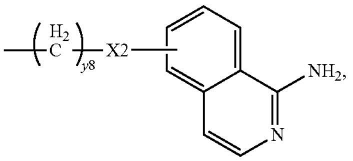

wherein each X2 is independently selected from a suitable linker and each y8 is independently selected from an integer from 0 and 6. In other embodiments, each $R^4$ is independently selected from:

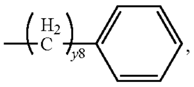
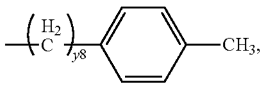
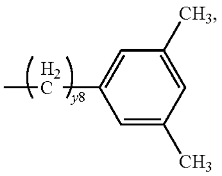
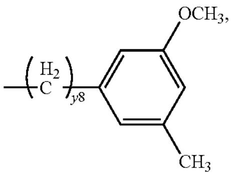
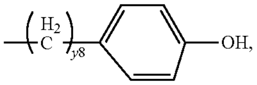
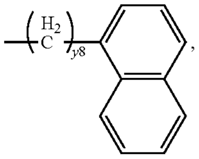
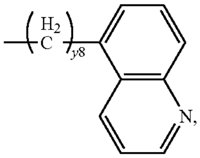
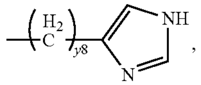
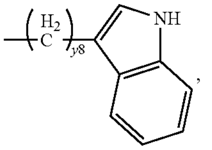
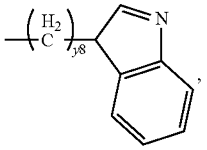
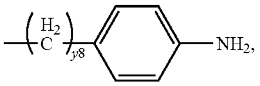
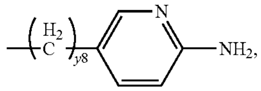
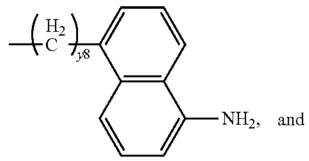
and
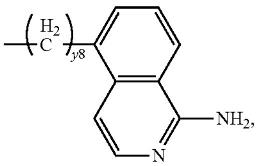

wherein each y8 is independently selected from an integer from 0 and 6. In other embodiments, each $R^4$ is independently selected from:

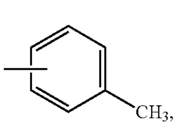
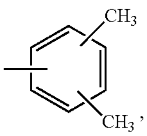
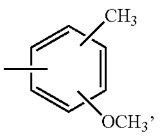

-continued
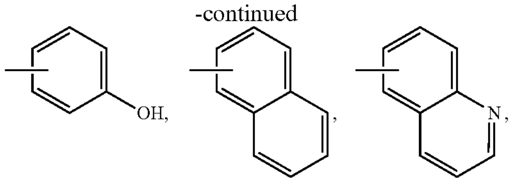
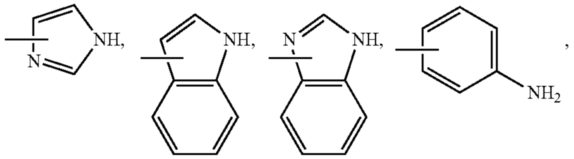
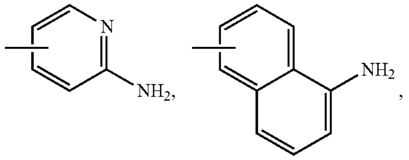
and
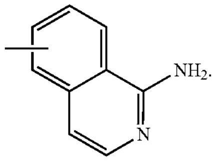
In other embodiments, each $R^4$ is independently selected from:
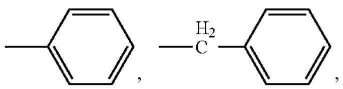
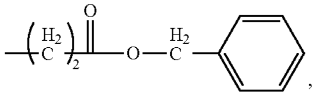
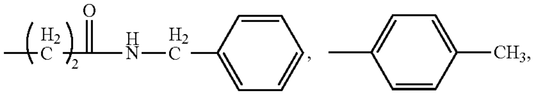
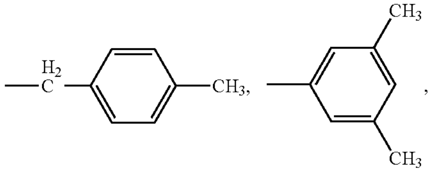
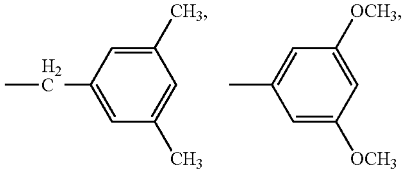
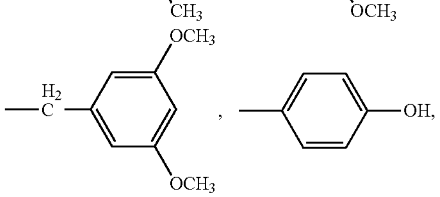
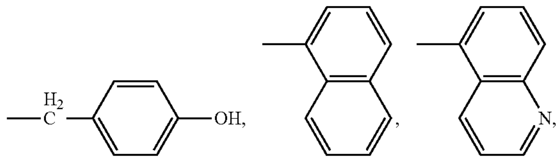
-continued
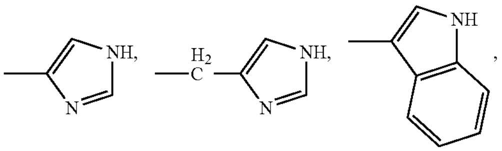
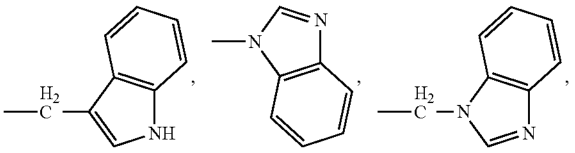
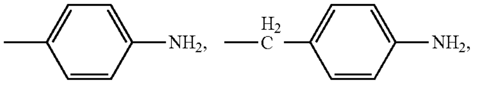
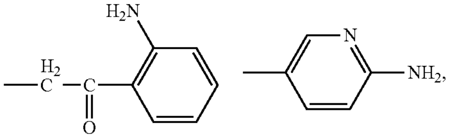
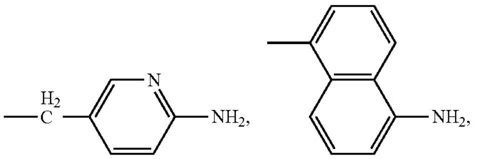
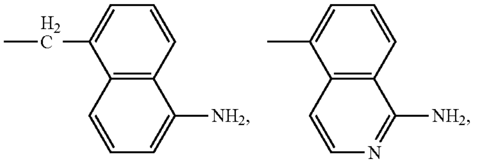
and
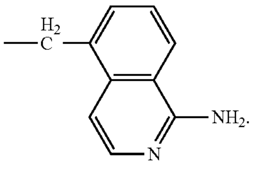
In preferred embodiments, each $R^4$ is independently selected from:
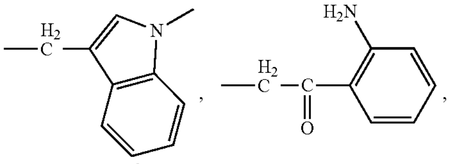
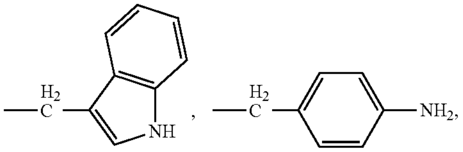
and
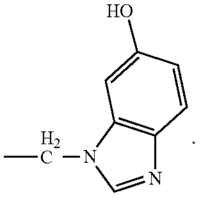

In some embodiments of the vaccine, wherein at least one D is:

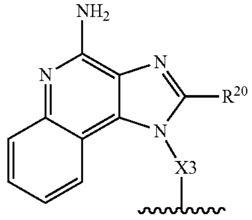

wherein, $R^{20}$ is selected from H, alkyl, alkoxyalkyl, aryl, heteroaryl, aminoalkyl, amide and ester; and X3 is selected from alkyl, alkoxyalkyl, aralkyl, heteroaralkyl, aryl, heteroaryl and carboxy.

In some embodiments of the vaccine, $R^{20}$ is selected from H, alkyl and alkoxyalkyl; and X3 is selected from alkyl and aralkyl. In other embodiments, $R^{20}$ is butyl.

In some embodiments of the vaccine, X3 is alkyl.

In some embodiments of the vaccine, m, n, o and p each independently denote an integer of 1 to 30 with the sum of m, n, o and p less than or equal to 30.

In some embodiments of the vaccine, m, n, o and p each independently denote an integer of 1 to 10 with the sum of m, n, o and p less than or equal to 10.

In some embodiments of the vaccine, B is present and is a hydrophilic polymer, e.g., a PEG group. In other embodiments, B is present and is a hydrophilic peptide.

In some embodiments of the vaccine, the PEG group comprises between 4 and 36 monomeric units. In other embodiments, the PEG group comprises between 4 and 12 monomeric units.

In some embodiments of the vaccine, the hydrophilic peptide comprises between 4 and 36 amino acids. In other embodiments, the hydrophilic peptide comprises between 4 and 12 amino acids.

In some embodiments of the vaccine, the amphiphile has the formula S-H. In other embodiments, the amphiphile has the formula S-B-U-H. In other embodiments, the amphiphile has the formula S-B-U-H-D.

In some embodiments of the vaccine, the vaccine comprises a peptide antigen conjugate to amphiphile molar ratio of between about 4:1 to about 1:20, preferably about 1:1.

In some embodiments of the vaccine, the vaccine is a cancer vaccine, an infectious disease vaccine, a tolerance inducing allergy vaccine, a tolerance inducing autoimmune disease vaccine, or a tolerance inducing transplant rejection vaccine.

In some embodiments of the vaccine, the peptide antigen (A) comprises a sequence wherein one or more cysteine residues have been replaced with alpha amino-butyric acid and/or one or more methionine residues have been replaced with norleucine. In some embodiments of the vaccine, the at least one peptide antigen conjugate comprises an A is selected from minimal immunogens. Minimal immunogens are, for example, small peptide fragments derived from a naturally occurring protein that comprises a B cell epitope. Minimal immunogens can be used for cancer, infectious disease and tolerance inducing vaccines, as well as for the treatment of cardiovascular or neurodegenerative diseases.

In some embodiments of the vaccine, A is a peptide antigen selected from

```
                                          (SEQ ID NO: 52)
RGYLTKILHVFHGLLPGFLVKMSGDLLE,

                                          (SEQ ID NO: 53)
PGFLVKMSGDLLE,

                                          (SEQ ID NO: 54)
PGFLVKnSGDLLE,
wherein n = norleucine;

                                          (SEQ ID NO: 55)
PGFLVKMSSDLLG,

                                          (SEQ ID NO: 56)
PGFLVKnSSDLLG,
wherein n is norleucine;

                                          (SEQ ID NO: 57)
SIPWNLERITPPR;

                                          (SEQ ID NO: 58)
SIPWNLERITPPR;

                                          (SEQ ID NO: 59)
SIPWNLE;

                                          (SEQ ID NO: 60)
SIPWNLEKVTPPR;

                                          (SEQ ID NO: 61)
SIPWNLDRVTPPR;

                                          (SEQ ID NO: 62)
NVPEEDGTRFHRQASKC;

                                          (SEQ ID NO: 63)
NVPEEDGTRFHRQASK;

                                          (SEQ ID NO: 64)
PEEDGTR,

                                          (SEQ ID NO: 65)
NVPEEDG;

                                          (SEQ ID NO: 66)
NVPEEDATRFHRQGSK;

                                          (SEQ ID NO: 67)
LFAPGEDIIGASSDCSTCFVSQSGTSQAAA;

                                          (SEQ ID NO: 68)
CSTCFVSQSGTSQAAA;

                                          (SEQ ID NO: 69)
STCFVSQSGTSQAAA,

                                          (SEQ ID NO: 70)
STBFVSQSGTSQAAA;

                                          (SEQ ID NO: 71)
STBFVSQ;

                                          (SEQ ID NO: 72)
MFTIKLLLFIVPLVISSRIDQDNSSFDSLSPEPKSRFAMLDDVKILANGL

LQLGHGLKDFVHKTKGQIND;

                                          (SEQ ID NO: 73)
EPKSRFAMLDDVKILANGLLQLGHGLKDFVHKTKGQIND;

                                          (SEQ ID NO: 74)
EPKSRFAMLDDVKI;

                                          (SEQ ID NO: 75)
MLDDVKILANGLLQ,

                                          (SEQ ID NO: 76)
```

-continued

LANGLLQLGHGLKD;

(SEQ ID NO: 77)
LGHGLKDFVHKTKG;

(SEQ ID NO: 78)
LKDFVHKTKGQIND;

(SEQ ID NO: 79)
RFAMLDDVKILANGLLQLGH;

(SEQ ID NO: 80)
GLLQLGHGLKDFVHKTKGQI;
and (SEQ ID NO: 81)
IFQKLNIFDQSFYDLSLQTSEIKEEEKELRRTTYKLQVKNEEVKNMSLEL

NSKLESLLEEKILLQQKVK.

In some embodiments of the vaccine, A is directly attached by a covalent bond to an E1 that is directly attached by a covalent bond or indirectly via U to H.

In some embodiments of the vaccine, A is directly attached by a covalent bond to an E2 that is directly attached by a covalent bond to or indirectly via U to H.

In some embodiments of the vaccine, E1 and E2 each comprise a PEG group between 4 and 36 monomeric units, e.g., the PEG group comprises between 4 and 24 monomeric units.

In some embodiments of the vaccine, E1 and E2 each comprise a peptide.

In some embodiments of the vaccine, the peptide comprises 4 to 24 amino acids.

In some embodiments of the vaccine, the at least one peptide antigen conjugate comprises an A selected from autoantigens, alloantigens, and allergens.

In some embodiments of the vaccine, the S of the amphiphile comprises two or more solubilizing groups (SGs) independently selected from carboxylic acids, phosphoserine, and/or sugar molecules, wherein the sugar molecules are independently selected from mannose, glucose, glucosamine, N-acetyl glucose, galactose, galactosamine, and N-acetyl galactosamine, and agonists of CD22a.

In some embodiments of the vaccine, the vaccine comprises at least one D selected from inhibitors of mTOR, RORγt, CDK8/19, and HDAC and agonists of AHR, RAR and A$_{2a}$. In some embodiments of the vaccine, the at least one D is selected from ATP-competitive mTOR inhibitors.

In some embodiments of the vaccine, the vaccine further comprises a second drug molecule (D2) independently selected from inhibitors of mTOR, RORγt, CDK8/19, and HDACs, agonists of AHR, RAR and A$_{2a}$, and immunostimulants selected from agonists of NLRs, CLRs, TLRs and STING, provided that D and D2 bind to different receptors.

In some embodiments of the vaccine, the at least one D is selected from inhibitors of mTOR and agonists of AHR, and the D2 is selected from agonists of NLRs, CLRs, TLRs and STING. In some embodiments of the vaccine, the at least one D is selected from ATP-competitive mTOR inhibitors and the D2 is selected from agonists of NLRs, CLRs, TLRs and STING.

In some embodiments of the vaccine, the D2 is selected from agonists of TLR-3, TLR-7, TLR-8, TLR-7/8, TLR-9 and STING. In some embodiments of the vaccine, the D2 is selected from RNA and imidazoquinoline agonists of TLR-7, TLR-8 and TLR-7/8.

In some embodiments of the vaccine, the vaccine further comprises a third drug molecule (D3) independently selected from inhibitors of mTOR, RORγt, CDK8/19, and HDACs, agonists of AHR, RAR and A$_{2a}$, and immunostimulants selected from agonists of NLRs, CLRs, TLRs and STING, provided that D, D2 and D3 bind to different receptors.

In some embodiments of the vaccine, the at least one D is selected from AZD-8055, AZD-2016, KU-0063794, CC223, Torin-1, Torin-2, INK-128, WYE354, WYE132, OSI-027, OXA-01, PI-103, NVP-BEZ235, GNE-493, GSK2126458, rapamycin, tacrolimus, everolimus, RAD001, CCI-779 and AP23573.

In some embodiments of the vaccine, the molar ratio of total peptide antigen conjugate to the at least one D is between about 20:1 to 1:2, or about 10:1 to about 1:1 or about 4:1 to about 2:1, preferably about 1:1.

In some embodiments of the vaccine, the at least one peptide antigen conjugate comprises an A selected from tumor antigens.

In some embodiments of the vaccine, the S of the amphiphile comprises two or more solubilizing groups (SGs) independently selected from amines or sugar molecules, wherein the sugar molecules are independently selected from mannose and sialyl lewix x, and combinations thereof.

In some embodiments of the vaccine, the S of the amphiphile comprises two or more solubilizing groups (SGs) independently selected from amines, carboxylic acids or sugar molecules, wherein the sugar molecules are independently selected from mannose, sialyl lewis x, sialyl lewis a, lewis y, lewis x, Tn, sTn, TF, sTF, Globo H, SSEA-3, GM2, GD2, GD3 and Fucosyl GM1 and combinations thereof.

In some embodiments of the vaccine, each H of the amphiphile and/or the peptide antigen conjugate independently comprise a poly(amino acid) comprising monomers of hydrophobic amino acids (M) selected from tryptophan, 1-methyl tryptophan and para-amino phenylalanine. In other embodiments, each H of the amphiphile and/or the peptide antigen conjugate comprises a poly(amino acid) comprising monomers of the reactive amino acid (N), wherein the monomers comprise a D selected from a Glu-TLR-7/8a. In some embodiments of the vaccine, at least one D is present and selected from agonists of TLR-3, TLR-7, TLR-8, TLR-7/8, TLR-9 and STING. In some embodiments of the vaccine, the vaccine further comprises a second drug molecule (D2) selected from inhibitors of mTOR. In other embodiments, D2 is selected from rapamycin, tacrolimus, everolimus, RAD001, CCI-779 and AP23573. In some embodiments of the vaccine, the molar ratio of peptide antigen conjugate to D2 is between about 20:1 to 1:2, or about 10:1 to about 1:1 or about 4:1 to about 2:1, preferably about 1:1.

In some embodiments of the vaccine, A is a glycopeptide. In other embodiments, A is selected from HGVT*S*APDT*RPAPGS*T*APPA (SEQ ID NO: 534), DT*RPAPGS*T*APPAHGVT*S*AP (SEQ ID NO: 535), GS*T*APPAHGVT*S*APDT*RPAPGS*T*APPA (SEQ ID NO: 536), GVT*S*APDT*RPAP (SEQ ID NO: 537), APDT*RPAPGS*T*A (SEQ ID NO: 538), GS*T*APPAHGVT*S*AP (SEQ ID NO: 539), VT*S*AP (SEQ ID NO: 540), DT*RPAP (SEQ ID NO: 541) and GS*T*AP (SEQ ID NO: 542), wherein * is an O-linked glycan and each occurrence is independently selected from sialyl lewis x, sialyl lewis a, lewis y, lewis x, Tn, sTn, TF, STF.

In some embodiments of the vaccine, S of the amphiphile comprises a second or third generation dendrimer; and B comprises from 4 to 36 PEG monomeric units.

In some embodiments of the vaccine, S of the amphiphile comprises a second or third generation dendrimer; and H of the amphiphile comprises a poly(amino acid) comprising hydrophobic amino acids (M).

In some embodiments of the vaccine, B comprises from 4 to 36 monomeric units; and H of the amphiphile comprises a poly(amino acid) comprising hydrophobic amino acids (M).

In some embodiments of the vaccine, S of the amphiphile comprises a second or third generation dendrimer; B comprises from 4 to 36 PEG monomeric units; and H of the amphiphile comprises a poly(amino acid) comprising hydrophobic amino acids (M).

In some embodiments of the vaccine, S of the amphiphile comprises a second or third generation dendrimer; and H of the amphiphile comprises a poly(amino acid) comprising para amino-phenylalanine.

In some embodiments of the vaccine, B comprises from 4 to 36 PEG monomeric units; and H of the amphiphile comprises a polymer of para amino-phenylalanine.

In some embodiments of the vaccine, S of the amphiphile comprises a second or third generation dendrimer; B comprises from 4 to 36 PEG monomeric units; and H of the amphiphile comprises a polymer of para amino-phenylalanine.

In some embodiments of the vaccine, S of the amphiphile comprises a second or third generation dendrimer; and H of the amphiphile comprises a poly(amino acid) comprising hydrophobic amino acids (M) and reactive amino acids (N) that comprise an imidazoquinoline.

In some embodiments of the vaccine, B comprises from 4 to 36 PEG monomeric units; and H of the amphiphile comprises a poly(amino acid) comprising hydrophobic amino acids (M) and reactive amino acids (N) that comprise an imidazoquinoline.

In some embodiments of the vaccine, S of the amphiphile comprises a second or third generation dendrimer; B comprises from 4 to 36 PEG monomeric units; and H of the amphiphile comprises a poly(amino acid) comprising hydrophobic amino acids (M) and reactive amino acids (N) that comprise an imidazoquinoline.

In some embodiments of the vaccine, S of the amphiphile comprises a second or third generation dendrimer; and H of the amphiphile comprises a poly(amino acid) of tryptophan and reactive amino acids (N) that comprise an imidazoquinoline.

In some embodiments of the vaccine, B comprises from 4 to 36 PEG monomeric units; and H of the amphiphile comprises a poly(amino acid) of tryptophan and reactive amino acids (N) that comprise an imidazoquinoline.

In some embodiments of the vaccine, S of the amphiphile comprises a second or third generation dendrimer; B comprises from 4 to 36 PEG monomeric units; and H of the amphiphile comprises a poly(amino acid) of tryptophan and reactive amino acids (N) that comprise an imidazoquinoline.

In some embodiments of the vaccine, S of the amphiphile comprises a second or third generation dendrimer; B comprises from 4 to 36 PEG monomeric units; and SG comprises mannose.

In some embodiments of the vaccine, S of the amphiphile comprises a second or third generation dendrimer; H of the amphiphile comprises a poly(amino acid) comprising hydrophobic amino acids (M); and SG comprises mannose.

In some embodiments of the vaccine, B comprises from 4 to 36 PEG monomeric units; H of the amphiphile comprises a poly(amino acid) comprising hydrophobic amino acids (M); and SG comprises mannose.

In some embodiments of the vaccine, S of the amphiphile comprises a second or third generation dendrimer; B comprises from 4 to 36 PEG monomeric units; H of the amphiphile comprises a poly(amino acid) comprising hydrophobic amino acids (M); and SG comprises mannose.

In some embodiments of the vaccine, S of the amphiphile comprises a second or third generation dendrimer; H of the amphiphile comprises a polymer of para amino-phenylalanine; and SG comprises mannose.

In some embodiments of the vaccine, B comprises from 4 to 36 PEG monomeric units; H of the amphiphile comprises a polymer of para amino-phenylalanine; and SG comprises mannose.

In some embodiments of the vaccine, S of the amphiphile comprises a second or third generation dendrimer; B comprises from 4 to 36 PEG monomeric units; H of the amphiphile comprises a polymer of para amino-phenylalanine; and SG comprises mannose.

In some embodiments of the vaccine, S of the amphiphile comprises a second or third generation dendrimer; and H of the amphiphile comprises a poly(amino acid) comprising hydrophobic amino acids (M) and reactive amino acids (N) that comprise an imidazoquinoline; and SG comprises mannose.

In some embodiments of the vaccine, B comprises from 4 to 36 PEG monomeric units; and H of the amphiphile comprises a poly(amino acid) comprising hydrophobic amino acids (M) and reactive amino acids (N) that comprise an imidazoquinoline; and SG comprises mannose.

In some embodiments of the vaccine, S of the amphiphile comprises a second or third generation dendrimer; B comprises from 4 to 36 PEG monomeric units; H of the amphiphile comprises a poly(amino acid) comprising hydrophobic amino acids (M) and reactive amino acids (N) that comprise an imidazoquinoline; and SG comprises mannose.

In some embodiments of the vaccine, S of the amphiphile comprises a second or third generation dendrimer; and H of the amphiphile comprises a poly(amino acid) of tryptophan and reactive amino acids (N) that comprise an imidazoquinoline; and SG comprises mannose.

In some embodiments of the vaccine, B comprises from 4 to 36 PEG monomeric units; and H of the amphiphile comprises a poly(amino acid) of tryptophan and reactive amino acids (N) that comprise an imidazoquinoline; and SG comprises mannose.

In some embodiments of the vaccine, S of the amphiphile comprises a second or third generation dendrimer; B comprises from 4 to 36 PEG monomeric units; and H of the amphiphile comprises a poly(amino acid) of tryptophan and reactive amino acids (N) that comprise an imidazoquinoline; and SG comprises mannose.

In some embodiments of the vaccine, S of the amphiphile comprises a second or third generation dendrimer; B comprises from 4 to 36 PEG monomeric units; and H of the peptide antigen conjugate comprises a poly(amino acid) comprising hydrophobic amino acids (M).

In some embodiments of the vaccine, S of the amphiphile comprises a second or third generation dendrimer; H of the amphiphile comprises a poly(amino acid) comprising hydrophobic amino acids (M); and H of the peptide antigen conjugate comprises a poly(amino acid) comprising hydrophobic amino acids (M).

In some embodiments of the vaccine, B comprises from 4 to 36 PEG monomeric units; H of the amphiphile comprises a poly(amino acid) comprising hydrophobic amino acids (M); and H of the peptide antigen conjugate comprises a poly(amino acid) comprising hydrophobic amino acids (M).

In some embodiments of the vaccine, S of the amphiphile comprises a second or third generation dendrimer; B comprises from 4 to 36 PEG monomeric units; H of the amphiphile comprises a poly(amino acid) comprising hydrophobic amino acids (M); and H of the peptide antigen conjugate comprises a poly(amino acid) comprising hydrophobic amino acids (M).

In some embodiments of the vaccine, S of the amphiphile comprises a second or third generation dendrimer; H of the amphiphile comprises a polymer of para amino-phenylalanine; and H of the peptide antigen conjugate comprises a poly(amino acid) comprising hydrophobic amino acids (M).

In some embodiments of the vaccine, B comprises from 4 to 36 PEG monomeric units; H of the amphiphile comprises a polymer of para amino-phenylalanine; and H of the peptide antigen conjugate comprises a poly(amino acid) comprising hydrophobic amino acids (M).

In some embodiments of the vaccine, S of the amphiphile comprises a second or third generation dendrimer; B comprises from 4 to 36 PEG monomeric units; H of the amphiphile comprises a polymer of para amino-phenylalanine; and H of the peptide antigen conjugate comprises a poly(amino acid) comprising hydrophobic amino acids (M).

In some embodiments of the vaccine, S of the amphiphile comprises a second or third generation dendrimer; H of the amphiphile comprises a poly(amino acid) comprising hydrophobic amino acids (M) and reactive amino acids (N), that comprise an imidazoquinoline; and H of the peptide antigen conjugate comprises a poly(amino acid) comprising hydrophobic amino acids (M).

In some embodiments of the vaccine, B comprises from 4 to 36 PEG monomeric units; H of the amphiphile comprises a poly(amino acid) comprising hydrophobic amino acids (M) and reactive amino acids (N), that comprise an imidazoquinoline; and H of the peptide antigen conjugate comprises a poly(amino acid) comprising hydrophobic amino acids (M).

In some embodiments of the vaccine, S of the amphiphile comprises a second or third generation dendrimer; B comprises from 4 to 36 PEG monomeric units; H of the amphiphile comprises a poly(amino acid) comprising hydrophobic amino acids (M) and reactive amino acids (N) that comprise an imidazoquinoline; and H of the peptide antigen conjugate comprises a poly(amino acid) comprising hydrophobic amino acids (M).

In some embodiments of the vaccine, S of the amphiphile comprises a second or third generation dendrimer; H of the amphiphile comprises a poly(amino acid) of tryptophan and reactive amino acids (N) that comprise an imidazoquinoline; and H of the peptide antigen conjugate comprises a poly (amino acid) comprising hydrophobic amino acids (M).

In some embodiments of the vaccine, B comprises from 4 to 36 PEG monomeric units; H of the amphiphile comprises a poly(amino acid) of tryptophan and reactive amino acids (N) that comprise an imidazoquinoline; and H of the peptide antigen conjugate comprises a poly(amino acid) comprising hydrophobic amino acids (M).

In some embodiments of the vaccine, S of the amphiphile comprises a second or third generation dendrimer; B comprises from 4 to 36 PEG monomeric units; H of the amphiphile comprises a poly(amino acid) of tryptophan and reactive amino acids (N) that comprise an imidazoquinoline; and H of the peptide antigen conjugate comprises a poly(amino acid) comprising hydrophobic amino acids (M).

In some embodiments of the vaccine, S of the amphiphile comprises a second or third generation dendrimer; B comprises from 4 to 36 PEG monomeric units; SG comprises mannose; and H of the peptide antigen conjugate comprises a poly(amino acid) comprising hydrophobic amino acids (M).

In some embodiments of the vaccine, S of the amphiphile comprises a second or third generation dendrimer; H of the amphiphile comprises a poly(amino acid) comprising hydrophobic amino acids (M); SG comprises mannose; and H of the peptide antigen conjugate comprises a poly(amino acid) comprising hydrophobic amino acids (M).

In some embodiments of the vaccine, B comprises from 4 to 36 PEG monomeric units; H of the amphiphile comprises a poly(amino acid) comprising hydrophobic amino acids (M); SG comprises mannose; and H of the peptide antigen conjugate comprises a poly(amino acid) comprising hydrophobic amino acids (M).

In some embodiments of the vaccine, S of the amphiphile comprises a second or third generation dendrimer; B comprises from 4 to 36 PEG monomeric units; H of the amphiphile comprises a poly(amino acid) comprising hydrophobic amino acids (M); SG comprises mannose; and H of the peptide antigen conjugate comprises a poly(amino acid) comprising hydrophobic amino acids (M).

In some embodiments of the vaccine, S of the amphiphile comprises a second or third generation dendrimer; H of the amphiphile comprises a polymer of para amino-phenylalanine; SG comprises mannose; and H of the peptide antigen conjugate comprises a poly(amino acid) comprising hydrophobic amino acids (M).

In some embodiments of the vaccine, B comprises from 4 to 36 PEG monomeric units; H of the amphiphile comprises a polymer of para amino-phenylalanine; SG comprises mannose; and H of the peptide antigen conjugate comprises a poly(amino acid) comprising hydrophobic amino acids (M).

In some embodiments of the vaccine, S of the amphiphile comprises a second or third generation dendrimer; B comprises from 4 to 36 PEG monomeric units; H of the amphiphile comprises a polymer of para amino-phenylalanine; SG comprises mannose; and H of the peptide antigen conjugate comprises a poly(amino acid) comprising hydrophobic amino acids (M).

In some embodiments of the vaccine, S of the amphiphile comprises a second or third generation dendrimer; and H of the amphiphile comprises a poly(amino acid) comprising hydrophobic amino acids (M) and reactive amino acids (N), that comprise an imidazoquinoline; SG comprises mannose; and H of the peptide antigen conjugate comprises a poly (amino acid) comprising hydrophobic amino acids (M).

In some embodiments of the vaccine, B comprises from 4 to 36 PEG monomeric units; and H of the amphiphile comprises a poly(amino acid) comprising hydrophobic amino acids (M) and reactive amino acids (N) that comprise an imidazoquinoline; SG comprises mannose; and H of the peptide antigen conjugate comprises a poly(amino acid) comprising hydrophobic amino acids (M).

In some embodiments of the vaccine, S of the amphiphile comprises a second or third generation dendrimer; B comprises from 4 to 36 PEG monomeric units; H of the amphiphile comprises a poly(amino acid) comprising hydrophobic amino acids (M) and reactive amino acids (N) that comprise an imidazoquinoline; SG comprises mannose; and H of the peptide antigen conjugate comprises a poly(amino acid) comprising hydrophobic amino acids (M).

In some embodiments of the vaccine, S of the amphiphile comprises a second or third generation dendrimer; and H of the amphiphile comprises a poly(amino acid) of tryptophan and reactive amino acids (N) that comprise an imidazoquinoline; SG comprises mannose; and H of the peptide antigen conjugate comprises a poly(amino acid) comprising hydrophobic amino acids (M).

In some embodiments of the vaccine, B comprises from 4 to 36 PEG monomeric units; H of the amphiphile comprises a poly(amino acid) of tryptophan and reactive amino acids (N) that comprise an imidazoquinoline; SG comprises mannose; and H of the peptide antigen conjugate comprises a poly(amino acid) comprising hydrophobic amino acids (M).

In some embodiments of the vaccine, S of the amphiphile comprises a second or third generation dendrimer; B comprises from 4 to 36 PEG monomeric units; H of the amphiphile comprises a poly(amino acid) of tryptophan and reactive amino acids (N) that comprise an imidazoquinoline; SG comprises mannose; and H of the peptide antigen conjugate comprises a poly(amino acid) comprising hydrophobic amino acids (M).

In some embodiments of the vaccine, S of the amphiphile comprises a second or third generation dendrimer; B comprises from 4 to 36 PEG monomeric units; the amphiphile comprises amino-hexanoic acid; and H of the peptide antigen conjugate comprises a poly(amino acid) comprising hydrophobic amino acids (M).

In some embodiments of the vaccine, S of the amphiphile comprises a second or third generation dendrimer; H of the amphiphile comprises a poly(amino acid) comprising hydrophobic amino acids (M); the amphiphile comprises amino-hexanoic acid; and H of the peptide antigen conjugate comprises a poly(amino acid) comprising hydrophobic amino acids (M).

In some embodiments of the vaccine, B comprises from 4 to 36 PEG monomeric units; H of the amphiphile comprises a poly(amino acid) comprising hydrophobic amino acids (M); the amphiphile comprises amino-hexanoic acid; and H of the peptide antigen conjugate comprises a poly (amino acid) comprising hydrophobic amino acids (M).

In some embodiments of the vaccine, S of the amphiphile comprises a second or third generation dendrimer; B comprises from 4 to 36 PEG monomeric units; H of the amphiphile comprises a poly(amino acid) comprising hydrophobic amino acids (M); the amphiphile comprises amino-hexanoic acid; and H of the peptide antigen conjugate comprises a poly(amino acid) comprising hydrophobic amino acids (M).

In some embodiments of the vaccine, S of the amphiphile comprises a second or third generation dendrimer; H of the amphiphile comprises a polymer of para amino-phenylalanine; the amphiphile comprises amino-hexanoic acid; and H of the peptide antigen conjugate comprises a poly(amino acid) comprising hydrophobic amino acids (M).

In some embodiments of the vaccine, B comprises from 4 to 36 PEG monomeric units; H of the amphiphile comprises a polymer of para amino-phenylalanine; the amphiphile comprises amino-hexanoic acid; and H of the peptide antigen conjugate comprises a poly(amino acid) comprising hydrophobic amino acids (M).

In some embodiments of the vaccine, S of the amphiphile comprises a second or third generation dendrimer; B comprises from 4 to 36 PEG monomeric units; H of the amphiphile comprises a polymer of para amino-phenylalanine; the amphiphile comprises amino-hexanoic acid; and H of the peptide antigen conjugate comprises a poly(amino acid) comprising hydrophobic amino acids (M).

In some embodiments of the vaccine, S of the amphiphile comprises a second or third generation dendrimer; and H of the amphiphile comprises a poly(amino acid) comprising hydrophobic amino acids (M) and reactive amino acids (N), that comprise an imidazoquinoline; the amphiphile comprises amino-hexanoic acid; and H of the peptide antigen conjugate comprises a poly(amino acid) comprising hydrophobic amino acids (M).

In some embodiments of the vaccine, B comprises from 4 to 36 PEG monomeric units; and H of the amphiphile comprises a poly(amino acid) comprising hydrophobic amino acids (M) and reactive amino acids (N) that comprise an imidazoquinoline; the amphiphile comprises amino-hexanoic acid; and H of the peptide antigen conjugate comprises a poly(amino acid) comprising hydrophobic amino acids (M).

In some embodiments of the vaccine, S of the amphiphile comprises a second or third generation dendrimer; B comprises from 4 to 36 PEG monomeric units; H of the amphiphile comprises a poly(amino acid) comprising hydrophobic amino acids (M) and reactive amino acids (N) that comprise an imidazoquinoline; the amphiphile comprises amino-hexanoic acid; and H of the peptide antigen conjugate comprises a poly(amino acid) comprising hydrophobic amino acids (M).

In some embodiments of the vaccine, S of the amphiphile comprises a second or third generation dendrimer; and H of the amphiphile comprises a poly(amino acid) of tryptophan and reactive amino acids (N) that comprise an imidazoquinoline; the amphiphile comprises amino-hexanoic acid; and H of the peptide antigen conjugate comprises a poly(amino acid) comprising hydrophobic amino acids (M).

In some embodiments of the vaccine, B comprises from 4 to 36 PEG monomeric units; H of the amphiphile comprises a poly(amino acid) of tryptophan and reactive amino acids (N) that comprise an imidazoquinoline; the amphiphile comprises amino-hexanoic acid; and H of the peptide antigen conjugate comprises a poly(amino acid) comprising hydrophobic amino acids (M).

In some embodiments of the vaccine, S of the amphiphile comprises a second or third generation dendrimer; B comprises from 4 to 36 PEG monomeric units; H of the amphiphile comprises a poly(amino acid) of tryptophan and reactive amino acids (N) that comprise an imidazoquinoline; the amphiphile comprises amino-hexanoic acid; and H of the peptide antigen conjugate comprises a poly(amino acid) comprising hydrophobic amino acids (M).

In some embodiments of the vaccine, S of the amphiphile comprises a second or third generation dendrimer; B comprises from 4 to 36 PEG monomeric units; the dendrimer monomers comprise hydroxy acids and amino alcohols; and H of the peptide antigen conjugate comprises a poly(amino acid) comprising hydrophobic amino acids (M).

In some embodiments of the vaccine, S of the amphiphile comprises a second or third generation dendrimer; H of the amphiphile comprises a poly(amino acid) comprising hydrophobic amino acids (M); the dendrimer monomers comprise hydroxy acids and amino alcohols; and H of the peptide antigen conjugate comprises a poly(amino acid) comprising hydrophobic amino acids (M).

In some embodiments of the vaccine, B comprises from 4 to 36 PEG monomeric units; H of the amphiphile comprises a poly(amino acid) comprising hydrophobic amino acids (M); the dendrimer monomers comprise hydroxy acids and amino alcohols; and H of the peptide antigen conjugate comprises a poly(amino acid) comprising hydrophobic amino acids (M).

In some embodiments of the vaccine, S of the amphiphile comprises a second or third generation dendrimer; B comprises from 4 to 36 PEG monomeric units; H of the amphiphile comprises a poly(amino acid) comprising hydrophobic amino acids (M); the dendrimer monomers comprise hydroxy acids and amino alcohols; and H of the peptide antigen conjugate comprises a poly(amino acid) comprising hydrophobic amino acids (M).

In some embodiments of the vaccine, S of the amphiphile comprises a second or third generation dendrimer; H of the amphiphile comprises a polymer of para amino-phenylalanine; the dendrimer monomers comprise hydroxy acids and amino alcohols; and H of the peptide antigen conjugate comprises a poly(amino acid) comprising hydrophobic amino acids (M).

In some embodiments of the vaccine, B comprises from 4 to 36 PEG monomeric units; H of the amphiphile comprises a polymer of para amino-phenylalanine; the dendrimer monomers comprise hydroxy acids and amino alcohols; and H of the peptide antigen conjugate comprises a poly(amino acid) comprising hydrophobic amino acids (M).

In some embodiments of the vaccine, S of the amphiphile comprises a second or third generation dendrimer; B comprises from 4 to 36 PEG monomeric units; H of the amphiphile comprises a polymer of para amino-phenylalanine; the dendrimer monomers comprise hydroxy acids and amino alcohols; and H of the peptide antigen conjugate comprises a poly(amino acid) comprising hydrophobic amino acids (M).

In some embodiments of the vaccine, S of the amphiphile comprises a second or third generation dendrimer; and H of the amphiphile comprises a poly(amino acid) comprising hydrophobic amino acids (M) and reactive amino acids (N), that comprise an imidazoquinoline; the dendrimer monomers comprise hydroxy acids and amino alcohols; and H of the peptide antigen conjugate comprises a poly(amino acid) comprising hydrophobic amino acids (M).

In some embodiments of the vaccine, B comprises from 4 to 36 PEG monomeric units; and H of the amphiphile comprises a poly(amino acid) comprising hydrophobic amino acids (M) and reactive amino acids (N) that comprise an imidazoquinoline; the dendrimer monomers comprise hydroxy acids and amino alcohols; and H of the peptide antigen conjugate comprises a poly(amino acid) comprising hydrophobic amino acids (M).

In some embodiments of the vaccine, S of the amphiphile comprises a second or third generation dendrimer; B comprises from 4 to 36 PEG monomeric units; H of the amphiphile comprises a poly(amino acid) comprising hydrophobic amino acids (M) and reactive amino acids (N) that comprise an imidazoquinoline; the dendrimer monomers comprise hydroxy acids and amino alcohols; and H of the peptide antigen conjugate comprises a poly(amino acid) comprising hydrophobic amino acids (M).

In some embodiments of the vaccine, S of the amphiphile comprises a second or third generation dendrimer; and H of the amphiphile comprises a poly(amino acid) of tryptophan and reactive amino acids (N) that comprise an imidazoquinoline; the dendrimer monomers comprise hydroxy acids and amino alcohols; and H of the peptide antigen conjugate comprises a poly(amino acid) comprising hydrophobic amino acids (M).

In some embodiments of the vaccine, B comprises from 4 to 36 PEG monomeric units; H of the amphiphile comprises a poly(amino acid) of tryptophan and reactive amino acids (N) that comprise an imidazoquinoline; the dendrimer monomers comprise hydroxy acids and amino alcohols; and H of the peptide antigen conjugate comprises a poly(amino acid) comprising hydrophobic amino acids (M).

In some embodiments of the vaccine, S of the amphiphile comprises a second or third generation dendrimer; B comprises from 4 to 36 PEG monomeric units; H of the amphiphile comprises a poly(amino acid) of tryptophan and reactive amino acids (N) that comprise an imidazoquinoline; the dendrimer monomers comprise hydroxy acids and amino alcohols; and H of the peptide antigen conjugate comprises a poly(amino acid) comprising hydrophobic amino acids (M).

The present disclosure relates to a vaccine for inducing tolerance comprising at least one peptide antigen conjugate having the formula selected from PEG-[E1]-A-[E2]-[U]-H and H-[U]-[E1]-A-[E2]-PEG wherein A is a peptide antigen;

E1 is an N-terminal extension;

E2 is a C terminal extension;

H, independently for each occurrence is a hydrophobic block, wherein one or more drug molecules (D) are optionally attached to each H directly or via a suitable linker X1;

U, independently for each occurrence, is a linker;

[ ] denotes that the group is optional, and

- denotes that the two adjacent groups are directly attached to one another by a covalent bond or indirectly to one another via a suitable linker X; and wherein at least one peptide antigen is selected from an autoantigen, alloantigen and allergen.

In some embodiments of the vaccine, wherein either (i) the average aqueous solubility of the peptide antigens (A) of the one or more peptide antigen conjugates is less than 1 mg/mL or (ii) the average GRAVY score of the peptide antigens (A) of the one or more peptide antigen conjugates is >0, the amphiphile is present.

The present disclosure also relates to a vaccine for inducing tolerance comprising at least one peptide antigen conjugate having the formula selected from PEG-[E1]-A-[E2]-[U]-H and H-[U]-[E1]-A-[E2]-PEG, and an amphiphile having the formula S-[B]-[U]-H, wherein A is a peptide antigen;

E1 is an N-terminal extension;

E2 is a C terminal extension;

H, independently for each occurrence is a hydrophobic block, wherein one or more drug molecules (D) are optionally attached to each H directly or via a suitable linker X1; S is a solubilizing block;

B is a spacer;

U, independently for each occurrence, is a linker;

[ ] denotes that the group is optional,

- denotes that the two adjacent groups are directly attached to one another by a covalent bond or indirectly to one another via a suitable linker X; and wherein the amphiphile comprises a dendron amplifier and at least one peptide antigen is selected from an autoantigen, alloantigen and allergen.

In one embodiments of the vaccine, the PEG group of the peptide antigen conjugate includes terminal functional groups selected from OH, MeO— and $NH_2$.

In a particular embodiment of the vaccine for inducing tolerance, the PEG group of the peptide antigen conjugate is polyethylene glycol.

In some embodiments of the vaccine for inducing tolerance, the PEG group of the peptide antigen conjugate comprises between 4 and 36 monomeric units.

In a particular embodiment of the vaccine for inducing tolerance, the PEG group of the peptide antigen conjugate comprises between 4 and 12 monomeric units, or between 12 to 36 monomeric units, preferably 24 monomeric units.

In some embodiments of the vaccine for inducing tolerance, A is an autoantigen. In other embodiments, A is an allergen. In other embodiments, A is an alloantigen.

In some embodiments of the vaccine for inducing tolerance, wherein the ampiphile is present, the amphiphile comprises a dendron amplifier.

In some embodiments of the vaccine for inducing tolerance, the S of the amphiphile comprises a dendron amplifier. In other embodiments, the S of the amphiphile has a dendritic architecture.

In some embodiments of the vaccine for inducing tolerance, the S of the amphiphile comprises two or more solubilizing groups (SGs). In other embodiments, the two or more SGs are connected to the remaining portion of the S by a dendron amplifier, e.g., 4 to 8 SGs are connected to the S.

In some embodiments of the vaccine for inducing tolerance, the SGs are independently selected from amines, hydroxyls, carboxylic acids and/or sugar molecules, wherein the sugar molecules are independently selected from mannose, glucose, glucosamine, N-acetyl glucose, galactose, galactosamine, N-acetyl galactosamine, N-acetyl glucosamine, phosphoserine and any derivatives thereof, agonists of CD22a, sialyl lewix x, and combinations thereof.

In some embodiments of the vaccine for inducing tolerance, at least one SG is galactose. In other embodiments, at least one SG is phosphoserine. In other embodiments, at least one SG is an agonist of CD22a.

In some embodiments of the vaccine for inducing tolerance, the dendron amplifier comprises repeating monomer units of 1 to 10 generations having between 2 to 6 branches per generation. In other embodiments, the dendron amplifier comprises repeating monomer units of 2 to 3 generations having between 2 to 3 branches per generation.

In some embodiments of the vaccine for inducing tolerance, the repeating monomer units are selected from FG1-$(CH_2)_{y2}CH(R^1)_2$, FG1-$(CH_2)_{y2}C(R^1)_3$, FG1-$(CH_2CH_2O)_{y2}CH(R^1)_2$, FG1-$(CH_2CH_2O)_{y2}C(R^1)_3$, and FG1-$CH(R^1)_2$, FG1-$C(R^1)_3$, wherein $R^1$, independently for each occurrence, is selected from $(CH_2)_{y3}$-FG2, $(OCH_2CH_2)_{y3}$-FG2, and $CH_2$ $(OCH_2CH_2)_{y3}$-FG2); y2 and y3, independently for each occurrence, is an integer of repeating units from 1 to 6; FG1 is a first functional group; and FG2 is a second functional group. In some embodiments, FG1 is $—NH_2$; and FG2, independently for each occurrence, is $—CO_2—$ or $—CO_2H$. In some embodiments, FG1 is $—CO_2—$ or $—CO_2H$; and FG2, independently for each occurrence, is $—NH_2$.

In some embodiments of the vaccine for inducing tolerance, the SGs are linked to S via a suitable linker X5. In some embodiments of the vaccine for inducing tolerance, the suitable linker X5 that links the SGs to S is selected from lower alkyl and PEG groups. In some embodiments of the vaccine for inducing tolerance, two or more SGs are connected to the remaining portion of the S by a dendron amplifier through a suitable linker X5, which links the two or more SGs to a terminal functional (FGt) group of the dendron amplifier through an amide bond. In some embodiments of the vaccine for inducing tolerance, the linker X5 joining the SGs to the dendron amplifier is selected from selected from $—NH—R^{19}$, $—NH—C(O)—R^{19}$, $—C(O)—NH—R^{19}—$ or $—C(O)—R^{19}$, wherein $R^{19}$ may be selected from but is not limited to $—(CH_2)_t—$, $—(CH_2CH_2O)_t—CH_2CH_2—$, $—(CH_2)_t—C(O)—NH—(CH_2)_u—$, $—(CH_2CH_2O)_tCH_2CH_2C(O)—NH—(CH_2)_u—$, $—(CH_2)_t—NH—C(O)—NH—(CH_2)_u—$, or $—(CH_2CH_2O)_tCH_2CH_2NH—C(O)—(CH_2)_u—$ where t and u are each independently an integer typically selected from between 1 to 6, such as 1, 2, 3, 4, 5 or 6.

In some embodiments of the vaccine for inducing tolerance, the dendron amplifier comprises a polyethylene oxide (PEG) group.

In some embodiments of the vaccine for inducing tolerance, the H of the amphiphile comprises a higher alkane, an aromatic group, a fatty acid, a sterol, a polyunsaturated hydrocarbon, squalene, saponins, and/or a polymer.

In some embodiments of the vaccine for inducing tolerance, the H of the peptide antigen conjugate comprises a higher alkane, an aromatic group, fatty acid, a sterol, a polyunsaturated hydrocarbon, and/or a polymer.

In some embodiments of the vaccine for inducing tolerance, each H independently comprises a poly(amino acid) comprising monomers selected from hydrophobic amino acids (M), reactive amino acids (N), spacer amino acids (O), charged amino acids (P) and combinations thereof provided that at least one of M or N is present.

In some embodiments of the vaccine for inducing tolerance, each H independently comprises a poly(amino acid) having the formula:

$$-(M)_m-(N)_n-(O)_o-(P)_p-R^3,$$

wherein M, N, O and P are each independently present or absent, provided that at least one of M or N is present;

m, n, o and p each independently denote an integer of 1 to 100 with the sum of m, n, o and p less than or equal to 100;

$R^3$ is selected from hydrogen, $NH_2$, $NH—CH_3$, $NH—(CH_2)_{y5}CH_3$, OH or a drug molecule (D) either connected directly or through a suitable linker X1; and y5 is an integer selected from 1 to 6.

In some embodiments of the vaccine for inducing tolerance, P is absent. In other embodiments, N, O, and P are each absent.

In some embodiments of the vaccine for inducing tolerance, P is

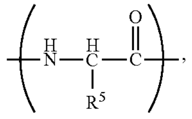

wherein each $R^5$, independently, is a group that comprises 1 to 2 charged functional groups.

In some embodiments of the vaccine for inducing tolerance, O is

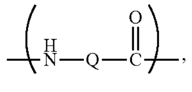

wherein each Q, independently, is selected from $(CH_2)_y$ and $(CH_2CH_2O)_iCH_2CH_2$; each y is independently selected from an integer from 1 to 6; and each i is independently selected from an integer from 1 to 4.

In some embodiments of the vaccine for inducing tolerance, N is

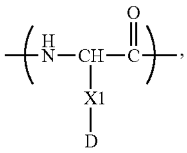

wherein each X1, independently, is a suitable linker; and each D, independently, is a drug molecule.

In some embodiments of the vaccine for inducing tolerance, M is

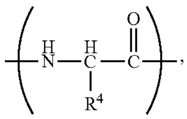

wherein each $R^4$ is, independently, a hydrophobic group.

In some embodiments of the vaccine for inducing tolerance, $R^4$ is

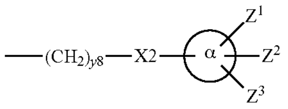

wherein

α is aryl or heteroaryl;

X2 is present or absent and when present is a suitable linker;

Y8 is selected from an integer from 0 and 6; and $Z^1$, $Z^2$, and $Z^3$ are each independently selected from H, F, hydroxy, amino, alkyl, and fluoroalkyl.

In some embodiments of the vaccine for inducing tolerance, a is an aryl, e.g., phenyl or naphthyl. In other embodiments, a is a heteroaryl, e.g., pyridinyl, quinolinyl, isoquinolinyl, indolyl, or benzimidazolyl.

In some embodiments of the vaccine for inducing tolerance, X is absent. In other embodiments, X2 is present and is selected from C(O), $CO_2$ $(CH_2)_{y9}$, $CO_2$, C(O) $NH(CH_2)_{y9}$, NHC(O) and $NHC(O)(CH_2)_{y9}$, wherein y9 is an integer typically selected from 1 to 6. In other embodiments, X2 is present and is selected from lower alkyl and PEG groups.

In some embodiments of the vaccine for inducing tolerance, each $R^4$ is independently selected from:

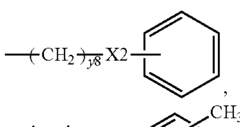

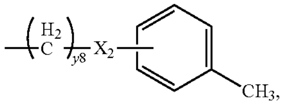

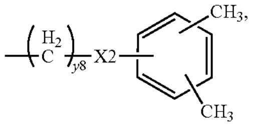

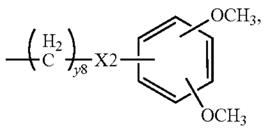

-continued

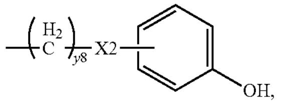

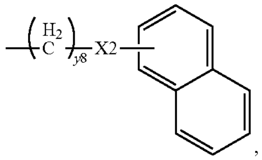

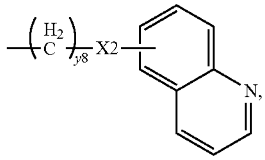

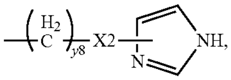

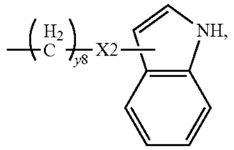

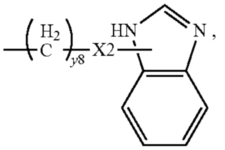

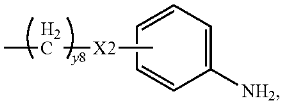

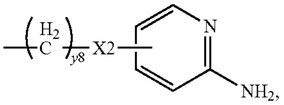

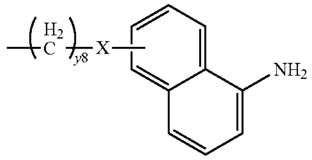

and

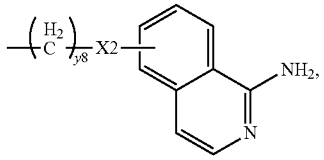

wherein each X2 is independently selected from a suitable linker and each y8 is independently selected from an integer from 0 and 6. In other embodiments, each $R^4$ is independently selected from:

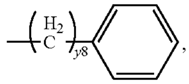

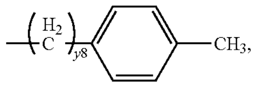

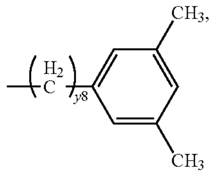

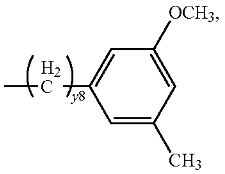

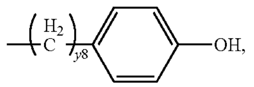

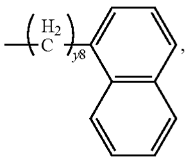

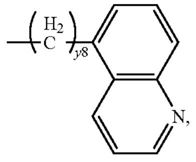

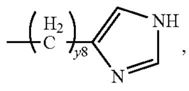

-continued
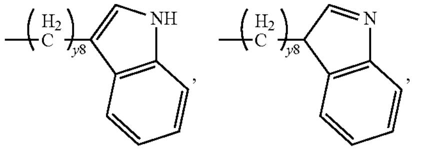
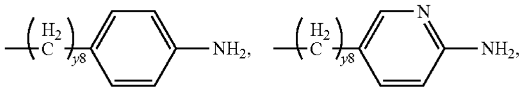
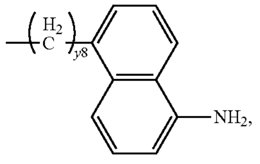
and
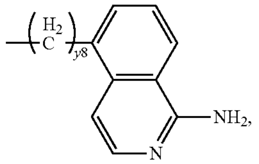
wherein each y8 is independently selected from an integer from 0 and 6. In other embodiments, each $R^4$ is independently selected from:
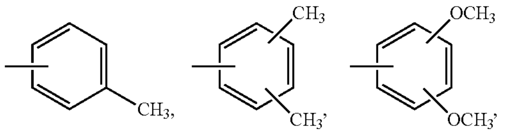
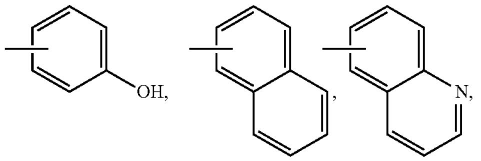
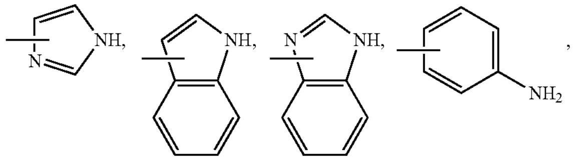
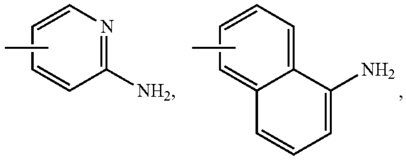
and
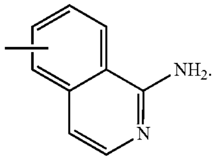
In other embodiments, each $R^4$ is independently selected from:
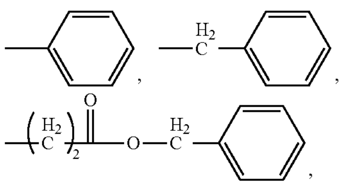
-continued
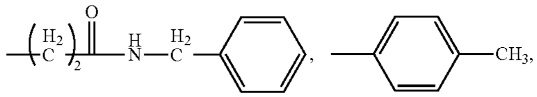
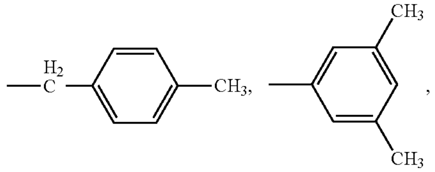
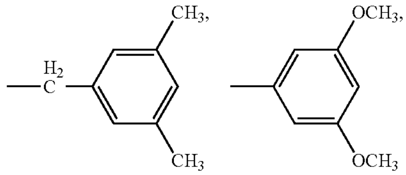
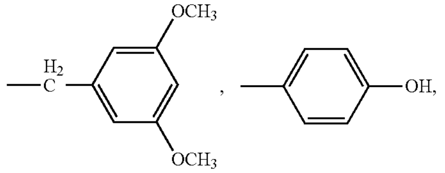
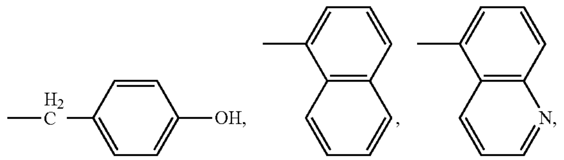
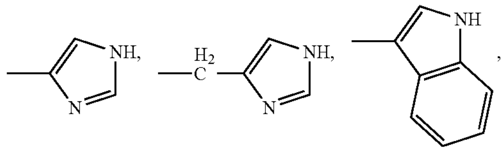
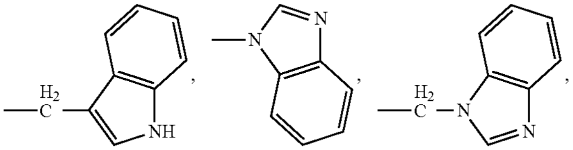
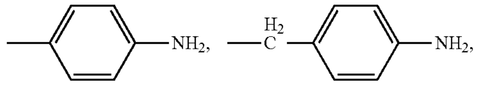
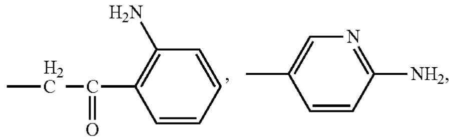
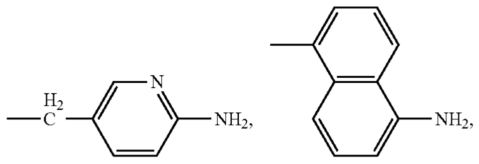
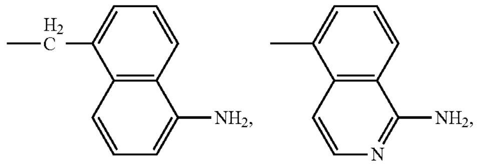
and -continued

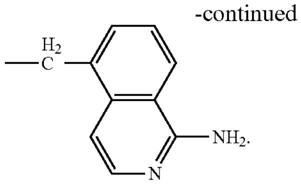

In preferred embodiments, each $R^4$ is independently selected from:

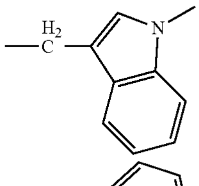,
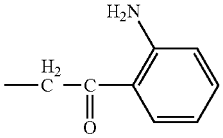

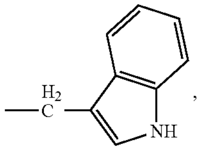,
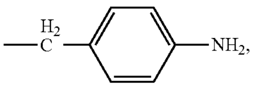 and

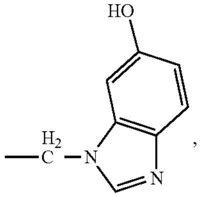, wherein y is selected from an integer from 1 and 6.

In some embodiments of the vaccine for inducing tolerance, wherein at least one D is:

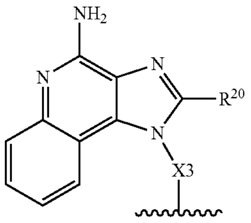

wherein, $R^{20}$ is selected from H, alkyl, alkoxyalkyl, aryl, heteroaryl, aminoalkyl, amide and ester; and X3 is selected from alkyl, alkoxyalkyl, aralkyl, heteroaralkyl, aryl, heteroaryl and carboxy.

In some embodiments of the vaccine for inducing tolerance, $R^{20}$ is selected from H, alkyl and alkoxyalkyl; and X3 is selected from alkyl and aralkyl. In other embodiments, $R^{20}$ is butyl.

In some embodiments of the vaccine for inducing tolerance, X3 is alkyl.

In some embodiments of the vaccine for inducing tolerance, m, n, o and p each independently denote an integer of 1 to 30 with the sum of m, n, o and p less than or equal to 30.

In some embodiments of the vaccine for inducing tolerance, m, n, o and p each independently denote an integer of 1 to 10 with the sum of m, n, o and p less than or equal to 10.

In some embodiments of the vaccine for inducing tolerance, B is present and is a hydrophilic polymer, e.g., a PEG group. In other embodiments, B is present and is a hydrophilic peptide.

In some embodiments of the vaccine for inducing tolerance, the PEG group comprises between 4 and 36 monomeric units. In other embodiments, the PEG group comprises between 4 and 12 monomeric units.

In some embodiments of the vaccine for inducing tolerance, the hydrophilic peptide comprises between 4 and 36 amino acids. In other embodiments, the hydrophilic peptide comprises between 4 and 12 amino acids.

In some embodiments of the vaccine for inducing tolerance, the amphiphile has the formula S—H. In other embodiments, the amphiphile has the formula S-B-U-H. In other embodiments, the amphiphile has the formula S-B-U-H-D.

In some embodiments of the vaccine for inducing tolerance, the vaccine comprises a peptide antigen conjugate to amphiphile molar ratio of between about 4:1 to about 1:20, preferable about 1:1.

In some embodiments of the vaccine for inducing tolerance, the peptide antigen (A) comprises a sequence wherein one or more cysteine residues have been replaced with alpha amino-butyric acid and/or one or more methionine residues have been replaced with norleucine.

In some embodiments of the vaccine for inducing tolerance, the peptide antigen (A) comprises alpha amino-butyric acid and/or norleucine.

In some embodiments of the vaccine for inducing tolerance, the vaccine comprises at least one D selected from inhibitors of mTOR, RORγt, CDK8/19, and HDAC and agonists of AHR, RAR and $A_{2a}$. In other embodiments, the at least one D is selected from ATP-competitive mTOR inhibitors.

In some embodiments of the vaccine for inducing tolerance, the vaccine further comprises a second drug molecule (D2) independently selected from inhibitors of mTOR, RORγt, CDK8/19, and HDACs, agonists of AHR, RAR and $A_{2a}$, and immunostimulants selected from agonists of NLRs, CLRs, TLRs and STING, provided that D and D2 bind to different receptors.

In some embodiments of the vaccine for inducing tolerance, the at least one D is selected from inhibitors of mTOR and agonists of AHR, and the D2 is selected from agonists of NLRs, CLRs, TLRs and STING.

In some embodiments of the vaccine for inducing tolerance, wherein the at least one D is selected from ATP-competitive mTOR inhibitors, and the D2 is selected from agonists of NLRs, CLRs, TLRs and STING.

In other embodiments of the vaccine for inducing tolerance, wherein the D2 is selected from agonists of TLR-3, TLR-7, TLR-8, TLR-7/8, TLR-9 and STING. In other embodiments of the vaccine for inducing tolerance, wherein the D2 is selected from RNA and imidazoquinoline agonists of TLR-7, TLR-8 and TLR-7/8.

In some embodiments of the vaccine for inducing tolerance, the vaccine further comprises a third drug molecule (D3) independently selected from inhibitors of mTOR, RORγt, CDK8/19, and HDACs, agonists of AHR, RAR and $A_{2a}$, and immunostimulants selected from agonists of NLRs, CLRs, TLRs and STING, provided that D, D2 and D3 bind to different receptors.

In some embodiments of the vaccine for inducing tolerance, the at least one D is selected from AZD-8055, AZD2016, KU-0063794, CC223, Torin-1, Torin-2, INK-128, WYE354, WYE132, OSI-027, OXA-01, PI-103, NVP- BEZ235, GNE-493, GSK2126458, rapamycin, tacrolimus, everolimus, RAD001, CCI-779 and AP23573.

In some embodiments of the vaccine for inducing tolerance, the molar ratio of total peptide antigen conjugate to the at least one D is between about 20:1 to 1:2, or about 10:1 to about 1:1 or about 4:1 to about 2:1, or preferably about 1:1.

In some embodiments of the vaccine for inducing tolerance, S of the amphiphile comprises a second or third generation dendrimer; and B comprises from 4 to 36 PEG monomeric units.

In some embodiments of the vaccine for inducing tolerance, S of the amphiphile comprises a second or third generation dendrimer; and H of the amphiphile comprises a poly(amino acid) comprising hydrophobic amino acids (M).

In some embodiments of the vaccine for inducing tolerance, B comprises from 4 to 36 PEG monomeric units; and H of the amphiphile comprises a poly(amino acid) comprising hydrophobic amino acids (M).

In some embodiments of the vaccine for inducing tolerance, S of the amphiphile comprises a second or third generation dendrimer; B comprises from 4 to 36 PEG monomeric units; and H of the amphiphile comprises a poly(amino acid) comprising hydrophobic amino acids (M).

In some embodiments of the vaccine for inducing tolerance, S of the amphiphile comprises a second or third generation dendrimer; and H of the amphiphile comprises a polymer of para amino-phenylalanine.

In some embodiments of the vaccine for inducing tolerance, B comprises from 4 to 36 PEG monomeric units; and H of the amphiphile comprises a polymer of para amino-phenylalanine.

In some embodiments of the vaccine for inducing tolerance, S of the amphiphile comprises a second or third generation dendrimer; B comprises from 4 to 36 PEG monomeric units; and H of the amphiphile comprises a polymer of para amino-phenylalanine.

In some embodiments of the vaccine for inducing tolerance, S of the amphiphile comprises a second or third generation dendrimer; and H of the amphiphile comprises a poly(amino acid) comprising hydrophobic amino acids (M) and reactive amino acids (N) that comprise an imidazoquinoline.

In some embodiments of the vaccine for inducing tolerance, B comprises from 4 to 36 PEG monomeric units; and H of the amphiphile comprises a poly(amino acid) comprising hydrophobic amino acids (M) and reactive amino acids (N) that comprise an imidazoquinoline.

In some embodiments of the vaccine for inducing tolerance, S of the amphiphile comprises a second or third generation dendrimer; B comprises from 4 to 36 PEG monomeric units; and H of the amphiphile comprises a poly(amino acid) comprising hydrophobic amino acids (M) and reactive amino acids (N) that comprise an imidazoquinoline.

In some embodiments of the vaccine for inducing tolerance, S of the amphiphile comprises a second or third generation dendrimer; and H of the amphiphile comprises a poly(amino acid) of tryptophan and reactive amino acids (N) that comprise an imidazoquinoline.

In some embodiments of the vaccine for inducing tolerance, B comprises from 4 to 36 PEG monomeric units; and H of the amphiphile comprises a poly(amino acid) of tryptophan and reactive amino acids (N) that comprise an imidazoquinoline.

In some embodiments of the vaccine for inducing tolerance, S of the amphiphile comprises a second or third generation dendrimer; B comprises from 4 to 36 PEG monomeric units; and H of the amphiphile comprises a poly(amino acid) of tryptophan and reactive amino acids (N) that comprise an imidazoquinoline.

In some embodiments of the vaccine for inducing tolerance, S of the amphiphile comprises a second or third generation dendrimer; B comprises from 4 to 36 PEG monomeric units; and SG comprises N-acetyl galactosamine.

In some embodiments of the vaccine for inducing tolerance, S of the amphiphile comprises a second or third generation dendrimer; H of the amphiphile comprises a poly(amino acid) comprising hydrophobic amino acids (M); and SG comprises N-acetyl galactosamine.

In some embodiments of the vaccine for inducing tolerance, B comprises from 4 to 36 PEG monomeric units; H of the amphiphile comprises a poly(amino acid) comprising hydrophobic amino acids (M); and SG comprises N-acetyl galactosamine.

In some embodiments of the vaccine for inducing tolerance, S of the amphiphile comprises a second or third generation dendrimer; B comprises from 4 to 36PEG monomeric units; H of the amphiphile comprises a poly(amino acid) comprising hydrophobic amino acids (M); and SG comprises N-acetyl galactosamine.

In some embodiments of the vaccine for inducing tolerance, S of the amphiphile comprises a second or third generation dendrimer; H of the amphiphile comprises a polymer of para amino-phenylalanine; and SG comprises N-acetyl galactosamine.

In some embodiments of the vaccine for inducing tolerance, B comprises from 4 to 36 PEG monomeric units; H of the amphiphile comprises a polymer of para amino-phenylalanine; and SG comprises N-acetyl galactosamine.

In some embodiments of the vaccine for inducing tolerance, S of the amphiphile comprises a second or third generation dendrimer; B comprises from 4 to 36 PEG monomeric units; H of the amphiphile comprises a polymer of para amino-phenylalanine; and SG comprises N-acetyl galactosamine.

In some embodiments of the vaccine for inducing tolerance, S of the amphiphile comprises a second or third generation dendrimer; and H of the amphiphile comprises a poly(amino acid) comprising hydrophobic amino acids (M) and reactive amino acids (N) that comprise an imidazoquinoline; and SG comprises N-acetyl galactosamine.

In some embodiments of the vaccine for inducing tolerance, B comprises from 4 to 36 PEG monomeric units; and H of the amphiphile comprises a poly(amino acid) comprising hydrophobic amino acids (M) and reactive amino acids (N) that comprise an imidazoquinoline; and SG comprises N-acetyl galactosamine.

In some embodiments of the vaccine for inducing tolerance, S of the amphiphile comprises a second or third generation dendrimer; B comprises from 4 to 36 PEG monomeric units; H of the amphiphile comprises a poly (amino acid) comprising hydrophobic amino acids (M) and reactive amino acids (N) that comprise an imidazoquinoline; and SG comprises N-acetyl galactosamine.

In some embodiments of the vaccine for inducing tolerance, S of the amphiphile comprises a second or third generation dendrimer; and H of the amphiphile comprises a poly(amino acid) of tryptophan and reactive amino acids (N) that comprise an imidazoquinoline; and SG comprises N-acetyl galactosamine.

In some embodiments of the vaccine for inducing tolerance, B comprises from 4 to 36 PEG monomeric units; and H of the amphiphile comprises a poly(amino acid) of tryptophan and reactive amino acids (N) that comprise an imidazoquinoline; and SG comprises N-acetyl galactosamine.

In some embodiments of the vaccine for inducing tolerance, S of the amphiphile comprises a second or third generation dendrimer; B comprises from 4 to 36 PEG monomeric units; and H of the amphiphile comprises a poly(amino acid) of tryptophan and reactive amino acids (N) that comprise an imidazoquinoline; and SG comprises N-acetyl galactosamine.

In some embodiments of the vaccine for inducing tolerance, S of the amphiphile comprises a second or third generation dendrimer; and B comprises from 4 to 36 PEG monomeric units; and the peptide antigen conjugate comprises an enzyme degradable linker.

In some embodiments of the vaccine for inducing tolerance, S of the amphiphile comprises a second or third generation dendrimer; and H of the amphiphile comprises a poly(amino acid) comprising hydrophobic amino acids (M); and the peptide antigen conjugate comprises an enzyme degradable linker.

In some embodiments of the vaccine for inducing tolerance, B comprises from 4 to 36 PEG monomeric units; and H of the amphiphile comprises a poly(amino acid) comprising hydrophobic amino acids (M); and the peptide antigen conjugate comprises an enzyme degradable linker.

In some embodiments of the vaccine for inducing tolerance, S of the amphiphile comprises a second or third generation dendrimer; B comprises from 4 to 36 PEG monomeric units; H of the amphiphile comprises a poly (amino acid) comprising hydrophobic amino acids (M); and the peptide antigen conjugate comprises an enzyme degradable linker.

In some embodiments of the vaccine for inducing tolerance, S of the amphiphile comprises a second or third generation dendrimer; and H of the amphiphile comprises a polymer of para amino-phenylalanine; and the peptide antigen conjugate comprises an enzyme degradable linker.

In some embodiments of the vaccine for inducing tolerance, B comprises from 4 to 36 PEG monomeric units; and H of the amphiphile comprises a polymer of para amino-phenylalanine; and the peptide antigen conjugate comprises an enzyme degradable linker.

In some embodiments of the vaccine for inducing tolerance, S of the amphiphile comprises a second or third generation dendrimer; B comprises from 4 to 36 PEG monomeric units; and H of the amphiphile comprises a polymer of para amino-phenylalanine; and the peptide antigen conjugate comprises an enzyme degradable linker.

In some embodiments of the vaccine for inducing tolerance, S of the amphiphile comprises a second or third generation dendrimer; and H of the amphiphile comprises a poly(amino acid) comprising hydrophobic amino acids (M) and reactive amino acids (N), that comprise an imidazoquinoline; and the peptide antigen conjugate comprises an enzyme degradable linker.

In some embodiments of the vaccine for inducing tolerance, B comprises from 4 to 36 PEG monomeric units; and H of the amphiphile comprises a poly(amino acid) comprising hydrophobic amino acids (M) and reactive amino acids (N), that comprise an imidazoquinoline; and the peptide antigen conjugate comprises an enzyme degradable linker.

In some embodiments of the vaccine for inducing tolerance, S of the amphiphile comprises a second or third generation dendrimer; B comprises from 4 to 36 PEG monomeric units; and H of the amphiphile comprises a poly(amino acid) comprising hydrophobic amino acids (M) and reactive amino acids (N) that comprise an imidazoquinoline; and the peptide antigen conjugate comprises an enzyme degradable linker.

In some embodiments of the vaccine for inducing tolerance, S of the amphiphile comprises a second or third generation dendrimer; and H of the amphiphile comprises a poly(amino acid) of tryptophan and reactive amino acids (N) that comprise an imidazoquinoline; and the peptide antigen conjugate comprises an enzyme degradable linker.

In some embodiments of the vaccine for inducing tolerance, B comprises from 4 to 36 PEG monomeric units; and H of the amphiphile comprises a poly(amino acid) of tryptophan and reactive amino acids (N) that comprise an imidazoquinoline; and the peptide antigen conjugate comprises an enzyme degradable linker.

In some embodiments of the vaccine for inducing tolerance, S of the amphiphile comprises a second or third generation dendrimer; B comprises from 4 to 36 PEG monomeric units; and H of the amphiphile comprises a poly(amino acid) of tryptophan and reactive amino acids (N) that comprise an imidazoquinoline; and the peptide antigen conjugate comprises an enzyme degradable linker.

In some embodiments of the vaccine for inducing tolerance, S of the amphiphile comprises a second or third generation dendrimer; B comprises from 4 to 36 PEG monomeric units; and H of the peptide antigen conjugate comprises a poly(amino acid) comprising hydrophobic amino acids (M).

In some embodiments of the vaccine for inducing tolerance, S of the amphiphile comprises a second or third generation dendrimer; H of the amphiphile comprises a poly(amino acid) comprising hydrophobic amino acids (M); and H of the peptide antigen conjugate comprises a poly (amino acid) comprising hydrophobic amino acids (M).

In some embodiments of the vaccine for inducing tolerance, B comprises from 4 to 36 PEG monomeric units; H of the amphiphile comprises a poly(amino acid) comprising hydrophobic amino acids (M); and H of the peptide antigen conjugate comprises a poly(amino acid) comprising hydrophobic amino acids (M).

In some embodiments of the vaccine for inducing tolerance, S of the amphiphile comprises a second or third generation dendrimer; B comprises from 4 to 36 PEG monomeric units; H of the amphiphile comprises a poly (amino acid) comprising hydrophobic amino acids (M); and H of the peptide antigen conjugate comprises a poly(amino acid) comprising hydrophobic amino acids (M).

In some embodiments of the vaccine for inducing tolerance, S of the amphiphile comprises a second or third generation dendrimer; H of the amphiphile comprises a polymer of para amino-phenylalanine; and H of the peptide antigen conjugate comprises a poly(amino acid) comprising hydrophobic amino acids (M).

In some embodiments of the vaccine for inducing tolerance, B comprises from 4 to 36 PEG monomeric units; H of the amphiphile comprises a polymer of para amino-phenylalanine; and H of the peptide antigen conjugate comprises a poly(amino acid) comprising hydrophobic amino acids (M).

In some embodiments of the vaccine for inducing tolerance, S of the amphiphile comprises a second or third generation dendrimer; B comprises from 4 to 36 PEG monomeric units; H of the amphiphile comprises a polymer of para amino-phenylalanine; and H of the peptide antigen conjugate comprises a poly(amino acid) comprising hydrophobic amino acids (M).

In some embodiments of the vaccine for inducing tolerance, S of the amphiphile comprises a second or third generation dendrimer; H of the amphiphile comprises a poly(amino acid) comprising hydrophobic amino acids (M) and reactive amino acids (N), that comprise an imidazoquinoline; and H of the peptide antigen conjugate comprises a poly(amino acid) comprising hydrophobic amino acids (M).

In some embodiments of the vaccine for inducing tolerance, B comprises from 4 to 36 PEG monomeric units; H of the amphiphile comprises a poly(amino acid) comprising hydrophobic amino acids (M) and reactive amino acids (N), that comprise an imidazoquinoline; and H of the peptide antigen conjugate comprises a poly(amino acid) comprising hydrophobic amino acids (M).

In some embodiments of the vaccine for inducing tolerance, S of the amphiphile comprises a second or third generation dendrimer; B comprises from 4 to 36 PEG monomeric units; H of the amphiphile comprises a poly (amino acid) comprising hydrophobic amino acids (M) and reactive amino acids (N) that comprise an imidazoquinoline; and H of the peptide antigen conjugate comprises a poly (amino acid) comprising hydrophobic amino acids (M).

In some embodiments of the vaccine for inducing tolerance, S of the amphiphile comprises a second or third generation dendrimer; H of the amphiphile comprises a poly(amino acid) of tryptophan and reactive amino acids (N) that comprise an imidazoquinoline; and H of the peptide antigen conjugate comprises a poly(amino acid) comprising hydrophobic amino acids (M).

In some embodiments of the vaccine for inducing tolerance, B comprises from 4 to 36 PEG monomeric units; H of the amphiphile comprises a poly(amino acid) of tryptophan and reactive amino acids (N) that comprise an imidazoquinoline; and H of the peptide antigen conjugate comprises a poly(amino acid) comprising hydrophobic amino acids (M).

In some embodiments of the vaccine for inducing tolerance, wherein S of the amphiphile comprises a second or third generation dendrimer; B comprises from 4 to 36 PEG monomeric units; H of the amphiphile comprises a poly (amino acid) of tryptophan and reactive amino acids (N) that comprise an imidazoquinoline; and H of the peptide antigen conjugate comprises a poly(amino acid) comprising hydrophobic amino acids (M).

In some embodiments of the vaccine for inducing tolerance, S of the amphiphile comprises a second or third generation dendrimer; B comprises from 4 to 36 PEG monomeric units; SG comprises N-acetyl galactosamine; and H of the peptide antigen conjugate comprises a poly (amino acid) comprising hydrophobic amino acids (M).

In some embodiments of the vaccine for inducing tolerance, S of the amphiphile comprises a second or third generation dendrimer; H of the amphiphile comprises a poly(amino acid) comprising hydrophobic amino acids (M); SG comprises N-acetyl galactosamine; and H of the peptide antigen conjugate comprises a poly(amino acid) comprising hydrophobic amino acids (M).

In some embodiments of the vaccine for inducing tolerance, B comprises from 4 to 36 PEG monomeric units; H of the amphiphile comprises a poly(amino acid) comprising hydrophobic amino acids (M); SG comprises N-acetyl galactosamine; and H of the peptide antigen conjugate comprises a poly(amino acid) comprising hydrophobic amino acids (M).

In some embodiments of the vaccine for inducing tolerance, S of the amphiphile comprises a second or third generation dendrimer; B comprises from 4 to 36 PEG monomeric units; H of the amphiphile comprises a poly (amino acid) comprising hydrophobic amino acids (M); SG comprises N-acetyl galactosamine; and H of the peptide antigen conjugate comprises a poly(amino acid) comprising hydrophobic amino acids (M).

In some embodiments of the vaccine for inducing tolerance, S of the amphiphile comprises a second or third generation dendrimer; H of the amphiphile comprises a polymer of para amino-phenylalanine; SG comprises N-acetyl galactosamine; and H of the peptide antigen conjugate comprises a poly(amino acid) comprising hydrophobic amino acids (M).

In some embodiments of the vaccine for inducing tolerance, B comprises from 4 to 36 PEG monomeric units; H of the amphiphile comprises a polymer of para amino-phenylalanine; SG comprises N-acetyl galactosamine; and H of the peptide antigen conjugate comprises a poly(amino acid) comprising hydrophobic amino acids (M).

In some embodiments of the vaccine for inducing tolerance, S of the amphiphile comprises a second or third generation dendrimer; B comprises from 4 to 36 PEG monomeric units; H of the amphiphile comprises a polymer of para amino-phenylalanine; SG comprises N-acetyl galactosamine; and H of the peptide antigen conjugate comprises a poly(amino acid) comprising hydrophobic amino acids (M).

In some embodiments of the vaccine for inducing tolerance, S of the amphiphile comprises a second or third generation dendrimer; H of the amphiphile comprises a poly(amino acid) comprising hydrophobic amino acids (M) and reactive amino acids (N), that comprise an imidazoquinoline; and SG comprises N-acetyl galactosamine; and H of the peptide antigen conjugate comprises a poly(amino acid) comprising hydrophobic amino acids (M).

In some embodiments of the vaccine for inducing tolerance, B comprises from 4 to 36 PEG monomeric units; H of the amphiphile comprises a poly(amino acid) comprising hydrophobic amino acids (M) and reactive amino acids (N) that comprise an imidazoquinoline; SG comprises N-acetyl galactosamine; and H of the peptide antigen conjugate comprises a poly(amino acid) comprising hydrophobic amino acids (M).

In some embodiments of the vaccine for inducing tolerance, S of the amphiphile comprises a second or third generation dendrimer; B comprises from 4 to 36 PEG monomeric units; H of the amphiphile comprises a poly (amino acid) comprising hydrophobic amino acids (M) and reactive amino acids (N) that comprise an imidazoquinoline; SG comprises N-acetyl galactosamine; and H of the peptide antigen conjugate comprises a poly(amino acid) comprising hydrophobic amino acids (M).

In some embodiments of the vaccine for inducing tolerance, S of the amphiphile comprises a second or third generation dendrimer; H of the amphiphile comprises a poly(amino acid) of tryptophan and reactive amino acids (N) that comprise an imidazoquinoline; SG comprises N-acetyl galactosamine; and H of the peptide antigen conjugate comprises a poly(amino acid) comprising hydrophobic amino acids (M).

In some embodiments of the vaccine for inducing tolerance, B comprises from 4 to 36 PEG monomeric units; H of the amphiphile comprises a poly(amino acid) of tryptophan and reactive amino acids (N) that comprise an imidazoquinoline; SG comprises N-acetyl galactosamine; and H of the peptide antigen conjugate comprises a poly(amino acid) comprising hydrophobic amino acids (M).

In some embodiments of the vaccine for inducing tolerance, S of the amphiphile comprises a second or third generation dendrimer; B comprises from 4 to 36 PEG monomeric units; H of the amphiphile comprises a poly (amino acid) of tryptophan and reactive amino acids (N) that comprise an imidazoquinoline; and SG comprises N-acetyl galactosamine; and H of the peptide antigen conjugate comprises a poly(amino acid) comprising hydrophobic amino acids (M).

In some embodiments of the vaccine for inducing tolerance, S of the amphiphile comprises a second or third generation dendrimer; B comprises from 4 to 36 PEG monomeric units; the peptide antigen conjugate comprises an enzyme degradable linker; and H of the peptide antigen conjugate comprises a poly(amino acid) comprising hydrophobic amino acids (M).

In some embodiments of the vaccine for inducing tolerance, S of the amphiphile comprises a second or third generation dendrimer; and H of the amphiphile comprises a poly(amino acid) comprising hydrophobic amino acids (M); the peptide antigen conjugate comprises an enzyme degradable linker; and H of the peptide antigen conjugate comprises a poly(amino acid) comprising hydrophobic amino acids (M).

In some embodiments of the vaccine for inducing tolerance, B comprises from 4 to 36 PEG monomeric units; H of the amphiphile comprises a poly(amino acid) comprising hydrophobic amino acids (M); the peptide antigen conjugate comprises an enzyme degradable linker; and H of the peptide antigen conjugate comprises a poly(amino acid) comprising hydrophobic amino acids (M).

In some embodiments of the vaccine for inducing tolerance, S of the amphiphile comprises a second or third generation dendrimer; B comprises from 4 to 36 PEG monomeric units; the amphiphile comprises amino-hexanoic acid; and H of the peptide antigen conjugate comprises a poly(amino acid) comprising hydrophobic amino acids (M).

In some embodiments of the vaccine for inducing tolerance, S of the amphiphile comprises a second or third generation dendrimer; H of the amphiphile comprises a poly(amino acid) comprising hydrophobic amino acids (M); the amphiphile comprises amino-hexanoic acid; and H of the peptide antigen conjugate comprises a poly(amino acid) comprising hydrophobic amino acids (M).

In some embodiments of the vaccine for inducing tolerance, B comprises from 4 to 36 PEG monomeric units; H of the amphiphile comprises a poly(amino acid) comprising hydrophobic amino acids (M); the amphiphile comprises amino-hexanoic acid; and H of the peptide antigen conjugate comprises a poly(amino acid) comprising hydrophobic amino acids (M).

In some embodiments of the vaccine for inducing tolerance, S of the amphiphile comprises a second or third generation dendrimer; B comprises from 4 to 36 PEG monomeric units; H of the amphiphile comprises a poly (amino acid) comprising hydrophobic amino acids (M); the amphiphile comprises amino-hexanoic acid; and H of the peptide antigen conjugate comprises a poly(amino acid) comprising hydrophobic amino acids (M).

In some embodiments of the vaccine for inducing tolerance, S of the amphiphile comprises a second or third generation dendrimer; H of the amphiphile comprises a polymer of para amino-phenylalanine; the amphiphile comprises amino-hexanoic acid; and H of the peptide antigen conjugate comprises a poly(amino acid) comprising hydrophobic amino acids (M).

In some embodiments of the vaccine for inducing tolerance, B comprises from 4 to 36 PEG monomeric units; H of the amphiphile comprises a polymer of para amino-phenylalanine; the amphiphile comprises amino-hexanoic acid; and H of the peptide antigen conjugate comprises a poly(amino acid) comprising hydrophobic amino acids (M).

In some embodiments of the vaccine for inducing tolerance, S of the amphiphile comprises a second or third generation dendrimer; B comprises from 4 to 36 PEG monomeric units; H of the amphiphile comprises a polymer of para amino-phenylalanine; the amphiphile comprises amino-hexanoic acid; and H of the peptide antigen conjugate comprises a poly(amino acid) comprising hydrophobic amino acids (M)

In some embodiments of the vaccine for inducing tolerance, S of the amphiphile comprises a second or third generation dendrimer; H of the amphiphile comprises a poly(amino acid) comprising hydrophobic amino acids (M) and reactive amino acids (N) that comprise an imidazoquinoline; the amphiphile comprises amino-hexanoic acid; and H of the peptide antigen conjugate comprises a poly(amino acid) comprising hydrophobic amino acids (M).

In some embodiments of the vaccine for inducing tolerance, B comprises from 4 to 36 PEG monomeric units; H of the amphiphile comprises a poly(amino acid) comprising hydrophobic amino acids (M) and reactive amino acids (N) that comprise an imidazoquinoline; the amphiphile comprises amino-hexanoic acid; and H of the peptide antigen conjugate comprises a poly(amino acid) comprising hydrophobic amino acids (M).

In some embodiments of the vaccine for inducing tolerance, S of the amphiphile comprises a second or third generation dendrimer; B comprises from 4 to 36 PEG monomeric units; H of the amphiphile comprises a poly (amino acid) comprising hydrophobic amino acids (M) and reactive amino acids (N) that comprise an imidazoquinoline; the amphiphile comprises amino-hexanoic acid; and H of the peptide antigen conjugate comprises a poly(amino acid) comprising hydrophobic amino acids (M).

In some embodiments of the vaccine for inducing tolerance, S of the amphiphile comprises a second or third generation dendrimer; H of the amphiphile comprises a poly(amino acid) of tryptophan and reactive amino acids (N) that comprise an imidazoquinoline; the amphiphile comprises amino-hexanoic acid; and H of the peptide antigen conjugate comprises a poly(amino acid) comprising hydrophobic amino acids (M).

In some embodiments of the vaccine for inducing tolerance, B comprises from 4 to 36 PEG monomeric units; H of the amphiphile comprises a poly(amino acid) of tryptophan and reactive amino acids (N) that comprise an imidazoquinoline; the amphiphile comprises amino-hexanoic acid; and H of the peptide antigen conjugate comprises a poly(amino acid) comprising hydrophobic amino acids (M).

In some embodiments of the vaccine for inducing tolerance, S of the amphiphile comprises a second or third generation dendrimer; B comprises from 4 to 36 PEG monomeric units; H of the amphiphile comprises a poly (amino acid) of tryptophan and reactive amino acids (N) that comprise an imidazoquinoline; the amphiphile comprises amino-hexanoic acid; and H of the peptide antigen conjugate comprises a poly(amino acid) comprising hydrophobic amino acids (M).

In some embodiments of the vaccine for inducing tolerance, S of the amphiphile comprises a second or third generation dendrimer; B comprises from 4 to 36 PEG monomeric units; the dendrimer monomers comprise hydroxy acids and amino alcohols; and H of the peptide antigen conjugate comprises a poly(amino acid) comprising hydrophobic amino acids (M).

In some embodiments of the vaccine for inducing tolerance, S of the amphiphile comprises a second or third generation dendrimer; H of the amphiphile comprises a poly(amino acid) comprising hydrophobic amino acids (M); the dendrimer monomers comprise hydroxy acids and amino alcohols; and H of the peptide antigen conjugate comprises a poly(amino acid) comprising hydrophobic amino acids (M).

In some embodiments of the vaccine for inducing tolerance, B comprises from 4 to 36 PEG monomeric units; H of the amphiphile comprises a poly(amino acid) comprising hydrophobic amino acids (M); the dendrimer monomers comprise hydroxy acids and amino alcohols; and H of the peptide antigen conjugate comprises a poly(amino acid) comprising hydrophobic amino acids (M).

In some embodiments of the vaccine for inducing tolerance, S of the amphiphile comprises a second or third generation dendrimer; B comprises from 4 to 36 PEG monomeric units; H of the amphiphile comprises a poly (amino acid) comprising hydrophobic amino acids (M); the dendrimer monomers comprise hydroxy acids and amino alcohols; and H of the peptide antigen conjugate comprises a poly(amino acid) comprising hydrophobic amino acids (M).

In some embodiments of the vaccine for inducing tolerance, S of the amphiphile comprises a second or third generation dendrimer; H of the amphiphile comprises a polymer of para amino-phenylalanine; the dendrimer monomers comprise hydroxy acids and amino alcohols; and H of the peptide antigen conjugate comprises a poly(amino acid) comprising hydrophobic amino acids (M).

In some embodiments of the vaccine for inducing tolerance, B comprises from 4 to 36 PEG monomeric units; H of the amphiphile comprises a polymer of para amino-phenylalanine; the dendrimer monomers comprise hydroxy acids and amino alcohols; and H of the peptide antigen conjugate comprises a poly(amino acid) comprising hydrophobic amino acids (M).

In some embodiments of the vaccine for inducing tolerance, S of the amphiphile comprises a second or third generation dendrimer; B comprises from 4 to 36 PEG monomeric units; H of the amphiphile comprises a polymer of para amino-phenylalanine; the dendrimer monomers comprise hydroxy acids and amino alcohols; and H of the peptide antigen conjugate comprises a poly(amino acid) comprising hydrophobic amino acids (M).

In some embodiments of the vaccine for inducing tolerance, S of the amphiphile comprises a second or third generation dendrimer; H of the amphiphile comprises a poly(amino acid) comprising hydrophobic amino acids (M) and reactive amino acids (N) that comprise an imidazoquinoline; the dendrimer monomers comprise hydroxy acids and amino alcohols; and H of the peptide antigen conjugate comprises a poly(amino acid) comprising hydrophobic amino acids (M).

In some embodiments of the vaccine for inducing tolerance, B comprises from 4 to 36 PEG monomeric units; H of the amphiphile comprises a poly(amino acid) comprising hydrophobic amino acids (M) and reactive amino acids (N) that comprise an imidazoquinoline; the dendrimer monomers comprise hydroxy acids and amino alcohols; and H of the peptide antigen conjugate comprises a poly(amino acid) comprising hydrophobic amino acids (M).

In some embodiments of the vaccine for inducing tolerance, S of the amphiphile comprises a second or third generation dendrimer; B comprises from 4 to 36 PEG monomeric units; H of the amphiphile comprises a poly (amino acid) comprising hydrophobic amino acids (M) and reactive amino acids (N) that comprise an imidazoquinoline; the dendrimer monomers comprise hydroxy acids and amino alcohols; and H of the peptide antigen conjugate comprises a poly(amino acid) comprising hydrophobic amino acids (M).

In some embodiments of the vaccine for inducing tolerance, S of the amphiphile comprises a second or third generation dendrimer; H of the amphiphile comprises a poly(amino acid) of tryptophan and reactive amino acids (N) that comprise an imidazoquinoline; the dendrimer monomers comprise hydroxy acids and amino alcohols; and H of the peptide antigen conjugate comprises a poly(amino acid) comprising hydrophobic amino acids (M).

In some embodiments of the vaccine for inducing tolerance, B comprises from 4 to 36 PEG monomeric units; H of the amphiphile comprises a poly(amino acid) of tryptophan and reactive amino acids (N) that comprise an imidazoquinoline; the dendrimer monomers comprise hydroxy acids and amino alcohols; and H of the peptide antigen conjugate comprises a poly(amino acid) comprising hydrophobic amino acids (M).

In some embodiments of the vaccine for inducing tolerance, S of the amphiphile comprises a second or third generation dendrimer; B comprises from 4 to 36 PEG monomeric units; H of the amphiphile comprises a poly (amino acid) of tryptophan and reactive amino acids (N) that comprise an imidazoquinoline; the dendrimer monomers comprise hydroxy acids and amino alcohols; and H of the peptide antigen conjugate comprises a poly(amino acid) comprising hydrophobic amino acids (M).

The present disclosure also relates to a vaccine comprising at least one peptide antigen conjugate having the formula selected from PEG-[E1]-A-[E2]-[U]-H and H-[U]-[E1]-A-[E2]-PEG, and an amphiphile having the formula S-[B]-[U]-H, wherein A is peptide antigen;

E1 is an N-terminal extension;

E2 is a C terminal extension;

H, independently for each occurrence is a hydrophobic block, wherein one or more drug molecules (D) are optionally attached to each H directly or via a suitable linker X1;

S is a solubilizing block;

B is a spacer;

U, independently for each occurrence, is a linker;

[ ] denotes that the group is optional, denotes that the two adjacent groups are directly attached to one another by a covalent bond or indirectly to one another via a suitable linker X;

wherein the amphiphile comprises a dendron amplifier; and at least one A comprises a sequence wherein one or more cysteine residues have been replaced with alpha amino-butyric acid and/or one or more methionine residues have been replaced with norleucine.

In some embodiments of the vaccine, the S of the amphiphile comprises carboxylic acids. In other embodiments of the vaccine, the S of the amphiphile comprises succinic acid or beta alanine.

In some embodiments of the vaccine, the molar ratio of peptide antigen conjugate to amphiphile is between about 4:1 to 1:20, preferably about 1:1.

In some embodiments of the vaccine, the average net charge of the at least one peptide antigen conjugate is positive at physiologic pH and the molar ratio of peptide antigen conjugate to amphiphile is between about 4:1 to about 2:1 or about 1:2 to about 1:16, or about 1:2 to about 1:4, preferably about 1:1.

The present disclosure also relates to a vaccine comprising at least one peptide antigen (A), wherein at least one peptide antigen (A) comprises a sequence wherein one or more cysteine residues have been replaced with alpha amino-butyric acid and/or one or more methionine residues have been replaced with norleucine.

In some embodiments of the vaccine, the vaccine further comprises a particle delivery system selected from lipid emulsions, liposomes, PLGA particles, inorganic salt particles and metal nanoparticles. In other embodiments of the vaccine, the vaccine further comprising at least one drug molecule (D) selected from immunostimulants and Treg promoting immunomodulators.

The present disclosure also relates to a vaccine comprising at least one peptide antigen conjugate having the formula selected from PEG-[E1]-A-[E2]-[U]-H and H-[U]-[E1]-A-[E2]-PEG, wherein H, independently for each occurrence, is a hydrophobic block, wherein one or more drug molecules (D) are optionally attached to each H directly or via a suitable linker X1;

A, independently for each occurrence, is a peptide antigen;

E1, independently for each occurrence, is an N-terminal extension;

E2, independently for each occurrence, is a C-terminal extension;

U, independently for each occurrence, is a linker;

wherein either:

(i) at least one A comprises alpha amino-butyric acid and/or norleucine;

(ii) at least one A is selected from tumor antigens, at least one D is present and is selected from agonists of TLR-7/8, and the vaccine further comprises a second drug molecule (D2) selected from inhibitors of mTOR;

(iii) at least one A is a glycopeptide; or (iv) at least one A is selected from autoantigens, allergens and alloantigens and at least one D is present and is selected from ATP-competitive mTOR inhibitors; [ ] denotes that the group is optional; and

- denotes that the two adjacent groups are directly attached to one another by a covalent bond or indirectly to one another via a suitable linker X.

In some embodiments of the vaccine, the at least one peptide antigen conjugate comprises at least one A selected from tumor antigens.

In some embodiments of the vaccine, at least one D is selected from agonists of TLR-3, TLR-7, TLR-8, TLR-9, and STING In some embodiments of the vaccine, each H of the amphiphile and/or the peptide antigen conjugate comprises a poly(amino acid) comprising monomers of the reactive amino acid (N), wherein the monomers comprise a D selected from agonists of TLR-7/8.

In some embodiments of the vaccine, D2 is present and selected from rapamycin, tacrolimus, everolimus, RAD001, CCI-779 and AP23573.

In some embodiments of the vaccine, the molar ratio of peptide antigen conjugate to the D2 is between about 20:1 to 1:2, or about 10:1 to about 1:1 or about 4:1 to about 2:1, preferably about 1:1.

In some embodiments of the vaccine, wherein at least one A is a glycopeptide, e.g. A is a glycopeptide selected from HGVT*S*APDT*RPAPGS*T*APPA (SEQ ID NO: 534), DT*RPAPGS*T*APPAHGVT*S*AP (SEQ ID NO: 535), GS*T*APPAHGVT*S*APDT*RPAPGS*T*APPA (SEQ ID NO: 536), GVT*S*APDT*RPAP (SEQ ID NO: 537), APDT*RPAPGS*T*A (SEQ ID NO: 538), GS*T*APPAHGVT*S*AP (SEQ ID NO: 539), VT*S*AP (SEQ ID NO: 540), DT*RPAP (SEQ ID NO: 541) and GS*T*AP (SEQ ID NO: 542), wherein * is an O-linked glycan and each occurrence is independently selected from sialyl lewis x, sialyl lewis a, lewis y, lewis x, Tn, sTn, TF, sTF.

In some embodiments of the vaccine wherein the A is a glycopeptide, S is absent. In other embodiments, S is present.

In some embodiments of the vaccine, the vaccine further comprises an amphiphile having the formula S-[B]-[U]-H, wherein S is a solubilizing block;

B is a spacer;

H is a hydrophobic block;

U is a linker;

[ ] denotes that the group is optional;

- denotes that the two adjacent groups are directly attached to one another by a covalent bond or indirectly to one another via a suitable linker X, and wherein the S of the amphiphile comprises a dendron amplifier.

In some embodiments of the vaccine, the S of the amphiphile comprises two or more solubilizing groups (SGs) independently selected from amines, carboxylic acids or sugar molecules, wherein the sugar molecules are independently selected from mannose, sialyl lewis x, sialyl lewis a, lewis y, lewis x, Tn, sTn, TF, sTF, Globo H, SSEA-3, GM2, GD2, GD3 and Fucosyl GM1 and combinations thereof.

In some embodiments of the vaccine, the at least one peptide antigen conjugate comprises at least one A selected from autoantigens, alloantigens, and allergens.

In some embodiments of the vaccine, the vaccine further comprises at least one D selected from inhibitors of mTOR, RORγt, CDK8/19, and HDAC and agonists of AHR, RAR and $A_{2a}$.

In some embodiments of the vaccine, the vaccine further comprises a second drug molecule (D2) independently selected from inhibitors of mTOR, RORγt, CDK8/19, and HDACs, agonists of AHR, RAR and $A_{2a}$, and immunostimulants selected from agonists of NLRs, CLRs, TLRs and STING, provided that D and D2 bind to different receptors.

In some embodiments of the vaccine, the D2 is selected from agonists of NLRs, CLRs, TLRs and STING. In other embodiments, the D2 is selected from agonists of TLR-3, TLR-7, TLR-8, TLR-7/8, TLR-9 and STING. In other embodiments, the D2 is selected from RNA and imidazoquinoline agonists of TLR-7, TLR-8 and TLR-7/8.

In some embodiments of the vaccine, the vaccine further comprises a third drug molecule (D3) independently selected from inhibitors of mTOR, RORY, CDK8/19, and HDACs, agonists of AHR, RAR and $A_{2a}$, and immunostimulants selected from agonists of NLRs, CLRs, TLRs and STING, provided that D, D2 and D3 bind to different receptors.

In some embodiments of the vaccine, the at least one D is selected from AZD-8055, AZD2016, KU-0063794, CC223, Torin-1, Torin-2, INK-128, WYE354, WYE132, OSI-027, OXA-01, PI-103, NVP-BEZ235, GNE-493, GSK2126458, rapamycin, tacrolimus, everolimus, RAD001, CCI-779 and AP23573.

In some embodiments of the vaccine, the molar ratio of total peptide antigen conjugate to the at least one D is between about 20:1 to 1:2, or about 10:1 to about 1:1 or about 4:1 to about 2:1, preferably about 1:1.

In a preferred embodiment of the vaccine for inducing tolerance, a vaccine comprises at least one peptide antigen conjugate having the formula selected from PEG-[E1]-A-[E2]-[U]-H and H-[U]-[E1]-A-[E2]-PEG, wherein H, independently for each occurrence, is a hydrophobic block, wherein one or more drug molecules (D) are optionally attached to each H directly or via a suitable linker X1;

A, independently for each occurrence, is a peptide antigen;

E1, independently for each occurrence, is an N-terminal extension;

E2, independently for each occurrence, is a C-terminal extension; U, independently for each occurrence, is a linker;

wherein at least one A is selected from autoantigens, allergens and alloantigens and at least one D is present and is selected from ATP-competitive mTOR inhibitors; [ ] denotes that the group is optional; and - denotes that the two adjacent groups are directly attached to one another by a covalent bond or indirectly to one another via a suitable linker X.

In some embodiments of the vaccine, the at least one D is selected from AZD-8055, AZD2016, KU-0063794, CC223, Torin-1, Torin-2, INK-128, WYE354, WYE132, OSI-027, OXA-01, PI-103, NVP-BEZ235, GNE-493, GSK2126458, rapamycin, tacrolimus, everolimus, RAD001, CCI-779 and AP23573.

In some embodiments of the vaccine, the vaccine further comprises an amphiphile having the formula S-[B]-[U]-H, wherein S is a solubilizing block;

B is a spacer;

H is a hydrophobic block;

U is a linker;

[ ] denotes that the group is optional; and

- denotes that the two adjacent groups are directly attached to one another by a covalent bond or indirectly to one another via a suitable linker X, wherein the S of the amphiphile comprises a dendron amplifier.

In some embodiments of the vaccine, the S of the amphiphile comprises two or more solubilizing groups (SGs) independently selected from carboxylic acids, phosphoserine and sugar molecules, wherein the sugar molecules are independently selected from mannose, glucose, glucosamine, N-acetyl glucose, galactose, galactosamine, N-acetyl galactosamine, and agonists of CD22a.

In some embodiments of the vaccine, the peptide antigen conjugate has a net positive charge between about +1 to about +10 at physiologic pH. In other embodiments, the peptide antigen conjugate has a net positive charge between about +2 to about +6 or between about +3 to about +5 at physiologic pH.

In some embodiments of the vaccine, the amphiphile is present and the molar ratio of peptide antigen conjugate to amphiphile is between about 4:1 to 1:20, preferably about 1:1.

In some embodiments of the vaccine, the amphiphile comprise carboxylic acids and has net negative charge. In other embodiments, the amphiphile comprises carboxylic acids selected from beta alanine and succinic acid.

In some embodiments of the vaccine, the average net charge of the at least one peptide antigen conjugate is positive at physiologic pH and the molar ratio of peptide antigen conjugate to amphiphile is between about 4:1 to about 2:1 or about 1:2 to about 1:16, or about 1:2 to about 1:4. In certain preferred embodiments, the molar ratio is about 1:1.

In some embodiments of the vaccine, the vaccine comprises particles further comprising an amphiphile and one or more peptide antigen conjugates. In preferred embodiments of the vaccine, the vaccine comprises particles that comprise an amphiphile having the formula S-[B]-[U]-H and at least one peptide antigen conjugate having the formula PEG-[E1]-A-[E2]-[U]-H or H-[U]-[E1]-A-[E2]-PEG, wherein A is a peptide antigen, S is a solubilizing block; E1 and E2 are N- and C-terminal extensions, respectively; B is a spacer; U is a linker molecule; H is hydrophobic block; [ ] denotes that the groups is optional; - denotes that the two adjacent groups are directly attached to one another by a covalent bond or indirectly to one another via a suitable linker X; and U and H of the amphiphile and the peptide antigen conjugate may be the same, different, or comprise one or more of the same functional groups or moieties.

In some embodiments of the vaccine, the amphiphiles and/or peptide antigen conjugates further comprise one or more drug molecules (D). The drug molecules (D) may either be linked directly or indirectly via X1 to the hydrophobic block (H) of the amphiphile and/or peptide antigen conjugate (e.g., S-[B]-[U]-H-D and/or PEG-[E1]-A-[E2]-[U]-H-D). The drug molecule (D) may be admixed with the amphiphile and/or peptide antigen conjugate (e.g., D+S-[B]—[U]-H+PEG-[E1]-A-[E2]-[U]-H) or the drug molecule (D) may be in form of a drug molecule conjugate (i.e. D-[U]-H or H-D) that is admixed with the amphiphile and/or peptide antigen conjugate (e.g., D-H+S-[B]—[U]-H+PEG-[E1]-A-[E2]—[U]—H). Preferred compositions of vaccines further comprising drug molecules (D) are described throughout the specification. The D is bonded directly or indirectly as a side chain or as part of a side chain group to the adjacent group.

In preferred embodiments of the vaccine, the vaccine comprises particles comprising amphiphiles and one or more peptide antigen conjugates, which further comprises a drug molecule (D) selected from immunomodulators. The drug molecule (D) selected from immunomodulators may either be linked directly or indirectly via X1 to the hydrophobic block (H) of the amphiphile and/or peptide antigen conjugate (e.g., S-[B]-[U]-H-D and/or PEG-[E1]-A-[E2]—[U]-HD); the drug molecule (D) may be admixed with the amphiphile and peptide antigen conjugate (e.g., D+S-[B]—[U]-H+PEG-[E1]-A-[E2]—[U]-H); or, the drug molecule (D) may be in the form of a drug molecule conjugate (i.e. D-[U]-H or H-D) that is admixed with the amphiphile and peptide antigen conjugate (e.g., D-H+S-[B]—[U]-H+PEG-[E1]-A-[E2]-[U]-H). Preferred compositions of vaccines further comprising drug molecules (D) are described throughout the specification.

In some embodiments of the vaccine for treating or preventing autoimmune diseases, the peptide antigen conjugate comprises an antigen (A) selected from a self-antigen (sometimes referred to as an autoantigen). In some embodiments of the vaccine for treating or preventing allergies, the peptide antigen conjugate comprises an antigen (A) selected from an allergen. In some embodiments of the vaccine for treating or preventing transplant rejection, the peptide antigen conjugate comprises an antigen (A) selected from an alloantigen. In some embodiments of the vaccine for treating or preventing cancer, the peptide antigen conjugate comprises an antigen (A) selected from self-antigens, neoantigens or viral antigens. In some embodiments of the vaccine for treating or infectious diseases, the peptide antigen conjugate comprises an antigen (A) selected from viruses, bacteria, protozoa or fungi. Preferred antigens as well as preferred methods for selecting antigens for treating different diseases are described throughout the specification.

It was found that particles comprising certain compositions of amphiphiles had particular utility for delivery of small molecule drugs for various applications, including treatment of cancer, inflammation, autoimmune diseases, macular degeneration as well as diseases of vital organs, including liver, and metabolic diseases.

In some embodiments of compositions for cancer treatment, the cancer treatment comprises particles comprising amphiphiles and drug molecules selected from chemotherapeutics and/or immunomodulators. In preferred embodiments of cancer treatments, the particle comprises amphiphiles having the formula S-[B]-[U]-H and a drug, D, wherein S is a solubilizing block; B is a spacer; U is a linker molecule; H is a hydrophobic block; [ ] denotes that the groups is optional; and, the drug, D, is associated with the particles through covalent or non-covalent interactions.

In some embodiments, the drug molecule (D) is linked to the hydrophobic block (H) of the amphiphile, when present, e.g., S-[B]-[U]-H-D, wherein one or more D are bonded directly or indirectly via X1 at the end(s) or as part of a side chain group to the adjacent group. In other embodiments, the drug molecule is admixed with the amphiphile (e.g., D+S-[B]-[U]-H) or linked to a hydrophobic block (H) and admixed with the amphiphile (e.g., D-[B]—[U]-H+S-[B]-[U]-H, or H-D+S-[B]-[U]-H) and the drug is incorporated within the particles formed by the amphiphile. Preferred compositions of cancer treatments comprising amphiphiles and at least one chemotherapeutic and/or immunostimulant are described throughout the specification.

The present disclosure also relates to a peptide antigen conjugate having the formula selected from PEG-[E1]-A-[E2]-[U]-H-[D] and [D]-H-[U]-[E1]-A-[E2]-PEG or a peptide antigen fragment having the formula selected from PEG-[E1]-A-[E2]—[U1] and [U1]-[E1]-A-[E2]-PEG.

The present disclosure also relates to a peptide antigen conjugate having the formula selected from PEG-[E1]-A-[E2]-[U]-H-[D] and [D]-H-[U]-[E1]-A-[E2]-PEG or a peptide antigen fragment having the formula selected from PEG-[E1]-A-[E2]—[U1] and [U1]-[E1]-A-[E2]-PEG, wherein H is a hydrophobic block, wherein one or more drug molecules (D) are optionally attached to each H directly or via a suitable linker X1;

A is a peptide antigen;

E1 is an N-terminal extension;

E2 is a C-terminal extension;

U is a linker;

U1 is a linker precursor;

[ ] denotes that the group is optional; and

- denotes that the two adjacent groups are directly attached to one another by a covalent bond or indirectly to one another via a suitable linker X.

In some embodiments, the peptide antigen fragment has the formula A-[E2]-PEG.

In some embodiments, E1 and/or E2 are present and selected from cathepsin cleavable tetrapeptides of the formula P4-P3-P2-P1.

In some embodiments, E1 and/or E2 are present and selected from Ser-Pro-Val-Arg, Ser-Pro-Val-Cit, Val-Cit, and Ser-Pro-Val-aBut.

In some embodiments, the peptide antigen (A) comprises at least one amino acid selected from norleucine and alpha-aminobutyric acid.

In some embodiments, disclosed herein is a vaccine comprising a peptide antigen conjugate having the formula selected from PEG-[E1]-A-[E2]-[U]-H-[D] and [D]-H-[U]-[E1]-A-[E2]-PEG or a peptide antigen fragment having the formula selected from PEG-[E1]-A-[E2]—[U1] and [U1]-[E1]-A-[E2]-PEG, wherein H is a hydrophobic block, wherein one or more drug molecules (D) are optionally attached to each H directly or via a suitable linker X1;

A is a peptide antigen;

E1 is an N-terminal extension;

E2 is a C-terminal extension;

U is a linker;

U1 is a linker precursor;

[ ] denotes that the group is optional; and

- denotes that the two adjacent groups are directly attached to one another by a covalent bond or indirectly to one another via a suitable linker X.

In some embodiments, vaccines for inducing tolerance can be used for preventing or treating autoimmune diseases. Non-limiting examples of autoimmune diseases include but are not limited to multiple sclerosis, anti-MOG, celiac disease (including refractory disease), type-1 diabetes, vitiligo, autoimmune hepatitis, neuromyelitis optica, autoimmune uveitis, rheumatoid arthritis, myasthenia gravis, lambert eaton syndrome, graves disease, optic neuritis, immune thrombocytopenia purpura, pemphigus vulgaris, bullous pemphigoid, Goodpasture syndrome, eczema, sjorgen syndrome, achalasia, myositis, dermatomyositis, systemic sclerosis, psoriasis, inflammatory bowel diseases, including Chron's disease and ulcerative colitis, primary sclerosing cholangitis, various vasculitides, including but not limited, Takayasus arteritis, giant cell arteritis, polyarteritis nodosa, Kawasaki disease, anti-GBM disease, ANCA vasculitides, systemic lupus erythematosus, amyotrophic lateral sclerosis (ALS), behcet's disease and birch pollen allergy.

The present disclosure also relates to method of treating or preventing an autoimmune disease in a subject in need thereof, the method comprising administering to the subject a vaccine comprising at least one peptide antigen conjugate having the formula selected from PEG-[E1]-A-[E2]-[U]-H and H-[U]-[E1]-A-[E2]-PEG, and an amphiphile having the formula S-[B]-[U]-H, wherein A is a peptide antigen;

E1 is an N-terminal extension;

E2 is a C terminal extension;

H, independently for each occurrence is a hydrophobic block, wherein one or more drug molecules (D) are optionally attached to each H directly or via a suitable linker X1;

S is a solubilizing block;

B is a spacer;

U, independently for each occurrence, is a linker;

[ ] denotes that the group is optional,

- denotes that the two adjacent groups are directly attached to one another by a covalent bond or indirectly to one another via a suitable linker X;

wherein the amphiphile comprises a dendron amplifier and at least one peptide antigen is selected from an autoantigen or tumour antigen.

In one embodiment of the method of treating autoimmune disease, the vaccine is administered intravenously, subcutaneously or intramuscularly.

The present disclosure also relates to a method for enhancing the efficacy and/or tolerability of vaccine said method comprising administering to the subject a vaccine comprising at least one peptide antigen conjugate having the formula selected from PEG-[E1]-A-[E2]-[U]-H and H-[U]-[E1]-A-[E2]-PEG, and an amphiphile having the formula S-[B]-[U]-H, wherein A is a peptide antigen;

E1 is an N-terminal extension;

E2 is a C terminal extension;

H, independently for each occurrence is a hydrophobic block, wherein one or more drug molecules (D) are optionally attached to each H directly or via a suitable linker X1;

S is a solubilizing block;

B is a spacer;

U, independently for each occurrence, is a linker;

[ ] denotes that the group is optional, and

- denotes that the two adjacent groups are directly attached to one another by a covalent bond or indirectly to one another via a suitable linker;

wherein the amphiphile comprises a dendron amplifier and at least one peptide antigen is selected from an autoantigen.

Vaccines for inducing tolerance can be used for preventing or treating inflammatory diseases, which may be characterized as diseases wherein an unwanted immune response in a subject is directed against an antigen, which may be an autoantigen, an alloantigen, a foreign antigen (e.g., allergen), drug molecule or device.

The present disclosure also relates to a method of inducing an immune response in a subject in need thereof, comprising administering to the subject at least one dose of a first vaccine (V1) followed by at least one dose of a second vaccine (V2), wherein V1 is a vaccine disclosed herein; and V2 is a viral vaccine.

In some embodiments, the T cell response in the subject is increased relative to the administration of only at least one dose of a first vaccine (V1).

In some embodiments, the T cell response in the subject is increased relative to the administration of only at least one dose of a second vaccine (V2).

In some embodiments, one dose of V1 is administered at a first time (V1T1). In other embodiments, two doses of V1 are administered at a first time (V1T1) and a second time (V1T2). In other embodiments, three doses of V1 are administered at a first time (V1T1), a second time (V1T2), and a third time (V1T3).

In some embodiments, one dose of V2 is administered at a first time (V2T1). In other embodiments, two doses of V2 are administered at a first time (V2T1) and a second time (V2T2). In other embodiments, three doses of V2 are administered at a first time (V2T1), a second time (V2T2), and a third time (V2T3).

In some embodiments, V1 is administered by intramuscular or intravenous route.

In some embodiments, V2 is administered by intravenous route.

In some embodiments, the initial dose of V2 is administered from 1 to 6 weeks following the final dose of V1. In other embodiments, the initial dose of V2 is administered from 1 to 12 weeks following the final dose of V1.

In some embodiments, V2 is an adenovirus vector vaccine.

In some embodiments, the adenovirus encodes for a peptide antigen (A) of V1.

In some embodiments, V2 is a ChAdOx vaccine.

Linkers

The term linker refers to any molecule that joins together any two or more molecules (or "moieties"), such as any two or more components of amphiphiles, peptide antigen conjugates, or drug conjugates, and may additionally perform any one or more of the following functions: I) increase or decrease water solubility; II) increase distance between any two components; III) impart rigidity or flexibility; or, IV) modulate the rate of degradation of the link between any two or more different molecules. As used herein, the term "linker" may be used to describe linkers (U), suitable linkers (X), such as X1, X2, X3, X4 and X5, and extensions (E1 or E2).

Linkers that have particular utility are named, and specific, preferred compositions of those named linkers are described throughout the specification. Accordingly, extensions E1 and E2 are optional peptide-based linkers extending from the N- and C-termini of the peptide antigen (A), respectively, which may be included between the solubilizing block(S), such as a PEG group or charged block (C), and the antigen (A) or between the antigen (A) and hydrophobic block (H) or between the antigen (A) and optional Linker U. The spacer (B) is a linker between the solubilizing block(S) and the hydrophobic block (H) on amphiphiles. The molecule that results from the reaction of Linker precursor 1 ("U1") linked either directly or indirectly to the solubilizing block or a drug (D) via a spacer (B) with Linker precursor 2 ("U2") on a hydrophobic block (H) is referred to as a Linker U. Suitable linker X refers to any linker suitable for linking two or more adjacent groups. Suitable linkers preferred for joining drug molecules (D) to hydrophobic blocks (H) are referred to as X1. Suitable linkers preferred for joining aryl or heteroaryl groups to the hydrophobic block are referred to as X2. Suitable linkers used to join reactive functional groups ("FG4") to the pharmacophore of drug molecules (D) are referred to as X3. Suitable linkers preferred for joining charged groups to hydrophobic block (H) are referred to as X4. Suitable linkers preferred for joining SG to S are referred to as X5.

The linker may use covalent or non-covalent means to join any two or more components. In preferred embodiments, a linker may join, i.e., link, any two components through a covalent bond. Covalent bonds are the preferred linkages used to join any two components and ensure that no component is able to immediately disperse from the other components following administration to a subject.

There are many suitable linkers that are well known to those of skill in the art and include, but are not limited to, straight or branched-chain carbon linkers, heterocyclic carbon linkers, rigid aromatic linkers, flexible ethylene oxide linkers, peptide linkers, or a combination thereof, which, for covalent linkers, further comprise two or more functional groups, which may be the same or different, that are used to link any two molecules, e.g., any two components of amphiphiles, peptide antigen conjugates and/or drug conjugates, though covalent bonds.

In some embodiments, the carbon linker can include a C1-C18 alkane linker, e.g., a lower alkyl linker, such as C1-C6 (i.e., from one to six methylene units), which can serve to increase the space between two or more molecules, i.e., different components, while longer chain alkane linkers can be used to impart hydrophobic characteristics. Alternatively, hydrophilic linkers, such as ethylene oxide linkers, may be used in place of alkane linkers to increase the space between any two or more heterologous molecules and increase water solubility. In other embodiments, the linker can be a cyclic and/or aromatic compound, or poly(aromatic) compound that imparts rigidity. The linker molecule may comprise a hydrophilic or hydrophobic linker. In several embodiments, the linker includes a degradable peptide sequence that is cleavable by an intracellular enzyme (such as a cathepsin or the immunoproteasome).

For linking two components of amphiphiles, peptide antigen conjugates and drug conjugates, wherein at least one of the components comprises a peptide, it was found that linkers comprising between 2 and 7 methylene groups improved coupling of the two or components. In non-limiting examples, increasing the number of methylene units between the amide and the amine of the N-terminal amino acid of peptide-based hydrophobic blocks (H) led to improved coupling to other molecules, including U2, antigens (A), extension E2, spacers (B) and solubilizing blocks (S), such as PEG and charged block (C). Therefore, in preferred embodiments, the N-terminal amino acid of poly (amino acid)-based hydrophobic blocks (H) comprises two or more, typically between 2 and 7, such as 1, 2, 3, 4, 5, 6, 7 methylene units. For clarity, an amino acid with 2 methylene units is beta-alanine and an amino acid with 5 methylene units is amino-hexanoic acid. In certain preferred embodiments, the N-terminal amino acid of peptide-based hydrophobic blocks (H) is amino-hexanoic acid (sometimes referred to as Ahx; CAS number 60-32-3). In other embodiments, the N-terminal amino acid of peptide-based hydrophobic blocks (H) is beta-alanine.

In some embodiments, the linker may comprise poly (ethylene oxide) (PEG). The length of the linker depends on the purpose of the linker. For example, the length of the linker, such as a PEG linker, can be increased to separate any two or more components, for example, to reduce steric hindrance, or in the case of a hydrophilic PEG linker can be used to improve water solubility. The linker, such as PEG, may be between about 1 and about 24 monomers in length, such as 1, 2, 3, 4, 5, 6, 7, 8, 9, 10, 11, 12, 13, 14, 15, 16, 17, 18, 19, 20, 21, 22, 23, 24 monomers in length or more. When used as a spacer (B), the PEG may be up to 45 monomers in length or more, though, typically between 4 and 36 monomers in length.

In some embodiments, wherein the linker comprises a carbon chain, the linker may comprise a chain of between about 1 or 2 and about 18 carbons, such as 1, 2, 3, 4, 5, 6, 7, 8, 9, 10, 11, 12, 13, 14, 15, 16, 17, 18 carbons in length or more. In some embodiments, wherein the linker comprises a carbon chain, the linker may comprise a chain of between about 12 and about 20 carbons. In some embodiments, wherein the linker comprises a carbon chain, the linker may comprise a chain of between no more than 18 carbons, typically between about 1 and 6 carbon atoms.

The linkage used to join any two or more molecules, e.g., any two or more components of amphiphiles, peptide antigen conjugates and/or drug conjugates may comprise any suitable functional group, including but not limited to amides, esters, ethers, thioethers, silyl ethers, disulfides, carbamates, carbamides, hydrazides, hydrazones, acetals and triazoles.

In non-limiting examples of a covalent linkage, a click chemistry reaction may result in a triazole that links, i.e., joins together, any two components of the amphiphile, peptide antigen conjugate, or drug molecule conjugate. In several embodiments, the click chemistry reaction is a strain-promoted [3+2] azide-alkyne cyclo-addition reaction. An alkyne group and an azide group may be provided on respective molecules to be linked by "click chemistry". In some embodiments, an antigen (A) bearing an azide functional group is coupled to a hydrophobic block (H) having an appropriate reactive group, such as an alkyne, for example, a dibenzylcyclooctyne (DBCO).

In some embodiments, an amine is provided on one molecule and may be linked to another molecule by reacting the amine with any suitable electrophilic group such as carboxylic acids, acid chlorides, activated esters (for example, NHS ester), which results in an amide bond; the amine may be reacted with alkenes (via Michael addition); the amine may be reacted with aldehydes and ketones (via Schiff base); or, the amine may be reacted with activated carbonates or carbamates to yield a carbamate.

In some embodiments, the linker is cleavable under intracellular conditions, such that cleavage of the linker results in the release of any component linked to the linker, for example, a drug molecule (D).

For example, the linker can be cleavable by enzymes localized in intracellular vesicles (for example, within a lysosome or endosome or caveolae) or by enzymes, in the cytosol, such as the proteasome, or immunoproteasome. The linker can be, for example, a peptide linker that is cleaved by protease enzymes, including, but not limited to proteases that are localized in intracellular vesicles, such as cathepsins in the lysosomal or endosomal compartments of cells.

The peptide linker is typically between 1-10 amino acids, such as 1, 2, 3, 4, 5, 6, 7, 8, 9, 10, or more (such as up to 20) amino acids long, such as 11, 12, 13, 14, 15, 16, 17, 18, 19, 20 or more amino acids long. When used as a spacer (B), the peptide linker may be up to about 45 amino acids. Certain dipeptides are known to be hydrolyzed by proteases that include cathepsins, such as cathepsins B and D and plasmin, (see, for example, Dubowchik and Walker, 1999, Pharm. Therapeutics 83:67-123). For example, a peptide linker that is cleavable by the thiol-dependent protease cathepsin-B, can be used (for example, a Phe-Leu or a Gly-Phe-Leu-Gly (SEQ ID NO:1) linker). Other examples of such linkers are described, for example, in U.S. Pat. No. 6,214,345, incorporated herein by reference. In certain such embodiments, the peptide linker cleavable by an intracellular protease is a Val-Cit linker or a Phe-Lys linker (see, for example, U.S. Pat. No. 6,214,345, which describes the synthesis of doxorubicin with the Val-Cit linker). Note: for examples of amino acids and peptides provided in throughout the specification (either within the text of figures), unless otherwise specified, it should be understood that the peptides and amino acids are L-amino acids.

The cleavable peptide linker can be selected to promote processing (i.e., hydrolysis) of the peptide linker following intracellular uptake by immune cells. The sequence of the cleavable peptide linker can be selected to promote processing by intracellular proteases, such as cathepsins in intracellular vesicles or the proteasome or immunoproteasome in the cytosolic space.

In several embodiments, linkers comprising peptide sequences of the formula Pn . . . P4-P3-P2-P1 are used to promote recognition by cathepsins, wherein P1 is selected from arginine, lysine, acetyl lysine (i.e., the epsilon amine is acetylated), boc protected lysine (i.e., the epsilon amine is boc protected), citrulline, glutamine, threonine, leucine, norleucine, alpha-aminobutyric acid (abbreviated as "a-But" herein) or methionine; P2 is selected from glycine, serine, leucine, valine or isoleucine; P3 is selected rom glycine, serine, alanine, proline, or leucine; and P4 is selected from glycine, serine, arginine, lysine, acetyl lysine (i.e., the epsilon amine is acetylated), boc protected lysine, aspartic acid, glutamic acid or beta-alanine. In non-limiting examples a tetrapeptide linker of the formula P4-P3-P2-P1 linked through an amide bond to another molecule and has the sequence Lys-Pro-Leu-Arg (SEQ ID NO:2). For clarity, the amino acid residues (Pn) are numbered from proximal to distal from the site of cleavage, which is C-terminal to the P1 residue, for example, the amide bond between P1-P1' is hydrolyzed. Suitable peptide sequences that promote cleavage by endosomal and lysosomal proteases, such as cathepsin, are well described in the literature (see: Choe, et al., J. Biol. Chem., 281:12824-12832, 2006).

In several embodiments, linkers comprising peptide sequences are selected to promote recognition by the proteasome or immunoproteasome. Peptide sequences of the formula Pn . . . P4-P3-P2-P1 are selected to promote recognition by proteasome or immunoproteasome, wherein P1 is selected from basic residues and hydrophobic, branched residues, such as arginine, lysine, leucine, isoleucine and valine; P2, P3 and P4 are optionally selected from leucine, isoleucine, valine, lysine and tyrosine. In non-limiting examples, a cleavable linker of the formula P4-P3-P2-P1 that is recognized by the proteasome is linked through an amide bond at P1 to another molecule and has the sequence Tyr-Leu-Leu-Leu (SEQ ID NO: 3). Sequences that promote degradation by the proteasome or immunoproteasome may be used alone or in combination with cathepsin cleavable linkers. In some embodiments, amino acids that promote immunoproteasome processing are linked to linkers that promote processing by endosomal proteases. A number of suitable sequences to promote cleavage by the immunoproteasome are well described in the literature (see: Kloetzel, et al., Nat. Rev. Mol. Cell Biol., 2:179-187), 2001, Huber, et al., Cell, 148:727-738, 2012, and Harris et al., Chem. Biol., 8:1131-1141, 2001).

In certain preferred embodiments, drug molecules (D) are linked to hydrophobic blocks (H) via linker X1 comprising an enzyme degradable peptide. A non-limiting example is shown here:

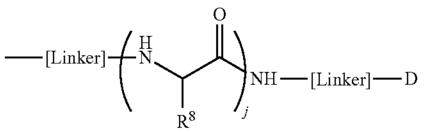

wherein D is a drug molecule; "Linker" is any suitable linker molecule; j denotes any integer, though, j is typically 1 to 6 amino acids, such as 1, 2, 3, 4, 5 or 6 amino acids; $R^8$ is any suitable amino acid side group; the N-terminal amine of the peptide is linked either directly or via the ends, e.g., to the N- or C-termini of a hydrophobic block (H) comprising poly(amino acids), either directly or via U, or through reactive monomers comprising the hydrophobic block (H); and, brackets "[ ]" denote that the group is optional.

In certain preferred embodiments of drug molecules linked to hydrophobic blocks (H) via linker X1 comprising an enzyme degradable peptide, the drug molecule (D) is linked directly to the peptide through an amide bond as shown here:

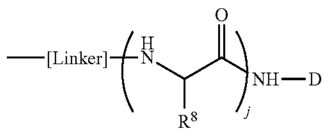

In non-limiting examples of the above structure, wherein the N-terminal Linker group is present and selected from beta alanine the structure is:

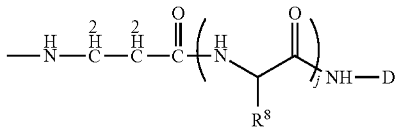

In some embodiments, the drug molecule (D) is linked to the peptide via a self-immolative carbamate linker. A non-limiting example is shown here:

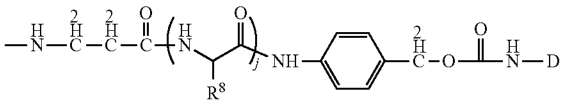

In the above example, wherein j is 4 and the amino acids are Serine-Lysine(Ac)-Valine-nor-Leucine, the structure is:

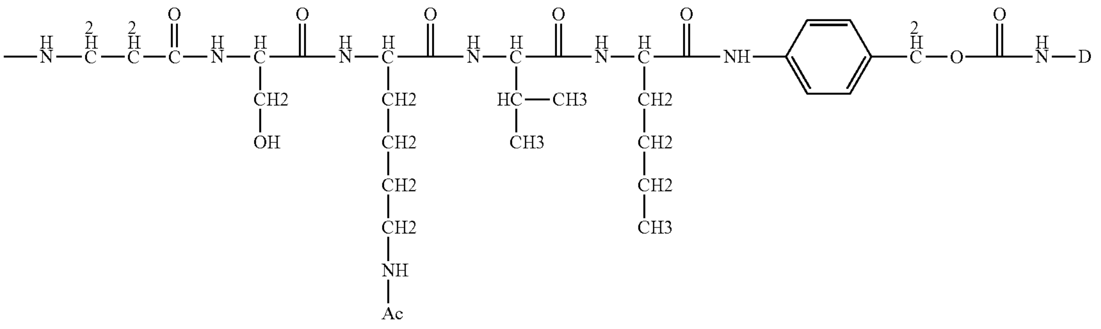

In some embodiments, drug molecules (D) are linked to hydrophobic blocks (H) through a sulfatase degradable linker X1, wherein hydrolysis of a sulfate by sulfatase results in release of the drug molecule from the linker. A number of arylsulfatase and alkysulfatase degradable linkers have recently been described (e.g., see: Bargh, et al., 2020, Chem. Sci. 11, 2375). In some embodiments of the present disclosure, drug molecules are linked to hydrophobic blocks (H) through sulfatase degradable linkers. Non-limiting examples are shown here for clarity:

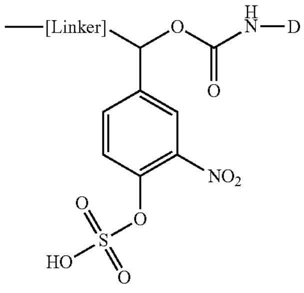

and

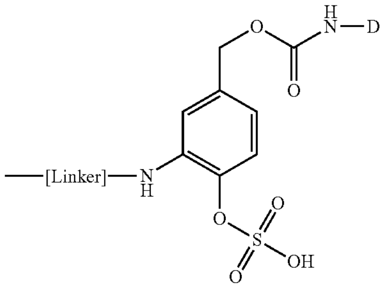

wherein D is a drug molecule; "Linker" is any suitable linker molecule linked either directly or via ends, e.g., to the N- or C-termini of a hydrophobic block (H) comprising poly (amino acids), either directly or via U, or through reactive monomers comprising the hydrophobic block (H); and, brackets "[ ]" denote that the group is optional.

Non-limiting examples of the above structures, wherein the "Linker" is present and selected from short alkyl linkers linked to the hydrophobic block through an amide are shown here for clarity:

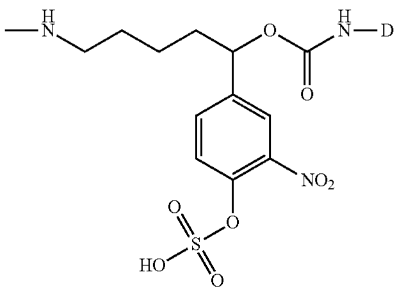

or

-continued

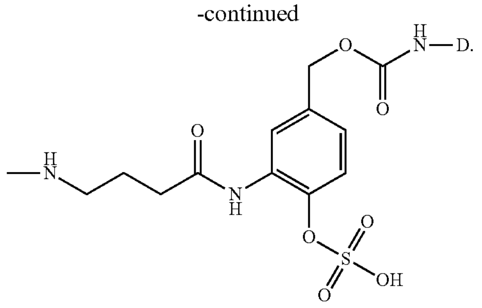

In other embodiments, any two or more components may be joined together through a pH-sensitive linker X that is sensitive to hydrolysis under acidic conditions. A number of pH-sensitive linkers are familiar to those skilled in the art and include for example, a hydrazone, carbohydrazone, semicarbazone, thiosemicarbazone, cis-aconitic amide, orthoester, acetal, ketal, silylether or the like (see, for example, U.S. Pat. Nos. 5,122,368; 5,824,805; 5,622,929; Dubowchik and Walker, 1999, Pharm. Therapeutics 83:67-123; Neville et al., 1989, Biol. Chem. 264:14653-14661).

In certain embodiments, different components (e.g., drug molecule and hydrophobic block (H)) are linked together through pH-sensitive linkers that are stable at blood pH, e.g., at a pH of about 7.4, but undergo more rapid hydrolysis at endosomal/lysosomal pH, ~ pH 5-6.5. In certain, preferred embodiments, drug molecules (D) are linked to hydrophobic blocks (H) through reactive monomers via a pH-sensitive bonds, such as hydrazone bonds that result from the reaction between a ketone and a hydrazine. The functional group hydrazine linked to a carbonyl is sometimes referred to as hydrazide, though, hydrazine is meant to broadly refer to —NH—$NH_2$ groups, including when linked to carbonyl, e.g., C(O)—NH—$NH_2$. pH-sensitive linkages, such as a hydrazone, provide the advantage that the bond is stable at physiologic pH, at about pH 7.4, but is hydrolyzed at lower pH values, such as the pH of intracellular vesicles.

In certain preferred embodiments, drug molecules are linked by a linker X1 comprising a ketone and may be represented by the formula:

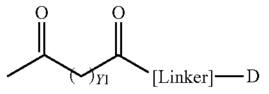

wherein D is any drug molecule; "Linker" is any suitable linker molecule; y1 denotes an integer between 1 to 6, preferably 4; brackets "[ ]" denote that the group is optional; and, wherein the ketone in the above example is used to link the linker linked drug molecule (D) to a reactive monomer through a hydrazone bond.

In the above example, wherein y1 is 4 and the drug molecule is linked directly (i.e., the "Linker" is absent) via an amide bond, the structure is:

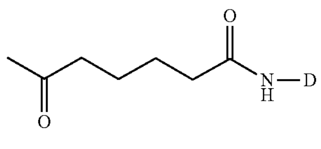

In preferred embodiments, drug molecules linked to ketones are linked to hydrophobic blocks (H) through hydrazone or carbohydrazone bonds. Non-limiting examples of drug molecules linked to a glutamic acid-based reactive monomer (N) through hydrazone and carbohydrazone bonds are shown here:

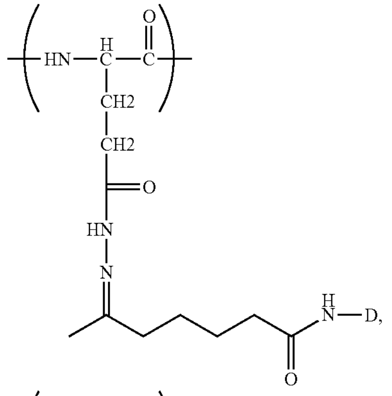

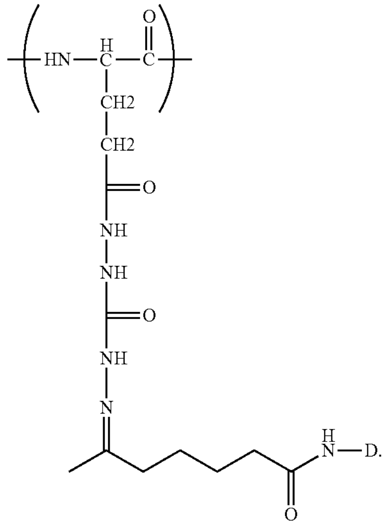

In some embodiments, the drug molecule comprises a ketone and may be linked directly to reactive monomers through hydrazone or carbohydrazone.

In other embodiments, the linker comprises a linkage that is cleavable under reducing conditions, such as a reducible disulfide bond. Many different linkers used to introduce disulfide linkages are known in the art (see, for example, Thorpe et al., 1987, Cancer Res. 47:5924-5931; Wawrzynczak et al., In Immunoconjugates: Antibody Conjugates in Radioimagery and Therapy of Cancer (C. W. Vogel ed., Oxford U. Press, 1987); Phillips et al., Cancer Res. 68:92809290, 2008). See also U.S. Pat. No. 4,880,935).

In preferred embodiments, the linker X1 linking a hydrophobic block (H) and one or more drug molecules (D) is a short alkyl or PEG linker. In other preferred embodiments, the linker X1 linking a hydrophobic block (H) and one or more drug molecules (D) is an enzyme degradable linker, such as a cathepsin degradable peptide or sulfatase degradable linker. In other preferred embodiments, the linker X1 linking a hydrophobic block (H) and one or more drug molecules (D) comprises an enzyme degradable peptide and a self-immolative linker.

X can be any suitable linker, though, in preferred embodiments, the linker X linking any two or more groups, is a short alkyl (i.e., lower alkyl) or PEG linker, e.g., a PEG linker with between about 1 to about 24 monomeric units.

Extensions (E1 and E2)

The optional N- and C-terminal extensions (E1 and E2) denote moieties linked to the N- and C-terminus of the peptide antigen (A), respectively. The N- and C-terminal extensions E1 and E2 may comprise any one or more of the following: amino acids, including non-natural amino acids; hydrophilic ethylene oxide monomers (e.g., PEG); hydrophobic alkane chains; or the like; or combinations thereof. The N- and C-terminal extensions E1 and E2 are attached to the peptide antigen (A) through any suitable means, e.g., through amide bonds.

In some embodiments, the extensions (E1 and E2) function to control the rate of degradation of the peptide antigen (A) but may also perform any one or more additional functions. In some embodiments, the N- or C-terminal extension (E1 or E2) may be free (wherein one end of the N- or C-terminal extension is linked to the peptide antigen (A) and the other end is not linked to another molecule) and serve to slow degradation of the peptide antigen; for example, a E1 peptide-based extension may be linked to the N-terminus of the peptide antigen through an amide bond to slow degradation. In other embodiments, the N- and/or C-terminal extensions (E1 and/or E2) may be linked to a heterologous molecule and may function as a linker as well as to modulate peptide antigen (A) degradation. The N- and/or C-terminal extensions providing a linker function may link the peptide antigen either directly or indirectly through a Linker U to a hydrophobic block (H) and or solubilizing block(S), such as PEG. In some embodiments, the extensions (E1 and/or E2) function to provide distance, i.e., space, between any two heterologous molecules. In other embodiments, the extensions (E1 and/or E2) function to impart hydrophobic or hydrophilic properties to the peptide antigen conjugate. In still other embodiments, the composition of the extensions (E1 and/or E2) may be selected to impart rigidity or flexibility. In other embodiments, the N- and/or C-terminal extensions (E1 and/or E2) may help stabilize the particles formed by the peptide antigen conjugate.

In some embodiments, the extensions (E1 and/or E2) comprise charged functional groups, e.g., charged amino acid residues (e.g., arginine, ornithine, lysine, glutamic acid, aspartic acid, etc.), that impart charge at pH 7.4. The number of charged residues present in the extension can be used to modulate the net charge of the peptide antigen conjugate. Peptide-based extensions (E1 and/or E2) that are recognized by proteases and impart a particular electrostatic charge to stabilize particles formed by peptide antigen conjugates are described later.

Additionally, in some embodiments, C-terminal extensions (E2) added to peptide antigens (A) are selected to facilitate manufacturing of a peptides comprising the formula PEG-[E1]-A-E2-[U1], wherein [ ] denotes the group is optional. Accordingly, the amino acid sequence of peptide-based E2 can be selected to disrupt peptide β-sheet formation and prevent sequence truncation during solid-phase peptide synthesis. In non-limiting examples, a C-terminal di-peptide linker (E2), Gly-Ser, is incorporated during solid-phase peptide synthesis as a pseudoproline dipeptide (e.g., Gly-Ser(Psi (Me,Me)pro)). In additional embodiments, a proline is included in E2, e.g., Ser-Pro-Leu-Arg (SEQ ID NO:4); whereby the proline is included to both facilitate manufacturing and promote processing of the extension by endosomal proteases.

In some embodiments, the peptide antigen (A) is linked at the C-terminus to an E2 extension that is linked either directly or indirectly through a Linker (U) to a hydrophobic block, e.g., wherein the peptide antigen conjugate has the structure A-E2-U-H or A-E2-H. In some embodiments, an E1 extension is linked to the N-terminus of the peptide antigen (A) and an E2 extension is linked at the C-terminus of the peptide antigen (A), wherein either E1 or E2 are linked either directly or via a Linker (U) to a hydrophobic block (H), e.g. wherein the peptide antigen conjugate has the structure E1-A-E2-U-H, H-U-E1-A-E2, E1-A-E2-H, or H-E1-A-E2. In other embodiments, a peptide antigen (A) is linked at the N-terminus to an E1 extension that is linked either directly or via a Linker (U) to a hydrophobic block (H), e.g., wherein the peptide antigen conjugate has the structure H-U-E1-A or H-E1-A. In some embodiments, a solubilizing block, such as PEG, is linked to an extension, E1 or E2, that is linked to the N- or C-terminus of the peptide antigen (A), respectively, wherein the extension that is not linked to the solubilizing block(S), such as PEG, is linked either directly or via a Linker (U) to the hydrophobic block (H), e.g., wherein the peptide antigen conjugate has the structure PEG-E1-A-E2-U-H, H-U-E1-A-E2-PEG, PEG-E1-A-E2-H, or H-E1-A-E2-PEG.

In additional embodiments, PEG groups are linked to both E1 and E2 extensions that are linked to both the N- and C-termini of the peptide antigen (A), respectively; or, PEG are linked to the E1 extension linked to the N-terminus of the peptide antigen (A) but not to the E2 extension attached to the C-terminus of the peptide antigen (A), which may be linked either directly or through a Linker (U) to a hydrophobic block (H). A linker precursor U1 or Linker (U) may be linked to either of the extensions (E1 or E2) through any suitable means, such as an amide bond.

In preferred embodiments, the extensions (E1 and E2) are peptide sequences that are selected for recognition and hydrolysis by enzymes, such as proteases. The extensions (E1 and E2) are preferably cleavable peptides, including amino acids recognized by either or both endosomal proteases and/or the immunoproteasome.

In some embodiments, the N-terminal extension (E1) is a peptide sequence between about 1 to 8 amino acids in length, such as 1, 2, 3, 4, 5, 6, 7, or 8 amino acids, typically no more than 10 amino acids in length that is linked to the peptide antigen (A) through an amide bond formed between a carboxyl group of the E1 and the alpha amine of the N-terminal residue of the peptide antigen (A). The amide bond between E1 and the peptide antigen (A) may be cleaved by enzymes.

It is customary to number the amino acid positions in order of proximal to distal from the cleavage site, with amino acid positions C-terminal to the cleavage site indicated by the prime symbol (e.g., Pn'). For example, for a tetrapeptide extension (PN4-PN3-PN2-PN1) linked to the N-terminus of a peptide antigen (A) that is an octapeptide (PA1'-PA2'-PA3'-PA4'-PA5'-PA6'-PA7'-PA8'), e.g., PN4-PN3-PN2-PN1-PA1'-PA2'-PA3'-PA4'-PA5'-PA6'-PA7'-PA8', the amide bond between PN1-PA1' is recognized and hydrolyzed by an enzyme.

In some embodiments, the N-terminal extension (E1) is an enzyme degradable tetrapeptide that is recognized by endosomal proteases, wherein the PN1 position of a tetrapeptide extension (e.g., PN4-PN3-PN2-PN1) is preferably selected from arginine, lysine, citrulline, glutamine, threonine, leucine, norleucine, or methionine, for example, PN4-PN3-PN2-Arg; PN2 is selected from glycine, valine, leucine or isoleucine; PN3 is selected from glycine, serine, alanine, proline or leucine; and, PN4 is selected from glycine, serine, arginine, lysine, aspartic acid or glutamic acid. In some embodiments, the N-terminal extension (E1) is an enzyme degradable tripeptide that is recognized by endosomal proteases, wherein the PN1 position of a tripeptide extension (e.g., PN3-PN2-PN1) is preferably selected from arginine, lysine, citrulline, glutamine, threonine, leucine, norleucine, or methionine; PN2 is selected from glycine, valine, leucine or isoleucine; and PN3 is selected from glycine, serine, alanine, proline or leucine. In some embodiments, the N-terminal extension (E1) is an enzyme degradable di-peptide that is recognized by endosomal proteases, wherein the PN1 position of a dipeptide extension (e.g., PN2-PN1) is preferably selected from arginine, lysine, citrulline, glutamine, threonine, leucine, norleucine, or methionine; and PN2 is selected from glycine, valine, leucine or isoleucine. In still additional embodiments, the N-terminal extension (E1) is an amino acid that is recognized by endosomal proteases, wherein the PN1 position is preferably selected from arginine, lysine, citrulline, glutamine, threonine, leucine, norleucine, or methionine. In preferred embodiments of the vaccine for inducing tolerance E1 comprising a dipeptide is valine-citrulline.

In other embodiments, the N-terminal extension (E1) is an enzyme degradable peptide that is recognized by the immunoproteasome, wherein the P1 position of a tetrapeptide extension (PN4-PN3-PN2-PN1) is preferably selected from isoleucine, leucine, norleucine or valine, for example, PN4-PN3-PN2-Leu.

In additional embodiments, the N-terminal extension (E1) is an enzyme degradable peptide that is recognized by both endosomal proteases and the immunoproteasome, wherein the PN5 and PN1 positions of an octapeptide extension (PN8-PN7-PN6-PN5-PN4-PN3-PN2-PN1) are selected from arginine, lysine, citrulline, glutamine, threonine, leucine, norleucine, or methionine for the PN5 position recognized by cathepsins, and isoleucine, leucine, norleucine or valine for the PN1 position recognized by the immunoproteasome; for example, PN8-PN7-PN6-Arg-PN4-PN3-PN2-Leu. A non-limiting example of an N-terminal extension (E1) recognized by cathepsins and the immunoproteasome is Lys-Pro-Leu-Arg-Tyr-Leu-Leu-Leu (SEQ ID NO:5).

Non-limiting examples of tetrapeptide N-terminal extensions (E1) that are recognized by the immunoproteasome include: Ser-Leu-Val-Cit (SEQ ID NO:6), Ser-Leu-Val-Leu (SEQ ID NO:7), Ser-Pro-Val-Cit (SEQ ID NO:8), Glu-Leu-Val-Arg (SEQ ID NO:9), Ser-Pro-Val-Arg (SEQ ID NO:10), Ser-Leu-Val-Arg (SEQ ID NO:11), Lys-Pro-Leu-Arg (SEQ ID NO:2), Lys-Pro-Val-Arg (SEQ ID NO:12), Glu-Leu-Val-Cit (SEQ ID NO:13), Glu-Leu-Val-Leu (SEQ ID NO:14), Glu-Pro-Val-Cit (SEQ ID NO: 15), and Lys-Pro-Val-Cit (SEQ ID NO:16). Non-limiting examples of tripeptide N-terminal extensions (E1) include: Leu-Val-Cit, Leu-Val-Leu, Pro-Val-Cit, Leu-Val-Arg, Pro-Val-Arg, Pro-Leu-Arg, Gly-Val-Ser. Non-limiting examples of di-peptide N-terminal extensions (E1) include: Val-Cit, Val-Leu, Val-Arg, Leu-Arg. Non-limiting examples of single amino acid N-terminal extensions (E1) include Cit, Arg, Leu or Lys. In the above examples, Arg can be replaced with Lys; Lys can be replaced with Arg; Glu can be replaced with Asp; and Asp can be replaced with Glu. Note that Cit=citrulline.

In some embodiments, the E2 is a degradable peptide linked to the C-terminal residue of the peptide antigen (A)

and comprises amino acid sequences that are recognized and hydrolyzed by certain proteases. In some embodiments, the C-terminal extension (E2) is a peptide sequence between about 1 to 8 amino acids in length, such as 1, 2, 3, 4, 5, 6, 7, or 8 amino acids, typically no more than 10 amino acids. In preferred embodiments, the C-terminal extension (E2) is linked to the peptide antigen (A) via an amide bond formed between the C-terminal carboxyl group of the peptide antigen (A) and the alpha amine of the N-terminal residue of the extension (E2). The amide bond between E2 and the peptide antigen (A) may be cleaved by enzymes. Note: that it is customary to number the amino acid positions in order of proximal to distal from the cleavage site, with amino acid positions C-terminal to the cleavage site indicated by the prime symbol (e.g., Pn'). For example, for a tetrapeptide extension (PC1'—PC2'—PC3'—PC4') linked to the C-terminus of an octapeptide antigen (PA8-PA7-PA6-PA5-PA4-PA3-PA2-PA1), e.g., PA8-PA7-PA6-PA5-PA4-PA3-PA2-PA1-PC1'—PC2'—PC3'—PC4', the amide bond between PA1-PC1' is recognized and hydrolyzed by an enzyme.

In preferred embodiments of C-terminal extensions (E2), the C-terminal extension (E2) comprises amino acid sequences that are selected to promote immunoproteasome recognition and cleavage and optionally endosomal protease recognition. As peptide antigens (A) typically contain a C-terminal residue, for example, leucine, that promotes hydrolysis by the immunoproteasome, e.g., at the amide bond proximal to the C-terminal residue of the peptide antigen (A), extensions linked to the C-terminus of the peptide antigen (A) should be selected to promote immunoproteasome recognition and cleavage at the amide bond proximal to the C-terminus of the peptide antigen (A). The immuno-proteasome favors small, non-charged amino acids at the PC1' position adjacent to the C-terminal amino acid, PA1, of the peptide antigen (A), e.g., the amide bond between PA1-PC1'. However, endosomal proteases favor bulky hydrophobic amino acids (e.g., leucine, norleucine, methionine or glutamine) and basic amino acids (i.e., arginine and lysine). Therefore, C-terminal extensions may be selected to promote recognition by either or both classes of proteases.

In some embodiments, a peptide antigen (A) with the sequence PA8-PA7-PA6-PA5-PA4-PA3-PA2-PA1 is linked to a C-terminal peptide extension (E2) with the sequence PC1' . . . . PCn', wherein n is an integer value from 1 to 8, for example, PA8-PA7-PA6-PA4-PA3-PA2-PA1-PC1' . . . . PCn'. The composition of the C-terminal extension (E2) depends on the length of the extension sequence used. In some embodiments, the C-terminal extension, E2, is a single amino acid PC1' selected from Gly, Ala, Ser, Arg, Lys, Cit, Gln, Thr, Leu, Nle or Met. In additional embodiments, the C-terminal extension, E2, is a dipeptide, PC1'—PC2', wherein PC1' is selected from Gly, Ala or Ser; and PC2' is selected from Gly, Ala, Ser, Pro, Arg, Lys, Cit, Gln, Thr, Leu, Nle, or Met. In additional embodiments, the C-terminal extension, E2, is a tripeptide, PC1'—PC2'—PC3', wherein P1' is selected from Gly, Ala, or Ser; PC2' is selected from Gly, Ala, Ser, or Pro; and PC3' is selected from Gly, Ser, Arg, Lys, Cit, Gln, Thr, Leu, Nle or Met.

In additional embodiments, the C-terminal extension, E2, is a tetrapeptide extension, PC1'—PC2'—PC3'—PC4', wherein PC1' is selected from glycine, alanine or serine; PC2' is selected from glycine, alanine, serine, proline or leucine; PC3' is selected from glycine, alanine, serine, valine, leucine or isoleucine; and PC4' is selected from arginine, lysine, citrulline, glutamine, threonine, leucine, norleucine or methionine. In additional embodiments, the C-terminal extension, E2, is a pentapeptide, PC1'—PC2'—PC3'—PC4'—PC5', wherein PC1' is selected from glycine, alanine or serine; PC2' is selected glycine, alanine, serine, proline, arginine, lysine, glutamic acid or aspartic acid; PC3' is selected from glycine, alanine, serine, proline or leucine; PC4' is selected from glycine, alanine, valine, leucine or isoleucine; and PC5' is selected from arginine, lysine, citrulline, glutamine, threonine, leucine, norleucine or methionine. In additional embodiments, the C-terminal extension, E2, is a hexapeptide, PC1'—PC2'—PC3'—PC4'—PC5'—PC6', wherein PC1' is selected from glycine, alanine or serine; PC2' is selected from glycine, alanine, serine or proline; PC3' is selected from glycine, serine, proline, arginine, lysine, glutamic acid or aspartic acid; PC4' is selected from proline or leucine; PC5' is selected from glycine, alanine, valine, leucine or isoleucine; and PC6' is selected from arginine, lysine, citrulline, glutamine, threonine, leucine, norleucine or methionine.

Non-limiting examples of hexapeptide C-terminal extensions (E2) include Gly-Gly-Lys-Leu-Val-Arg (SEQ ID NO:17), Gly-Gly-Lys-Pro-Leu-Arg (SEQ ID NO: 18), Gly-Gly-Ser-Leu-Val-Arg (SEQ ID NO: 19), Gly-Gly-Ser-Leu-Val-Cit (SEQ ID NO:20), Gly-Gly-Ser-Pro-Val-Cit (SEQ ID NO:21), Gly-Gly-Ser-Leu-Val-Leu (SEQ ID NO:22), Gly-Gly-Glu-Leu-Val-Arg (SEQ ID NO:23), Gly-Gly-Glu-Leu-Val-Leu (SEQ ID NO:24).

Non-limiting examples of pentapeptide C-terminal extensions (E2) include Gly-Ser-Leu-Val-Arg (SEQ ID NO:25), Gly-Ser-Leu-Val-Cit (SEQ ID NO:26), Gly-Lys-Pro-Val-Cit (SEQ ID NO:27), Gly-Lys-Pro-Val-Arg (SEQ ID NO:28), Gly-Ser-Leu-Val-Leu (SEQ ID NO:29), Gly-Glu-Leu-Val-Leu (SEQ ID NO:30).

Non-limiting examples of tetrapeptide C-terminal extensions (E2) include Ser-Leu-Val-Cit (SEQ ID NO:6), Ser-Leu-Val-Leu (SEQ ID NO:7), Ser-Pro-Val-Cit (SEQ ID NO:8), Glu-Leu-Val-Arg (SEQ ID NO:9), Ser-Pro-Val-Arg (SEQ ID NO: 10), Ser-Leu-Val-Arg (SEQ ID NO:11), Lys-Pro-Leu-Arg (SEQ ID NO:2), Glu-Leu-Val-Cit (SEQ ID NO:13), Glu-Leu-Val-Leu (SEQ ID NO:14), Glu-Pro-Val-Cit (SEQ ID NO:15), Glu-Gly-Val-Cit (SEQ ID NO:31).

Non-limiting examples of tripeptide C-terminal extensions (E2) include Gly-Ser-Gly, Gly-Ser-Arg, Gly-Ser-Leu, Gly-Ser-Cit, Gly-Pro-Gly, Gly-Pro-Arg, Gly-Pro-Leu, Gly-Pro-Cit. Non-limiting examples of di-peptide C-terminal extensions (E2) include Gly-Ser, Gly-Pro, Val-Cit, Gly-Arg, Gly-Cit. Non-limiting examples of single amino acid C-terminal extensions (E2) include Gly, Ser, Ala, Arg, Lys, Cit, Val, Leu, Met, Thr, Gln or Nle. In the above examples, Arg can be replaced with Lys; Lys can be replaced with Arg; Glu can be replaced with Asp; and Asp can be replaced with Glu.

The C-terminal linker (E2) linked to the C-terminus of the peptide antigen (A) may be selected for recognition (i.e., hydrolysis) by both the immunoproteasome and endosomal proteases. In non-limiting examples, a peptide antigen (A) with the sequence PA8-PA7-PA6-PA5-PA4-PA3-PA2-PA1 is linked at the C-terminus to a C-terminal tetrapeptide extension (E2) with the sequence PC1'—PC2'—PC3'—PC4', wherein PC1' is selected from glycine, alanine or serine and PC4' is selected from arginine, lysine, citrulline, glutamine, threonine, leucine, norleucine, or methionine, for example, Ser-P3-P2-Arg. In some embodiments, an antigen with the sequence PA8-PA7-PA6-PA5-PA4-PA3-PA2-PA1 is linked at the C-terminus to a C-terminal hexapeptide extension (E2) with the sequence PC1'—PC2'—PC3'—PC4'—PC5'—PC6', wherein PC1' and PC2' are selected from glycine, alanine, proline or serine and PC6' is selected from arginine, lysine, citrulline, glutamine, threonine, leucine, norleucine, or methionine, for example, Gly-Gly-PC3'—PC4'—PC5'-Arg. A non-limiting example of a C-terminal extension (E2) that promotes processing by both the immuno-proteasome and cathepsins that is linked to the C-terminus of the peptide antigen (A) is Gly-Gly-Lys-Pro-Leu-Arg (SEQ ID NO:18). An additional non-limiting example of a C-terminal extension (E2) that is linked at the C-terminus of a peptide antigen (A) that favors processing by the immunoproteasome and cathepsins is Gly-Gly-Ser-Leu-Val-Cit (SEQ ID NO:20) or Gly-Gly-Ser-Pro-Val-Cit (SEQ ID NO:21).

Spacer (B)

The spacer (B) is an optional component of amphiphiles that links the solubilizing block(S) to the hydrophobic block (H) either directly or via a Linker (U), e.g., wherein the amphipile has the structure S-B-H or S-B-U-H. The spacer (B) may comprise any one or more of the following: amino acids, including non-natural amino acids; hydrophilic polymers, e.g., polymers based on ethylene oxide (PEG), acrylate, methacrylate, acrylamide or methacrylamide based monomers; alkane chains; or the like; or combinations thereof. The spacer (B) may be linked to the solubilizing block(S) and hydrophobic block (H) through any suitable means, e.g., directly or indirectly via linkers, though the linkages typically comprise covalent bonds, e.g., amide bonds.

In some embodiments, the spacer (B) functions to provide distance, i.e., space, between the heterologous molecules, S and H. In other embodiments, the spacer (B) functions to impart hydrophobic or hydrophilic properties. In still other embodiments, the composition of the spacer may be selected to impart rigidity or flexibility. In other embodiments, the composition of the spacer may be selected for recognition by enzymes and promote degradation.

In some embodiments, the spacer (B) is a hydrophilic polymer, with monomer units selected from acrylates, (meth)acrylates, acrylamides, (meth)acrylamides, allyl ethers, vinyl acetates, vinyl amides, substituted styrenes, amino acids, acrylonitrile, heterocyclic monomers (e.g., ethylene oxide), saccharides, phosphoesters, phosphonamides, sulfonate esters, sulfonamides, or combinations thereof.

In some embodiments, the spacer (B) is a peptide sequence between about 1 to 45 amino acids in length, such as 1, 2, 3, 4, 5, 6, 7, 8, 9, 10, 11, 12, 13, 14, 15, 16, 17, 18, 19, 29, 21, 22, 23, 24, 25, 26, 27, 28, 29, 30, 31, 32, 33, 34, 35, 36, 37, 38, 39, 40, 41, 42, 43, 44 or 45 amino acids, typically no more than 45 amino acids in length, that is linked to the hydrophobic block (H) and solubilizing block (S) through, e.g., an amide bond formed between the N- and C-terminal carboxyl group of the spacer (B), respectively. The amide bond between the spacer (B) and the solubilizing block(S) and/or hydrophobic block (H) may be recognized by enzymes or may be selected for resistance to enzyme-mediated hydrolysis.

In other embodiments, the spacer (B) is a hydrophilic polymer comprising monomer units selected from non-natural, hydrophilic monomers, e.g., ethylene oxide (PEG), HPMA, poly(sarcosine), or HEMA, that is about 1 to 48 monomers in length (i.e. degree of polymerization), such as 1, 2, 3, 4, 5, 6, 7, 8, 9, 10, 11, 12, 13, 14, 15, 16, 17, 18, 19, 29, 21, 22, 23, 24, 25, 26, 27, 28, 29, 30, 31, 32, 33, 34, 35, 36, 37, 38, 39, 40, 41, 42, 43, 44, 45, 46, 47 or 48 monomers, typically no more than 48 monomers in length, that is linked to the hydrophobic block (H) and solubilizing block(S) either directly or through linkers.

Specific compositions of spacers that lead to unexpected improvements in biological activity are described throughout the specification. Note: spacer groups (B) and solubilizing blocks(S) may both comprise hydrophilic polymers (e.g., hydrophilic poly(amino acids); hydrophilic methacrylate-based polymers, such as HEMA; hydrophilic methacrylamide-based polymers, such as HPMA, PEG, etc.); however, the distinction between S and B is based in part on function and called attention to in specific examples of amphiphiles. Similarly, the PEG group of peptide antigen conjugates of formula PEG-[E1]-A-[E2]-[U]-H and H-[E1]-A-[E2]—[U]-PEG is a hydrophilic polymer and type of solubilizing block. Linker (U)

A linker (U) optionally joins solubilizing block(S) fragments (S-[B]-U1) to hydrophobic block (H) fragments (U2-H) through the reaction of U1 with U2 to form amphiphiles (S-[B]-U-H).

A linker (U) also, independently of the amphiphile linker U, joins peptide antigen conjugate fragments (PEG-[E1]-A-[E2]—U1 or U1-[E1]-A-[E2]-PEG) to hydrophobic block (H) fragments (U2-H) through the reaction of U1 with U2 to form peptide antigen conjugates (PEG-[E1]-A-[E2]-U-H or H-U-[E1]-A-[E2]-PEG).

While peptide antigens (A) may be joined directly to hydrophobic blocks (H), i.e., A-H, or via an extension, i.e., A-E2-H (or H-E1-A), entirely on-resin by solid-phase peptide synthesis, it may be beneficial under certain circumstances to produce the antigen (A) and hydrophobic block (H) as separate fragments comprising Linker Precursor U1 (PEG-[E1]-A-[E2]—U1 or U1-[E1]-A-[E2]-PEG) and Linker Precursor U2 (U2-H), which may be joined on-resin or in solution to yield PEG-[E1]-A-[E2]-U-H (or H-U-[E1]-A-[E2]-PEG).

Similarly, while solubilizing blocks(S) on the amphiphile may be joined directly to hydrophobic blocks (H), i.e., S-H, or via a spacer, i.e., S-B-H, entirely on-resin by solid-phase peptide synthesis, it may be beneficial under certain circumstances to produce the solubilizing block(S) and hydrophobic block (H) as separate fragments comprising Linker Precursor U1 (S-[B]-U1) and Linker Precursor U2 (U2-H), which may be joined on-resin or in solution to yield S-[B]-U-H.

In preferred embodiments, the Linker Precursors used to form Linker U are selected for site-selectivity, i.e., a reaction only takes place between U1 and U2 and between no other groups. In some embodiments, Linker Precursor U1 comprises an activated carboxylic acid and is reacted with a Linker Precursor U2 that comprises an amine to form Linker U comprising an amide; or, U1 comprises an amine and is reacted with U2 that comprises an activated carboxylic acid to form Linker U comprising an amide. In some embodiments, Linker Precursor U1 comprises a maleimide and is reacted with Linker Precursor U2 that comprises a thiol to form a Linker U comprising a thioether bond; or, U1 comprises a thiol and is reacted with U2 that comprises a maleimide to form a Linker U comprising a thioether bond. In some embodiments, Linker Precursor U1 comprises an azide and is reacted with Linker Precursor U2 that comprises an alkyne to form a Linker U that comprises a triazole; or, U1 comprises an alkyne and is reacted with a U2 that comprises an azide to form a Linker US comprising a triazole.

In preferred embodiments, the amphiphile of formula S-[B]-U-H is joined together by linking a solubilizing block fragment (S-[B]-U1) to a hydrophobic block fragment (U2-H), wherein the Linker Precursor U1 comprises a strained alkyne (e.g., dibenzocyclooctyne (DBCO), bicyclononyne (BCN) or the like) that is reacted with Linker Precursor U2 which comprises an azide to form the Linker U that comprises a triazole.

In preferred embodiments, the peptide antigen conjugates of formulas PEG-[E1]-A-[E2]-U-H or H-U-[E1]-A-[E2]-PEG are joined together by linking a peptide antigen fragment PEG-[E1]-A-[E2]—U1 or U1-[E1]-A-[E2]-PEG to a hydrophobic block fragment (U2-H), wherein the Linker Precursor U1 comprises a strained alkyne (e.g., dibenzocyclooctyne (DBCO), bicyclononyne (BCN) or the like) that is reacted with Linker Precursor U2 which comprises an azide to form the Linker U which comprises a triazole.

In preferred methods of manufacturing the peptide antigen conjugates of formulas PEG-[E1]-A-[E2]-U-H or H-U-[E1]-A-[E2]-PEG are joined together by linking a peptide antigen fragment PEG-[E1]-A-[E2]—U1 or U1-[E1]-A-[E2]-PEG to a hydrophobic block fragment (U2-H), wherein the Linker Precursor U1 comprises DBCO and the Linker Precursor U2 comprises an azide by (i) adding 1 molar equivalent of peptide antigen fragment in DMSO at concentrations greater than 10 mM, preferably greater than 25 mM, to at least 1.05 equivalents of the hydrophobic block fragment in DMSO at concentrations greater than 25 mM, most preferably greater than 50 mM; and (ii) upon reaction completion removing any unreacted hydrophobic block fragment by adding an azide-resin, such as agarose-azide, to the reaction mixture; and then (iii) removing the resin to generate pure peptide antigen conjugate.

In other preferred embodiments, Linker Precursor U1 comprises an azide that is reacted with the Linker Precursor U2 that comprises a strained alkyne (e.g., dibenzocyclooctyne (DBCO), bicyclononyne (BCN) or the like) to form the Linker U which comprises a triazole. In non-limiting examples, the Linker Precursor U2 comprising DBCO is linked to the hydrophobic block (H) via a suitable linker X (e.g., DBCO-NHS, CAS number 1353016-71-3) and the Linker Precursor U1 (e.g. azido acid, such as azidopentanoic acid; azido amino acid, such as azido-lysine (abbreviated Lys (N3), CAS number 159610-92-1; or, azido amine, such as azido-butylamine) is linked to the solubilizing block fragment (S-[B]-U1) or peptide antigen fragment (PEG-[E1]-A-[E2]—U1 or U1-[E1]-A-[E2]-PEG) via a suitable linker X.

In preferred embodiments, the Linker U preferably comprises an amide, thioether or triazole.

Dendron Amplifier

Dendron amplifiers are a specific type of linker moiety that functions to increase the valency (i.e., the number) of groups present on any components of amphiphiles, peptide antigen conjugates or drug molecule conjugates described herein. For instance, in preferred embodiments of solubilizing blocks (S), dendron amplifiers are used to increase the valency of solubilizing groups (referred to as "SG" in formulae) that are present on the surface of the solubilizing block (S). In other embodiments, dendron amplifiers are used to increase the valency of solubilizing blocks (S) and spacers (B) linked to a hydrophobic block (H).

Dendron amplifiers (also referred to as "dendrons") are regularly branched molecules that are often symmetric and typically comprise repeating units of monomers that comprise three or more functional groups (FG) and a branch point. Dendron amplifiers may be expressed by the formula, (FG')-T-(FGt)d, wherein FG' and FGt are the focal point and terminal functional groups, respectively, which are selected from any suitable functional group; T is any suitable linker and "d" is any integer greater than 1, typically between 2 to 32, though, more preferably between 2 and 8, such as 2, 3, 4, 5, 6, 7, and 8. The multiple by which dendron amplifiers increase the terminal functional group (FGt) can be expressed as $FGt=\beta^{\gamma}$, wherein $\beta$ is the number of branches that occur for each generation of the dendron and the symbol y is the number of generations, wherein the number of branches is any integer, though, typically between 2 to 6, and the number of generations is any integer, though, typically between 1 to 10. Terminal functional groups present on solubilizing blocks that are free (i.e., unreacted), may also be referred to as solubilizing groups (SG).

Dendron amplifiers may comprise repeats of a monomer comprising a first functional group (FG1) and a second functional group (FG2), wherein the first functional group is reactive towards the second functional group. For instance, a non-limiting example of a 2$^{nd}$ generation dendron amplifier with $\beta$=2 comprising repeats of a monomer comprising a first functional group (FG1) and a second functional group (FG2), wherein the first functional group is reactive towards the second functional group, is shown here for clarity:

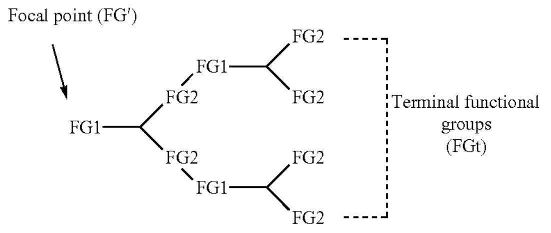

wherein, the first functional group at the starting point is also referred to as the focal point functional group (FG') and the terminal FG2 are referred to as the terminal functional groups or FGt.

A non-limiting example of a 3$^{rd}$ generation dendron formed from monomers comprising a first and second functional group wherein $\beta$=2 is shown here for clarity:

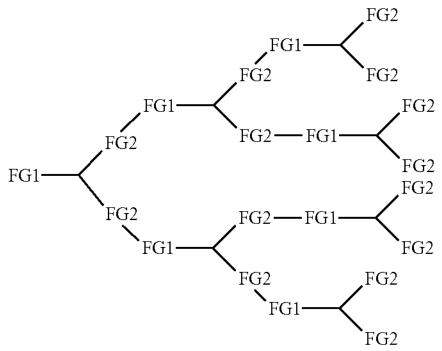

A non-limiting example of a $2^{nd}$ generation dendron amplifier with $\beta$=3 comprising repeats of a first monomer comprising a first functional group (FG1) and a second functional group (FG2), wherein the first functional group is reactive towards the second functional group, is shown here for clarity:

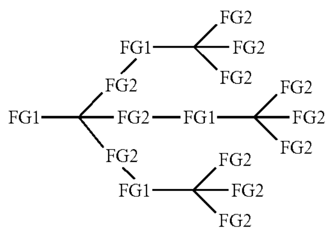

Monomers comprising a first functional group and a second functional group, wherein the first functional group is reactive towards the second functional group, and the monomer comprises at least one first functional group and two or more second functional groups may be selected from any suitable monomer. Non-limiting examples include FG1-$(CH_2)_{y2}CH(R^1)_2$, FG1-$(CH_2)_{y2}C(R^1)_3$, FG1-$(CH_2CH_2O)_{y2}CH(R^1)_2$, FG1-$(CH_2CH_2O)_{y2}C(R^1)_3$, FG1-$CH(R^1)_2$, FG1-$C(R^1)_3$, wherein $R^1$ is independently selected from $(CH_2)_{y3}$-FG2, $(OCH_2CH_2)_{y3}$-FG2 or $CH_2$ $(OCH_2CH_2)_{y3}$-FG2) and y2 and y3 are each an integer number of repeating units selected from between 1 to 6.

A non-limiting example of FG1-$CH(R^1)_2$, wherein FG1 is $NH_2$, $R^1$ is $CH_2$ $(OCH_2CH_2)_{y3}$-FG2, y3 is 1 and FG2 is COOH is shown here for clarity:

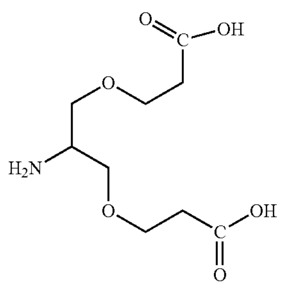 [SMILES: NC(COCCC(=O)O)COCCC(=O)O]

wherein the above monomer is used to produce a 2nd generation amplifying linker, the structure is:

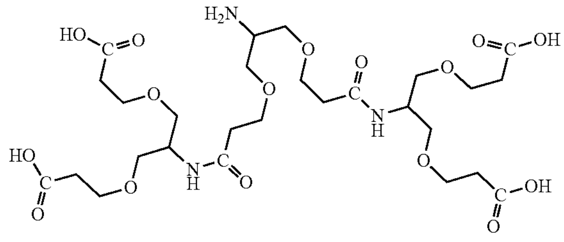 [SMILES: NC(COCCC(=O)NC(COCCC(=O)O)COCCC(=O)O)COCCC(=O)NC(COCCC(=O)O)COCCC(=O)O]

Additional non-limiting examples of monomers comprising a first functional group and a second functional group, wherein the first functional group is reactive towards the second functional group, and the monomer comprises at least one first functional group and two or more second functional groups include FG1-$(CH_2)_{y2}N(R^2)_2$, FG1-$(CH_2CH_2O)_{y2}CH_2CH_2N(R^2)_2$, wherein $R^2$ is independently selected from $(CH_2)_{y3}$-FG2, $(CH_2CH_2O)_{y3}(CH_2)_{y4}$-FG2, $(CH_2OCH_2CH_2)_{y3}$-FG2) and y2, y3 and y4 are each an integer of repeating units selected from between 1 to 6. Note: in the above example, FG' is an amine and the 4 FGt are carboxylic acids.

A non-limiting example of FG1-$(CH_2CH_2O)_{y1}CH_2CH_2N(R^2)_2$, wherein FG1 is $NH_2$, $R^2$ is $(CH_2CH_2O)_{y3}(CH_2)_{y4}$-FG2, y2 is 2, y3 is 1, y4 is 2 and FG2 is COOH is shown here for clarity:

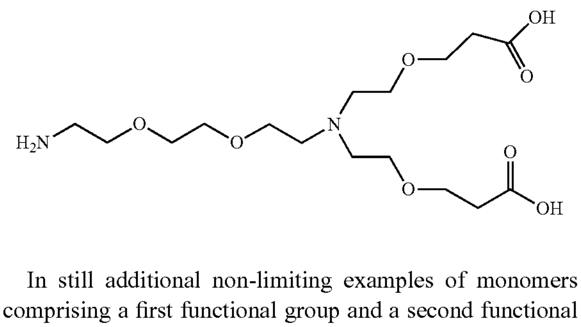

In still additional non-limiting examples of monomers comprising a first functional group and a second functional group, wherein the first functional group is reactive towards the second functional group, and the monomer comprises at least one first functional group and two or more second functional groups include certain amino acids, such as glutamic acid, aspartic acid, lysine or ornithine. A non-limiting example of a 3rd generation lysine dendron is shown here for clarity:

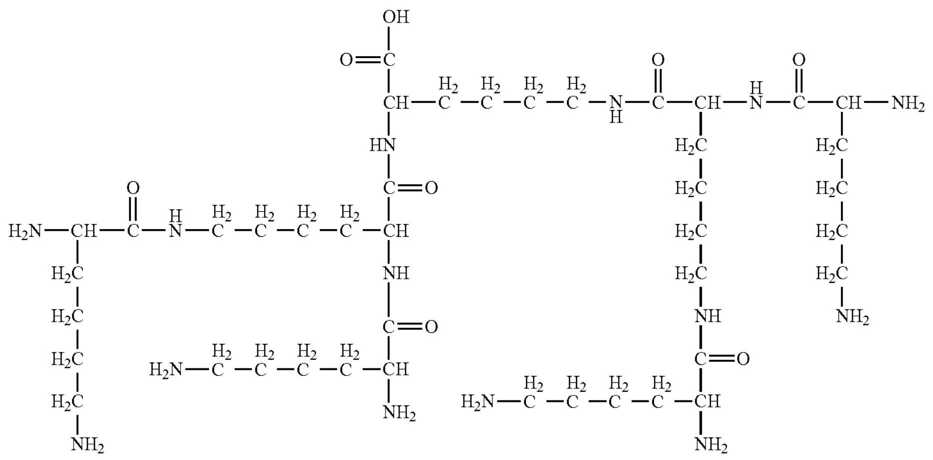 [SMILES: NCCCCC(N)C(=O)NCCCCC(NC(=O)C(N)CCCCN)C(=O)NCCCCC(NC(=O)C(CCCCNC(=O)C(N)CCCCN)NC(=O)C(N)CCCCN)C(=O)O]

Dendron amplifiers may comprise repeats of two monomers, wherein a first monomer comprises three or more first functional groups (FG1) and the second monomer comprises two or more second functional groups (FG2), wherein the first functional group is reactive towards the second functional group. For instance, a non-limiting example of a 2nd generation dendron amplifier with β=2 comprising repeats of a first and second monomer, wherein the first monomer comprises three first functional groups (FG1) and the second monomer comprises two second functional groups (FG2), wherein the first functional group is reactive towards the second functional group, is shown here for clarity:

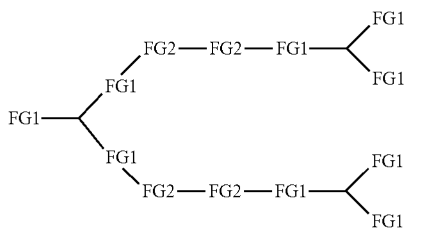

A non-limiting example of a 1st generation dendron amplifier with β=2 comprising repeats of a first and second monomer, wherein the first monomer comprises three first functional groups (FG1) and the second monomer comprises three second functional groups (FG2), wherein the first functional group is reactive towards the second functional group, is shown here for clarity:

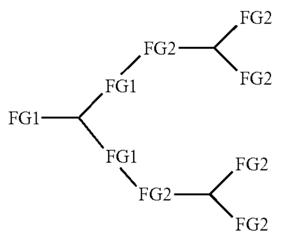

Dendron amplifiers may be used to join together any three or more components of amphiphiles, peptide antigen conjugates and drug molecule conjugates. The focal point functional group (FG') and the terminal functional groups (FGt) may be further functionalized, i.e., reacted to fit a particular purpose.

In preferred embodiments of amphiphiles of formula S-[B]-[U]-H, the solubilizing block(S) comprises a dendron amplifier wherein the focal point is linked to the hydrophobic block (H) either directly or indirectly via a spacer (B) and/or Linker U and the terminal functional groups (FGt) either are unlinked and serve as the solubilizing groups or are linked to a solubilizing group (SG). Solubilizing groups (SG) are any molecules that are hydrophilic and/or charged; preferred solubilizing groups (SG) are described throughout the specification.

In some embodiments of amphiphiles of formula S-[B]-[U]-H-D, peptide antigen conjugates of formula PEG-[E1]-A-[E2]-[U]-H-D or H-D-[U]-[E1]-A-[E2]-PEG) and drug molecule conjugates of formula H-D, the hydrophobic block (H) comprises a dendron amplifier wherein the focal point is linked to either (i) a solubilizing block(S) either directly or indirectly via a spacer (B) and/or Linker U, (ii) an antigen (A) either directly or indirectly via an extension (E1 or E2) and/or Linker U; or (iii) a drug molecule either directly or via a Linker X1.

In some embodiments, the hydrophobic block (H) comprises a dendron amplifier and the terminal functional groups (FGt) are linked to hydrophobic drug molecules. In such embodiments, the focal point is linked to either (i) a solubilizing block(S) either directly or indirectly via a spacer (B) and/or Linker U, (ii) an antigen (A) either directly or indirectly via an extension (E1 or E2) and/or Linker U; or (iii) is unreacted or capped with a terminal group, such as an acetyl group. Capped or capping refers to the modification of a functional group, such as FGt, to make it less reactive and/or have neutral charge at pH 7.4. For example, an amine may be capped with an activated carboxylic acid (e.g., acetyl chloride) to result in a relatively less reactive amide; or, e.g., a strained alkyne may be capped with an alkyl-azide to result in a relatively less reactive triazole.

Hydrophobic Block (H)

The hydrophobic block (sometimes designated "H" in formulae) is a molecule with substantially limited water solubility, or is amphiphilic in properties, and capable of assembling into supramolecular structures, e.g., micellar, nano- or micro-particles in aqueous solutions. In certain embodiments, the hydrophobic block (H) is insoluble, or forms micelles, in aqueous solutions at concentrations less than about 1.0 mg/mL, e.g., about 0.1 mg/mL or about 0.01 mg/mL. In some embodiments, the hydrophobic block is soluble in aqueous solutions at certain concentrations, temperatures and/or pH ranges but becomes insoluble in response to a change in concentration, temperature and/or pH. For instance, in some embodiments, the hydrophobic block is a hydrophobic polymer that is temperature-responsive, i.e., the hydrophobic polymer is soluble in aqueous solutions at temperatures below a transition temperature (Ttr) but becomes insoluble at temperatures above the transition temperature. Preferred hydrophobic blocks (H) are molecules that have a solubility of at least less than about 1.0 mg/mL, such as less than about 0.1 mg/mL or less than about 0.01 mg/mL, at or near physiologic pH (~ pH 7.4), between about pH 6.5 to pH 8.5 or between about pH 6.0 and pH 9.0, and at or near physiologic temperature (~ 37° C.) and physiologic salt concentrations (~10 g/L) and salt composition.

The hydrophobic block (H) may be chosen from any molecule comprising higher alkanes, cyclic aromatics, fatty acids, compounds deriving from terpenes/isoprenes, or polymers or oligomers that have limited water solubility and/or amphiphilic characteristics.

Exemplary higher alkanes include but are not limited to octane, nonane, decane, undecane, dodecane, tridecane, tetradecane, pentadecane, hexadecane, heptadecane and octadecane. Exemplary cyclic aromatics include but are not limited to phenyl. Exemplary saturated and unsaturated fatty acids include but are not limited to myristic acid, palmitic acid, stearic acid or oleic acid. In some embodiments, the hydrophobic block (H) is a fatty acid, for example myristic acid. In other embodiments, the hydrophobic block (H) comprises a diacyl lipid, such as 1,2-dioleoyl-sn-glycero-3-phosphoethanolamine or 1,2-distearoyl-sn-glycero-3-phosphoethanolamine or a lipopeptide, e.g., Pam2Cys. In some embodiments, the fatty acid or lipid based hydrophobic block (H) may further comprise a PEG. Exemplary compounds deriving from terpenes/isoprene include sterol derivatives, such as cholesterol, and squalene. In some embodiments, the hydrophobic block (H) comprises cholesterol. In some embodiments, the hydrophobic block (H) comprises a saponin, e.g., QS-21.

In some embodiments the hydrophobic block (H) is a linear, branched or brush polymer (or oligomer). The hydrophobic block (H) can be a homopolymer or copolymer. The hydrophobic block (H) can comprise one or many different types of monomer units. The hydrophobic block (H) can be a statistical copolymer or alternating copolymer. The hydrophobic block (H) can be a block copolymer, such as the A-B type, or the polymer can comprise a grafted copolymer, whereby two or more polymers are linked through polymer analogous reaction.

The hydrophobic block (H) may comprise polymers comprising naturally occurring and/or non-natural monomers and combinations thereof.

In some embodiments, the hydrophobic block (H) is selected from natural biopolymers. Natural biopolymers may include peptides (sometimes referred to as poly(amino acids)) which comprise hydrophobic amino acids. Non-limiting examples of hydrophobic amino acids include leucine, isoleucine, norleucine, valine, tryptophan, phenylamine, tyrosine and methionine, as well as hydrophilic amino acids that have been modified, such as by acetylation or benzoylation to have hydrophobic characteristics. Natural biopolymers that are water soluble in their native form may be used but must be modified chemically to make such natural biopolymers water insoluble and suitable for use as hydrophobic block (H). For example, biopolymers which comprise of hydrophilic amino acids, such as glutamic acid or lysine residues may be modified at the gamma carboxyl or epsilon amine groups, respectively, for the attachment of a hydrophobic molecule, such as a hydrophobic drug molecule, to increase the hydrophobicity of the resulting modified biopolymer. Similarly, biopolymers can be selected from hydrophilic polysaccharides, which may include but are not limited to glycogen, cellulose, dextran, alginate and chitosan, but such polysaccharides should be modified chemically, for example via acetylation or benzoylation of hydrophilic functional groups to render the resulting modified polysaccharide water insoluble. In still further embodiments the hydrophobic block comprises monomers selected from lactic acid and/or glycolic acid.

Monomers comprising the hydrophobic block (H) can be selected from acrylates, (meth)acrylates, acrylamides, (meth)acrylamides, allyl ethers, vinyl acetates, vinyl amides, substituted styrenes, amino acids, acrylonitrile, heterocyclic monomers (e.g., ethylene oxide), saccharides, phosphoesters, phosphonamides, sulfonate esters, sulfonamides, or combinations thereof. Specific examples of (meth)acrylates and (meth)acrylamides include benzyl methacrylamide (BnMAM) and benzyl methacrylate (BnMA), respectively.

Certain monomers described herein as hydrophobic monomers may be water soluble under certain conditions but are hydrophobic and water insoluble at certain conditions in aqueous solutions. Non-limiting examples include temperature-responsive monomers, such as N-isopropylmethacrylamide (NIPMAM); a homopolymer comprising entirely of NIPMAM may be water soluble at room temperature but may become insoluble and form particles at elevated temperatures. Such distinctions are made to facilitate description of certain embodiments. In some embodiments, the hydrophobic block comprises a majority of monomer units selected from hydrophobic monomers that are temperature-responsive (sometimes referred to as "temperature-responsive monomers"), such as NIPAM, NIPMAM, N,N'-diethylacrylamide (DEAAM), N-(L)-(1-hydroxymethyl) propyl methacrylamide (HMPMAM), N,N'-dimethylaminoethylmethacrylate (DMEMA), N—(N-ethylcarbamido) propylmethacrylamide, N-vinylisobutyramide (PNVIBA), N-vinyl-n-butyramide (PNVBA), N-acryloyl-N-propylpiperazine (PNANPP), N-vinylcaprolactam (PVCa), DEGMA, TEGMA, or poly (amino acids) or γ-(2-methoxyethoxy) esteryl-L-glutamate. In still other embodiments, the hydrophobic block (H) may comprise monomers of ethylene oxide, propylene oxide or combinations thereof.

Hydrophobic blocks (H) comprising a polymer typically comprise hydrophobic monomers and one or more other types of monomers, such as reactive monomers optionally linked to a drug molecule, spacer monomers and/or charged monomers. In some embodiments of hydrophobic blocks (H) comprising a polymer (or oligomer), a majority of monomer units are selected from hydrophobic monomers. In other embodiments of hydrophobic blocks (H) comprising a polymer (or oligomer), a majority of monomer units are selected from reactive monomers linked to hydrophobic drug molecules. In still other embodiments of hydrophobic blocks (H) comprising a polymer (or oligomer), the polymer comprises hydrophobic monomers and reactive monomers linked to hydrophobic drug molecules. In still further embodiments of hydrophobic blocks (H) comprising a polymer (or oligomer), the polymer comprises hydrophobic monomers and charged monomers and optionally reactive monomers linked to hydrophobic drug molecules.

In preferred embodiments, the hydrophobic block (H) comprises a polymer (or oligomer) that comprises hydrophobic monomers that further comprise aryl groups. In certain embodiments, the hydrophobic block (H) comprises heteroaryl groups. In still other embodiments, the aryl or heteroaryl groups of the hydrophobic block (H) comprise an amino substituent. The present inventors found that hydrophobic blocks (H) comprising aminoaryl or aminoheteroaryl groups lead to improved manufacturability and solubility in water-miscible solvents. The present inventors also found that amphiphiles with hydrophobic blocks (H) comprising aromatic amines lead to formation of stable particles with low CMC.

In preferred embodiments, the hydrophobic block (H) comprises monomers that comprise aryl or heteroaryl groups. Exemplary aryl groups (sometimes referred to as "aromatics" or "aromatic rings") include but are not limited to phenyl, naphthyl, and quinolinyl. Non-limiting examples include:

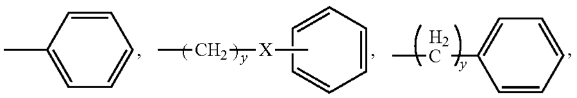

where y = 1 to 6 where y = 1 to 6

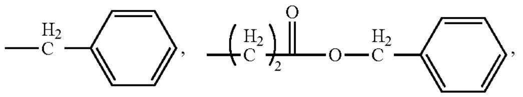

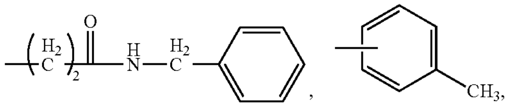

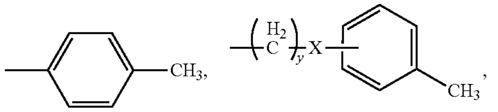

where y = 1 to 6

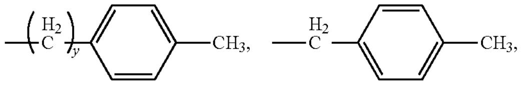

where y = 1 to 6

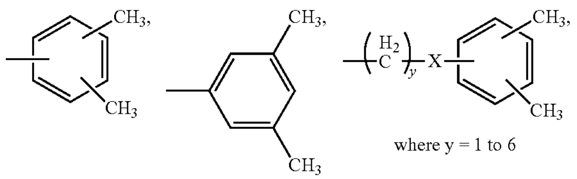

where y = 1 to 6

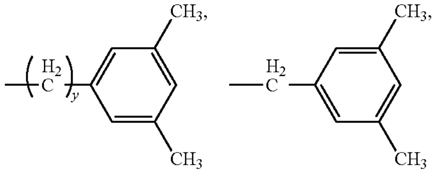

where y = 1 to 6

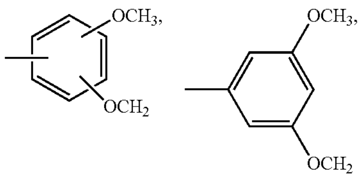

-continued

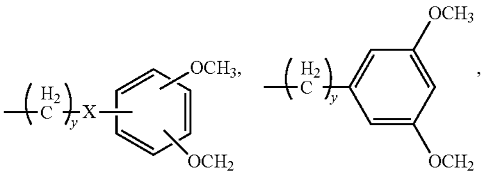

where y = 1 to 6 where y = 1 to 6

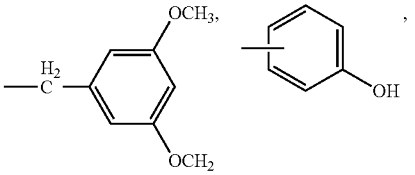

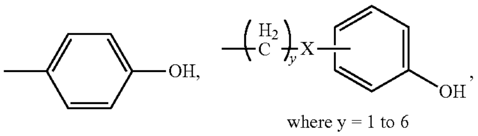

where y = 1 to 6

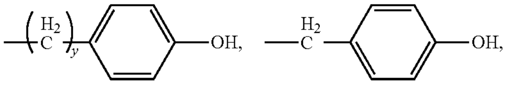

where y = 1 to 6

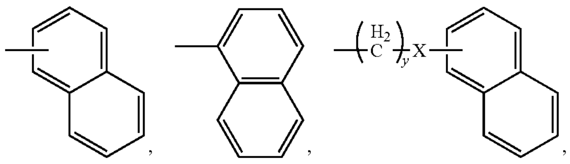

where y = 1 to 6

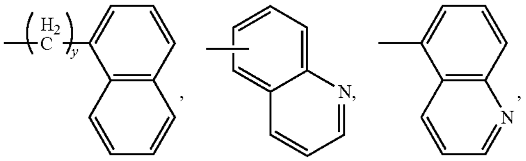

where y = 1 to 6

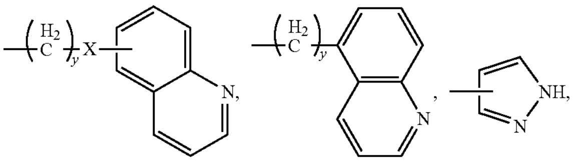

where y = 1 to 6 where y = 1 to 6

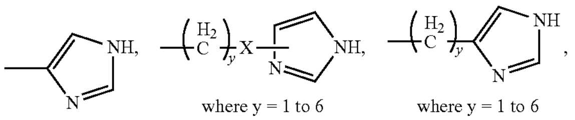

where y = 1 to 6 where y = 1 to 6

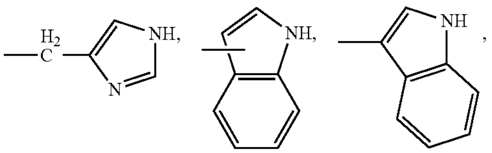

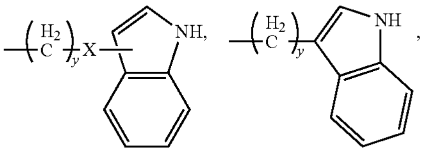

where y = 1 to 6 where y = 1 to 6

-continued

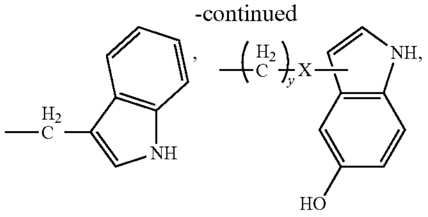

where y = 1 to 6

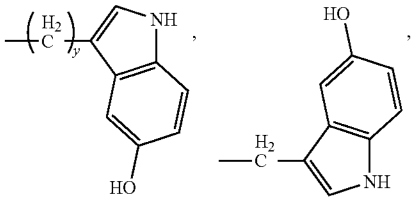

where y = 1 to 6

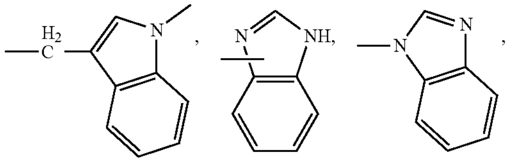

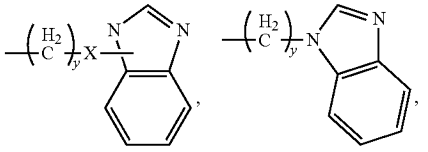

where y = 1 to 6 where y = 1 to 6

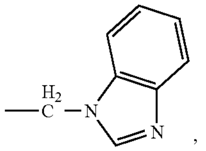

wherein X is any suitable linker molecule and y is an integer value, typically between 1 and 6.

In preferred embodiments, aryl or heteroaryl groups include but are not limited to

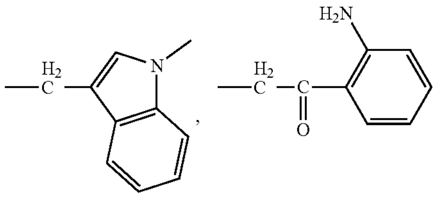

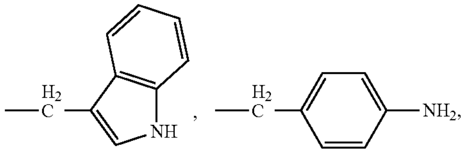

and

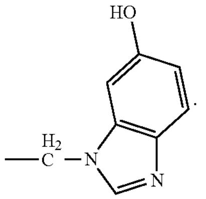

Furthermore, in the aforementioned aryl or heteroaryl groups one or more hydrogen atoms may be substituted for one or more fluorine atoms. In certain embodiments, the hydrophobic block comprises fluorinated aliphatic, aryl or heteroaryl groups, wherein one or more hydrogen atoms of the aforementioned groups comprising the hydrophobic monomer may be substituted for one or more fluorine atoms. The following non-limiting examples of fluorinated aryl groups may be present in hydrophobic monomers:

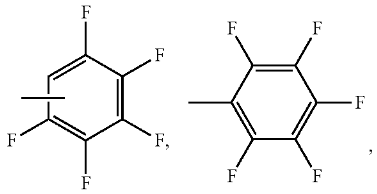

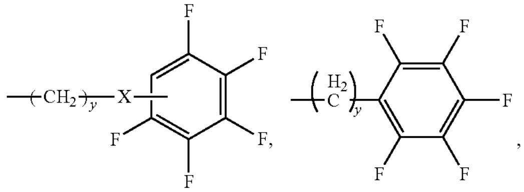

where y = 1 to 6 where y = 1 to 6

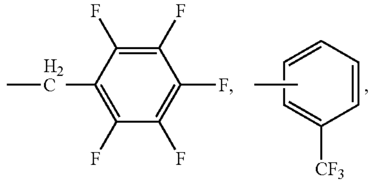

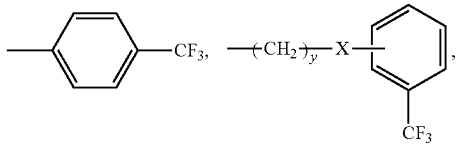

where y = 1 to 6

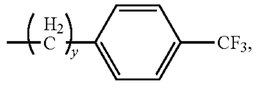

where y = 1 to 6

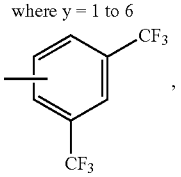

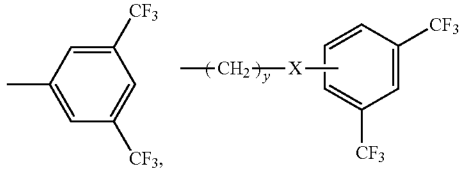

and where y = 1 to 6

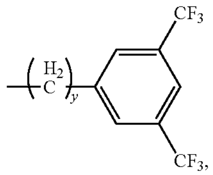

where y = 1 to 6 wherein X is any suitable linker molecule and y is an integer value, typically between 1 and 6.

The present inventors have unexpectedly found that hydrophobic blocks (H) comprising aminoaryl or aminoheteroaryl groups lead to improved manufacturing and solubility in polar aprotic solvents and alcohols. Therefore, in certain preferred embodiments, the hydrophobic block (H) comprises moieties of the formula —Ar-NHR, where Ar can be a aryl or heteroaryl, and R is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl. Non-limiting examples of aminoaryl or aminoheteroaryl groups include but are not limited to:

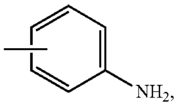 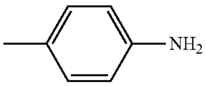,

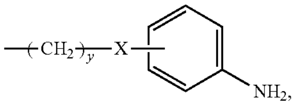 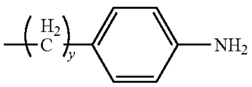, where y = 1 to 6 where y = 1 to 6

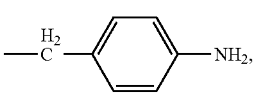 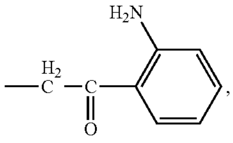,

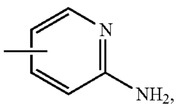 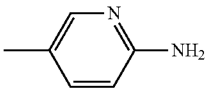,

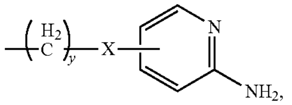 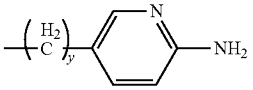, where y = 1 to 6 where y = 1 to 6

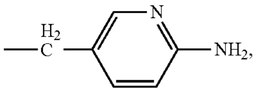 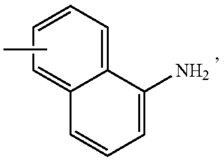,

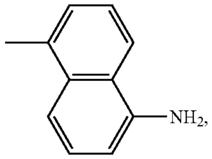 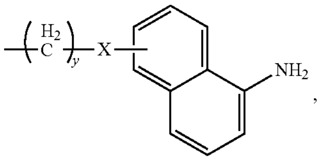, where y = 1 to 6

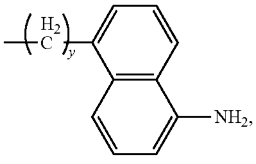 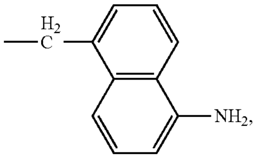

where y = 1 to 6

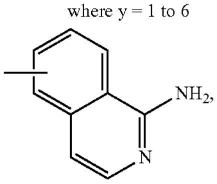 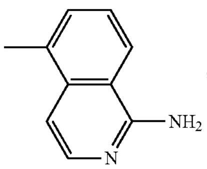,

-continued

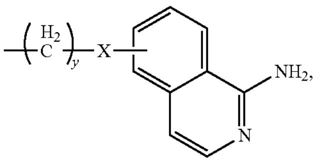

where y = 1 to 6

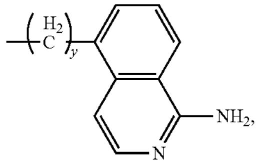 and 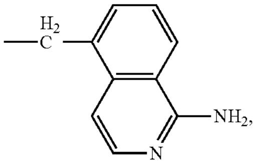

where y = 1 to 6 wherein X is any suitable linker molecule and y is an integer value, typically between 1 and 6.

In some embodiments, the hydrophobic block (H) comprises polymers (or oligomers) that further comprise hydrophobic monomers with fused aryl groups (e.g., naphthyl) or fused heteroaryl groups (e.g., xanthenyl or quinolinyl). In some embodiments, the hydrophobic block (H) comprises reactive monomers linked to hydrophobic drug molecules. In some embodiments, the hydrophobic drug molecules (e.g., imidazoquinolines) are aromatic and thus the reactive monomers linked to hydrophobic drug molecules comprising aromatic groups may also be described as hydrophobic monomers comprising aromatic groups or reactive monomers linked to drugs.

In some embodiments, the hydrophobic block (H) comprises a poly(amino acid) of Formula I:

$$(M)_m\text{-}(N)_n\text{-}(O)_o\text{-}(P)_p\text{-}R^3$$

wherein the poly(amino acid) of Formula I comprises monomers selected from hydrophobic amino acids (M), reactive amino acids (N), spacer amino acids (O), charged amino acids (P) and combinations thereof provided that at least monomer M or N are present; m, n, o and p denote that there are an integer of repeat units of monomers M, N, O and P, respectively, which may be distributed along the polymer in a specific or random order; and $R^3$ is typically selected from hydrogen, $NH_2$, $NH_2$—$CH_3$, $NH_2$—$(CH_2)_{y5}CH_3$, OH, or drug molecules (D) either linked directly or through X1.

In some embodiments, P is absent. In other embodiments, N, O, and P are each absent.

In some embodiments, P

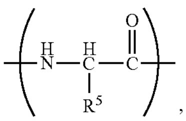, is wherein each $R^5$, independently, is a group that comprises 1 to 2 charged functional groups.

In some embodiments, O is

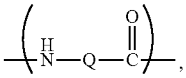, wherein each Q, independently, is selected from $(CH_2)_{y6}$ and $(CH_2CH_2O)_{y7}CH_2CH_2$; each y6 is independently selected from an integer from 1 to 6; and each y7 is independently selected from an integer from 1 to 4.

In some embodiments, N is

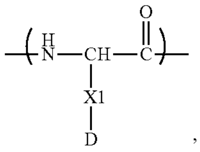
, wherein each X1, independently, is a suitable linker; and each D, independently, is a drug molecule.

In some embodiments, M is

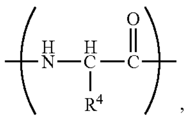
, wherein each $R^4$ is, independently, a hydrophobic group.

In some embodiments, the hydrophobic block (H) comprises a poly(amino acid) of Formula I:

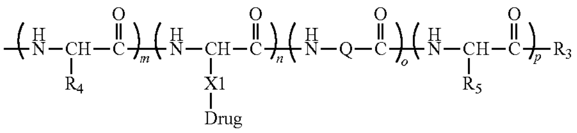

wherein the poly(amino acid) of Formula I comprises monomers selected from hydrophobic amino acids (M), reactive amino acids (N), spacer amino acids (O), charged amino acids (P) and combinations thereof provided that at least monomer M or N are present; m, n, o and p denote that there are an integer of repeat units of monomers M, N, O and P, respectively, which may be distributed along the polymer in a specific or random order; $R^3$ is typically selected from hydrogen, $NH_2$, $NH_2$—$CH_3$, $NH_2$—$(CH_2)_{y5}CH_3$, OH, or drug molecules (D) either linked directly or through X1; $R^4$ is any hydrophobic group typically selected from aryl or heteroaryl groups; $R^5$ is any group that comprises one or more functional groups that are charged in aqueous solutions or are pH-responsive and charged in aqueous solutions at certain pH ranges; Q is typically selected from any lower alkyl or heteroalkyl including but not limited to $(CH_2)_{y6}$ and $(CH_2CH_2O)_{y7}CH_2CH_2$, where y6 is any integer from 1 to 6 and y7 is an integer typically selected from 1 to 4; and, the N-terminus is linked to either (i) a solubilizing block(S) directly or indirectly via a spacer (B) and/or a Linker U; (ii) a peptide antigen (A) either directly or indirectly via an extension (E1 or E2) and/or Linker U; or (iii) a drug molecule either directly or via X1. Note: hydrophobic amino acids, reactive amino acids, spacer amino acids and charged amino acids are sometimes described more generally as hydrophobic monomers, reactive monomers, spacer monomers and charged monomers, respectively.

In preferred embodiments of poly(amino acids) of Formula I, $R^4$ is

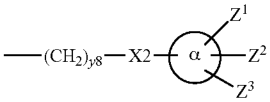

wherein,

α is aryl or heteroaryl;

X2 is present or absent and when present is a suitable linker;

y8 is selected from an integer from 0 and 6; and $Z^1$, $Z^2$, and $Z^3$ are each independently selected from H, F, hydroxy, amino, alkyl, and fluoroalkyl.

In preferred embodiments of poly(amino acids) of Formula I, a is aryl, e.g., phenyl or naphthyl. In other embodiments, a is heteroaryl, e.g., imidazolyl, pyridinyl, quinolinyl, isoquinolinyl, indolyl, and benzimidazolyl.

In preferred embodiments of poly(amino acids) of Formula I, X2 is absent. In other embodiments, X2 is present and is selected from C(O), $CO_2$ $(CH_2)_{y9}$, and C(O) NH $(CH_2)_{y9}$, NHC(O) and NHC(O)$(CH_2)_{y9}$, wherein y9 is an integer typically selected from 1 to 6. In other embodiments, X2 is present and is selected from lower alkyl and PEG groups.

In preferred embodiments of poly(amino acids) of Formula I, the poly(amino acid) of Formula I comprises hydrophobic amino acids, M, selected from any natural or non-natural amino acid that comprises a hydrophobic group, $R^4$. In preferred embodiments, $R^4$ is selected from hydrophobic groups comprising aryl groups, heteroaryl groups, aminoaryl, and/or aminoheteroaryl. Non-limiting examples of $R^4$ include but are not limited to:

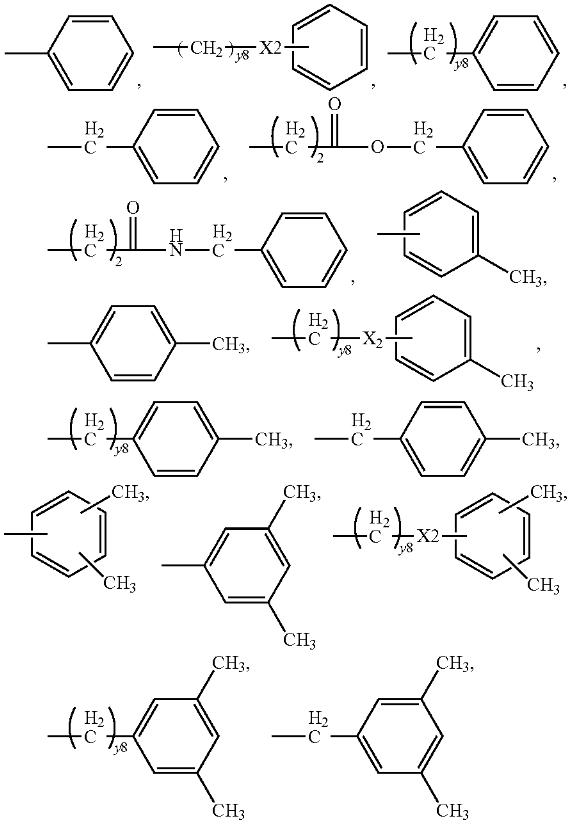

-continued
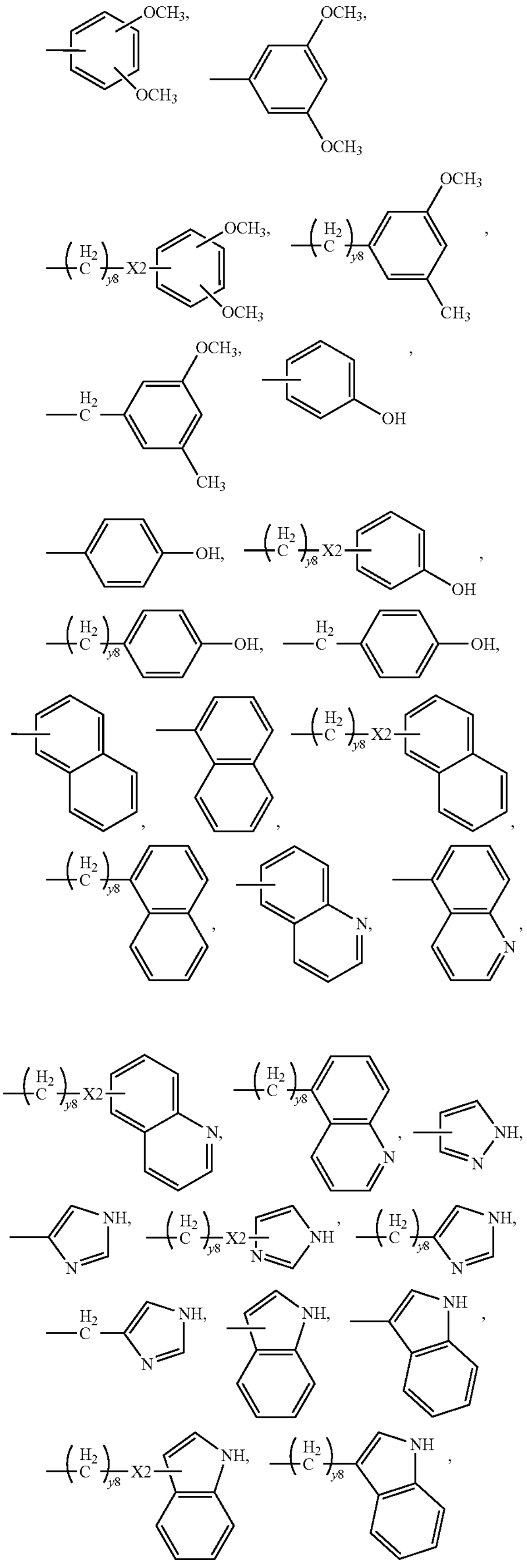
-continued
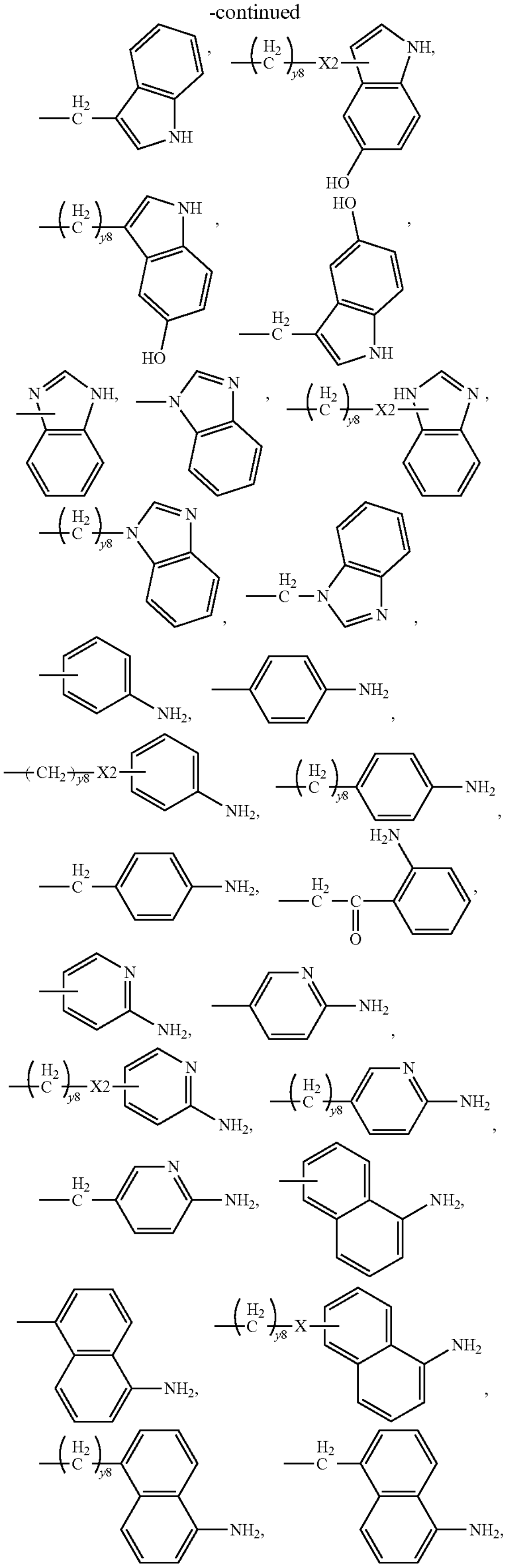

-continued

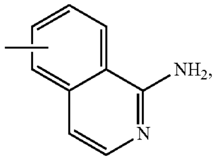

,

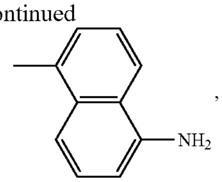

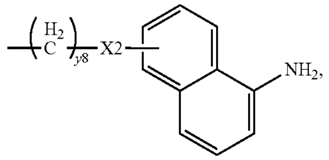

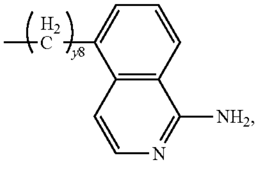

and

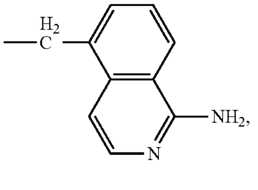

wherein X2 is any suitable linker molecule and y8 is an integer value, typically between 0 and 6. In preferred embodiments y8 is 1.

In non-limiting examples, wherein $R^4$ is

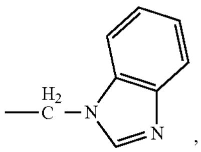

, monomer M is:

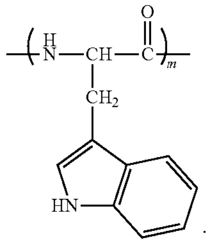

.

In some embodiments, the poly(amino acid)-based hydrophobic block (H) of Formula I comprises reactive amino acids, N, that are selected from any natural or non-natural amino acid, wherein a drug molecule (D) is linked directly or through X1 to the monomer. Suitable reactive amino acids include but are not limited to any amino acids bearing a group suitable for attachment of drug molecules, include amino acids with azide, alkyne, tetrazine, transcyclooctyne (TCO), protected hydrazine, ketone, aldehyde, certain hydroxyl groups, isocyanate, isothiocyanate, carboxylic acids, activated carboxylic acids, activated carbamates, activated carbamates, protected maleimide, thiol and/or amine groups.

X1 is any suitable linker for linking drug molecules, D, to the hydrophobic block (H), including to the reactive amino acid, N, of poly(amino acids) and is typically selected from —$(CH_2)_{y10}$-FG3 and —$(CH_2)_{y10}$—$R^6$ (or —C(O)—$(CH_2)_{y10}$-FG3 and —C(O)—$(CH_2)_{y10}$—$R^6$ when drugs are linked at the N-terminus or off of amine groups, or —NH—$(CH_2)_{y10}$-FG3 and —NH—$(CH_2)_{y10}$—$R^6$ when drugs are linked at the C-terminus or off of carbonyl groups), wherein y10 is any integer, typically selected from 1 to 6, and $R^6$ is typically selected from any one or more of —C(O)—NH—$R^7$, —NH—C(O)—$R^7$, —NH—C(O)—O—$R^7$, —O—C(O)—NH—$R^7$, —O—C(O)—$R^7$, —C(O)—O—$R^7$, —O—$R^7$, O—C(O)—W, or —C(O)—W, wherein $R^7$ is typically selected from any one or more of —$(CH_2)_{y11}$—W, —$(CH_2)_{y11}$—$(OCH_2CH_2)_{y12}$—W, —$(CH_2)_{y11}$—$(OCH_2CH_2)_{y12}$—$(CH_2)_{y13}$—W, —$CHR^8$—C(O)—W, —$CHR^8$—C(O)—(NH—$CHR^8$—C(O))$_j$—W, —$(CH_2)_{y11}$—C(O)—NH—$CHR^8$—C(O)—W, —$(CH_2)_{y11}$—C(O)—NH—$CHR^8$—C(O)—(NH—$CHR^8$—C(O))$_j$—W, —$(CH_2)_{y11}$—$(OCH_2CH_2)_{y12}$—C(O)—NH—$CHR^8$—C(O)—W, —$(CH_2)_{y11}$—$(OCH_2CH_2)_{y12}$—$(CH_2)_{y13}$C(O)—NH—$CHR^8$—C(O)—W, —$(CH_2)_{y11}$—$(OCH_2CH_2)_{y12}$—C(O)—NH—$CHR^8$—C(O)—(NH—$CHR^8$—C(O))$_j$—W, —$(CH_2)_{y11}$—$(OCH_2CH_2)_{y12}$—$(CH_2)_{y13}$—C(O)—NH—$CHR^8$—C(O)—(NH—$CHR^8$—C(O))$_j$—W, —$CHR^8$—C(O)—NH—$C_6H_4$—$CH_2$—O—C(O)—W, —$CHR^8$—C(O)—NH($CH_3$)$(CH_2)_2$—O—C(O)—W, —$CHR^8$—C(O)—(NH—$CHR^8$—C(O))$_j$—NH—$C_6H_4$—$CH_2$—O—C(O)—W, —$CHR^8$—C(O)—(NH—$CHR^8$—C(O))$_j$—NH($CH_3$)$(CH_2)_2$—O—C(O)—W, —$(CH_2)_{y11}$—C(O)—(NH—$CHR^8$—C(O))$_j$—NH—$C_6H_4$—$CH_2$—O—C(O)—W, —$(CH_2)_{y11}$—C(O)—(NH—$CHR^8$—C(O))$_j$—NH($CH_3$)$(CH_2)_2$—O—C(O)—W, —$(CH_2)_{y11}$—$(OCH_2CH_2)_{y12}$—C(O)—(NH—$CHR^8$—C(O))$_j$—NH—$C_6H_4$—$CH_2$—O—C(O)—W, —$(CH_2)_{y11}$—$(OCH_2CH_2)_{y12}$—C(O)—(NH—$CHR^8$—C(O))$_j$—NH($CH_3$)$(CH_2)_2$—O—C(O)—W, —$(CH_2)_{y11}$—$(OCH_2CH_2)_{y12}$—$(CH_2)_{y13}$C(O)—(NH—$CHR^8$—C(O))$_j$—NH—$C_6H_4$—$CH_2$—O—C(O)—W, —$(CH_2)_{y11}$—$(OCH_2CH_2)_{y12}$—$(CH_2)_{y13}$C(O)—(NH—$CHR^8$—C(O))$_j$—NH($CH_3$)$(CH_2)_2$—O—C(O)—W, —$(CH_2)_{y11}$—$(OCH_2CH_2)_{y12}$—$(CH_2)_{y13}$—C(O)—NH—$(CH_2)_{y14}$—C(O)—(NH—$CHR^8$—C(O))$_j$—NH—$C_6H_4$—$CH_2$—O—C(O)—W, —$(CH_2)_{y11}$—$(OCH_2CH_2)_{y12}$—$(CH_2)_{y13}$C(O)—NH—$(CH_2)_{y14}$—C(O)—(NH—$CHR^8$—C(O))$_j$—NH($CH_3$)$(CH_2)_2$—O—C(O)—W, —$(CH_2)_{y11}$—$(OCH_2CH_2)_{y12}$—C(O)—NH—$(CH_2)_{y14}$—C(O)—(NH—$CHR^8$—C(O))$_j$—NH—$C_6H_4$—$CH_2$—O—C(O)—W, —$(CH_2)_{y11}$—$(OCH_2CH_2)_{y12}$—C(O)—NH—$(CH_2)_{y14}$—C(O)—(NH—$CHR^8$—C(O))$_j$—NH($CH_3$)$(CH_2)_2$—O—C(O)—W, —$CHR^8$—C(O)—NH—$(CH_2)_{y15}$—W, —$CHR^8$—NH—C(O)—$(CH_2)_{y15}$—W, —$CHR^8$—C(O)—(NH—$CHR^8$—C(O))$_j$—NH—$(CH_2)_{y15}$—W, —$CHR^8$—NH—(C(O)—$CHR^8$—NH)$_j$—C(O)—$(CH_2)_{y15}$—W, where y11, y12, y13, y14, y15 and j are each independently selected from any integer typically selected from 1 to 6, $R^8$ is any amino acid side group, and W can be independently selected from H (hydrogen), FG3, LG and w; wherein FG3 is any suitable functional group for attachment to the drug molecule, which may be selected from, but not limited to, carboxylic acid, activated carboxylic acids (e.g., carbonylthiazolidine-2-thione ("TT"), NHS or nitrophenol esters), carboxylic acid anhydrides, amine and protected amines (e.g., tert-butyloxycarbonyl protected amine), $OSi(CH_3)$, alkene, azide, alkyne, stained-alkyne, halogen (e.g., fluoride, chloride), olefins and endo cyclic olefins (e.g., allyl), CN, OH, and epoxy, hydrazines (including hydrazides), carbohydrazides, aldehydes, ketones, carbamates and activated carbamates, LG is any suitable leaving group, which may be selected from, but not limited to any suitable leaving group (e.g., NHS, TT, nitrophenol, etc.), and, w is a group that results from either the reaction of FG4 with FG3 or the displacement of LG with FG4, and is typically selected from NH—, C(O)—, NH—C(O)—, C(O)—NH—, O—C(O)—NH—, C(O)—NH—N═C($CH_3$)—, NH—N═C($CH_3$)— or —$C(CH_3)$=N—NH—C(O)—, wherein w is always linked to D either directly (i.e., w-D) or indirectly via X3 (i.e., w-X3-D).

Drug molecules (D) may be attached to the reactive amino acid, N, directly or via X1 through reaction of FG4 with FG3, wherein FG4 is any suitable functional group on the drug (D) that is reactive with FG3. Alternatively, drug molecules (D) may be linked to the reactive amino acid, N, via X1 through displacement of LG with any suitable FG4 comprising a nucleophile, e.g., a primary amine, or drug molecules (D) may be linked to the reactive amino acid, N, via X1 through displacement of an LG present on the drug molecule with any suitable FG3 comprising a nucleophile.

In preferred embodiments, FG3 is a carboxylic acid and FG4 is an amine, which react to form an amide. In non-limiting examples, X1 is selected from —$(CH_2)_{y10}$-FG3, y10 is 2, FG3 is a carboxylic acid, and FG4 present on the drug is an amine (i.e., $NH_2$-D), which react to form an amide, which may be represented as —$(CH_2)_2$—C(O)-D (amine not shown) or —$(CH_2)_2$—C(O)—NH-D (amine shown), indicating that the drug is linked via an amide bond at the carbonyl of X1, which (after amide bond formation) may be described as —$(CH_2)_{y10}$—$R^6$, wherein y10 is 2, $R^6$=C(O)—W, and W is the group w, which is NH— and is linked to D to give-$(CH_2)_2$—C(O)—NH-D.

The drug may additionally comprise a linker, X3, between the reactive functional group FG4 and the pharmacophore, e.g., FG4-X3-D. Specific, preferred compositions of X3 are described elsewhere.

In other embodiments, FG3 is an amine and FG4 is a carboxylic acid, which react to form an amide. In non-limiting examples, X1 is —$(CH_2)_{y10}$-FG3, y10 is 4, FG3 is an amine, and FG4 present on the drug is a carboxylic acid (i.e., COOH-D), which react to form an amide, which may be represented as $(CH_2)_4$—NH-D (carbonyl not shown) or —$(CH_2)_4$—NH—C(O)-D (carbonyl shown), indicating that the drug is linked via an amide bond at the amine of X1.

In still other embodiments, FG3 is a ketone or aldehyde and FG4 is a hydrazide or carbohydrazide, which react to form a hydrazone. In non-limiting examples, X1 is —$(CH_2)_{y10}$—$R^6$, y10 is 4, $R^6$ is —NH—C(O)—$R^7$, $R^7$ is $(CH_2)_{y11}$—W, y11 is 2 and W is C(O)—$CH_3$, and FG4 present on the drug molecule is a hydrazide ($NH_2$—$NH_2$—C(O)-D), which reacts with X1, i.e., —$(CH_2)_4$—NH—C(O)—$(CH_2)_2$—C(O)—$CH_3$ to form a hydrazone bond, i.e., —$(CH_2)_4$—NH—C(O)—$(CH_2)_2$—$C(CH_3)$=N—NH—C(O)-D. In still other embodiments, FG3 is a hydrazide or carbohydrazide and FG4 is a ketone or aldehyde that reacts to form a hydrazone. In non-limiting examples, X1 is —$(CH_2)_{y10}$—$R^6$, y10 is 2, $R^6$ is —C(O)—W, W is FG3 and FG3 is-NH—$NH_2$ and FG4 present on the drug molecule is a ketone $CH_3C(O)$-D (or optionally $CH_3C(O)$-X3-D), which reacts with X1 to form-$(CH_2)_4$—C(O)—NH—$NH_2$ to form a hydrazone bind, i.e., form-$(CH_2)_4$—C(O)—NH—N=C$(CH_3)$-D.

In certain preferred compositions, drug molecules (D) are linked directly to the reactive amino acid, N. A non-limiting example of a reactive amino acid comprising a linker selected from —$(CH_2)_{y10}$-FG3, wherein y10=2, FG3 is carboxylic acid (i.e., the reactive amino acid is glutamic acid) linked to a drug molecule is shown below for clarity:

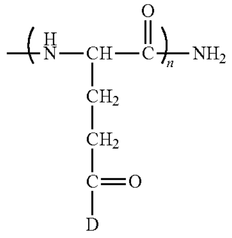

In certain other preferred embodiments, drug molecules (D) are linked to the reactive amino acid (N) via an enzyme degradable peptide and/or self-immolative linker, wherein the self-immolative linker is typically selected from —NH—$C_6H_4$—$CH_2$—O—C(O)— or —$NH(CH_3)(CH_2)_2$—O—C(O)— and FG4 present on the drug is an amine, e.g., $NH_2$-D or $NH_2$-X3-D, which results in a carbamate bond between the linker and the drug. In non-limiting examples, the reactive monomer comprises a linker selected from $(CH_2)_{y10}$—$R^6$, wherein y10=2, $R^6$ is —C(O)—NH—$R^7$ and $R^7$ is $(CH_2)_{y11}$—C(O)—(NH—$CHR^8$—C(O))$_j$—NH—$C_6H_4$—$CH_2$—O—C(O)—W, wherein y11 is 2, $R^8$ is any amino acid group, j is an integer typically selected from 1 to 6, W is selected from the group w, which is NH-linked to the drug (D), as shown here:

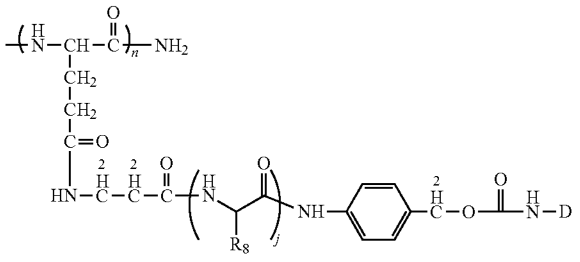

In preferred compositions of X1 comprising enzyme degradable linkers, the enzyme degradable linker typically comprises between 1 and 6 amino acids, such as 1, 2, 3, 4, 5 or 6 amino acids selected from single amino acids, dipeptides, tripeptides, tetrapeptides, pentapeptides and hexapeptides recognized and cleaved by enzymes, such as cathpesins and/or the immunoproteasome.

Reactive amino acids (N) may comprise functional groups that can impart charge; however, the classification of an amino acid as a reactive amino acid monomer is context-dependent and based on its intended use. For example, monomers comprising carboxylic acids may be referred to as charged monomers if the carboxylic acid is not used for drug attachment, whereas the same monomers linked to an amine bearing drug molecule, e.g., via an amide bind, would be considered a reactive monomer.

In some embodiments, the poly(amino acid)-based polymer of Formula I comprises spacer amino acids, O, that are selected from any natural or non-natural amino acid that are non-bulky and near neutral, such as a PEG amino acid spacer, e.g., Q of monomer O is a lower alkyl or PEG, e.g., —$(CH_2)_{y6}$—, —$CH_2$—$CH_2$—O— or —$(CH_2$—$CH_2$—O$)_{y7}CH_2$—$CH_2$—, wherein y6 and y7 are each independently an integer typically between 1 and 6. Alternatively, monomer O, is selected from amino acids with a small, i.e., non-bulky, substituent selected from hydrogen, lower alkyl or a lower alkyl comprising a hydroxyl and is provided to increase the spacing or flexibility of the polymer backbone.

Non-limiting examples include:

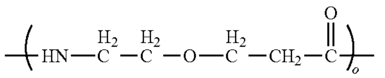

or

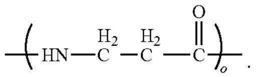

In some embodiments, the poly(amino acid)-based polymer of Formula I comprises optional co-monomer(s), P, that are selected from any natural or non-natural amino acid, wherein $R^5$ is selected from any group comprising a functional group that carries charge either permanently or at a specific pH in aqueous solutions. Non-limiting examples of charged amino acids include any natural or non-natural amino acid that comprise amine, quaternary ammonium, sulfonic acid, sulfuric acid, sulfonium, phosphoric acid, phosphonic acid, phosphonium, carboxylic acid, boronic acid functional groups and/or combination thereof, including zwitterions, which may be linked either directly or via a suitable linker molecule, as well as any composition of salts thereof. Non-limiting examples of salts include, e.g., positively charged functional groups, e.g., ammonium ions paired with halide (e.g., chloride) ions. Other non-limiting examples of suitable salts of charged amino acids include conjugate bases of carboxylic, sulfonic and phosphonic acids, paired with group 1 metals, such as sodium, or ammonium or guanidinium ions.

In some preferred embodiments of amphiphiles for nucleic acid delivery, the amphiphile comprises a hydrophobic block (H) further comprising a poly(amino acid)-based polymer of Formula I that includes $R^5$ selected from groups that have net positive charge, which include but are not limited to:

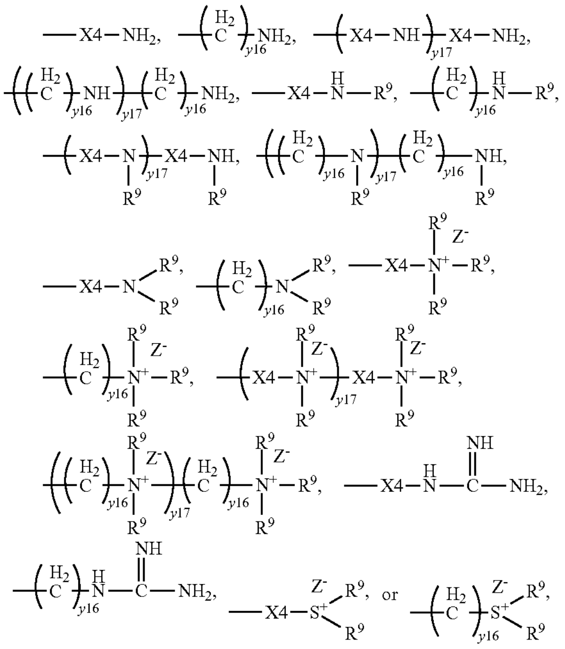

or wherein X4 is any suitable linker, y16 and y17 are each independently any integer, typically selected from between 1 to 6, $R^9$ is selected from lower alkyl or branched alkyl groups, such as $CH_3$, $CH_2CH_3$, $CH_2CH_2CH_3$, $CH(CH_3)_2$, $H_2CH(CH_3)_2$ or the like, and Z is any suitable counter anion, which is typically selected from conjugate bases of weak acids or halide ions, such as $Cl^-$, $I^-$, or $Br^-$.

The hydrophobic block (H) functions to drive particle assembly in aqueous solutions and therefore, in preferred embodiments of amphiphiles, peptide antigen conjugate or drug molecule conjugates, the hydrophobic block (H) comprises hydrophobic amino acids and/or reactive amino acids linked to hydrophobic drug molecules. In preferred embodiments of poly(amino acid)-based polymers of Formula I, the poly(amino acid)-based polymer (or oligomer) of Formula I comprises hydrophobic amino acids (M) and/or reactive amino acids (N) linked to hydrophobic drug molecules, and optionally spacer amino acids (O) and/or charged amino acids (P). In preferred embodiments of amphiphiles, peptide antigen conjugate or drug molecule conjugates used for peptide antigen delivery and/or for the delivery of neutral drug molecules, the hydrophobic block (H) is typically selected from poly(amino acid)-based polymers of Formula I comprising hydrophobic amino acids (M) and/or reactive amino acids (N) linked to hydrophobic drug molecules, and optionally spacer amino acids (O), but not charged amino acids (P). In contrast, wherein the amphiphiles, peptide antigen conjugate or drug molecule conjugates are used for nucleic acid delivery or for the delivery of charged drug molecules, the hydrophobic block (H) is typically selected from poly(amino acid)-based polymers of Formula I comprising hydrophobic amino acids (M) and/or charged amino acids (P), wherein the charge of the charge amino acid is opposite that of the nucleic acid or charged drug molecule, and optionally reactive amino acids (N) linked to hydrophobic drug molecules and spacer amino acids (O). Particular compositions of hydrophobic blocks (H) based on poly (amino acid)-based polymers or oligomers of Formula I that led to unexpected improvements in biological activity are described throughout the specification.

In some embodiments, the hydrophobic block (H) is a poly(amino acid) of Formula I comprising entirely hydrophobic monomers (m):

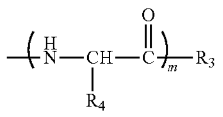

Non-limiting examples include:

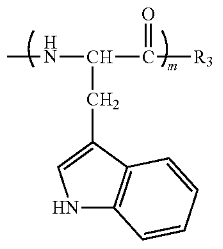

A non-limiting example of a poly(amino acid) of Formula I composed entirely of hydrophobic monomers (M) selected from tryptophan, wherein m is equal to 5 (i.e., 5 monomeric units), $R^3$ is an amine and the N-terminal amine is linked to a solubilizing block(S) either directly or indirectly through a spacer (B) and/or linker U, is shown here for clarity:

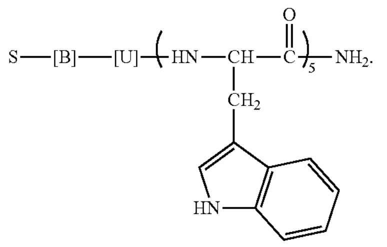

In some embodiments drug molecules (D) are linked via the N-terminus or C-terminus of hydrophobic blocks (H) comprising poly(amino acids) of Formula I. A non-limiting example is shown here for clarity:

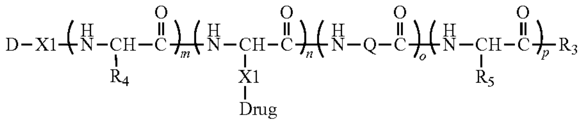

wherein the poly(amino acid) comprises hydrophobic amino acids selected from tryptophan and $R^3$ is $NH_2$ the structure is:

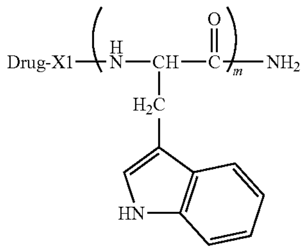

wherein when X1 comprises a PAB-Cit-Val linked to the poly(amino acid) via a succinate linker the structure is:

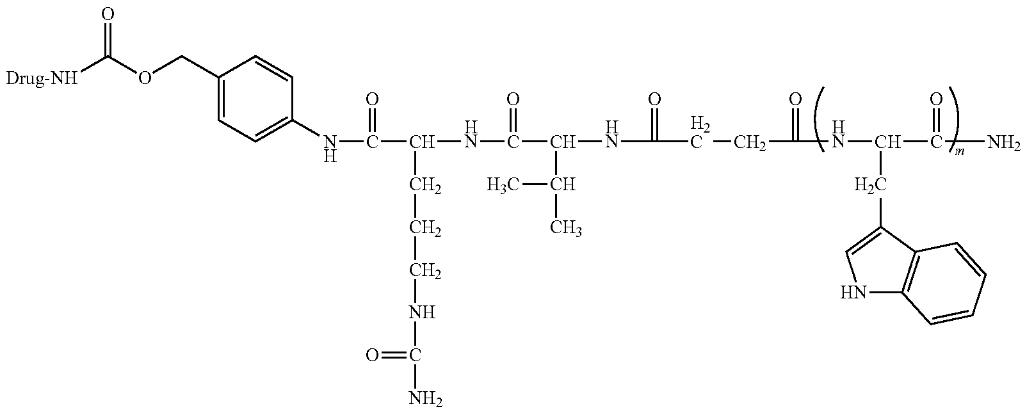

Alternatively, wherein X1, comprises a PAB-Cit-Val linked to the poly(amino acid) via Linker U resulting from the reaction between azide and DBCO, an exemplary strained alkyne, wherein the DBCO moiety is linked to poly(amino acid) via Ahx, the structure is:

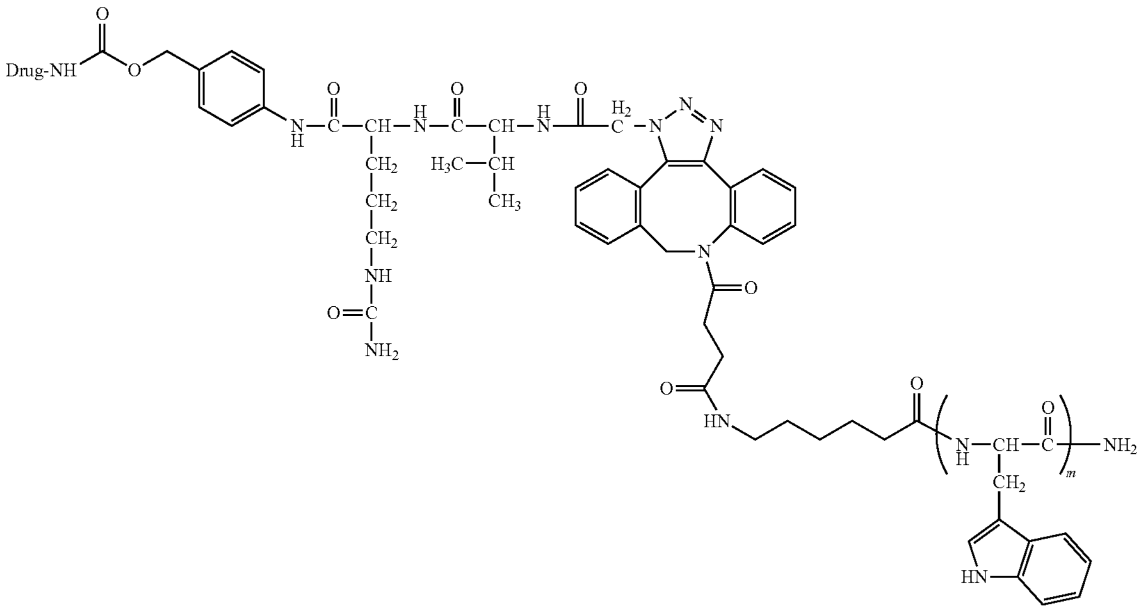

Amphiphilic copolymers with hydrophobic polymers or oligomers (H) which comprise poly(amino acid)-based copolymers that include aromatic amino acids (e.g., phenylalanine, amino phenylalanine, histidine, tryptophan, tyrosine, benzyl glutamate) and/or aromatic drug molecules (e.g., imidazoquinolines), have unexpected improvements in manufacturability through improved solubility in polar aprotic solvents and alcohols as well as improved particle stability as compared with poly(amino acids) comprising hydrophobic amino acids selected from aliphatic amino acids as reported in WO2022/177993, which is incorporated by reference herein.

An additional notable finding relates to how the number of monomer units comprising the hydrophobic block (H) impacts particle formation. For example, poly(amino acid)-based hydrophobic blocks (H) which comprise at least 5 hydrophobic amino acids were typically needed to ensure stable assembly of particles comprising amphiphiles of formula S-[B]-[U]-H (optionally further comprising a drug molecule, e.g., S-[B]—[U]-HD). Though, unexpectedly, poly(amino acid)-based hydrophobic blocks (H) which comprise oligomers with as few as 3 monomers that included aromatic rings were found to be sufficient to drive stable particle assembly. Notably, increasing the number of hydrophobic monomers comprising the poly(amino acid)-based hydrophobic block (H) from 3 to 5 and from 5 to 10 hydrophobic monomers led to improved particle assembly. While increasing the total number of monomers comprising hydrophobic blocks (H) (i.e. total number of monomers or degree of polymerization) led to improved particle stability, both the total number of monomers and composition of the poly(amino acids) of Formula I also impacted manufacturability as well as stability. For example, poly(amino acids) of Formula I comprising between 10-30 consecutive monomers selected from hydrophobic amino acids comprising aryl groups and/or heteroaryl groups were more reliably manufactured than poly(amino acids) of Formula I comprising between 10-30 consecutive monomers selected from hydrophobic amino acids comprising aliphatic groups.

Therefore, in preferred embodiments of poly(amino acid)-based hydrophobic blocks (H), the hydrophobic block (H) comprises 3 or more, preferably about 3 to about 100 hydrophobic amino acids (M) and/or reactive amino acids linked to drug molecules (D), though, more preferably between about 3 to 30 hydrophobic amino acids (M) and/or reactive amino acids linked to drug molecules (D), more preferably wherein the hydrophobic amino acids and/or reactive amino acids linked to drug molecules (D) further comprise aryl groups, heteroaryl, aminoaryl and/or aminoheteroaryl. Hydrophobic blocks (H) with branched architecture In some embodiments, the amphiphilic block copolymer comprises a hydrophobic block (H) that is branched. In certain preferred embodiments, the hydrophobic block (H) comprises a dendron, wherein the focal point is linked to either (i) a solubilizing block(S) either directly or indirectly via a spacer (B) and/or Linker U, (ii) an antigen (A) either directly or indirectly via an extension (E1 or E2) and/or Linker U; (iii) a drug molecule either directly or via a Linker U; or, (iv) a capping group, and the terminal functional groups (FGt) are linked to hydrophobic molecules, e.g., hydrophobic drug molecules, more preferably hydrophobic molecules comprising aromatic groups, e.g., hydrophobic drug molecules comprising aromatic groups.

Non-limiting examples of amphiphiles, peptide antigen conjugates or drug molecule conjugates comprising hydrophobic blocks (H) with dendron architecture, wherein the terminal functional groups (FGt) are linked to hydrophobic drug molecules are provided below for clarity:

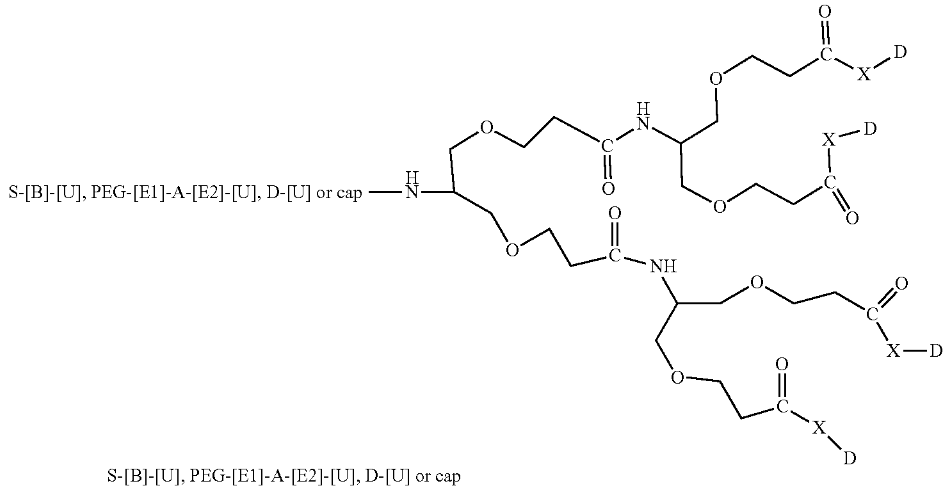

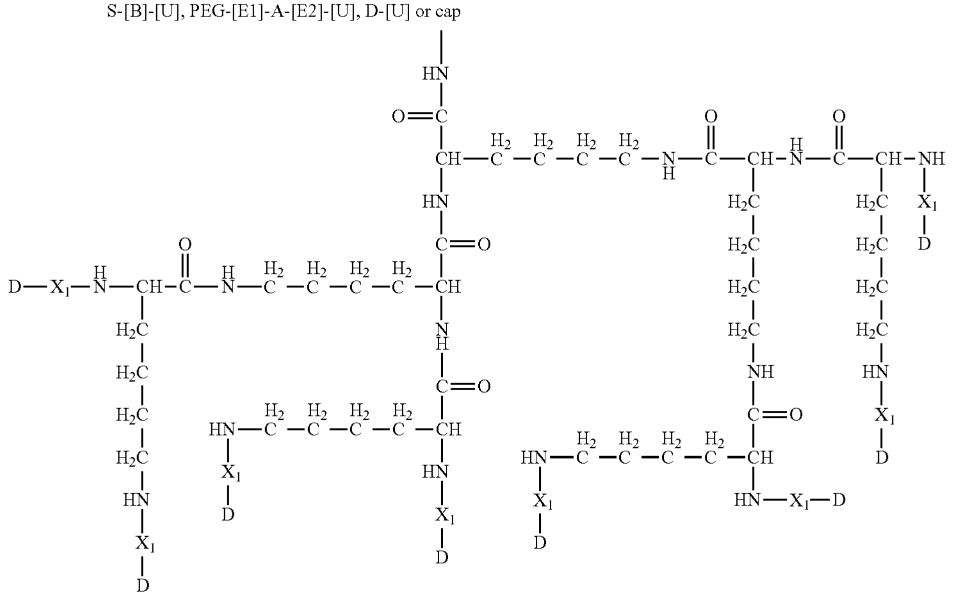

wherein X1 is either present or absent and when present is any suitable linker and D is any suitable drug molecule, preferably selected from hydrophobic drug molecules comprising aromatic groups, and the focal point is attached to either (i) a solubilizing block(S) either directly or indirectly via a spacer (B) and/or Linker U, (ii) an antigen (A) either directly or indirectly via an extension (E1 or E2) and/or Linker U; (iii) a drug molecule either directly or via a Linker U; or, (iv) a capping group.

Additional examples of hydrophobic blocks (H) with dendron architecture that have particular utility for certain applications and/or lead to unexpected improvements in manufacturing and/or biological activity are provided throughout the specification.

Density (mol %) of hydrophobic groups and/or drug molecules

The density (i.e., mol %) of the hydrophobic monomers (e.g., hydrophobic amino acids or reactive monomers linked to hydrophobic drug molecules) incorporated into polymer-based hydrophobic blocks (H), e.g., poly(amino acids) of Formula I, were found by the inventors of the present disclosure to have a major impact on particle stability and biological activity. Thus, the density (i.e., mol %) of hydrophobic monomers (e.g., hydrophobic amino acids or reactive monomers linked to hydrophobic drug molecules) incorporated into polymer-based hydrophobic blocks should be carefully selected. In general, the density (mol %) of hydrophobic monomers (e.g., hydrophobic amino acids or reactive monomers linked to hydrophobic drug molecules) required is inversely proportional to the length (i.e. degree of polymerization) of the polymer.

For instance, the preferred density (mol %) of hydrophobic monomers (e.g., hydrophobic amino acids, M) and/or reactive monomers linked to hydrophobic drug molecules (e.g., reactive amino acids (N) linked to hydrophobic drug molecules) is typically 100 mol % for polymers (or "oligomers") with 3 monomers; 75-100 mol % for polymers (or "oligomers") with 4 monomers, such as 75 mol % or 100 mol % for polymers with 4 monomers; 60-100 mol % for polymers (or "oligomers") with 5 monomers, such as 60 mol %, 80 mol % or 100 mol %; 50-100 mol % for polymers (or "oligomers") with 6 monomers, such as 50 mol %, 66.6 mol %, 83.3 mol % and 100 mol %; 42-100 mol % for polymers (or "oligomers") with 7 monomers, such as 42 mol %, 57 mol %, 71 mol %, 85.7 mol % and 100 mol %; 37.5-100 mol % for polymers (or "oligomers") with 8 monomers, such as 37.5 mol %, 50 mol %, 75 mol %, 87.5 mol % and 100 mol %; 33.3-100 mol % for polymers (or "oligomers") with 9 monomers, such as 33.3 mol %, 44.4 mol %, 55.6 mol %, 66.6 mol %, 77.9 mol %, 88.9 mol % and 100 mol %; 30-100 mol % for polymers (or "oligomers") with 10 monomers, such as 30 mol %, 40 mol %, 50 mol %, 60 mol %, 70 mol %, 80 mol %, 90 mol % and 100 mol %. The preferred density (mol %) of hydrophobic monomers (e.g., hydrophobic amino acids, M) and/or reactive monomers linked to hydrophobic drug molecules (e.g., reactive amino acids (N) linked to hydrophobic drug molecules) for polymers with between 11 and 20 monomers is typically between 20 mol % to 100 mol %, such as 20 mol %, 21 mol %, 22 mol %, 23 mol %, 24 mol %, 25 mol %, 26 mol %, 27 mol %, 28 mol %, 29 mol %, 30 mol %, 31 mol %, 32 mol %, 33 mol %, 34 mol %, 35 mol %, 36 mol %, 37 mol %, 38 mol %, 39 mol %, 40 mol %, 41 mol %, 42 mol %, 43 mol %, 44 mol %, 45 mol %, 46 mol %, 47 mol %, 48 mol %, 49 mol %, 50 mol %, 51 mol %, 52 mol %, 53 mol %, 54 mol %, 55 mol %, 56 mol %, 57 mol %, 58 mol %, 59 mol %, 60 mol %, 61 mol %, 62 mol %, 63 mol %, 64 mol %, 65 mol %, 66 mol %, 67 mol %, 68 mol %, 69 mol %, 70 mol %, 71 mol %, 72 mol %, 73 mol %, 74 mol %, 75 mol %, 76 mol %, 77 mol %, 78 mol %, 79 mol %, 80 mol %, 81 mol %, 82 mol %, 83 mol %, 84 mol %, 85 mol %, 86 mol %, 87 mol %, 88 mol %, 89 mol %, 90 mol %, 91 mol %, 92 mol %, 93 mol %, 94 mol %, 95 mol %, 96 mol %, 97 mol %, 98 mol %, 99 mol % or 100 mol %, provided that at least 3 hydrophobic monomers (M) or reactive monomers (N) linked to hydrophobic drugs are present; 10-100 mol %, more preferably 20-80 mol %, such as 20 mol %, 21 mol %, 22 mol %, 23 mol %, 24 mol %, 25 mol %, 26 mol %, 27 mol %, 28 mol %, 29 mol %, 30 mol %, 31 mol %, 32 mol %, 33 mol %, 34 mol %, 35 mol %, 36 mol %, 37 mol %, 38 mol %, 39 mol %, 40 mol %, 41 mol %, 42 mol %, 43 mol %, 44 mol %, 45 mol %, 46 mol %, 47 mol %, 48 mol %, 49 mol %, 50 mol %, 51 mol %, 52 mol %, 53 mol %, 54 mol %, 55 mol %, 56 mol %, 57 mol %, 58 mol %, 59 mol %, 60 mol %, 61 mol %, 62 mol %, 63 mol %, 64 mol %, 65 mol %, 66 mol %, 67 mol %, 68 mol %, 69 mol %, 70 mol %, 71 mol %, 72 mol %, 73 mol %, 74 mol %, 75 mol %, 76 mol %, 77 mol %, 78 mol %, 79 mol % or 80 mol % for polymers with between 21 and 30 monomers, provided that at least 3 hydrophobic monomers (M) or reactive monomers (N) linked to hydrophobic drugs are present; and, 5-60 mol %, more preferably, 10-40 mol % for polymers with >30 monomers, such as 10 mol %, 11 mol %, 12, mol %, 13 mol %, 14 mol %, 15 mol %, 16 mol %, 17 mol %, 18 mol %, 19 mol %, 20 mol %, 21 mol %, 22 mol %, 23 mol %, 24 mol %, 25 mol %, 26 mol %, 27 mol %, 28 mol %, 29 mol %, 30 mol %, 31 mol %, 32 mol %, 33 mol %, 34 mol %, 35 mol %, 36 mol %, 37 mol %, 38 mol %, 39 mol % and 40 mol % for polymers with >30 monomers.

In the above examples, in preferred embodiments, the polymer is a poly(amino acid) and the monomer is selected from hydrophobic monomers (e.g., hydrophobic amino acid and/or reactive monomers linked to hydrophobic drug molecules) that comprise an aryl group, and, more preferably, a heteroaryl, aminoaryl, and/or aminoheteroaryl. Additionally, in the above examples, the hydrophobic monomer may be selected from two or more monomers, e.g., two or more distinct hydrophobic monomers (e.g., hydrophobic amino acids), or one or more hydrophobic monomers and one or more reactive monomers (e.g., reactive amino acids) linked to hydrophobic drugs, such that the total mol % of hydrophobic monomers falls within the preferred ranges.

General Properties of Polymer-Based Hydrophobic Blocks (H)

The average molecular weight of polymer-based hydrophobic blocks (H) can be readily estimated based on the number and composition of monomers (e.g., amino acids for poly(amino acids) and is typically between about 500 g/mol to about 20,000 g/mol. In some embodiments, the polymer molecular weight is between about 1,000 and 5,000, or between about 5,000 and 10,000, or between about 10,000 and 20,000 g/mol.

The polydispersity, Mw/Mn, of the hydrophobic polymer or oligomer (H) typically ranges from about 1.0 to 2.0 and depends on the polymerization technique used. For instance, poly(amino acid)-based hydrophobic polymers or oligomers (H) are typically prepared by solid phase peptide synthesis and will have polydispersity of 1.0 as the polymers are molecularly defined. Polymers formed by chain growth polymerization will have polydispersities >1.0. The hydrophobic polymer or oligomer (H) may also comprise polymers based on cyclic monomers, such as poly(amino acid)-based hydrophobic polymers or oligomers (H) based on amino acid N-carboxyanhydrides (NCAs).

The size of the polymer-based hydrophobic block (H) may either be expressed by the molecular weight or degree of polymerization. For molecularly defined, monodisperse polymers, the length (or degree or degree polymerization) of the polymer can be calculated by dividing the molecular weight (e.g., theoretical or experimentally determined by mass spectrometry) by the average molecular weight of the monomer unit(s) comprising the polymer. For polydisperse polymers, the number-average molecular weight, abbreviated Mn, is preferred for estimating the degree of polymerization. As a non-limiting example, a polydisperse polymer with a Mn of 25 kDa and an average monomer molecular weight of 250 g/mol would have a degree of polymerization of 100. The molecular weight of a polymer can also be calculated by multiplying the degree of polymerization by the average monomer molecular weight.

In preferred embodiments of hydrophobic blocks (H), the molecular weight or Mn, is preferably between about 0.5 kDa and 60 kDa, such as about 0.5 kDa, 1 kDa, 1.5 kDa, 2 kDa, 2.5 kDa, 3 kDa, 3.5 kDa, 4 kDa, 4.5 kDa, 5 kDa, 6 kDa, 7 kDa, 8 kDa, 9 kDa, 10 kDa, 11 kDa, 12 kDa, 13, kDa, 14 kDa, 15 kDa, 16 kDa, 17 kDa, 18 kDa, 19 kDa, 20 kDa, 21 kDa, 22 kDa, 23 kDa, 24 kDa, 25 kDa, 26 kDa, 27 kDa, 28 kDa, 29 kDa, 30 kDa, 31 kDa, 32 kDa, 33 kDa, 34 kDa, 35 kDa, 36 kDa, 37 kDa, 38 kDa, 39 kDa, 40 kDa, 41 kDa, 42 kDa, 43 kDa, 44 kDa, 45 kDa, 46 kDa, 47 kDa, 48 kDa, 49 kDa, 50 kDa, 51 kDa, 52 kDa, 53 kDa, 54 kDa, 55 kDa, 56 kDa, 57 kDa, 58 kDa, 59 kDa or 60 kDa. More preferably, the molecular weight of the hydrophobic block is between about 0.5 kDa to about 20 kDa. In certain embodiments, the hydrophobic block (H) is a poly(amino acid) and has a molecular weight of between about 0.5 kDa and about 10 kDa or about 1.5 kDa to about 5 kDa.

Polymers described herein can be synthesized by any suitable means and should preferably have low or no polydispersity. For instance, poly(amino acids) described herein are typically produced by solid-phase peptide synthesis and are molecularly defined with no polydispersity. Similarly, PEG based spacers and dendrons described herein are produced by controlled processed and have little to no polydispersity. In contrast, polymers produced by radical polymerization will have some degree of polydispersity, which may be calculated by dividing the weight-average molecular weight Mw by Mn, i.e., polydispersity index (PDI)=Mw/Mn. Though, the polydispersity of polymers produced by radical polymerization may be controlled by the polymerization technique utilized. Therefore, in preferred embodiments, living polymerization, e.g., RAFT polymerization, is used to synthesize polymers with PDI less than 2.0, typically between about 1.01 and 1.2.

Solubilizing Block

The amphiphiles disclosed herein comprise a solubilizing block(S) that functions to impart solubility in aqueous solutions at certain temperature, pH and salt concentration. Peptide antigen conjugates may also comprise a solubilizing block. Accordingly, the PEG group of peptide antigen conjugates of formula PEG-[E1]-A-[E2]-[U]-H and H-[E1]-A-[E2]—[U]-PEG and charged block (C) of peptide antigen conjugates of formula C-[E1]-A-[E2]-[U]-H and H-[E1]-A-[E2]—[U]—C are subsets of solubilizing blocks(S). Preferred solubilizing blocks of peptide antigen conjugates are discussed in detail later and delineated for clarity.

In certain embodiments, the solubilizing block(S) is soluble in aqueous solutions up to about 1-1,000 mg/mL, e.g., up to about 1 mg/mL, about 10 mg/mL, about 100 mg/mL, about 200 mg/mL, or about 500 mg/mL, though, typically not more than 1,000 mg/mL. In some embodiments, the solubilizing block(S) is soluble in aqueous solutions at certain concentrations, temperatures and/or pH ranges but becomes insoluble or less soluble in response to a change in concentration, temperature and/or pH. Preferred solubilizing blocks(S) are molecules that are soluble at concentrations up to at least 1 mg/mL or up to at least about 10 mg/mL or up to at least about 100 mg/mL at or near physiologic pH (~ pH 7.4), between about pH 6.5 to pH 8.5 or between about pH 6.0 and pH 9.0, and at or near physiologic temperature (~ 37° C.), such as between about 32-40° C., and at physiologic salt concentrations (~10 g/L) and salt composition, such as normal saline (0.9% NaCl).

The solubilizing block may be chosen from any molecule that is water soluble and/or has hydrophilic characteristics. In some embodiments the solubilizing block(S) is selected from a linear, branched or brush polymer (or oligomer). The solubilizing block(S) can be a homopolymer or copolymer. The solubilizing block(S) can comprise one or many different types of monomer units. The solubilizing block(S) can be a statistical copolymer or alternating copolymer. The solubilizing block(S) can be a block copolymer, such as the A-B type, or the polymer can comprise a grafted copolymer, whereby two or more polymers are linked through a polymerization-type reaction.

The solubilizing block(S) may comprise polymers comprising naturally occurring and/or non-natural monomers and combinations thereof.

In some embodiments, the solubilizing block(S) is selected from natural biopolymers. Natural biopolymers selected as solubilizing blocks(S) may include peptides (sometimes referred to as poly(amino acids)) comprising hydrophilic amino acids. Non-limiting examples of hydrophilic amino acids include serine, sulfo-serine, glutamic acid, aspartic acid, lysine, ornithine, arginine. Biopolymers can be selected from hydrophilic polysaccharides, which may include but are not limited to glycogen, cellulose, dextran, alginate and chitosan.

Monomers comprising the solubilizing block(S) can be selected from acrylates, (meth)acrylates, acrylamides, (meth)acrylamides, allyl ethers, vinyl acetates, vinyl amides, substituted styrenes, amino acids, acrylonitrile, heterocyclic monomers (e.g., ethylene oxide used to make PEG polymers), saccharides, phosphoesters, phosphonamides, sulfonate esters, sulfonamides, or combinations thereof. Specific examples of (meth)acrylate and (meth)acrylamide monomers include N2hydroxypropyl(methacrylamide) (HPMA) and hydroxyethyl(methacrylate) (HEMA). Various monomers suitable for the solubilizing block(S) are described below.

In certain embodiments, the solubilizing block(S) comprises hydrophilic polymers selected from synthetic or natural poly(saccharides), such as glycogen, cellulose, dextran, alginate and chitosan. Hydrophilic polymers used as the solubilizing block(S) should have sufficient length to provide adequate surface coverage to stabilize particles formed by amphiphiles, e.g., amphiphiles of formula S-[B]-[U]-H. In preferred embodiments of solubilizing blocks comprising hydrophilic polymers, the hydrophilic polymer comprises 50 or monomer units, such as between 50 to 300, though, preferably between 50 and 100.

Solubilizing blocks(S) comprising linear polymers may comprise homopolymers comprising a single monomer composition or copolymers having two or more distinct compositions of monomers. In some embodiments, the homopolymer comprises neutral, hydrophilic monomers or charged monomers, e.g., positive, negative or zwitterion monomers. In other embodiments, the copolymer comprises neutral, hydrophilic monomers, and positive, negative or zwitterion monomers, or any combination thereof. Solubilizing blocks comprising linear polymers may comprise monomers linked to any solubilizing groups (SG) (or "moieties"), which generally refers to any hydrophilic groups, including neutral hydrophilic groups that do not carry a full integer value of charge; zwitterions, which are neutral but carry a whole number value of positive charge and a whole number value of negative charge; positively charged groups; and negatively charged groups; or a combination thereof.

In some embodiments, the solubilizing block(S) comprises neutral hydrophilic monomers, which may be described generically as hydrophilic monomers. In some embodiments, the hydrophilic monomers are selected from (meth)acrylates or (meth)acrylamides (inclusive of acrylates, methacrylates, acrylamides and methacrylamides) of the chemical formula $CH_2{=}CR^{11}—C(O)—R^{10}$ ("Formula II"), wherein the acryl side group $R^{10}$ may be selected from one or more of $—OR^2$, $—NHR^{12}$ or $—N(CH_3)\ R^{12}$, where $R^{11}$ can be H or $CH_3$, and $R^{12}$ is independently selected from any hydrophilic substituent. Non-limiting examples of $R^{12}$ include but are not limited to H (except for $OR^{13}$), $CH_3$, $CH_2CH_3$, $CH_2CH_2OH$, $CH_2\ (CH_2)_2OH$, $CH_2CH(OH)CH_3$, $CHCH_3CH_2OH$ or $(CH_2CH_2O)_yH$, where y is an integer number of repeating units, typically 1 to 6, such as 1, 2, 3, 4, 5 or 6.

A non-limiting example of a neutral hydrophilic monomer of Formula II wherein $R^{10}{=}NHR^{12}$, $R^{11}{=}CH_3$, and $R^{13}{=}CH_2CH(OH)CH_3$ is N2hydroxypropyl(methacrylamide) (HPMA):

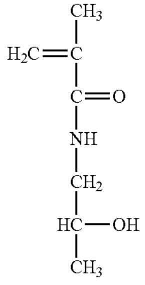

The above example, N-(2-hydroxpropyl(methacrylamide)) (HPMA), is an example of a neutral hydrophilic monomer of Formula II.

In some embodiments, the solubilizing block(S) comprises charged monomers that contain one or more functional groups ("charged functional group") that either have a fixed charge or have net charge under certain physiological conditions. Non-limiting examples of charged monomers include any monomer that comprises amine, quaternary ammonium, sulfonic acid, sulfuric acid, sulfonium, phosphoric acid, phosphonic acid, phosphonium, carboxylic acid and/or boronic acid functional groups, as well as any combinations or salt forms thereof.

In some embodiments, charged monomers are selected from (meth)acrylates and (meth)acrylamides with chemical formula $CH_2{=}CR^{14}{-}C(O){-}R^{13}$ ("Formula III"). The acryl side group $R^{13}$ may be selected from one or more of the groups consisting of $-OR^{15}$, $-NHR^{15}$ or $-N(CH_3)\ R^{15}$, where $R^{14}$ can be H or $CH_3$ and $R^{15}$ can be selected from, but is not limited to, H, linear alkyl structures such as $(CH_2)_y NH_2$, $(CH_2)_y$-imidazole, $(CH_2)_y$-pyridine amine, $(CH_2)_y$-(quinoline-amine), $(CH_2)_y$-pyridine amine, $(CH_2)_y$-naphthalene amine, $(CH_2)_yCH(NH_2)COOH$, $(CH_2)_yCOOH$, $(CH_2)_y CH(CH_3)COOH$, $(CH_2)_yC(CH_3)_2COOH$, $(CH_2)_yPO_3H_2$, $(CH_2)_yOPO_3H_2$, $(CH_2)_ySO_3H$, $(CH_2)_yOSO_3H$, $(CH_2)_yB(OH)\ 2$, $CH_2N(CH_3)_2$, $CH_2CH_2N(CH_3)_2$, $CH_2CH_2CH_2N(CH_3)_2$, $CH_2N(CH_2CH_3)_2$, $CH_2CH_2N(CH_2CH_3)_2$, $CH_2CH_2CH_2N(CH_2CH_3)_2$, $CH_2N(CH(CH_3)_2)$, $CH_2CH_2N((CH(CH_3)_2)$, $CH_2CH_2CH_2N(CH(CH_3)_2)$, $CH[CH_2N(CH_3)_2]_2$, $CH(COOH)\ CHCH_2COOH$, $(CH_2)_yNH(CH_2)_j COOH$, $(CH_2)_yN(CH_3)(CH_2)_yCOOH$, $(CH_2)_yN^+(CH_3)_2(CH_2)_yCOOH$, $(CH_2)_yN^+(CH_2{-}CH_3)_2\ (CH_2)_yCOOH$, $[CH_2CH(CH_3)O]_5PO_3H_2$, $C(CH_3)_2CH_2SO_3H$, and $C_6H_4B(OH)_2$ where y is an integer number of a repeating units, typically between 1 to 6, such as 1, 2, 3, 4, 5 or 6. In some embodiments of (meth)acrylates and (meth)acrylamides of Formula III, the acryl side group comprises tetraalkyl ammonium salts, nitrogen containing heterocycles, aminoaryl, or aminoheteroaryl, which may be linked to the monomer through any suitable means either directly or via a linker. Non-limiting examples of aryls, nitrogen containing heteroaryls and/or aminoheteroaryls include pyrrolyl, imidazolyl, pyridinyl, pyrimidinyl, pyrazinyl, diazepinyl, indolyl, quinolinyl, amino quinolinyl, amino pyridinyl, purinyl, pteridinyl, anilinyl, amino naphthyl or the like. In certain preferred embodiments of (meth)acrylates and (meth)acrylamides of Formula III, the acryl side group comprises carboxylic acid(s), which may be linked to the monomer through any suitable means either directly or via a linker. A non-limiting example of a charged monomer of Formula III wherein $R^{13}{=}{-}OR^{15}$, $R^4{=}CH_3$ and $R^{15}{=}H$ is:

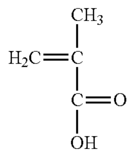

Dendron-Based Solubilizing Blocks

Certain preferred embodiments of solubilizing blocks(S) comprise dendron amplifiers ("dendrons"), wherein the focal point of the solubilizing block(S) is linked either directly or indirectly via a spacer (B) and/or Linker U to a hydrophobic block (H), and the terminal groups (FGt) are either blind ended (unlinked) and function as solubilizing groups, or the terminal functional groups (FGt) are linked to solubilizing groups, wherein the solubilizing groups (SG) (or "moieties") generally refer to any hydrophilic groups, including neutral hydrophilic groups that do not carry a full integer value of charge; zwitterions, which are neutral but carry a whole number value of positive charge and a whole number value of negative charge; positively charged groups; and negatively charged groups; or a combination thereof. In some embodiments, the solubilizing block (B) comprises dendron architecture and the terminal functional groups (FGt) are unlinked and therefore FGt are the solubilizing groups (SG). In other embodiments, the solubilizing block (B) comprises dendron architecture and the terminal functional groups (FGt) are linked either directly or via a linker to a solubilizing group (SG).

Architecture and composition of amphiphiles of formula S-[B]-[U]-H had a marked impact on particle stability and drug loading into such particles. Previously it has reported that amphiphiles of formula S-[B]-[U]-H comprising solubilizing blocks with dendron architecture formed nanoparticles with improved hydrodynamic stability, higher drug loading and increased biological activity as compared with amphiphiles of formula S-[B]-[U]-H comprising solubilizing blocks(S) with linear architecture. Therefore, in preferred embodiments of amphiphiles, the amphiphile comprising a solubilizing block(S) further comprising a dendron amplifier, with a single ("core" or "focal point") functional group linked either directly or indirectly via a spacer (B) and/or linker (U) to a hydrophobic block (H), additionally wherein the dendron has 2 or more solubilizing groups (SG), preferably, between 2 and 32 solubilizing groups, though more preferably between 4 and 8 solubilizing groups. Preferred compositions of dendron-based solubilizing blocks(S) are described throughout the specification as well as in WO 2022/177993, which is incorporated by reference herein.

The solubilizing groups (SG) comprising solubilizing blocks(S) with dendron architecture function to improve solubility and therefore stability of particles formed by amphiphiles but also impact blood protein interactions, cellular uptake and intracellular trafficking, which impact pharmacokinetics as well as safety and efficacy. Therefore, solubilizing groups (SG) should be carefully selected to meet the demands of the application.

It was identified that particular solubilizing group (SG) compositions that led to unexpected improvements in biological activity. Accordingly, particles comprising amphiphiles with solubilizing groups comprising dendrons with solubilizing groups (SG) selected from carboxylic acids with net negative charge (at pH 7.4) were found to be efficiently phagocytosed by monocyte populations. In contrast, particles comprising amphiphiles with solubilizing groups comprising linear polymers or dendrons with net neutral or near neutral charge were generally found to be poorly phagocytosed by immune cells, e.g., antigen presenting cells, and other cell populations, unless the linear polymers or dendrons comprise neutral sugar molecules that bind C-type lectin receptors that promote uptake by immune cell populations or other sugar molecules, such as glucose or galactose, which promote uptake via GLUT1 and asialglycoprotein, respectively, by various cell populations. Furthermore, particles comprising amphiphiles with solubilizing groups comprising linear polymers or dendrons with net positive charge were found to be broadly taken up by various cell populations, particularly by antigen presenting cells. Thus, the solubilizing block(S) charge and composition can be tuned by varying the solubilizing groups (SG) to modulate biological activity. Preferred compositions of solubilizing groups are described below and throughout the specification.

Charged Blocks (C)

A subset of solubilizing blocks(S) selected from linear poly(amino acid) comprising charged amino acids are referred to as charged blocks (C). In some embodiments, the charged block (C) is a linear poly(amino acid) comprising charged amino acids, hydrophilic amino acids or a combination thereof. Charged blocks (C) comprising poly(amino acids) may be linked via the N- or C-termini or a side chain either directly or indirectly via an extension (E1 or E2) and/or linker (U). Charged blocks comprising poly(amino acids) may comprise amino acids linked to any hydrophilic groups, including neutral hydrophilic groups that do not carry a full integer value of charge; zwitterions, which are neutral but carry a whole number value of positive charge and a whole number value of negative charge; positively charged groups; and negatively charged groups; or a combination thereof.

In certain embodiments, the charged block (C) has a net negative charge and comprises 1 or more negatively charged amino acids. In certain embodiments, the charged block (C) with a net negative charge comprises between 1 to 20 negatively charged amino acids, e.g., 1, 2, 3, 4, 5, 6, 7, 8, 9, 10, 11, 12, 13, 14, 15, 16, 17, 18, 19 or 20, though, more preferably between about 2 to 12 negatively charged amino acids.

In non-limiting examples, a poly(amino acid) comprising 12 aspartic acid monomers, e.g., Asp-Asp-Asp-Asp-Asp-Asp-Asp-Asp-Asp-Asp-Asp-Asp (SEQ ID NO:32), is used to prepare a charged block (C) with a net negative charge of −12; a poly(amino acid) comprising 11 aspartic acid monomers, e.g., Asp-Asp-Asp-Asp-Asp-Asp-Asp-Asp-Asp-Asp-Asp (SEQ ID NO:33), is used to prepare a charged block (C) with a net negative charge of −11; a poly(amino acid) comprising 10 aspartic acid monomers, e.g., Asp-Asp-Asp-Asp-Asp-Asp-Asp-Asp-Asp-Asp (SEQ ID NO:34), is used to prepare a charged block (C) with a net negative charge of −10; a poly(amino acid) comprising 9 aspartic acid monomers, e.g., Asp-Asp-Asp-Asp-Asp-Asp-Asp-Asp-Asp (SEQ ID NO:35), is used to prepare a charged block (C) with a net negative charge of −9; a poly(amino acid)) comprising 8 aspartic acid monomers, e.g., Asp-Asp-Asp-Asp-Asp-Asp-Asp-Asp (SEQ ID NO:36), is used to prepare a charged block (C) with a net negative charge of −8; a poly(amino acid) comprising 7 aspartic acid monomers, e.g., Asp-Asp-Asp-Asp-Asp-Asp-Asp (SEQ ID NO:37), is used to prepare a charged block (C) with a net negative charge of −7; a poly(amino acid) comprising 6 aspartic acid monomers, e.g., Asp-Asp-Asp-Asp-Asp-Asp (SEQ ID NO: 38), is used to prepare a charged block (C) with a net negative charge of −6; a poly(amino acid) comprising 5 aspartic acid monomers, e.g., Asp-Asp-Asp-Asp-Asp (SEQ ID NO:39), is used to prepare a charged block (C) with a net negative charge of −5; a poly(amino acid) comprising 4 aspartic acid monomers, e.g., Asp-Asp-Asp-Asp (SEQ ID NO:40), is used to prepare a charged block (C) with a net negative charge of −4; a poly(amino acid) comprising 3 aspartic acid monomers, e.g., Asp-Asp-Asp, is used to prepare a charged block (C) with a net negative charge of −3; a poly(amino acid) comprising 2 aspartic acid monomers, e.g., Asp-Asp, is used to prepare a charged block (C) with a net negative charge of −2. In the above examples, aspartic acid (Asp) may be replaced with any suitable negatively charged amino acid, including but not limited to glutamic acid, sulfo-serine, or phospho-serine, wherein the negatively charged amino acids may be the same or different.

In certain embodiments, the charged block (C) has a net positive charge and comprises 1 or more positively charged amino acids. In certain embodiments, the charged block (C) with a net positive charge comprises between 1 to 20 positively charged amino acids, e.g., 1, 2, 3, 4, 5, 6, 7, 8, 9, 10, 11, 12, 13, 14, 15, 16, 17, 18, 19 or 20, though, more preferably between about 2 to 12 positively charged amino acids. In preferred embodiments of the vaccine, wherein the at least one peptide antigen conjugate has net positive charge, the peptide antigen conjugate comprises a charged block (C) that further comprises between 1 to 20 positively charged amino acids.

In non-limiting examples, a poly(amino acid) comprising 12 lysine monomers, e.g., Lys-Lys-Lys-Lys-Lys-Lys-Lys-Lys-Lys-Lys-Lys-Lys (SEQ ID NO:41), is used to prepare a charged block (C) with a net positive charge of +12; a poly(amino acid) comprising 11 lysine monomers, e.g., Lys-Lys-Lys-Lys-Lys-Lys-Lys-Lys-Lys-Lys-Lys (SEQ ID NO:42), is used to prepare a charged block (C) with a net positive charge of +11; a poly(amino acid) comprising 10 lysine monomers, e.g., Lys-Lys-Lys-Lys-Lys-Lys-Lys-Lys-Lys-Lys (SEQ ID NO:43), is used to prepare a charged block (C) with a net positive charge of +10; a poly(amino acid) comprising 9 lysine monomers, e.g., Lys-Lys-Lys-Lys-Lys-Lys-Lys-Lys-Lys (SEQ ID NO:44), is used to prepare a charged block (C) with a net positive charge of +9; a poly(amino acid) comprising 8 lysine monomers, e.g., Lys-Lys-Lys-Lys-Lys-Lys-Lys-Lys (SEQ ID NO:45), is used to prepare a charged block (C) with a net positive charge of +8; a poly(amino acid) comprising 7 lysine monomers, e.g., Lys-Lys-Lys-Lys-Lys-Lys-Lys (SEQ ID NO:46), is used to prepare a charged block (C) with a net positive charge of +7; a poly(amino acid) comprising 6 lysine monomers, e.g., Lys-Lys-Lys-Lys-Lys-Lys (SEQ ID NO:47), is used to prepare a charged block (C) with a net positive charge of +6; a poly(amino acid) comprising 5 lysine monomers, e.g., Lys-Lys-Lys-Lys-Lys (SEQ ID NO:48), is used to prepare a charged block (C) with a net positive charge of +5; a poly(amino acid) comprising 4 lysine monomers, e.g., Lys-Lys-Lys-Lys (SEQ ID NO:49), is used to prepare a charged block (C) with a net positive charge of +4; a poly(amino acid) comprising 3 lysine monomers, e.g., Lys-Lys-Lys, is used to prepare a charged block (C) with a net positive charge of +3; a poly(amino acid) comprising 2 lysine monomers, e.g., Lys-Lys, is used to prepare a charged block (C) with a net positive charge of +2. In the above examples, Lysine (Lys) may be replaced with any suitable positively charged amino acid, including but not limited to trimethyl-lysine, ornithine or arginine, wherein the positively charged amino acids may be the same or different. In preferred embodiments of the vaccine, wherein the at least one peptide antigen conjugate has net positive charge, the peptide antigen conjugate comprises a charged block (C) that further comprises between 1 to 20 positively charged amino acids that comprise primary amines, including but not limited to lysine and ornithine.

Zwitterion Peptides

In additional embodiments, the charged block (C) comprises both negatively and positively charged amino acids, or amino acids with both positively and negatively charged functional groups. Dipeptides comprising amino acids of opposite charge, e.g., Lys-Asp, are referred to as zwitterion dipeptides because they are predicted to have a net neutral, 0, charge at pH 7.4. One or more zwitterion dipeptides can be included in the charged block (C) as a means to i) improve water solubility and ii) provide a prevailing charge (e.g., net negative or net positive) over certain pH ranges.

For instance, a zwitterion di-peptide can be used to increase the hydrophilic character of a peptide sequence without increasing or decreasing the charge of a peptide sequence at pH 7.4. However, the zwitterion can be used to impart a net charge at a particular pH. For instance, excluding the contribution of the N-terminal amine and the C-terminal carboxylic acid in this example, the zwitterion di-peptide, Lys-Asp, has a net charge of 0 at pH 7.4, but a net charge of +1 at pH <4 and a net charge of −1 at pH >10. One or more zwitterion di-peptides can be added to the sequence of poly(amino acid)-based charged blocks; for example, one di-peptide, Lys-Asp; two di-peptides Lys-Asp-Lys-Asp (SEQ ID NO:50); three di-peptides, Lys-Asp-Lys-Asp-Lys-Asp (SEQ ID NO:51) and so forth. In the above examples, Lysine (Lys) may be replaced with any suitable positively charged amino acid, including but not limited to trimethyl-lysine, ornithine or arginine, and aspartic acid (Asp) may be replaced with any suitable negatively charged amino acid, including but not limited to glutamic acid, sulfo-serine, or phospho-serine, wherein the positively or negatively charged amino acids may be the same or different.

The charged block (C) comprising poly(amino acids) may additionally comprise small non-charged, hydrophilic amino acids, or hydrophilic linkers, e.g., ethylene oxide that function to i) improve water solubility and ii) increase the distance between charged functional groups to prevent incomplete ionization. For instance, ionization of one functional group on a polymer may impact the pKa of neighboring functional groups through local effects. For example, protonation of an amine in close proximity to a second amine may cause a reduction in the pKa of the conjugate acid of the second amine. To reduce the impact of local effects on the ionization potential of neighboring functional groups, a linker molecule may be used to increase the distance between charged functional groups. The linker molecule may comprise between 1 to 5 small, non-charged hydrophilic amino acids, e.g., 1, 2, 3, 4, and 5 amino acids. Alternatively, the linker may comprise an ethylene oxide (i.e., PEG) linker between 1 to 4, or more, monomer units, e.g., 1, 2, 3, or 4 ethylene oxide monomers in length. In certain embodiments of charged blocks comprising poly (amino acids), 1 to 2 non-bulky, non-charged hydrophilic amino acids are placed between neighboring charged amino acids, wherein the amino acids are linked through amide bonds. In certain embodiments, a serine is placed between all or some of the charged amino acids comprising the poly(amino acid)-based charged block (C).

Solubilizing Groups (SG)

Solubilizing groups (SG) (or "moieties") are defined broadly as any hydrophilic groups, including neutral hydrophilic groups that do not carry a full integer value of charge; zwitterions, which are neutral but carry a whole number value of positive charge and a whole number value of negative charge; positively charged groups; and negatively charged groups; or a combination thereof.

In certain preferred embodiments, the solubilizing block (B) comprises solubilizing groups (SG) selected from sugar molecules comprising one or more sugar monomers, e.g., monosaccharides, disaccharides, trisaccharides, oligosaccharides and the like. Non-limiting examples of solubilizing groups selected from sugar molecules include but are not limited to glucose, glucosamine, N-acetyl glucosamine, galactose, galactosamine, N-acetyl galactosamine, mannose and sialyl lewis$^x$ (sLeX), which may be linked to solubilizing blocks through any suitable linker at any suitable attachment point, e.g.:

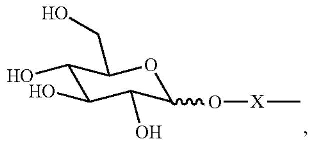
,
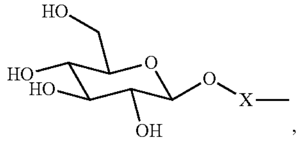
,
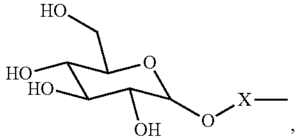
,
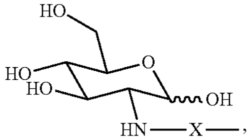
,
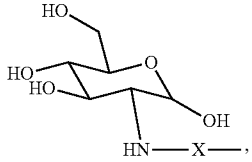
,
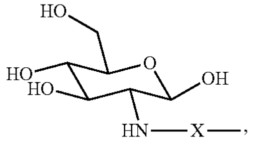
,
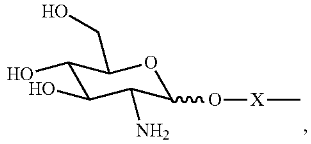
,
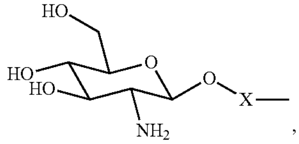
,
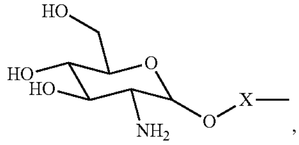
,
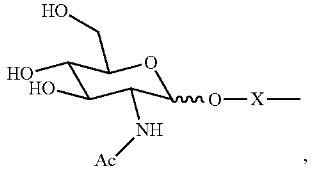
,
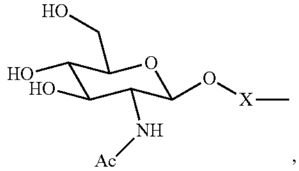
,
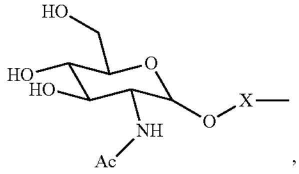
,
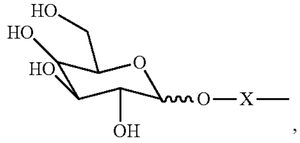
, -continued

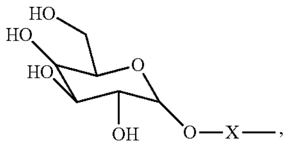

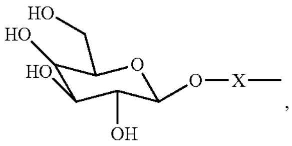

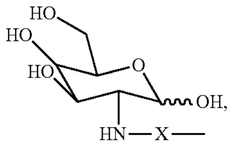

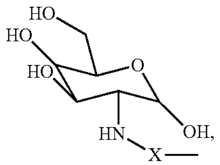

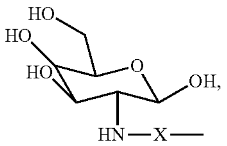

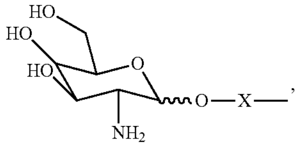

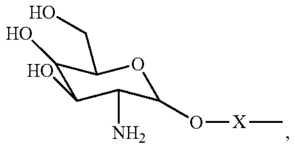

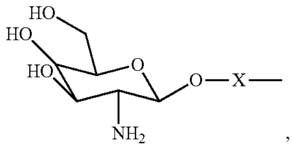

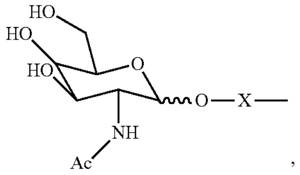

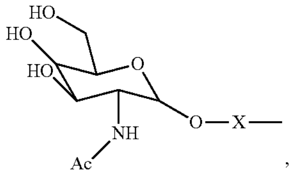

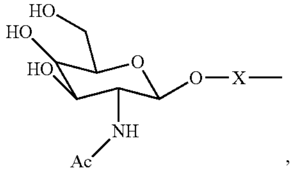

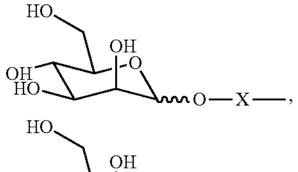

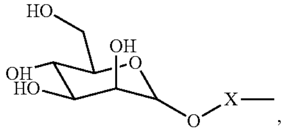

-continued

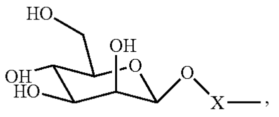

or

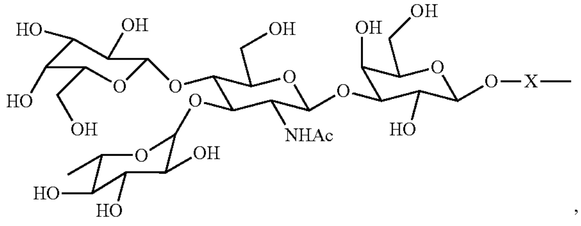

wherein X is any suitable linker molecule, which may be present or absent, and when present is typically selected from lower alkyl or PEG groups.

In some embodiments, the solubilizing block(S) comprises solubilizing groups (SG) that have net positive or net negative charge in aqueous buffers at a pH of about 7.4. The charge of the solubilizing groups (SG) may be dependent or independent of the pH of the solution in which the solubilizing block (S) is dispersed, such is the case, for example, for tertiary amines and quaternary ammonium compounds that are pH dependent and pH independent, respectively. Non-limiting examples of solubilizing groups that have net positive or net negative charge at certain pH in aqueous solutions or have pH independent charge are provided here for clarity:

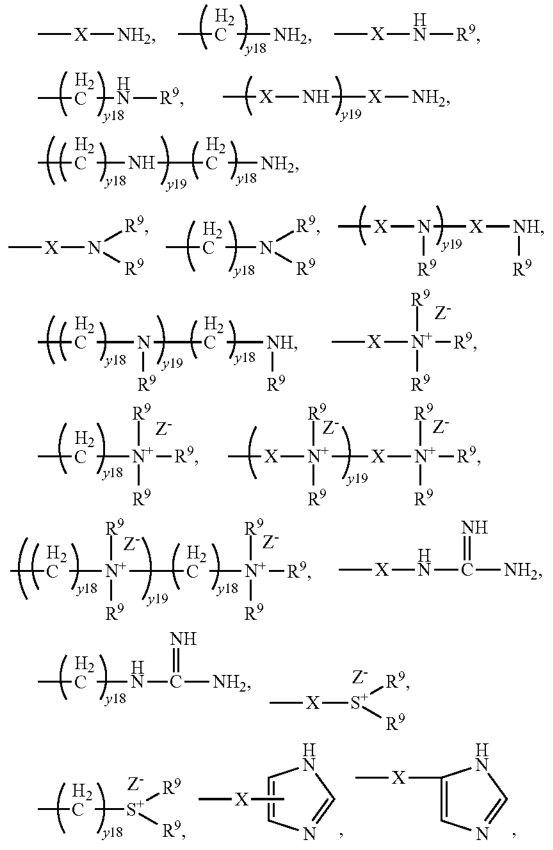

-continued

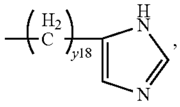
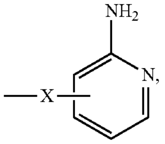
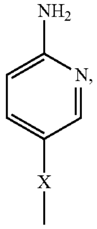

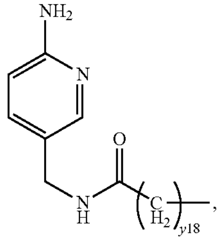

—X—COOH,

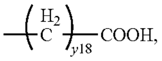

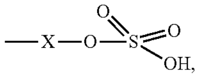
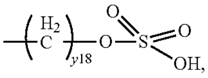

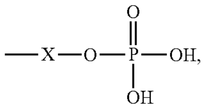
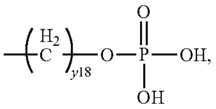

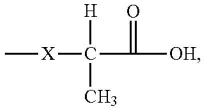
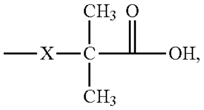

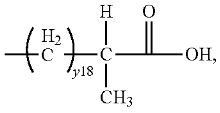
or
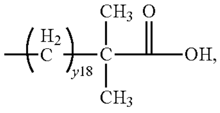

wherein X is any suitable linker molecule, which may be present or absent, and when present is typically selected from lower alkyl or PEG, y18 and y19 are each independently any integer, typically selected from between 1 to 6, $R^9$ is selected from lower alkyl or branched alkyl groups, such as $CH_3$, $CH_2CH_3$, $CH_2CH_2CH_3$, $CH(CH_3)_2$, $H_2CH(CH_3)_2$ or the like, and Z is any suitable counter anion, which is typically selected from conjugate bases of weak acids or halide ions, such as $Cl^-$, $I^-$, or $Br^-$.

In certain preferred embodiments, the solubilizing block (S) comprises solubilizing groups (SG) selected from zwitterions that have 0 net charge, or net 0 charge in aqueous conditions at certain pH. In some embodiments, the solubilizing block(S) comprises solubilizing groups (SG) selected from zwitterions that have 0 net charge at pH 7.4, but have net positive charge at reduced pH, e.g., tumor pH between about 5.5 to 7.0. Non-limiting examples of solubilizing groups comprising zwitterions are provided here for clarity:

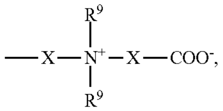
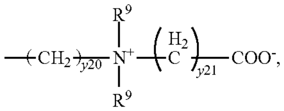

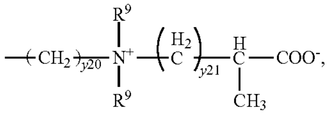

-continued

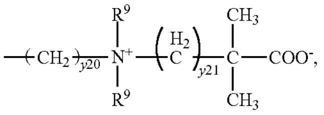

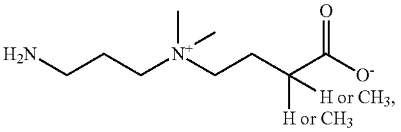

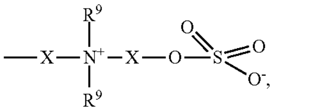

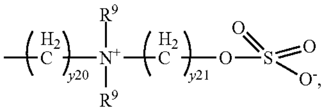

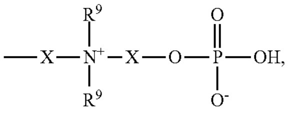

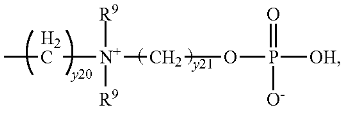

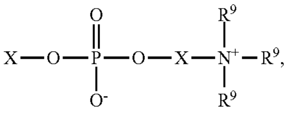

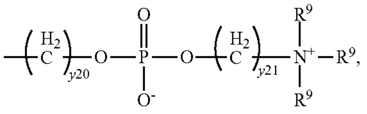

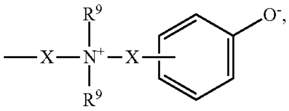

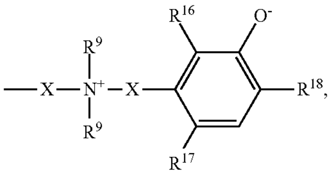

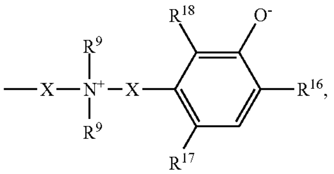

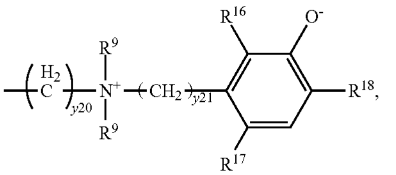

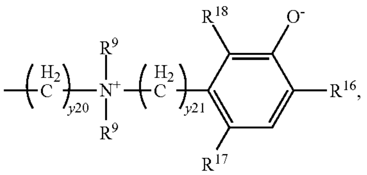

-continued

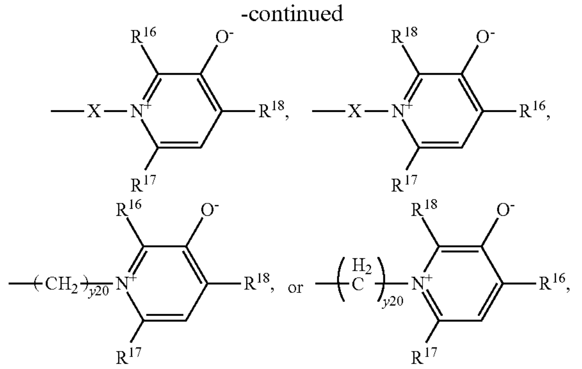

wherein X is any suitable linker, which may be present or absent, and when present is typically selected from lower alkyl or PEG groups, y20 and y21 are each independently any integer, typically selected from between 1 to 6, $R^9$ is selected from lower alkyl or branched alkyl groups, such as $CH_3$, $CH_2CH_3$, $CH_2CH_2CH_3$, $CH(CH_3)_2$, $H_2CH(CH_3)_2$ or the like, $R^{16}$, $R^{17}$ and $R^{18}$ are each independently selected from —H, $CH_3$, F and —$NO_2$.

In some embodiments, the solubilizing group (SG) may further comprise a targeting moiety and/or drug molecule. As a non-limiting example, certain sugar molecules may improve solubility and therefore function as a solubilizing group; additionally, the sugar molecule may bind to cell surface receptors and/or exert a physiological effect and therefore also function as a targeting moiety and/or drug molecule (D). Accordingly, solubilizing groups (SG) comprising mannose bind to mannose receptors and therefore target cells and tissues expressing such receptors; additionally, binding to the mannose receptor can promote phagocytosis and may therefore exert a physiological effect. Additional non-limiting examples of solubilizing groups (SG) that may perform two or more functions include targeting molecules comprising hydrophilic peptides, glycopeptides, antibodies, fragments of antibodies, nanobodies, nucleic acid aptamers and related molecules that are both hydrophilic and bind to specific cells or tissues.

Linkage of Solubilizing Group (SG) to the Solubilizing Block

Solubilizing groups (SG) may be linked to the solubilizing block(S) through any suitable means, including any suitable linker molecule. In certain preferred embodiments of dendron-based solubilizing blocks(S), the terminal functional group is a carboxylic acid, and the solubilizing group is linked via an ester or, more preferably, an amide bond. In certain other preferred embodiments of dendron-based solubilizing blocks(S), the terminal functional group is an amine, and the solubilizing group is linked to the terminal functional group via an amide or carbamate bond.

In preferred embodiments, solubilizing groups (SG) are linked to the solubilizing block(S) through a covalent bond via a suitable linker X, which is typically selected from lower alkyl or PEG groups. Particular suitable linkers X that are preferred for joining SG to S are referred to as X5. In non-limiting examples, solubilizing blocks(S) selected from either polymers comprising monomers comprising amines or dendrons comprising terminal functional groups (FGt) comprising amines, e.g., —$NH_2$, are covalently linked to solubilizing groups (SG) via a suitable linker, X5, through reaction with activated carboxylic acids (LG-C(O)—$R^{19}$) to yield-NH—C(O)—$R^{19}$; activated mixed carbonates (LG-C(O)—O—$R^{19}$) or chloroformates (Cl—C(O)—O—$R^{19}$) to yield NH—C(O)—O—$R^{19}$; aldehydes or ketones ($CR^{22}$(O)—$R^{19}$) to yield Schiff base of formula $CR^{22}$ (—NH)—$R^{19}$; alkenes (C($R^{22}$)($R^{23}$)═C($R^{24}$)($R^{19}$) to yield Michael-addition products (e.g., NH—C($R^{22}$)($R^{23}$)—CH($R^{24}$)($R^{19}$) or —N(C($R^{22}$)($R^{23}$)—CH($R^{24}$)($R^{19}$)) 2); or, alkyl or aryl halide (LG-$R^{19}$, wherein LG=Cl, Br or I), to yield —NH—$R^{19}$, —N(—$R^{19}$)$_2$ and/or —N+(—$R^{19}$)$_3$. In additional non-limiting examples, solubilizing blocks(S) selected from either polymers comprising monomers comprising carboxylic acids or dendrons comprising terminal functional groups (FGt) comprising carboxylic acids, e.g., —COOH (or —C(O)-LG), are covalently linked to solubilizing groups (SG) via a suitable linker, X5, through reaction with an amine ($NH_2$—$R^{19}$) to yield-C(O)—NH—$R^{19}$ or methylamine ($R^{19}$—N($CH_3$)(H) or $R^{19}$—NHMe) to yield —C(O)—N($CH_3$)($R^{19}$).

In the above non-limiting examples, LG is any suitable leaving group, and $R^{19}$ may be selected from but is not limited to —$(CH_2)_t$-SG, —$(CH_2CH_2O)_t$—$CH_2CH_2$-SG, —$(CH_2)_t$—C(O)—NH—$(CH_2)_u$-SG, —$(CH_2CH_2O)_t$ $CH_2CH_2$C(O)—NH—$(CH_2)_u$-SG, —$(CH_2)_t$—NH—C(O)—NH—$(CH_2)_u$-SG and $(CH_2CH_2O)_t CH_2CH_2$NH—C(O)—$(CH_2)_u$-SG where t and u are each independently an integer typically selected from between 1 to 6, such as 1, 2, 3, 4, 5 or 6. Preferred X5 for linking S to SG (i.e., S-X5-SG) are typically selected from —NH—$(CH_2)_t$—, —NH—$(CH_2CH_2O)_t$—$CH_2CH_2$—, —NH—$(CH_2)_t$—C(O)—NH—$(CH_2)_u$—, —NH—$(CH_2CH_2O)_t CH_2CH_2$C(O)—NH—$(CH_2)_u$—, NH—$(CH_2)_t$—NH—C(O)—NH—$(CH_2)_u$—, —NH$(CH_2CH_2O)_t CH_2CH_2$NH—C(O)—$(CH_2)_u$—, —C(O)—$(CH_2)_t$—, —C(O)—$(CH_2CH_2O)$—$CH_2CH_2$—, —C(O)—$(CH_2)_t$—C(O)—NH—$(CH_2)_u$—, C(O)—$(CH_2CH_2O)_t CH_2CH_2$C(O)—NH—$(CH_2)_u$—, C(O)—$(CH_2)$—NH—C(O)—NH—$(CH_2)_u$— or —C(O)—$(CH_2CH_2O)_t CH_2CH_2$NH—C(O)—$(CH_2)_u$—, where t and u are each independently an integer typically selected from between 1 to 6, such as 1, 2, 3, 4, 5 or 6.

A non-limiting example of an amphiphile comprising a solubilizing block(S) with dendron architecture, wherein the dendron is second generation and comprises monomeric units selected from FG1-CH($R^1$)$_2$, wherein FG1 (and the focal point) is $NH_2$, $R^1$ is $(OCH_2CH_2)_y$-FG2, y is 1 and FG2 (and FGt) is COOH, wherein the terminal functional group (FGt) carboxylic acids are linked to $NH_2$—$R^{19}$ to yield-C(O)—$NH_2$—$R^{19}$ wherein $R^{19}$ is —$(CH_2CH_2O)_t$—$CH_2CH_2$-SG, t=1 and the solubilizing group is selected from a glucose is provided below for clarity:

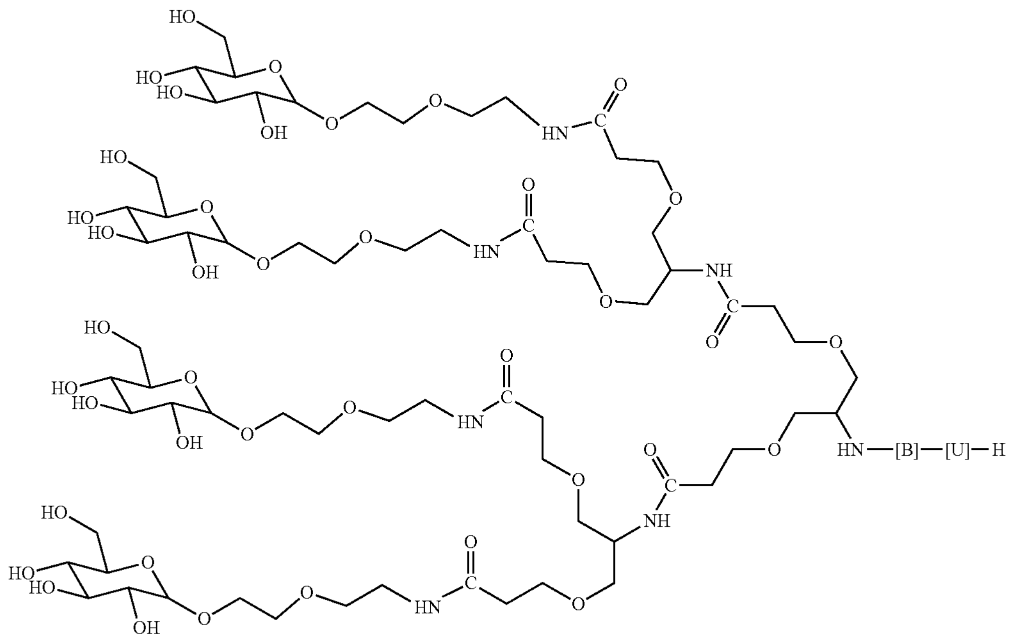

wherein the solubilizing block(S) is linked either directly or indirectly via a spacer (B) and/or Linker U to the hydrophobic block (H), which may further comprise a drug molecule (e.g., H-D). In the above example, X5 is —NH—$R^{19}$ and $R^{19}$ is —$(CH_2CH_2O)_t$—$CH_2CH_2$-SG, which may be written as —NH—$(CH_2CH_2O)_t$—$CH_2CH_2$—(SG not shown), wherein t=1 and SG is α glucose.

Additional examples of hydrophobic blocks (H) with dendron architecture that have particular utility for certain applications and/or lead to unexpected improvements in manufacturing and/or biological activity are provided throughout the specification.

Impact of the Number of Charged Functional Groups

In some embodiments, the solubilizing block(S) has a net negative charge and comprises one or more functional groups that carry a negative charge at pH 7.4. Suitable solubilizing blocks(S) that carry a net negative charge include molecules bearing functional groups (e.g., functional groups with a pKa of about 7.4 or less) that occur as the conjugate base of an acid at physiologic pH, at a pH of about 7.4 or less. These include but are not limited to molecules bearing carboxylates, sulfates, phosphates, phosphoramidates, and phosphonates. The solubilizing block(S) bearing a carboxylate may be selected from but is not limited to carboxylic acids selected from glutamic acid, aspartic acid, pyruvic acid, lactic acid, glycolic acid, glucuronic acid, citrate, isocitrate, alpha-keto-glutarate, succinate, fumarate, malate, oxaloacetate, butyrate, methylbutyrate, dimethylbutyrate and derivatives thereof. In certain embodiments, the solubilizing block(S) comprises a molecule with between 1 to 20 negatively charged functional groups, such as 1, 2, 3, 4, 5, 6, 7, 8, 9, 10, 11, 12, 13, 14, 15, 16, 17, 18, 19 or 20 negatively charged functional groups, though, typically no more than 8 negatively charged functional groups, preferably between 4 and 8 negatively charged functional groups.

In some embodiments, the solubilizing block(S) has a net positive charge and comprises positively charged functional groups. Suitable solubilizing blocks(S) that carry a net positive charge include molecules that occur as the conjugate acid of weak bases at pH 7.4, wherein the pKa of the conjugate acid of the base is greater than 7.4. These include but are not limited to molecules bearing primary, secondary and tertiary amines, as well as quaternary ammonium, guanidinium, phosphonium and sulfonium functional groups. Suitable molecules bearing ammonium functional groups include, for example, imidazolium, and tetra-alkyl ammonium compounds. In some embodiments, the solubilizing block comprises quaternary ammonium or sulfonium compounds that carry a permanent positive charge that is independent of pH.

In some embodiments, the solubilizing group(S) comprises between 1-20 positively charged functional groups, such as 1, 2, 3, 4, 5, 6, 7, 8, 9, 10, 11, 12, 13, 14, 15, 16, 17, 18, 19 or 20 positively charged functional groups. For amphiphiles, the solubilizing block(S) typically has no more than 8 charged functional groups, preferably between 4 and 8 positively charged functional groups.

For peptide antigen conjugates, the number of charged functional groups of the charged block (C) is typically selected to ensure net charge of the peptide antigen conjugate at physiologic pH 7.4 is greater than or equal to +2 or greater than or equal to +3, and the charged block is typically selected from poly(amino acids) comprising lysine or ornithine. For compositions of vaccines comprising at least one peptide antigen conjugate comprising a charged block, wherein the vaccine further comprises an amphiphilic carrier molecule ("amphiphile," e.g., of formula S-[B]-[U]-H), the number of charged functional groups present on the charged block (C) of the peptide antigen conjugate is typically selected to ensure net charge of the peptide antigen conjugate at physiologic pH 7.4 is greater than or equal to +2 or greater than equal to +3, though, typically no more than +10, and the charged block is typically selected from poly(amino acids) comprising lysine or ornithine. The process for designing and manufacturing peptide antigen conjugates to achieve a specific net charge has been described by Lynn and colleagues (see: Lynn et al., Nature Biotechnology. 2020) and in patent application WO2018187515, which are incorporated by reference herein in their entirety.

Solubilizing Blocks of Peptide Antigen Conjugates

In typical embodiments, the vaccine comprises one or more peptide antigen conjugate(s) comprising a solubilizing block(S), e.g., S-[E1]-A-[E2]-[U]-H-[D] and [D]-H-[E1]-A-[E2]—S and an amphiphile of formula S-[B]-[U]-H, wherein for each occurrence, S and H are independently selected. In certain preferred embodiments of the vaccine, the amphiphile is absent and vaccine comprises one or more peptide antigen conjugate(s) comprising a solubilizing block (S), e.g., S-[E1]-A-[E2]-[U]-H-[D] and [D]-H-[E1]-A-[E2]—S. In certain other embodiments, the vaccine comprises one or more peptide antigen conjugate(s) without a solubilizing block(S), e.g., [E1]-A-[E2]-[U]-H-[D] and [D]-H-[E1]-A-[E2] and an amphiphile of formula S-[B]-[U]-H, wherein for each occurrence, H is independently selected.

The solubilizing block of peptide antigen conjugates is typically selected from hydrophilic linear polymers, with either neutral or negative charge that are typically between 10 and 50 monomeric units in length, or charged blocks (C).

In certain preferred embodiments, the hydrophilic, linear polymer is PEG, attached either directly or indirectly via an extension (E1 or E2) and/or linker (U) to the N- or C-terminus of the peptide antigen conjugate through an amide bond. A notable finding disclosed herein is that peptide antigen conjugates with PEG-based solubilizing blocks, e.g., PEG-[E1]-A-[E2]-[U]-H-[D] and [D]-H-[E1]-A-[E2]—[U]-PEG, were more well tolerated and led to improved immune responses, such as tolerance induction when used in vaccines for inducing tolerance, as compared with peptide antigen conjugates with solubilizing blocks selected from positively charged blocks (C). This was unexpected because PEG is typically used to prevent cell uptake and block immune responses but PEG up to 36 monomeric units in length was effective at stabilizing nanoparticles formed by peptide antigen conjugates of formula PEG-[E1]-A-[E2]-[U]-H-[D] and [D]-H-[E1]-A-[E2]—[U]-PEG while permitting enhanced immune responses, such as tolerance induction. Based on these findings, PEG was selected as the preferred solubilizing block for peptide antigen conjugates of formula PEG-[E1]-A-[E2]-[U]-H-[D] and [D]-H-[E1]-A-[E2]—[U]-PEG. The PEG group is typically selected from a PEG having between 12 and 36 monomeric units, more preferably between 20 and 28 monomeric, and most preferably 24 monomeric units, and is capped with either an amine (e.g., $NH_2—(CH_2—CH_2—O)_n—$), methoxy (e.g., $CH_3—O_2—(CH_2—CH_2—O)_n—$), ethoxy (e.g., $CH_3—CH_2—O_2—(CH_2—CH_2—O)_n—$) or hydroxyl group (e.g., $HO—(CH_2—CH_2—O)_n—$). In preferred embodiments the PEG comprises 24 monomeric units and is capped with a hydroxyl group based on unexpected findings that PEG with 24 monomeric units ("PEG24") and hydroxyl cap (end group) provided adequate solubility to enable the peptide antigen conjugates of formula PEG-[E1]-A-[E2]-[U]-H-[D] and [D]-H-[E1]-A-[E2]—[U]-PEG to form stable nanoparticle micelles without adversely impacting immune responses, e.g., tolerance induction.

In certain other embodiments, the solubilizing block of the one or more peptide antigen conjugates is selected from linear polymers comprising hydrophilic or charged monomers, wherein the charged monomers are selected from those having carboxylic acids. In certain preferred embodiments, the linear polymers comprising hydrophilic monomers are selected from, poly(lactic acid), poly(glycolic acid), poly(lactic-co-glycolic acid), poly(aspartic acid), poly (glutamic acid), poly(methyl acrylic acid), poly(ethyl acrylic acid), poly(HPMA) or poly(HEMA), poly(HEMAM) or poly(HEAA). In a non-limiting example, the linear polymers comprising hydrophilic monomers is selected from polym (HPMA) and the peptide antigen conjugates have the formula poly (HPMA)-[E1]-A-[E2]-[U]-H-[D] or [D]-H-[E1]-A-[E2]—[U]-poly (HPMA).

Counter-Ion Selection

In some embodiments of the vaccine, the peptide antigen conjugate, amphiphile, drug and/or formulation buffer may comprise a charge molecule. An important consideration regarding charged molecules is the counterion selected. Suitable counterions for charged molecules bearing functional groups with negative charge include but are not limited to hydrogen and alkali and alkaline earth metals, including, for example, sodium, potassium, magnesium and calcium, or conjugate acids of weak bases, such as ammonium compounds. Suitable amines used to form the ammonium salt include but are not limited to ammonium, primary amines, such as tris(hydroxymethyl) aminomethane ("TRIS" or "Tris"), secondary amines based on di-alkyl amines, such as dimethyl amine and diethyl amine, tertiary amines based on tri-alkyl amines, such as trimethylamine, di-isopropyl ethylamine (DIPEA) and triethylamine (TEA), as well as quaternary ammonium compounds.

Unexpectedly, tris(hydroxymethyl) aminomethane (or Tris) as the ammonium salt of acids as the counterion of amphiphiles and/or peptide antigen conjugates with negative charge had improved solubility in both water-miscible organic solvents, such as DMSO, DMF, acetone and ethanol, and aqueous solutions. For these reasons, the protonated form of tris(hydroxymethyl) aminomethane is a preferred counter-ion to use in formulations of vaccines disclosed herein.

Antigens

The antigen of immunogenic compositions, e.g., vaccines, may be any antigen that is useful for inducing an immune response in a subject and is often selected from peptide antigens (A). The peptide antigen (A) may be used to induce either a proinflammatory or tolerogenic immune response depending on the nature of the immune response required for the application. In some embodiments, the peptide antigen (A) is a tumor-associated antigen, such as a self-antigen, neoantigen or tumor-associated viral antigen (e.g., HPV E6/E7). In other embodiments, the peptide antigen (A) is an infectious disease antigen, such as a peptide derived from a protein isolated from a virus, bacteria, fungi or protozoan microbial pathogen. In some embodiments, the peptide antigen (A) is a peptide derived from an allergen or an autoantigen, which is known or suspected to cause allergies or autoimmunity. In other embodiments, the peptide antigen (A) is a peptide derived from an alloantigen.

The peptide antigen (A) comprises a sequence of amino acids or a peptide mimetic that can induce an immune response, such as a T cell or B cell response in a subject. In some embodiments, the peptide antigen (A) comprises an amino acid or amino acids with a post-translational modification (e.g., glycosylation, oxidation, phosphorylation, citrullination and/or homocitrullination), non-natural amino acids or peptide-mimetics. The peptide antigen may be any sequence of natural, non-natural or post-translationally modified amino acids, peptide-mimetics, or any combination thereof, that have an antigen or predicted antigen, i.e., an antigen with a T cell and/or B cell epitope. Peptide antigens (A) also include post-translationally modified peptide antigens (A), including glycopeptides.

The inventors of the present disclosure found unexpectedly that replacing certain amino acids, e.g., Cysteine and Methionine, found in naturally occurring peptide antigen sequences with amino acids that are not naturally found in those sequences, e.g., alpha aminobutyric acid (aBut) and norleucine (nLeu), respectively, led to unexpected improvements in vaccine manufacturing and in vivo immunogenicity. Therefore, in preferred embodiments of peptide antigens (A), naturally occurring cysteine amino acids are replaced with alpha aminobutyric acid and methionine amino acids are replaced with norleucine.

Immunogenic compositions, including compositions of vaccines, e.g., vaccine for inducing tolerance, may comprise one or more different peptide antigen conjugates each having a different peptide antigen (A) composition. In some embodiments, the immunogenic compositions, e.g., vaccines, comprise particles with up to 50 different peptide antigen conjugates each having a unique peptide antigen (A) composition. In some embodiments, the immunogenic compositions comprise mosaic particles that comprise two or more different peptide antigen conjugates, e.g., up to about 100 different peptide antigen conjugates, typically no more than about 40 peptide antigen conjugates, such as 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 peptide antigen conjugates. In other embodiments, the immunogenic compositions comprise mosaic particles that comprise 5 different peptide antigen conjugates. In still other embodiments, the immunogenic compositions comprise a single particle composition comprising of a single (1) peptide antigen conjugate composition.

The length of the peptide antigen (A) depends on the specific application and is typically between about 5 to about 100 amino acids. In preferred embodiments, the peptide antigen (A) is between about 7 to 45 amino acids, e.g., 7, 8, 9, 10, 11, 12, 13, 14, 15, 16, 17, 18, 19, 20, 21, 22, 23, 24, 25, 26, 27, 28, 29, 30, 31, 32, 33, 34, 35, 37, 38, 39, 40, 41, 42, 43, 44 or 45 amino acids. In still other cases, the peptide antigen is a full-length polypeptide, such as a protein antigen that may be recombinantly expressed.

In some embodiments, the peptide antigen (A) is 7 to 35 amino acids, typically about 25 amino acids. Thus, for an autoantigen, allergen, alloantigen, tumor-associated antigen or infectious disease antigen greater than 25 amino acids in length, e.g., a 100 amino acid antigen, the antigen may be divided into multiple peptide sequences of 7 to 35 amino acid, e.g., 25 amino acid, peptide antigens (A) wherein each peptide antigen (A) contains a unique composition of amino acids; or, the peptide antigens (A) can be overlapping peptide pools wherein an antigen is divided into a set number of 7 to 35 amino acid, e.g., 25 amino acid, peptide antigens (A) that have overlapping sequences. For example, an overlapping peptide pool comprising a 100 amino acid antigen may be divided into eight 25 amino acid peptide antigens (A) that are each offset by 12 amino acids (i.e., each subsequent 25 amino acid peptide comprising a 100 amino acid peptide sequence starts at the 13th amino acid position from the prior peptide). Those skilled in the art understand that many permutations exist for generating a peptide pool from an antigen.

In some embodiments, the peptide antigen (A) is a minimal CD8 or CD4 T cell epitope that comprises the portions of a tumor-associated antigen, infectious disease antigen, allergen, alloantigen or autoantigen that are predicted in silico (or measured empirically) to bind MHC-I or MHC-II molecules. Algorithms for predicting MHC-I or MHC-II binding are widely available (see Lundegaard et al., Nucleic Acids Res., 36: W509-W512, 2008 and http://www.cbs.dtu.dk/services/NetMHC/). In some embodiments of a personalized therapy for a particular subject, the peptide antigen (A) comprising a peptide antigen conjugate may comprise a minimal CD8 T cell epitope from a tumor-associated antigen, infectious disease antigen, allergen, alloantigen or autoantigen that is typically a 7-13 amino acid peptide that is predicted to have <1,000 nM binding affinity for a particular MHC-I allele that is expressed by that subject. In some embodiments of a personalized therapy for a particular subject, the peptide antigen (A) may comprise a minimal CD4 T cell epitope from a tumor-associated antigen, infectious disease antigen, allergen, alloantigen or autoantigen that is an 8-20 amino acid peptide, or more preferably a 10-16 amino acid peptide, that is predicted to have <1,000 nM binding affinity for a particular MHC-II allele that is expressed by that subject. In certain preferred embodiments, when a minimal CD8 or CD4 T cell epitope cannot be identified for a tumor-associated antigen, infectious disease antigen, allergen, alloantigen or autoantigen, or when the tumor-associated antigen, infectious disease antigen, allergen or autoantigen contains multiple CD8 and CD4 T cell epitopes, the peptide antigen (A) may be between 16-35 amino acids, e.g., up to 35 amino acids such that it may contain all possible CD8 or CD4 T cell epitopes.

In some embodiments, the peptide antigen (A) is derived from tumor antigens. Tumor antigens include self-antigens that are present on healthy cells but are preferentially expressed by tumor cells, or neoantigens, which are aberrant proteins that are specific to tumor cells and are unique to individual patients. Tumor antigens may also include viral antigens.

Preferred self-antigens include antigens that are preferentially expressed by tumor cells, such as CLPP, Cyclin-A1, MAGE-A1, MAGE-C1, MAGE-C2, SSX2, XAgE1b/GAGED2a, Melan-A/MART-1, TRP-1, Tyrosinase, CD45, glypican-3, IGF2B3, Kallikrein 4, KIF20A, Lengsin, Meloe, MUC5AC, survivin, prostatic acid phosphatase, NY-ESO-1 and MAGE-A3.

Neoantigens arise from the inherent genetic instability of cancers, which can lead to mutations in DNA, RNA splice variants and changes in post-translational modification, all potentially leading to de novo protein products that are referred to collectively as neoantigens or sometimes predicted neoantigens. DNA mutations include changes to the DNA including nonsynonymous missense mutations, nonsense mutations, insertions, deletions, chromosomal inversions and chromosomal translocations, all potentially resulting in novel gene products and therefore neoantigens. RNA splice site changes can result in novel protein products and missense mutations can introduce amino acids permissive to post-translational modifications (e.g., phosphorylation) that may be antigenic. The instability of tumor cells can furthermore result in epigenetic changes and the activation of certain transcription factors that may result in selective expression of certain antigens by tumor cells that are not expressed by healthy, non-cancerous cells.

Peptide antigen conjugates used in personalized cancer vaccines should include peptide antigens (A) that comprise the portions of tumor-associated antigens that are unique to tumor cells. Peptide antigens (A) comprising neoantigens arising from a missense mutation should encompass the amino acid change encoded by 1 or more nucleotide polymorphisms. Peptide antigens (A) comprising neoantigens that arise from frameshift mutations, splice site variants, insertions, inversions and deletions should encompass the novel peptide sequences and junctions of novel peptide sequences. Peptide antigens (A) comprising neoantigens with novel post-translational modifications should encompass the amino acids bearing the post-translational modification(s), such as a phosphate or glycan. In preferred embodiments, the peptide antigen (A) comprises the up to 25 amino acids on either side flanking the amino acid change or novel junction that arises due to a mutation. In certain embodiments, the peptide antigen (A) is a neoantigen sequence that comprises the 12 amino acids on either side flanking the amino acid change that arises from a single nucleotide polymorphism, for example, a 25 amino acid peptide, wherein the 13th amino acid is the amino acid residue resulting from the single nucleotide polymorphism. In some embodiments, the peptide antigen (A) is a neoantigen sequence that comprises the 12 amino acids on either side flanking an amino acid with a novel post-translational modification, for example, a 25 amino acid peptide, wherein the $13^{th}$ amino acid is the amino acid residue resulting from the novel post-translational modification site. In other embodiments, the peptide antigen (A) is a neoantigen sequence that comprises 0-12 amino acids on either side flanking a novel junction created by an insertion, deletion or inversion. In some cases, the peptide antigen (A) comprising neoantigens resulting from novel sequences can encompass the entire novel sequence, including 0-25 amino acids on either side of novel junctions that may also arise.

Tumor-associated antigens suitable as peptide antigens (A) for immunogenic compositions of the present disclosure can be identified through various techniques that are familiar to one skilled in the art. Tumor-associated antigens can be identified by assessing protein expression of tumor cells as compared with healthy cells, i.e., non-cancerous cells from a subject. Suitable methods for assessing protein expression include but are not limited to immunohistochemistry, immunofluorescence, western blot, chromatography (i.e., size-exclusion chromatography), ELISA, flow cytometry and mass spectrometry. Proteins preferentially expressed by tumor cells but not healthy cells or by a limited number of healthy cells (e.g., CD20) are suitable tumor-associated antigens. DNA and RNA sequencing of patient tumor biopsies followed by bioinformatics to identify mutations in protein-coding DNA that are expressed as RNA and produce peptides predicted to bind to MHC-I or MHC-II alleles on patient antigen presenting cells (APCs), may also be used to identify tumor-associated antigens that are suitable as peptide antigens (A) for immunogenic compositions of the present disclosure.

In preferred embodiments, tumor-associated antigens suitable as peptide antigens (A) for immunogenic compositions are identified using mass spectrometry. Suitable peptide antigens (A) are peptides identified by mass spectrometry following elution from the MHC molecules from patient tumor biopsies but not from healthy tissues from the same subject (i.e., the peptide antigens are only present on tumor cells but not healthy cells from the same subject). Mass spectrometry may be used alone or in combination with other techniques to identify tumor-associated antigens. Those skilled in the art recognize that there are many methods for identifying tumor-associated antigens, such as neoantigens (see Yadav et al., Nature, 515:572-576, 2014) that are suitable as peptide antigens (A) for the practice of the disclosed invention.

In preferred embodiments, the tumor-associated antigens used as peptide antigens (A) are clonal or nearly clonal within the population of neoplastic cells, which may be considered heterogeneous in other respects.

Tumor-associated antigens selected for use as peptide antigens (A) in personalized cancer vaccination schemes may be selected based on mass spectrometry confirmation of peptide-MHC binding and/or in silico predicted MHC binding affinity and RNA expression levels within tumors. These data provide information on whether or not a tumor-associated antigen is expressed and presented by tumor cells and would therefore be a suitable target for T cells. Such criteria may be used to select the peptide antigens (A) used in a personalized cancer vaccine.

For patients with highly mutated tumors that have more than 50 tumor-associated neoantigens, a down-selection process may be used to select peptide antigens (A) for use in personalized cancer vaccines comprising peptide antigen conjugates. In some embodiments, a down-selection process is used to select peptide antigens (A) comprising epitopes predicted to have the highest MHC binding affinity and RNA expression levels within tumor cells. Additional criteria may be applied for the selection of tumor-associated self-antigens or neoantigens. For example, predicted immunogenicity or predicted capacity of the peptide antigen (A) to lead to T cells that react with other self-antigens, which may lead to autoimmunity, are additional criteria considered. For instance, peptide antigens (A) that comprise tumor-associated antigens and have high predicted immunogenicity but also low potential to lead to autoimmunity are criteria used to select potential peptide antigens (A) for use in personalized cancer vaccines. In some embodiments, neoantigens that that would be expected to result in T cell or antibody responses that react with self-antigens found on healthy cells are not selected for use as peptide antigens (A). For patients with less than, for example, 20-50 predicted neoantigens, a down selection process may not be critical and so all 20-50 predicted neoantigens might be used as peptides antigens (A) in a personalized cancer vaccine.

Cancer vaccines may include peptide antigens (A) that comprise tumor-associated antigens that are patient-specific and/or tumor-associated antigens that are shared between patients. For example, the tumor-associated antigen can be a conserved self-antigen, such as NY-ESO-1 (testicular cancer) or gp100 (melanoma), or the antigen may be a cryptic epitope, such as Na17 (melanoma) that is not typically expressed by healthy cells but is conserved between certain cancer patients. Immunogenic compositions of the present disclosure may include peptide antigens (A) that arise from so-called hot-spot mutations that are frequent mutations in certain genes or gene regions that occur more frequently than would be predicted by chance. Non-limiting examples of hot spot mutations include the V600E mutation in BRAF protein, which is common to melanoma, papillary thyroid and colorectal carcinomas, or KRAS G12 mutations, which are among the most common mutations, such as KRAS G12C. A number of suitable self-antigens as well as neoantigens that arise from hotspot mutations are known and are incorporated herein by reference: see Chang et al., Nature Biotechnology, 34:155-163, 2016; Vigneron, N., et al, Cancer Immunology, 13:15-20, 2013.

In some embodiments, the peptide antigen (A) can be from a hematological tumor. Non-limiting examples of hematological tumors include leukemias, including acute leukemias (such as 11q23-positive acute leukemia, acute lymphocytic leukemia, acute myelocytic leukemia, acute myelogenous leukemia and myeloblastic, promyelocytic, myelomonocytic, monocytic and erythroleukemia), chronic leukemias (such as chronic myelocytic (granulocytic) leukemia, chronic myelogenous leukemia, and chronic lymphocytic leukemia), polycythemia vera, lymphoma, Hodgkin's disease, non-Hodgkin's lymphoma (indolent and high grade forms), multiple myeloma, Waldenstrom's macroglobulinemia, heavy chain disease, myelodysplastic syndrome, hairy cell leukemia and myelodysplasia.

In some embodiments, the peptide antigen (A) can be from a solid tumor. Non-limiting examples of solid tumors, such as sarcomas and carcinomas, include fibrosarcoma, myxosarcoma, liposarcoma, chondrosarcoma, osteogenic sarcoma, and other sarcomas, synovioma, mesothelioma, Ewing's tumor, leiomyosarcoma, rhabdomyosarcoma, colon carcinoma, lymphoid malignancy, pancreatic cancer, breast cancer (including basal breast carcinoma, ductal carcinoma and lobular breast carcinoma), lung cancers, ovarian cancer, prostate cancer, hepatocellular carcinoma, squamous cell carcinoma, basal cell carcinoma, adenocarcinoma, sweat gland carcinoma, medullary thyroid carcinoma, papillary thyroid carcinoma, pheochromocytomas sebaceous gland carcinoma, papillary carcinoma, papillary adenocarcinomas, medullary carcinoma, bronchogenic carcinoma, renal cell carcinoma, hepatoma, bile duct carcinoma, choriocarcinoma, Wilms' tumor, cervical cancer, testicular tumor, seminoma, bladder carcinoma, and CNS tumors (such as a glioma, astrocytoma, medulloblastoma, craniopharyngioma, ependymoma, pinealoma, hemangioblastoma, acoustic neuroma, oligodendroglioma, meningioma, melanoma, neuroblastoma and retinoblastoma). In several examples, a tumor is melanoma, lung cancer, lymphoma breast cancer or colon cancer.

In some embodiments, the peptide antigen (A) is a tumor-associated antigen from a breast cancer, such as a ductal carcinoma or a lobular carcinoma. In some embodiments, the peptide antigen (A) is a tumor-associated antigen from a prostate cancer. In some embodiments, peptide antigen (A) is a tumor-associated antigen from a skin cancer, such as a basal cell carcinoma, a squamous cell carcinoma, a Kaposi's sarcoma, or a melanoma. In some embodiments, the peptide antigen (A) is a tumor-associated antigen from a lung cancer, such as an adenocarcinoma, a bronchiolaveolar carcinoma, a large cell carcinoma, or a small cell carcinoma. In some embodiments, the peptide antigen (A) is a tumor-associated antigen from a brain cancer, such as a glioblastoma or a meningioma. In some embodiments, the peptide antigen (A) is a tumor-associated antigen from a colon cancer. In some embodiments, the peptide antigen (A) is a tumor-associated antigen from a liver cancer, such as a hepatocellular carcinoma. In some embodiments, the peptide antigen (A) is a tumor-associated antigen from a pancreatic cancer. In some embodiments, peptide antigen (A) is a tumor-associated antigen from a kidney cancer, such as a renal cell carcinoma. In some embodiments, the peptide antigen (A) is a tumor-associated antigen from a testicular cancer.

In some embodiments, the peptide antigen (A) is a tumor-associated antigen derived from premalignant conditions, such as variants of carcinoma in situ, or vulvar intraepithelial neoplasia, cervical intraepithelial neoplasia, or vaginal intraepithelial neoplasia.

In some embodiments, the peptide antigen (A) is an antigen from an infectious agent, such as a virus, a bacterium, or a fungus. In additional embodiments, the peptide antigen (A) is a peptide or glycopeptide derived from an infectious agent; for example, the HIV Envelope fusion peptide or a V3 or V1/V2 glycopeptide from HIV. In some embodiments, the antigen is a peptide antigen derived from a flavivirus, such as dengue, West Nile virus, Zika virus, hepatitis C or others; a coronavirus, such as MERS, SARS or SARS-COV-2 viruses; a paramyxovirus, such as a mumps, measles, respiratory syncytial virus (RSV), human parainfluenza viruses, as well as zoonotic viruses, such a Newcastle disease virus; a filovirus, such as Ebola or Marburg viruses; human papillomaviruses; hepadnaviruses, such as hepatitis B; orthomyxovirus, such as influenza; lentiviruses, such as HIV; and other viral derived proteins or glycoproteins.

In certain preferred embodiments of the vaccine against HPV, the peptide antigens are selected from MHQKRTAMFQDPQERPRKLPQLCTELQTT (SEQ ID NO:82), PRKLPQLCTELQTTIHDIILECVYCKQQL (SEQ ID NO:83), HDIILECVYCKQQLLRREVYDFAFRDLCI (SEQ ID NO:84), RREVYDFAFRDLCIVYRDGNPYAVCDKCL (SEQ ID NO:85), YRDGNPYAVCDKCLKFYSKISEYRHYCYS (SEQ ID NO:86), FYSKISEYRHYCYSLYGTTLEQQYNKPLC (SEQ ID NO:87), YGTTLEQQYNKPLCDLLIRCINCQKPLCP (SEQ ID NO:88), LLIRCINCQKPLCPEEKQRHLDKKQRFHN (SEQ ID NO:89), EKQRHLDKKQRFHNIRGRWTGRCMSCCR (SEQ ID NO:90), IRGRWTGRCMSCCRSSRTRRETQL (SEQ ID NO:91), MHGDTPTLHEYMLDLQPETTDLYCYEQ (SEQ ID NO:92) DLQPETTDLYCYEQLNDSSEEEDEI (SEQ ID NO:93), YEQLNDSSEEEDEIDGPAGQAEPDR (SEQ ID NO:94), DEIDGPAGQAEPDRAHYNIVTFCCKCD (SEQ ID NO:95), RAHYNIVTFCCKCDSTLRLCVQSTHVDIRTLE (SEQ ID NO:96), LCVQSTHVDIRTLEDLLMGTLGIVCPICSQKP (SEQ ID NO:97) and QLYQTCKAAGTCPSDVIPKI (SEQ ID NO:98). In preferred embodiments of the vaccine against HPV, one or more cysteine and/or methionine residues of naturally occurring peptide antigens are replaced with alpha-aminobutyric acid ("B") and/or norleucine ("n"), respectively. Non-limiting examples include nHQKRTAnFQDPQERPRKLPQLBTELQTT (SEQ ID NO: 143) nHQKRTAnFQDPQERPRKLPQLCTELQTT (SEQ ID NO:99), MHQKRTAMFQDPQERPRKLPQLBTELQTT (SEQ ID NO: 100), PRKLPQLBTELQTTIHDIILEBVYBKQQL (SEQ ID NO:101), HDIILEBVYBKQQLLRREVYDFAFRDLBI (SEQ ID NO:102), RREVYDFAFRDLBIVYRDGNPYAVBDKBL (SEQ ID NO:103), YRDGNPYAVBDKBLKFYSKISEYRHYBYS (SEQ ID NO:104), FYSKISEYRHYBYSLYGTTLEQQYNKPLB (SEQ ID NO:105), YGTTLEQQYNKPLDLLIRBINBQKPLBP (SEQ ID NO:106), LLIRBINBQKPLBPEEKQRHLDKKQRFHN (SEQ ID NO:107), EKQRHLDKKQRFHNIRGRWTGRCnSCCR (SEQ ID NO:108), EKQRHLDKKQRFHNIRGRWTGRBnSBBR (SEQ ID NO:109), EKQRHLDKKQRFHNIRGRWTGRBMSBBR (SEQ ID NO:110), IRGRWTGRCnSCCRSSRTRRETQL (SEQ ID NO:111), IRGRWTGRBnSBBRSSRTRRETQL (SEQ ID NO: 112), IRGRWTGRBMSBBRSSRTRRETQL (SEQ ID NO:113), nHGDTPTLHEYnLDLQPETTDLYCYEQ (SEQ ID NO:114), nHGDTPTLHEYnLDLQPETTDLYBYEQ (SEQ ID NO:115), nHGDTPTLHEYnLDLQPETTDLYMYEQ (SEQ ID NO:116), DLQPETTDLYBYEQLNDSSEEEDEI (SEQ ID NO:117), YEQLNDSSEEEDEIDGPAGQAEPDR (SEQ ID NO:118), DEIDGPAGQAEPDRAHYNIVTFBBKBD (SEQ ID NO:119), RAHYNIVTFBBKBDSTLRLBVQSTHVDIRTLE (SEQ ID NO:120), LCVQSTHVDIRTLEDLLnGTLGIVCPICSQKP (SEQ ID NO:121), LBVQSTHVDIRTLEDLLnGTLGIVBPIBSQKP (SEQ ID NO:122), LBVQSTHVDIRTLEDLLMGTLGIVBPIBSQKP (SEQ ID NO:123), and QLYQTBKAAGTBPSDVIPKI (SEQ ID NO:124) or any fragments thereof having at least 6 amino acids in length, preferably at least 9 amino acids, or derivatives thereof.

In certain other preferred embodiments of the vaccine against HPV, including HPV+ cancers, the peptide antigens are selected from ALQAIELQLTLETIYNSQYSNEKWTLQDV (SEQ ID NO:125), NSQYSNEKWTLQDVSLEVYLTAPTGCIKK (SEQ ID NO:126), SVTVVEGQVDYYGLYYVHEGIRTYFVQFK (SEQ ID NO:127), LKGDANTLKCLRYRFKKHCTLYTAVSSTWHWT (SEQ ID NO:128), KHKSAIVTLTYDSEWQRDQFLSQVKIPKT (SEQ ID NO: 129), MHQKRTAMFQDPQERPRKLPQLCTELQTT (SEQ ID NO:130), PRKLPQLCTELQTTIHDIILECVYCKQQL (SEQ ID NO:131), HDIILECVYCKQQLLRREVYDFAFRDLCI (SEQ ID NO:132), RREVYDFAFRDLCIVYRDGNPYAVCDKCL (SEQ ID NO:133), YRDGNPYAVCDKCLKFYSKISEYRHYCYS (SEQ ID NO:134), FYSKISEYRHYCYSLYGTTLEQQYNKPLC (SEQ ID NO:135), YGTTLEQQYNKPLCDLLIRCINCQKPLCP (SEQ ID NO:136), CPEEKQRHLDKKQRFHNIRGRWTGRCMSCCR (SEQ ID NO:137), MHGDTPTLHEYMLDLQPETTDLYCYEQ (SEQ ID NO:138), AGQAEPDRAHYNIVTFCCKCDSTLRLCVQ (SEQ ID NO:139). and LCVQSTHVDIRTLEDLLMGTLGIVCPICSQKP (SEQ ID NO: 140), wherein in preferred embodiments one or more cysteine and/or methionine residues are replaced with alpha-aminobutyric acid and/or norleucine, respectively, for example, ALQAIELQLTLETIYNSQYSNEKWTLQDV (SEQ ID NO:125), NSQYSNEKWTLQDVSLEVYLTAPTGBIKK (SEQ ID NO:141), SVTVVEGQVDYYGLYYVHEGIRTYFVQFK (SEQ ID NO: 127), LKGDANTLKBLRYRFKKHBTLYTAVSSTWHWT (SEQ ID NO:142), KHKSAIVTLTYDSEWQRDQFLSQVKIPKT (SEQ ID NO: 129), nHQKRTAnFQDPQERPRKLPQLBTELQTT (SEQ ID NO:143), PRKLPQLBTELQTTIHDIILEBVYBKQQL (SEQ ID NO:144), HDIILEBVYBKQQLLRREVYDFAFRDLBI (SEQ ID NO:145), RREVYDFAFRDLBIVYRDGNPYAVBDKBL (SEQ ID NO:146), YRDGNPYAVBDKBLKFYSKISEYRHYBYS (SEQ ID NO:147), FYSKISEYRHYBYSLYGTTLEQQYNKPLB (SEQ ID NO:148), YGTTLEQQYNKPLBDLLIRBINBQKPLBP (SEQ ID NO: 149), BPEEKQRHLDKKQRFHNIRGRWTGRBnSBBR (SEQ ID NO:150), nHGDTPTLHEYnLDLQPETTDLYBYEQ (SEQ ID NO:151), AGQAEPDRAHYNIVTFBBKBDSTLRLBVQ (SEQ ID NO:152) and LBVQSTHVDIRTLEDLLnGTLGIVBPIBSQKP (SEQ ID NO:153).

In some embodiments of cancer vaccines for prostate cancer, the cancer vaccine comprises peptide antigens selected from fragments of prostate specific antigen (PSA), APLILSRIVGGWECEKHSQPWQVLVASRGRAVCGGVLVHPQWVLTAAHCIRNKSVILLGRHSLF HPEDTGQVFQVSHSFPHPLYDMSLLKNRFLRPGDDS SHDLMLLRLSEPAELTDAVKVMDLPTQE PALGTTCYASGWGSIEPEEFLTPKKLQCVDLHVISNDVCAQVHPQKVTKFMLCAGRWTGGKST CSGDSGGPLVCNGVLQGITSWGSEPCALPERPSLYTKVVHYRK WIKDTIVANP. (SEQ ID NO: 154). In certain preferred embodiments, the peptide antigens (A) selected from fragments of PSA are typically selected from 7 to 55 amino acid stretches of PSA that may optionally overlap. Non-limiting examples include but are not limited to: CGGVLVHPQWVLTAAHCIRNKSVILLGRHSLFHPE (SEQ ID NO: 155), SLFHPEDTGQVFQVSHSFPHPLYDMSLLKNRFLRP (SEQ ID NO: 156), PCALPERPSLYTKVVHYRKWIKDTIVANP (SEQ ID NO:157).

In some embodiments of cancer vaccines for prostate cancer, the cancer vaccine comprises peptide antigens selected from fragments of prostatic acid phosphatase (PAP), FFWLDRSVLAKELKFVTLVFRHGDRSPIDTFPTDPIKESSWPQGFGQLTQLGMEQHYELGEYIRK RYRKFLNESYKHEQVYIRSTDVDRTLMSAMTNLAALFPPEGVSIWNPILLWQPIPVHTVPLSEDQ LLYLPFRNCPRFQELESETLKSEEFQKRLHPYKDFIATLGKLSGLHGQDLFGIWSKVYDPLYCES VHNFTLPSWATEDTMTKLRELSELSLLSLYGIHKQKEKSRLQGGVLVNEILNHMKRATQIPSYK KLIMYSAHDTTVSGLQMALDVYNGLLPPYASCHLTELYFEKGEYFVEMYYRNETQHEPYPLML PGCSPSCPLERFAELVGPVIPQDWSTECMTTNSHQGTEDSTD (SEQ ID NO:158). In certain preferred embodiments, the peptide antigens (A) selected from fragments of PAP are typically selected from 7 to 55 amino acid stretches of PAP that may optionally overlap. Non-limiting examples include but are not limited to: RTLMSAMTNLAALFPPEGVSIWNPILLWQPIPVHT (SEQ ID NO:159), PILLWQPIPVHTVPLSEDQLLYLPFRNCPRFQELE (SEQ ID NO:160), ATEDTMTKLRELSELSLLSLYGIHKQKEKSRLQGG (SEQ ID NO:161), LOGGVLVNEILNHMKRATQIPSYKKLIMYSAHDTT (SEQ ID NO:162), MALDVYNGLLPPYASCHLTELYFEKGEYFVEMYYR (SEQ ID NO:163), YFEKGEYFVEMYYRNETQHEPYPLMLPGCSPSCPL (SEQ ID NO:164).

In some embodiments of cancer vaccines for prostate cancer, the cancer vaccine comprises peptide antigens selected from fragments of STEAP1, MESRKDITNQEELWKMKPRRNLEEDDYLHKDTGETSMLKRPVLLHLHQTAHADEFDCPSELQH TQELFPQWHLPIKIAAIIASLTFLYTLLREVIHPLATSHQQYFYKIPILVINKVLPMVSITLLALVYL PGVIAAIVQLHNGTKYKKFPHWLDKWMLTRKQFGLLSFFFAVLHAIYSLSYPMRRSYRYKLLN WAYQQVQQNKEDAWIEHDVWRMEIYVSLGIVGLAILALLAVTSIPSVSDSLTWREFHYIQSKLG IVSLLLGTIHALIFAWNKWIDIKQFVWYTPPTFMIAVFLPIVLIFKSILFLPCLRKKILKIRHGWEDV TKINKTEICSQL (SEQ ID NO: 165). In certain preferred embodiments, the peptide antigens (A) selected from fragments of STEAP1 are typically selected from 7 to 55 amino acid stretches of STEAP1 that may optionally overlap. Non-limiting examples include but are not limited to:

```
                                          (SEQ ID NO: 166)
LFPQWHLPIKIAAIIASLTFLYTLLREVIHPLATS,

                                          (SEQ ID NO: 167)
YTLLREVIHPLATSHQQYFYKIPILVINKVLPMVS,

                                          (SEQ ID NO: 168)
RKQFGLLSFFFAVLHAIYSLSYPMRRSYRYKLLNWAYQ,

                                          (SEQ ID NO: 169)
EDAWIEHDVWRMEIYVSLGIVGLAILALLAVTSIP,

                                          (SEQ ID NO: 170)
LAVTSIPSVSDSLTWREFHYIQSKLGIVSLLLGTI,

                                          (SEQ ID NO: 171)
DIKQFVWYTPPTFMIAVFLPIVLIFKSILFLPCLR.
```

In some embodiments of cancer vaccines for prostate cancer, the cancer vaccine comprises peptide antigens selected from fragments of 5T4, SSPTSSASSESSSAPFLASAVSAQPPLPDQCPALCECSEAARTVKCVNRNLTE- VPTDLPAYVRNLF LTGNQLAVLPAGAFARRPPLAEL-AALNLSGSRLDEVRAGAFEHLPSLRQLDLSHNPLADL-SPFAF SGSNASVSAPSPLVELILNHIVPPEDERQNRS-FEGMVVAALLAGRALQGLRRLELASNHFLYLPR DVLAQLPSLRHLDLSNNSLVSLTYVSFRNLTH-LESLHLEDNALKVLHNGTLAELQGLPHIRVFLD NNPWVCDCHMADMVTWLKETEVVQGKDRLTCAY-PEKMRNRVLLELNSADLDCDPILPPSLQT SYVFLGIV-LALIGAIFLLVLYLNRKGIKKWMHNIRDACRDHM-EGYHYRYEINADPRLTNLSSNSD V (SEQ ID NO:172). In certain preferred embodiments, the peptide antigens (A) selected from fragments of 5T4 are typically selected from 7 to 55 amino acid stretches of 5T4 that may optionally overlap. Non-limiting examples include but are not limited to:

```
                                    (SEQ ID NO: 173)
SPTSSASSESSSAPFLASAVSAQPPLPDQCPALCE,

                                    (SEQ ID NO: 174)
RNLTEVPTDLPAYVRNLFLTGNQLAVLPAGAFARR,

                                    (SEQ ID NO: 175)
ALQGLRRLELASNHFLYLPRDVLAQLPSLRHLDLS,

                                     (SEQ ID NO: 176
LSNNSLVSLTYVSFRNLTHLESLHLEDNALKVLHN,

                                    (SEQ ID NO: 177)
DCDPILPPSLQTSYVFLGIVLALIGAIFLLVLYLN.
```

In certain preferred embodiments of the vaccine against influenza, the peptide antigens are selected from minimal immunogens, including but not limited to RNNILRTQESE (SEQ ID NO:178) and LNDKHSNGTIKDRSPYR (SEQ ID NO:179), SWRNNILRTQES (SEQ ID NO:180), DNWHG-SNRP (SEQ ID NO:181), DNPRPNDKTGS (SEQ ID NO:182) and DPNGWTGTDNNFSI (SEQ ID NO:183) or any fragments thereof having at least 6 amino acids in length, preferably at least 9 amino acids, or derivatives thereof.

In certain preferred embodiments of the vaccine against hepatitis B, the peptide antigens are selected from minimal immunogens, including but not limited to QLDPAFRAG (SEQ ID NO:184), RGLYFPAGL (SEQ ID NO:185) and STGPCRTCMTK (SEQ ID NO:186) or any fragments thereof having at least 6 amino acids in length, preferably at least 9 amino acids, or derivatives thereof.

In certain preferred embodiments of the vaccine against HIV, the peptide antigens are selected from minimal immunogens, including but not limited to AVGIGAVFL (SEQ ID NO:187), EINCTRPNNNTRPGEIIGDIRQAHCNISRA (SEQ ID NO:188) or YNKRKRIHIGPGRAFYTTKNIIG (SEQ ID NO:189).

In certain preferred embodiments of the vaccine against malaria, the peptide antigens are selected from minimal immunogens including but not limited to PADGNPDPNANPNVD (SEQ ID NO: 190), NPDPNANPNVDPNAN (SEQ ID NO:191), NANPNVDPNANPNVD (SEQ ID NO:192), NANPNANPNANPNAN (SEQ ID NO:193), DPNANPNVDPNA (SEQ ID NO:194), KQPADGNPDPNANPNV (SEQ ID NO:195), EDNEKLRKPKHKKLKQPADGNPDPNANPNVDPNAN (SEQ ID NO:196), KLRKPKHKKLKQPADGNPDP (SEQ ID NO:197) or any fragments thereof having at least 6 amino acids in length, preferably at least 9 amino acids, or derivatives thereof.

In preferred embodiments of the vaccine against SARS the peptide antigens are selected from TES-NKKFLPFQQFGRDIA (SEQ ID NO:198), SQIL-PDPSKPSKRSFIEDLLFNKVTLADAGF (SEQ ID NO: 199), SQILPDPSKPSKRSFIEDLLFNKVT (SEQ ID NO:200), PSKPSKRSFIEDLLFNKVTLADAGF (SEQ ID NO:201), DYSVLYNSASF-STFKCYGVSPTKLNDLCFTN (SEQ ID NO:202), LYN-SASFSTFKCYGVSPTKL (SEQ ID NO:203), SNNLD-SKVGGNYNYLYRLFRKSNLK (SEQ ID NO:204), YRLFRKSNLKPFERDISTEIYQAGS (SEQ ID NO:205), ISTEIYQAGSTPCNGVEGENCYFPL (SEQ ID NO: 206), VEGFNCYFPLQSYGFQPTNGVGYQ (SEQ ID NO:207) and SNNLDSKVGGNYNYLYRLFRGSGIYQAG-STPCNGVEGENCYFPLQSYGFQPTNGVGYQ (SEQ ID NO: 208) or any fragments thereof having at least 6 amino acids in length, preferably at least 9 amino acids, or derivatives thereof.

In some embodiments, the peptide antigen (A) represents an autoantigen. The autoantigen may be identified and selected on the basis of screening a subject's own T cells for autoreactivity against self-antigens presented in the context of a patient's own MHC-I and/or MHC-II molecules. Alternatively, the peptide antigens may be selected using in silico methods to predict potential autoantigens that (i) have a predicted high affinity for binding a subjects' own MHC-I and/or MHC-II molecules and (ii) are expressed and/or known to be associated with pathology accounting for a subject's autoimmune syndrome. In other embodiments, the peptide antigen represents a CD4 epitope derived from an allergen and is selected on the basis of the peptide antigen having a high binding affinity for a patient's own MHC-II molecules.

In some embodiments, the autoantigen is specific for the tissue that is being damaged by the autoimmune response. In some embodiments, the autoantigen is widely expressed. In some embodiments, the autoantigen is induced by inflammation, such as a heat shock protein. In all cases, the peptide antigen(s) may be selected from protein sequences comprising one or more isoforms as a result of splice variants or post-translational modifications or proteolytic processing. In some embodiments the antigen is an alloantigen selected from donor tissue and used to prevent or treat transplant rejection. Vaccine compositions for inducing tolerance described herein for autoantigens can also be used for alloantigens for preventing or treating transplant rejection. Compositions for inducing tolerance generally apply to any class of antigen useful for treating inflammatory diseases, which includes autoantigens, allergens and alloantigens.

Peptide antigens for treating autoimmune diseases are generally selected from proteins expressed in abundance by the tissues most affected by the disease, or proteins that trigger an inflammatory response, such as gluten proteins involved in celiac disease. In certain embodiments of the vaccines for inducing tolerance, for a given disease indication, peptide antigens may be selected from proteins implicated in disease accordingly. Non-limiting examples are provided in the below Table 1A, wherein the full sequence associated with each protein can be accessed based on the referenced accession numbers provided.

TABLE 1A

Peptide antigens selected from proteins implicated in disease

| Disease indication | Proteins implicated in disease | Example accession numbers |
|---|---|---|
| Multiple sclerosis | Myelin, myelin basic peptide (MBP), proteo lipoprotein (PLP), Myelin oligodendrocyte glycoprotein (MOG) Additional examples provided later | P25189, P02686, P60201, Q04941, P23515, Q13875, Q16653 |
| Celiac disease | Gluten, Transglutaminase 2 (TG2), Protein-glutamine gamma-glutamyltransferase 2 Additional examples provided later | P21980 |
| Type-1 diabetes | Insulin peptide, Chromogranin | P01308, Q9Y5Q6, P51460, G3V2Q7, A0A0A0MT66, G5E968, Q9BZL6, Q8WXD2, P10645, P05060, P13521, B4DQJ6 |
| Vitiligo | Pmel (gp100), Tyrosinase, Tyrosinase-related protein 1, Tyrosinase-related protein 2, Melanoma antigen recognized by T cells 1 (MART-1 or melan-A), Melanin concentrating hormone receptor 1 (MHCR1), Melanin concentrating hormone receptor 2 (MHCR2) | P40967, P14679, C9JZ52, E7EQI3, Q16655, Q99705, Q969V1 |
| Neuromyeltitis optica | Aquaporin-4 (AQP4) | P55087, P78564 |
| Optic neuritis | Myelin oligodendrocyte glycoprotein (MOG), Aquaporin-4 (AQP4) | Q16653, P55087, P78564 |
| Autoimmune uveitis | Arrestin, interphotoreceptor retinoid binding protein (IRBP), retinol-binding protein 3 (RBP3), recoverin | P36575, P10745, P35243 |
| Immune thrombocytopenia purpura | Acetylcholine receptor, muscarinic acetylcholine receptor, muscle specific kinase | P08173, P08912, P20309, P11229, P08172 |
| Graves disease | Thyrotropin receptor (TSHR) | P16473 |

In some embodiments wherein the composition is used to treat multiple sclerosis and related neuro-inflammatory diseases, the antigens are selected from peptide sequences from the myelin sheath proteins, including myelin basic protein (MBP), myelin oligodendrocyte protein (MBP), and/or myelin proteolipid protein (PLP). In some embodiments wherein the composition is used to treat type 1 diabetes, the antigens are selected from peptides that are expressed in pancreatic islet cells, including insulin, glutamic acid decarboxylase, chromogranin A, and/or neuropilin. In some embodiments wherein the composition is used to treat neuromyelitis optica, the antigen is aquaporin 4. In some embodiments wherein the composition is used to treat celiac disease, the antigen is gluten proteins and/or transglutaminase. In some embodiments wherein the composition is used to treat pemphigus vulgaris, the antigen is epidermal cadherin. In some embodiments wherein the composition is used to treat myasthenia gravis, the antigen is acetylcholine receptor. In some embodiments wherein the composition is used to treat allergy, the antigen is the allergen.

In some embodiments of tolerance vaccines used to treat multiple sclerosis, the antigen comprises one or more peptide fragments having at least six amino acids in length, more preferably at least 9 or more amino acids in length, derived from any isoform of myelin oligodendrocyte glycoprotein (MOG), such as (SEQ ID NO: 209)
MASLSRPSLPSCLCSFLLLLLLQVSSSYAGQFRVIGPRHPIRALVGDEVE
LPCRISPGKNATGMEVGWYRPPFSRVVHLYRNGKDQDGDQAPEYRGRTEL
LKDAIGEGKVTLRIRNVRFSDEGGFTCFFRDHSYQEEAAMELKVEDPFYW
VSPGVLVLLAVLPVLLLQITVGLIFLCLQYRLRGKLRAEIENLHRTFDPH
FLRVPCWKITLFVIVPVLGPLVALIICYNWLHRRLAGQFLEELRNPF.

In some embodiments of tolerance vaccines used to treat multiple sclerosis, the antigen comprises one or more peptide fragments having at least six amino acids in length, more preferably at least 9 or more amino acids in length, derived from any isoform of myelin basic proteins, such as (SEQ ID NO: 210)
MGNHAGKRELNAEKASTNSETNRGESEKKRNLGELSRTTSEDNEVFGEAD
ANQNNGTSSQDTAVTDSKRTADPKNAWQDAHPADPGSRPHLIRLFSRDAP
GREDNTFKDRPSESDELQTIQEDSAATSESLDVMASQKRPSQRHGSKYLA
TASTMDHARHGFLPRHRDTGILDSIGRFFGGDRGAPKRGSGK.

In some embodiments of tolerance vaccines used to treat multiple sclerosis, the antigen comprises one or more peptide fragments having at least six amino acids in length, more preferably at least 9 or more amino acids in length, derived from any isoform of myelin proteolipid protein, such as (SEQ ID NO: 211)
MGLLECCARCLVGAPFASLVATGLCFFGVALFCGCGHEALTGTEKLIETY
FSKNYQDYEYLINVIHAFQYVIYGTASFFFLYGALLLAEGFYTTGAVRQI
FGDYKTTICGKGLSATVTGGQKGRGSRGQHQAHSLERVCHCLGKWLGHPD
KFVGITYALTVVWLLVFACSAVPVYIYFNTWTTCQSIAFPSKTSASIGSL
CADARMYGVLPWNAFPGKVCGSNLLSICKTAEFQMTFHLFIAAFVGAAAT
LVSLLTFMIAATYNFAVLKLMGRGTKF.

In certain preferred embodiments of tolerance vaccines for treating multiple sclerosis, the tolerance vaccine comprises peptide antigens consisting of overlapping peptides derived from myelin oligodendrocyte glycoprotein, myelin basic protein and/or myelin proteolipid protein, wherein the overlapping peptides consist of 35 amino acid peptide antigens that have between 13 to 19 amino acid overlap with at least one other peptide antigen in the overlapping peptide pool. In some embodiments of tolerance vaccines for treating multiple sclerosis, the tolerance vaccine comprises peptide antigens derived from myelin oligodendrocyte glycoprotein, myelin basic protein and/or myelin proteolipid protein selected on the basis of having epitopes with predicted high binding affinity for MHC-I and/or MHC-II. A non-limiting example of a tolerance vaccine for treating multiple sclerosis comprising peptide antigens derived from myelin oligodendrocyte glycoprotein, myelin basic protein and/or myelin proteolipid that have predicted high binding affinity for MHC-II includes but is not limited to peptide antigens selected from SLPSCLCSFLLLLLLQVSSSYAGQFRVIGPRHPIR (SEQ ID NO:212), VSSSYAGQFRVIGPRHPIRALVGDEVELPCRISPG (SEQ ID NO:213), EEAAMELKVEDPFYWVSPGVLVLLAVLPVLLLQIT (SEQ ID NO:214), SPGVLVLLAVLPVLLLQITVGLIFLCLQYRLRGKL (SEQ ID NO:215), QITVGLIFLCLQYRLRGKLRAEIENLHRTFDPHFL (SEQ ID NO:216), GKLRAEIENLHRTFDPHFLRVPCWKITLFVIVPVL (SEQ ID NO:217), HFLRVPCWKITLFVIVPVLGPLVALIICYNWLHRR (SEQ ID NO:218), PVLGPLVALIICYNWLHRRLAGQFLEELRNPF (SEQ ID NO:219), DPGSRPHLIRLFSRDAPGREDNTFKDRPSESDELQ (SEQ ID NO:220), GRTQDENPVVHFFKNIVTPRTPPPSQGKGRGLSLS (SEQ ID NO:221), GGRASDYKSAHKGFKGVDAQGTLSKIFKLGGRDSR (SEQ ID NO:222), FSKNYQDYEYLINVIHAFQYVIYGTASFFFLYGAL (SEQ ID NO:223), AFQYVIYGTASFFFLYGALLLAEGFYTTGAVRQIF (SEQ ID NO:224), GALLLAEGFYTTGAVRQIFGDYKTTICGKGLSATV (SEQ ID NO:225), HPDKFVGITYALTVVWLLVFACSAVPVYIYFNTWT (SEQ ID NO:226), LLVFACSAVPVYIYFNTWTTCQSIAFPSKTSASIG (SEQ ID NO:227), TWTTCQSIAFPSKTSASIGSLCADARMYGVLPWNA (SEQ ID NO:228), SICKTAEFQMTFHLFIAAFVGAAATLVSLLTFMIA (SEQ ID NO:229), AAFVGAAATLVSLLTFMIAATYNFAVLKLMGRGTK (SEQ ID NO:230), MIAATYNFAVLKLMGRGTKF (SEQ ID NO:231) or any fragments thereof having at least 6 amino acids in length, preferably at least 9 amino acids, or derivatives thereof.

In some embodiments of the vaccine for inducing tolerance for treatment of celiac disease, peptide antigens are selected from specific epitopes or fragments of proteins implicated in celiac disease pathogenesis, optionally wherein the peptide antigens are modified, e.g., partially or fully deamidated. The peptide antigens may be derived from known pathogenic cereal proteins, including but not limited to gliadins, glutenins, prolamins, secalins and hordeins. Examples of secalins include alleles of rye gamma or omega secalins. Examples of hordeins include alleles of barley hordeins. Examples of gliadins include alleles of alpha gliadin, gamma gliadin or omega gliadins from wheat, durum wheat, spelt, or rye.

Examples of glutenins include alleles of low molecular weight glutenins or high molecular weight glutenins from wheat, spelt, or rye. Examples of non-gliadin or non-secalin prolamins include alleles of barley alpha or gamma prolamin. The peptide antigen sequences derived from these allele amino acid sequences were produced as consensus sequences from one or more genbank protein sequence entries using clustal omega amino acid alignment. Pathogenic cereal protein sequences from which the vaccine for inducing tolerance may be derived included but are not limited to:

```
                                                     (SEQ ID NO: 232)
MKTFLILALLAIVATTATIAVRVPVPQLQPONTSQQQPQEQVPLVQQQQFPGQQQPFPPQQPYPQ

PQPFPSQQPYLQLQPFPQPQLPYPQPQPFRPQQPYPQPQPQYSQPQQPISQQQQQQQQQQQQQQQ

QQQILQQILQQQLIPCRDVVLQQHNIAHGSSQILQQSTYQLVQQLCCQQLWQIPEQSRCQAIHNV

VHAIILHQQQQQPLSQVSFQQPQQQYPSGQGSFQPSQQNPQAQGSVQPQQLPQFEEIRNLALETL

PAMCNVYIPPYCTIAPVGIFGTN,

                                                     (SEQ ID NO: 233)
MKTFLILALLAIVATTATIAVRVPVPQLQPQNPSQQQPQEQVPLVQQQQFPGQQQPFPPQQPYPQ

PQPFPSQQPYLQLQPFPQPQLPYPQPQLPYPQPQPFRPQQPYPQPQPQYSQPQQPISQQQQQQQQ

QQQQQQILQQILQQQLIPCRDVVLQQHSIAHGSSQVLQQSTYQLVQQLCCQQLWQIPEQSRCQAI

HNVVHAIILHQQQQQQQQQQQQPLSQVSFQQPQQQYPSGQGSFQPSQQNPQAQGSVQPQQLPQFEE

IRNLALETLPAMCNVYIPPYCTIAPVGIFGTN,

                                                     (SEQ ID NO: 234)
MKTFLILALLAIVATTATIAVRVPVPQLQPQNPSQQQPQEQVPLVQQQQFPGQQQPFPPQQPYPQ

PQPFPSQQPYLQLQPFPQPQLPYPQPQLPYPQPQLPYPQPQPFRPQQPYPQSQPQYSQPQQPISQ

QQQQQQQQQQQKQQQQQQQQILQQILQQQLIPCRDVVLQQHSIAYGSSQVLQQSTYQLVQQLCCQ

QLWQIPEQSRCQAIHNVVHAIILHQQQQQQQQQQQQQPLSQVSFQQPQQQYPSGQGSFQPSQQNP

QAQGSVQPQQLPQFEEIRNLALETLPAMCNVYIPPYCTIAPVGIFGTNYR,

                                                     (SEQ ID NO: 235)
MKTFLILALLAIVATTATIAVRVPVPQLQPQNPSQQQPQEQVPLVQQQQFPGQQQPFPPQQPYPQ

LQPFPSQQPYMQLQPFPQPQLPYPQPQLPYPQPQPFRPQQSYPQPQPQYSQPQQPISQQQQQQQQ

QQQQQQILQQILQQQLIPCRDVVLQQHSIAHGSSQVLQQSTYQLVQQLCCQQLWQIPEQSRCQAI

HNVVHAIILHQQQQQQQQQQQQPLSQVCFQQPQQQYPSGQGSFQPSQQNPQAQGSVQPQQLPQFEE

IRNLALETLPAMCNVYIPPYCTIAPVGIFGTNYR,
```

-continued (SEQ ID NO: 236)
MKTFLILALLAIVATTATTAVRVPVPQLQPQNPSQQQPQEQVPLVQQQQFPGQQQQFPPQQPYPQ
PQPFPSQQPYLQLQPFPQPQPFPPQLPYPQPQSFPPQQPYPQQQPQYLQPQQPISQQQAQQQQQQ
QQQQQQQQQILQQILQQQLIPCRDVVLQQHNIAHASSQVLQQSTYQLLQQLCCQQLWQIPEQSRC
QAIHNVVHAIILHQQQQQQQQQQQQQQQQQPSSQVSFQQPQQQYPSGQGSFQPSQQNPQAQGSVQ
PQQLPQFEEIRNLALQTLPAMCNVYIPPYCSTTIAPFGIFGTNXR, (SEQ ID NO: 237)
MKTFLILALLAIVATTATSAVRVPVPQLQPQNPSQQQPQEQVPLMQQQQQFPGQQEQFPPQQPYP
HQQPFPSQQPYPQPQPFPPQLPYPQTQPFPPQQPYPQPQPQYPQPQQPISQQQAQQQQQQQQILQ
QILQQQLIPCRDVVLQQHNIAHASSQVLQQSSYQQLQQLCCQQLFQIPEQSRCQAIHNVVHAIIL
HHHQQQQQQQPSSQVSYQQPQEQYPSGQGSFQSSQQNPQAQGSVQPQQLPQFQEIRNLALQTLPA
MCNVYIPPYCSTTIAPFGIFGTNYR, (SEQ ID NO: 238)
MKTFLILALLAIVATTATTAVRVPVPQLQPQNPSQQQPQEQVPLVQQQQFLGQQQPFPPQQPYPQ
PQPFPSQQPYLQLQPFPQPQLPYSQPQPFRPQQPYPQPQPQYSQPQQPISQQQQQQQQQQQQQQQ
QQQILQQILQQQLIPCMDVVLQQHNIAHGRSQVLQQSTYQLLQELCCQHLWQIPEQSQCQAIHNV
VHAIILHQQQKQQQQPSSQVSFQQPLQQYPLGQGSFRPSQQNPQAQGSVQPQQLPQFEEIRNLAL
QTLPAMCNVYIPPYCTIAPFGIFGTNYR, (SEQ ID NO: 239)
MKTFLILALLAIVATTTTTAVRVPVPQLQPQNPSQQQPQEQVPLVQQQQFLGQQQQQFPGQQQPF
PPQQPYPQPQPFLPQLPYPQPQPFPPQQSYPQPQPQYPQPQQPISQQQAQLQQQQQQQQQQQQQI
LQQILQQQLIPCRDVVLQQPNIAHASSQVSQQSYQLLQQLCCQQLWQTPEQSRCQAIHNVIHAII
LHQQQQQQQQQQQQQQQQQPSSQVSYQQPQQQYPSGQGFFQPSQQNPQAQGFVQPQQLPQFEEIR
NLALQTLPAMCNVYIPPYCSTTIAPFGIMSTN, (SEQ ID NO: 240)
MKTFLILALLAIVATTATIAVRVPVPQLQPQNPSQQQPQEQVPLVQQQQFPGQQQPFPPQQPYPQ
PQPFPSQQPYLQLQPFPQPQLPYPQPQLPYPQPQLPYPQPQPFRPQQPYPQSQPQYSQPQQPISQ
QQQQQQQQQQQQQQQQQQQILQQILQQQLIPCRDVVLQQHSIAYGSSQVLQQSTYQLVQQLCCQQ
LWQIPEQSRCQAIHNVVHAIILHQQQQQQQQQQQQQPLSQVSFQQPQQQYPSGQGSFQPSQQNPQ
AQGSVQPQQLPQFEEIRNLALETLPAMCNVYIPPYCTIAPVGIFGTN, (SEQ ID NO: 241)
MKTFLILALLAIVATTATIAVRVPVPQLQPQNPSQQQPQEQVPLVQQQQFPGQQQPFPPQQPYPQ
XQPFPSQQPYMQLQPFPQPQLPYPQPQLPYPQPQPFRPQQSYPQPQPQYSQPQQPISQQQQQQQ
QQQQQILQQILQQQLIPCRDVVLQQHSIAHGSSQVLQQSTYQLVQQLCCQQLWQIPEQSRCQAIH
NVVHAIILHQQQQQQQQQQQPLSQVSFQQPQQQYPSGQGSFQPSQQNPQAQGSVQPQQLPQFEEI
RNLALETLPAMCNVYIPPYCTIAPVGIFGTN, (SEQ ID NO: 242)
MKTFLILALLAIVATTATTAVRVPVPQLQPQNPSQQQPQEQVPLVQQQQFPGQQQQFPPQQPYPQ
PQPFPSQQPYLQLQPFPQPQPFPPQLPYPQPQSFPPQQPYPQQQPQYLQPQQPISQQQAQQQQQQ
QQILQQILQQQLIPCRDVVLQQHNIAHASSQVLQQSSYQQLQQLCCQQLFQIPEQSRCQAIHNVV
HAIILHHHQQQQQQPSSQVSYQQPQEQYPSGQGSFQSSQQNPQAQGSVQPQQLPQFQEIRNLALQ
TLPAMCNVYIPPYCSTTIAPFGIFGTN, -continued (SEQ ID NO: 243)
MKTFLILALLAIVATTATTAVRVPVPQLQPQNPSQQQPQEQVPLVQQQQFPGQQQQFPPQQPYPQ
PQPFPSQQPYLQLQPFPQPQPFPPQLPYPQPQSFPPQQPYPQQQPQYLQPQQPISQQQQQQQQQQ
QQQQQQQQILQQILQQQLIPCRDVVLQQHNIAHASSQVLQQSTYQLLQQLCCQQLLQIPEQSRCQ
AIHNVAHAIIMHQQQQQQQEQQQQLQQQQQQQLHQQRQQPSSQVSFQQPQQQYPSSQVSFQPSQL
NPQAQGSVQPQQLPQFAEIRNLALQTLPAMCNVYIPPHCSTTIAPFGIFGTN, (SEQ ID NO: 244)
MKTFLILALLAIVATTATSAVRVPVPQLQPQNPSQQQPQEQVPLMQQQQFPGQQEQFPPQQPYP
HQQPFPSQQPYPQPQPFPPQLPYPQTQPFPPQQPYPQPQPQYPQPQQPISQQQAQQQQQQQQILQ
QILQQQLIPCRDVVLQQHNIAHASSQVLQQSSYQQLQQLCCQQLFQIPEQSRCQAIHNVVHAIIL
HHHQQQQQQPSSQVSYQQPQEQYPSGQGSFQSSQQNPQAQGSVQPQQLPQFQEIRNLALQTLPAM
CNVYIPPYCSTTIAPFGIFGTNYR, (SEQ ID NO: 245)
MKTFLILALLAIVATTATTAVRVPVPQLQPQNPSQQQPQEQVPLVQQQQFLGQQQPFPPQQPYPQ
PQPFPSQQPYLQLQPFPQPQLPYSQPQPFRPQQPYPQPQPQYSQPQQPISQQQQQQQQQQQQQQQ
QQQQILQQILQQQLIPCMDVVLQQHNIAHGRSQVLQQSTYQLLQELCCQHLWQIPEQSQCQAIHN
VVHAIILHQQQKQQQQPSSQVSFQQPQQQYPLGQGSFRPSQQNPQAQGSVQPQQLPQFEEIRNLA
LQTLPAMCNVYIPPYCTIAPFGIFGTN, (SEQ ID NO: 246)
MKTFLILALLAIVATTATTAVRVPVPQLQPQNPSQQQPQEQVPLVQQQQFPGQQQQFPPQQPYPQ
PQPFPSQQPYLQLQPFPQPQPFPPQLPYPQPQSFPPQQPYPQQQPQYLQPQQPISQQQAQQQQQQ
QQQQQQQQQILQQILQQQLIPCRDVVLQQHNIAHASSQVLQQSTYQLLQQLCCQQLLQIPEQSRC
QAIHNVVHAIIMHQQQQQQQEQQQQXQQQQQQQLHQQRQQPSSQVSFQQPQQQYPSSQVSFQPSQ
LNPQAQGSVQPQQLPQFAEIRNLALQTLPAMCNVYIPPHCSTTIAPFGIFGTN, (SEQ ID NO: 247)
MKTFLILALLAIVATTATTAVRVPVPQLQPQNPSQQQPQEQVPLVQQQQFLGQQQPFPPQQPYPQ
PQPFPSQQPYLQLQPFPQPQLPYSQPQPFRPQQPYPQPQPQYSQPQQPISQQQQQQQQQQQQQQQ
EQQILQQILQQQLIPCMDVVLQQHNIAHGRSQVLQQSTYQLLQELCCQHLWQIPEQSQCQAIHNV
VHAIILHQQQKQQQQPSSQVSFQQPLQQYPLGQGSFRPSQQNPQAQGSVQPQQLPQFEEIRNLAL
QTLPAMCNVYIPPYCTIAPFGIFGTN, (SEQ ID NO: 248)
METFLILSLIAIVATTATTAVRVPVPQLQLQNPSMQQPQEQVPLVQQQQFLGQQQTFPPQQPYPQ
PQPFPTQQPYPQPQPFPQPQPFPPQLPYPQPQPFPPQQPYPQPQTQHLQPQQPISQQQAQQQQQQ
QQQQQQQQQQQLQQQILQQILQQYPLGQGSFRPSQQNPQAQGSVQPQQQPQFEEIRNLALQTLPA
MCNAYIPPYCTIAPFGIFGTN, (SEQ ID NO: 249)
PQQPFFPLQPQQSFLWQSQQPFLQQPQQPSPQPQQVVQIISPATPTTIPSAGKPTSAPFPQQQQQH
QQLAQQQIPVVQPSILQQLNPCKVFLQQQCSPVAMPQRLARSQMLQQSSCHVMQQQCCQQLPQIP
QQSRYQAIRAIIYSIILQEQQQVQGSIQSQQQQPQQLGQCVSQPQQQSQQQLGQQPQQQQLAQGT
FLQPHQIAQLEVMTSIALRILPTMCSVNVPLYRTTTSVPFGVGTGVGAY, (SEQ ID NO: 250)
MKTLLILTILAMAITIGTANIQVDPSGQVQWLQQQLVPQLQQPLSQQPQQTFPQPQQTFPHQPQQ
QVPQPQQPQQPFLQPQQPFPQQPQQPFPQTQQPQQPFPQQPQQPFPQTQQPQQPFPQQPQQPFPQ
TQQPQQPFPQLQQPQQPFPQPQQQLPQPQQPQQSFPQQQRSFIQPSLQQQLNPCKNILLQQCKPA -continued

SLVSSLWSIIWPQSDCQVMRQQCCQQLAQIPQQLQCAAIHSVVHSIIMQQQQQQQQQQGMHIFLP

LSQQQQVGQGSLVQGQGIIQPQQPAQLEAIRSLVLQTLPSMCNVYVPPECSIMRAPFASIVAGIG

GQYR, (SEQ ID NO: 251)
MKTLLIQTILVMAITIATANMQVDPSGQVPWPQQQPFPQPHQPFSQQPQQTFPQPQQTFPHQPQQ

QFSQPQQPQQQFIQPQQPFPQQPQQTYPQRPQQPFPQTQQPQQPFPQSQQPQQPFPQPQQQFPQP

QQPQQSFPQQQPSLIQQSLQQQLNPCKNFLLQQCKPVSLVSSLWSMILPRSDCQVMRQQCCQQLA

QIPQQLQCAAIHSIVHSIIMQQEQQEQRQGVQILVPLSQQQQVGQGTLVQGQGIIQPQQPAQLEV

IRSLVLQTLATMCNVYVPPECSIIKAPFSSVVAGIGGQYR, (SEQ ID NO: 252)
MKTLLILTILAMAITISTANMQVDPSGQVQWPQQQLVPQPQQPLSQQPQQAFPQPQQTFPHQPQQ

QVPQPQQPQQQPFLQPQQAFPQQPQQPFPQTQQPQQPFPQQPQQPFPQTQQPQQPFPQQPQQPFPQ

QXQQPFPQTQQPQQPFPQQPQQPFPQTQQPQQPFPQFQQPHQPFPQPQQQFPQPQQPQQSFPQQQ

RPFIQPSLQQRLNPCKNILLQQCKPASLVSSLWSIIWPQSDCQVMQQQCCQELAQIPQQLQCAAI

HSVVHSIIXQQQQQQQQQQQQQQGMHILLPLSQQQQLGQGTLVQGQGIIQPQQLAQLEAIRSLVL

QTLPTMCNVYVPPECSIIRAPFASIRASSGHHLPALVAGIGGQ, (SEQ ID NO: 253)
MKTLLILTIIAVALTTTTANIQVDPSGQVQWPQQQQPFPQPQQPQQIFPQPQQTFPHQPQQAFPQ

PQQTFPHQPQQQFPQPQQPQQPFPQQPQQQFPQPQQPQQPFPQQPQQQFPQPQQPQQPFPQPQQP

QLPFPQQPQQPFPQPQQPQQPFPQLQQPQQPLPQPQQPQQPFPQQQQPLIQPYLQQQMNPCKNYL

LQQCNPVSLVSSLVSMILPRSDCKVMRQQCCQQLAQIPQQLQCAAIHGVVHSIIMQQEQQQQXQQ

QQQGIQIMRPLFQLVQGQGIIQPQQPAQLEVIRSLVLGTLPTMCNVFVPPECSTTKAPFASIVAD

IGGQ, (SEQ ID NO: 254)
MKTLFILTILAMATTIATANMQVDPSGQVQWPQQQPFRQPQQPFYQQPQQTFPQPQQTFPHQPQQ

QFPQPQQPQQQFPQPQQPQQPFPQPQQAQLPFPQQPQQPFPQPQQPQQPFPQSQQPQQPFPQPQQ

PQQSFPQQQQPLIQPYLQQQMNPCKNYLLQQCNPVSLVSSLVSMILPRSDCQVMQQQCCQQLAQI

PRQLQCAAIHSVVHSIVMQQEQQQGIQILRPLFQLVQGQGIIQPQQPAQYEVIRSLVLRTLPNMC

NVYVRPDCSTINAPFASIVAGISGQ, (SEQ ID NO: 255)
MKTLFILTILAMATTIATANMQVDPSGQVQWPQQQPFRQPQQPFYQQPQQTFPQPQQAFPHQPQQ

QFPQPQQPQQQFPQPQQPQQPFPQPQQAQLPFPQQPQQPFPQPQQPQQPFPQSQQPQQPFPQPQQ

PQQSFPQQQQPLIQPYLQQQMNPCKNYLLQQCNPVSLVSSLVSMILPRSDCQVMQQQCCQQLAQI

PRQLQCAAIHSVVHSIVMQQEQQQGIQILRPLFQLVQGQGIIQPQQPAQYEVIRSLVLRTLPNMC

NVYVRPDCSTINAPFASIVAGISGQ, (SEQ ID NO: 256)
MKTLLILTIFAAALTIATANIQVDPSGQVQWPQQQPFPQPQPFSQQPQQAFLQPQHTFPLQPQQV

FPQPQQPQQQFPQPQQPQQQPFPQPQQPQLPFPQQPQQPFPQPQQPQQPFPQSQQPQQPFPQPQQQ

FPQPQQPQQSFPQQQPPLIQPYLQQQMNPCKNYLLQQCNPVSLVSSLVSMILPRNDCQVMQQQCC

QQLAQIPRQLQCTAIHSVVHAIIMQQEQQGIQILRPLFQLVQGQGIIQPQQPAQYEVIRSLVLRT

LPNMCNVYVRPDCSTINAPFASIVAGIGGQYR, (SEQ ID NO: 257)
MKTLLILTILAMATTIATANMQVDPSGQVQWPQQQPFPQPQQPFCQQPQRTIPQPHQTFHHQPQQ

TFPQPEQTYPHQPQQQFPQTQQPQQPFPQPQQTFPQQPQLPFPQQPQQPFPQPQQPQQPFPQSQQ

-continued

PQQPFPQPQQQFPQPQQPQQSFPQQQQPAIQSFLQQQMNPCKNFLLQQCNHVSLVSSLVSIILPR

SDCQVMQQQCCQQLAQIPQQLQCAAIHSVAHSIIMQQEQQQGVPILRPLFQLAQGLGIIQPQQPA

QLEGIRSLVLKTLPTMCNVYVPPDCSTINVPYANIDAGIGGQ, (SEQ ID NO: 258)

MKTLLILTILAMATTIATANMQVDPSGQVQWPQQQPFPQPQQPFCQQPQRTIPQPHQTFHHQPQQ

TFPQPQQTYPHQPQQQFPQTQQPQQPFPQPQQTFPQQPQLPFPQQPQQPFPQPQQPQQPFPQSQQ

PQQPFPQPQQQFPQPQQPQQSFPQQQQPAIQSFLQQQMNPCKNELLQQCNHVSLVSSLVSIILPR

SDCQVMQQQCCQQLAQIPQQLQCAAIHSVAHSIIMQQEQQQGVPILRPLFQLAQGLGIIQPQQPA

QLEGIRSLVLKTLPTMCNVYVPPDCSTINXPYANIDAGIGGQ, (SEQ ID NO: 259)

MKTLLILTILVMAITIATANMQVDPSGQVPWPQQQPFPQPHQPFSQQPQQTFPQPQQTFPHQPQQ

QFSQPQQPQQQFIQPQQPFPQQPQQTYPQRPQQPFPQTQQPQQPFPQSQQPQQPFPQPQQQFPQP

QQPQQSFPQQQPSLIQQSLQQQLNPCKNFLLQQCKPVSLVSSLWSMILPRSDCQVMRQQCCQQLA

QIPQQLQCAAIHSIVHSIIMQQEQQEQRQGVQILVPLSQQQQVGQGTLVQGQGIIQPQQPAQLEV

IRSLVLQTLATMCNVYVPPYCSTIRAPFASIVAGIGGQYR, (SEQ ID NO: 260)

MKTFIILTILAMATTIATANMQVGSSGQVEWPQHQQLPQPQQPLYHQPQQIFPQPRQTFPHLPQQ

TFPQPQQTIPHQPQQQFPQTQQPLQPFPQPQQTFPQQPQQPLPQPQQPQQPFPQSQQPQPQQPFP

QPQQQFPQPQQPQQSIPQQQQPLIQSSLQQQMNPCKNFLLQQCNPVSLVSSLVSLIFPRSDCQVM

QLQCCQQLAQIPQQLQCAAIHSVVHSIMMQQEQQQPQQLAHLEVIRSLVLKTLQTXCNVYVRPDC

STIRTPFASTVAGIGGQ, (SEQ ID NO: 261)

MKTLLILTILAMAITIATANMQVDPSGQVQWPQQQPFLQPHQPFSQQPQQIFPQPQQTFPHQPQQ

QFPQPQQPQQQFLQPRQPFPQQPQQPYPQQPQQPFPQTQQPQQPFPQSKQPQQPFPQPQQPQQSF

PQQQPSLIQQSLQQQLNPCKNFLLQQCKPVSLVSSLWSIILPPSDCQVMRQQCCQQLAQIPQQLQ

CAAIHSVVHSIIMQQEQQEQLQGVQILVPLSQQQQVGQGILVQGQGIIQPQQPAQLEVIRSLVLQ

TLPTMCNVYVPPYCSTIRAPFASIVASIGGQE, (SEQ ID NO: 262)

MKTLFILTILAMATTIATANMQVDPSGQVQWPQQQPFRQPQQPFYQQPQHTFPQPQQTFPHQPQQ

QFPQPQQPQQQFPQPQQPQQPFPQPQQAQLPFPQQPQQPFPQPQQPQQPFPQSQQPQQPFPQPQQ

PQQSFPQQQQPLIQPYLQQQMNPCKNYLLQQCNPVSLVSSLVSMILPRSDCQVMQQQCCQQLAQI

PRQLQCAAIHSVVHSIVMQQEQQQGIQILRPLFQLVQGQGIIQPQQPAQYEVIRSLVLRTLPNMC

NVYVRPDCSTINAPFASIVAGISGQ, (SEQ ID NO: 263)

MKTLLILTILAMATTIATANMQVDPSSRVQWPQEQPPPQSQQPFSQQPQQIFPQPQQTFPHQPQQ

AFLQPQQTFPRRPQQQFPQPQQPQQPFPQPQQPQLPFPQQPQQPFPQPQQPQQPFPQSQQPQQPF

PQPQQQFPQPQQPQQSFPQQQQWMIQSFLQQQMNPCKNELLQQCNPVSLVSSLVSIILPRSDCQL

MQQQCCQQLAQIPQQLQCAAIHNVAHSIIMQQEQQRGVQILRPLFQLAQGLGIIQPQQPAQLEGI

RSLVLKTLPTMCNVYV, (SEQ ID NO: 264)

MKTLLILTILAMAITIGTANMQVDPSSQVQWPQQQPVPQPHQPFSQQPQRTIPQPHQTFHHQPQQ

TFPQPQQTFPHQPQQQFPQPQQPQQQFLQPQQPFPQQPQQPYPQQPQQPFPQTQQPQQLFPQSQQ

PQQQFSQPQQQFPQPQQPQQSFPQQQPPFIQPSLQQQVNPCKNFLLQQCKPVSLVSSLWSMIWPQ

-continued

SDCQVMRQQCCQQLAQIPQQLQCAAIHTVIHSIIMQQQQQQQEQQEQQQGMHILLPLYQQQQVGQ

GTLVQGQGIIQPQQPAQLEAIRSLVLQTLPTMCNVYVPPECSIIKAPFSSVVAGIGGQYR, (SEQ ID NO: 265)
MKTLLILTILAMATTIATANMQVDPSGQVQWPQQQPFPQPQQPFCEQPQRTIPQPHQTFHHQPQQ

TFPQPEQTYPHQPQQQFPQTQQPQQPFPQPQQTFPQQPQLPFPQQPQQPFPQPQQPQQPFPQSQQ

PQQPFPQPQQQFPQPQQPQQSFPQQQQPAIQSFLQQQMNPCKNFLLQQCNHVSLVSSLVSIILPR

SDCQVMQQQCCQQLAQIPQQLQCAAIHSVAHSIIMQQEQQQGVPILRPLFQLAQGLGIIQPQQPA

QLEGIRSLVLKTLPTMCNVYVPPDCSTINVPYANIDAGIGGQ, (SEQ ID NO: 266)
MKTLLMLAILAMATTIATANMQVNPSGQVQCPQQQPFPQPQQSSPQQPQQPFPQQSQQPFPQQPQ

QSSPQPQQPYPQQPFPQQPQQPYPQQPQQPFPQQPQQPYPQQPQQPFPQQPQQPVPQQPQQQFPQ

QPQQPVPQQPLQXFPQQPQQPVPQQPLQQFPQQPQQPFPQQPQQPVPQQSQQPFPQTQQPQQPFP

QPQQPQQLFPQTQQSSPQQPQQVTSQPQQPFPQAQPPQQSSPQSQQPYPQEPQQLFPQSQQPQQP

FPQPQQPQQPFPQPQPQTQQSIPQPQQPFPQPQQPFPQSQEPFPQVHQPQQPSPQQQQPSIQLSL

QQQLNPCKNVLLQQCSPVALVSSLRSKIFPQSECQVMQQQCCQQLAQIPQQLQCAAIHSVVHAII

MQQEQREGVQILLPQSHKQHVGQGALAQVQGIIQPQQLSQLEVVRSLVLQNLPTMCNVYVPRQCS

TIQAPFASIVTGIVGH, (SEQ ID NO: 267)
MKTLLMLAILAMATTIATANMQVNPSGQVQCPQQQPFPQPQQSSPQQPQQPFPQQSQQPFPQQPQ

QSSPQPQQPYPQQPFPQQPQQPYPQQPQQPFPQQPQQXXXXXXXXXXXXXXXXXXXXXXXXXXXX

XXXXXXXXXXXXXXXXXXXXXXXXXXXXXXXXXXXXXXXXXXXXPFPQQPQQPVPQQSQQPFPQT

QQPQQPFPQPQQPQQLFPQTQQSSPQQPQQVTSQPQQPFPQAQPPQQSSPQSQQPYPQEPQQLFP

QSQQPQQPFPQPQQPQQPFPQPXXQTQQSIPQPQQPFPQPQQPFPQSQEQFPQVHQPQQPSPQQQ

QPSIQLSLQQQLNPCKNVLLQQCSPVALVSSLRSKIFPQSECQVMQQQCCQQLAQIPQQLQCAAI

HSVVHAIIMQQEQREGVQILLPQSHQQHVGQGALAQVQGIIQPQQLSQLEVVRSLVLQNLPTMCN

VYVPRQCSTIQAPFASIVTGIVGH, (SEQ ID NO: 268)
MKTLLMLAILAMVTTIATANMQVNPSGQVQCPQQQPFPQPQQSSPLQPQQPFPQQSQQPFPHQPQ

QSSPQPQQPYPQQPFPQQPQQPYPQQPQQPFPQQPQQPYPQQPQQPFPQQPQQPVPQQPQQQFPQ

QPQQPVPQQPLQQFPQQPQQPFPQQPQQPVPQQPLQQFPQQPQQPFPQQPQQLVPQQSQQPFPQT

QQPQQPFPQPQQPQQLFPQTQQSSPQQPQQVTSQPQQPFPQAQPPQQSSPQSQQPYPQEPQQLFP

QSQQPQQPXPQPQQPFPQPQQPFPQSQEQFPQVHQPQQPSPQQQQPSIQLSLQQQLNPCKNVLLQ

QCSPVALVSSLRSKIFPQSECQVMQQQCCQQLAQIPQQLQCAAIHSVVHAIIMQQEQREGVQILL

PQSHQQHVGQGALAQVQGIIQPQQLSQLEVVRSLVLQNLPTMCNVYVPRQCSTIQAPFASIVTGI

VGH, (SEQ ID NO: 269)
MKTLLMLAILAMVTTIATANMQVNPSGQVQCPQQQPFPQPQQSSPLQPQQPFPQQSQQPFPHQPQ

QSSPQPQQPYPQQPFPQQPQQPYPQQPQQPFPQQPQQPYPQQPQQPFPQQPQQPVPQQPQQQFPQ

QPQQPVPQQPLQQFPQQPQQPFPQQPQQPVPQQPLQQFPQQPQQPFPQQPQQLVPQQSQQPFPQT

QQPQQPFPQPQQPQQLFPQTQQSSPQQPQQVTSQPQQPFPQAQPPQQSSPQSQQPYPQEPQQLFP

QSQQPQQPFPQPQQPFPQPQQPFPQSQEQFPQVHQPQQPSPQQQQPSIQLSLQQQLNPCKNVLLQ

-continued

QCSPVALVSSLRSKIFPQSECQVMQQQCCQQLAQIPQQLQCAAIHSVVHAIIMQQEQREGVQILL
PQSHQQHVGQGALAQVQGIIQPQQLSQLEVVRSLVLQNLPTMCNVYVPRQCSTIQAPFASIVTGI
VGH, (SEQ ID NO: 270)
MKTLLMLAILAMVTTIATANMQVNPSGQVQCPQQQPFPQPQQSSPLQPQQPFPQQSQQPFPHQPQ
QSSPQPQQPYPQQPFPQQPQQPYPQQPQQPQQPQQLVPQQSQQPFPQTQQPQQPFPQPQQPQQLF
PQTQQSSPQQPQQVTSQPQQPFPQAQPPQQSSPQSQQPYPQEPQQLFPQSQQPQQPFPQPQQPQQ
PFPQPQPQTQQSIPQPQQPFPQPQQPFPQSQEQFPQVHQPQQPSPQQQQPSIQLSLQQQLNPCKN
VLLQQCSPVALVSSLRSKIFPQSECQVMQQQCCQQLAQIPQQLQCAAIHSVVHAIIMQQEQREGV
QILLPQSHQQHVGQGALAQVQGIIQPQQLSQLEVVRSLVLQNLPTMCNVYVPRQCSTIQAPFASI
VTGIVGH, (SEQ ID NO: 271)
MKTLLMLAILAMVTTIATANMQVNPSGQVQCPQQQPFPQPQQSSPLQPQQPFPQQSQQPFPQQPQ
QSSPQPQQPYPQQPFPQQPQQQPQQQQPFPQPQPQTQQSIPQPQQPFPQPQQPFPQSQEPFPQVH
QPQQPSPQQQQPSIQLSLQQQLNPCKNVLLQQCSPVALVSSLRSKIFPQSECQVMQQQCCQQLAQ
IPQQLQCAAIHSVVHAIIMQQEQREGVQILLPQSHQQHVGQGALAQVQGIIQPQQLSQLEVVRSL
VLQNLPTMCNVYVPRQCSTIQAPFASIVTGIVGH, (SEQ ID NO: 272)
ARELNPSEQELQSPQPRFQKGQQPVPKEQSYPQQPYPSHQPFPTPQQYSPYQPQQPFPQPQQPTP
IQPQQPFPQQPQQPQQPFPQPQQQLPLQPQQPFPQPQQPIPQQPQQSFPQQPFPQPLQRPEQQFP
QQPQQIIPQQTQQPFPLQPQQPFPQQPQRPFAQQPEQIISQQPFPLQPQQPFSQPQQPFPQQPGQ
IIPQQPQQPSPLQPQQPFSQQPQRPQQPFPQQPQQIIPQQPQQPFPLQPQQPVPQQPQRPFGQQP
EQIISQRPQQPFPLQPQQPFSQPQQPFPQQPGQIIPQQPQQPFPLQPQQPFPQQPEQIIPQQPQQ
PFPLQPQQPFPQQPEQIISQQPQQPFPLQPQQPSPQQPPHQQLPFPQPQQPFVVVETSIGGQ, (SEQ ID NO: 273)
MAKQLVLFAAVVVALVALTVAEGEASGQLQCERELQERELEACRQIVDQQLRDTSPGCRPVAVSP
GTGQHEQQTVVPLKGGSFYPDETSPPQQLEQRILWGIPTLLKRYYPSVTSPHQGSYYPGQTSLQQ
PGQAQQPGQGQQPGQAQQPGQGQQPGQGQQPKKGQQGYYPTTPQQPGQEQQPGQGQQPGQGQPGY
YLTSSQQPGQGQQPGQGQPGYYPTSPQQSGQGQQLGQGQQGQQPGQGQPGYYPTSPQQPGQGQQP
GQGQRPGQGQQGQQPGQGQQGQQSGQGQQPGEGQQGYYPTFPQQPGQVQQPGEGQQPGQGQPGYY
PTSPQQPGQGQQPGQRQQPGQGKPGYYPTSPQQSGQGQQPGQGQSGYYPTSPQQPGQEQQPGQGQ
QVQQPGQGQQPGQGQQGYYPTSPQQSGQAQQPGQWQQPGQGQSGYYPTSQQQPGQGQQPGQGQQG
QQQGQGQQPGQGQQGYYPTSPQQPGQGQQPGQGQQPGQGQPGYYPTSPQQPGQGQQTGQGQQPGQ
GQQPGQGQQGQQPGQGQQGQQPGQGQQPGQGQQGYYPTSPQQPGQGQLEYYPTSPQQPGQGQPGY
YPTSPQLPXQLQQPAQGQQGYYSTSPRQPGQGQQEYYPTSPQQPGQWQQPGQGQQGYYITSPQQS
GQGQQPGQGQQPGQWLQPEQGQEGYYPTSGQQPGQWLQIGQGQQGYYLTSPQQPGQGQQGYDSPY
HVSAEHQAASLKVAKAQQLAAQLPAMCRLEGGDALSASQ, (SEQ ID NO: 274)
MAKRLVLFGIVVIALVALTAAEGEASRQLQCERELQESSLEACRQVVDQQLAGRLPWSTGLQMRC
CQQLRDVSAKCRHVAVSQVARQYEQTAVPPKGGSIYPGETTPLQQLQQGIFWGTSSQTVQGYYPS
VTSPQQGSYYPGQASPQQPGQGQQQGKWQEPGQGQQGYYPTSQQQPGQGQQGHYPASQQQPGQGQ
QGHYPASLQQPGQGQQGHYPASLQQPGQGQQTEQPGQMQQPGQGQQIGQGQQPGQGQQIGQGQQI
RQGQQPGQGQQGYYQTHPQQPGQGQQPGQGQQGYYPTSPQQPGQGQQGHYPGSLQQPGQGQPGQR

-continued

QQPGQGQQTGQGQQPEQEQQPGQGQQGYYPTSPQQPGQGQQPGQGQQGYYPTSLQQPGQGQQPHY
PASQQQPGQGQQGHYPTSLLQPGQGQQGHYPASSLQPGQGQQGHYPASLQQPGQGQQTEQPGQGQ
QPAQEQQSGQGQQGHYPTSLQQPGQGQPGQRQQPGQGQQIGQGQQPEQEQQPGQGQPGHYPASVQ
QPGQGQQTEQTGQGQQPGQGQQPEQEQQPGQGQQGYYITSLQQPGQGKQLGQWQQPGQGQEGYYP
TSPQQPGQGQQGHCPTSRQQPGQAQQPGQGQQIGQAQKPGQGQQGYYPTSLQQPGQGQQSGQGNQ
PGQGHQPGQGQQSGQDQQGYDSPCHVSAEQKATSPKVAKAQQPVAQLPTMCQMEGGDTLSASQ, (SEQ ID NO: 275)
MAKRLVLFATVVIGLVSLTVAEGEASKQLQCERELQESSLEACRLVVDQQLAGRLPWSTGLQMRC
CQQLRDISAKCRPVALSQVARQYGQTAVPPKGGSFYHRETTQLQQLQQGIFGGTSSQTVQGYYPS
VISPQQGSYYPGQASPQQPGKWQELGQGQQWYYPTSLQQPGQGQQGYYRTSLQQPGQRQQGYYRT
SRQQPGQGQQIGQWQQGYYPTSPQHPGQGQQPGQVQKIGQGQQPEKGQQLGQEQQIGQGQQPEQG
QQPGQGQQGYYPTSPQQPGQGQQPGQXXXXXXXXXXXXXXXXXXXXXXXXXXXXXGQQGYYPTSL
QQPGQEQQSGQGQQLGQGHQPGQGQQSGQEQQGYGTPYHVSVEQQAASPKVAKAHHPVAQLPTMC
QMEGGDALSASQ, (SEQ ID NO: 276)
MTKRLVLFAAVVVALVALTAAEGEASGQLQCERELQEHSLKACRQVVDQQLRDVSPECQPVGGGP
VARQYEQQVVVPPKGGSFYPGETTPPQQLQQSILWGIPALLRRYYLSVTSPQQVSYYPGQASSQR
PGQGQQPGQGQQEYYLTSPQQSGQWQQPGQGQSGYYPTSPQQSGQEQPGYYPTSPWQPEQLQQPT
QGQQRQQPGQGQQLRQGQQGQQSGQGQPRYYPTSSQQPGQLQQLAQGQQGQQPERGQQGQQSGQG
QQLGQGQQGQQPGQKQQSGQGQQGYYPISPQQLGQGQQSGQGQLGYYPTSPQQSGQGQSGYYPTS
AQQPGQLQQSTQEQQLGQEQQDQQSGQGRQGQQSGQRQQDQQSGQGQQPGQRQPGYYSTSPQQLG
QGQPRYYPTSPQQPGQEQQPRQLQQPEQGQQGQQPEQGQQGQQPGQGEQGQQPGQGQQGQQPGQG
QPGYYPTSPQQSGQGQPGYYPTSPQQSGQLQQPAQGQQPGQEQQGQQPGQGQQGQQPGQGQQPGQ
GQPGYYPTSPQQSGQEQQLEQWQQSGQGQPGHYPTSPLQPGQGQPGYYPTSPQQIGQGQQPGQLQ
QPTQGQQGQQPGQGQQGQQPGQGQQGQQPGQGQQPGQGQPGYYPTSLQQSGQGQQPGQWQQPGQG
QPGYYPTSSLQPEQGQQGYYPTSQQQPGQGPQPGQWQQSGQGQQGYYPTSPQQSGQGQQPGQWLQ
PGQWLQSGYYLTSPQQLGQGQQPRQWLQPRQGQQGYYPTSPQQSGQGQQLGQGQQGYYPTSPQQS
GQGQQGYDSPYHVSAEHQAASLKVAKAQQLAAQLPAMCRLEGGDALLASQ, (SEQ ID NO: 277)
MAKRLVLFVAVVVALVALTVAEGEASEQLQCERELKACQQVMDQQLRDISPECHPVVVSPVAGQY
EQQIVVPPKGGSFYPGETTPPQQLQQRIFWGIPALLKRYYPSVTSPQQVSYYPGQASPQRPGQGQ
QPGQGQQSGQGQQGYYPTSPQQPGQWQQPEQGQPGYYPTSPQQPGQLQQPAQGQQPGQGQQGRQP
GQGQPGYYPTSSQLQPGQLQQPAQGQQGQQPGQGQQGQQPGQGQQPGQGQQGQQPGQGQQPGQGQ
QGQQLGQGQQGYYPTSLQQSGQGQPGYYPTSLQQLGQGQSGYYPTSPQQPGQGQQPGQLQQPAQG
QQPEQGQQGQQPGQGQQGQQPGQGQQPGQGQPGYYPTSPQQSGQGQPGYYPTSSQQPTQSQQPGQ
GQQGQQVGQGQQAQQPGQGQQPGQGQPGYYPTSPLQSGQGQPGYYLTSPQQSGQGQQPGQLQQSA
QGQKGQQPGQGQQPGQGQQGQQPGQGQQGQQPGQGQPGYYPTSPQQSGQGQQPGQWQQPGQGQPG
YYPTSPLQPGQGQPGYDPTSPQQPGQGQQPGQLQQPAQGQQGQQLAQGQQGQQPAQVQQGQQPAQ
GQQGQQLGQGQQGQQPGQGQQPAQGQQGQQPGQGQQGQQPGQGQQPGQGQPWYYPTSPQESGQGQ
QPGQWQQPGQWQQPGQGQPGYYLTSPXQPGQGQQXYYPTSXQQPGQWQQPGQGQQGYYPTSPQQS
GQXQQXGQGQQPGQWLQPGQGQQGYYPTSXQQXGQGQQXGQWLQXGQGQQGYYXTSXQQPGQGQQ
SGQGQQGYDSPYHVSAEHQAASLKVAKAQQLAAQLPAMCRLEGGDALSASQ,

-continued (SEQ ID NO: 278)
MAKRLVLFVAVVVALVALTVAEGEASEQLQCERELQELQERELKACQQVMDQQLRDISPECHPVV

VSPVAGQYEQQIVVPPKGGSFYPGETTPPQQLQQRIFWGIPALLKRYYPSVTSPQQVSYYPGQAS

PQRPGQGQQPGQGQQSGQGQQGYYPTSPQQPGQWQQPEQGQPGYYPTSPQQPGQLQQPAQGQQPG

QGQQGRQPGQGQPGYYPTSSQLQPGQLQQPAQGQQGQQPGQGQQGQQPGQGQQPGQGQQGQQPGQ

GQQPGQGQQGQQLGQGQQGYYPTSLQQSGQGQPGYYPTSLQQLGQGQSGYYPTSPQQPGQGQQPG

QLQQPAQGQQPEQGQQGQQPGQGQQGQQPGQGQQPGQGQPGYYPTSPQQSGQGQPGYYPTSSQQP

TQSQQPGQGQQGQQVGQGQQAQQPGQGQQPGQGQPGYYPTSPLQSGQGQPGYYLTSPQQSGQGQQ

PGQLQQSAQGQKGQQPGQGQQPGQGQQGQQPGQGQQGQQPGQGQPGYYPTSPQQSGQGQQPGQWQ

QPGQGQPGYYPTSPLQPGQGQPGYDPTSPQQPGQGQQPGQLQQPAQGQQGQQLAQGQQGQQPAQV

QQGQQPAQGQQGQQLGQGQQGQQPGQGQQPAQGQOGQQPGQGQQGQQPGQGQQPGQGQPWYYPTS

PQESGQGQQPGQWQQPGQWQQPGQGQPGYYLTSPLQLGQGQQGYYPTSLQQPGQGQQPGQWQQSG

QGQHGYYPTSPQLSGQGQRPGQWLQPGQGQQGYYPTSPQQSGQGQQLGQWLQPGQGQQGYYPTSL

QQTGQGQQSGQGQQGYYSSYHVSVEHQAASLKVAKAQQLAAQLPAMCRLEGGDALSASQ, (SEQ ID NO: 279)
MAKRLVLFATVVITLVALTAAEGEASRQLQCERELQESSLEACRQVVDQQLAGRLPWSTGLQMRC

CQQLRDVSAKCRPVAVSQVVRQYEQTVVPPKGGSFYPGETTPLQQLQQVIFWGTSSQTVQGYYPS

VSSPQQGPYYPGQASPQQPGQGQQPGKWQELGQGQQGYYPTSLHQSGQGQQGYYPSSLQQPGQGQ

QIGQGQQGYYPTSLQQPGQGQQIGQGQQGYYPTSPQHPGQRQQPGQGQQIGQGQQLGQGRQIGQG

QQSGQGQQGYYPTSPQQLGQGQQPGQWQQSGQGQQGYYPTSQQQPGQGQQGQYPASQQQPGQGQQ

GQYPASQQQPGQGQQGQYPASQQQPAQGQQGQYPASQQQPGQGQQGHYLASQQQPGQGQQRHYPA

SLQQPGQGQQGHYTASLQQPGQGQQGHYPASLQQVGQGQQIGQLGQRQQPGQGQQTRQGQQLEXX

XXXXXXXXXXXQQLEQGQQPGQGQQGYYPTSPQQSGQGQQPGQSQQPGQGQQGYYSSSLQQPGQ

GLQGHYPASLQQPGQGHPGQRQQPGQGQQPEQGQQPGQGQQGYYPTSPQQPGQGKQLGQGQQGYY

PTSPQQPGQGQQPGQGQQGHCPTSPQQTGQAQQPGQGQQIGQVQQPGQGQQGYYPISLQQSGQGQ

QSGQGQQSGQGHQLGQGQQSGQEQQGYDNPYHVNTEQQTASPKVAKVQQPATQLPIMCRMEGGDA

LSASQ, (SEQ ID NO: 280)
MAKRLVLFAAVVIALVALTTAEGEASRQLQCERELQESSLEACRQVVDQQLAGRLPWSTGLQMRC

CQQLRDVSAKCRSVAVSQVARQYEQTVVPPKGGSFYPGETTPLQQLQQGIFWGTSSQTVQGYYPS

VTSPRQGSYYPGQASPQQPGQGQQPGKWQEPGQGQQWYYPTSLQQPGQGQQIGKGKQGYYPTSLQ

QPGQGQQIGQGQQGYYPTSPQHTGQRQQPVQGQQIGQGQQPEQGQQPGQWQQGYYPTSPQQLGQG

QQPGQWQQSGQGQQGHYPTSLQQPGQGQQGHYLASQQQPAQGQQGHYPASQQQPGQGQQGHYPAS

QQQPGXXXGHYPASQQQPGQGQQGHYPASQQEPGQGQQGQIPASQQQPGQGQQGHYPASLQQPGQ

QGHYPTSLQQLGQGQQIGQPGQKQQPGQGQQTGQGQQPEQEQQPGQGQQGYYPTSLQQPGQGQQQ

GQGQQGYYPTSLQQPGQGQQGHYPASLQQPGQGQPGQRQQPGQGQHPEQGQQPGQGQQGYYPTSP

QQPGQGQQLGQGQQGYYPTSPQQPGQGQQPGQGQQGHCPMSPQQTGQAQQLGQGQQIGQVQQPGQ

GQQGYYPTSLQQPGQGQQSGQGQQSGQGHQPGQGQQSGQEKQGYDSPYHVSAEQQAASPMVAKAQ

QPATQLPTVCRMEGGDALSASQ, (SEQ ID NO: 281)
MAKRLVLFAAVVVALLALTAAEGEASGQLQCERELQESSLEACRRVVDQQLAGQLPWSTGLQMRC

CQQLRDVSPECRPIAVSQVARQYEQQIVVPPKGGSFYPGETTPPQQLQQRIFWGRSSQTVQGYYP

-continued

SVTSPQQGSYYPGQASPQQPGQGQQPGQWQEPGQGIQGYGLTSPQQPGQGQQLGQRQQPEQGQQG
YCPISPQQPGQWQQSGQGQQGYYQTSPQQPAQGQQGYDLTSPQQSGQGQQLGQRQQPGQGQQGYY
PISPQQPGQWQQPGQGQQGYYPTSPQQPGQGQQGYYPTSPQQSGQGQQPGQGYYPTXPQSPQQPG
QWQQPGQGQQGYYPTSPQQPGQGQQGYYPTSPQQPGQWQQLGQGYYPTFPQQSGQGQQPGQGYYP
TFPQQPGQGQQGYYPTSPQQSGQWQQSGQWQQGYYPTFPQQPGQGQQLGQEPQGYNSPYHVSAEQ
QAASLMVAKAQQLAAQLPAMCRLEGSGALSASQ, (SEQ ID NO: 282)

MAKRLVLFAAVVIALVALTTAEGEASRQLQCERELQESSLEACRQVVDQQLAGRLPWSTGLQMRC
CQQLRDVSAKCRSVAVSQVARQYEQTVVPPKGGSFYPGETTPLQQLQQGIFWGTSSQTVQGYYPG
VTSPRQGSYYPGQASPQQPGQGQQPGKWQEPGQGQQWYYPTSLQQPGQGQQIGKGQQGYYPTSLQ
QPGQGQQGYYPTSLQHTGQRQQPVQGQQPEQGQQPGQWQQGYYPTSPQQLGQGQQPRQWQQSGQG
QQGHYPTSLQQPGQGQQGHYLASQQQPGQGQQGHYPASQQQPGQGQQGHYPASQQQPGQGQQGHY
PASQQEPGQGQQGQIPASQQQPGQGQQGHYPASLQQPGQGQQGHYPTSLQQLGQGQQTGQPGQKQ
QPGQGQQTGQGQQPEQEQQPGQGQQGYYPTSLQQPGQGQQQGQGQQGYYPTSLQQPGQGQQGHYP
ASLQQPGQGQPGQRQQPGQGQHPEQGKQPGQGQQGYYPTSPQQPGQGQQLGQGQQGYYPTSPQQP
GQGQQPGQGQQGHCPTSPQQSGQAQQPGQGQQIGQVQQPGQGQQGYYPTSVQQPGQGQQSGQGQQ
SGQGHQPGQGQQSGQEQQGYDSPYHVSAEQQAASPMVAKAQQPATQLPTVCRMEGGDALSASQ, (SEQ ID NO: 283)

MAKRLVLFATVVIGLVSLTVAEGEASRQLQCXRELXESSLEACRLVVDQQLAGRLPWSTGLQMRC
CQQLRDISAKCRPVAVSQVARQYGQTAVPPKGGSFYPRETTPLQQLQQEIFGGTSSQTVQGYYPS
VISPQQGSYYPGQASPQQPGKWQELGQEQQGYYPTSLQQPGQGQQGYYRTSLQQSGQGQQGYYRT
SLQQPGQGQQIGQWQQGYYPTSPQHPGQGQQPGQVQKIGQGQQPEKGQQLGQEQQIGQGQQPEQG
QQPGQGQQPGQGQQGYYPTSLQQPGQGQQPGQWQQPGQGQQGYYPTSLQQPGQGQQGHYPASQHQ
PGQGQQGHHPASLQQSGQGQQGHHPASLQQPGQGKQTGQREQRQQPGQGQQTGQGQQPEQEQQPG
QGQQGYYPTYMQQPGQGQQPEQWQQPGQGQQGHYPASLQQSGQGQQGHYPASLQQPGQGQPGQTQ
QPGQGQQPEQEEQSGQGQQGYYPTSPQQPGQGQQPGQGQQGHFPTSGQAQQPGQGQQIGQAQQLG
QGQQGYYPTSLQQPGQEQQSRQGQQLGQGHQPGQGQQSGQEQQGYDSPYHVSVEQQAASPKVAKA
HHPVAQLPTMCQMXGGDALSASQ, (SEQ ID NO: 284)

MAKRLVLFAAVVVALVALTVAEGEASGQLQCERELQERELEACRQIVDQQLRDTSPGCRPVAVSP
GTGQQEQQTVVPLKGGSFYPDETSPPQQLEQRILWGIPTLLKRYYPSVTSPHQGSYYPGQTSLQQ
PGQAQQPGQGQQPGQAQQPGHGQQSGQGQQPEKGQQGYYPTTPQQPGXXXXQGQQPGQGQPGYYL
TSSQQPGQGQQPGQGQPGYYPTSSQQXGQGQQLGQGQQGQQPGQGQPGYYPTSPQQPGQGQQPGQ
GQQPGQGQQGQQPGQGQQGQQPGQGQQPGEGQQGYYPTFPQQPGQVQQPGQGQQPGQGQPGYYPT
SPQQPGQGQQPGQEQQPGQRQQPGQGKPGYYPTSPQQSGQGQSGYYPTSPQQPGQXQQPGQGQQV
QQPGQGQQPGQGQQGYYPTSPQQSGQAQQPGQWQQPGQGQSGYYPTSQQQPGQGQQPGQGQQPGQ
GQQPGQGQQGQQPXQGQQXGQGQQGYYPTSPQQXGQGQQPGQXQQPGQGQPGYYPTSPQQSGQGQ
QPGQGQXGYXXTSPQQPGQXQQPGQGQQGQQPGQGQQPGQGQQGYYPTSPQQPXQGQQPGQGQLE
YYPTSPQQPGQGQPGYYPTXPQLPGQLQQPAQGQQGYYXTSPXQPGQGQQXYYPTSPQQPGQWQQ
PGQGQQGYYITSPQQSGQGQQPGQGQQPGQWLQPGQGQEGYYPTSGQQPGQWLQIGQGQQGYYXT
SPQQQGYYXTSPQQPGQGXQPGQGQQGYDSPYHVSAEHQAASLKVAKAQQLAAQLPAMCRLEGGD
ALSASQ,

-continued (SEQ ID NO: 285)
MAKRLVLFAAVVVALVALTAAEGEASGQLQCEHELEACQQVVDQQLRDVSPGCRPITVSPGTRQY

EQQPVVPSKAGSFYPSETTPSQQLQQMIFWGIPALLRRYYPSVTSSQQGSYYPGQASPQQSGQGQ

QPGQEQQPGQGQQDQQPGQRQQGYYPTSPQQPGQGQQLGQGQPGYYPTSQQPGQKQQAGQGQQSG

QGQQGYYPTSPQQSGQGQQPGQGQPGYYPTSPQQSGQWQQPGQGQQPGQGQQSGQGQQGQQPGQG

QRPGQGQQGYYPXSPQQPGQGQQSGQGQPGYYPTSLRQPGQWQQPGQGQQPGQGQQGQQPGQGQQ

SGQGQQGYYPTSLQQPGQGQQLGQGQPGYYPTSQQSEQGQQPGQGKQPGQGQQGYYPTSPQQSGQ

GQQLGQGQPGYYPTSPQQSGQGQQSGQGQQGYYPTSPQQSGQGQQPGQGQSGYFPTSRQQSGQGQ

QPGQGQQSGQGQQGQQPGQGQQAYYPTSSQQSRQRQQAGQWQRPGQGQPGYYPTSPQQPGQEQQS

GQAQQSGQWQLVYYPTSPQQPGQLQQPAQGQQPAQGQQSAQEQQPGQAQQSGQWQLVYYPTSPQQ

PGQLQQPXQGQQGYYPTSPQQSGQGQQGYYPTSPQQSGQGQQGYYPTSPQQSGQGQQPGQGQQPR

QGQQGYYPISPQQSGQGQQPGQGQQGYYPTSPQQSGQGQQPGHEQQPGQWLQPGQGQQGYYPTSS

QQSGQGQQSGQGQQGYYPTSLWQPGQGQQXGQGQQGYDSPYHVSAEYQAARLKVAKAQQLAAQLP

AMCRLEGSDALSARQ, (SEQ ID NO: 286)
MAKRLVLFVAVVVALVALTVAEGEASEQLQCERELQELQERELKACQQVMDQQLRDISPECHPVV

VSPVAGQYEQQIVVPPKGGSFYPGETTPPQQLQQRIFWGIPALLKRYYPSVTCPQQVSYYPGQAS

PQRPGQGQQPGQGQQGYYPTSPQQPGQWQQPEQGQPRYYPTSPQQSGQLQQPAQGQQPGQGQQGQ

QPGQGQPGYYPTSSQLQPGQLQQPAQGQQGQQPGQGQQGQQPGQGQQPGQGQQGQQPGQGQQPGQ

GQQGQQLGQGQQGYYPTSLQQSGQGQPGYYPTSLQQLGQGQSGYYPTSPQQPGQGQQPGQLQQPA

QGQQPGQGQQGQQPGQGQQGQQPGQGQQPGQGQPGYYPTSPQQSGQGQPGYYPTSSQQPTQSQQP

GQGQQGQQVGQGQQAQQPGQGQQPGQGQPGYYPTSPQQSGQGQPGYYLTSPQQSGQGQQPGQLQQ

SAQGQKGQQPGQGQQPGQGQQGQQPGQGQQGQQPGQGQPGYYPTSPQQSGQGQQPGQWQQPGQGQ

PGYYPTSPLQPGQGQPGYDPTSPQQPGQGQQPGQLQQPAQGQQGQQLAQGQQGQQPAQVQQGQRP

AQGQQGQQPGQGQQGQQLGQGQQGQQPGQGQQGQQPAQGQQGQQPGQGQQGQQPGQGQQGQQPGQ

GQQPGQGQPWYYPTSPQESGQGQQPGQWQQPGQGQPGYYLTSPLQLGQGQQGYYPTSLQQPGQGQ

QPGQWQQSGQGQHWYYPTSPQLSGQGQRPGQWLQPGQGQQGYYPTSPQQPGQGQQLGQWLQPGQG

QQGYYPTSLQQTGQGQQSGQGQQGYYSSYHVSVEHQAASLKVAKAQQLAAQLPAMCRLEGGDALS

ASQ, (SEQ ID NO: 287)
MAKRLVLFAAVVVALVALTAAEGEASGQLQCERELRKRELEACQQVVDQQLRDVSPGCRPITVSP

GTRQYEQQPVVPSKAGSFYPSETTPSQQLQQMIFWGIPALLRRYYPSVTSSQQG, (SEQ ID NO: 288)
MKTFLIFALLAIAATNTIAQQQPFPQQPQPYPQQPQPYPQQPFPPQQPFPQQPPFWWQQPVQSQQ

QPCQQQQTPLPQGQQYQPLLQQQIPFVHPSXLQQLNPCKVFLQQQCSPVPMPQRIARSQMLQQSS

CHVLQQQCCQQLPQIPEQFRHEAIRAIIYSIILQEQQQVQDFVQPQQQQPQQSVQGVSQSQQQSQ

QPQLGQCSFQQPQLQQLGQQPQQQQVPLWAFLQPQQMAQLEVMTSVALRTLPTMCNVNVPLYGIT

TSVPLSVGTGVGPY, (SEQ ID NO: 289)
MKTFLIFALLAIVATSTIAQQQPYPQQPQPFPQQPIPQXXXXXXXXXXXXXXXXXXXXPIPQQPQ

PYPQQPQPFPQQPIPQQPQPYPQQPQPFPLQPFPSQQPFPQQPPFWQQQPVLSQQQPCTQEQTPL

LQEQQDQMLXQVQIPFVHPSILQQLNPCKVFLQQQCSPVAMSQRIARSQMLQQSSCHVLQQQCCQ

-continued

QLPQIPEQLRHEAVRAIVYSIVLQEQSLQLVQGVSQPQQQSQQQQVGQCSFQQPQPQQGQQQQVP

QSVXLQPHQIAQLEATTSIALRTLPTMCSVNVPLYRIVPLAIDTRVGV, (SEQ ID NO: 290)
MKTFLIFALLAIVATSTIAQQQPYPQQPQPFPQQPIPQQPQPFPQQPQPFPQQPFPSRQPFPQQP

PFWQQQPVLSQQQPCTQDQTPLLQEQQDQMLLQVQIPFVHPSILQQLNPCKVFLQQQCSPVAMSQ

RIARSQMLQQSSCHVLQQQCCQQLPQIPEQIRHEAVRAIVYSIVLQEQPLQLVQGVSQPQQQSQQ

QQVGQCSFQQPQPQQGQQQQVPQSVFLQPHQIAQLEATASIALRTLPTMCSVNVPLYRIVPLAID

TRVGV, (SEQ ID NO: 291)
MKTFLIFALLAIAATSTIAQQQPFPQQPIPQQPQPYPQQPQPYPQQPFQPQQPFPQQTIPQQPQP

YPQQPQPYPQQPFPPQQAFPQQPPFWPQQPFPQQPPFGLQQPILSQQQPCTPQQTPLPQGQLYQT

LLQLQIPNVQPSILQQLNPCKVFLQQQCSPVRMQQLIARSQMLQQSSCHVLQQQCCQQLPQIPEQ

FRHEAIRAIVYSIFLQEQPQQSVQGVSQPQQQLQQEQVGQCYFQQPQPQQLGQPQQVPQSVFLQP

HQIAQLEATTSIALRTLPTMCNVNVPLYDIMPFGVGTRVGV, (SEQ ID NO: 292)
MKTFLIFALLVIAATSTIAQQQPFPQQPFPQQPQPYPQQPQPYPQQPFQPQQPFPQQTIPQQPQP

YPQQPFPPQQEFPQQPPFWPQQPFPQQPPFGLQQPILSQQQPCTPQQTPLPQGQLYQTLLQLQIP

YVHPSILQQLNPCKVFLQQQCSPVRMPQLIARLQMLQQSSCHVLQQQCCQQLPQISEQFRHEAIR

AIVYSIFLQEQPQQSVQGVSQTQQQLQQEQVGQCSFQQPQPQQLGQAQQVPQSVFLQPHQIAQLE

ATTSIALRTLPRMCNVNVPLYDIMPPDFWHXVXV, (SEQ ID NO: 293)
MKTFLIFALLAIAATSTIAQQQPFPQQPQQIPQQPQPYPQQPQPYPQQPFPPQQEFPQQPPFWPQ

QPFPQQPPFGLQQPILSQQQPCTPQQTPLPQGQLYQTLLQLQIPYVHPSILQQLNPCKVFLQQQC

SPVRMPQLIARLQMLQQSSCHVLQQQCCQQLPQISEQFRHEAIRAIVYSIFLQEQPQQSVQGVSQ

TQQQLQQEQVGQCSFQQPQPQQLGQPQQVPQSVFLQPHQIAQLEATTSIALRTLPRMCNVNVPLY

DIMPPDFWHRVGV, (SEQ ID NO: 294)
MKTFLTFVLLAMAMSIVTTARQLNPSXQELQSPQQXXXXXXSYLQQPYPQXPYLPQQPFPTPQQF

FPYLPQQTFPQSQQPTPLQPQQPFPLQPQQPXPXXQQPFXWQPQQPFPQPQQPXPQQPQQPFXXQ

PQQIXXQQPQQPFPQQPQQPFPQPQQPFXWQPQQPFXQPXQXFPLQPQQPFPWQPQQPFPQPQQP

IAHQPQQPFSFSQQPQQPFPLQPQQPFPQQPQQPFPQQPQQIIFQQPQQSYPVQPQQPFPQPQQP

FPQIPQQPFPLQPQPFPQQPQQPLPQPQQPFRQQAELIIPQQPQQPFPLQPHQPYTQQTIWSMVA

LLG, (SEQ ID NO: 295)
MAKRLVLFVAVIVALVALTTAEREINGNNIFLDSRSRQLQCERELQESSLEACRRVVDQQLVGQL

PWSTGLQMQCCQQLRDVSPECRPVALSQVVRQYEQQTEVPSKGGSFYPGGTAPPLQQGGWWGTSV

KWYYPDQTSSQQSWQGQQGYHQSVTSSQQPGQGQQGSYPGSTFPQQPGQGQQPGQRQPWSYPSAT

FPQQPGQGQGQQGYYPGATSLLQPGQGQQGPYQSATSPQQPGQGQGQQETYPIATSPHQPGQWQQ

PGQGQQGYYPSVTSPQQSGQGQQGYPSTTSPQQSGQGQQLGQGQQPGQGQQGYPSATFPQQPGQW

QQGSYPSTTSPQQSGQGQQGYNPSGTSTQQPGQVQQLGQGQQGYYPIATSPQQPGQGQQLGQGQQ

PGHGQQLVQGQQQGQGQQGHYPSMTSPHQTGQGQKGYYPSAISPQQSGQGQQGYQPSGASSQGSV

QGACQHSTSSPQQQAQGCQASSPKQGLGSLYYPSGAYTQQKPGQGYNPGGTSPLHQQGGGFGGGL

TTEQPQGGKQPFHCQQTTVSPHQGQQTTVSPHQGQQTTVSPHQGQQTTVSPHQGQQTTVSPHQGQ

-continued

```
QTTVSPHQGQQTTVSPHPGQQTTVSPHQGQQTTVSPHPGQQTTVSPHQGQQTTVSPHQGQQTTVS

PHQGQQTTVSPHQGQQTTVSPHQGQQPGEQPCGFPGQQTTVSLHHGQQSNELYYGSPYHVSVEQP

SASLKVAKAQQLAAQLPAMCRLEGGGGLLASQ,
```

(SEQ ID NO: 296)
```
MKILIILTILAMATTFATSEMQVNPSVQVQPTQQQPYPESQQPFISQSQQQFPQPQQPFPQQPQQ

PFPQSQQQCLQQPQHQFPQPTQQFPQRPLLPFTHPFLTFPDQLLPQPPHQSFPQPPQSYPQPPLQ

PFPQPPQQKYPEQPQQPFPWQQPTIQLYLQQQLNPCKEFLLQQCRPVSLLSYLWSKIVQQSSCRV

MQQQCCLQLAQIPEQYKCTAIDSIVHAIFMQQGQRQGVQIVQQQPQPQQVGQCVLVQGQGVVQPQ

QLAQMEAIRTLVLQSVPSMCNFNVPPNCSTIKAPFVGVVTGVGGQ,
```

(SEQ ID NO: 297)
```
MKIFLLFSLLGVATAITTTTMQFNPSGLELERPQQLFPQWQPLPQQPPFLQQEPEQPYPQQQPLP

QQQPFPQQPQLPHQHQFPQQLPQQQFPQQMPLQPQQQFPQQMPLQPQQQPQFPQQKPFGQYQQPL

TQQPYPQQQPLAQQQPSIEEQHQLNLCKEFLLQQCTLDEKVPLLQSVISFLRPHISQQNSCQLKR

QQCCQQLANINEQSRCPAIQTIVHAIVMQQQVQQQVGHGFVQSQLQQLGQGMPIQLQQQPGQAFV

LPQQQAQFKVVGSLVIQTLPMLCNVHVPPYCSPFGSMATGSGGQ,
```

(SEQ ID NO: 298)
```
MKTFLIFALLAIAATNTIAQQQPFPQQPQPYPQQPQPYPQQPFPPQQPFPQQPPFWWQQPVQSQQ

QPCQQQQTPLPQGQQYQPLLQQQIPFVHPSXLQQLNPCKVFLQQQCSPVPMPQRIARSQMLQQSS

CHVLQQQCCQQLPQIPEQFRHEAIRAIIYSIILQEQQQVQDFVQPQQQQPQQSVQGVSQSQQQSQ

QPQLGQCSFQQPQLQQLGQQPQQQQVPLWAFLQPQQMAQLEVMTSVALRTLPTMCNVNVPLYGIT

TSVPLSVGTGVGPY,
```

(SEQ ID NO: 299)
```
MKTFLIFALLAIVATSTIAQQQPYPQQPQPFPQQPIPQXXXXXXXXXXXXXXXXXXXXXPIPQQPQ

PYPQQPQPFPQQPIPQQPQPYPQQPQPFPLQPFPSQQPFPQQPPFWQQQPVLSQQQPCTQEQTPL

LQEQQDQMLXQVQIPFVHPSILQQLNPCKVFLQQQCSPVAMSQRIARSQMLQQSSCHVLQQQCCQ

QLPQIPEQLRHEAVRAIVYSIVLQEQSLQLVQGVSQPQQQSQQQQVGQCSFQQPQPQQGQQQQVP

QSVXLQPHQIAQLEATTSIALRTLPTMCSVNVPLYRIVPLAIDTRVGV,
```

(SEQ ID NO: 300)
```
MKTFLIFALLAIVATSTIAQQQPYPQQPQPFPQQPIPQQPQPFPQQPQPFPQQPFPSRQPFPQQP

PFWQQQPVLSQQQPCTQDQTPLLQEQQDQMLLQVQIPFVHPSILQQLNPCKVFLQQQCSPVAMSQ

RIARSQMLQQSSCHVLQQQCCQQLPQIPEQIRHEAVRAIVYSIVLQEQPLQLVQGVSQPQQQSQQ

QQVGQCSFQQPQPQQGQQQQVPQSVFLQPHQIAQLEATASIALRTLPTMCSVNVPLYRIVPLAID

TRVGV,
```

(SEQ ID NO: 301)
```
MKTFLIFALLAIAATSTIAQQQPFPQQPIPQQPQPYPQQPQPYPQQPFQPQQPFPQQTIPQQPQP

YPQQPQPYPQQPFPPQQAFPQQPPFWPQQPFPQQPPFGLQQPILSQQQPCTPQQTPLPQGQLYQT

LLQLQIPNVQPSILQQLNPCKVFLQQQCSPVRMQQLIARSQMLQQSSCHVLQQQCCQQLPQIPEQ

FRHEAIRAIVYSIFLQEQPQQSVQGVSQPQQQLQQEQVGQCYFQQPQPQQLGQPQQVPQSVFLQP

HQIAQLEATTSIALRTLPTMCNVNVPLYDIMPFGVGTRVGV,
```

(SEQ ID NO: 302)
```
MKTFLIFALLVIAATSTIAQQQPFPQQPFPQQPQPYPQQPQPYPQQPFQPQQPFPQQTIPQQPQP

YPQQPFPPQQEFPQQPPFWPQQPFPQQPPFGLQQPILSQQQPCTPQQTPLPQGQLYQTLLQLQIP

YVHPSILQQLNPCKVFLQQQCSPVRMPQLIARLQMLQQSSCHVLQQQCCQQLPQISEQFRHEAIR
```

-continued

AIVYSIFLQEQPQQSVQGVSQTQQQLQQEQVGQCSFQQPQPQQLGQAQQVPQSVFLQPHQIAQLE
ATTSIALRTLPRMCNVNVPLYDIMPPDFWHXVXV, (SEQ ID NO: 303)
MKTFLIFALLAIAATSTIAQQQPFPQQPQQIPQQPQPYPQQPQPYPQQPFPPQQEFPQQPPFWPQ
QPFPQQPPFGLQQPILSQQQPCTPQQTPLPQGQLYQTLLQLQIPYVHPSILQQLNPCKVFLQQQC
SPVRMPQLIARLQMLQQSSCHVLQQQCCQQLPQISEQFRHEAIRAIVYSIFLQEQPQQSVQGVSQ
TQQQLQQEQVGQCSFQQPQPQQLGQPQQVPQSVFLQPHQIAQLEATTSIALRTLPRMCNVNVPLY
DIMPPDFWHRVGV, (SEQ ID NO: 304)
MKTFLTFVLLAMAMSIVTTARQLNPSXQELQSPQQXXXXXXSYLQQPYPQXPYLPQQPFPTPQQF
FPYLPQQTFPQSQQPTPLQPQQPFPLQPQQPXPXXQQPFXWQPQQPFPQPQQPXPQQPQQPFXXQ
PQQIXXQQPQQPFPQQPQQPFPQPQQPFXWQPQQPFXQPXQXFPLQPQQPFPWQPQQPFPQPQQP
IAHQPQQPFSFSQQPQQPFPLQPQQPFPQQPQQPFPQQPQQIIFQQPQQSYPVQPQQPFPQPQQP
FPQIPQQPFPLQPQPFPQQPQQPLPQPQQPFRQQAELIIPQQPQQPFPLQPHQPYTQQTIWSMVA
LLG, (SEQ ID NO: 305)
MAKRLVLFVAVIVALVALTTAEREINGNNIFLDSRSRQLQCERELQESSLEACRRVVDQQLVGQL
PWSTGLQMQCCQQLRDVSPECRPVALSQVVRQYEQQTEVPSKGGSFYPGGTAPPLQQGGWWGTSV
KWYYPDQTSSQQSWQGQQGYHQSVTSSQQPGQGQQGSYPGSTFPQQPGQGQQPGQRQPWSYPSAT
FPQQPGQGQGQQGYYPGATSLLQPGQGQQGPYQSATSPQQPGQGQGQQETYPIATSPHQPGQWQQ
PGQGQQGYYPSVTSPQQSGQGQQGYYPSTTSPQQSGQGQQLGQGQQPGQGQQGYPSATFPQQPGQW
QQGSYPSTTSPQQSGQGQQGYNPSGTSTQQPGQVQQLGQGQQGYYPIATSPQQPGQGQQLGQGQQ
PGHGQQLVQGQQQGQGQQGHYPSMTSPHQTGQGQKGYYPSAISPQQSGQGQQGYQPSGASSQGSV
QGACQHSTSSPQQQAQGCQASSPKQGLGSLYYPSGAYTQQKPGQGYNPGGTSPLHQQGGGFGGGL
TTEQPQGGKQPFHCQQTTVSPHQGQQTTVSPHQGQQTTVSPHQGQQTTVSPHQGQQTTVSPHQGQ
QTTVSPHQGQQTTVSPHPGQQTTVSPHQGQQTTVSPHPGQQTTVSPHQGQQTTVSPHQGQQTTVS
PHQGQQTTVSPHQGQQTTVSPHQGQQPGEQPCGFPGQQTTVSLHHGQQSNELYYGSPYHVSVEQP
SASLKVAKAQQLAAQLPAMCRLEGGGGLLASQ, (SEQ ID NO: 306)
MKILIIILTILAMATTFATSEMQVNPSVQVQPTQQQPYPESQQPFISQSQQQFPQPQQPFPQQPQQ
PFPQSQQQCLQQPQHQFPQPTQQFPQRPLLPFTHPFLTFPDQLLPQPPHQSFPQPPQSYPQPPLQ
PFPQPPQQKYPEQPQQPFPWQQPTIQLYLQQQLNPCKEFLLQQCRPVSLLSYLWSKIVQQSSCRV
MQQQCCLQLAQIPEQYKCTAIDSIVHAIFMQQGQRQGVQIVQQQPQPQQVGQCVLVQGQGVVQPQ
QLAQMEAIRTLVLQSVPSMCNFNVPPNCSTIKAPFVGVVTGVGGQ, (SEQ ID NO: 307)
MKIFLLFSLLGVATAITTTTMQFNPSGLELERPQQLFPQWQPLPQQPPFLQQEPEQPYPQQQPLP
QQQPFPQQPQLPHQHQFPQQLPQQQFPQQMPLQPQQQFPQQMPLQPQQQPQFPQQKPFGQYQQPL
TQQPYPQQQPLAQQQPSIEEQHQLNLCKEFLLQQCTLDEKVPLLQSVISFLRPHISQQNSCQLKR
QQCCQQLANINEQSRCPAIQTIVHAIVMQQQVQQQVGHGFVQSQLQQLGQGMPIQLQQQPGQAFV
LPQQQAQFKVVGSLVIQTLPMLCNVHVPPYCSPFGSMATGSGGQ, (SEQ ID NO: 308)
MKTFLIFVLLAMAMKIATAARELNPSNKELQSPQQSFSHQQQPFPQQPYPQQPYPSQQPYPSQQP
FPTPQQQFPQQSQQPFTQPQQPTPLQPQQPFPQQPQQPQQPFPQPQQPFPWQPQQPFPQTQQSFP

-continued

LQPQQPFPQQPQQPFPQPQLPFPQQSEQIIPQQPQQPFPLQPQQPFPQQPQQPFPQQIPQPQQFP

QQSQQSQQPFPQQLFPELQQPIPQQPQQPFPLQPQQPFPQQPQQPFPQQPQQPFPQQPQQPFPXX

QQPFPLRPQQPFPQQPQQSQQSFPQPQPQQPQQPSILQPQXXXXXQPQQPFQQPQQQLSQQPEQT

ISQQPQQPFPQQPHQPQQPYPQQQPYGSSLTSIGGQ, (SEQ ID NO: 309)
ARZLNPSEQELQSPQQAVPKEQSYPQQPYPSHQPFPTPQQYSPYQPQQPFPQPQQPTPIQPQQPF

PQQXXXPQQPFPQPQQQLPLQPQQPFPQPQQPIPQQPQQSFPQQPQRPZQQFPQQPQQIIPQQTQ

QPFPLQPQQPFPQQPQRPFAQQPEQIISQQPFPLQPQQPFSQPQQPFPQQPGQIIPQQPQQPSPL

QPQQPFSQQPQRPQQPFPQQPQQIIPQQPQQPFPLQPQQPVPQQPQRPFGQQPEQIISQRPQQPF

PLQPQQPFSQPQQPFPQQPGQIIPQQPQQPFPLQPQQPFPXXXXXQPEQIIXQQPQQPFPLQPQQ

PSPQQPXXXQLPFPQPQQPFVXXXTXIGGQ, (SEQ ID NO: 310)
MKTLFILTILAMATTIATANMQVDPSGQVQWPQQQPFRQPQQPFYQQPQHTFPQPQQTFPHQPQQ

QFPQPQQPQQQFPQPQQPQQPFPQPQQAQLPFPQQPQQPFPQPQQPQQPFPQSQQPQQPFPQPQQ

PQQSFPQQQQPLIQPYLQQQMNPCKNYLLQQCNPVSLVSSLVSMILPRSDCQVMQQQCCQQLAQI

PRQLQCAAIHSVVHSIVMQQEQQQGIQILRPLFQLVQGQGIIQPQQPAQYEVIRSLVLRTLPNMC

NVYVRPDCSTINAPFASIVAGISGQ, (SEQ ID NO: 311)
MKTFIIFVLLAMAMNIASASRLLSPRGKELHTPQEQFPQQQQFXXXQLTQQQFPQPQQSPEQQQF

PQQQFPQQPPQQFPQQQFPIPYPPQQSQEPSPYQQYPQQQPSGSDVISISGL, (SEQ ID NO: 312)
MKTFIIFVLLAMAMNIASASRLLSPRGKELHTPQEQFPQQQQFPQPQQFPQQQIPQQHQIPQQPQ

QFPQQQQFQQQXXXXXXXQFXXQQQFPRPQQSPEQQQFPQQQFPQQPPQQFPQQQFPIPYPPQQS

QEPSPYQQYPQQQPSGSDVISISGL, (SEQ ID NO: 313)
MKTFLIFVLAMTMSIITTARQLNPSEQELQSPQQPVPKEQSYPQQPYPSHQPFPTPQQYSPYQPQ

QPFPQPQQPTPIQPQQPFPQQPQQPFPQPQQQLPLQPQQPFPQPQQPIPQQPQQSFPQQPQRPEQ

QFPQQPQQIIPQQTQQPFPLQPQQPFPQQPQRPFAQQPEQJISQQPFPLQPQQPFSQPQQPFPQQ

PGQIIPXQPQQPSPLQPQQPFSQQPQRPQQPFPQQPQQIIPQQPQQPFPLQPQQPVPQQPQRPFG

QQPEQIISQRPQQPFPLQPQQPFSQPQQPFPQQPGQIIPQQPQQPFPLQPQQPFPQQPEQIISQQ

PQQPFPLQPQQPSPQQPQLPFPQPQQPFVVVV,
or (SEQ ID NO: 314)
MKTFLIFVLAMTMSIITTARQLNPSEQELQSPQQPVPKEQSYPQQPYPSHQPFPTPQQYSPYQPQ

QPFPQPQQPTPIQPQQPFPQQPQQPFPQPQQQLPLQPQQPFPQPQQPIPQQPQQXFPQQQRPSXL

QPXQPXSQQPQRPQQPFPQQPQQIIPQQPQQPFPLQPQQPVPQQPQRPFGQQPEQIISQRPQQPF

PLQPQQPFSQPQQPFPQQPGQIIPQQPQQPFPLQPQQPFPQQPEQIIPQQPQQPFPLQPQQPSPQ

QPQLPFPQPQQPFVVVV, wherein, independently for each instance of glutamine, (Q), the one or more glutamines may be deamidated, i.e., Gln (Q) is replaced with Glu (E).

In one embodiment of a vaccine for inducing tolerance, the peptide antigen A is derived from an amino acid sequence derived from one or more specific regions of interest identified within any given allele. These regions of interest are partial amino acid sequences from alleles of gliadins, glutenins, prolamins, secalins and hordeins from wheat, durum wheat, spelt, rye, or barley. Regions of interest contain amino acid sequences with known T cell epitopes. The regions of interest for use as peptide antigens in vaccines for inducing tolerance for treating celiac disease include but are not limited to:

(SEQ ID NO: 315)
PYLQLQPFPQPQLPYPQPQPFRPQQPYPQPQPQYSQPQQPISQQ, (SEQ ID NO: 316)
YPSGQGSFQPSQQNPQAQGSVQPQQLPQFE, (SEQ ID NO: 317)
PYLQLQPFPQPQLPYPQPQLPYPQPQPFRPQQPYPQPQPQYSQPQQPISQQ, (SEQ ID NO: 318)
YPSGQGSFQPSQQNPQAQGSVQPQQLPQF, (SEQ ID NO: 319)
PYLQLQPFPQPQLPYPQPQLPYPQPQLPYPQPQPFRPQQPYPQSQPQYSQPQQPISQQ, (SEQ ID NO: 320)
YPSGQGSFQPSQQNPQAQGSVQPQQLPQF, (SEQ ID NO: 321)
PYMQLQPFPQPQLPYPQPQLPYPQPQPFRPQQSYPQPQPQYSQPQQPISQQ, (SEQ ID NO: 322)
QYPSGQGSFQPSQQNPQAQGSVQPQQLPQF, (SEQ ID NO: 323)
QYPSGQGSFQSSQQNPQAQGSVQPQQLPQF, (SEQ ID NO: 324)
PYLQLQPFPQPQLPYSQPQPFRPQQPYPQPQPQYSQPQQPISQQ, (SEQ ID NO: 325)
QYPLGQGSFRPSQQNPQAQGSVQPQQLPQF, (SEQ ID NO: 326)
QYPSSQVSFQPSQLNPQAQGSVQPQQLPQF, (SEQ ID NO: 327)
PWPQQQPFPQPHQPFSQQPQQTFPQPQQTFPHQPQQQFSQPQQPQQQFIQPQQPFPQQP

QQTYPQRPQQPFPQTQQPQQPFPQSQQPQQPFPQPQQQFPQPQQPQQSFPQQQPSLI, (SEQ ID NO: 328)
GQGTLVQGQGIIQPQQPAQLEVIRSLVLQT, (SEQ ID NO: 329)
FPQPQQPQQQFPQPQQPQQPFPQPQQAQLPFPQQPQQPFPQPQQPQQPFPQSQQPQQPFPQPQQP

QQSFPQQQQPLI, (SEQ ID NO: 330)
FPQPQQPQQQFPQPQQPQQPFPQPQQPQLPFPQQPQQPFPQPQQPQQPFPQSQQPQQPFP

QPQQQFPQPQQPQQSFPQQQPPLI, (SEQ ID NO: 331)
GQVQWPQQQPFPQPQQPFCQQPQRTIPQPH, (SEQ ID NO: 332)
QPQQQFPQTQQPQQPFPQPQQTFPQQPQLPFPQQPQQPFPQPQQPQQPFPQSQQPQQPFP

QPQQQFPQPQQPQQSFPQQQQPAI, (SEQ ID NO: 333)
GVPILRPLFQLAQGLGIIQPQQPAQLEGIRSLVLKT, (SEQ ID NO: 334)
GQVPWPQQQPFPQPHQPFSQQPQQTFP, (SEQ ID NO: 335)
FSQPQQPQQQFIQPQQPFPQQPQQTYPQRPQQPFPQTQQPQQPFPQSQQPQQPFPQPQQQ

FPQPQQPQQSFPQQQPSLI, (SEQ ID NO: 336)
GQGTLVQGQGIIQPQQPAQLEVIRSLVLQ, (SEQ ID NO: 337)
FPQQPQQPLPQPQQPQQPFPQSQQPQPQQPFPQPQQQFPQPQQPQQSIP,

-continued (SEQ ID NO: 338)
FPQPQQPQQQFLQPRQPFPQQPQQPYPQQPQQPFPQTQQPQQPFPQSKQPQQPFPQPQQPQQSFPQQQPSLI, (SEQ ID NO: 339)
GQGILVQGQGIIQPQQPAQLEVIRSLVLQ, (SEQ ID NO: 340)
FPRRPQQQFPQPQQPQQPFPQPQQPQLPFPQQPQQPFPQPQQPQQPFPQSQQPQQPFPQPQQQFPQPQQPQQSFPQQQQWMI, (SEQ ID NO: 341)
GVQILRPLFQLAQGLGIIQPQQPAQLEGIRSLVLK, (SEQ ID NO: 342)
DPSGQVQWPQQQPFPQPQQPFCEQPQRTIPQP, (SEQ ID NO: 343)
YPHQPQQQFPQTQQPQQPFPQPQQTFPQQPQLPFPQQPQQPFPQPQQPQQPFPQSQQPQQPFPQPQQQFPQPQQPQQSFPQQQQPAI, (SEQ ID NO: 344)
PQQPFPQPQQPFPWQPQQ, (SEQ ID NO: 345)
FPQPQQPQQPFPQPQQAQLPFPQQPQQPFPQPQQPQQPFPQSQQPQQPFPQPQQPQQSFPQQQQPI, (SEQ ID NO: 346)
QQPFISQSQQQFPQPQQPFPQQPQQPFPQSQQQCLQ, (SEQ ID NO: 347)
PFPQPPQQKYPEQPQQPFPWQQPTIQLYLQ, (SEQ ID NO: 348)
PQPQQPFPQPQQPFPQSQEQFP, (SEQ ID NO: 349)
LFPQSQQPQQPFPQPQQPFPQPQQPFPQSQEQFPQV, (SEQ ID NO: 350)
FPQPQQSSPLQPQQPFPQQSQQPFP, (SEQ ID NO: 351)
QSIPQPQQPFPQPQQPFPQSQEQFPQVHQP, (SEQ ID NO: 352)
PQPQQSSPLQPQQPFPQQSQQPFPQQPQQSSPQPQQPYPQQPFPQQPQQQPQQ, (SEQ ID NO: 353)
QSIPQPQQPFPQPQQPFPQSQEPFP, (SEQ ID NO: 354)
GQGQQPGQGQPGYYPTSPQQSGQGQQLGQGQQGQQPGQGQPGYYPTSPQQPGQG, (SEQ ID NO: 355)
GQGQPGYYPTSPQQPGQGQQPGQRQQPGQGKPGYYPTSPQQSGQGQQPGQGQSGYYPTSPQQPGQEQQPGQGQQVQQPGQGQQPGQGQQGYYPTSPQQSG, (SEQ ID NO: 356)
GQGQQGYYPTSPQQPGQGQQPGQGQQPGQGQPGYYPTSPQQPGQG, (SEQ ID NO: 357)
GQGQQGYYPTSPQQPGQGQLEYYPTSPQQPGQGQPGYYPTSPQLP, (SEQ ID NO: 358)
GQGQQGYYPTSPQQPGQGQQGHYPGSLQQPGQGQPGQRQQPGQGQQTGQGQQPEQEQQPGQGQQGYYPTSPQQPGQG, (SEQ ID NO: 359)
GQGQEGYYPTSPQQPGQG, (SEQ ID NO: 360)
QIGQWQQGYYPTSPQHPGQGQQPGQVQKIGQGQQPEKGQQLGQEQQIGQGQQPEQGQQPGQGQQGYYPTSPQQPGQG, -continued (SEQ ID NO: 361)
GQGQSGYYPTSPQQSGQE, (SEQ ID NO: 362)
GQGQLGYYPTSPQQSGQG, (SEQ ID NO: 363)
GQGQPGYYPTSPQQSGQGQPGYYPTSPQQSGQLQQPAQGQQPGQEQQGQQPGQGQQ
GQQPGQGQQPGQGQPGYYPTSPQQSGQEQQLEQWQQSGQGQPGHYPTSPLQPGQGQPGYYPTS
PQQIGQG, (SEQ ID NO: 364)
GQGQQGYYPTSPQQSGQGQQPGQWLQPGQWLQSGYYLTSPQQLGQGQQPRQWLQPR
QGQQGYYPTSPQQSGQGQQLGQGQQGYYPTSPQQSG (SEQ ID NO: 365)
GQGQQGYYPTSPQQPGQWQQPEQGQPGYYPTSPQQPGQ, (SEQ ID NO: 366)
GQGQSGYYPTSPQQPGQGQQPGQLQQPAQGQQPEQGQQGQQPGQGQQGQQPGQGQQPG
QGQPGYYPTSPQQSG, (SEQ ID NO: 367)
GQGQQGYYPTSPQQPGQWQQPEQGQPGYYPTSPQQPGQL, (SEQ ID NO: 368)
GQGQSGYYPTSPQQPGQGQQPGQLQQPAQGQQPEQGQQGQQPGQGQQGQQPGQGQQPG
QGQPGYYPTSPQQSGQG, (SEQ ID NO: 369)
GQGQHGYYPTSPQLSGQGQRPGQWLQPGQGQQGYYPTSPQQSGQG, (SEQ ID NO: 370)
GQGQQGYYPTSPQHPGQRQQPGQGQQIGQGQQLGQGRQIGQGQQSGQGQQGYYPTSPQQ
LGQG, (SEQ ID NO: 371)
GQGQQGYYPTSPQQPGQGKQLGQGQQGYYPTSPQQPGQG, (SEQ ID NO: 372)
GQGQQGYYPTSPQHTGQRQQPVQGQQIGQGQQPEQGQQPGQWQQGYYPTSPQQLGQ
G, (SEQ ID NO: 373)
GQGQQGYYPTSPQQPGQGQQLGQGQQGYYPTSPQQPG, (SEQ ID NO: 374)
GQGQQGYYPISPQQPGQWQQPGQGQQGYYPTSPQQPGQGQQGYYPTSPQQSGQGQQPGQGYY
PTXPQSPQQPGQWQQPGQGQQGYYPTSPQQPGQGQQGYYPTSPQQPGQWQQLGQGYYPTFPQ
QSGQGQQPGQGYYPTFPQQPGQGQQGYYPTSPQQSG, (SEQ ID NO: 375)
GQGQQGYYPTSPQQPGQGQQLGQGQQGYYPTSPQQPGQG, (SEQ ID NO: 376)
GQWQQGYYPTSPQHPGQG, (SEQ ID NO: 377)
EKGQQGYYPTTPQQPG, (SEQ ID NO: 378)
GQGQPGYYPTSPQQPGQGQQPGQEQQPGQRQQPGQGKPGYYPTSPQQSGQGQSGYYPTSP
QQPGQXQQPGQGQQVQQPGQGQQPGQGQQGYYPTSPQQSG, (SEQ ID NO: 379)
GQRQQGYYPTSPQQPGQG, (SEQ ID NO: 380)
GQGQQGYYPTSPQQSGQGQQPGQGQPGYYPTSPQQSGQ, -continued (SEQ ID NO: 381)
GQGQQGYYPTSPQQSGQGQQLGQGQPGYYPTSPQQSGQGQQSGQGQQGYYPTSPQQSGQG, (SEQ ID NO: 382)
QGQQGYYPTSPQQSGQGQQGYYPTSPQQSGQGQQGYYPTSPQQSGQGQQPGQGQQPR

QGQQGYYPISPQQSGQGQQPGQGQQGYYPTSPQQSGQG, (SEQ ID NO: 383)
QQQPYPQQPQPFPQQPIPQQPQPFPQQPQPFPQQ, (SEQ ID NO: 384)
PQQPIPQQPQPYPQQPQPYPQQPFQPQQPFPQQTIPQQPQPYPQQPQPYPQQ, (SEQ ID NO: 385)
QPFPQQPFPQQPQPYPQQPQPYPQQP, (SEQ ID NO: 386)
TIAQQQPFPQQPQQIPQQPQPYPQQPQPYPQQP, (SEQ ID NO: 387)
PIPQQPQPYPQQPQPFPQQPIPQQPQPYPQQPQPFPLQ, (SEQ ID NO: 388)
IAQQQPFPQQPQPYPQQPQPYPQQ, (SEQ ID NO: 389)
SQQQFPQPQQPFPQQPQQPFPQSQQ, (SEQ ID NO: 390)
PLPQQQPFPQQPQLPHQ, (SEQ ID NO: 391)
PQQPQLPFPQPQQPFVVV, (SEQ ID NO: 392)
PILSQQPPFSQQQQPVLPQQSP, (SEQ ID NO: 393)
QQPPFSQQQQSPESQQ, (SEQ ID NO: 394)
PQQPPFSQQQQPVLPPQ, (SEQ ID NO: 395)
LQQSPFSQQQQPVLPQQQPVIILQQPPFSQQQQPVLPQQPPFSQQQQQQQQQQPPFSQQQQPVLP

QQ, (SEQ ID NO: 396)
QQSPFSQQQQPVLPQQQPVIILQQPPFSQQQQPVLPQQPPFSQQQQQQQQQQPPESQQQ

QPVLPQ, (SEQ ID NO: 397)
QQPPFSQQQQPVLPQQPSFSQQQLPPFSQQQPPFSQQQQPVLPQQPPFSQQQQPILPQQ, (SEQ ID NO: 398)
QQPPFSQQQQPVLPQQPSFSQQQLPPFSQQQQPPFSQQQQPVLPQQPSFSQQQLPPFSQQLPPFSQ

QQQPVLPQQPPFSQQQLPPFSQQLPPFSQQQQPVLPQQPPFSQQQQQPILPQQPPESQQQQPVLLQ, (SEQ ID NO: 399)
QQSPFSQQQQPVLPQQQPVIILQQPPFSQQQQPVLPQQPPFSQQQQQQQQQQPPFSQQQQPVLPQ

Q
and (SEQ ID NO: 400)
QQPPFSQQQQPVLPQQPSFSQQQLPPFSQQQPPFSQQQQPVLPQQ, wherein, independently for each instance of glutamine, (Q), the one or more glutamines may be deamidated, i.e., Gln (Q) is replaced with Glu (E).

In some embodiments of the vaccine for inducing tolerance, the peptide antigen (A) contains the amidated or deamidated forms of known T cell epitopes for celiac disease. Amidated celiac disease associated T cell epitopes include but are not limited to the following: PFPQPQLPY (SEQ ID NO:401), PYPQPQLPY (SEQ ID NO:402), PQPQLPYPQ (SEQ ID NO:403), FRPQQPYPQ (SEQ ID NO:404), PQQSFPQQQ (SEQ ID NO:405), IQPQQPAQL (SEQ ID NO:406), QQPQQPYPQ (SEQ ID NO:407), SQPQQQFPQ (SEQ ID NO:408), PQPQQQFPQ (SEQ ID NO:409), QQPQQPFPQ (SEQ ID NO:410), PQPQQPFCQ (SEQ ID NO:411), LQPQQPFPQ (SEQ ID NO:412), QQPFPQQPQ (SEQ ID NO:413), PFPQPQQPF (SEQ ID NO:414), PQPQQPFPW (SEQ ID NO:415), PFSQQQQPV (SEQ ID NO:416), FSQQQQSPF (SEQ ID NO:417), PQPQQPFPQ (SEQ ID NO:418), PIPQQPQPY (SEQ ID NO:419), PYPQQPQPY (SEQ ID NO:420), PFPQQPQQI (SEQ ID NO:421), PYPQQQQPF (SEQ ID NO:422), PYPQQQQPI (SEQ ID NO:423), QGSVQPQQL (SEQ ID NO 424), QYSQPQQPI (SEQ ID NO:425), QGSFQPSQQ (SEQ ID NO:426) and QGYYPTSPQ (SEQ ID NO:427). Deamidated celiac disease associated T cell epitopes include but are not limited to the following: PFPQPELPY (SEQ ID NO:428), PYPQPELPY (SEQ ID NO:429), PQPELPYPQ (SEQ ID NO:430), FRPEQPYPQ (SEQ ID NO:431), PQQSFPEQQ (SEQ ID NO:432), IQPEQPAQL (SEQ ID NO:433), QQPEQPYPQ (SEQ ID NO:434), SQPEQEFPQ (SEQ ID NO:435), PQPEQEFPQ (SEQ ID NO:436), QQPEQPFPQ (SEQ ID NO:437), PQPEQPFCQ (SEQ ID NO:438), LQPEQPFPQ (SEQ ID NO:439), QQPFPEQPQ (SEQ ID NO:440), PFPQPEQPF (SEQ ID NO:441), PQPEQPFPW (SEQ ID NO:442), PFSEQEQPV (SEQ ID NO:443), FSQQQESPF (SEQ ID NO:444), PQPEQPFPQ (SEQ ID NO:445), PIPEQPQPY (SEQ ID NO:446), PYPEQPQPY (SEQ ID NO:447), PFPEQPEQI (SEQ ID NO:448), PYPEQEEPF (SEQ ID NO:449), PYPEQEQPF (SEQ ID NO:450), PYPEQEQPI (SEQ ID NO:451), QYSQPEQPI (SEQ ID NO:452), EGSFQPSQE (SEQ ID NO:453), EQPQQPFPQ (SEQ ID NO:454), EQPQQPYPE (SEQ ID NO:455), and PQQSFPEQE (SEQ ID NO:456).

In some embodiments of the vaccine for inducing tolerance for treating celiac disease, peptide antigen(s) (A) comprise amino acid sequences flanking the known deamidated T cell epitopes contained within each peptide conjugate. In general, leading and trailing amino acid sequences affect the binding of any peptide epitope to MHC. Here, three N-terminal leading (−3) and C-terminal trailing (+3) amino acids for each known deamidated T cell epitope are chosen based on peptide sequence analysis. These embodiments may include a +3 amino acid sequence reflecting the most highly represented or a lower frequency +3 leading amino acid sequence for each specific known deamidated T cell epitope reflected by peptide sequence analysis. These embodiments may include a −3 amino acid sequence reflecting the most highly represented or a lower frequency −3 trailing amino acid sequence for each specific known deamidated T cell epitope reflected by peptide sequence analysis. This embodiment includes known deamidated T cell epitope sequences included in the tolerance vaccine peptide antigen sequences flanked by leading and trailing amino acids selected from the following: QLQPFPQPELPYPQP (SEQ ID NO: 457), PQLPYPQPELPYPQP (SEQ ID NO:458), QPFPQPELPYPQPQL (SEQ ID NO:459), LPYPQPELPYPQPQP (SEQ ID NO:460), PQP-FRPEQPYPQPQP (SEQ ID NO:461), PQQPQQSFPEQQPPL (SEQ ID NO:462), PQQPQQSFPEQQPPF (SEQ ID NO:463), QGIIQPEQPAQLEVI (SEQ ID NO:464), PFPQQPEQPYPQQPE (SEQ ID NO:465), QQFSQPEQEFPQPQQ (SEQ ID NO:466), QPFPQPEQEFPQPQQ (SEQ ID NO:467), PQPQQPEQPFPQPEQ (SEQ ID NO:468), PYPQQPEQPFPQPQQ (SEQ ID NO:469), QPFPQPEQPFCQQPQ (SEQ ID NO:470), QPFLQPEQPFPQQPQ (SEQ ID NO:471), SSPLQPEQPFPQQPE (SEQ ID NO:472), PTPLQPEQPFPQQPQ (SEQ ID NO:473), QQPQQPFPEQPQQPF (SEQ ID NO:474), PEQPFPQPEQPFPQS (SEQ ID NO:475), PQQPFPQPEQPFPWQ (SEQ ID NO:476), PQQPFPQPEQPFCQQ (SEQ ID NO:477), QPFPQPEQPFPWQPQ (SEQ ID NO:478), QSIPQPEQPFPQPEQ (SEQ ID NO:479), QPFPQPEQPFPQSQE (SEQ ID NO:480), PQQPIPEQPQPYPEQ (SEQ ID NO:481), QPQPYPEQPQPYPQQ (SEQ ID NO:482), PQQPFPEQPEQIIPQ (SEQ ID NO:483), QQPPFSE-QEQPVLPQ (SEQ ID NO:484), or QPPFSQQQESPFSQQ (SEQ ID NO:485), wherein, independently for each instance of glutamine, (Q), the one or more glutamines may be deamidated, i.e., Gln (Q) is replaced with Glu (E).

In one embodiment, one or more peptide antigen (A) sequence is derived from one or more regions of interest wherein zero, one, or multiple specific Q residues are replaced with E. These replacements reflect the conversion to pathogenic T cell epitopes resulting from in vivo deamidase activity associated with celiac disease.

In preferred embodiments the peptide antigen (A) includes any amino acid sequence between 5 and 100 amino acids selected from the celiac disease associated protein sequence, or any deamidated form thereof. In more preferred embodiments these peptide antigens (A) are 7-45 amino acids in length.

In some embodiments, the vaccine for inducing tolerance for treating celiac disease comprises peptide antigens (A) selected from QLQPFPQPELPYPQPQLPYPQPQPFR (SEQ ID NO:486), PQLPYPQPELPYPQPQP-FRPEQPYPQPQP (SEQ ID NO:487), QGIIQPEQPAQLEVI (SEQ ID NO: 464), PQPQQPEQPFPQPEQEFPQPQQPQQSFPEQQPPL (SEQ ID NO:488), PQQPFPQPEQPFCQQPQ (SEQ ID NO: 489), QQFLQPEQPFPQQPEQPYPQQPEQPFPQPQQ (SEQ ID NO: 490), QQFSQPEQEFPQPQQPQQSFPEQQPPF (SEQ ID NO:491), PTPLQPEQPFPQQPQQPQQPFPQPEQPFPWQPQ (SEQ ID NO:492), SSPLQPEQPFPQQPQQPFPEQPQQPQ (SEQ ID NO:493), QSIPQPEQPFPQPEQPFPQSQE (SEQ ID NO: 494), PQQPFPQQPQQIIPQ (SEQ ID NO:495), PQQPIPEQPQPYPEQPQPYPQQ (SEQ ID NO: 496), QQPPFSEQEQPVLPQ (SEQ ID NO:484), QPPFSQQQESPFSQQ (SEQ ID NO:485) and PQQPFPQPEQPFBQQPQ (SEQ ID NO: 497), wherein, independently for each instance of glutamine, (Q), the one or more glutamines may be deamidated, i.e., Gln (Q) is replaced with Glu (E).

In some embodiments, a vaccine for inducing tolerance for preventing or treating diabetes may comprise peptide antigens derived from proteins found in beta islet cells, including but not limited chromogranin and insulin.

In some embodiments, a vaccine for inducing tolerance for preventing or treating neuromyelitis optica may comprise peptide antigens derived from aquaporin-4.

In some embodiments, a vaccine for inducing tolerance for preventing or treating vitiligo may comprise peptide antigens derived from gp100 (pmel), tyrosinase, TRP1, TRP2, MART1 or MHCR1.

Vaccines for inducing tolerance can be used for preventing or treating transplant rejection. Non-limiting examples of transplants include both allogeneic and xenogeneic transplants of any organ, including skin, heart, lungs, liver and kidneys. In preferred embodiments of the vaccine for preventing or treating transplant rejection, the vaccine comprises antigens derives from major and minor histocompatibility antigens from the host from which the transplanted organ is derived.

Vaccines for inducing tolerance may also be used for preventing or treating allergies. Non-limiting examples of allergies include food allergies, such as tree nut allergies, soy allergy, shellfish allergy, tree pollens allergy, milk allergy, soy allergy, eggs allergy, wheat allergy, peanut allergy. In preferred embodiments of the vaccine for preventing or treating allergies, the vaccine comprises fragments of the antigen(s) that cause the allergy.

Those skilled in the art recognize that any peptide, protein or post-translationally modified protein (e.g., glycoprotein) that leads to an immune response and is useful in the prevention or treatment of a disease can be selected for use as a peptide antigen (A) for use in the immunogenic compositions of the present invention.

Molar Ratio of Peptide Antigen Conjugate to Amphiphile

In certain embodiments of immunogenic compositions comprising vaccines that further comprise one or more peptide antigen conjugates of formula PEG-[E1]-A-[E2]-[U]-H and/or H-[E1]-A-[E2]—[U]-PEG an amphiphile of formula S-[B]-[U]-H is present; in other embodiments of the vaccine, the amphiphile is absent and the vaccine comprise one or more peptide antigen conjugates of formula PEG-[E1]-A-[E2]-[U]-H and/or H-[E1]-A-[E2]—[U]-PEG.

In general, the amphiphile is included if the vaccine comprising one or more peptide antigen conjugates of formula PEG-[E1]-A-[E2]-[U]-H and/or H-[E1]-A-[E2]—[U]-PEG at total peptide antigen conjugate concentrations ≥0.5 mM, or ≥1 mM, in an aqueous solution (e.g., formulation buffer such as buffered normal saline or PBS) with no more than 20% organic solvent (e.g., DMSO) exhibits a tendency to aggregate after 24 hours at room temperature as evidenced by average hydrodynamic diameter ≥50 nm diameter, turbidity (OD at 490 nm)>0.1, direct evidence of aggregation by visual inspection or >10% loss after sterile filtration through 0.2 micron filters. Additional tests to determine whether to include the amphiphile may be based on:

Average GRAVY score: For a vaccine comprising one or more peptide antigen conjugates, if the average GRAVY score of the peptide antigens is ≤0 then the amphiphile is not included; whereas if the average GRAVY score of the peptide antigens is >then 0 then the peptide antigen conjugates may exhibit a tendency to aggregate an therefore the amphiphile is generally included.

Solubility in aqueous solutions at pH between 6 to 8 or 5.5 to 8.5: for a vaccine comprising one or more peptide antigen conjugates, if the average peptide antigen solubility in aqueous solution at pH between 6 to 8 or pH between 5.5 to 8.5 is >1 mg/mL then the amphiphile is not included; whereas for a vaccine comprising one or more peptide antigen conjugates, if the average peptide antigen solubility in aqueous solution at pH between 6 to 8 or pH between 5.5 to 8.5 is <1 mg/mL then the amphiphile is included.

The above algorithm for electing to use or exclude an amphiphile is based on the unexpected findings that vaccines comprising amphiphiles and total peptide antigen conjugates at concentrations ≥0.5 mM in aqueous solutions exhibit a tendency to undergo non-covalent cross-linking and can form hydrogels that can be detrimental to manufacturing. An unexpected finding was that the cross-linking and hydrogel formation were less likely to occur when the amphiphile was absent. However, for vaccines comprising peptide antigen conjugates that (i) exhibit a tendency to aggregate after 24 hours at room temperature when total peptide antigen conjugate concentrations are ≥0.5 mM, or ≥1 mM, in an aqueous solution (e.g., formulation buffer such as buffered normal saline or PBS) with no more than 20% organic solvent (e.g., DMSO); and/or comprise peptide antigens that (ii) have average GRAVY score >0 and/or (iii) have average solubility in aqueous solution less than 1.0 mg/mL in at pH between 6 to 8 or pH between 5.5 to 8.5, removing the amphiphile was observed to lead to a tendency of the peptide antigen conjugates to aggregate. Therefore, based on these unexpected findings, the amphiphile is included if any of (i), (ii) or (iii) conditions are met, and the amphiphile is excluded if (i), (ii) and (iii) are not met.

In preferred embodiments of immunogenic compositions comprising vaccines, the vaccines comprise particles that further comprise one or more peptide antigen conjugates (e.g., PEG-[E1]-A-[E2]—[U]-H) and an amphiphile (e.g., S-[B]-[U]-H). In certain preferred embodiments of immunogenic compositions comprising vaccines, the amphiphile is absent and the vaccine comprise particles that further comprise one or more peptide antigen conjugates (e.g., PEG-[E1]-A-[E2]-[U]-H), The amphiphile includes a solubilizing block(S) that functions to stabilize particles and account for hydrophobic properties of some peptide antigens (A). However, the molar ratio of the peptide antigen conjugate to amphiphile was found to affect the stability and hydrodynamic behavior of particles comprising peptide antigen conjugates and amphiphiles. Accordingly, total peptide antigen conjugate to amphiphile molar ratios of between about 4:1 to 1:1,000 were found to be generally well-tolerated. While higher proportions of amphiphiles tended to result in improved particle stability, there was an inverse relationship between amphiphile percent molar amount and immunogenicity, with higher amphiphile proportions generally leading to lower immunogenicity, possibly due to relatively lower peptide antigen (A) loading in particles. Additionally, increasing the amphiphile too much also resulted in a propensity for non-covalent cross-linking to occur. Therefore, the amphiphile proportion should be tuned to ensure particle stability without sacrificing biological activity. Thus, in preferred embodiments of the vaccine that comprise an amphiphile, the peptide antigen conjugate to amphiphile molar ratio is typically selected from between about 4:1 to about 1:20, such as 4:1, 3:1, 2:1, 1:1, 1:2, 1:3, 1:4, 1:5, 1:6, 1:7, 1:8, 1:9, 1:10, 1:11, 1:12, 1:13, 1:14, 1:15, 1:16, 1:17, 1:18, 1:19, 1:20, though more preferably between about 2:1 to about 1:4, such as about 1:1.

For vaccines comprising peptide antigen conjugates with average GRAVY scores that are moderate, or high, e.g., GRAVY ≥0, or ≥1, respectively, the molar ratio of peptide antigen conjugate to amphiphile should generally be higher, such as between 2:1 to about 1:20, or more preferably about 1:1 to about 1:20, such as 1:1 to about 1:4. However, the net charge of the peptide antigen conjugate also contributes to particle stability and affects the amount of amphiphile that may be needed. For instance, for vaccines comprising peptide antigen conjugates with average net charge greater than or equal to +3 or less than or equal to −3, less amphiphile may be required to form nanoparticles of stable size. For such compositions, the molar ratio of peptide antigen conjugate to amphiphile is preferably between about 4:1 to about 1:4, more preferably between about 3:1 to 1:3 or between about 2:1 to 1:2, most preferably 1:1.

Immunomodulatory Drug Molecules (D) for Use in Vaccine Compositions

Preferred compositions of vaccines include one or more immunomodulatory drug molecules selected from immunostimulants and/or immunosuppressants.

The selection of the immunomodulatory drug molecules for use in vaccines depends on the application. For compositions of vaccines for treating or preventing cancer ("cancer vaccines"), the one or more immunomodulatory drug molecules are typically selected from immunostimulants, more preferably immunostimulants that induce Type-I IFNs, including agonists of TLR-3, TLR-7, TLR-8, TLR-9, RLR and STING. For compositions of vaccines for treating or preventing infectious diseases ("infectious disease vaccines"), the one or more immunomodulatory drug molecules are typically selected from immunostimulants that induce proinflammatory cytokines and/or Type-I IFNs, including agonists of TLR-1, TLR-2, TLR-3, TLR-4, TLR-5, TLR-6, TLR-7, TLR-8, TLR-9, CLRs, NLRs or combinations thereof. For compositions of vaccines for inducing tolerance to treat allergies or autoimmune diseases, the one or more immunomodulatory drug molecules are typically selected from immunosuppressants such as Treg promoting immunomodulators (defined below) or a combination of Treg promoting immunomodulators and immunostimulants selected from agonists of TLR-1, TLR-2, TLR-3, TLR-4, TLR-5, TLR-6, TLR-7, TLR-8, TLR-9, CLRs, NLRs or combinations thereof. Preferred compositions and combinations of specific immunomodulatory drugs are described in greater detail in later sections.

Compositions of immunostimulants suitable for use in vaccines are typically selected from PRR agonists. Non-limiting examples of pattern recognition receptor (PRR) agonists include TLR-1/2/6 agonists (e.g., lipopeptides and glycolipids, such as Pam2cys or Pam3cys lipopeptides); TLR-3 agonists (e.g., dsRNA, such as PolyI:C, and nucleotide base analogs); TLR-4 agonists (e.g., lipopolysaccharide (LPS) derivatives, for example, monophosphoryl lipid A (MPL) and small molecule derivatives or analogs of pyrimidoindole); TLR-5 agonists (e.g., Flagellin); TLR-7 &-8 agonists (e.g., ssRNA and nucleotide base analogs, including derivatives of imidazoquinolines, hydroxy-adenine, 180eadenylate180ridine and loxoribine); and TLR-9 agonists (e.g., unmethylated CpG); Stimulator of Interferon Genes (STING) agonists (e.g., cyclic dinucleotides, such as cyclic 180eadenylate monophosphate and diABZI or derivatives thereof); C-type lectin receptor (CLR) agonists (such as various mono, di, tri and polymeric sugars that can be linear or branched, e.g., mannose, Lewis-X trisaccharides, etc.); RIG-I-like receptor (RLR) agonists; NOD-like receptor (NLR) agonists (such as peptidogylcans and structural motifs from bacteria, e.g., meso-diaminopimelic acid and muramyl dipeptide); and combinations thereof. In some embodiments, the immunostimulant selected for use in a vaccine is selected from inorganic salts, including aluminum salts and or oils, such as squalene and its derivatives (e.g., MF59 and the like).

In several embodiments of the vaccine, the vaccine comprises an immunostimulant selected from a TLR agonist, such as an imidazoquinoline-based TLR-7/8 agonist. For example, the immunostimulant can be Imiquimod (R2137) or Resiquimod (R2148), which are approved by the FDA for human use for certain indications and uses.

In several embodiments of the vaccine, the vaccine comprises a TLR-7 agonist, a TLR-8 agonist and/or a TLR-7/8 agonist. Numerous such agonists are known, including many different imidazoquinoline compounds.

Imidazoquinolines are of use in the methods disclosed herein. Imidazoquinolines are synthetic immunomodulatory drugs that act by binding Toll-like receptors −7 and/or −8 (TLR-7/TLR-8) on antigen presenting cells (e.g., dendritic cells), structurally mimicking these receptors' natural ligand, viral single-stranded RNA. Imidazoquinolines are heterocyclic compounds comprising a fused quinoline-imidazole skeleton. Derivatives, salts (including hydrates, solvates, and N-oxides), and prodrugs thereof also are contemplated by the present disclosure. Particular imidazoquinoline compounds are known in the art, see for example, U.S. Pat. Nos. 6,518,265; and 4,689,338. In some non-limiting embodiments, the imidazoquinoline compound is not imiquimod or resiquimod.

In some embodiments, the immunostimulant is a small molecule having a 2-aminopyridine fused to a five membered nitrogen-containing heterocyclic ring, including but not limited to imidazoquinoline amines and substituted imidazoquinoline amines such as, for example, amide substituted imidazoquinoline amines, sulfonamide substituted imidazoquinoline amines, urea substituted imidazoquinoline amines, aryl ether substituted imidazoquinoline amines, heterocyclic ether substituted imidazoquinoline amines, amido ether substituted imidazoquinoline amines, sulfonamido ether substituted imidazoquinoline amines, urea substituted imidazoquinoline ethers, thioether substituted imidazoquinoline amines, hydroxylamine substituted imidazoquinoline amines, oxime substituted imidazoquinoline amines, 6-, 7-, 8-, or 9-aryl, heteroaryl, aryloxy or arylalkyleneoxy substituted imidazoquinoline amines, and imidazoquinoline diamines; tetrahydroimidazoquinoline amines including but not limited to amide substituted tetrahydroimidazoquinoline amines, sulfonamide substituted tetrahydroimidazoquinoline amines, urea substituted tetrahydroimidazoquinoline amines, aryl ether substituted tetrahydroimidazoquinoline amines, heterocyclic ether substituted tetrahydroimidazoquinoline amines, amido ether substituted tetrahydroimidazoquinoline amines, sulfonamido ether substituted tetrahydroimidazoquinoline amines, urea substituted tetrahydroimidazoquinoline ethers, thioether substituted tetrahydroimidazoquinoline amines, hydroxylamine substituted tetrahydroimidazoquinoline amines, oxime substituted tetrahydroimidazoquinoline amines, and tetrahydroimidazoquinoline diamines; imidazopyridine amines including but not limited to amide substituted imidazopyridine amines, sulfonamide substituted imidazopyridine amines, urea substituted imidazopyridine amines, aryl ether substituted imidazopyridine amines, heterocyclic ether substituted imidazopyridine amines, amido ether substituted imidazopyridine amines, sulfonamido ether substituted imidazopyridine amines, urea substituted imidazopyridine ethers, and thioether substituted imidazopyridine amines; 1,2-bridged imidazoquinoline amines; 6,7-fused cycloalkylimidazopyridine amines; imidazonaphthyridine amines; tetrahydroimidazonaphthyridine amines; oxazoloquinoline amines; thiazoloquinoline amines; oxazolopyridine amines; thiazolopyridine amines; oxazolonaphthyridine amines; thiazolonaphthyridine amines; pyrazolopyridine amines; pyrazoloquinoline amines; tetrahydropyrazoloquinoline amines;

pyrazolonaphthyridine amines; tetrahydropyrazolonaphthyridine amines; and 1H-imidazo dimers fused to pyridine amines, quinoline amines, tetrahydroquinoline amines, naphthyridine amines, or tetrahydronaphthyridine amines.

In some embodiments, the immunostimulant is an imidazoquinoline with the formula:

Formula IV

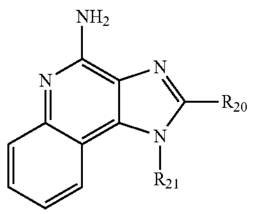

In Formula IV, $R^{20}$ is selected from one of hydrogen, optionally-substituted lower alkyl, or optionally-substituted lower ether; and $R^{21}$ is selected from one of optionally substituted arylamine, or optionally substituted lower alkylamine. $R^{21}$ may be optionally substituted to a linker that links to a polymer. An unexpected finding was that in some compounds wherein $R^{21}$ was selected from a lower alkylamine, while the compound was less potent than $R^{21}$ selected from an arylamine, the quality of response was improved. Thus, moderate potency Adjuvants of Formula IV led to better quality responses. Note: Adjuvant(s) of Formula IV are a type of Ligand and may be referred to as Adjuvants of Formula IV or Ligands with adjuvant properties.

In some embodiments, the $R^{20}$ included in Formula IV can be selected from hydrogen,

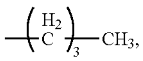 or 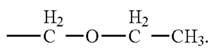

In some embodiments, $R^{21}$ can be selected from,

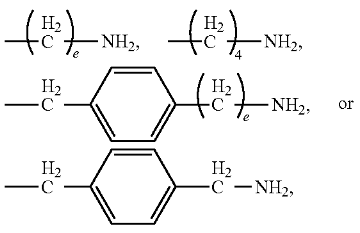

wherein e denotes the number of methylene unites is an integer from 1 to 4.

In some embodiments, $R^{21}$ can be

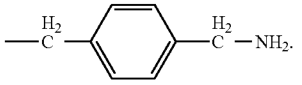

In some embodiments, $R^{21}$ can be

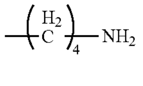

In some embodiments, $R^{20}$ can be

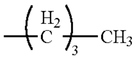

and $R^{21}$ can be

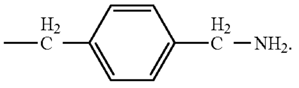

In some embodiments, at least one D is

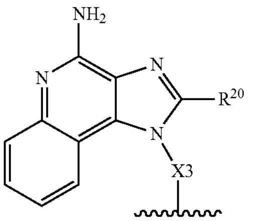

wherein $R^{20}$ is selected from H, alkyl, alkoxyalkyl, aryl, heteroaryl, aminoalkyl, amide and ester; and X3 is selected from alkyl, alkoxyalkyl, aralkyl, heteroaralkyl, aryl, heteroaryl and carboxy.

In some embodiments, wherein, $R^{20}$ is selected from H, alkyl and alkoxyalkyl; and X3 is selected from alkyl and aralkyl. In other embodiments, $R^{20}$ is butyl.

In some embodiments, X3 is alkyl.

In preferred embodiments of the vaccine, the vaccine comprises nanoparticles further comprising amphiphiles, one or more peptide antigen conjugates and immunomodulatory drug molecules. In such embodiments, the immunomodulatory drug molecules may be incorporated into the nanoparticles through any suitable means.

In some embodiments, immunomodulatory drugs molecules that are hydrophobic and/or amphiphilic are incorporated into the nanoparticles comprising amphiphiles and one or more peptide antigen conjugates through non-covalent interactions, such as hydrophobic interactions with the hydrophobic blocks comprising the core of the nanoparticles. Non-limiting examples include, squalene-based immunostimulants; lipid-based PRR agonists, such as mincle receptor agonists (e.g., trehalose dimycolate and trehalose dibehenate) lipopolysaccharide-based agonists of TLR-4, and lipopeptide-based agonists of TLR-1/2 and TLR-2/6; heteroaryl-based agonists of TLR-4 (e.g., pyrimidoindole); agonists of TLR-7/8 (e.g., imidazoquinolines and benzonaphthyridines) and STING (e.g., diABZI); and various hydrophobic immunosuppressants, including but not limited to certain inhibitors of mTOR/PI3K/AKT (e.g., KU-0062794, Torin 1, Torin 2, etc.), CDK8/19 (e.g., Cortistatin), retinoic acid-related orphan gamma t (RORγt) (e.g., SR1555) and histone deacetylase (HDACs) (e.g., TMP269), as well as certain agonists of aryl hydrocarbon receptors (AHR) (e.g., indole, indolo[3,2-b]carbazole (ICZ) and 3,3 diindolomethane), retinoic acid receptors (RAR) (e.g., all-trans retinoic acid, TTNPB (cas: 71441-28-6), AM580, BMS753, BMS961 and the like) and adenosine receptor (e.g., UK-432,097).

In some embodiments, immunomodulatory drugs molecules are linked to hydrophobic blocks to form drug molecule conjugates that are incorporated into nanoparticles comprising amphiphiles and one or more peptide antigen conjugates through non-covalent interactions. In still other embodiments, immunomodulatory drugs molecules are incorporated into the nanoparticles comprising amphiphiles and one or more peptide antigen conjugates through covalent attachment to the amphiphiles and/or peptide antigen conjugates. In preferred embodiments of the vaccine for cancer and infectious diseases, the vaccines comprise nanoparticles that comprise amphiphiles, one or more peptide antigen conjugates and immunostimulants selected from imidazoquinolines, wherein the imidazoquinolines are linked to the hydrophobic blocks of the amphiphiles and/or peptide antigen conjugates. Preferred compositions of vaccines are described in greater detail elsewhere.

Compositions of Amphiphiles and Peptide Antigen Conjugates for Use in Vaccines

In preferred embodiments of the vaccine, the vaccine comprises nanoparticles comprising one or more peptide antigen conjugates. In some embodiments, the vaccine further comprises an amphiphile and/or one or more immunomodulatory drug molecules.

The one or more peptide antigen conjugates included in vaccine compositions are selected to ensure that an adequate immune response can be induced in each subject. In preferred embodiments, vaccines typically include up to about 40 peptide antigens conjugates each comprising a unique antigen composition, though, typically no more than about 100 unique peptide antigen conjugates. Each peptide antigen conjugate comprises a unique peptide antigen (A) that comprises one or more known or predicted T cell epitopes (e.g., CD4 and/or CD8 T cell epitopes) and/or B cell epitopes. In general, vaccines for cancer treatment ("cancer vaccines") include peptide antigen conjugates further comprising antigens with CD4 and/or CD8 T cell epitopes derived from tumor or viral antigens; vaccines for inducing tolerance ("tolerance vaccines") include peptide antigen conjugates further comprising antigens with CD4 and/or CD8 T cell epitopes derived from autoantigens, alloantigens or allergens. Additionally, in preferred compositions of cancer vaccines, the vaccine typically comprises cancer at least one or more additional peptide antigen conjugates comprising antigens selected from infectious disease antigens (e.g. flu antigens) and/or non-natural CD4 helper peptides, such as PADRE (e.g., AKFVAAWTLKAAA and related peptide sequences, e.g., wherein F is replaced with cyclohexylalanine), which function to enhance the response by inducing CD4 T cell responses. A more detailed process for selecting antigens to include in peptide antigen conjugates, including the appropriate length and chemical composition is described in greater detail elsewhere.

In some embodiments of the vaccine, the one or more peptide antigen conjugates comprise a PEG and have the formula PEG-[E1]-A-[E2]-[U]-H-[D] or [D]-H-[U]-[E1]-A-[E2]-PEG), wherein the PEG may function to improve solubility of the peptide antigen conjugate during manufacturing and/or to promote nanoparticle micellization when solubilized in an aqueous solution.

In some embodiments of the vaccine, the one or more peptide antigen conjugates comprise an N-terminal and/or C-terminal extension. In preferred compositions of vaccines, an extension is included between the hydrophobic block and the antigen, either directly or via a linker, e.g., PEG-[E1]-A-E2-[U]—H-[D] or [D]-H-[U]-E1-A-[E2]-PEG, and an extension is typically included between the PEG and antigen, e.g., PEG-E1-A-[E2]-[U]-H-[D] or [D]-H-[U]-[E1]-A-E2-PEG. Preferred compositions and uses of extensions are described in greater detail elsewhere.

Peptide antigen conjugates may be manufactured by any suitable means. Typically, peptide antigen conjugates are either manufactured entirely on-resin by solid-phase peptide synthesis (SPPS) or are manufactured by convergent assembly of a peptide antigen fragment produced by SPPS and a hydrophobic block fragment, wherein the coupling of the peptide antigen fragment and hydrophobic block fragment may occur in solution or on-resin. The preference for the manufacturing process typically depends on the composition of the hydrophobic block. For instance, wherein the hydrophobic block of the peptide antigen conjugate comprises amino acids selected from tryptophan (and any analogs or derivatives thereof), para-aminophenylalanine, glutamic acid (any derivatives thereof), lysine or ornithine (and any derivatives thereof) and the like, the peptide antigen conjugate is typically produced entirely by SPPS. Wherein the hydrophobic block comprises drug molecules, particularly drug molecules that are of relatively high cost (relative to standard amino acid costs), the peptide antigen conjugate is typically manufactured by convergent assembly of two separately produced components (i.e., PEG-[E1]-A-[E2]-U1+U2-H-[D]) using linker chemistries described in greater detail elsewhere.

The incorporation of peptide antigen conjugates in nanoparticles of uniform size and composition is critical to ensuring consistent manufacturing and reliable induction of immune responses in subjects. The inventors of the present disclosure previously reported (see: Lynn et al. Nat. Biotech. 2020) that incorporation of one or more charged amino acid residues (referred to as charge-modifying groups) directly or indirectly via an extension to peptide antigens linked to hydrophobic blocks resulted in amphiphilic peptide antigen conjugates that self-assembled into uniform nanoparticle micelles if the peptide antigen conjugate had appropriate net charge. Potential limitations of this approach (i.e., incorporating a solubilizing block onto each peptide antigen conjugate) are that it is generally preferred to manufacture charge-modifying groups onto each antigen during SPPS to reduce manufacturing complexity and costs, but the reliance on SPPS for introducing the SPPS can limit the scope of chemical compositions that are practicable. For instance, it was found that net positive charge-modifying groups based on lysine, but not net negative charge-modifying groups based on glutamic acid, aspartic acid, or phosphoserine, could be readily incorporated into any peptide antigen during manufacturing by SPPS, thus limiting the scope of potential charge-modifying groups that could be practically utilized.

The authors of the present disclosure synthesized and evaluated amphiphiles of formula S-[B]—[U]-H-[D] with varying architecture (linear, cone and brush), charge (net positive, net negative or net neutral charge), chemical composition and size (e.g., length of linear polymers or oligomers, or generation of dendrons) and evaluated how various properties of the amphiphile combined with one or more peptide antigen conjugates (at a range of molar ratios of amphiphile to peptide antigen conjugate) impact hydrodynamic behavior and immunogenicity in vivo.

Peptide antigen conjugates admixed with amphiphiles with linear and cone (or "dendron") architecture formed stable nanoparticle micelles with greater consistency and with up to higher peptide antigen conjugate to amphiphile ratios as compared with amphiphiles having brush architecture, provided that the amphiphiles with linear architecture had net charge ≥+4 or net charge ≤−4, or contained at least two or more sugar molecules, preferably between 2 to 8 or more sugar molecules (i.e., 2 to 8 or more monosacahrides as either individual monosaccharides or more complex structures, e.g., 1 to 4 or more disaccharides). In contrast to the amphiphiles with linear architecture requiring net positive or net negative charge, or high sugar molecule content, the amphiphiles with cone architecture were found to form stable nanoparticle micelles independent of charge, i.e., stable nanoparticle formation was observed with amphiphiles with cone architecture having net positive, net negative and neutral charge at ratios of peptide antigen conjugate to amphiphile ranging from 4:1 to 1:1,000, though, higher ratios (i.e., greater proportions of peptide antigen conjugate) could be achieved when the peptide antigen conjugates had average net charge greater than or equal to +6 or less than or equal to −6.

Importantly, the ability of dendrons to enable nanoparticle micellization independent of net charge allowed for a thorough investigation of how different solubilizing groups impact vaccine formulation properties as well as biological activity. Accordingly, amphiphiles with cone architecture generally required up to 4 or more solubilizing groups, (e.g., saccharides, amines, carboxylic acids or hydroxyls) to ensure stable nanoparticle formation when combined with peptide antigen conjugates at molar ratios of 4:1 or less of peptide antigen conjugate to amphiphile. Thus, in preferred embodiments of amphiphiles with cone architecture, the amphiphile comprises 4 or more solubilizing groups, though, typically no more than 16 or 32 solubilizing groups per amphiphile. While amphiphiles having cone architecture and 4 or more solubilizing groups generally formed stable nanoparticle micelles with high ratios of peptide antigen conjugate to amphiphile, the specific chemical composition of the dendron amplifier, spacer and hydrophobic block also had an impact on hydrodynamic behavior. Accordingly, generation 2 to 4 PEG-based dendron amplifiers and PEG-based spacers (B) with between 4 to 36 monomeric units were found to lead to more uniform nanoparticle compositions as compared with amphiphiles with cone architecture comprising similar generation and length of peptide-based amplifying linkers and peptide-based spacers, respectively. Moreover, vaccines comprising amphiphiles with PEG-based spacers (B) with greater than 48 monomeric units tended to lead to less stable nanoparticle micelles and reduced immunogenicity than vaccines comprising amphihiles with short PEG-spacers. However, the spacer length selected for the amphiphile also impacted the capacity of the amphiphile to prevent hemolysis when the vaccine composition further comprised peptide antigen conjugates with average net positive charge. Accordingly, amphiphiles with PEG spacers greater than or equal to 12 monomeric units were found to mitigate hemolysis more effectively than amphiphiles with shorter spacers.

In preferred embodiments of the vaccine, the amphiphile is absent and the vaccine comprises one or more, typically between 1 to 40, peptide antigen conjugates of formula PEG-[E1]-A-[E2]-[U]-H-[D] or [D]-H-[U]-[E1]-A-[E2]-PEG. In certain preferred embodiments of the vaccine, the vaccine comprises one or more, typically between 1 to 40, peptide antigen conjugates of formula PEG-[E1]-A-[E2]-[U]-H-[D] or [D]-H-[U]-[E1]-A-[E2]-PEG and an amphiphile of formula S-B-[U]-H-[D] with cone architecture, wherein the amphiphile with cone architecture further comprises a solubilizing block comprising a PEG-based dendron with between 4 to 16 solubilizing groups and a PEG-based spacer with between 4 and 48 monomer units, more preferably 4 to 36 monomer units, most preferably 24 monomers units, additionally wherein the solubilizing groups comprise sugar molecules, carboxylic acids, amines and/or hydroxyls, and the hydrophobic block comprises a poly(amino acid) of Formula I. A non-limiting example is provided here for clarity:

(PEG—[E1]—A—[E2]—[U]—H—[D])$_{1\ to\ 40}$

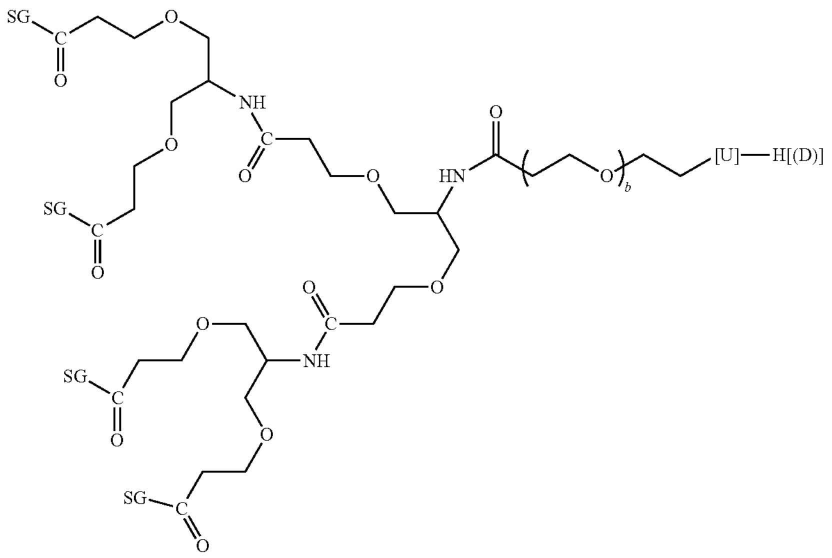

wherein b is an integer number of monomeric units comprising the spacer and is typically between 4 and 48, such as 4, 5, 6, 7, 8, 9, 10 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 22, 43, 44, 45, 46, 47 or 48 monomeric units, preferably between about 4 and 36 monomer units, most preferably 24 monomeric units; SG is selected from sugar molecules, carboxylic acids, amines and/or hydroxyls that are linked to S either directly or via a suitable linker X, or, more preferably, X5; the hydrophobic block (H) is typically selected from poly(amino acids) of Formula I; PEG is typically 24 monomeric units and capped with a hydroxyl group; E1 is a N-terminal extension; A is an antigen; E2 is a C-terminal extension; U is a linker; D is drug molecule; and [ ] denotes that the groups are optional. In some alternative embodiments the peptide antigen conjugates have the formula H-[U]-[E1]-A-[E2]-PEG. For clarity, each occurrence of any of the components of vaccines described herein, e.g., H, S, A, E1, E2, B, D and any linkers (e.g., U) are independently selected.

While the intended used of the vaccine should be considered in selecting the composition of the solubilizing groups, the inventors of the present disclosure identified that for vaccines comprising one or more peptide antigen conjugates of formula PEG-[E1]-A-[E2]-[U]-H-[D] or [D]-H-[U]-[E1]-A-[E2]-PEG and an amphiphile of formula S-B-[U]-H-[D] with cone architecture, the solubilizing groups of the solubilizing block of the amphiphile selected from mannose generally led to higher magnitude T cell responses as compared with the use of amphiphiles with solubilizing groups comprising carboxylic acids, amines or hydroxyls. A non-limiting example of a vaccine comprising one or more, typically between 1 to 40, peptide antigen conjugates of formula PEG-[E1]-A-[E2]-[U]-H-[D] and an amphiphile of formula S-B-[U]-H-[D] with cone architecture, wherein the amphiphile with cone architecture further comprises a solubilizing block comprising a PEG-based dendron with 4 solubilizing groups (SG) and a PEG-based spacer with between 4 and 36 monomer units, additionally wherein the solubilizing groups comprise sugar molecules selected from mannose and the hydrophobic block comprises a poly(amino acid) of Formula I, is provided here for clarity:

$$\left(\text{PEG}—[\text{E1}]—\text{A}—[\text{E2}]—[\text{U}]—\text{H}—[\text{D}]\right)_{1\ to\ 40}$$

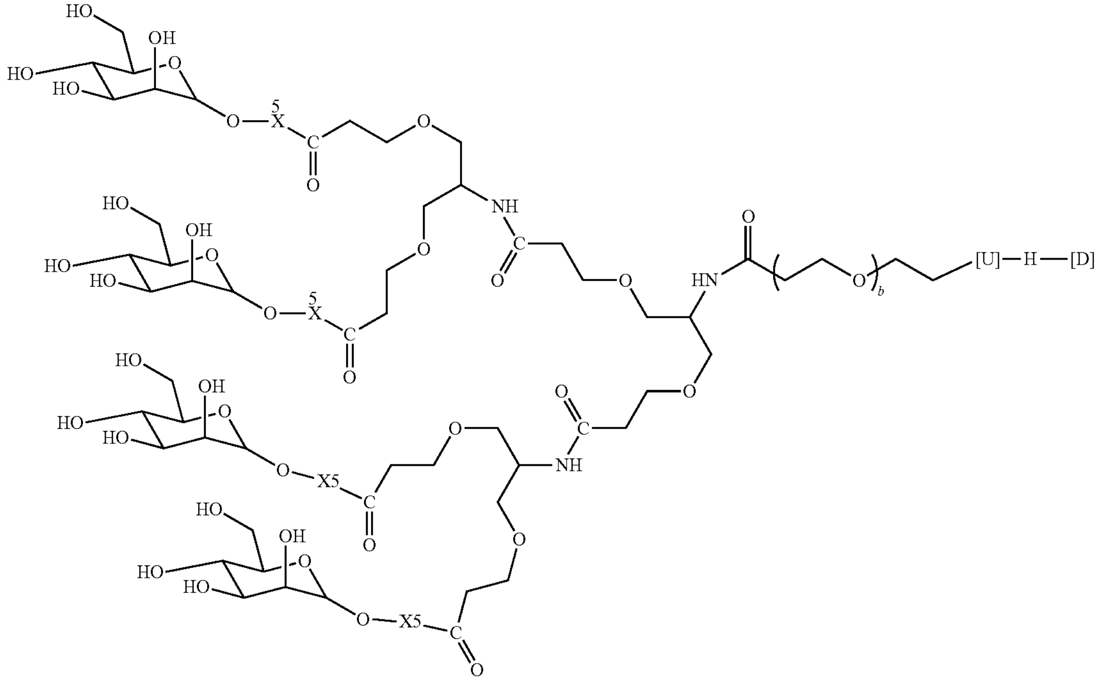

X5 is a suitable linker; b is an integer number of monomeric units comprising the spacer and is preferably between 4 and 36, such as 4, 5, 6, 7, 8, 9, 10 11, 12, 13, 14, 15, 16, 17, 18, 19, 20, 21, 22, 23, 24, 25, 26, 27, 28, 29, 30, 31, 32, 33, 34, 35 or 36 monomeric units; the hydrophobic block (H) comprises a poly(amino acid) of Formula I; PEG is typically 24 monomeric units and capped with a hydroxyl group; E1 is a N-terminal extension, A is an antigen, E2 is a C-terminal extension, U is a linker, D is a drug molecule and [ ] denotes that the groups are optional. In some alternative embodiments, the peptide antigen conjugates have the formula H-[U]-[E1]-A-[E2]-PEG.

The intended use of the vaccine should also be considered when selecting suitable peptide antigen conjugate compositions as well as the hydrophobic block composition for both the peptide antigen conjugate and the amphiphile (if present), yet the authors of the present disclosure identified certain features of peptide antigen conjugates and hydrophobic block compositions that were generally preferred across different vaccine applications.

Accordingly, for vaccines comprising preferred compositions of amphiphiles of formula S-[B]—[U]-H-[D] and one or more peptide antigen conjugates, it was found that the peptide antigens (A) could be linked directly or indirectly via an extension and or Linker U to a hydrophobic block (H) without use of a solubilizing block(S) (e.g., [D]-H-[U]-[E1]-A or A-[E2]-[U]-H [(D)]) and the resulting formulations of amphiphile and at least one peptide antigen conjugate generally led to nanoparticle micelles with consistent size particles that were stable over time and immunogenic in vivo.

WO 2022/177993 discloses that vaccines comprising peptide antigen conjugates with net positive charge and solubilizing blocks selected from poly(amino acids) with positively charged groups, e.g., lysine and ornithine, generally had improved manufacturability and formulation properties (e.g., particle size uniformity and stability) as compared with vaccines comprising peptide antigen conjugates lacking solubilizing groups (e.g., solubilizing blocks) or having solubilizing groups with net negative charge.

An additional notable finding was that the manufacturing process of certain peptide antigen conjugates could be further simplified based on the composition of the hydrophobic block (H). Accordingly, it was observed that for peptide antigen conjugates comprising hydrophobic blocks based on poly(amino acids) of Formula I comprising hydrophobic monomers M with aromatic groups further comprising aryl, heteroaryl, aminoaryl and/or aminoheteroaryl groups, and optionally charged amino acids (P) comprising amines, the entire peptide antigen conjugate could be produced by SPPS. Thus, in certain preferred embodiments of the vaccine, the peptide antigen conjugate is selected from peptide antigen conjugates of formula [D]-H-[E1]-A-[E2]-PEG or PEG-[E1]-A-[E2]—H-[D] and the hydrophobic block of the peptide antigen conjugate comprises hydrophobic monomers M with aryl, heteroaryl, aminoaryl and/or aminoheteroaryl groups, and optionally charged amino acids (P) comprising amines, wherein the number of amino acids comprising the hydrophobic block is typically between 3 to 30.

Additionally, it was observed that peptide antigen conjugates and amphiphiles with hydrophobic blocks selected from poly(amino acids) of Formula I comprising hydrophobic monomers M with aryl, heteroaryl, aminoaryl and/or aminoheteroaryl groups improved manufacturability and led to more consistent nanoparticle formulations than those with hydrophobic blocks comprising higher alkanes or aromatic groups lacking nitrogen. Thus, in preferred embodiments of the vaccine, the vaccine comprises one or more, typically between 1 to 40, peptide antigen conjugates of formula PEG-[E1]-A-[E2]-[U]-H-[D] or [D]-H-[U]-[E1]-A-[E2]-PEG, and an amphiphile of formula S-B-[U]-H-[D] with cone architecture, wherein the amphiphile with cone architecture further comprises a solubilizing block comprising a PEG-based dendron with 4 solubilizing groups (SG) and a PEG-based spacer with between 4 and 36 monomer units, additionally wherein the solubilizing groups comprise sugar molecules selected from mannose and the hydrophobic block of both the peptide antigen conjugate and the amphiphile comprises a poly(amino acid) of Formula I comprising hydrophobic monomers, M, with aryl, heteroaryl, aminoaryl and/or aminoheteroaryl groups:

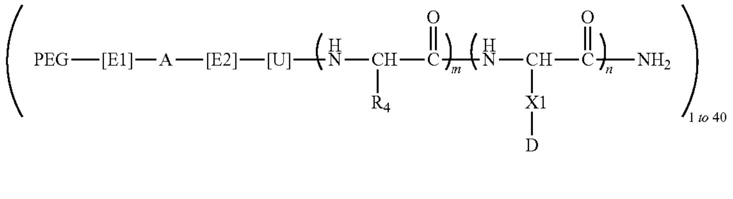

-continued

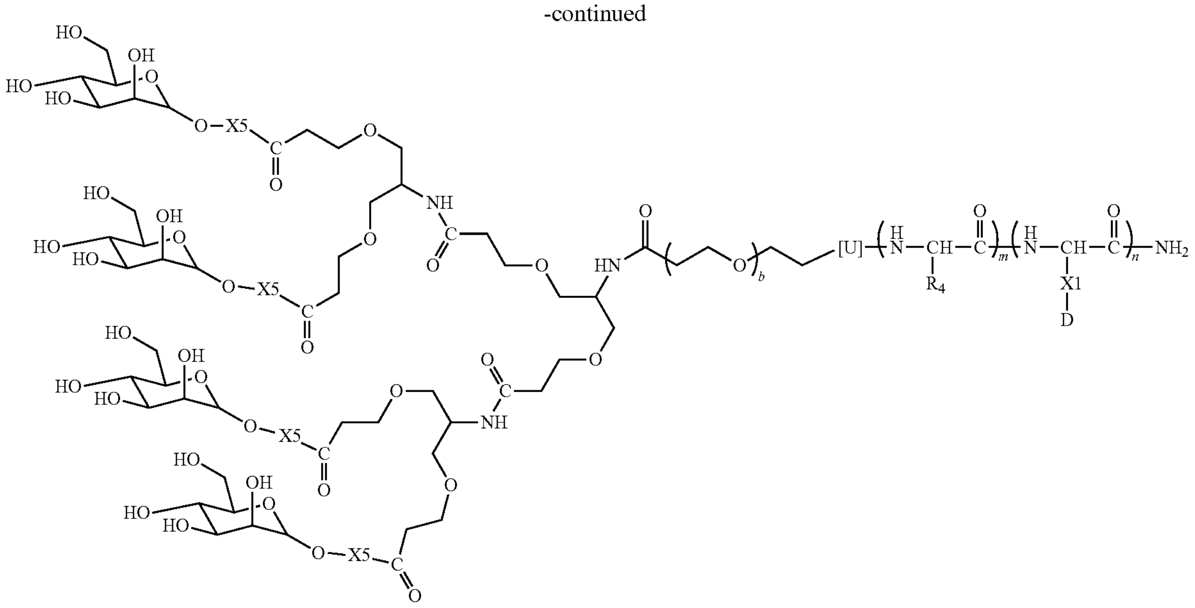

wherein X5 is a suitable linker; b is an integer number of monomeric units comprising the spacer and is typically between 4 and 36, such as 4, 5, 6, 7, 8, 9, 10 11, 12, 13, 14, 15, 16, 17, 18, 19, 20, 21, 22, 23, 24, 25, 26, 27, 28, 29, 30, 31, 32, 33, 34, 35 or 36 monomeric units; the hydrophobic block (H) comprises a poly(amino acid) of Formula I, wherein $R^4$ is selected from aryl, heteroaryl, aminoaryl and/or aminoheteroaryl groups and m is typically between 3 and 30; A is an antigen, block, PEG is typically 24 monomeric units and capped with a hydroxyl group, E1 is a N-terminal extension, E2 is a C-terminal extension, U is a linker and [ ] denotes that the groups are optional. In certain preferred embodiments of the vaccine, the amphiphile is absent and the vaccine comprises one or more, typically between 1 to 40, peptide antigen conjugates of formula PEG-[E1]-A-[E2]-[U]-H-[D] or [D]-H-[U]-[E1]-A-[E2]-PEG. In some alternative embodiments the peptide antigen conjugates have the formula H-[U]-[E1]-A-[E2]-PEG.

In the above example, wherein the hydrophobic monomer is para-aminophenylalanine (sometimes abbreviated "F") the structures of the peptide antigen conjugate and amphiphile are:

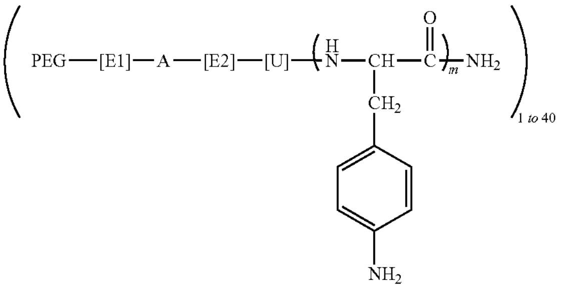

-continued
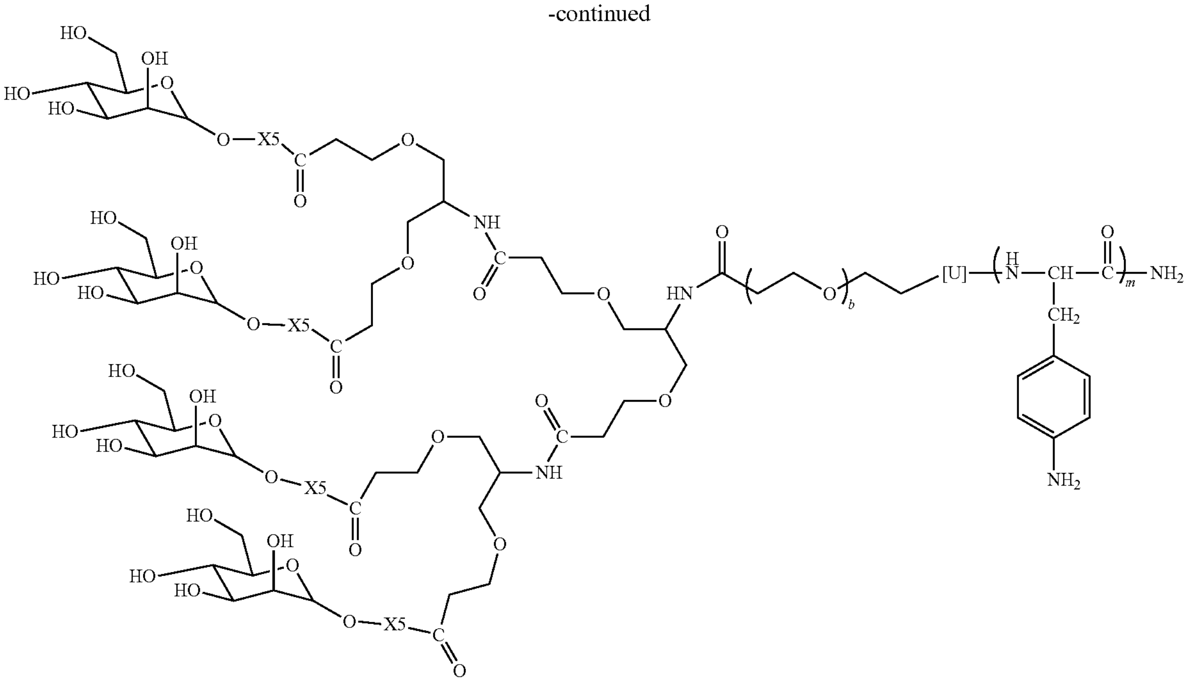
In certain preferred embodiments of the vaccine, a drug molecule is included in the hydrophobic block of the peptide antigen conjugate and/or amphiphile. A non-limiting example is provided here for clarity:
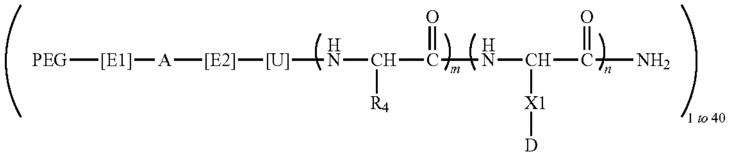
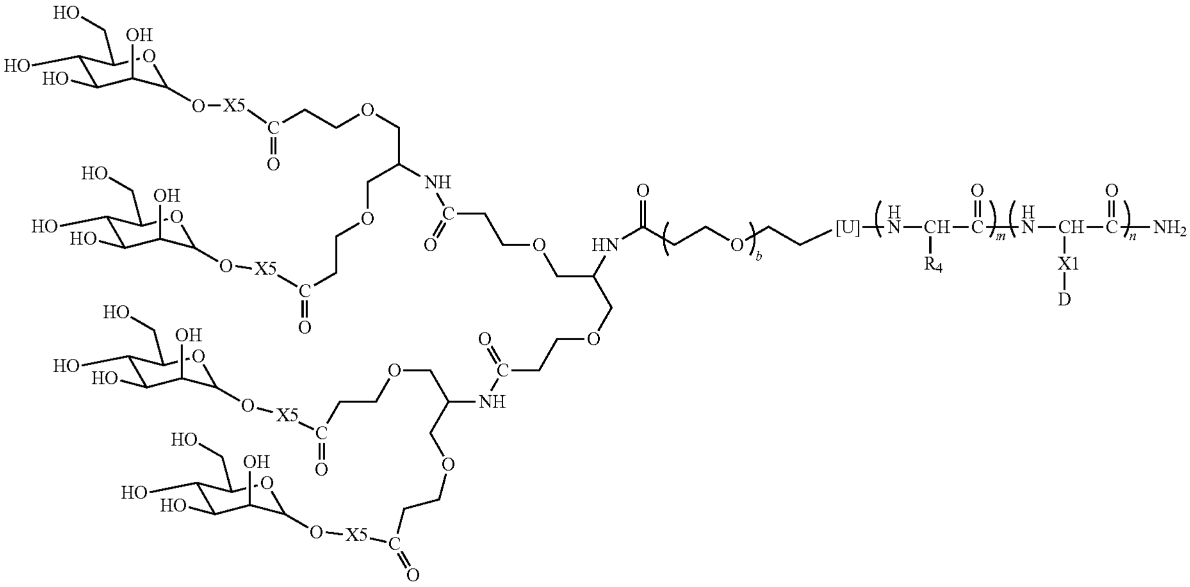

wherein X1 and X5 are suitable linkers; b is an integer number of monomeric units comprising the spacer and is typically between 4 and 36, such as 4, 5, 6, 7, 8, 9, 10 11, 12, 13, 14, 15, 16, 17, 18, 19, 20, 21, 22, 23, 24, 25, 26, 27, 28, 29, 30, 31, 32, 33, 34, 35 or 36 monomeric units; the hydrophobic block (H) comprises a poly(amino acid) of Formula I, wherein $R^4$ is selected from aryl, heteroaryl, aminoaryl and/or aminoheteroaryl groups; the drug (D) is any suitable immunomodulatory drug; m and n are an integer number of repeating units of monomers M and N, wherein the sum of m and n is typically between 3 and 30; A is an antigen, PEG is typically 24 monomeric units and capped with a hydroxyl group, E1 is a N-terminal extension, E2 is a C-terminal extension, U is a linker and [ ] denotes that the groups are optional. In certain preferred embodiments of the vaccine, the amphiphile is absent and the vaccine comprises one or more, typically between 1 to 40, peptide antigen conjugates of formula PEG-[E1]-A-[E2]-[U]-H-[D] or [D]-H-[U]-[E1]-A-[E2]-PEG. In some alternative embodiments the peptide antigen conjugates have the formula [D]-H-[U]-[E1]-A-[E2]-PEG.

In preferred embodiments of the vaccine for cancer treatment, and in some compositions of vaccines for inducing tolerance that further comprise drug molecules selected from inhibitors of mTOR, the vaccine comprises drug molecules selected from imidazoquinolines that are covalently linked to the hydrophobic block of the peptide antigen conjugate and/or amphiphile. A non-limiting example is shown here for clarity:

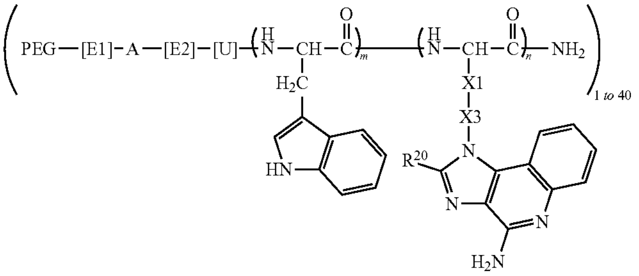

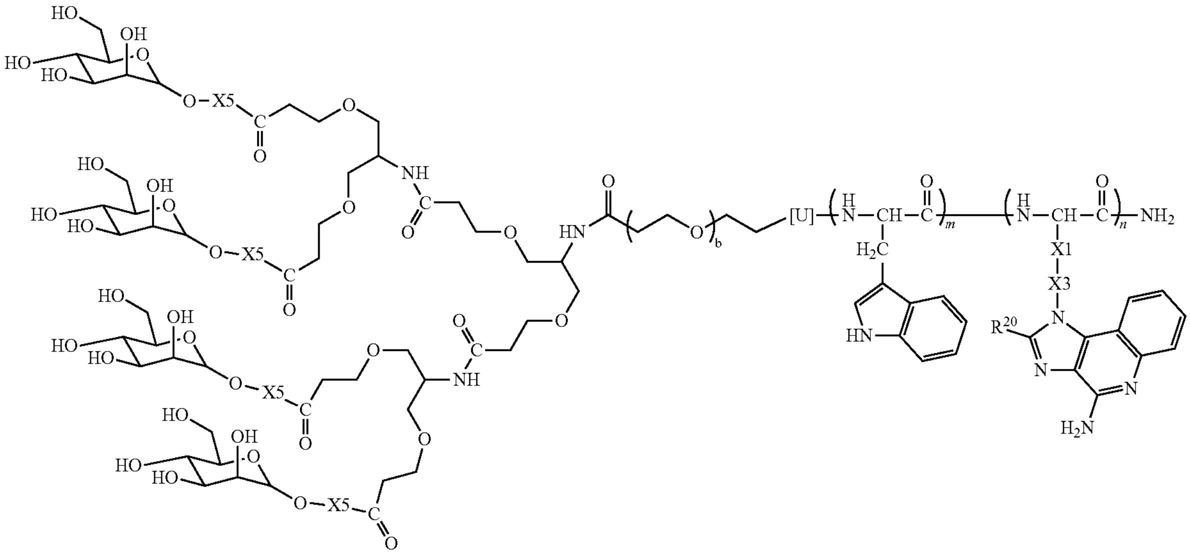

In preferred embodiments of the vaccine wherein the hydrophobic block of the peptide antigen conjugate and/or amphiphile comprises a drug molecule, the hydrophobic block is linked to the antigen and amphiphile through a Linker U comprising a triazole. A non-limiting example is provided here for clarity:

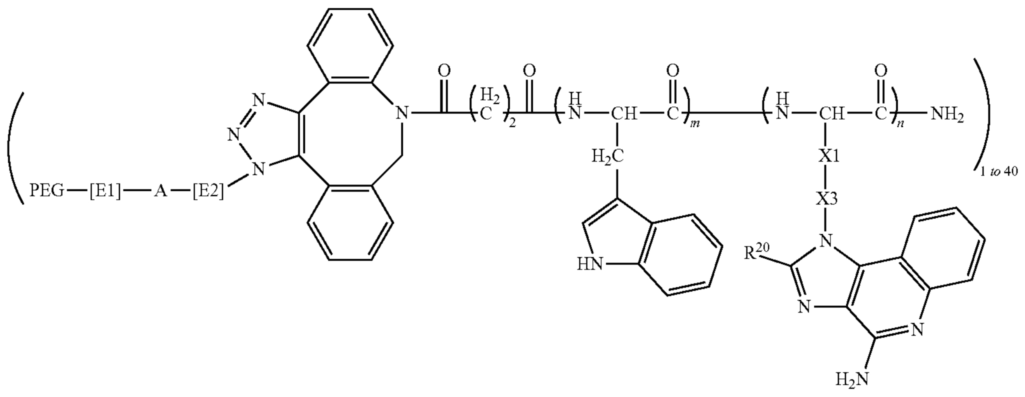

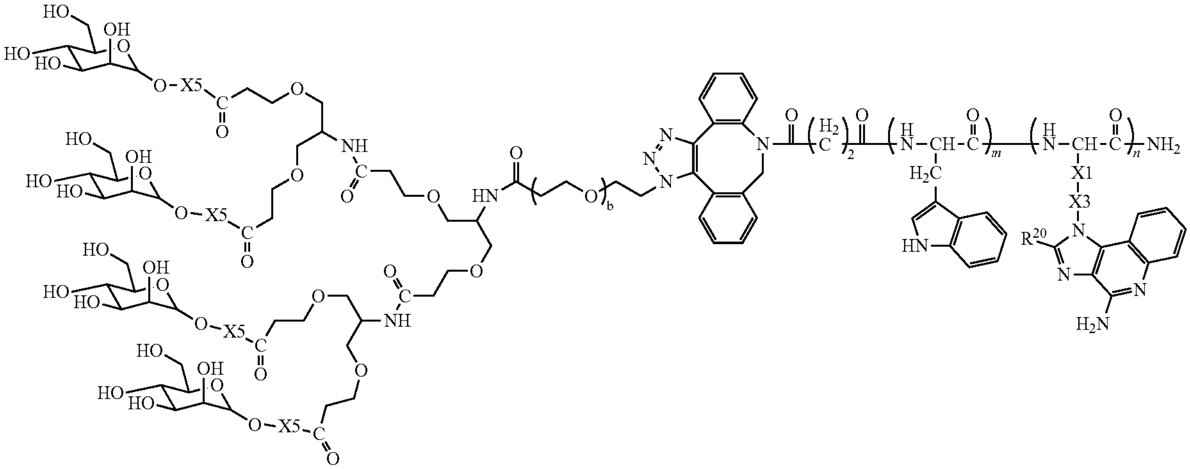

For certain preferred embodiments of the vaccine, particularly for personalized vaccines, the inventors of the present disclosure found it preferable to use different hydrophobic block compositions for the peptide antigen conjugate and the amphiphile. For instance, for vaccines wherein a unique set of peptide antigen conjugates is provided to each patient, the inventors of the present disclosure found that it was preferred to use conjugates with hydrophobic blocks comprising poly(amino acids) of Formula I further comprising hydrophobic monomers, M, with aryl, heteroaryl, aminoaryl and/or aminoheteroaryl groups, and optionally charged amino acids (P) comprising amines, wherein the number of amino acids comprising the hydrophobic block is typically between 3 to 30; and to use amphiphiles with hydrophobic blocks comprising drug molecules. A non-limiting example is provided here for clarity:

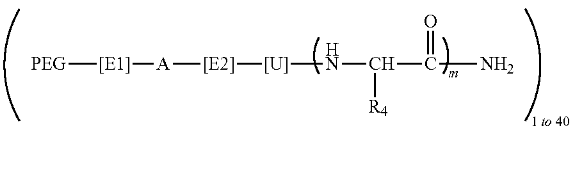

-continued

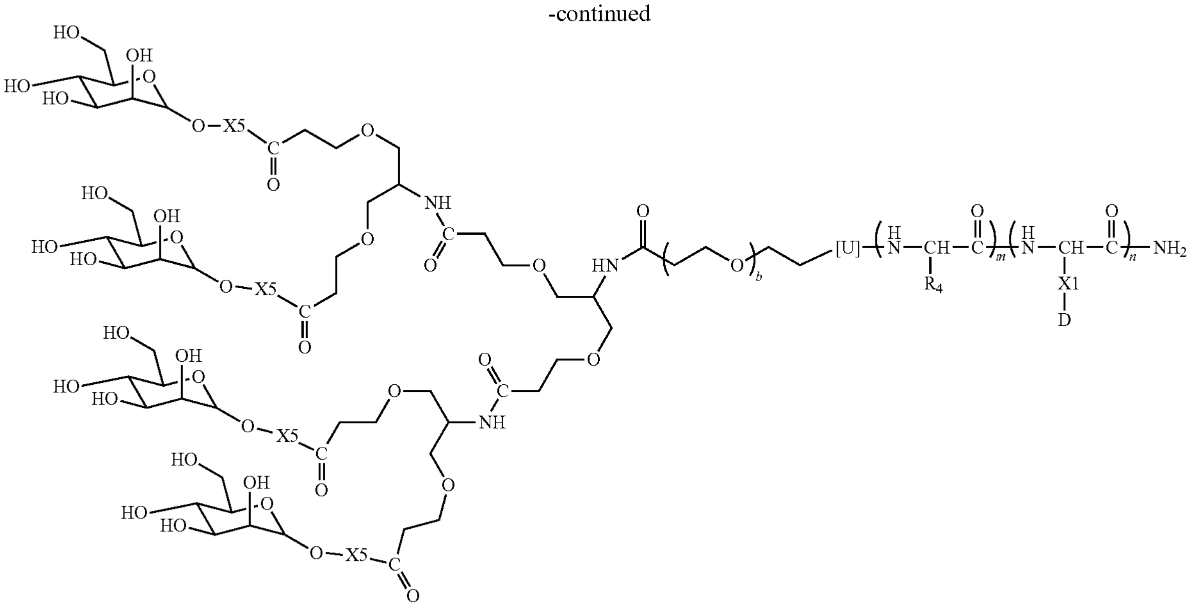

wherein X1 and X5 are each independently any suitable linker; b is an integer number of monomeric units comprising the spacer and is typically between 4 and 36, such as 4, 5, 6, 7, 8, 9, 10 11, 12, 13, 14, 15, 16, 17, 18, 19, 20, 21, 22, 23, 24, 25, 26, 27, 28, 29, 30, 31, 32, 33, 34, 35 or 36 monomeric units; the hydrophobic block of the peptide antigen conjugate comprises a poly(amino acid) of Formula I, wherein $R^4$ is selected from aryl, heteroaryl, aminoaryl and/or aminoheteroaryl groups and m is typically between 3 and 30; the hydrophobic block of the amphiphile comprises a poly(amino acid) of Formula I, wherein $R^4$ is selected from aryl, heteroaryl, aminoaryl and/or aminoheteroaryl groups; the drug (D) is any suitable immunomodulatory drug; m and n are an integer number of repeating units of monomers M and N, wherein the sum of m and n is typically between 3 and 30; A is an antigen, PEG is typically 24 monomeric units and capped with a hydroxyl group, E1 is a N-terminal extension, E2 is a C-terminal extension; U is a linker and [ ] denotes that the groups are optional. In some alternative embodiments the peptide antigen conjugates have the formula H-[U]-[E1]-A-[E2]-PEG.

In still other embodiments of the vaccine for cancer treatment and inducing antibodies and in some embodiments of the vaccine for inducing tolerance that further comprise drug molecules selected from inhibitors of mTOR, the vaccine comprises drug molecules selected from imidazoquinolines that are covalently linked to the hydrophobic block of the peptide antigen conjugate but not the amphiphile. A non-limiting example is shown here for clarity:

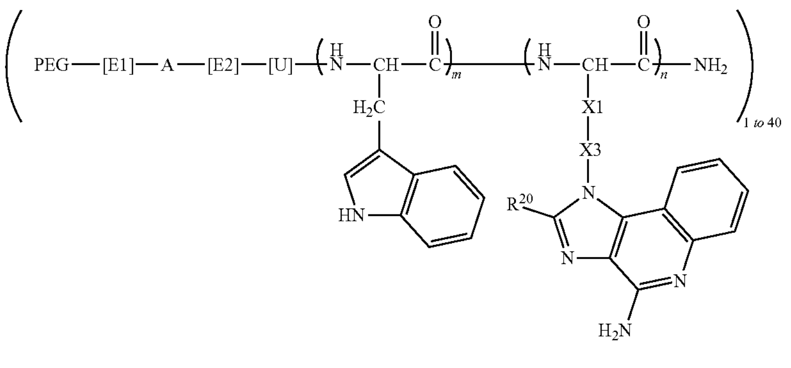

and/or

-continued
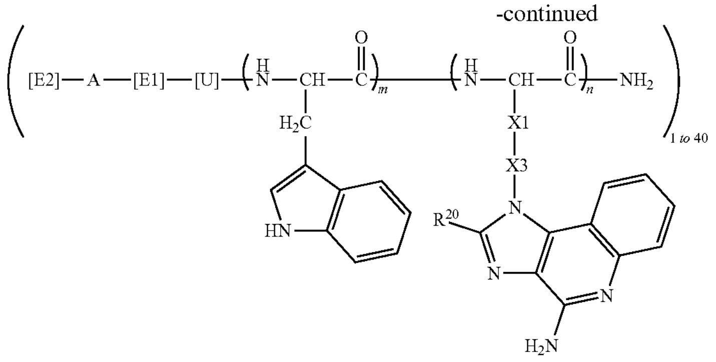
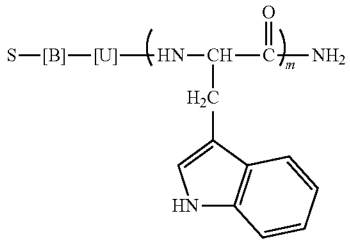
For example, wherein the ampiphile has dendron architecture and comprises a solubilizing block comprising a PEG-based dendron with 4 solubilizing groups (SG) and a PEG-based spacer with between 4 and 36 monomer units, additionally wherein the solubilizing groups comprise sugar molecules selected from mannose:
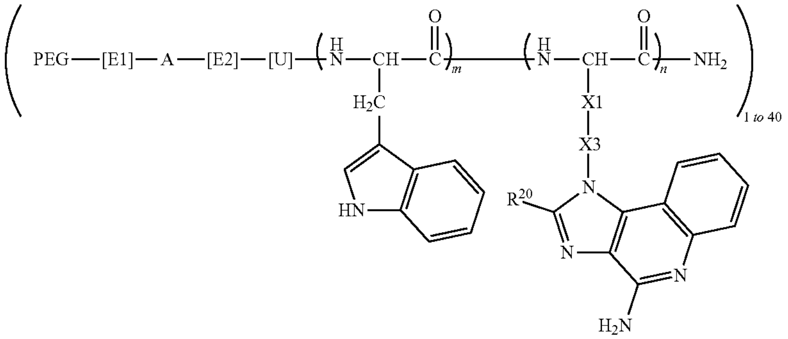
and/or
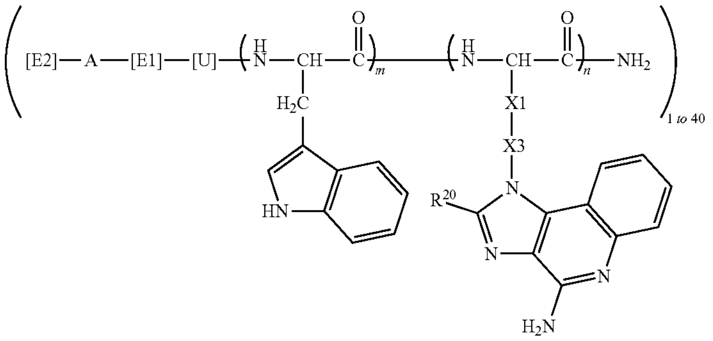

-continued

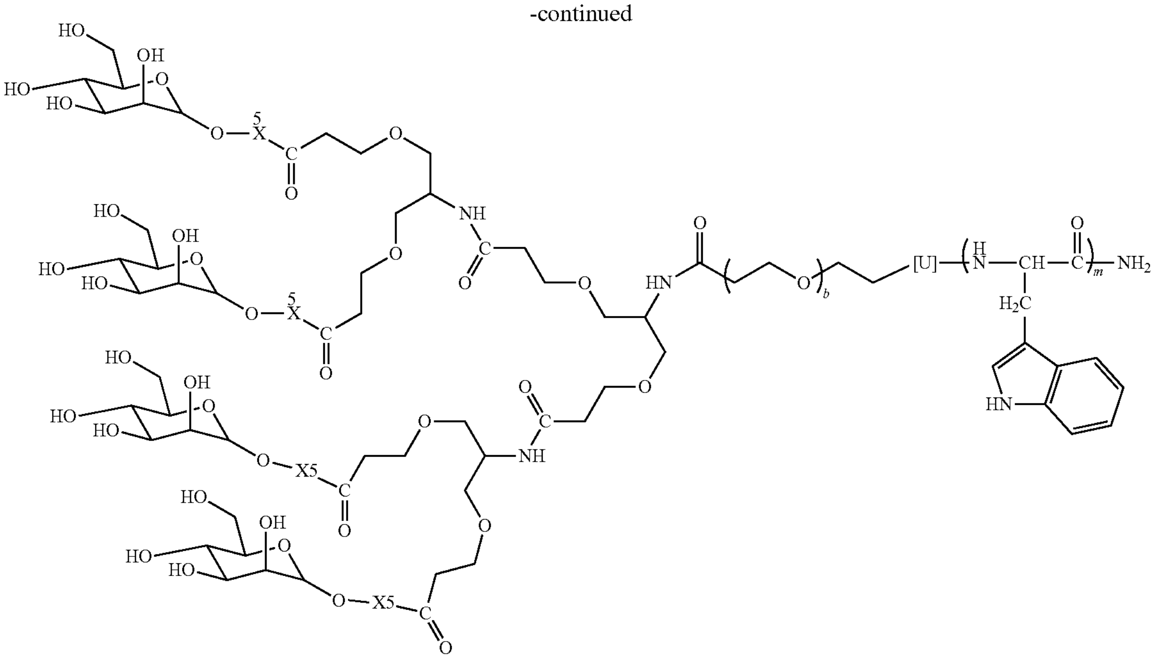

Compositions of Vaccines for Preventing or Treating Cancer

Earlier sections provided general descriptions of vaccines, including compositions of peptide antigen conjugates, amphiphiles and drug molecules (including drug molecule conjugates) that are generally preferred for use in vaccines. This section describes specific, preferred embodiments of the vaccine for preventing or treating cancer ("cancer vaccines").

Cancer vaccines comprises nanoparticles comprising one or more peptide antigen conjugates. In preferred embodiments of cancer vaccines, the vaccine further comprises an amphiphile and an immunostimulatory drug molecule.

The one or more peptide antigen conjugates, typically between 1 and 40, each comprise an antigen (A), which is typically selected from tumor antigens, including self-antigens, neoantigens and viral antigens. In preferred compositions of cancer vaccines, at least one of the peptide antigen conjugates comprises an antigen (A) selected from tumor antigens, though, the cancer vaccine may also include one or more additional peptide antigen conjugates comprising antigens (A) selected from infectious disease antigens as well as non-natural CD4 helper peptides, such as PADRE. In some embodiments, the cancer vaccine comprises at least one peptide antigen conjugate comprising an antigen selected from neoantigens. In other embodiments, the cancer vaccine comprises at least one peptide antigen conjugate comprising an antigen selected from self-antigens. In other embodiments, the cancer vaccine comprises at least one peptide antigen conjugate comprising an antigen selected from viral antigens, more preferably viral antigens associated with a malignancy (e.g., HPV, HCV, polyoma virus, etc.).

The number of peptide antigen conjugates is selected to ensure that an adequate immune response can be induced in each subject. In preferred embodiments, vaccines for cancer treatment typically include up to about 40, though typically no more than 100, peptide antigen conjugates each comprising a unique peptide antigen (A) that comprises one or more CD4, CD8 T cell and/or B cell epitopes or predicted epitopes. A more detailed process for selecting antigens is described in greater detail elsewhere.

In preferred embodiments of cancer vaccines, the vaccine further comprises a drug molecule selected from immunostimulants that induce type-I IFNs and is typically selected from agonists of TLR-3, TLR-7, TLR-8, TLR-7/8, TLR-9, RLR and STING. In preferred embodiments of cancer vaccines, the immunostimulant is selected from an imidazoquinoline of Formula IV, which is linked to the peptide antigen conjugates and/or amphiphile via a covalent bond.

In certain preferred embodiments of cancer vaccines, the amphiphile is absent and the vaccine comprises one or more, typically between 1 to 40, peptide antigen conjugates of formula PEG-[E1]-A-[E2]-[U]-H-[D] or [D]-H-[U]-[E1]-A-[E2]-PEG. In a preferred embodiments of cancer vaccines, the vaccine comprises one or more, typically between 1 to 40, peptide antigen conjugates of formula PEG-[E1]-A-[E2]-[U]-H-[D] or [D]-H-[U]-[E1]-A-[E2]-PEG and an amphiphile of formula S-B-[U]-H-[D] with cone architecture, wherein the amphiphile with cone architecture further comprises a solubilizing block comprising a PEG-based dendron with between 4 to 16 solubilizing groups and a PEG-based spacer with between 4 and 36 monomer units, additionally wherein the solubilizing groups comprise sugar molecules, carboxylic acids, amines and/or hydroxyls, and the hydrophobic block comprises a poly(amino acid) of Formula I. A non-limiting example is provided here for clarity:

$$(\text{PEG}-[\text{E1}]-\text{A}-[\text{E2}]-[\text{U}]-\text{H}-[\text{D}])_{1\ to\ 40}$$

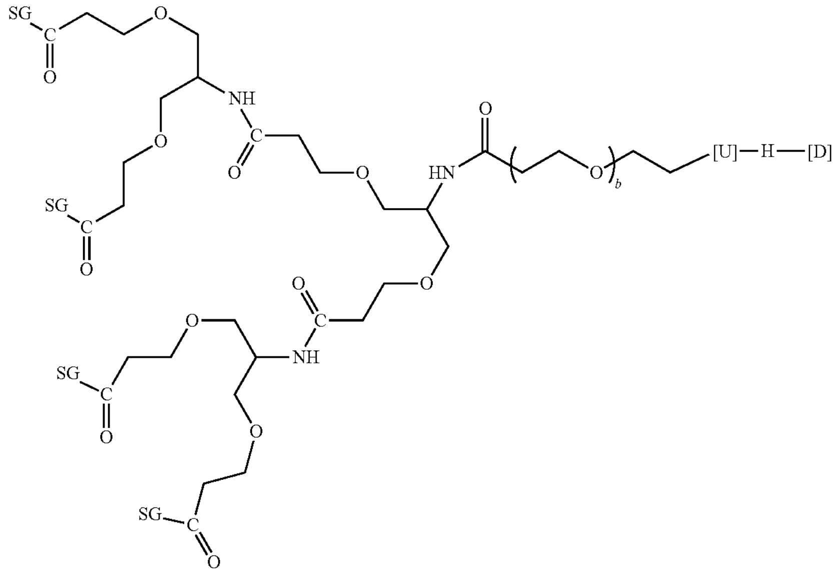

wherein b is an integer number of monomeric units comprising the spacer and is typically between 4 and 36, such as 4, 5, 6, 7, 8, 9, 10 11, 12, 13, 14, 15, 16, 17, 18, 19, 20, 21, 22, 23, 24, 25, 26, 27, 28, 29, 30, 31, 32, 33, 34, 35 or 36 monomeric units; SG is selected from sugar molecules, carboxylic acids, amines and/or hydroxyls that are linked to S either directly or via a suitable linker X, or, more preferably, X5; the hydrophobic block (H) is typically selected from poly(amino acids) of Formula I; PEG is typically 24 monomeric units and capped with a hydroxyl group, E1 is a N-terminal extension, A is an antigen selected from tumor antigens, E2 is a C-terminal extension, U is a linker, D is drug molecule and [ ] denotes that the groups are optional. In some alternative embodiments, the peptide antigen conjugates have the formula H-[U]-[E1]-A-[E2]-PEG. In preferred embodiments, the molar ratio of the peptide antigen conjugate to amphiphile is between 4:1 and 1:4, more preferably between 2:1 and 1:2 or about 1:1; and b comprises between 24 to 36 monomeric units.

In certain preferred embodiments of cancer vaccines, the amphiphile is absent and the vaccine comprises one or more, typically between 1 to 40, peptide antigen conjugates of formula PEG-[E1]-A-[E2]-[U]-H-[D] or [D]-H-[U]-[E1]-A-[E2]-PEG. In certain other preferred embodiments of cancer vaccines, the vaccine comprises one or more, typically between 1 to 40, peptide antigen conjugates of formula PEG-[E1]-A-[E2]-[U]-H-[D] or [D]-H-[U]-[E1]-A-[E2]-PEG and an amphiphile of formula S-B-[U]-H-[D] with linear architecture, wherein the amphiphile with linear architecture further comprises a solubilizing block comprising a peptide with between 3 to 12 charged amino acids and a PEG-based spacer with between 4 and 36 monomer units, and the hydrophobic block comprises a poly(amino acid) of Formula I.

In certain preferred embodiments of cancer vaccines, the amphiphile is absent and the vaccine comprises an immunostimulatory drug molecule and one or more, typically between 1 to 40, peptide antigen conjugates of formula PEG-[E1]-A-[E2]-[U]-H-[D] or [D]-H-[U]-[E1]-A-[E2]-PEG. In preferred embodiments of cancer vaccines, the vaccine comprises an immunostimulatory drug molecule and one or more, typically between 1 to 40, peptide antigen conjugates of formula PEG-[E1]-A-[E2]-[U]-H-D or [D]-H-[U]-[E1]-A-[E2]-PEG and an amphiphile of formula S-B-[U]-H-D with cone architecture, wherein the amphiphile with cone architecture further comprises a solubilizing block comprising a PEG-based dendron with between 4 to 16 solubilizing groups and a PEG-based spacer with between 4 and 36 monomer units, additionally wherein the solubilizing groups comprise sugar molecules selected from mannose or Sialyl Lewis$^x$ (sLeX), and the hydrophobic block comprises a poly(amino acid) of Formula I further comprising an imidazoquinoline of Formula IV. A non-limiting example is provided here for clarity:

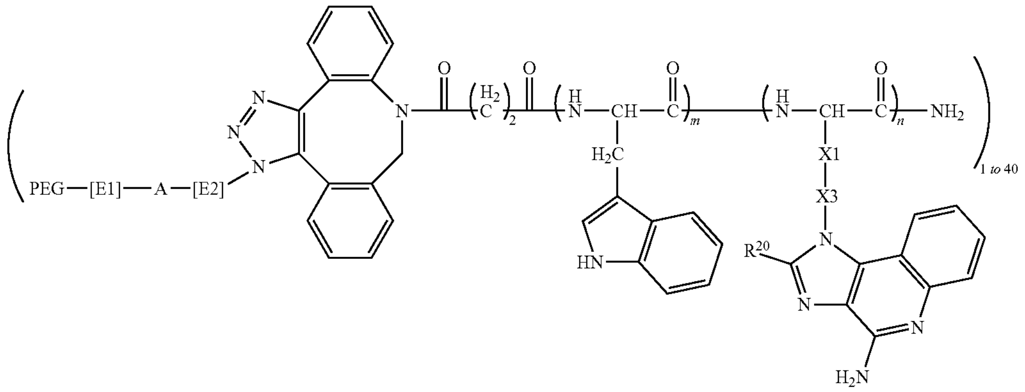

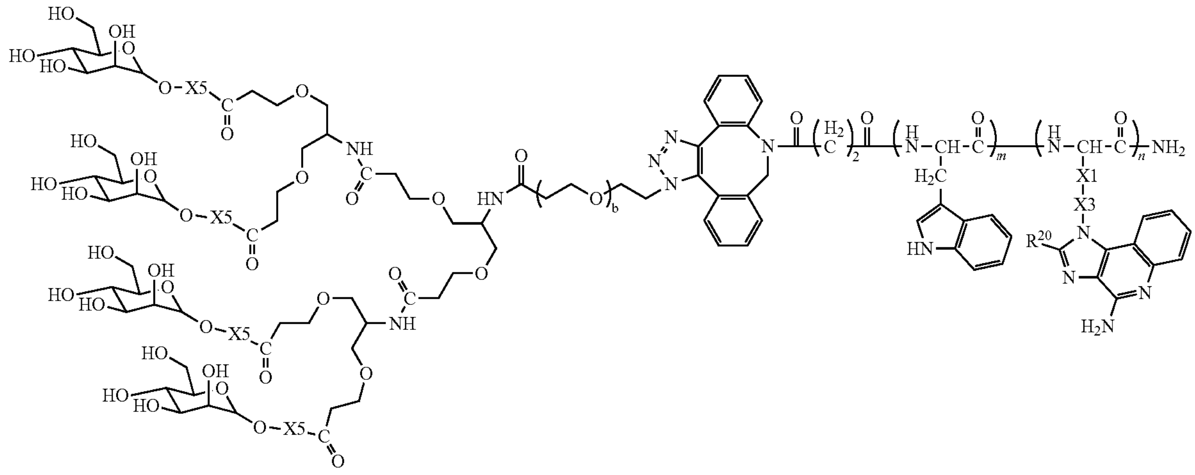

wherein X1, X3 and X5 are each independently any suitable linker molecule; b is an integer number of monomeric units comprising the spacer and is typically between 4 and 36, such as 4, 5, 6, 7, 8, 9, 10 11, 12, 13, 14, 15, 16, 17, 18, 19, 20, 21, 22, 23, 24, 25, 26, 27, 28, 29, 30, 31, 32, 33, 34, 35 or 36 monomeric units; PEG is typically 24 monomeric units and capped with a hydroxyl group, E1 is a N-terminal extension, E2 is a C-terminal extension, A is an antigen selected from tumor antigens, and [ ] denotes that the groups are optional. In some alternative embodiments the peptide antigen conjugates have the formula D-H-U-[E1]-A-[E2]-PEG. In preferred embodiments, wherein the amphiphile is present, the molar ratio of the peptide antigen conjugate to amphiphile is between 4:1 and 1:4, more preferably between 2:1 and 1:2 or about 1:1; and b comprises between 12 to 36 monomeric units, preferably 24 monomeric units.

For certain preferred compositions of cancer vaccines used as personalized on-demand therapies ("personalized cancer vaccines" or "PCVs"), drug molecules may be incorporated into the hydrophobic block of the amphiphile but not the hydrophobic block of the peptide antigen conjugate, such as:

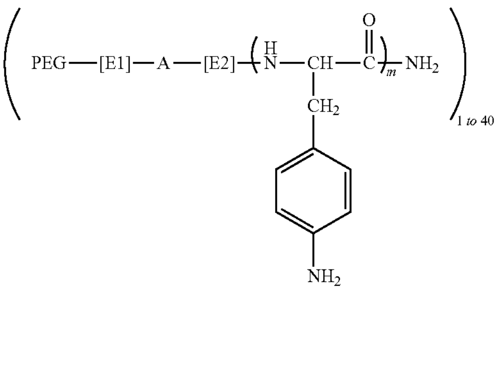

-continued

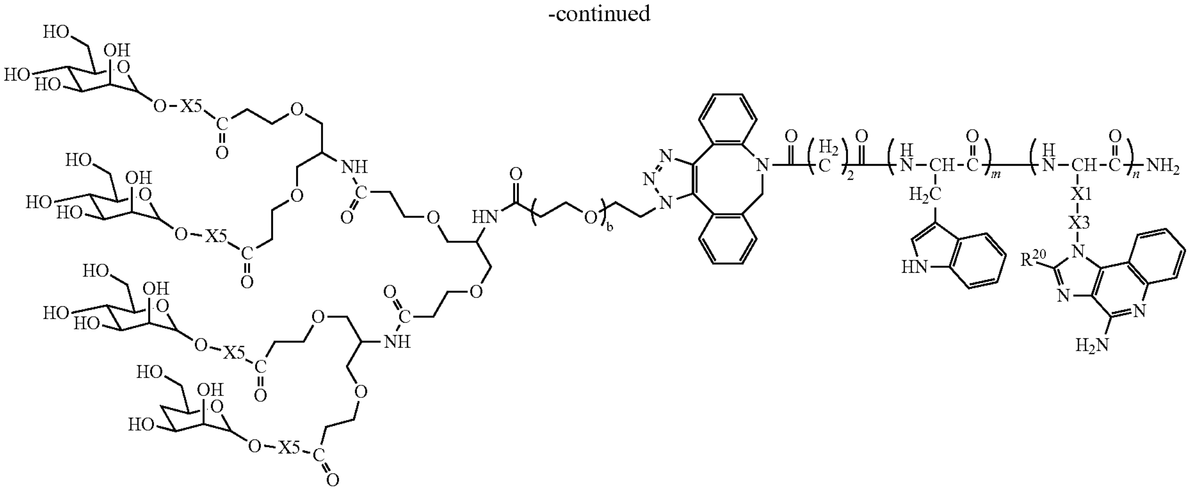

In some embodiments of cancer vaccines, the preferred composition of the first vaccine ("prime") given to a subject is different from the preferred composition of the second vaccine ("boost") given to a subject.

In preferred cancer treatment regimens, a subject is provided a prime immunization and at least one boost immunization, wherein each immunization is separated by an interval of between 1 and 64 days, more preferably between about 7 to 21 days. For instance, for certain cancer treatment regimens, a prime immunization is provided followed by a boost immunization at between 7 to 21 days following the prime.

In certain preferred embodiments of cancer treatment regimens, a subject is provided a prime immunization that comprise nanoparticles further comprising one or more, typically between 1 to 40, peptide antigen conjugates of formula PEG-[E1]-A-[E2]-[U]-H-[D] or [D]-H-[U]-[E1]-A-[E2]-PEG, and at least one immunostimulatory drug molecule, which is followed by a boost immunization that comprises a biological adjuvant selected from bacteria, viruses, cytokines, chemokines or the like, and nanoparticles comprising one or more, typically between 1 and 40, peptide antigen conjugates of formula PEG-[E1]-A-[E2]-[U]-H-[D] or H-[D]-U-[E1]-A-[E2]-PEG, and optionally an immunostimulatory drug molecule. In certain preferred cancer treatment regimens, a subject is provided a prime immunization that comprises nanoparticles further comprising one or more, typically between 1 and 40, peptide antigen conjugates of formula PEG-[E1]-A-[E2]-[U]-H-[D] or [D]-H-[U]-[E1]-A-[E2]-PEG, an amphiphile of formula S-[B]-[U]-H-[D], and at least one immunostimulatory drug molecule, which is followed by a boost immunization that comprises a biological adjuvant selected from bacteria, viruses, cytokines, chemokines or the like, and nanoparticles comprising one or more, typically between 1 and 40, peptide antigen conjugates of formula PEG-[E1]-A-[E2]-[U]-H-[D] or [D]-H-[U]-[E1]-A-[E2]-PEG, an amphiphile of formula S-[B]-[U]-H-[D] and optionally an immunostimulatory drug molecule. An unexpected finding disclosed herein is that boost immunizations comprising biological adjuvants, such as viruses, led to higher magnitude immune responses when the following criteria were met: the nanoparticles comprising one or more peptide antigen conjugates were (i) administered by the intravenous route and (ii) did not include an immunostimulant drug. Non-limiting examples of prime and boost compositions that meet these criteria are provided here below.

Non-limiting examples of the prime include:

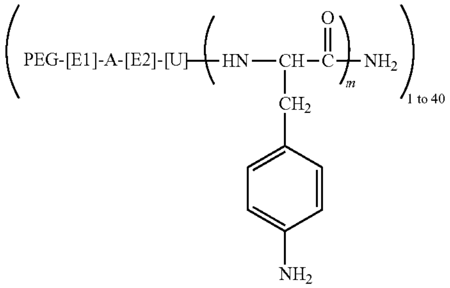

-continued
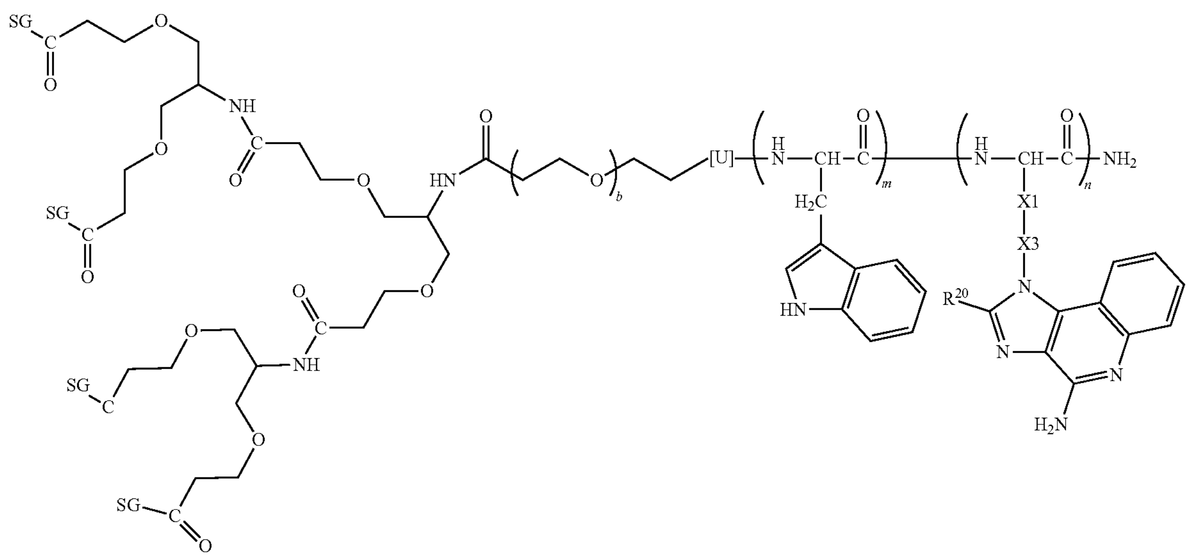
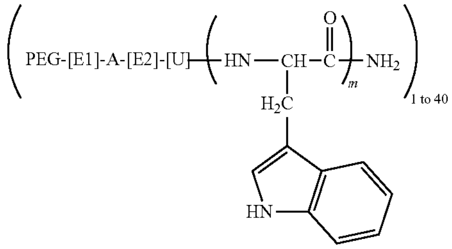
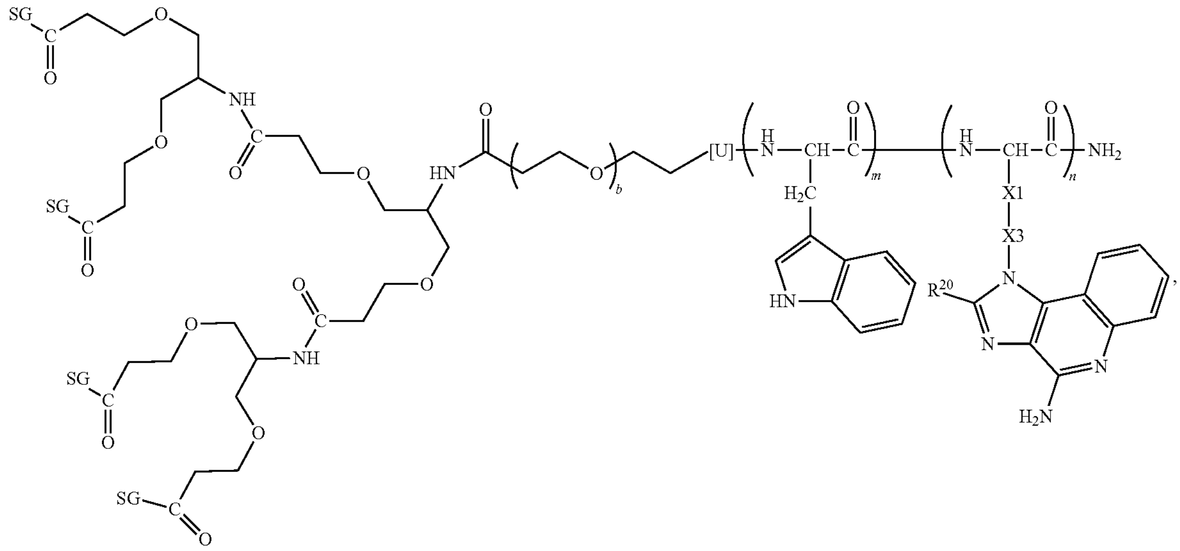
, or
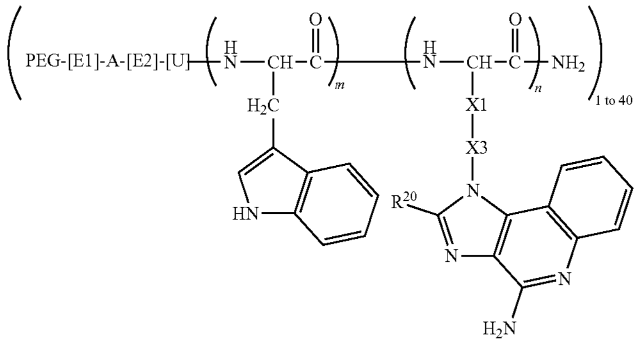
225                                                    226
$$\left( PEG\text{-}[E1]\text{-}A\text{-}[E2]\text{-}[U] \left( HN\text{-}CH\text{-}C \right)_m NH_2 \right)_{1\,to\,40}$$
$$\left( PEG\text{-}[E1]\text{-}A\text{-}[E2]\text{-}[U] \left( N\text{-}CH\text{-}C \right)_m \left( N\text{-}CH\text{-}C \right)_n NH_2 \right)_{1\,to\,40}$$

-continued
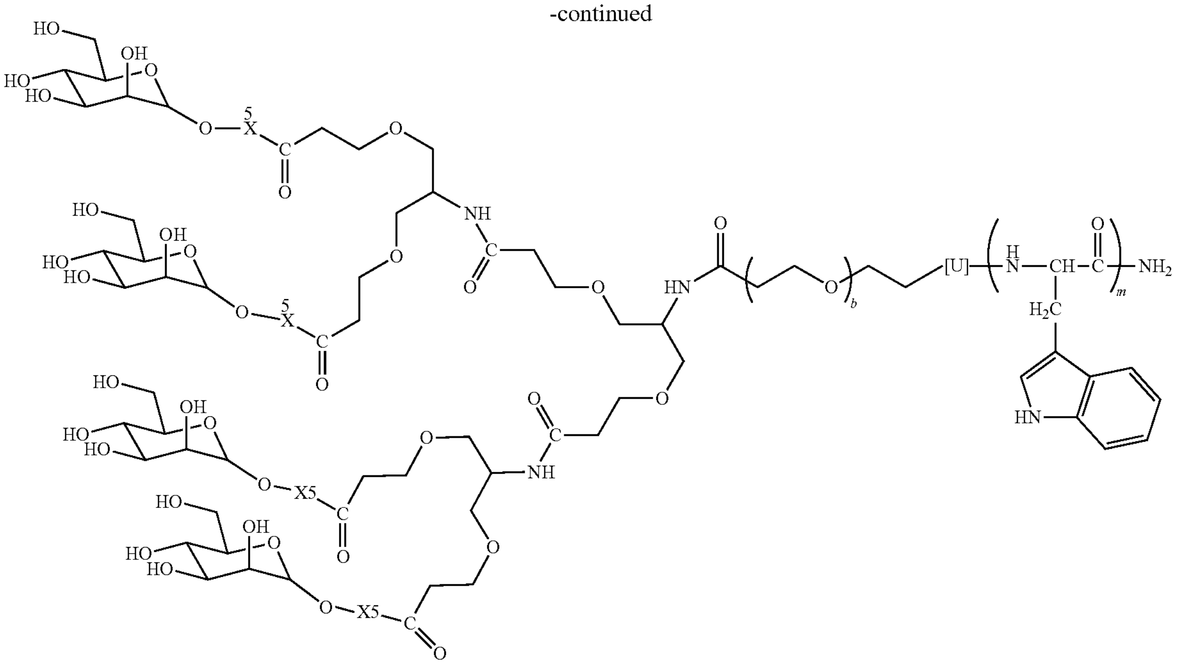
Non-limiting examples of the boost composition included for use in combination with a biological adjuvant include:
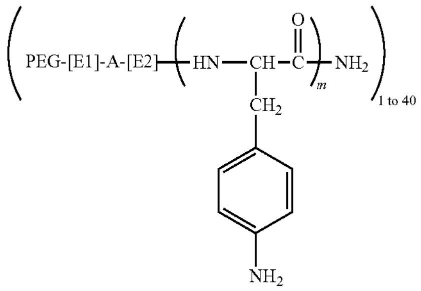
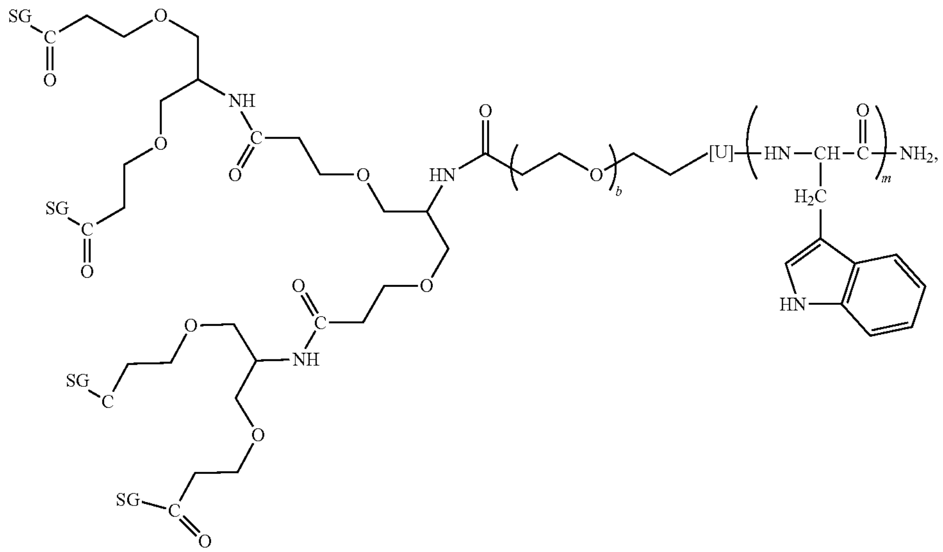

-continued
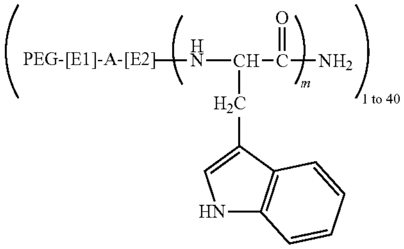
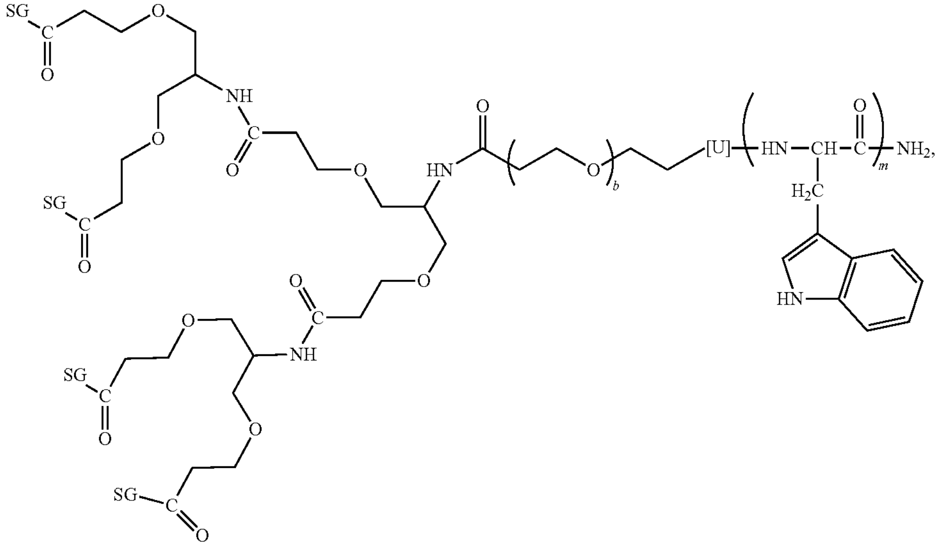
or
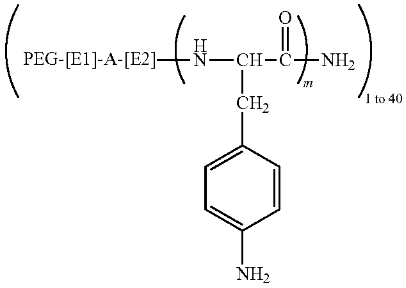
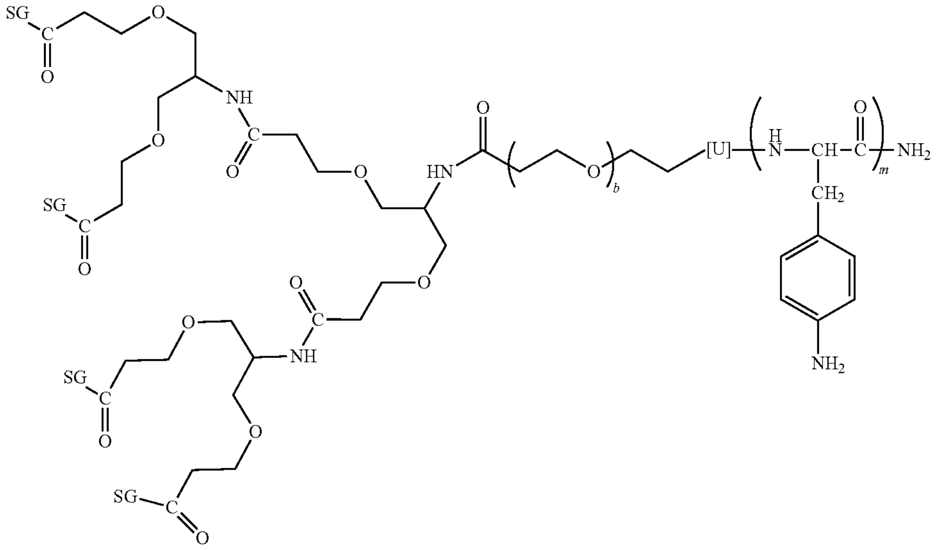

-continued

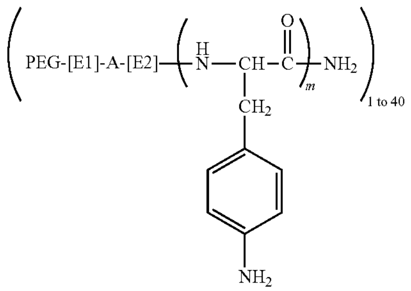

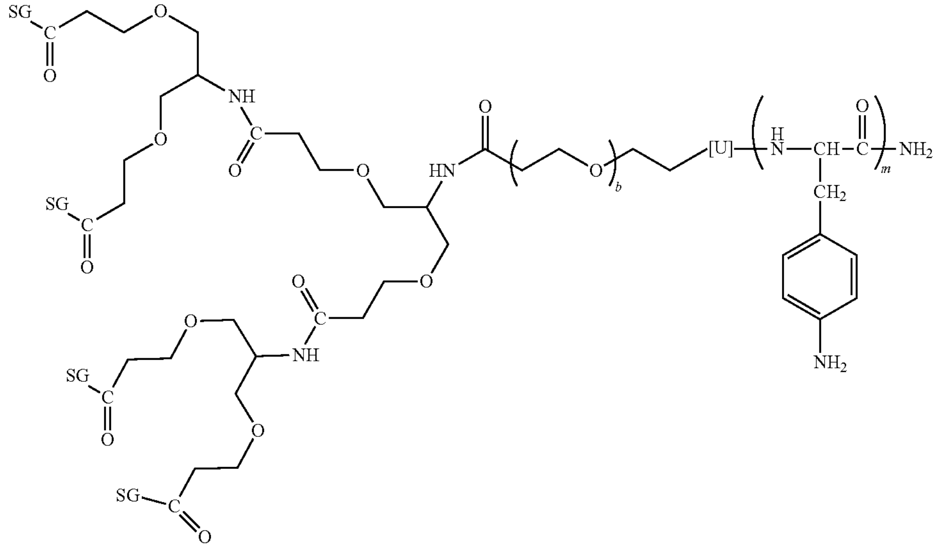

wherein X1, X3 and X5 are each independently any suitable linker molecule; b is an integer number of monomeric units comprising the spacer and is typically between 4 and 36, such as 4, 5, 6, 7, 8, 9, 10 11, 12, 13, 14, 15, 16, 17, 18, 19, 20, 21, 22, 23, 24, 25, 26, 27, 28, 29, 30, 31, 32, 33, 34, 35 or 36 monomeric units; SG is selected from sugar molecules, carboxylic acids, amines and/or hydroxyls that are linked to S either directly or via a suitable linker X, or, more preferably, X5; m is an integer number of repeating units of hydrophobic amino acids, which is typically selected from between 3 to 30, E1 is an N-terminal extension, A is an antigen selected from tumor antigens, E2 is a C-terminal extension, U is a linker and [ ] denotes that the groups are optional. In some alternative embodiments the peptide antigen conjugates have the formula [D]-H-[U]-[E1]-A-[E2]-PEG.

In certain preferred embodiments of compositions of cancer vaccines comprising a hydrophobic block H further comprising tryptophan, the tryptophan is N-methylated (CAS number: 21339-55-9) such that the R group is:

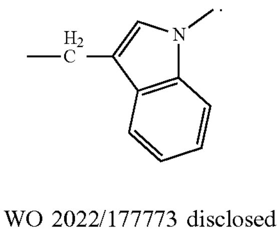

WO 2022/177773 disclosed that amphiphiles with solubilizing blocks further comprising sugar molecules and/or carboxylic acids led to reduced toxicity, including hemolytic activity, when included in vaccines comprising one or more peptide antigen conjugates with average net positive charge, particularly peptide antigen conjugates with solubilizing blocks comprising charged blocks (C) that include positively charged amino acids, such as lysine. These findings led to the design of cancer vaccines for intravenous administration that include both positively charged peptide antigen conjugates and neutral or negative amphiphile that are safer and better tolerated than cancer vaccines that lack the amphiphile. An additional notable finding reported therein was that the safety and tolerability of cancer vaccine compositions for intravenous administration could be further improved by including a drug molecule that solely blocks mTORC1 signalling. For instance, while ATP-competitive mTOR inhibitors that inhibit signalling downstream of both mTORC1 and mTORC2 were found to block the capacity of immunostimulants selected from TLR-3, TLR-7, TLR-8, TLR-7/8, TLR-9, RIGI and STING to induce CD4 T cells with Th1 phenotype, a notable finding was that rapamycin and related molecules that inhibit mTORC1, but not mTORC2, could be used to reduce the toxicity of cancer vaccines administered by the intravenous route of administration without having a deleterious impact on immunogenicity and efficacy. Therefore, in certain preferred embodiments of the vaccine for preventing or treating cancer, the vaccine comprises an inhibitor of mTORC1, including but not limited to Rapamycin (Sirolimus), tacrolimus, everolimus, RAD001 (Everolimus), CCI-779 (Temsirolimus) and AP23573 (Deferolimus), and the molar ratio of total peptide antigen conjugate (i.e., the total molar amount of peptide antigen conjugate) to inhibitor of mTOR is selected from about 100:1 to about 1:4 were suitable with molar ratios of about 10:1 to 1:2 being preferred and molar ratios of about 5:1 to about 1:1 or about 4:1 to about 2:1 being most preferred.

Amphiphiles with solubilizing groups (SG) selected from sugars were found to have utility as carriers to ensure stable nanoparticle formulations as well as to reduce hemolytic activity of peptide antigen conjugates with positive net charge. In addition to these characteristics, it was found that the amphiphile could also serve a role in inducing antibody responses against tumor-associated glycans. Accordingly, it was observed that amphiphiles with SG selected from sTn, TF, sTF, Globo H, SSEA-3, GM2, GD2, GD3, Fucosyl GM1, NeuGcGM3 and poly(sialic acid) tumor associated glycans could both serve as a carrier.

Compositions of Vaccines for Treating or Preventing Infectious Diseases

In preferred embodiments of a vaccine for preventing or treating an infectious disease, the vaccine comprises an amphiphile of formula S-B-[U]-H-[D] and one or more peptide antigen conjugates of formula PEG-[E1]-A-[E2]-[U]-H-[D] and/or [D]-H-[U]-[E1]-A-[E2]-PEG. Wherein the antigen sleeted for preventing or treating an infectious disease is a B cell epitope, the peptide antigen conjugate does not have a solubilizing block and the peptide antigen conjugate has the formula A-[E2]-[U]-H-[D] or [D]-H-[U]-[E1]-A.

A non-limiting example of a vaccine for preventing or treating infectious diseases that comprises peptide antigen conjugates further comprising one or more antigens (A) that comprise a B cell epitope is provided here for clarity, wherein the vaccine comprises one or more peptide antigen conjugates of formula:

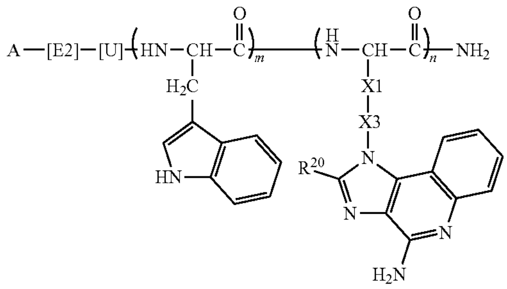

and/or

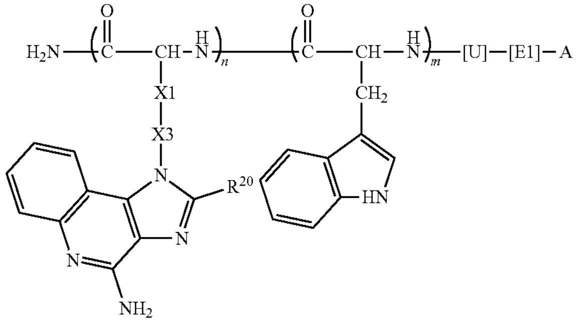

and an amphiphilic carrier of formula:

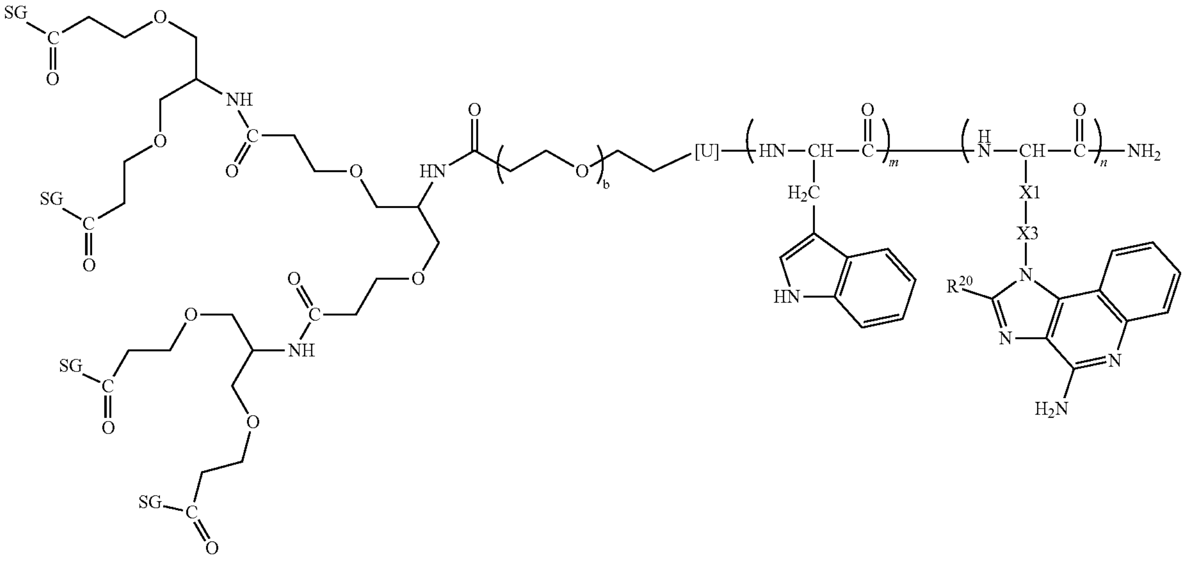

wherein X1 and X3 are each independently any suitable linker molecule, b is an integer number of monomeric units comprising the spacer and is typically between 4 and 36, such as 4, 5, 6, 7, 8, 9, 10 11, 12, 13, 14, 15, 16, 17, 18, 19, 20, 21, 22, 23, 24, 25, 26, 27, 28, 29, 30, 31, 32, 33, 34, 35 or 36 monomeric units; SG is selected from sugar molecules, preferably mannose or Sialyl Lewis x sugars, carboxylic acids, amines and/or hydroxyls that are linked to S either directly or via a suitable linker X, or, more preferably, X5; U is a linker preferably selected from triazole (if present); E1 (or E2) are typically present and selected from PEG or peptides of between 1 and 36 monomer units in length, though typically, between about 4 to 24 monomer units in length; A is a peptide antigen selected from peptide sequences derived from infectious organisms; and [ ] denotes that the groups are optional.

General Features of Vaccines that are Useful for Promoting Tolerance

The inventors of the present disclosure identified compositions that provided unexpected improvements in manufacturability, safety and/or efficacy of vaccines for inducing tolerance, including vaccines for the treatment of allergies, transplant rejection and autoimmunity.

In certain preferred embodiments of the vaccine for inducing tolerance, the vaccine comprises one or more peptide antigen conjugates of formula PEG-[E]-A-[E2]-[U]-H or H-[E]-A-[E2]—[U]-PEG, and optionally one or more distinct immunomodulatory drug molecules, which may be either linked to the hydrophobic block of the peptide antigen conjugate (e.g., PEG-[E]-A-[E2]-[U]-H-D), amphiphile (e.g., S-[B]-[U]-H-D) or both, or provided as a drug molecule conjugate (e.g., D-[B]-[U]-H), or free drug, D. In preferred embodiments of the vaccine for inducing tolerance, the vaccine comprises one or more peptide antigen conjugates of formula PEG-[E]-A-[E2]-[U]-H or H-[E]-A-[E2]—[U]-PEG, an amphiphile of formula S-[B]-[U]-H and optionally one or more distinct immunomodulatory drug molecules, which may be either linked to the hydrophobic block of the peptide antigen conjugate (e.g., PEG-[E]-A-[E2]—[U]-H-D), amphiphile (e.g., S-[B]-[U]-H-D) or both, or provided as a drug molecule conjugate (e.g., D-[B]-[U]-H), or free drug, D.

The one or more peptide antigen conjugates each comprise an antigen (A) selected from autoantigens, alloantigens or allergens that preferably comprise one or more T cell epitopes. In preferred embodiments, vaccines for inducing tolerance typically comprise more than one composition of peptide antigen conjugate, preferably between 1 and 40 unique peptide antigen conjugates, such as 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 peptide antigens conjugates each with a distinct peptide antigen (A) composition. In certain preferred embodiments of the vaccine for inducing tolerance to treat celiac disease, the number of unique peptide antigen conjugates is 12 or 14. The process for selecting antigens (A) is described in detail elsewhere.

While various options for solubilizing blocks(S) exist and are described in greater detail elsewhere in the specification, the authors of the present disclosure identified specific architectures and compositions of solubilizing blocks(S) of amphiphiles that led to improved manufacturing as well as enhanced safety and efficacy of vaccines for inducing tolerance. Accordingly, solubilizing blocks(S) with dendron architecture having between 2 and 32 solubilizing groups, preferably between about 4 and 8 solubilizing groups, were found to be optimal for generally improving manufacturing and peptide antigen conjugate loading into vaccines as compared with solubilizing blocks with linear or brush architectures, which tended to require higher net surface charge for particle stabilization. Additionally, the specific solubilizing group (SG) composition was found to have a substantial impact on the efficacy of vaccines for inducing tolerance. Indeed, an unexpected finding by the inventors of the present disclosure was that vaccines for inducing tolerance comprising amphiphiles of formula S-[B]-[U]-H optionally comprising a drug molecule (e.g., S-[B]-[U]-H-D) with solubilizing blocks(S) comprising dendrons comprising negatively charged solubilizing groups and/or saccharides and having net negative or near neutral charge led to enhanced efficacy for treating autoimmune diseases.

Therefore, in preferred embodiments, the solubilizing block of amphiphiles used in vaccines for inducing tolerance typically comprises dendron architecture with solubilizing groups (SG) selected from carboxylic acid, phosphoserine (or glycerophosphoserine), glucose, mannose, glucosamine, n-acetylglucosamine, galactose, galactosamine, n-acetyl-galactosamine and/or agonists of CD22a, which may be linked either directly or indirectly via a linker to the terminal functional groups (FGt) of the solubilizing block(S) with dendron architecture through any suitable means, though, in preferred embodiments the solubilizing group is linked to FGt via an amide bond. In certain preferred embodiments, solubilizing groups (SG) comprising sugar molecules are linked to the solubilizing block(S) via an alpha- or/beta-linkage at the anomeric carbon. In still other embodiments, the solubilizing group (SG) is the terminal functional group of the dendron, as may be the case, e.g., for FGt comprising a carboxylic acid.

A non-limiting example of a solubilizing block(S) comprising solubilizing groups (SG) further comprising carboxylic acids, wherein the solubilizing block(S) is linked either directly or indirectly via a spacer (B) and/or Linker U to a hydrophobic block (H) is shown here for clarity:

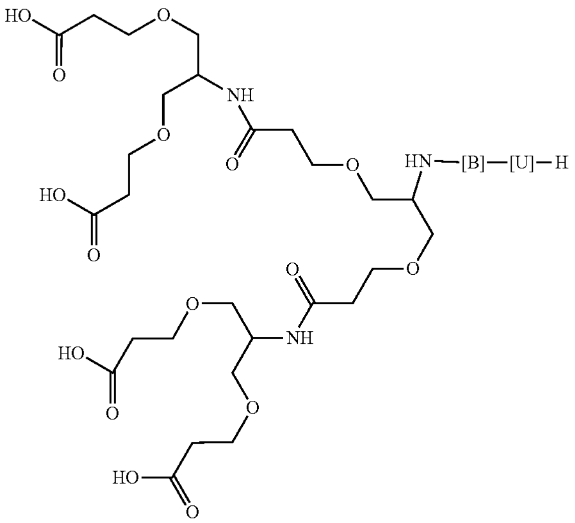

The amphiphiles of the above structure were found to be pH-responsive at pH near physiologic pH 7.4 leading to reduced solubility and aggregation when dispersed in solution at or near pH 7.4, e.g., between pH 7.0 and 7.3. However, subtle changes to the chemical composition of solubilizing blocks with dendron architecture having carboxylic acids were found to affect the range over which the resulting amphiphiles were pH-responsive. In non-limiting examples, substitution of the terminal functional groups FGt with beta-alanine yielded amphiphiles of the following structure that were not found to exhibit pH responsive properties down to at least pH 6.0:

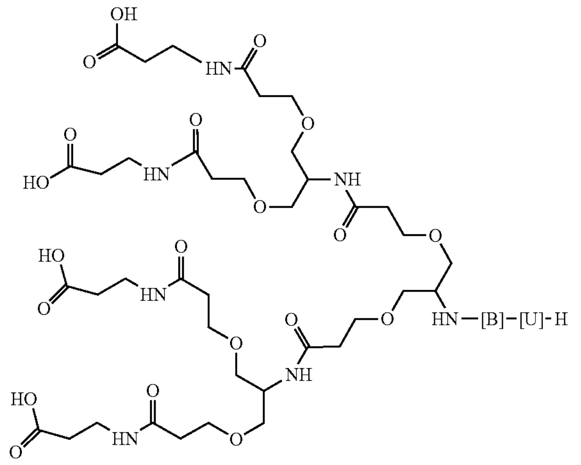

Similarly, amphiphiles comprising lysine-based dendrons wherein the primary amines of the lysine, i.e., FGt, were substituted with succinic acid led to amphiphiles that formed nanoparticles that were stable near physiologic pH 7.4. A non-limiting example of an amphiphile comprising lysine-based dendrons wherein the primary amines of the lysine, i.e., FGt, were substituted with succinic acid is shown here for clarity:

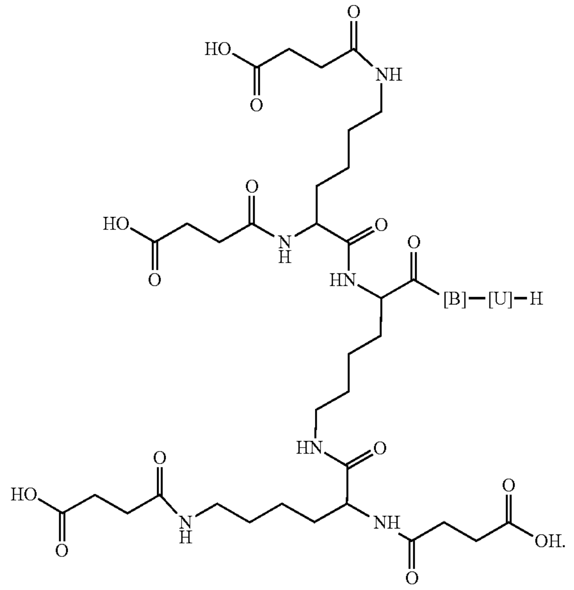

Based on these findings, preferred embodiments of the vaccine, including vaccine for inducing tolerance, that comprise amphiphiles with negative charge comprise dendrons with terminal functional groups substituted with beta-alanine and/or succinic acid.

An additional non-limiting example of a solubilizing block(S) comprising solubilizing groups (SG) further comprising a saccharide, wherein the solubilizing block(S) is linked either directly or indirectly via a spacer (B) and/or Linker U to a hydrophobic block (H) is shown here for clarity:

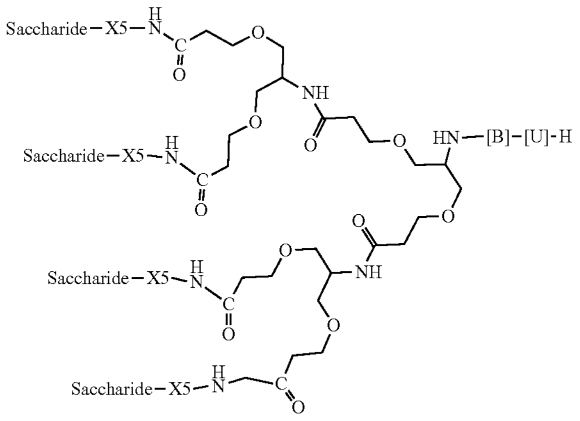

wherein X5 is any suitable linker, typically selected from lower alkyl and/or ethylene oxide and the saccharide is typically selected from

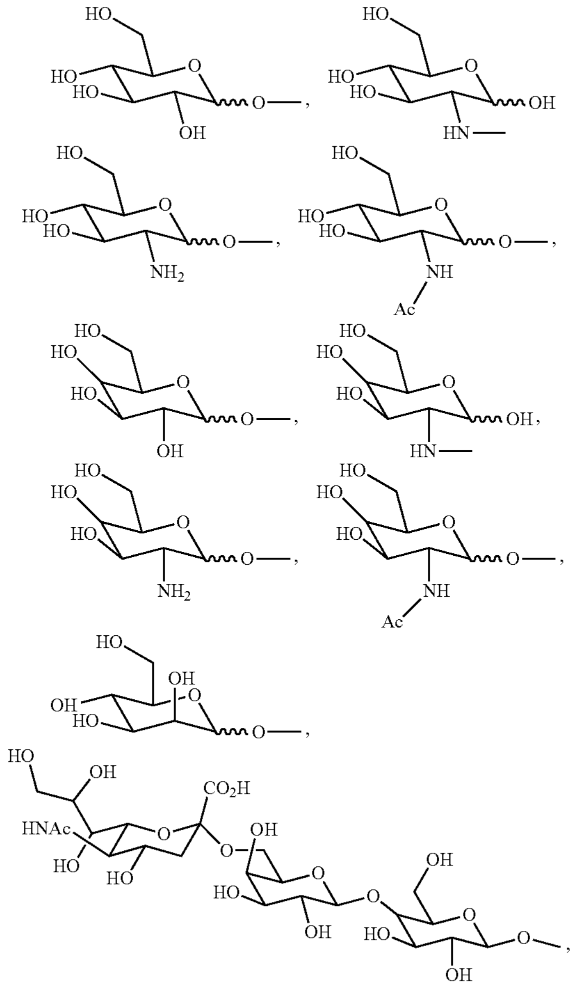

or a combinations thereof.

Both the peptide antigen conjugate and amphiphile comprise a hydrophobic block (H). Various options for hydrophobic blocks (H) exist and are described in greater detail elsewhere in the specification; however, the authors of the present disclosure identified hydrophobic blocks (H) that have utility for use with tolerance vaccines. In preferred embodiments, the hydrophobic block (H) comprises a poly (amino acid) of Formula I comprising monomer units selected from hydrophobic amino acids (M) further comprising aryl or heteroaryl groups and/or reactive amino acids (N) linked to hydrophobic drug molecules (D). In some embodiments of the vaccine for inducing tolerance, the hydrophobic block (H) of amphiphiles and/or peptide antigen conjugates comprises a poly(amino acid) of Formula I, wherein the poly(amino acid) is comprised entirely of hydrophobic amino acids (M). Non-limiting examples are provided here for clarity:

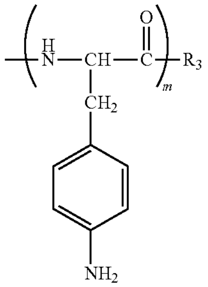

and

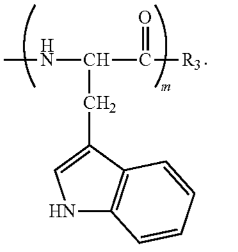

Additional non-limiting examples include poly(amino acids) of Formula I comprising hydrophobic amino acids M that are AHR agonists, including:

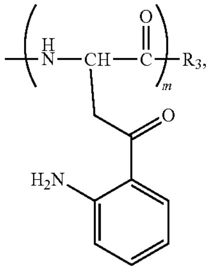

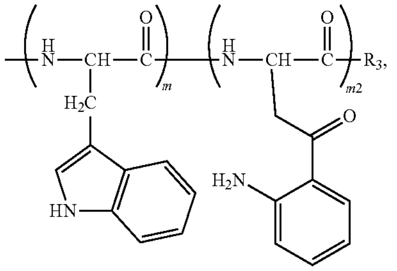

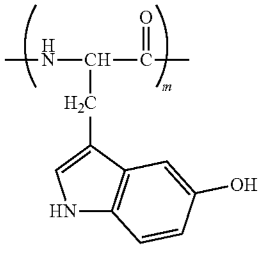

or

-continued

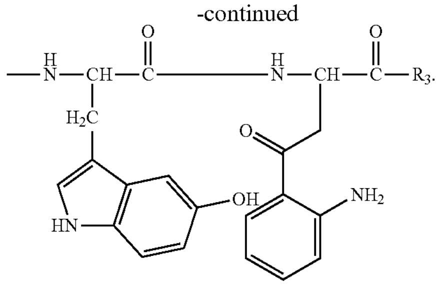

Drug molecules (D) with immunomodulatory properties, referred to as immunomodulatory drugs, may be added to or co-administered with vaccines for inducing tolerance to further improve efficacy. Suitable drug molecules include immunomodulators that can promote regulatory T cell priming, trans-differentiation, expansion or stabilization ("Treg promoting immunomodulators"), which includes phosphoinositide-3-kinase (PI3K), AKT and mammalian target of rapamycin (mTOR) inhibitors, such rapamycin, everolimus, torin 1, torin 2, INK-128, dactolisib, AZD8055, KU-00639874 and any analogs, derivatives or salt forms thereof; cyclin dependent kinase (CDK8) and/or CDK19 inhibitors, such as Cortistatin, CCT251545, CCT251921, Senexin A and BRD6968; retinoic acid-related orphan gamma t (RORγt) inhibitors, such as SR1555 or SR1001; certain histone deacetylases (HDACs), such as trichostatin-A (TsA), suberoylanilide hydroxamic acid (SAHA, or "vorinostat"), or butyrate, or, more preferably inhibitors of HDAC9, such as TMP269; agonists of aryl hydrocarbon receptor (AHR), such as indole, indolo[3,2-b]carbazole (ICZ), kynurenine, kynurenic acid, 5-hydroxy tryptophan, tryptamine, indol-3-acetic acid and ITE (cas: 448906-42-1) (see: Gutierrez-Vazquez, C., et al. Immunity Review, 2018); substrates for indoleamine 2,3-dioxygenase (IDO); agonists of retinoic acid receptors (RAR), such as all-trans retinoic acid, TTNPB (cas: 71441-28-6), AM580, BMS753, BMS961 and the like; certain adenosine receptor agonists, e.g., agonists of $A_{2A}$, such as ATL-146e, YT-146, (N6-(2-(3,5-dimethoxyphenyl)-2-(2-methylphenyl)ethyl) adenosine (DPMA), regadenoson, UK-432,097, zeatin; and, agonists of TGF-β, IL-17, IL-2 and IL-10 receptors, including naturally occurring proteins and/or antibodies. Note: "Treg promoting immunomodulators" may also be described more generally as immunosuppressants.

An unexpected finding by the inventors of the present disclosure is that compositions of vaccines for inducing tolerance that include certain compositions of immunostimulants and one or more Treg promoting immunomodulators led to significantly higher magnitude of T cell induction as compared with vaccine compositions without the immunostimulants. This was unexpected because immunostimulants are believed to oppose regulatory T cell induction and immune suppression.

Non-limiting examples of immunostimulants that were found to be effective for use in combination with Treg promoting immunomodulators include but are not limited to: agonists of C-type lectin receptors (CLR), such as trehalose-6,6-dibenhenate, agonists of nucleotide-binding oligomerization domain (NOD)-like, such as muramyl dipeptide; agonists of TLR-7, such as imidazoquinolines; agonists of TLR-4 such as lipopolysaccharide or derivatives thereof, such as monophosphoryl lipid A (MPL-A); and agonists of STING, such as CDNs (e.g., c-di-AMP) and diABZI.

The preferred means of incorporating drug molecules into vaccines for inducing tolerance depends, in part, on the composition of the drug molecule.

Immunostimulants and/or Treg promoting immunomodulators that are poorly water soluble, i.e., hydrophobic drug molecules, may be admixed with amphiphiles and/or peptide antigen conjugates (e.g., D+S-[B]-[U]-H and/or PEG-[E1]-A-[E2]-[U]-H) and incorporated into the hydrophobic core of particles comprising the amphiphiles and/or peptide antigen conjugates through non-covalent interactions. Non-limiting examples include immunostimulants comprising fatty acids, such as lipopeptide-based agonists of TLR-1, -2 and/or -6 as well as lipid-based agonists of TLR-4 and CLRs (e.g., mincle); immunostimulants comprising polycyclic heteroaryls, such as imidazoquinoline based agonists of TLR-7 and -8, as well as diABZI-based agonists of STING, and any derivatives thereof, such imidazoquinoline or pip-diABZI molecules linked to fatty acid, cholesterol or other hydrophobic moieties through the N1 of imidazoquinoline or nitrogen of piperazine, respectively; macrolide-based inhibitors of mTOR, such as rapamycin, and any of the various heterocyclic aromatic inhibitors of mTOR/PI3K/AKT (e.g., KU-0062794, Torin 1, Torin 2, etc.), CDK8/19 (e.g., Cortistatin), retinoic acid-related orphan gamma t (RORγt) inhibitors, such as SR1555; certain histone deacetylases (HDACs), such as TMP269; certain agonists of aryl hydrocarbon receptors (AHR), such as indole, indolo [3,2-b]carbazole (ICZ), 3,3 diindolomethane and ITE; agonists of retinoic acid receptors (RAR), such as all-trans retinoic acid, TTNPB (cas: 71441-28-6), AM580, BMS753, BMS961 and the like; and certain hydrophobic adenosine receptor agonists, such as UK-432,097.

Alternatively, immunostimulants and/or Treg promoting immunomodulators that are poorly water soluble, i.e., hydrophobic drug molecules, may be linked to the hydrophobic block (H) of the amphiphiles and/or peptide antigen conjugates (e.g., S-[B]-[U]-H-D and/or PEG-[E1]-A-[E2]-[U]-H-D) and may therefore be incorporated into the core of the particles comprising the amphiphiles and/or peptide antigen conjugates through covalent bonds between the drugs and the hydrophobic block (H) comprising the particle core. Non-limiting examples include immunostimulants and Treg promoting immunomodulators that are (i) poorly water soluble (ii) suitable for covalent conjugation; (iii) have severe dose-limiting toxicities when used systemically and therefore require a delivery platform to restrict biodistribution; and/or (iv) require covalent attachment to the amphiphile and/or peptide antigen conjugate to ensure adequate co-delivery with the peptide antigen (A). Non-limiting examples include immunostimulants such as imidazoquinoline based agonists of TLR-7 and -8, as well as diABZI-based agonists of STING; certain, conjugatable heterocyclic aromatic inhibitors of mTOR/PI3K/AKT, such as Torin 2; certain histone deacetylases (HDACs), such as butyric acid; certain agonists of aryl hydrocarbon receptors (AHR), such as tryptamine, kynurenine, kynurenic acid, 5-hydroxy tryptophan, indol-3-acetic acid and ITE; substrates for IDO, such as tryptophan; agonists of retinoic acid receptors (RAR), such as all-trans retinoic acid, TTNPB (cas: 71441-28-6), AM580, BMS753, BMS961 and the like; and, certain adenosine receptor agonists, such as UK-432,097.

In some embodiments of the vaccine for inducing tolerance, the hydrophobic block (H) of amphiphiles and/or peptide antigen conjugates comprises a poly(amino acid) of Formula I, wherein the poly(amino acid) of Formula I comprises reactive amino acids (N) linked to hydrophobic drug molecules and optionally hydrophobic amino acids (M). Non-limiting examples are provided here for clarity:

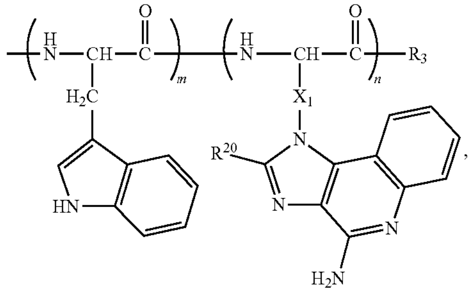

,

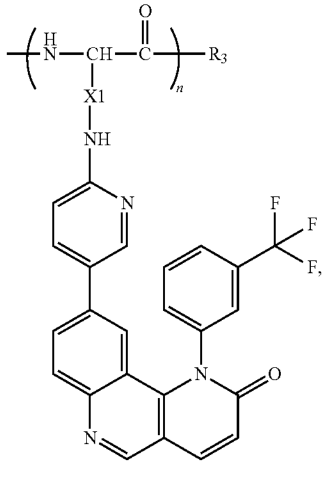

D = Torin 2

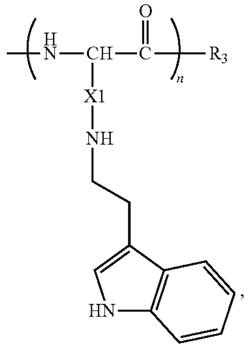

,

D = Tryptamine

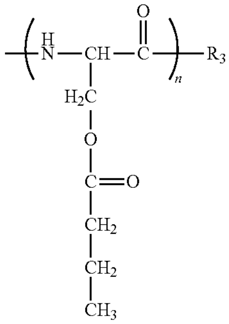

D = Butyric acid (linked via ester)

or

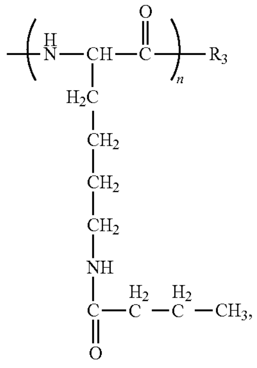

D = Butyric acid (linked via amide)

-continued

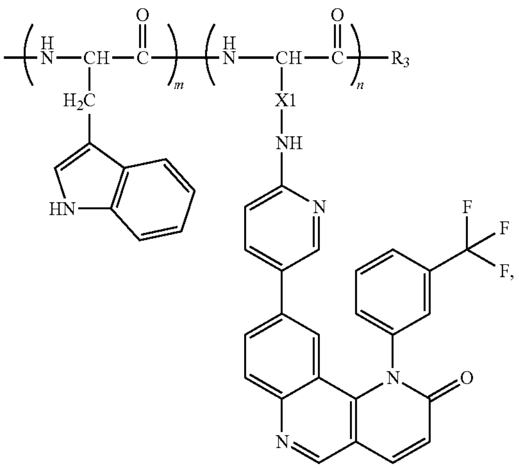

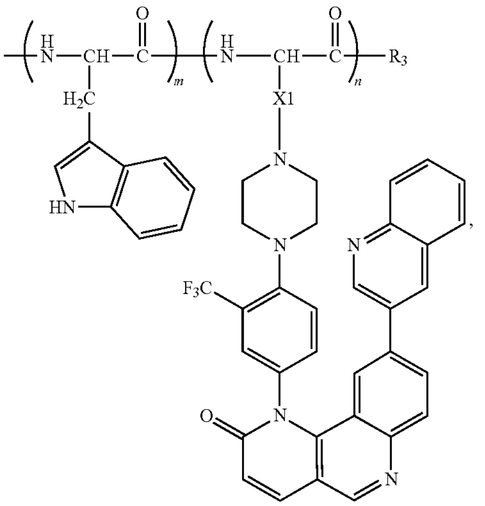

-continued

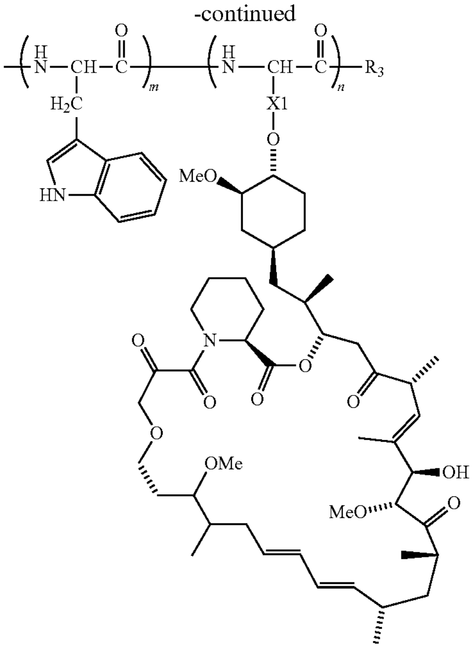

wherein X1 is any suitable linker and $R^3$ is typically selected from hydrogen, $NH_2$, $NH_2—CH_3$, $NH_2—(CH_2)_jCH_3$, OH, or drug molecules (D) either linked directly or through any suitable linker molecule (X1); n and m are any integers, wherein the sum of n and m (when present) is greater than 3, typically between about 3 and 30; and, the N-terminal amino acid is attached to either (i) a solubilizing block(S) either directly or indirectly via a spacer (B) and/or Linker U; (ii) an antigen (A) either directly or indirectly via an extension (E1 or E2) and/or Linker U; (iii) a drug molecule either directly or via a Linker U; or, (iv) a capping group.

In some embodiments, the drug molecule (D) is linked to the hydrophobic block (H) through an enzyme degradable peptide, which may further comprise a self-immolative linker. A non-limiting example is provided her for clarity:

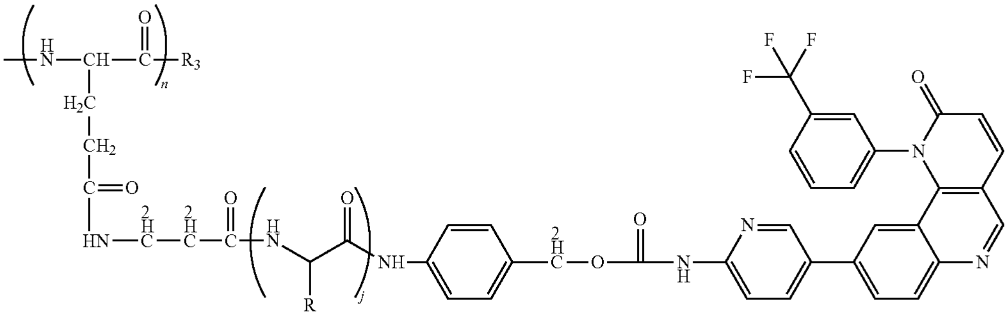

wherein j is any integer and R is any suitable amino acid composition, though, in preferred embodiments j is between 2 to 4 amino acids that are recognized by cathepsins.

In some embodiments, hydrophobic drug molecules selected from Treg promoting immunomodulators are used as the hydrophobic block of the peptide antigen conjugate and/or amphiphile. Non-limiting examples include but are not limited to:

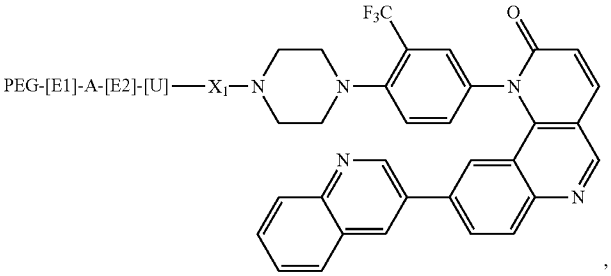

,

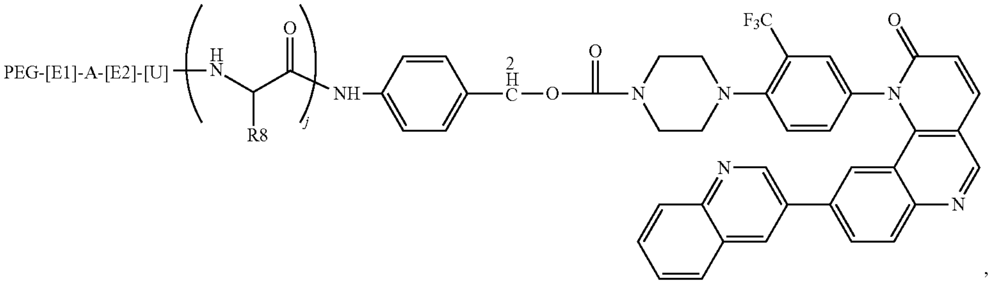

,

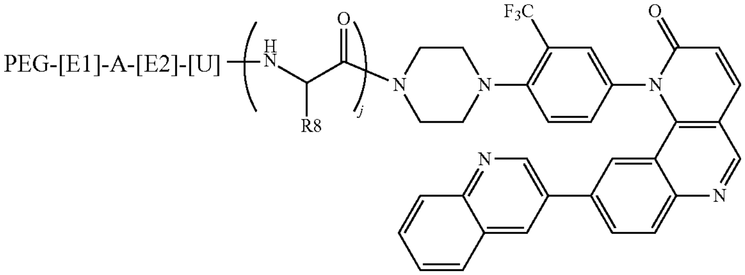

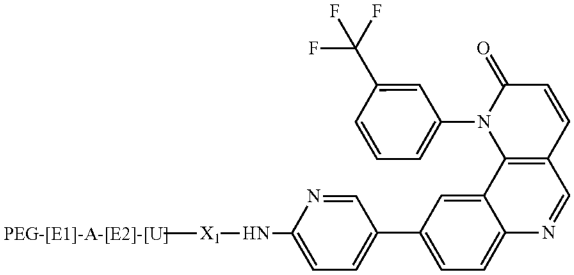

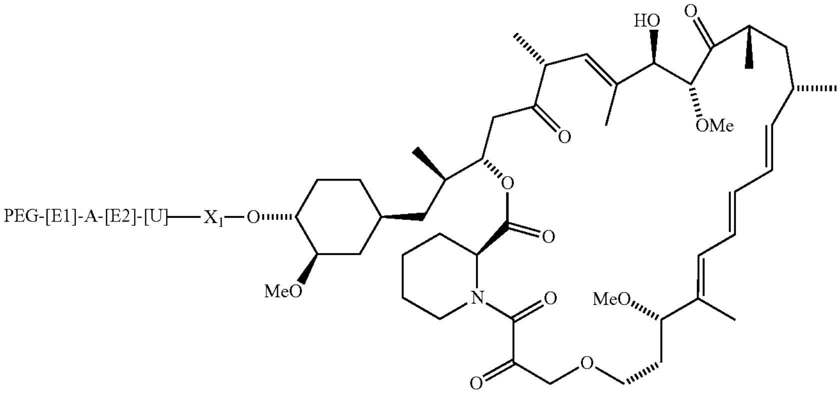

,

-continued

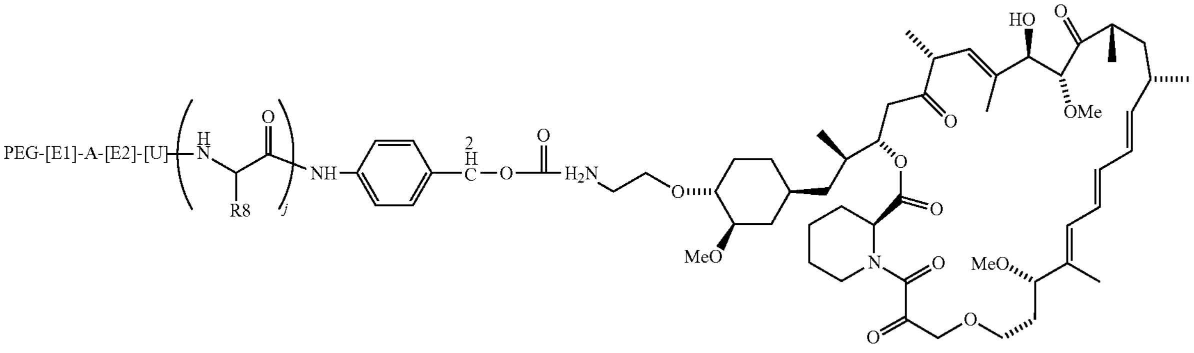

or

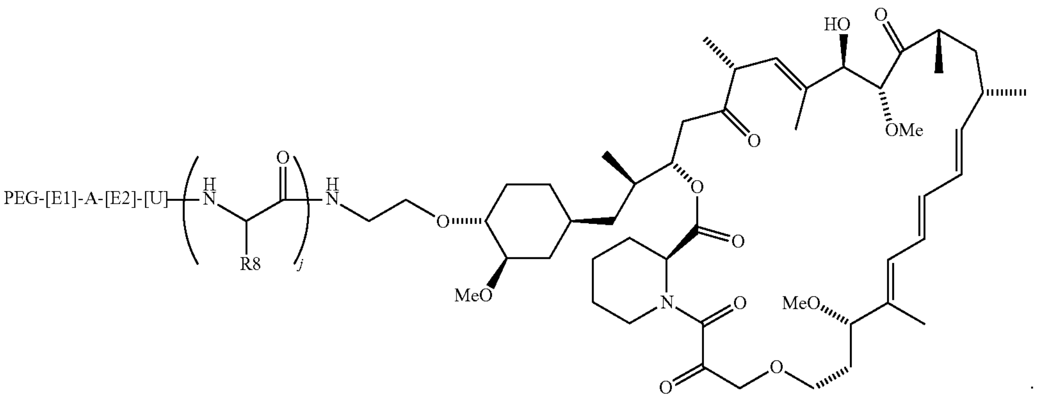

An unexpected finding disclosed herein is that vaccines comprising peptide antigen conjugates, a hydrophobic Treg promoting immunomodulator and optionally an amphiphile formed more stable nanoparticle formulations with the hydrophobic Treg promoting immunomodulator covalently attached to the hydrophobic block of the peptide antigen conjugate and/or amphiphile as compared to vaccines wherein the hydrophobic Treg promoting immunomodulator was not covalently linked to the hydrophobic block. Non-limiting examples of hydrophobic Treg promoting immunomodulator include macrolides, such as rapamycin or everolimus, as well as torins, such as Torin-1 or Torin-2, or derivatives of macrolides and torins, linked to the hydrophobic block of peptide antigen conjugates, or serving as the hydrophobic block.

Note: moderate to highly water soluble amphiphilic or hydrophilic drug molecules (D) may also be linked to the hydrophobic block (H) of the amphiphiles and/or peptide antigen conjugates (e.g., S-[B]-[U]-H-D and/or PEG-[E1]-A-[E2]-[U]-H-D), but the solubilizing effects of the drug molecule (D) should be compensated for by the composition of the hydrophobic block. In some embodiments of the vaccine for inducing tolerance, the hydrophobic block (H) of amphiphiles and/or peptide antigen conjugates comprises a poly(amino acid) of Formula I, wherein the poly(amino acid) of Formula I comprises hydrophobic amino acids (M) and reactive amino acids (N) linked to hydrophobic drug molecules.

In other embodiments of the vaccine for inducing tolerance, the hydrophobic block (H) of amphiphiles and/or peptide antigen conjugates comprises a dendron, wherein the terminal functional groups are linked to hydrophobic drug molecules. A non-limiting example is provided here for clarity:

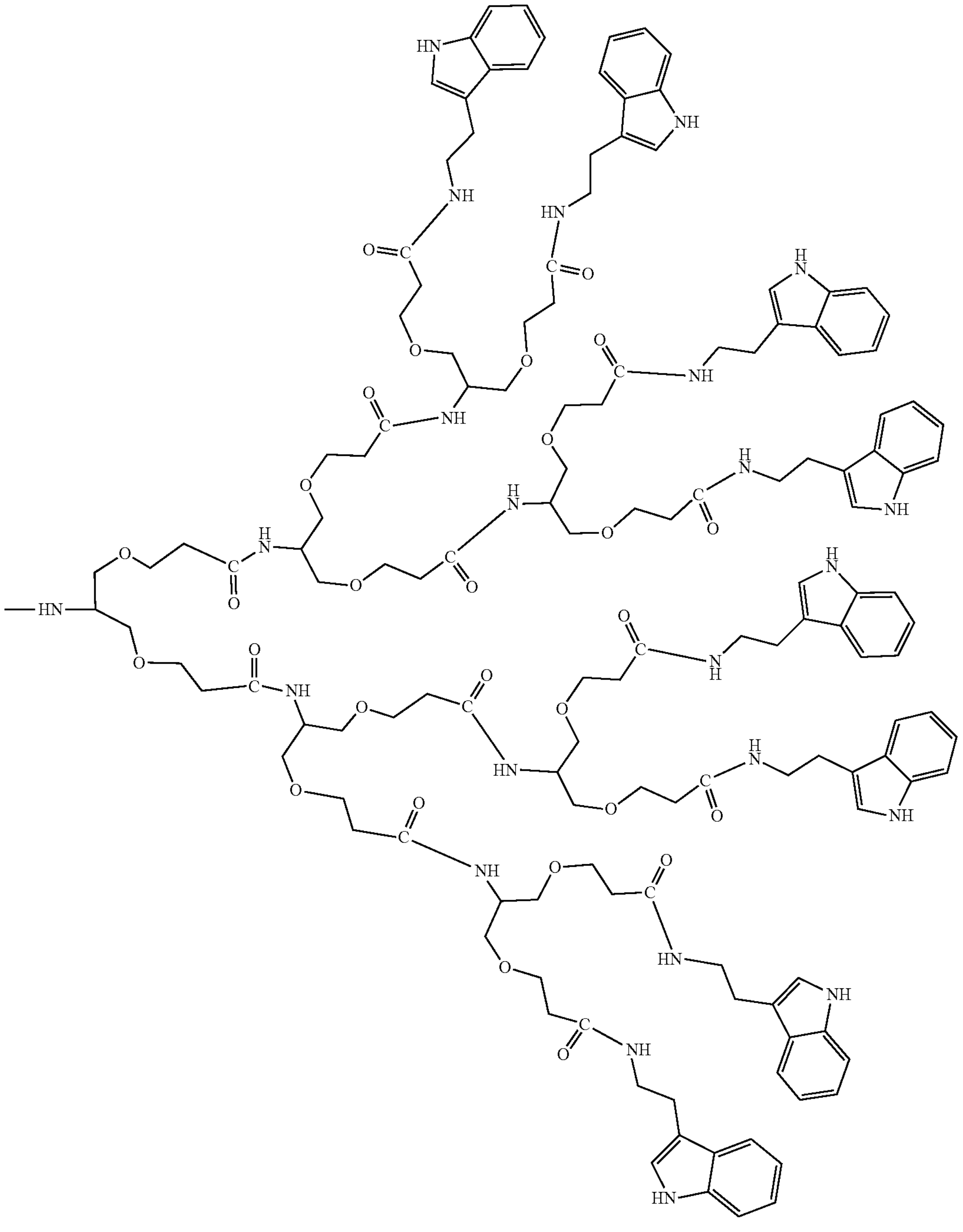 [SMILES: CNC(COCCC(=O)NC(COCCC(=O)NC(COCCC(=O)NCCc1c[nH]c2ccccc12)COCCC(=O)NCCc1c[nH]c2ccccc12)COCCC(=O)NC(COCCC(=O)NCCc1c[nH]c2ccccc12)COCCC(=O)NCCc1c[nH]c2ccccc12)COCCC(=O)NC(COCCC(=O)NC(COCCC(=O)NCCc1c[nH]c2ccccc12)COCCC(=O)NCCc1c[nH]c2ccccc12)COCCC(=O)NC(COCCC(=O)NCCc1c[nH]c2ccccc12)COCCC(=O)NCCc1c[nH]c2ccccc12]

wherein the drug molecule is tryptamine.

In preferred embodiments of the vaccine for inducing tolerance wherein the immunostimulants and/or Treg promoting immunomodulators are moderate or highly water soluble, i.e., amphiphilic or hydrophilic drug molecules, the immunostimulants and/or Treg promoting immunomodulators are linked to hydrophobic blocks (H) to yield drug molecule conjugates (e.g., D-H or H-D) that may be admixed with amphiphiles and/or peptide antigen conjugates (e.g., D-H+S-[B]-[U]-H and/or [S]-[E1]-A-[E2]—[U]-H) and incorporated into the hydrophobic core of particles comprising the amphiphiles and/or peptide antigen conjugates through non-covalent interactions. Immunostimulants and Treg promoting immunomodulators that are water soluble and are preferred for attachment to hydrophobic molecules for admixing with amphiphiles and/or peptide antigen conjugates include but are not limited to peptide-based NLRs, such as muramyl dipeptide and any derivatives thereof; adenine-based agonists of TLR-7, as well as highly-water soluble nucleic acid-based agonists of TLR-3, TLR-7, TLR-9, STING and MDA5; certain agonists of aryl hydrocarbon receptor (AHR), such as kynurenine and kynurenic acid; moderately water soluble adenosine receptor agonists, e.g., agonists of $A_{2A}$, such as ATL-146e, YT-146, (N6-(2-(3,5-dimethoxyphenyl)-2-(2-methylphenyl)ethyl) adenosine (DPMA), regadenoson or zeatin; and protein and peptide-based agonists of TGF-β, IL-17, IL-2 and IL-10 receptors.

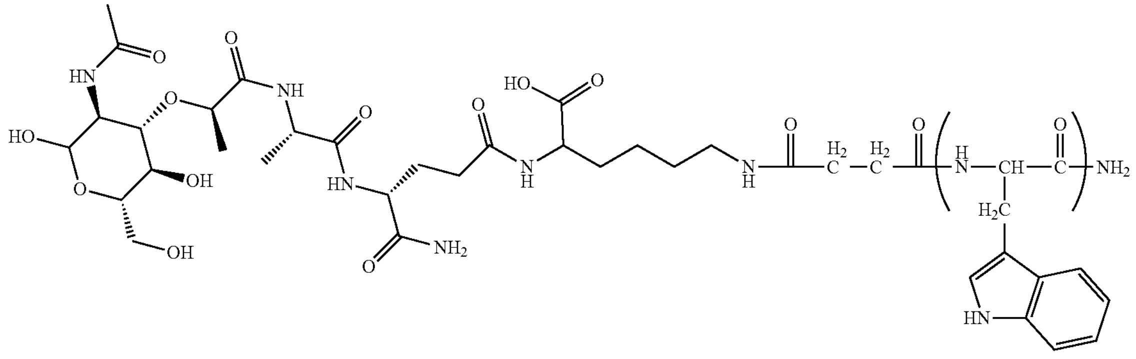

While admixing drug molecule conjugates (e.g., D-H or H-D) with amphiphiles and/or peptide antigen conjugates (e.g., D-H+S-[B]-[U]-H and/or PEG-[E1]-A-[E2]-[U]-H) is the preferred means to incorporate amphiphilic or hydrophilic drug molecules into the hydrophobic core of particles comprising the amphiphiles and/or peptide antigen conjugates for vaccines for inducing tolerance, such an approach is also effective for incorporating hydrophobic drug molecules, particularly when two or more different drug molecules are included in the vaccine for inducing tolerance.

An alternative means of incorporating nucleic acid-based drug molecules, such as nucleic acid-based agonists of TLR-3, TLR-7, TLR-9, STING and MDA5, includes electrostatic complexation with a positively charged hydrophobic block. Preferred compositions of amphiphiles and/or hydrophobic blocks for complexing nucleic acids are described elsewhere.

The inventors of the present disclosure identified compositions of vaccines for inducing tolerance that comprise specific, preferred combinations of drug molecules selected from immunostimulants and Treg promoting immunomodulators that led to unexpected improvements in the induction of regulatory T cells (Tregs) and/or trans-differentiation of Thl/Th2/Th17 cells to Tregs. Specifically, it was observed that, for vaccines for inducing tolerance comprising one or more peptide antigen conjugate of formula PEG-[E]-A-[E2]-[U]-H, an amphiphile of formula S-[B]-[U]-H and a drug molecule (D) comprising a Treg promoting immunomodulator selected from inhibitors of mTOR (e.g., Rapamycin, KU-0063794), RORγt (e.g., SR1555), CDK8/19 (e.g., CCT251921) and HDACs (e.g., SAHA, TMP269, etc.), as well as agonists of AHR (e.g., Kynurenine, Tryptamine, etc.), RAR (e.g., all-trans retinoic acid, BMS961, etc.) and $A_{2a}$ (e.g., Zeatin or UK 432,097), and a second drug molecule (D2) comprising an immunostimulant selected from agonists of NLRs (e.g., muramyl dipeptide), CLRs (e.g., TDB), TLR-1, -2 and -6 (lipopeptides), TLR-4 (LPS and any derivatives thereof), TLR-7/8a (e.g., imidazoquinolines) and STING (e.g., CDNs, diABZI, etc.) that the magnitude of Tregs was lower than if the immunostimulant was not included. Non-limiting explanations are that the immunostimulant is needed to promote native T cell activation and/or T cell expansion, but that the Treg promoting immunomodulator blocks T cell differentiation towards T helper (Th) phenotypes.

Including immunostimulants in tolerance vaccines generally led to higher magnitude antigen-specific T cell responses; however, the portion of antigen-specific CD4 T cells with Treg phenotype (i.e., FOXP3 expression) depended on the specific combination of Treg promoting immunomodulators and immunostimulants present during T cell priming. For instance, vaccine compositions comprising antigens and immunostimulants generally induced CD4 T cells with Thl, Th2 and/or Th17 phenotypes. Induction of Tregs typically required the addition of a Treg promoting immunomodulator; however, the presence of both an immunostimulant and Treg promoting immunomodulator in vaccine compositions led to CD4 T cells with a distribution of phenotypes that depended on the specific compositions and combinations of immunostimulants and Treg promoting immunomodulators used.

Accordingly, the inventors of the present disclosure found that, when used in vaccines for inducing tolerance, immunostimulants that induced IL-12 and/or Type I IFNs, such as agonists of TLR-3, TLR-4, TLR-7, TLR-8, TLR-9, STING and MDA5 were highly Thl polarizing and typically required the addition of Treg promoting immunomodulators selected from dual mTOR complex 1 (mTORC1) and mTOR complex 2 (mTORC2) inhibitors, including Torin 1 (Cas: 1222998-36-8), KU-0063794 (Cas: 938440-64-3) and omipalisib (Cas: 1086062-66-9), to block differentiation of CD4 T cells to Thl, Th2 and Th17 phenotypes, thus promoting CD4 T cell differentiation to Tregs. In contrast, immunostimulants that that induced lower or no IL-12 and/or Type I IFNs, such as agonists of CLRs, NLRs, TLR-1, TLR-2, TLR-5 and/or TLR-6 typically required the addition of Treg promoting immunomodulators selected from inhibitors of mTORC1 (e.g. Rapamcyin, Dactolisib, Everolimus and Temsirolimus, etc.), inhibitors of RORγt or agonists of AHR and/or RAR to promote CD4 T cell differentiation to Tregs. Thus, in preferred embodiments of the vaccine for inducing tolerance comprising an immunostimulant, the vaccine further comprises at least one Treg promoting immunomodulator selected from dual inhibitors of mTORC1 and mTORC2, such as Torin 1, KU-0063794, and omipalisib. In still other embodiments of the vaccine for inducing tolerance comprising an immunostimulant, wherein the immunostimulant is selected from agonists of CLRs, NLRs, TLR-1, TLR-2, TLR-5 and/or TLR-6, the vaccine further comprises at least one Treg promoting immunomodulator selected from dual inhibitors of mTORC1 and mTORC2, such as Torin 1, KU-0063794, and omipalisib, or inhibitors of mTORC1 (e.g. Rapamcyin, Dactolisib, Everolimus and Temsirolimus, etc.), inhibitors of RORγt or agonists of AHR and/or RAR. Compositions of vaccines for inducing tolerance In certain preferred embodiments of the vaccine for inducing tolerance, the amphiphile is absent and the vaccine comprises one or more, typically between 1 to 40, peptide antigen conjugates of formula PEG-[E1]-A-[E2]-[U]-H-[D]

(or [D]-H-[U]-[E1]-A-[E2]-PEG), wherein each peptide antigen conjugate typically comprises an antigen (A) selected from autoantigens, alloantigens or allergens. In preferred embodiments of the vaccine for inducing tolerance the vaccine comprises one or more, typically between 1 to 40, peptide antigen conjugates of formula PEG-[E1]-A-[E2]-[U]-H-[D] (or [D]-H-[U]-[E1]-A-[E2]-PEG) and an amphiphile of formula S-[B]-[U]-H-[D], wherein each peptide antigen conjugate typically comprises an antigen (A) selected from autoantigens, alloantigens or allergens, which is linked either directly or via an extension (E1 or E2) and/or Linker U to a hydrophobic block (H), which is typically selected from poly(amino acids) of Formula I comprising hydrophobic amino acids (M) and/or reactive amino acids (N) linked to drug molecules (D); and, additionally when present the amphiphile is selected from amphiphiles with dendron or linear architecture comprising a solubilizing block(S) linked either directly or via a spacer (B) and/or Linker U to a hydrophobic block (H) typically selected from poly(amino acids) of Formula I comprising hydrophobic amino acids (M) and/or reactive amino acids (N) linked to drug molecules (D); and, wherein the amphiphile has dendron architecture the solubilizing block is selected from dendron amplifiers with between 2 and 32, more preferably between 4 and 8, solubilizing groups (SG) selected from carboxylic acid, phosphoserine (or glycerophosphoserine), glucose, mannose, glucosamine, n-acetylglucosamine, galactose, galactosamine, n-acetyl-galactosamine and/or agonists of CD22a, which may be linked either directly or indirectly via a linker (X) to the terminal functional groups (FGt) of the solubilizing block(S) with dendron architecture through any suitable means, though, in preferred embodiments the solubilizing group is linked to FGt via an amide bond. A non-limiting example is provided here for clarity:

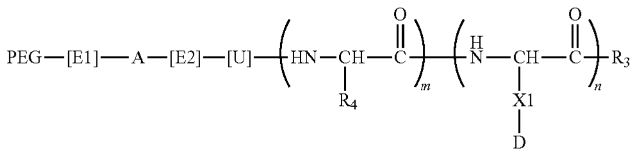

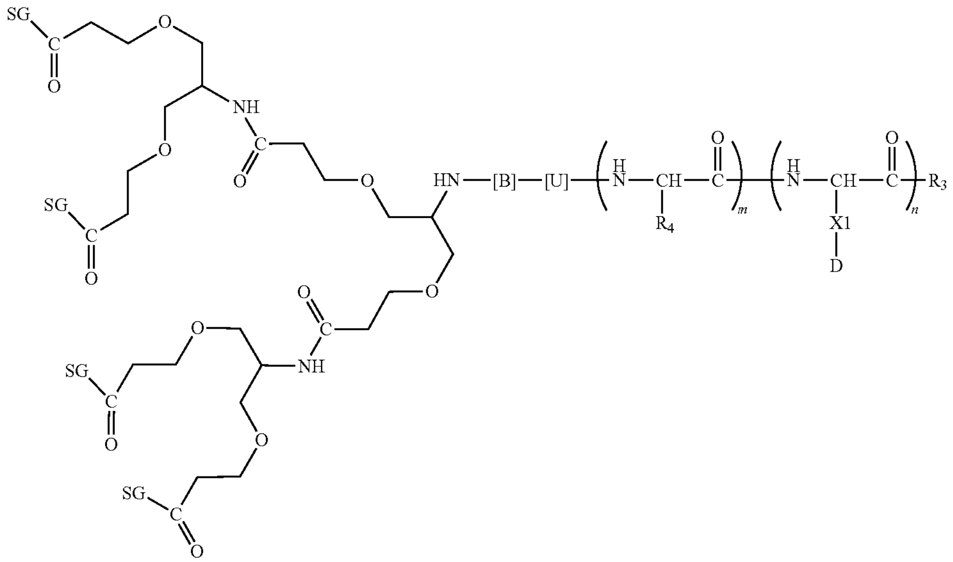

wherein PEG typically comprises between 12 and 36 monomeric units, more preferably between 20 and 28 monomeric unites, and most preferably 24 monomeric units and is capped with a hydroxyl group; X1 is any suitable linker molecule, D is any suitable drug molecule typically selected from immunostimulants and/or Treg promoting immunomodulators, $R^3$ is typically selected from hydrogen, $NH_2$, $NH_2—CH_3$, $NH_2—(CH_2)_{y5}CH_3$, OH, or drug molecules (D) either linked directly or through any suitable linker molecule (X); m and n are any integers, wherein the sum of m and n (when present) is greater than 3, typically between about 3 and 30.

In preferred embodiments, the hydrophobic block (H) comprises poly(amino acids) of Formula I is typically selected from hydrophobic amino acids (M) selected from AHR agonists (e.g., kynurenine or 5HT) or IDO substrates (e.g., tryptophan) and/or reactive amino acids linked to hydrophobic immunomodulators (e.g., tryptamine). In the above example, wherein the hydrophobic block comprises hydrophobic amino acids selected from tryptophan, and wherein $R^3$ is an amine, the structure is:

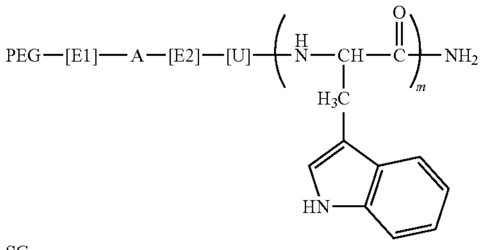

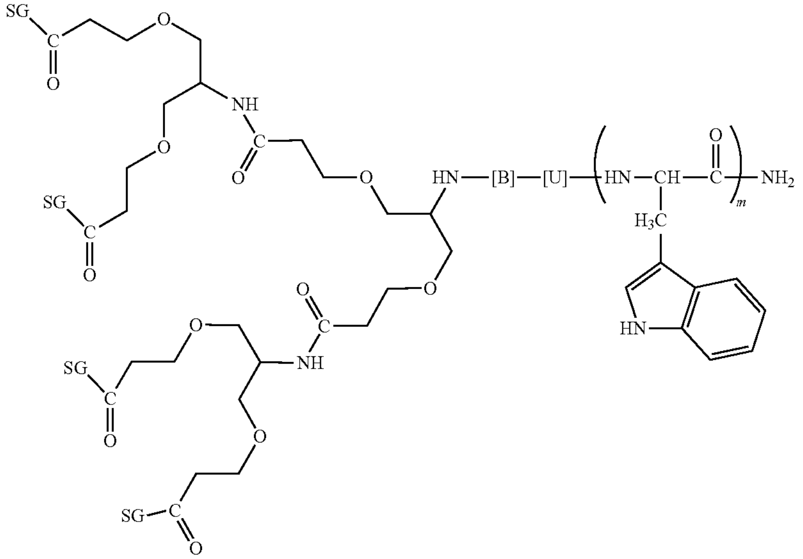

wherein PEG typically comprises between 12 and 36 monomeric units, more preferably between 20 and 28 monomeric unites, and most preferably 24 monomeric units and is capped with a hydroxyl group; U is present and selected from triazoles, e.g., a triazole resulting from the reaction of DBCO with azide; E1 is typically selected from Val-Cit and E2 is typically selected from Ser-Pro-Val-Cit; and D, is present and is typically selected from Rapamycin or Torin-1. In certain preferred embodiments of the vaccine for inducing tolerance, the amphiphile is absent and the vaccine comprises one or more, typically between 1 to 40, peptide antigen conjugates of formula PEG-[E1]-A-[E2]-[U]-H-[D] (or [D]-H-[U]-[E1]-A-[E2]-PEG), In some preferred embodiments of the vaccine for inducing tolerance, the solubilizing group of the amphiphile, when present, is selected from groups comprising carboxylic acids, mannose, phosphoserine (or glycerophosphoserine), glucose, glucosamine, n-acetylglucosamine, galactose, galactosamine, n-acetyl-galactosamine and/or agonists of CD22a, that are linked to S either directly or via a suitable linker X, or, more preferably, X5, typically selected from a lower alkyl or ethylene oxide linker. In the above example, wherein the solubilizing group comprises a carboxylic acid and is selected from beta-alanine and the spacer B is selected from PEG the structure is:

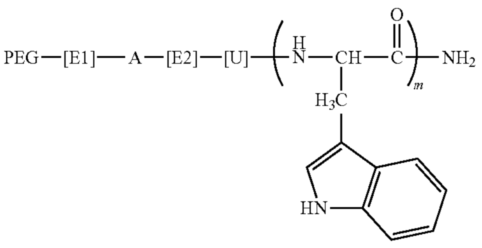
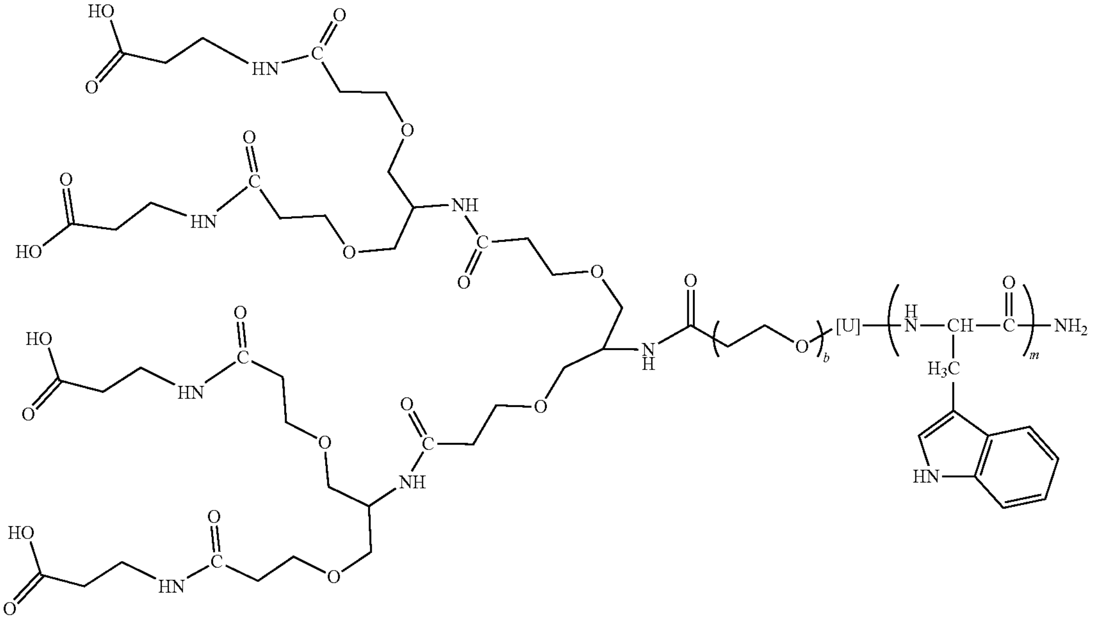
In the above example, wherein the solubilizing group comprises β-GalNAc linked via X5 to the terminal functional group (FGt) of the dendron-based solubilizing block, the structure is:
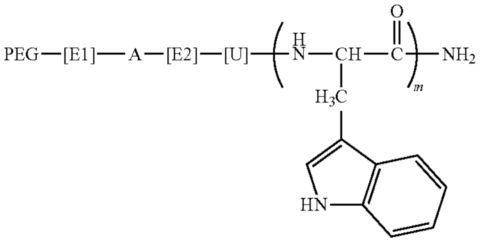

-continued
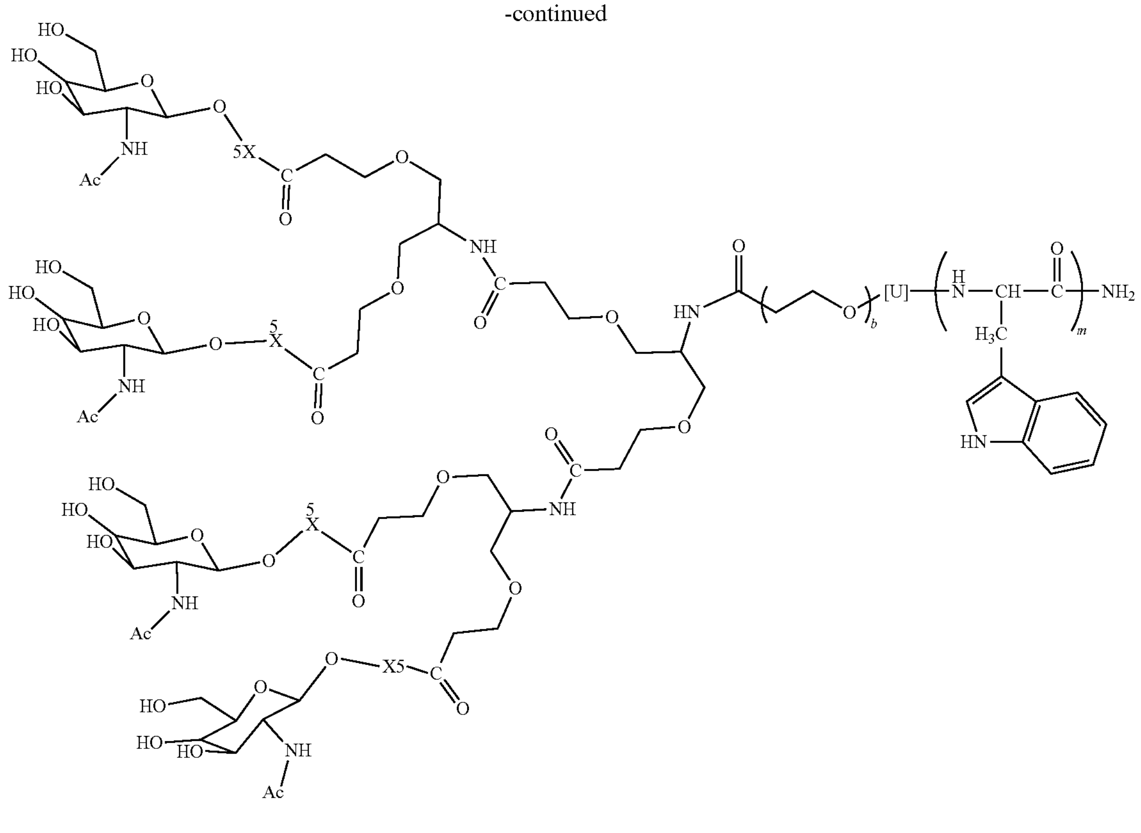
In the above example, wherein the solubilizing group comprises mannose linked via X5 to the terminal functional group (FGt) of the dendron-based solubilizing block, the structure is:
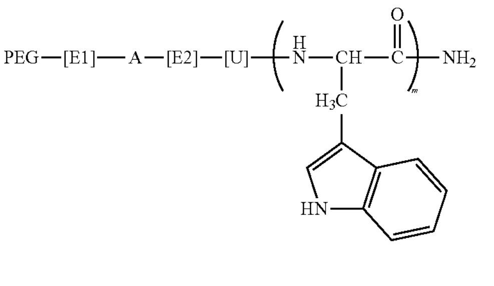

-continued

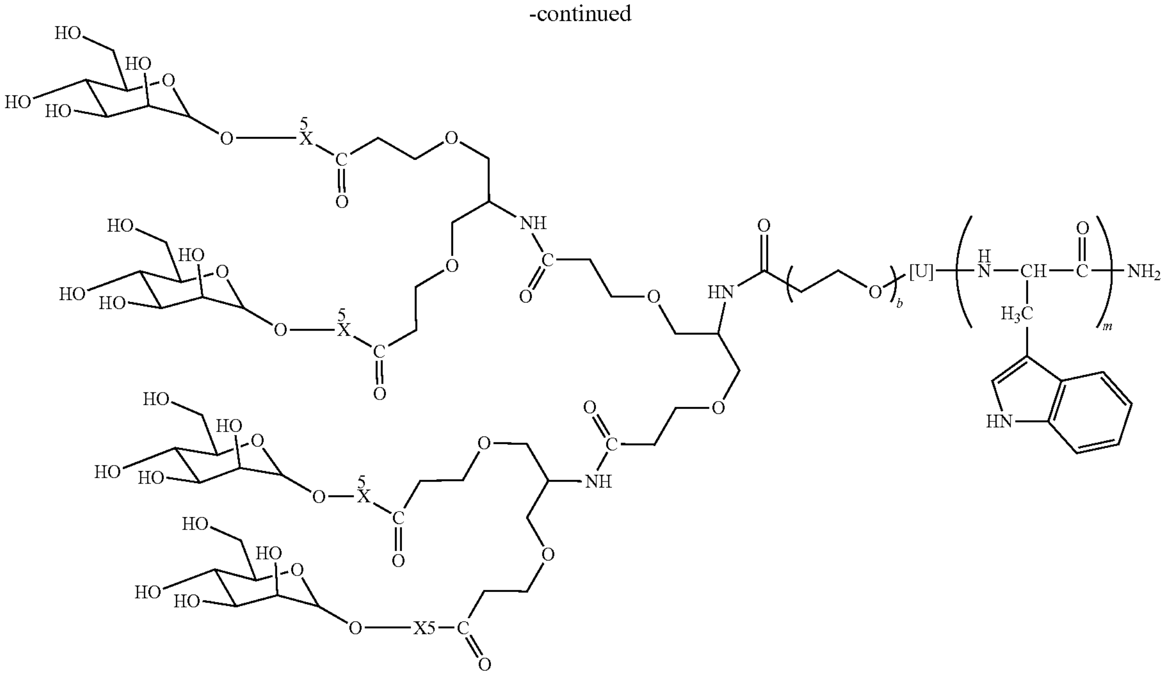

In preferred embodiments of the vaccine for inducing tolerance, the vaccine comprises one or more peptide antigen conjugates of formula PEG-E1-A-E2-U-H, typically between 1 and 40, each comprising a unique peptide antigen; the PEG comprises 24 monomeric units and is capped with a hydroxyl, E1 is selected from Val-Cit and E2 is selected from Ser-Pro-Val-Cit; U is present and selected from triazoles, e.g., a triazole resulting from the reaction of DBCO with azide. D is present and is typically selected from Rapamycin. In certain embodiment of the vaccine, the amphiphile is absent. The amphiphile when present comprises a solubilizing block(S) comprising a dendron amplifier, preferably selected from lysine dendron amplifiers, with 4 solubilizing groups (SG) selected from mannose, which are linked to the terminal functional groups (FGt) of the solubilizing block(S) with dendron architecture through an amide bond. A non-limiting example is provided here for clarity:

Peptide antigen conjugate of formula PEG-E1-A-E2-U-H

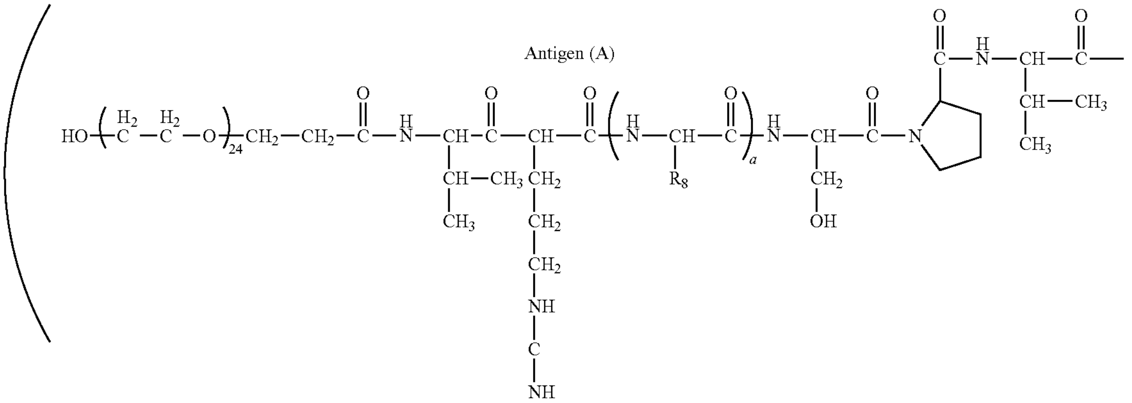

-continued
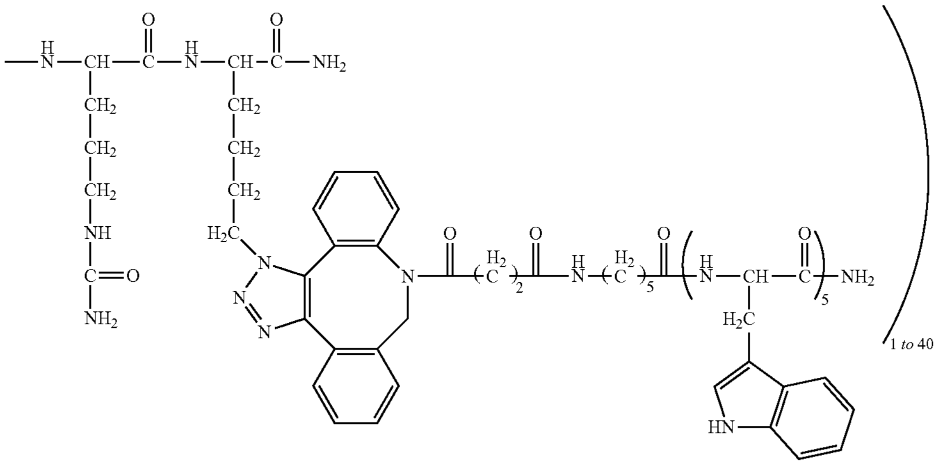
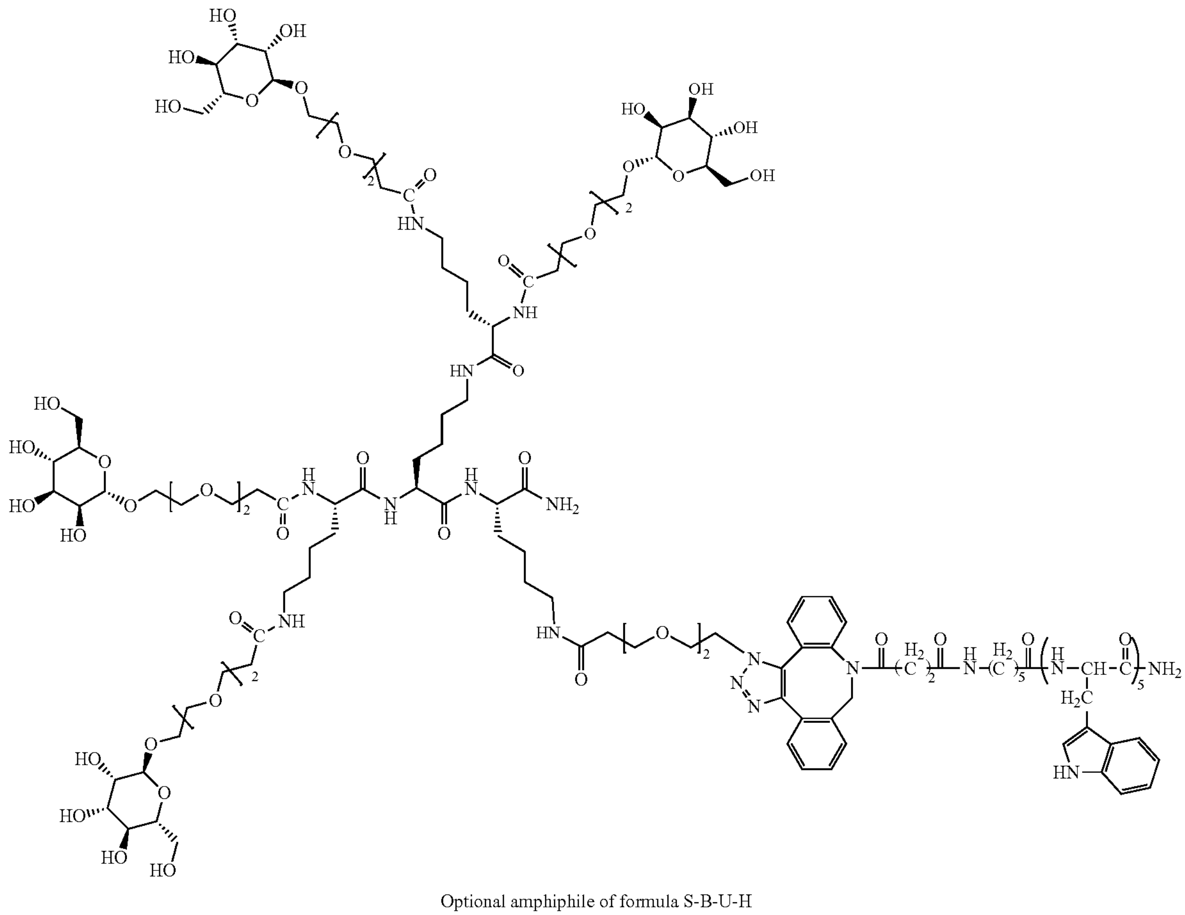
Optional amphiphile of formula S-B-U-H

-continued

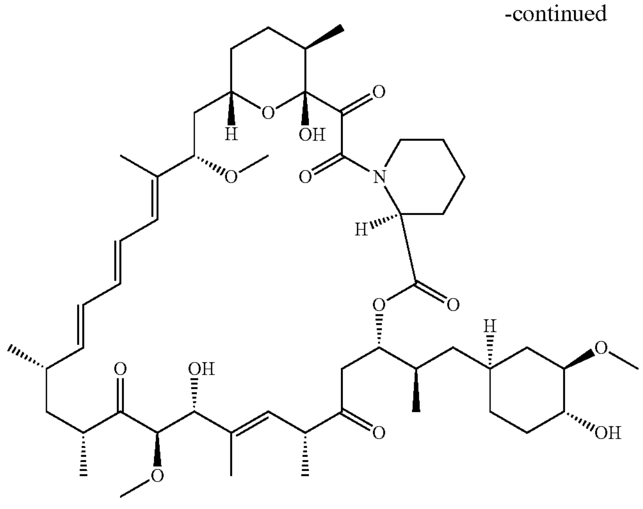

Drug (D), rapamycin

Wherein in the above example the amphiphile is optional; the total peptide antigen conjugate to amphiphile (when present) to drug molecule (D) (e.g., rapamycin) molar ratio is 1:1:1; the concentration of peptide antigen conjugate is ≥0.5 or ≥1 mM; and the vaccine comprises up to 12.5% DMSO in aqueous solution, e.g., formulation buffer, at pH between 5.5 and 8.5, more preferably pH between 6.0 and 8.0 or pH between 6.5 and 8.0.

In the above (immediately preceding) example, wherein the vaccine is used to treat celiac disease, up to 15 unique peptide antigen conjugates are selected and comprise peptide antigens (A) selected from QLQPFPQPELPYPQPQLPYPQPQPFR (SEQ ID NO:486), PQLPYPQPELPYPQPQPFRPEQPYPQPQP (SEQ ID NO:487), QGIIQPEQPAQLEVI (SEQ ID NO: 464), PQPQQPEQPFPQPEQEFPQPQQPQQSFPEQQPPL (SEQ ID NO:488), PQQPFPQPEQPFCQQPQ (SEQ ID NO: 489), QQFLQPEQPFPQQPEQPYPQQPEQPFPQPQQ (SEQ ID NO: 490), QQFSQPEQEFPQPQQPQQSFPEQQPPF (SEQ ID NO:491), PTPLQPEQPFPQQPQQPQQPFPQPEQPFPWQPQ (SEQ ID NO:492), SSPLQPEQPFPQQPQQPFPEQPQQPQ (SEQ ID NO:493), QSIPQPEQPFPQPEQPFPQSQE (SEQ ID NO: 494), PQQPFPQQPQQIIPQ (SEQ ID NO:495), PQQPIPEQPQPYPEQPQPYPQQ (SEQ ID NO: 496), QQPPFSEQEQPVLPQ (SEQ ID NO:484), QPPFSQQQESPFSQQ (SEQ ID NO:485) and PQQPFPQPEQPFBQQPQ (SEQ ID NO: 497) wherein, independently for each instance of glutamine, (Q), the one or more glutamines may be deamidated, i.e., Gln (Q) is replaced with Glu (E); the drug molecule (D) rapamycin is present, and the amphiphile is absent; the total peptide antigen conjugate to rapamycin molar ratio is 1:1; the concentration of peptide antigen conjugate is ≥1 mM; and the vaccine comprises up to 12.4% DMSO, preferably less than 10% DMSO in formulation buffer consisting of 50 mM Tris in normal saline (0.9% NaCl) at pH between 5.5 and 8.5, more preferably pH between 6.0 and 8.0 or 6.5 and 8.0. In some embodiments, the vaccine comprises 12 unique peptide antigens conjugates that comprise peptide antigens selected from QLQPFPQPELPYPQPQLPYPQPQPFR (SEQ ID NO: 486), PQLPYPQPELPYPQPQP-FRPEQPYPQPQP (SEQ ID NO:487), PQPQQPEQPFPQPEQEFPQPQQPQQSFPEQQPPL (SEQ ID NO: 488), PQQPFPQPEQPFBQQPQ (SEQ ID NO: 497), QQFLQPEQPFPQQPEQPYPQQPEQPFPQPQQ (SEQ ID NO:490), QQFSQPEQEFPQPQQPQQSFPEQQPPF (SEQ ID NO:491), PTPLQPEQPFPQQPQQPQQPFPQPEQPFPWQPQ (SEQ ID NO:492), SSPLQPEQPFPQQPQQPFPEQPQQPQ (SEQ ID NO:493), QSIPQPEQPFPQPEQPFPQSQE (SEQ ID NO: 494), PQQPFPQQPQQIIPQ (SEQ ID NO:495), PQQPIPEQPQPYPEQPQPYPQQ (SEQ ID NO: 496), and QQPPFSEQEQPVLPQ (SEQ ID NO:484).

In some embodiments of the vaccine for inducing tolerance, the vaccine comprises at least one peptide antigen conjugate having the formula selected from PEG-[E1]-A-[E2]-[U]-H and H-[U]-[E1]-A-[E2]-PEG, wherein A is QLQPFPQPELPYPQPQLPYPQPQPFR (SEQ ID NO:486).

In some embodiments of the vaccine for inducing tolerance, the vaccine comprises at least one peptide antigen conjugate having the formula selected from PEG-[E1]-A-[E2]-[U]-H and H-[U]-[E1]-A-[E2]-PEG, wherein A is PQLPYPQPELPYPQPQPFRPEQPYPQPQP (SEQ ID NO:487).

In some embodiments of the vaccine for inducing tolerance, the vaccine comprises at least one peptide antigen conjugate having the formula selected from PEG-[E1]-A-[E2]-[U]-H and H-[U]-[E1]-A-[E2]-PEG, wherein A is QGIIQPEQPAQLEVI (SEQ ID NO: 464).

In some embodiments of the vaccine for inducing tolerance, the vaccine comprises at least one peptide antigen conjugate having the formula selected from PEG-[E1]-A-[E2]-[U]-H and H-[U]-[E1]-A-[E2]-PEG, wherein A is PQPQQPEQPFPQPEQEFPQPQQPQQSFPEQQPPL (SEQ ID NO:488).

In some embodiments of the vaccine for inducing tolerance, the vaccine comprises at least one peptide antigen conjugate having the formula selected from PEG-[E1]-A-[E2]-[U]-H and H-[U]-[E1]-A-[E2]-PEG, wherein A is PQQPFPQPEQPFCQQPQ (SEQ ID NO:489).

In some embodiments of the vaccine for inducing tolerance, the vaccine comprises at least one peptide antigen conjugate having the formula selected from PEG-[E1]-A-[E2]-[U]-H and H-[U]-[E1]-A-[E2]-PEG, wherein A is QQFLQPEQPFPQQPEQPYPQQPEQPFPQPQQ (SEQ ID NO:490).

In some embodiments of the vaccine for inducing tolerance, the vaccine comprises at least one peptide antigen conjugate having the formula selected from PEG-[E1]-A-[E2]-[U]-H and H-[U]-[E1]-A-[E2]-PEG, wherein A is QQFSQPEQEFPQPQQPQQSFPEQQPPF (SEQ ID NO:491).

In some embodiments of the vaccine for inducing tolerance, the vaccine comprises at least one peptide antigen conjugate having the formula selected from PEG-[E1]-A-[E2]-[U]-H and H-[U]-[E1]-A-[E2]-PEG, wherein A is SSPLQPEQPFPQQPQQPFPEQPQQPQ (SEQ ID NO:493).

In some embodiments of the vaccine for inducing tolerance, the vaccine comprises at least one peptide antigen conjugate having the formula selected from PEG-[E1]-A-[E2]-[U]-H and H-[U]-[E1]-A-[E2]-PEG, wherein A is QSIPQPEQPFPQPEQPFPQSQE (SEQ ID NO:494).

In some embodiments of the vaccine for inducing tolerance, the vaccine comprises at least one peptide antigen conjugate having the formula selected from PEG-[E1]-A-[E2]-[U]-H and H-[U]-[E1]-A-[E2]-PEG, wherein A is PQQPFPQQPQQIIPQ (SEQ ID NO:495).

In some embodiments of the vaccine for inducing tolerance, the vaccine comprises at least one peptide antigen conjugate having the formula selected from PEG-[E1]-A-[E2]-[U]-H and H-[U]-[E1]-A-[E2]-PEG, wherein A is PQQPIPEQPQPYPEQPQPYPQQ (SEQ ID NO: 496).

In some embodiments of the vaccine for inducing tolerance, the vaccine comprises at least one peptide antigen conjugate having the formula selected from PEG-[E1]-A-[E2]-[U]-H and H-[U]-[E1]-A-[E2]-PEG, wherein A is QQPPFSEQEQPVLPQ (SEQ ID NO:484).

In some embodiments of the vaccine for inducing tolerance, the vaccine comprises at least one peptide antigen conjugate having the formula selected from PEG-[E1]-A-[E2]-[U]-H and H-[U]-[E1]-A-[E2]-PEG, wherein A is QPPFSQQQESPFSQQ (SEQ ID NO:485).

In some embodiments of the vaccine for inducing tolerance, the vaccine comprises at least one peptide antigen conjugate having the formula selected from PEG-[E1]-A-[E2]-[U]-H and H-[U]-[E1]-A-[E2]-PEG, wherein A is PQQPFPQPEQPFBQQPQ (SEQ ID NO: 497).

In some embodiments of the vaccine for inducing tolerance, the vaccine comprises at least one peptide antigen conjugate having the formula selected from PEG-[E1]-A-[E2]-[U]-H and H-[U]-[E1]-A-[E2]-PEG, wherein A is QLQPFPQPELPYPQPQLPYPQPQPFR (SEQ ID NO:486).

In some embodiments of the vaccine for inducing tolerance, the vaccine comprises at least one peptide antigen conjugate having the formula selected from PEG-[E1]-A-[E2]-[U]-H and H-[U]-[E1]-A-[E2]-PEG, wherein A is selected from QLQPFPQPELPYPQPQLPYPQPQPFR (SEQ ID NO:486), PQLPYPQPELPYPQPQP-FRPEQPYPQPQP (SEQ ID NO:487), QGIIQPEQPAQLEVI (SEQ ID NO: 464), PQPQQPEQPFPQPEQEFPQPQQPQQSFPEQQPPL (SEQ ID NO:488), PQQPFPQPEQPFCQQPQ (SEQ ID NO: 489), QQFLQPEQPFPQQPEQPYPQQPEQPFPQPQQ (SEQ ID NO: 490), QQFSQPEQEFPQPQQPQQSFPEQQPPF (SEQ ID NO:491), PTPLQPEQPFPQQPQQPQQPFPQPEQPFPWQPQ (SEQ ID NO:492), SSPLQPEQPFPQQPQQPFPEQPQQPQ (SEQ ID NO:493), QSIPQPEQPFPQPEQPFPQSQE (SEQ ID NO: 494), PQQPFPQQPQQIIPQ (SEQ ID NO:495), PQQPIPEQPQPYPEQPQPYPQQ (SEQ ID NO: 496), QQPPFSEQEQPVLPQ (SEQ ID NO:484), QPPFSQQQESPFSQQ (SEQ ID NO:485), PQQPFPQPEQPFBQQPQ (SEQ ID NO: 497) and combinations thereof.

In certain preferred embodiments of tolerance vaccines, the peptide antigen conjugate comprises a charged block (C) that further comprises a poly(amino acid) selected from lysine and the above structure becomes:

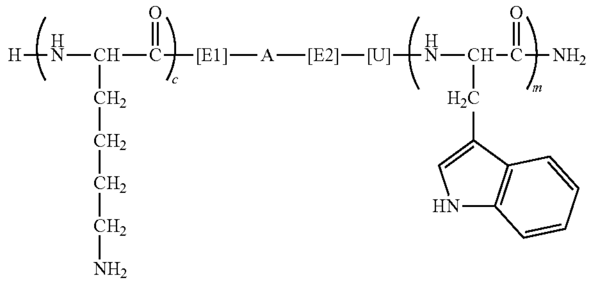

-continued

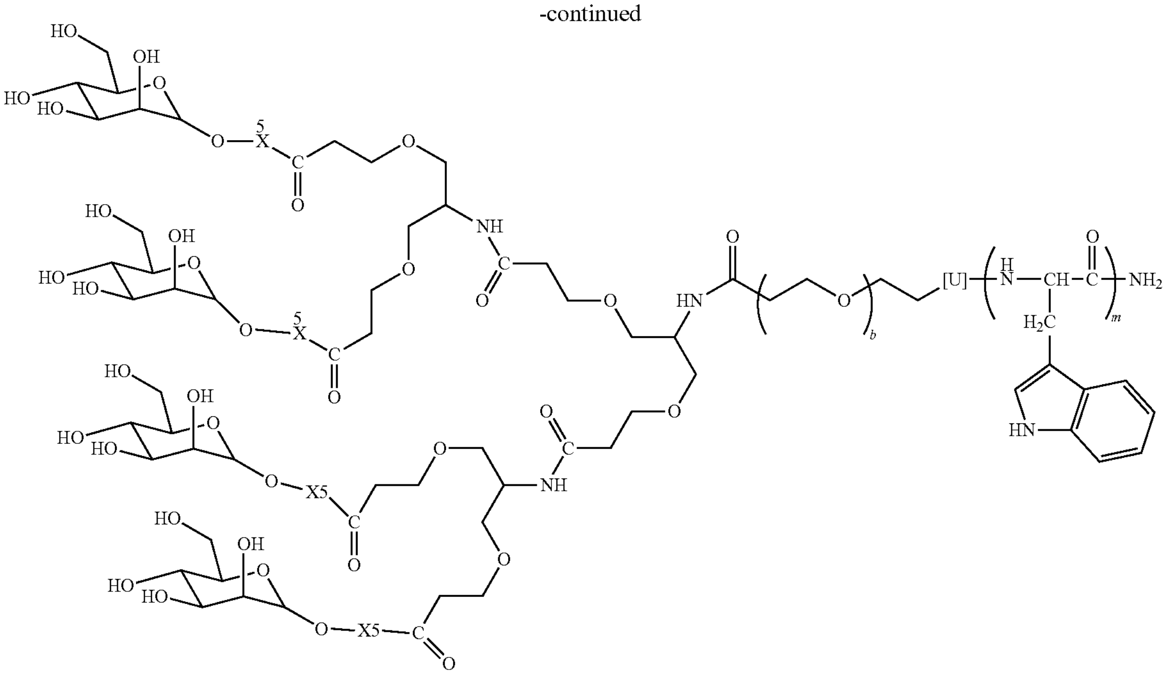

wherein c represents an integer number of repeat units that is selected such that the peptide antigen conjugate net charge at physiologic pH is greater than 2, preferably between 2 and 6, such as 1, 2, 3, 4, 5 or 6, most preferably between 3 and 5, such as 3; A is a peptide antigen, E1 is an N-terminal extension, E2 is a C-terminal extension; m is typically between 3 and 30; X5 is a linker typically selected from PEG or short aliphatic groups and b is an integer number of repeating units typically selected from between about 4 to about 36 monomeric units, though, more preferably between about 12 to 24 units.

In some preferred embodiments of the vaccine for inducing tolerance, the peptide antigen conjugate and/or amphiphile comprises a Linker U, preferably selected from linkers comprising a triazoline ring that results from the reaction of an azide with an alkyne. In the above example, wherein the peptide antigen conjugate and the amphiphile comprise a Linker U further comprising a triazole, a non-limiting example of a possible resulting structure is:

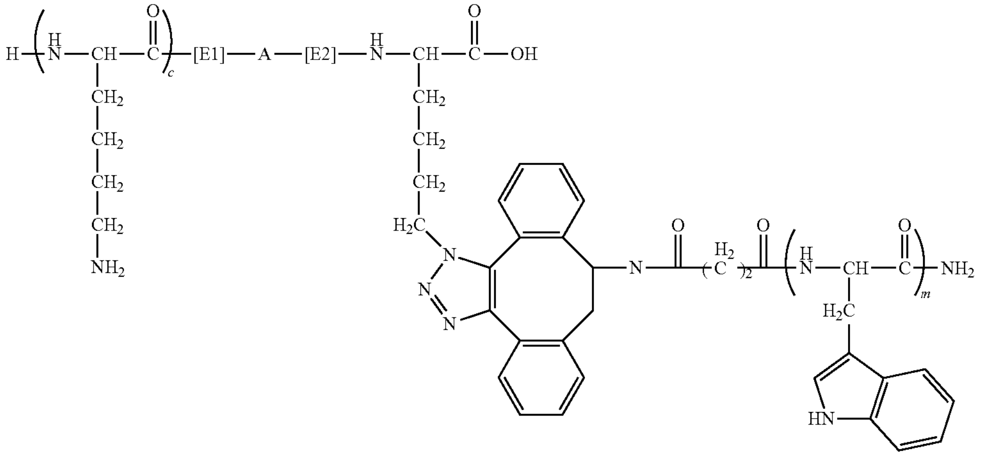

-continued
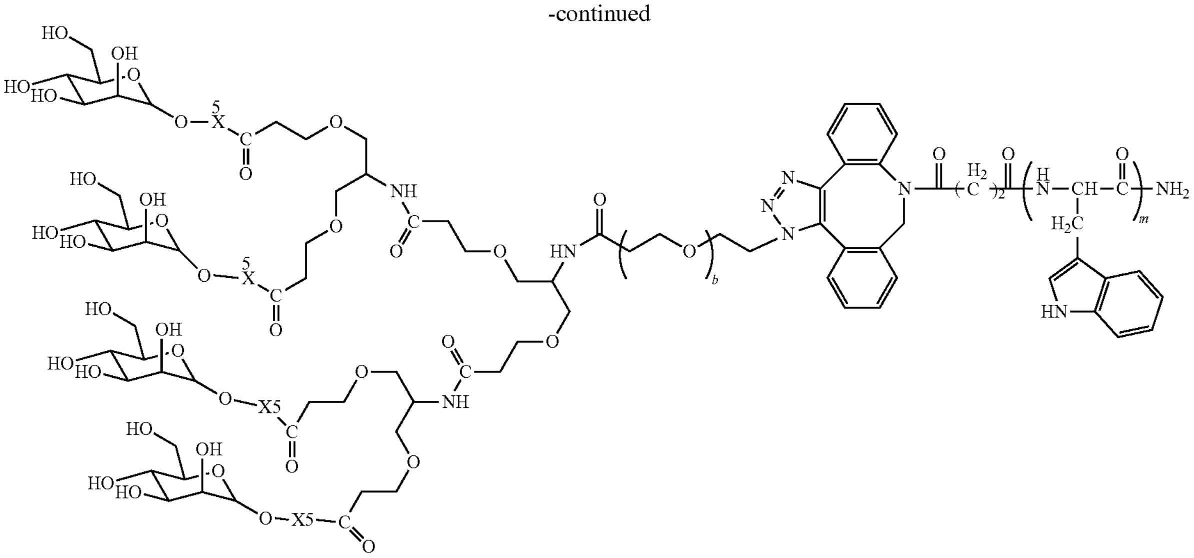
In still further preferred embodiments, the peptide antigen conjugate comprises an E1 N-terminal extension, typically selected from Val-Arg and an E2 C-terminal extension typically selected from Ser-Pro-Val-Cit and a X5 linker selected from PEG3, and the structure becomes:
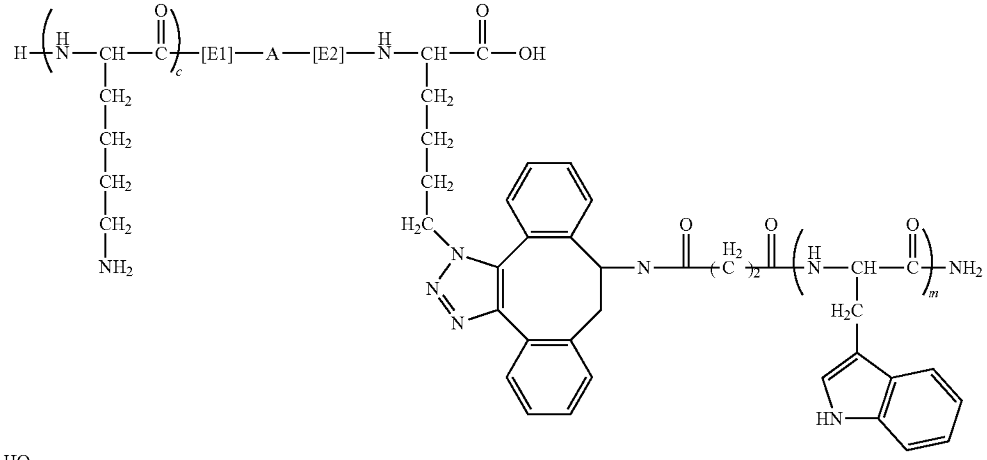
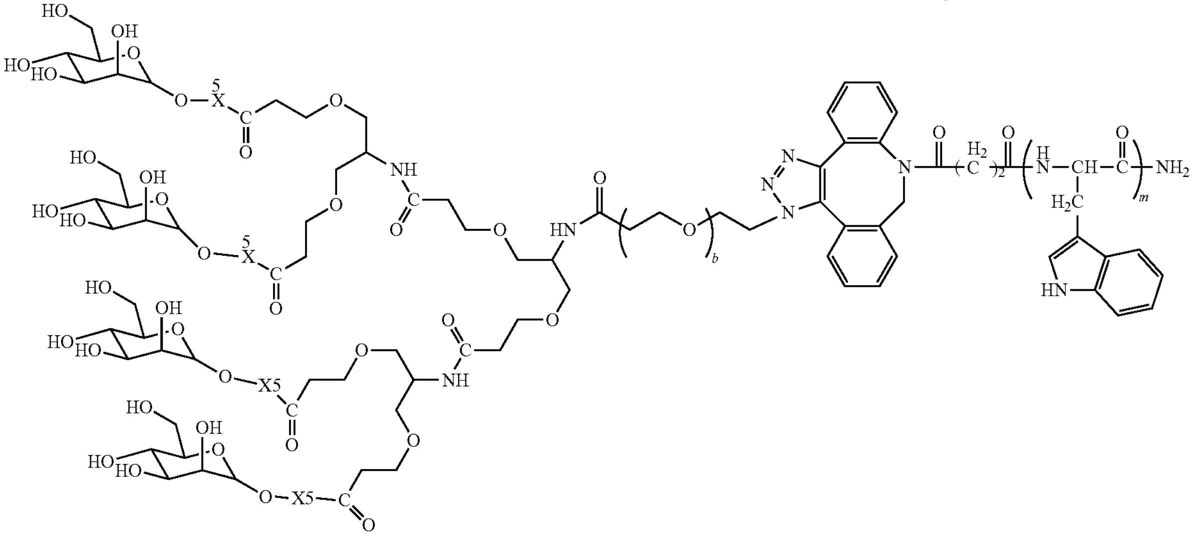

wherein c represents an integer number of repeat units that is selected such that the peptide antigen conjugate net charge at physiologic pH is greater than 2, preferably between 2 and 6, such as 1, 2, 3, 4, 5 or 6, most preferably between 3 and 5, such as 3; A is a peptide antigen with an integer, a, number of repeat units typically selected from 7 to 35, wherein R8 is any amino acid side chain; and b is an integer number of repeating units typically selected from between about 4 to about 36 monomeric units, though, more preferably between about 12 to 24 units. In certain preferred embodiments, the solubilizing group is GalNAc the above structure becomes:

Antigen (A)

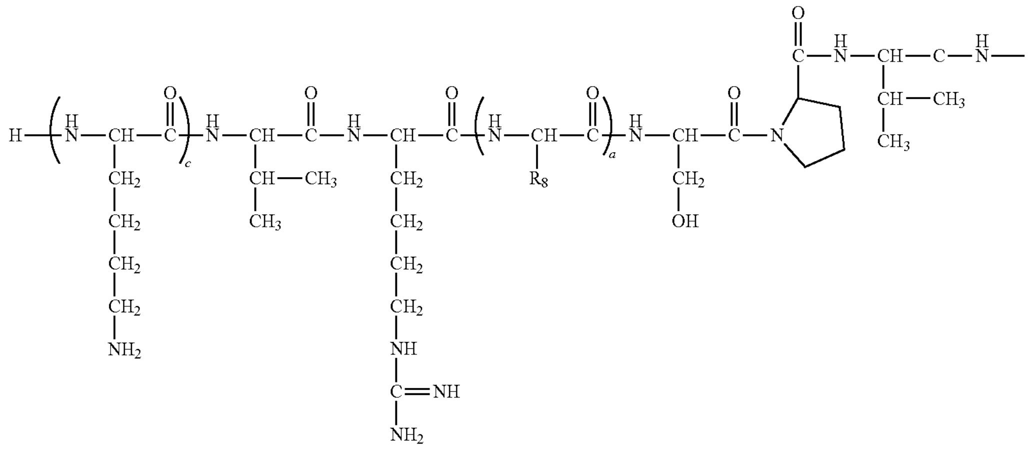

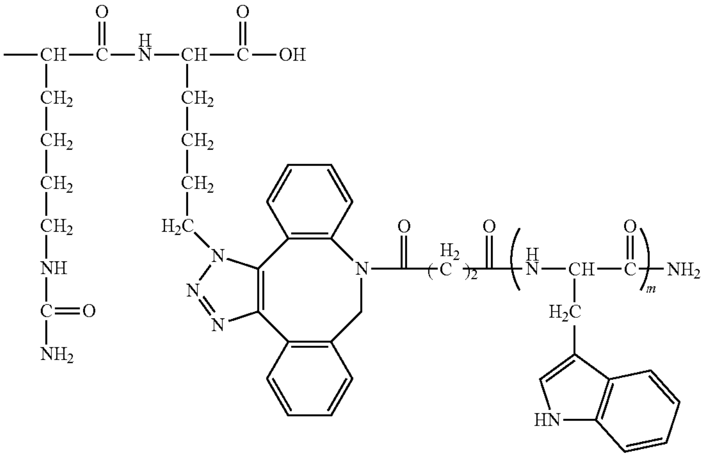

-continued
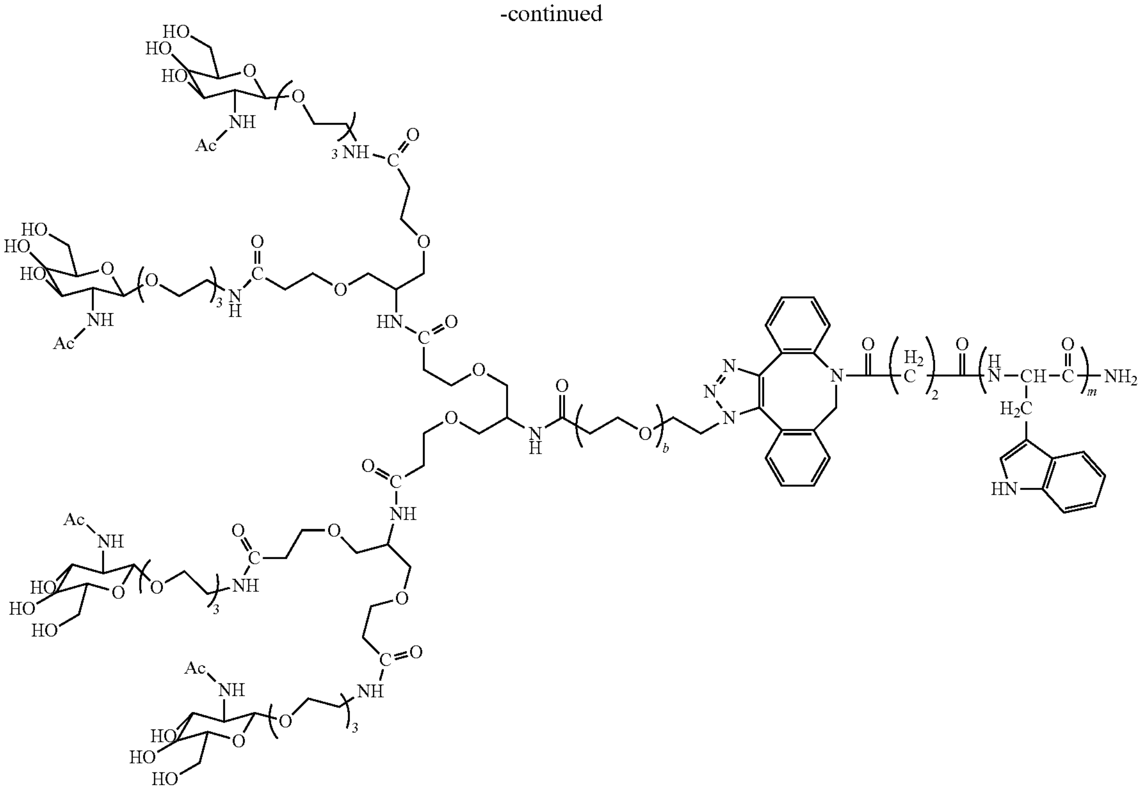
In still other embodiments, the solubilizing block comprises beta-alanine and the structure is:
Antigen (A)
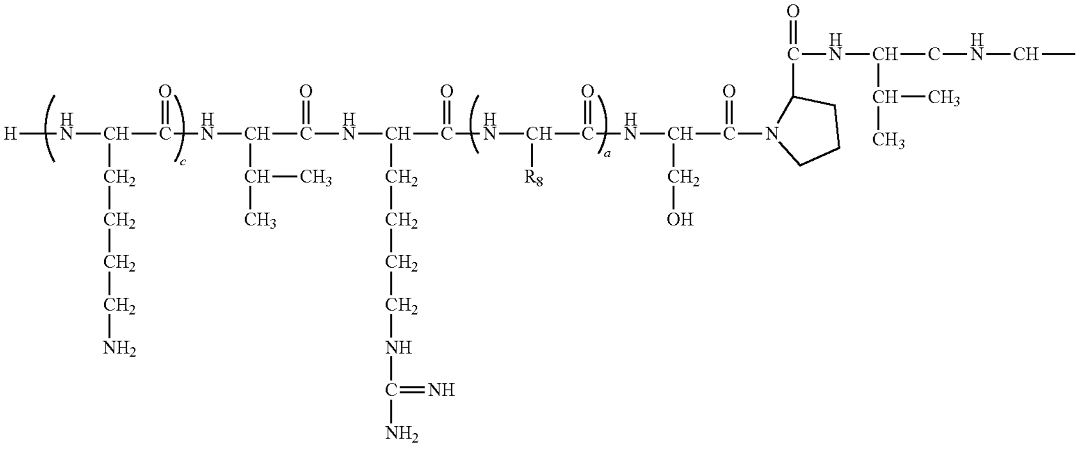

-continued
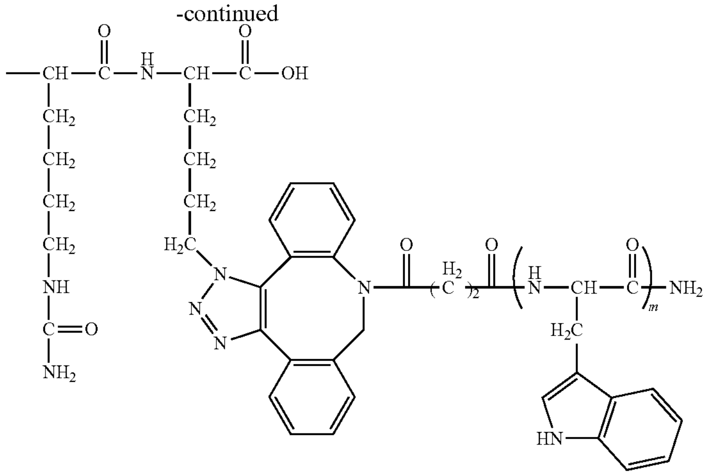
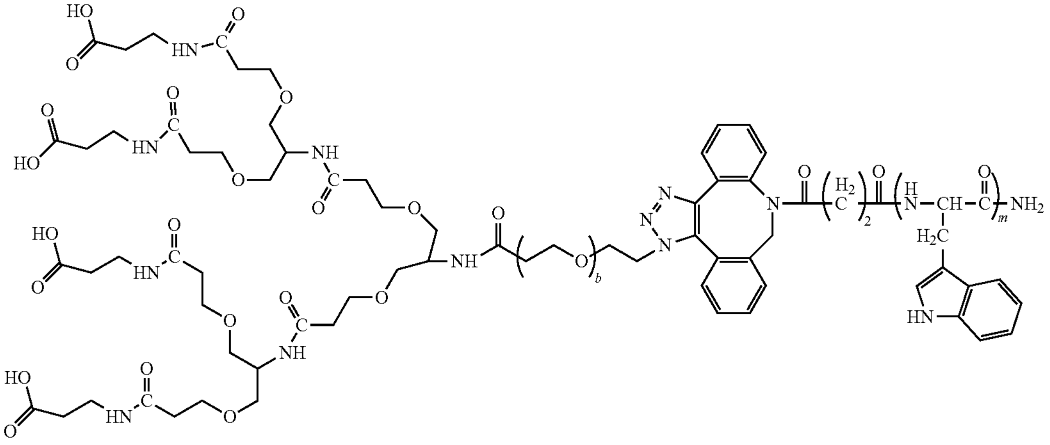
Or, the solubilizing block comprises succinic acid linked to a dendron-based amplifier and the structure is:
Antigen (A)
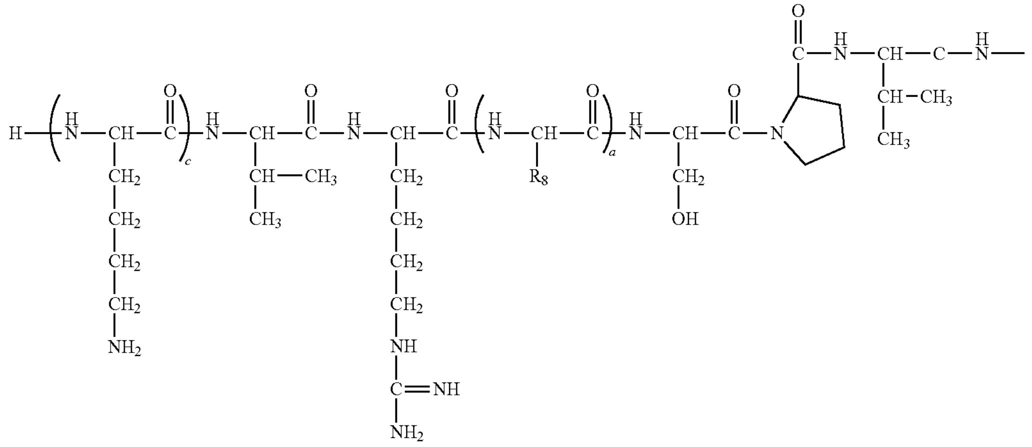

-continued

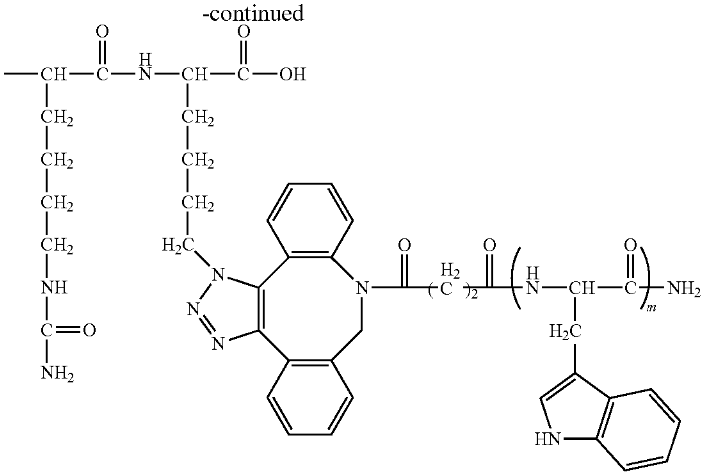

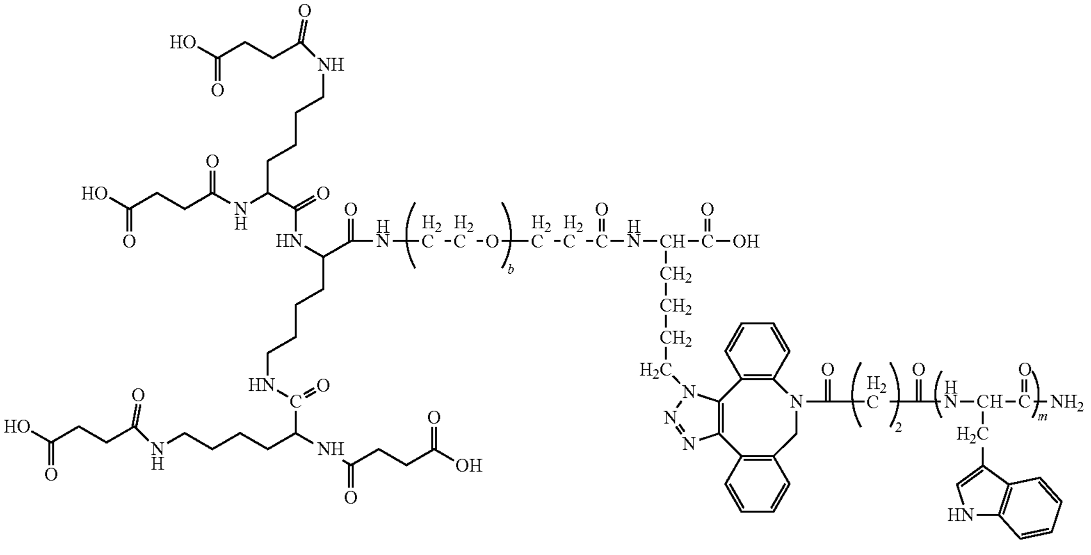

In certain preferred embodiments of the vaccine for inducing tolerance, the vaccine comprises one or more, typically no more than 40, peptide antigen conjugates of formula PEG-[E1]-A-[E2]-[U]-H-[D] (or -[D]-H-[U]-[E1]-A-[E2]-PEG), an amphiphile of formula S-[B]-[U]-H-[D] and a drug molecule (D) selected from inhibitors of mTOR (e.g., rapamycin) or agonists of AHR (e.g., kynurenine or ITE). In certain preferred embodiments of the vaccine for inducing tolerance, the amphiphile is absent and the vaccine comprises one or more, typically no more than 40, peptide antigen conjugates of PEG-[E1]-A-[E2]-[U]-H-[D] (or -[D]-H-[U]-[E1]-A-[E2]-PEG) and a drug molecule (D) selected from inhibitors of mTOR (e.g., rapamycin) or agonists of AHR (e.g., kynurenine or ITE).

In still other preferred embodiments of the vaccine for inducing tolerance, the vaccine comprises one or more, typically no more than 40, peptide antigen conjugates of formula PEG-[E1]-A-[E2]-[U]-H-[D] (or [D]-H-[U]-[E1]-A-[E2]-PEG), an amphiphile of formula S-[B]-[U]-H-[D], a drug molecule (D) comprising a Treg promoting immunomodulator and a second drug molecule (D2) comprising an immunostimulant. In certain preferred embodiments of the vaccine for inducing tolerance, the amphiphile is absent and the vaccine comprises one or more, typically no more than 40, peptide antigen conjugates of formula PEG-[E1]-A-[E2]-[U]-H-[D] (or [D]-H-[U]-[E1]-A-[E2]-PEG, a drug molecule (D) comprising a Treg promoting immunomodulator and a second drug molecule (D2) comprising an immunostimulant. In preferred embodiments, the drug molecule (D) comprising a Treg promoting immunomodulator is selected from inhibitors of mTOR (e.g., rapamycin) or agonists of AHR (e.g., kynurenine) and a second drug molecule (D2) comprising an immunostimulant is selected from muramyl dipeptide (MDP), TDB, TLR4 agonists (e.g., MPL or LPS), lipopeptide TLR-1-2 and -6 agonists (e.g., Pam2Cys or Pam3Cys), or TLR-7 agonists, provided that if D2 is selected from agonists of TLRs, the Treg promoting immunomodulator is selected from inhibitors of mTOR that inhibit both mTORC1 and mTORC2, such as such as Torin 1, KU-0063794, and omipalisib. Non-limiting exemplary combinations of D and D2 that fit these criteria include but are not limited to: (a) rapamycin and MDP, (b) rapamycin and TDB, (c) ITE and MDP, (d) ITE and TDB, (e) Torinl and MPL, (f) Torin 1 and Pam2Cys and (g) Torin 1 and an imidazoquinoline.

In still other preferred embodiments of the vaccine for inducing tolerance, the vaccine comprises one or more, typically no more than 40, peptide antigen conjugates of formula PEG-[E1]-A-[E2]-[U]-H-[D] (or [D]-H-[U]-[E1]-A-[E2]-PEG), an amphiphile of formula S-[B]-[U]-H-[D], a drug molecule (D) comprising a Treg promoting immunomodulator and a second drug molecule (D2) comprising a Treg promoting immunomodulator. In preferred embodiments, the drug molecule (D) comprising a Treg promoting immunomodulator is selected from an inhibitor of mTOR (e.g., rapamycin) or an inhibitor RORγt (e.g., SR1555) and the second drug molecule (D2) comprising a Treg promoting immunomodulator is selected from an agonist of AHR (e.g., kynurenine), RAR (e.g., retinoic acid) or $A_{2a}$ (e.g., zeatin or UK 432,097), or an inhibitor of HDACs (e.g., SAHA, TMP269, etc.). Non-limiting exemplary combinations of D and D2 that fit these criteria include but are not limited to: (a) rapamycin and kynurenine, (b) rapamycin and ITE, (c) rapamycin and retinoic acid, (d) rapamycin and SAHA.

In some additional embodiments, both the drug molecule (D) and second drug molecule (D2) comprise a Treg promoting immunomodulator selected from agonists of AHR (e.g., Kynurenine), RAR (e.g., retinoic acid) or $A_{2a}$ (e.g., Zeatin or UK 432,097), or an inhibitor of HDACs (e.g., SAHA, TMP269, etc.).

In still other preferred embodiments of the vaccine for inducing tolerance, the vaccine comprises one or more, typically no more than 40, peptide antigen conjugates of formula PEG-[E1]-A-[E2]-[U]-H-[D] (or [D]-H-[U]-[E1]-A-[E2]-PEG), an amphiphile of formula S-[B]-[U]-H-[D], a first drug molecule (D) a second drug molecule (D2) and a third drug molecule, (D3), wherein D D2 and D3 comprise Treg promoting immunomodulators independently selected from AHR (e.g., Kynurenine), RAR (e.g., retinoic acid) or $A_{2a}$ (e.g., Zeatin or UK 432,097), or an inhibitor of HDACs (e.g., SAHA, TMP269, etc.). In some additional embodiments, D is selected from inhibitors of mTOR (e.g., rapamycin) or RORγt (e.g., SR1555) and D2 and D3 are each independently selected from agonists of AHR (e.g., Kynurenine), RAR (e.g., retinoic acid) or $A_{2a}$ (e.g., Zeatin or UK 432,097), or an inhibitor of HDACs (e.g., SAHA, TMP269, etc.). Non-limiting exemplary combinations of D, D2 and D3 that fit these criteria include but are not limited to: (a) kynurenine, retinoic acid and SAHA and (b) rapamycin, kynurenine and SAHA.

In still other preferred embodiments of the vaccine for inducing tolerance, the vaccine comprises one or more, typically no more than 40, peptide antigen conjugates of formula PEG-[E1]-A-[E2]-[U]-H-[D] (or [D]-H-[U]-[E1]-A-[E2]-PEG), an amphiphile of formula S-[B]-[U]-H-[D], a drug molecule (D) comprising an immunostimulant, a second drug molecule (D2) comprising a Treg promoting immunomodulator and a third drug molecule (D3) comprising a Treg promoting immunomodulator. In preferred embodiments, D1 is selected from agonists of NLRs (e.g., muramyl dipeptide), CLRs (e.g., TDB), TLR-1, -2 and -6 (lipopeptides), TLR-4 (LPS and any derivatives thereof), TLR-7/8a (e.g., imidazoquinolines) and STING (e.g., CDNs, diABZI, etc.), and D2 and D3 are selected from inhibitors of mTOR (e.g., rapamycin) and RORγt (e.g., SR1555). In some embodiments, D1 is selected from agonists of NLRs (e.g., muramyl dipeptide), CLR (e.g., TDB), TLR-1, -2 and -6 (lipopeptides), TLR-4 (LPS and any derivatives thereof), TLR-7/8a (e.g., imidazoquinolines) and STING (e.g., CDNs, diABZI, etc.), D2 is selected from inhibitors of mTOR (e.g., rapamycin) and RORγt (e.g., SR1555) and D3 is selected from agonists of AHR (e.g., Kynurenine), RAR (e.g., retinoic acid) or $A_{2a}$ (e.g., Zeatin or UK 432,097), or an inhibitor of HDACs (e.g., SAHA, TMP269, etc.). In still other embodiments, D1 is selected from agonists of NLRs (e.g., muramyl dipeptide), CLRs (e.g., TDB), TLR-1, -2 and -6 (lipopeptides), TLR-4 (LPS and any derivatives thereof), TLR-7/8a (e.g., imidazoquinolines) and STING (e.g., CDNs, diABZI, etc.), and both D2 and D3 are each independently selected from agonists of AHR (e.g., Kynurenine), RAR (e.g., retinoic acid) or $A_{2a}$ (e.g., Zeatin or UK 432,097), or inhibitors of HDACs (e.g., SAHA, TMP269, etc.). Non-limiting exemplary combinations of D, D2 and D3 that fit these criteria include but are not limited to: (a) TDB, rapamycin and SR1555, (b) TDB, rapamycin and kynurenine, (c) an imidazoquinoline, Torin 1 and kynurenine, (d) TDB, kynurenine and retinoic acid and (e) TDB, kynurenine and SAHA.

In still other preferred embodiments of the vaccine for inducing tolerance, the vaccine comprises one or more, typically no more than 40, peptide antigen conjugates of formula PEG-[E1]-A-[E2]-[U]-H-[D] (or (or [D]-H-[U]-[E1]-A-[E2]-PEG), optionally an amphiphile of formula S-[B]-[U]-H-[D], a drug molecule (D) comprising an immunostimulant, a second drug molecule (D2) comprising an immunostimulant and a third drug molecule (D3) comprising a Treg promoting immunomodulator. In preferred embodiments, D1 and D2 are each independently selected from agonists of NLRs (e.g., muramyl dipeptide), CLRs (e.g., TDB), TLR-1, -2 and -6 (lipopeptides), TLR-4 (LPS and any derivatives thereof), TLR-7/8a (e.g., imidazoquinolines) and STING (e.g., CDNs, diABZI, etc.), and D3 is selected from inhibitors of mTOR (e.g., rapamycin) and RORγt (e.g., SR1555). Non-limiting exemplary combinations of D, D2 and D3 that fit these criteria include but are not limited to (a) TDB, LPS and torin1 and (b) MDP, TDB and torin1.

An unexpected finding reported herein is that Treg promoting immunomodulators selected from drug molecules (D) that inhibit both mTORC1 and mTORC2 included in vaccines for inducing tolerance led to a higher proportion of CD4 T cells with Treg phenotype as compared with use of inhibitors that solely inhibit signalling downstream of mTORC1. Moreover, vaccines for inducing tolerance comprising Treg promoting immunomodulators selected from inhibitors that inhibit both mTORC1 and mTORC2 and immunostimulants that induce IL-12 and/or IFNs, including agonists of TLR-3, TLR-7, TLR-8, TLR-9, RIGI and STING, were found to increase the number as well as proportion of CD4 T cells with Treg phenotype as compared with vaccines for inducing tolerance that lacked the immunostimulant. This is highly unexpected because immunostimulants that induce IL-12 and IFNs are considered some of the most potent immunostimulants for use as vaccine adjuvants for inducing cytotoxic T cells. Thus, it was highly unexpected and seemingly paradoxical that such immunostimulants could be included in a vaccine for inducing tolerance for inducing regulatory T cells.

Based on these findings, certain preferred compositions of vaccines for inducing tolerance comprise Treg promoting immunomodulators selected from inhibitors of both mTORC1 and mTORC2 and optionally an immunostimulant selected from TLR-3, TLR-7, TLR-8, TLR-7/8, TLR-9, RIGI and STING.

In preferred embodiments of the vaccine for inducing tolerance, the Treg promoting immunomodulator is selected from an ATP-competitive mTOR inhibitor that inhibits signalling downstream of both mTORC1 and mTORC2. Non-limiting examples of ATP-competitive mTOR inhibitors include those described in US2008/0081809A1. Non-limiting examples include AZD-8055, AZD2016, KU-0063794. Additional examples of ATP-competitive inhibitors include those of the pyrazino (2,3-b) pyrazine class such as the molecules described in U.S. Pat. No. 8,492,381 B2, including CC223. In certain preferred embodiments, the ATP-competitive inhibitor is a benzonaphthridinone as described in U.S. Pat. No. 8,394,818 B2 and by Liu and colleagues (Liu, et al. J. Med. Chem. 2010. Non-limiting examples of benzonaphthridinone class molecules includes Torin-1 and Torin-2. Other examples include pyrazolopyrimidine analogs, including those described in US 2008/0234262 A1, such as WYE354 and WYE132; fused bicyclic mTOR inhibitors as described in U.S. Pat. No. 8,796,455 B2, including OSI-027 and OXA-01; and other ATP-competitive inhibitors such as PP242, PI-103, NVP-BEZ235, GNE-493 and GSK2126458.

In preferred embodiments of the vaccine for inducing tolerance comprising a Treg promoting immunomodulator and an immunostimulant, the Treg promoting immunomodulator is an ATP-competitive inhibitor selected from AZD-8055, AZD2016, KU-0063794, CC223, Torin-1, Torin-2, INK-128, WYE354, WYE132, OSI-027, OXA-01, PI-103, NVP-BEZ235, GNE-493 and GSK2126458, and the immunostimulant is an agonist of TLR-3, TLR-3, TLR-7, TLR-8, TLR-7/8, TLR-9, RIGI and STING. In non-limiting examples of a vaccine for inducing tolerance comprising a Treg promoting immunomodulator and an immunostimulant, the Treg promoting immunomodulator is Torin-1 and the immunostimulant is an imidazoquinoline TLR-7, TLR-8 and/or TLR-7/8 agonist.

For vaccines comprising peptide antigen conjugates and Treg promoting immunomodulators selected from inhibitors of mTOR, the molar ratio of total peptide antigen conjugate (i.e., the total molar amount of peptide antigen conjugate) to Treg promoting immunomodulator was found to have a significant impact on particle hydrodynamic behavior as well as toxicity and efficacy. Accordingly, it was observed that molar ratio of total peptide antigen conjugate (i.e., the total molar amount of peptide antigen conjugate) to inhibitor of mTOR from about 100:1 to about 1:4 were suitable with molar ratios of about 10:1 to 1:4 being preferred and molar ratios of about 5:1 to about 1:3, such as 5:1, 4:1, 3:1, 2:1, 1:1, 1:2 and 1:3 more preferred, and molar ratios of about 5:1 to about 1:2 or about 5:1 to about 1:1 or about 2:1 to about 1:2 being even more preferred and ratios of about 1:1, such as 0.75:1, 0.8:1, 0.85:1, 0.9:1, 0.95:1, 1:1, 1:0.95, 1:0.9, 1:0.85, 1:0.8, 1:0.75 being most preferred. In some embodiments wherein the Treg promoting immunomodulator is linked to the peptide antigen conjugate, the preferred molar ratio of peptide antigen conjugate to Treg promoting immunomodulators selected from inhibitors of mTOR is about 1:1 to about 1:3, such as 1:1, 1:2 or 1:3.

Examples

Example 1: Synthesis of Amphiphiles, Peptide Antigen Conjugates, Drug Molecule Conjugates and any Precursors Thereof Hydrophobic blocks (H) based on poly(amino acids) produced by solid phase peptide synthesis (SPPS) provide the advantage over hydrophobic polymers produced by radical polymerization that the resulting material obtained is chemically defined, i.e. a single product with an exact composition can be obtained.

However, a potential limitation of producing hydrophobic poly(amino acids) by SPPS is that highly hydrophobic peptides may not be soluble in the solvents commonly used for peptide coupling (e.g., DMF) and/or the hydrophobic peptides may not be suitable for purification using common HPLC mobile (e.g., acetonitrile and water) and stationary (e.g., C18) phases.

Compound 1, DBCO-Ahx-W5

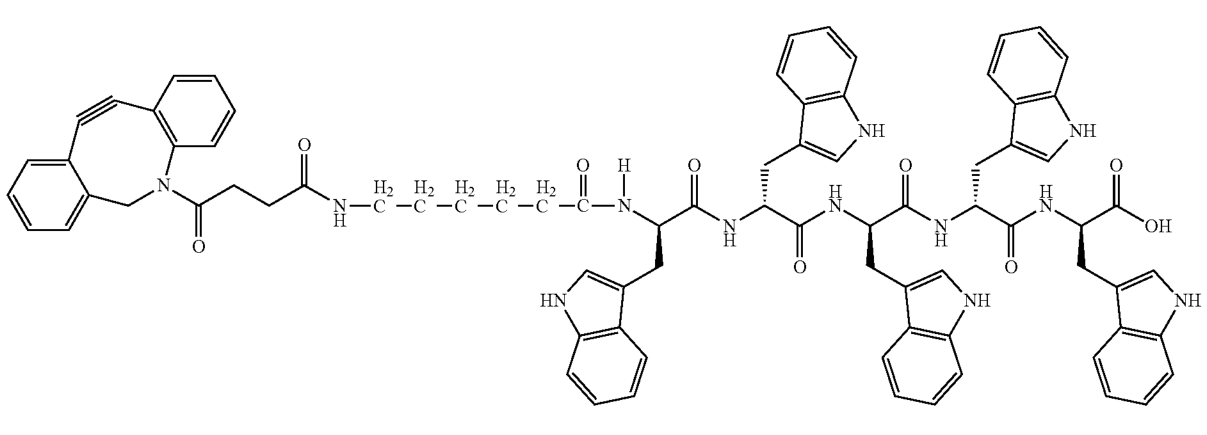 [SMILES: O=C(CCC(=O)N1Cc2ccccc2C#Cc2ccccc21)NCCCCCC(=O)N[C@H](Cc1c[nH]c2ccccc12)C(=O)N[C@H](Cc1c[nH]c2ccccc12)C(=O)N[C@H](Cc1c[nH]c2ccccc12)C(=O)N[C@H](Cc1c[nH]c2ccccc12)C(=O)N[C@H](Cc1c[nH]c2ccccc12)C(=O)O]

Compound 1, referred to as DBCO-Ahx-WWWWW or DBCO-Ahx-W5 was synthesized by reacting 14.2 mg (0.035 mmol, 1 eq) of the precursor DBCO-NHS, with 37.5 mg of Ahx-$(W)_5$-$NH_2$ (SEQ ID NO: 62) (0.035 mmol, 1 eq) that was prepared by solid phase peptide synthesis and 3.93 mg of triethylamine (0.039 mmol, 1.1 eq) in 0.5 mL of DMSO. The reaction was run overnight at room temperature and HPLC indicated that the reaction was complete by 24 hours. Compound 1 was precipitated out in twice with 1M HCL and once in H2O to obtain 34.3 mg (71.9% yield) of a spectroscopically pure (92.6% AUC at 254 nm) pink powder. MS (ESI) calculated for $C_{80}H_{76}N_{12}O_9$ m/z 1348.59, found 1348.4 $(M+H)^+$.

Compound 2, 2B

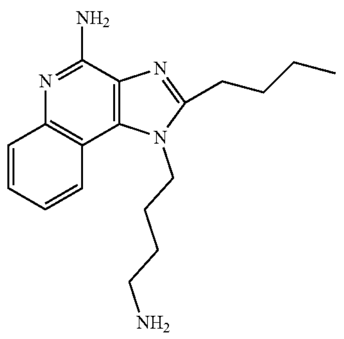 [SMILES: CCCCc1nc2c(N)nc3ccccc3c2n1CCCCN]

Compound 2, 1-(4-aminobutyl)-2-butyl-1H-imidazo[4,5-c]quinolin-4-amine, also referred to as 2B, was synthesized starting from 3-nitro-2,4-dichloroquinoline, 2-b, which was prepared as previously described (Lynn G M, et al., Nat Biotechnol 33(11):1201-1210, 2015). To 21 g of 2-b (87.8 mmol, 1 eq) in 210 mL of triethylamine (TEA) (10% w/w) was added 16.34 g (87.8 mmol, 1 eq) of N-boc-1,4-butanediamine while stirring vigorously. The reaction mixture was heated to 70° C. and monitored by HPLC, which confirmed that the reaction was complete after 2 hours. The triethylamine was removed under vacuum and the resulting oil was dissolved in 200 mL of dichloromethane and then washed with 3×100 mL DI $H_2O$. The organic layer was dried with $Na_2SO_4$ and then removed under vacuum and the resulting oil was triturated with 1:1 (v:v) hexane and diethyl ether to yield 30.7 g of yellow crystals of intermediate 2-c. MS (APCI) calculated for $C_{18}H_{23}ClN_4O_4$, m/z 394.1 found, 394.9.

2-d. 30.7 g (76.4 mmol) of intermediate 2-c was dissolved in 300 mL of ethyl acetate in a Parr Reactor vessel that was bubbled with argon, followed by the addition of 3 g of 10% platinum on carbon. The reaction vessel was kept under argon and then evacuated and pressurized with $H_2$ (g) several times before pressurizing to 55 PSI $H_2$ (g) while shaking vigorously. The $H_2$ (g) was continually added until the pressure stabilized at 55 PSI, at which point the reaction was determined to be complete. The reaction mixture from the Parr Reactor was then filtered through celite end evaporated to dryness to obtain a yellow oil that was triturated with 1:1 hexanes/ether to yield white crystals that were collected by filtration to obtain 27.4 g of spectroscopically pure white crystals of 2-d. MS (APCI) calculated for $C_{18}H_{25}ClN_4O_2$, m/z 364.2, found 365.2.

2-e. To 10 g (27.4 mmol, 1 eq) of 2-d in 50 mL of THF was added 7.7 mL of triethylamine (54.8 mmol, 2 eq) followed by the dropwise addition of 3.6 g of valeroyl chloride (30.1 mmol, 1.1 eq) in 30 mL of THF while stirring vigorously while the reaction mixture was on ice. After 90 minutes, the ice bath was removed and the THF was removed under vacuum, resulting in a yellow oil that was dissolved in 100 mL of dichloromethane (DCM) that was washed with 3×50 mL of pH 5.5 100 mM acetate buffer. The DCM was removed under vacuum in an oil that was triturated with ethyl acetate to obtain 10.4 g of a white solid that was dissolved in methanol with 1 g of CaO(s), which was heated at 100° C. for 5 hours while stirring vigorously. The reaction mixture was filtered and dried to yield 10.2 g of an off-white solid, intermediate, 2-e. MS (ESI) calculated for $C_{23}H_{31}ClN_4O_2$, m/z 430.21, found 431.2.

2-f. To 10.2 g (23.7 mmol, 1 eq) of 2-e was added 30.4 g (284 mmol, 12 eq) of benzylamine liquid, which was heated to 110° C. while stirring vigorously. The reaction was complete after 10 hours and the reaction mixture was added to 200 mL ethyl acetate and washed 4×100 mL with 1 M HCl. The organic layer was dried with $Na_2SO_4$ and then removed under vacuum and the resulting oil was recrystallized from ethyl acetate to obtain 10.8 g of spectroscopically pure white crystals of intermediate, 2-f. MS (ESI) calculated for $C_{30}H_{39}N_5O_2$, m/z 501.31, found 502.3

Compound 2. 10.8 g (21.5 mmol) of 2-f was dissolved in 54 mL of concentrated (>98%) $H_2SO_4$ and the reaction mixture was stirred vigorously for 3 hours. After 3 hours, viscous red reaction mixture was slowly added to 500 mL of DI $H_2O$ while stirring vigorously. The reaction mixture was stirred for 30 minutes and then filtered through Celite, followed by the addition of 10 M NaOH until the pH of the solution was ~ pH 10. The aqueous layer was then extracted with 6×200 mL of DCM and the resulting organic layer was dried with $Na_2SO_4$ and reduced under vacuum to yield a spectroscopically pure white solid . . . 1H NMR (400 MHZ, DMSO-$d_6$) δ 8.03 (d, J=8.1 HZ, 1H), 7.59 (d, J=8.1 Hz, 1H), 7.41 (t, J=7.41 Hz, 1H), 7.25 (t, J=7.4 Hz, 1H), 6.47 (s, 2H), 4.49 (t, J=7.4 Hz, 2H), 2.91 (t, J=7.78 Hz, 2H), 2.57 (t, J=6.64 Hz, 1H), 1.80 (m, 4H), 1.46 (sep, J=7.75 Hz, 4H), 0.96 (t, J=7.4 Hz, 3H). MS (ESI) calculated for $C_{18}H_{25}N_5$, m/z 311.21, found 312.3.

Compound 3, DBCO-Ahx-$E_3W_2$

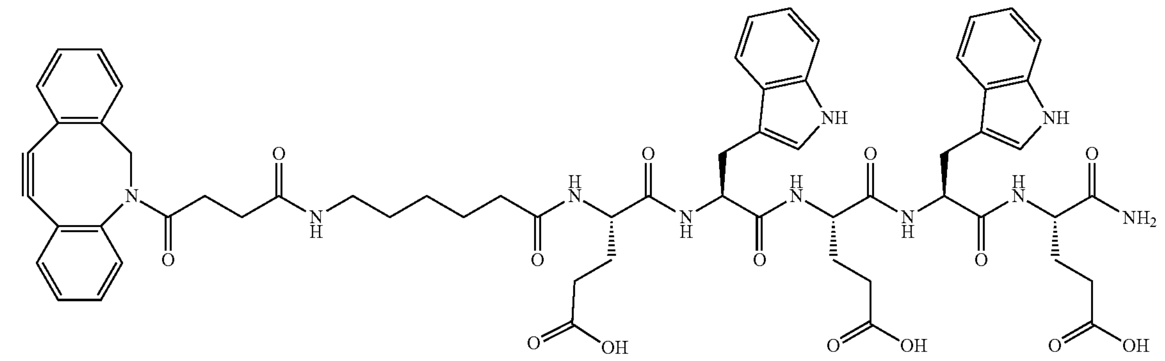

Compound 3, referred to as DBCO-Ahx-E3W2 or DBCO-Ahx-$(Glu)_3(Trp)_2$, was synthesized from a 6-amino-hexanoic-Glu-Trp-Glu-Trp-Glu-$NH_2$ or Ahx-$E_3W_2$ precursor prepared by solid-phase peptide synthesis. 105 mg of Ahx-E3W2 (0.12 mmol, 1 eq) and 65.8 uL triethylamine (TEA) (0.47 mmol, 4 eq) were added to 525 uL anhydrous DMF and stirred at room temperature under ambient air for 5 minutes. 52.2 mg of DBCO-NHS ester (Scottsdale, Arizona, USA) (0.13 mmol, 1.1 eq) was then added while stirring vigorously and reacted for 1 hour. The reaction progress was monitored by HPLC (AUC 254 nm). After 1 hour the reaction was complete, and the reaction was quenched by adding amino-PEG24-OH (San Diego, California, USA) (1 eq) and stirring for 1 hour. The reaction mixture was added dropwise to 5 mL of 0.2 M HCl to precipitate an off-white powder which was collected by centrifuging the solution at 4000 g at 4° C. for 5 minutes. The HCl solution was discarded and Compound 3 was collected as a solid off-white pellet. The off-white solid was re-suspended in 525 uL DMF and added dropwise to 5 mL of DI water and spun at 3000 g at 4° C. for 5 minutes; the DI water solution was discarded, and Compound 3 was collected as a solid pellet. This process was repeated and then the solid was collected and dried under vacuum to yield 117 mg of a spectroscopically pure (>95% AUC at 220 nm) white powder. MS (ESI) calculated for $C_{62}H_{68}N_{10}O_{14}$ m/z 1176.5, found 588.8 (M/2+H)+.

Compound 4, DBCO-Ahx-$2B_3W_2$

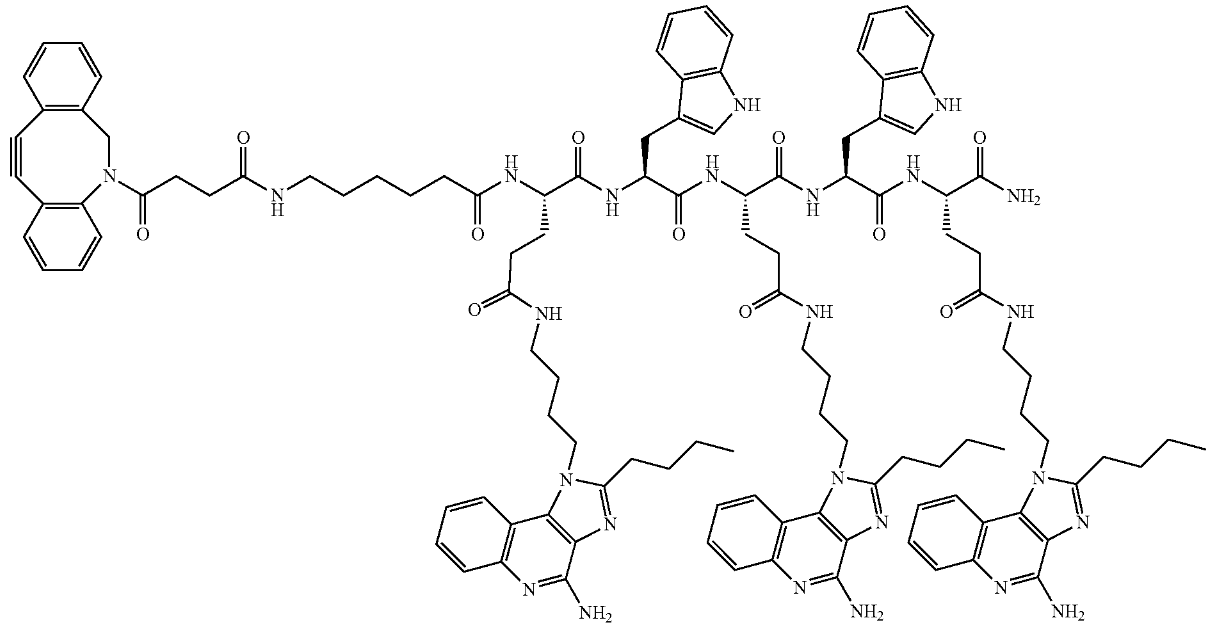

Compound 4, referred to as DBCO-Ahx-2B3W2, DBCO-Ahx-E(2B)$_3$W$_2$ or DBCO-Ahx-Glu (2B) 3 (Trp) 2 was synthesized by reacting Compound 3 and Compound 2 in the presence of HATU. 142.2 uL triethylamine (TEA) (1.02 mmol, 12 eq) was diluted in 1 mL anhydrous DMF, and 100 mg of Compound 3 (0.09 mmol, 1 eq) and 103 mg of Compound 2 (0.33 mmol, 3.9 eq) were added while stirring vigorously until fully dissolved. The reaction mixture was cooled to 4° C. by immersion in an ice bath for 5 minutes, then 106.6 mg of HATU (0.28 mmol, 3.3 eq) was added. The reaction mixture stirred vigorously for 1 hour at 4° C. and the reaction progress was monitored by HPLC (AUC 254 nm). The resulting product was purified on a preparative HPLC system using a gradient of 30-45% acetonitrile/H2O (0.05% TFA) over 12 minutes on an Agilent Prep C-18 column, 30×100 mm, 5 μm. The product eluted at ~ 40% acetonitrile and the resulting fractions were combined, frozen and lyophilized to give 99.1 mg (60% yield) of a spectroscopically pure white powder (>95% AUC at 220 nm). MS (ESI) Calculated for $C_{116}H_{137}$N25011 m/z 2056.1, found 685.4 (M/3+H)+.

Example 1A: Amphiphiles with Dendron-Based S Blocks Having Cone Architecture

Compound 5, (COOH) 2-PEG$_{24}$-N$_3$

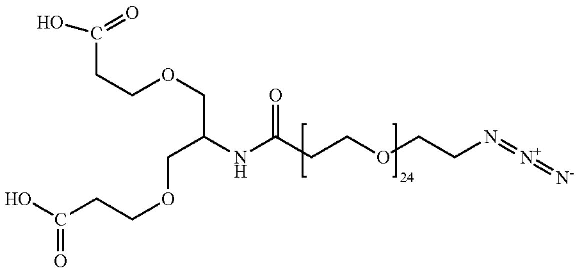

Compound 5, referred to as (COOH) 2-PEG$_{24}$-N$_3$ or bis (COOH)-PEG$_{24}$-N$_3$ was synthesized by reacting 2.8 g of N3-P24-NHS ester (2.2 mmol, 1 eq) and 0.57 g of 2-amino-1,3-bis(carboxylethoxy) propane HCl salt (2.1 mmol, 0.95 eq) dissolved in 30 mL anhydrous DCM. Triethylamine (3 mL, 22.1 mmol, 10 eq) was added to the reaction mixture. The reaction was stirred at room temperature for 3 hours until HPLC indicated the reaction was complete. The reaction solvent was removed under vacuum and the reaction mixture was redissolved in 1:1 DMSO/H2O w/0.05% TFA. The product was purified by flash C18 chromatography on a 12 g Biotage SNAP C18 column using a 2-step gradient: 0% acetonitrile in H2O (0.05% TFA) over 3 column volumes (CVs), followed by 0-60% acetonitrile in H2O (0.05% TFA) over 20 CVs. The product eluted at ~ 25% acetonitrile and the resulting fractions were collected and the solvent removed under vacuum to yield 2.0 g (65.2% yield) of a spectroscopically pure (>97% AUC at 220 nm) white oil. MS (ESI) calculated for $C_{60}H_{116}N_4O_{31}$ m/z 1388.8, found 1412.6 $(M+Na+H)^+$.

Compound 6, (TT)$_2$-PEG$_{24}$-N$_3$

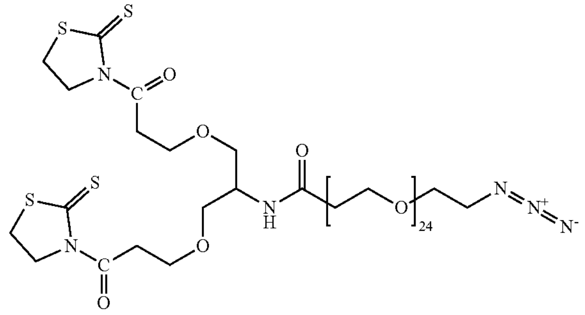

Compound 6, referred to as (TT) 2-PEG24-N3 or bis (TT)-PEG24-N3 was synthesized by reacting 2.0 g of Compound 5 (1.5 mmol, 1 eq) and 1.2 g of HATU (3.2 mmol, 2.2 eq) in 24 mL of DCM. The mixture was cooled on ice for 5 min and 1.6 mL of triethylamine (11.7 mmol, 8 eq) was added. The mixture was stirred on ice for 5 min and 0.45 g of thizoline-2-thiol (TT) (3.8 mmol, 2.6 eq) was added. The reaction mixture was stirred at room temperature for 2 hours until HPLC indicated the reaction was complete. The product was purified by flash chromatography on a 100 g Biotage Safar SilicaD column over a 2-step gradient: 0% methanol in DCM over 3 column volumes (CVs), followed by 0-8% methanol in DCM over 20 CVs. The product eluted at ~ 5% methanol and the resulting fractions were collected and the solvent removed to obtain 2.0 g (85.3% yield) of a spectroscopically pure (96.1% AUC at 220 nm) yellow oil. MS (ESI) Calculated for $C_{66}H_{122}N_9O_{29}$S4 m/z 1590.7, found 782.3 ((M-N3)/2)+.

Compound 7, $(COOH)_4$-$PEG_{24}$-$N_3$

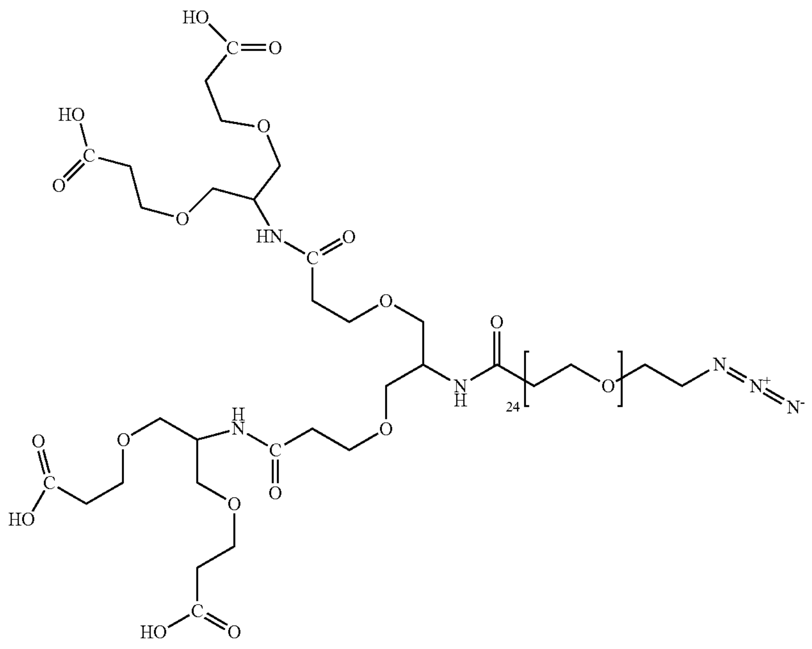

Compound 7, referred to as (COOH) 4-PEG24-N3 or tetra (COOH)-PEG24-N3 was synthesized by reacting 1.5 g of Compound 6 (0.9 mmol, 1 eq) and 0.4 g of 2-amino-1,3-bis(carboxylethoxy) propane HCl salt (1.4 mmol, 1.6 eq) dissolved in 35 mL of anhydrous DCM. Triethylamine (2.5 mL, 18.3 mmol, 19 eq) was added to the reaction mixture. The reaction was stirred at room temperature for 4 hours until HPLC indicated the reaction was complete. Compound 7 was not purified. MS (ESI) Calculated for $C_{78}H_{146}N_6O_{41}$ m/z 1823.0, found 912.4 (M/2+H)+.

Compound 8, $(TT)_4$-$PEG_{24}$-$N_3$

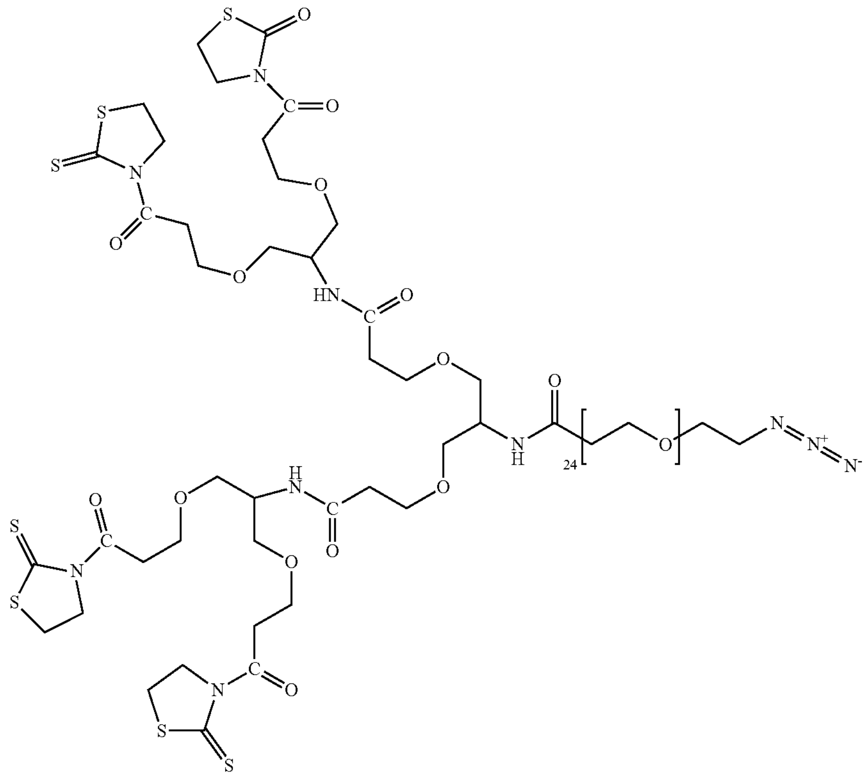

Compound 8, referred to as (TT) 4-PEG24-N3 was synthesized by reacting 1.5 g of Compound 7 (0.8 mmol, 1 eq) and 1.4 g of HATU (3.7 mmol, 4.4 eq) in 3 mL of DCM. Triethylamine (1.9 mL, 13.5 mmol, 16 eq) was added and the reaction mixture was stirred for 5 min. Thiazoline-2-thio (TT) (0.5 g, 4.4 mmol, 5 eq) was added and the reaction mixture was stirred at room temperature for 3 hours until HPLC indicated the reaction was complete. The product was purified by flash chromatography on a 100 g Biotage Safar SilicaD column over a 2-step gradient: 0% methanol in DCM over 3 column volumes (CVs), followed by 0-8% methanol in DCM over 20 CVs. The product eluted at ~5% methanol and the resulting fractions were collected and the solvent removed to obtain 0.8 g (42% yield) of a yellow oil (70% AUC at 220 nm). MS (ESI) Calculated for $C_{90}H_{158}N_{10}O_{37}S_8$ m/z 2228.8, found 962.8 (M/2)+.

Compound 9, (Mannose-PEG3)$_4$-PEG$_{24}$-N$_3$

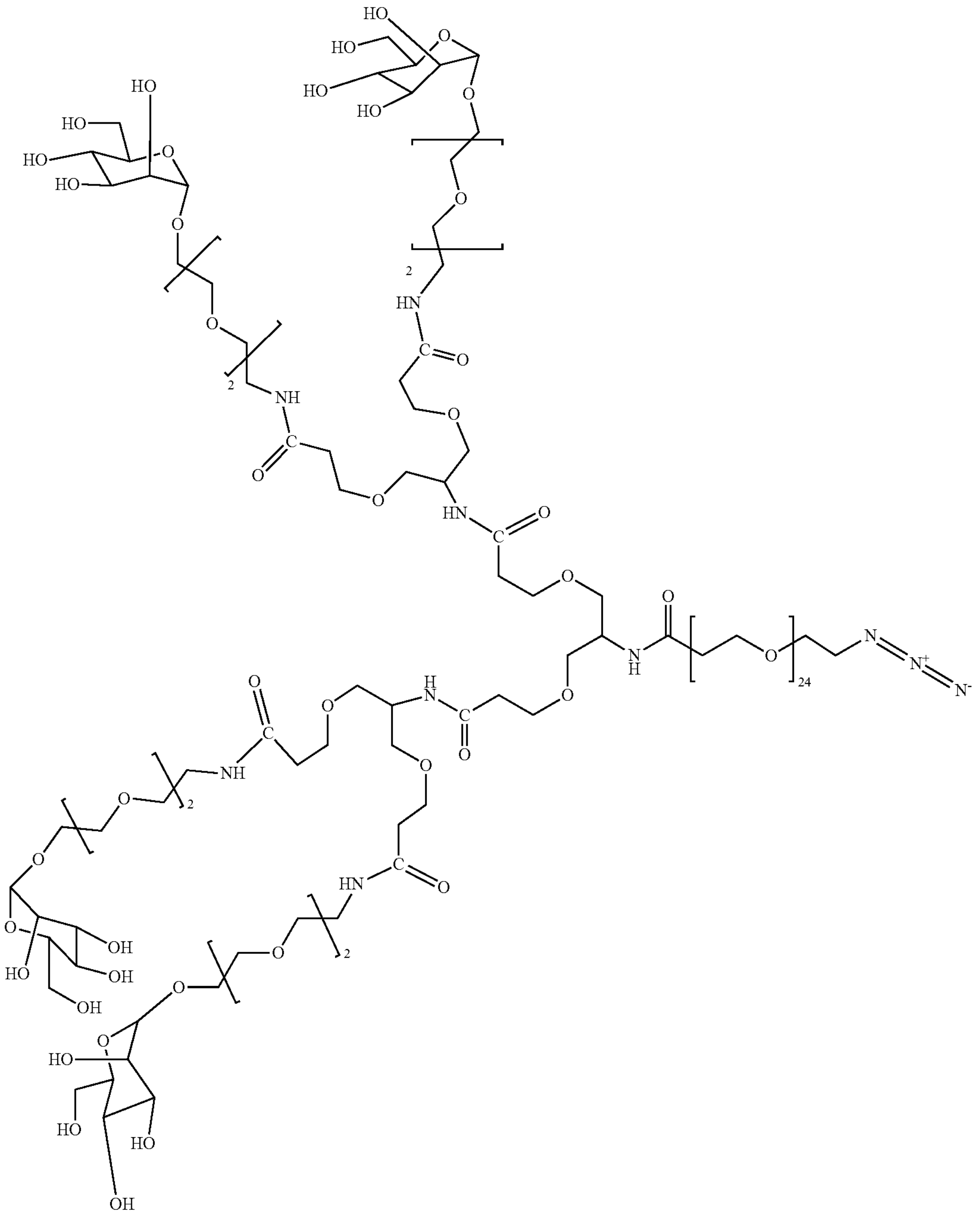

Compound 9, referred to as (Mannose-PEG3)$_4$-PEG24-N3 or Tetra(Mannose-PEG3)-PEG24-N3 was synthesized by reacting 65 mg of Compound 8 (0.029 mmol, 1 eq) and 62 mg of a-Mannose-PEG3-amine (CarboSynthUSA (San Diego, CA)) (0.20 mmol, 6.8 eq) in 240 μL of DMSO. Triethylamine (20 uL, 0.20 mmol, 6.8 eq) was added the reaction mixture was stirred at room temperature for 1 hour until HPLC indicated the reaction was complete. Compound 9 was purified on a preparatory HPLC system using a gradient of 15-35% acetonitrile/$H_2O$ (0.05% TFA) over 12 minutes on an Agilent Prep-$C_{18}$ column, 50×100 mm, 5 μm. The product eluted at ~ 7.3 minutes and the resulting fractions were collected, frozen and then lyophilized to obtain a 49.5% yield of a spectroscopically pure (97.2% AUC at 220 nm) white solid. MS (ESI) Calculated for $C_{126}H_{238}N_{10}O_{69}$ m/z 2995.5, found 999.9 (M/3)+.

Compound 10, (GalNAc-PEG3)$_4$-PEG$_{24}$-N$_3$

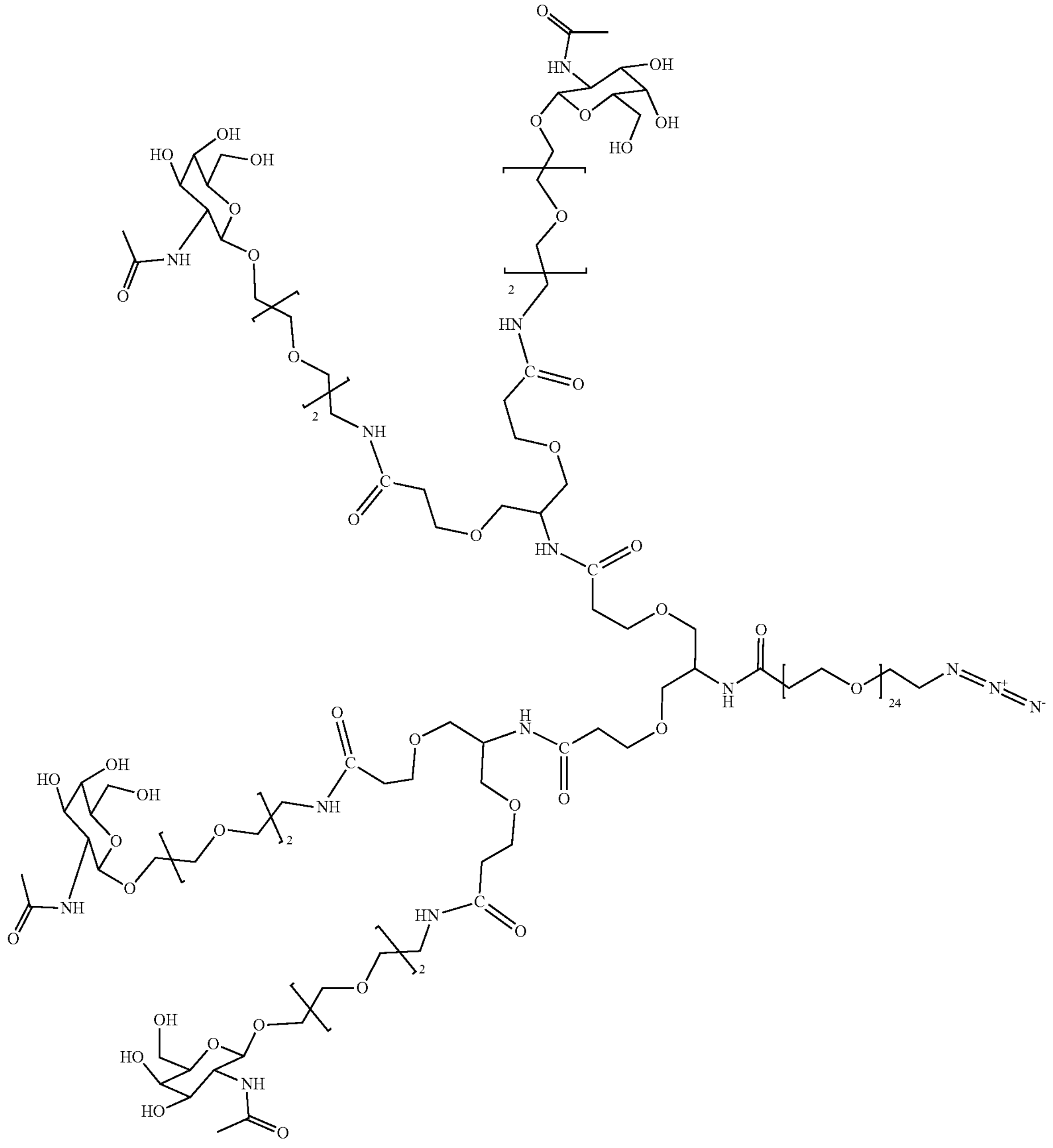

Compound 10, referred to as $(GalNAc-PEG3)_4-PEG_{24}-N_3$ or Tetra(GalNAc-PEG3)-PEG24-N3 was synthesized following the same procedure as Compound 9, except b-n-acetylgalactose-PEG3-amine (CarboSynthUSA (San Diego, CA)) was used instead of a-Mannose-PEG3-amine. Compound 98 was purified on a preparatory HPLC system using a gradient of 15-35% acetonitrile/$H_2O$ (0.05% TFA) over 12 minutes on an Agilent Prep-$C_{18}$ column, 30×100 mm, 5 μm. The product eluted at ~ 6.7 minutes and the resulting fractions were collected, frozen and then lyophilized to obtain a 51.6% yield of a spectroscopically pure (97.0% AUC at 220 nm) white solid. MS (ESI) Calculated for $C_{134}H_{250}N_{14}O_{69}$ m/z 3159.7, found 1054.8 $(M/3)^+$.

Compound 11, $(Glu-PEG3)_4-PEG_{24}-N_3$

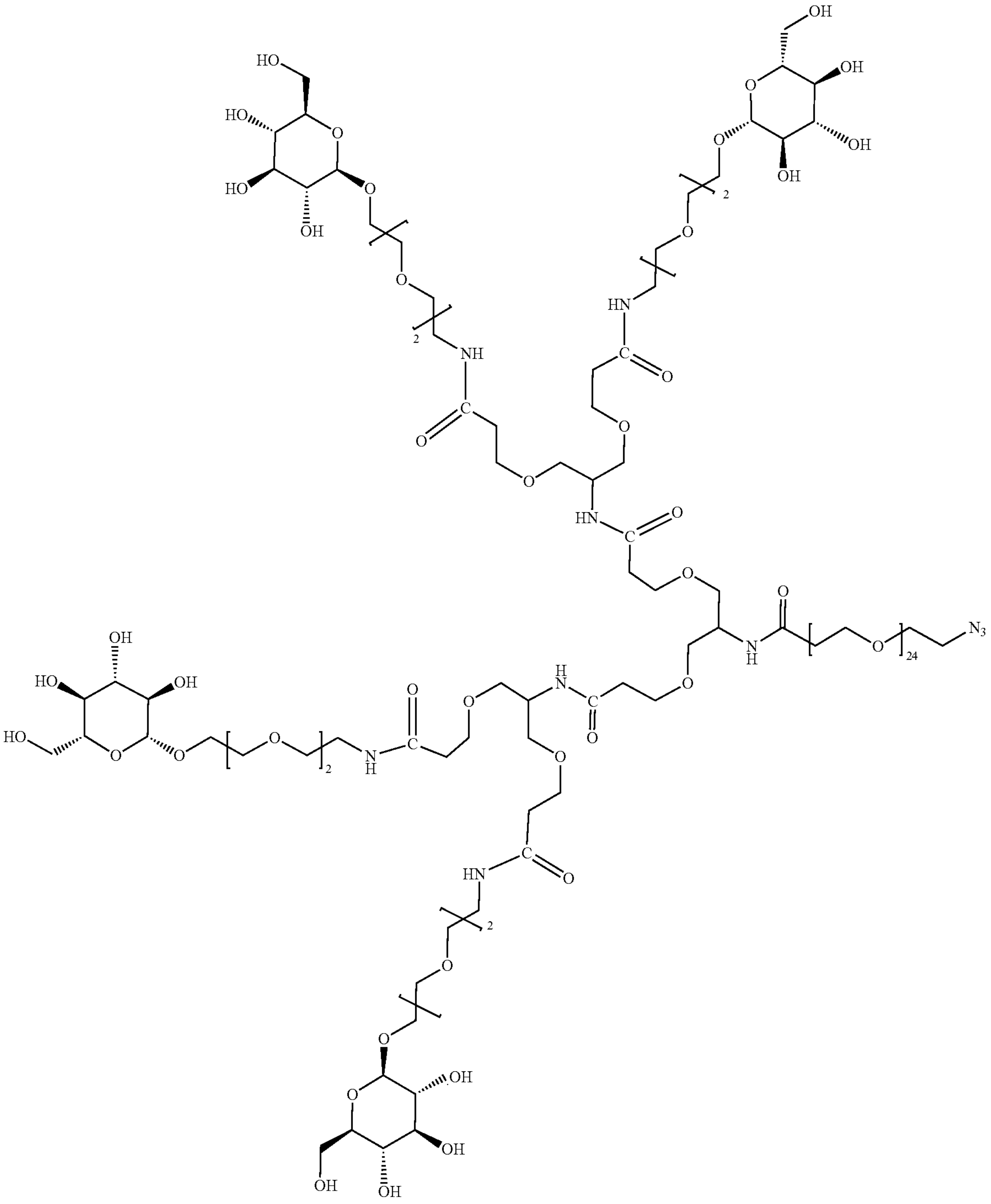

Compound 11, referred to as (Glu-PEG3)$_4$-PEG$_{24}$-N$_3$ or Tetra(Glu-PEG3)-PEG24-N3 was synthesized following the same procedure as Compound 9, except b-glucose-PEG3-Amine (CarboSynthUSA (San Diego, CA)) was used instead of a-Mannose-PEG3-amine. Compound 1 was purified on a preparatory HPLC system using a gradient of 15-35% acetonitrile/$H_2O$ (0.05% TFA) over 12 minutes on an Agilent Prep-$C_{18}$ column, 30×100 mm, 5 μm. The product eluted at ~ 7.0 minutes and the resulting fractions were collected, frozen and then lyophilized to obtain a 34% yield of a spectroscopically pure (99.0% AUC at 220 nm) white solid. MS (ESI) Calculated for $C_{126}H_{238}N_{10}O_{69}$ m/z 2995.5, found 999.9 $(M/3)^+$.

Compound 12, (OH-ethyl)$_4$-PEG$_{24}$-N$_3$

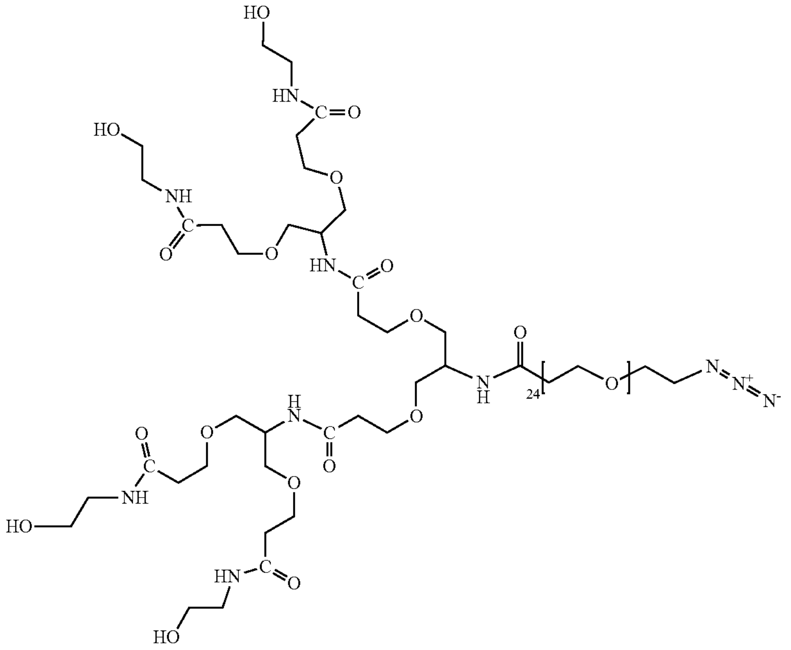

Compound 12, referred to as $(OH\text{-ethyl})_4\text{-PEG}_{24}\text{-N}_3$ was synthesized following the same procedure as Compound 9, except ethanolamine was used instead of a-Mannose-PEG3-amine. Compound 12 was purified on a preparatory HPLC system using a gradient of 17-37% acetonitrile/$H_2O$ (0.05% TFA) over 12 minutes on an Agilent Prep-$C_{18}$ column, 30×100 mm, 5 μm. The product eluted at ~ 7.0 minutes and the resulting fractions were collected, frozen and then lyophilized to obtain a 43.6% yield of a spectroscopically pure (97.2% AUC at 220 nm) white solid. MS (ESI) Calculated for $C_{86}H_{166}N_{10}O_{41}$ m/z 1995.1, found 998.6 $(M/2+H)^+$.

Example 1B: Amphiphilic Block Copolymers of Formula S-B-U-H-[D] Having Cone Architecture Compound 13, $(\text{Mannose-PEG}_3)_4\text{-PEG}_{24}\text{-(N}_3\text{-DBCO)}$-Ahx-W5

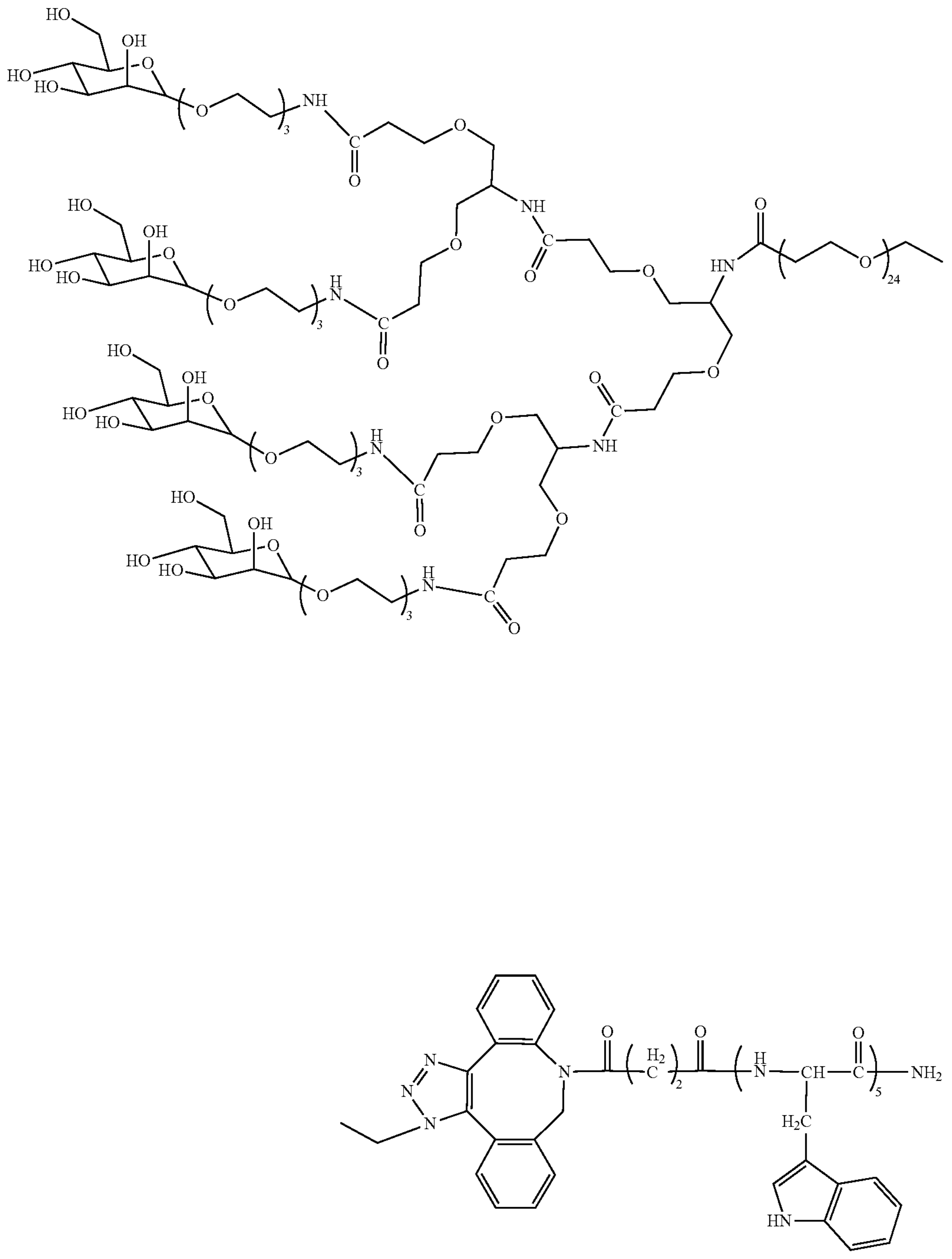

Compound 13, referred to as $(Mannose-PEG_3)_4-PEG_{24}-(N_3-DBCO)-Ahx-W5$ was synthesized by reacting Compound 9 (0.001 mmol, 1.0 eq) with Compound 1 (0.001 mmol, 1.05 eq) in anhydrous DMSO for 16 hours at room temperature. HPLC was monitored to evaluate reaction progress and indicated complete conversion of Compound 9 to Compound 13, resulting in a spectroscopically pure (87.8% AUC at 220 nm) colorless solution. MS (ESI) calculated for $C_{206}H_{314}N_{22}O_{78}$ m/z 4344.1, found 1086.6 $(M/4+H)^+$.

Compounds 14-17 were produced in a similar manner as that described for Compound 13. Table 1B provides a summary of the synthesis and characterization of compounds 14-17.

TABLE 1B

Amphiphiles of formula S-B-U-H-[D] having dendron architecture, i.e., having a solubilizing block (S) comprising a dendron amplifier.

| Cmpd # | (S-B-U1) Compound # / Product S-B-U-H-[D] | U2-H[D] Compound # | m/z Theo. | MS (ESI) m/n Found |
|---|---|---|---|---|
| 14 | Compound 9<br>$(Mannose-PEG_3)_4-PEG_{24}-(N_3-DBCO)-Ahx-2B_3W_2$ | Compound 4 | 5051.6 | 1264.6<br>(M/4 + H)+. |
| 15 | Compound 10<br>$(GalNAc-PEG_3)_4-PEG_{24}-(N_3-DBCO)-Ahx-W_5$ | Compound 1 | 4510.7 | 1503.8<br>$(M/3)^+$ |
| 16 | Compound 10<br>$(GalNAc-PEG_3)_4-PEG_{24}-(N_3-DBCO)-Ahx-2B_3W_2$ | Compound 4 | 5217.6 | 1305.4<br>$(M/4 + H)^+$ |
| 17 | Compound 12<br>$(OH-ethyl)_4-PEG_{24}-(N_3-DBCO)-Ahx-2B_3W_2$ | Compound 4 | 4051.2 | 1351.9<br>$(M/3 + H)^+$ |

Single letter abbreviations are used for amino acid sequences in the above table; Peptide-based starting materials were manufactured by solid-phase peptide synthesis by Genscript (Piscataway, NJ).

Compound 18, $TT-PEG_{12}-N_3$

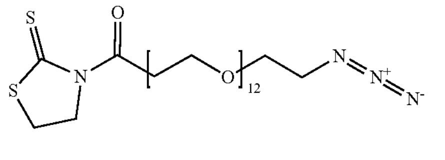

Compound 18, referred to as TT-PEG12-N3 was synthesized by reacting 50 mg of N3-PEG12-COOH (0.08 mmol, 1 eq) with 33.0 mg of HATU (0.09 mmol, 1.4 eq) in 330 µL of DCM. To the mixture, 43.3 uL of triethylamine (0.31 mmol, 4 eq) was added. The mixture was stirred for 5 minutes and 12.6 mg of thizoline-2-thiol (TT) (0.11 mmol, 1.4 eq) was added. The reaction mixture stirred at room temperature for 2 hours until HPLC indicated the reaction was complete. The product was purified by flash chromatography on a 10 g Biotage Safar Silica HC column over a 2-step gradient: 0% methanol in DCM over 3 column volumes (CVs), followed by 0-7% methanol in DCM over 20 CVs. The product eluted at ~ 5% methanol and the resulting fractions were collected and the solvent removed to obtain 24 mg (41.0% yield) of a spectroscopically pure (92.0% AUC at 220 nm) yellow oil. MS (ESI) Calculated for $C_{30}H_{56}N_4O_{13}S_2$ m/z 744.3, found 745.3 $(M+H)^+$.

Compound 19, $TT-PEG_{12}-(N_3-DBCO)-Ahx-W_5$

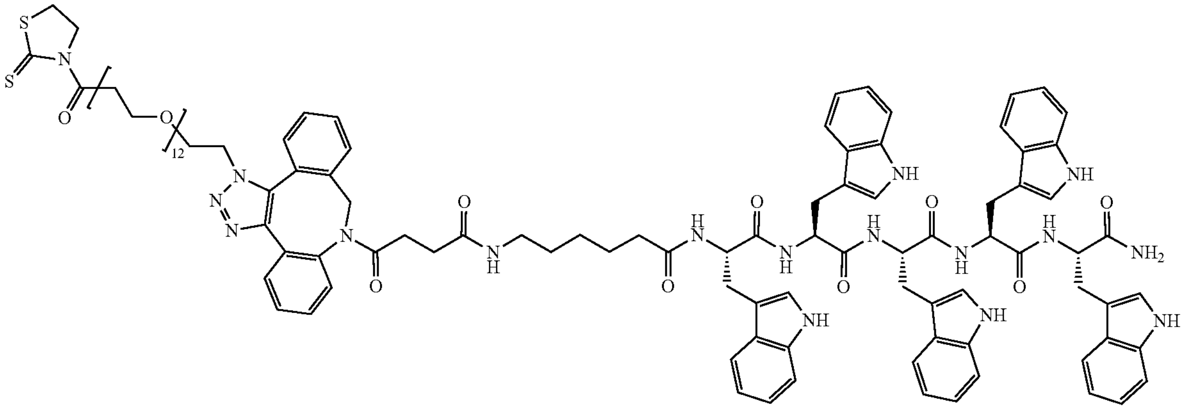

Compound 19, referred to as TT-PEG$_{12}$-($N_3$-DBCO)-Ahx-$W_5$ was synthesized by reacting 14.2 mg of Compound 18 (0.02 mmol, 1 eq) with 28.4 mg of Compound 1 (0.02 mmol, 1.1 eq) in 400 μL of anhydrous DMSO. The reaction was mixed at room temperature for 16 hours, until HPLC indicated the reaction was complete. The reaction was not purified and resulted in an 83% pure (AUC at 220 nm) product. MS (ESI) Calculated for $C_{110}H_{133}17O_{21}S2$ m/z 2091.9, found 1048.4 $(M/2+H)^+$.

Compound 20, TT-PEG$_{24}$-$N_3$

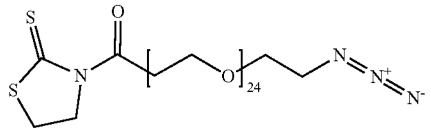

Compound 20, referred to as TT-PEG$_{24}$-$N_3$ was synthesized by reacting 2.55 g of N3-PEG24-COOH (2.2 mmol, 1 eq) with 0.92 g of HATU (2.4 mmol, 1.1 eq) in 24 mL of DCM. To the mixture, 1.2 mL of triethylamine (8.7 mmol, 4 eq) was added. The mixture was stirred for 5 minutes and 0.29 g of thizoline-2-thiol (TT) (2.5 mmol, 1.1 eq) was added. The reaction mixture was stirred at room temperature for 2 hours until HPLC indicated the reaction was complete. The reaction mixture was diluted with 200 mL of dichloromethane (DCM) and then washed with 2×200 mL 0.1 M HCl and the 1×200 mL DI $H_2O$. The organic layer was dried with $Na_2SO_4$ and then removed under vacuum, resulting in a yellow oil. The product was then purified by flash chromatography on a 100 g Biotage Safar Silica HC column over a 2-step gradient: 0% methanol in DCM over 3 column volumes (CVs), followed by 0-8% methanol in DCM over 20 CVs. The product eluted at ~ 5% methanol and the resulting fractions were collected and the solvent removed to obtain 1.8 g (62.5% yield) of an 84% pure (AUC at 220 nm) yellow oil. MS (ESI) Calculated for $C_{54}H_{104}N_4O_{28}S_2$ m/z 1272.6, found 1273.6 $(M+H)^+$.

Compound 21, TT-PEG$_{24}$-($N_3$-DBCO)-Ahx-$W_5$

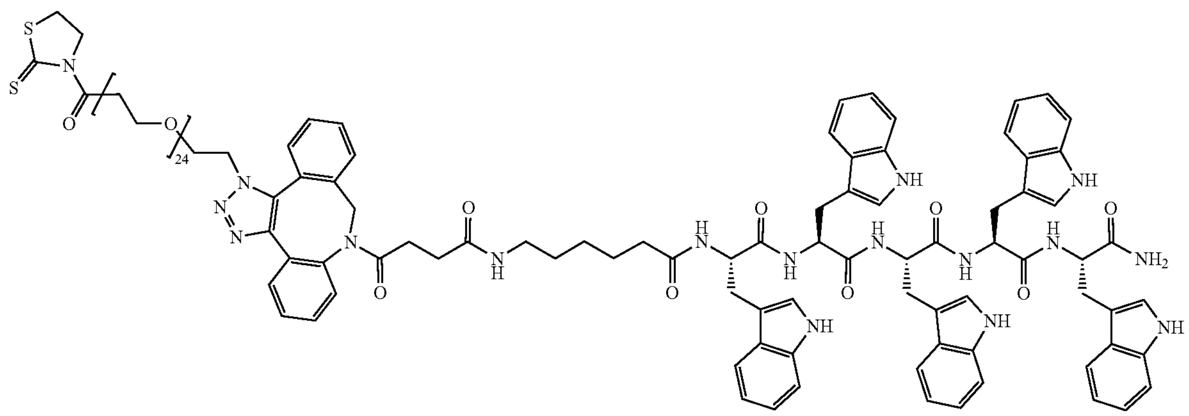

Compound 21, referred to as TT-$PEG_{24}$-($N_3$-DBCO)-Ahx-$W_5$ was synthesized by reacting 12.7 mg of Compound 20 (0.01 mmol, 1 eq) with 14.8 mg of Compound 1 (0.01 mmol, 1.1 eq) in 500 μL of DMSO. The reaction was mixed at room temperature for 16 hours, until HPLC indicated the reaction was complete. The reaction was not purified and resulted in an 84% pure (AUC at 220 nm) product. MS (ESI) Calculated for $C_{134}H_{181}N_{17}O_{33}S_2$ m/z 2622.1, found 1311.8 $(M/2+H)^+$.

Compound 22, (Mannose-$PEG_3$)$_4$-$PEG_{36}$-($N_3$-DBCO)-Ahx-$W_5$

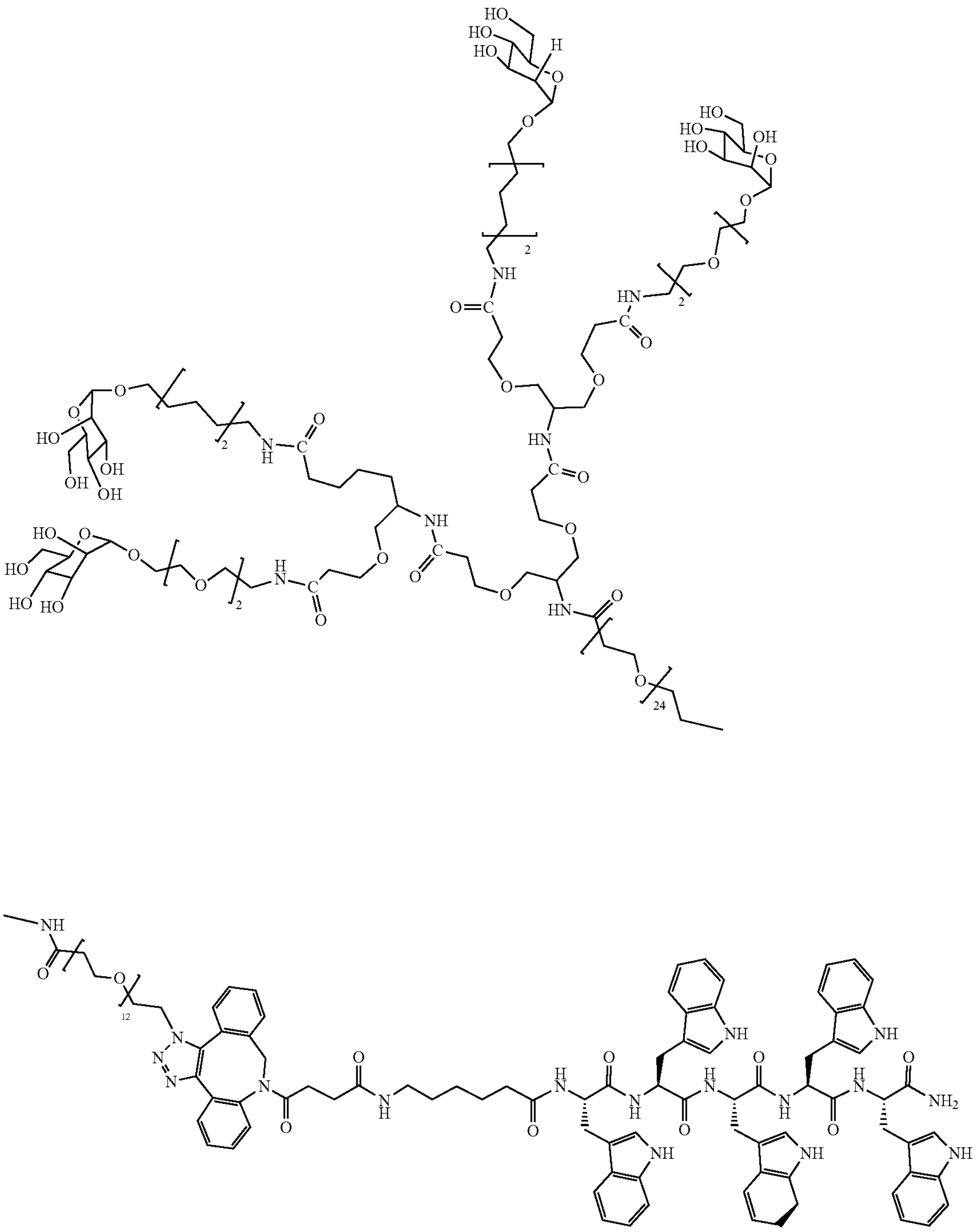

Compound 22, referred to as (Mannose-$PEG_3$)$_4$-$PEG_{24}$-$PEG_{12}$-($N_3$-DBCO)-Ahx-$W_5$, (Mannose-$PEG_3$)$_4$-$PEG_{36}$-Ahx-$W_5$ or Tetra(Mannose-$PEG_3$)-$PEG_{36}$-Ahx-$W_5$, was synthesized by first synthesizing (Mannose-$PEG_3$)$_4$-$PEG_{24}$-$NH_2$ by reacting 45 mg Compound 9 (15 umol, 1 eq) with 43 mg tris(2-carboxyethyl) phosphine hydrochloride (TCEP) (150 umol, 10 eq) in 1 mL anhydrous DMSO. The reaction was mixed for 16 hours at room temperature, when HPLC indicated that all of Compound 9 was converted to (Mannose-$PEG_3$)-$PEG_{24}$-$NH_2$. To the reaction mixture 28.9 mg of Compound 19 (13.8 umol, 1 eq) and 40 uL triethylamine (TEA) (287 umol, 20 eq) was added. The reaction was stirred for 1 hour at room temperature, when HPLC indicated the reaction was complete. Compound 22 was purified on a preparative HPLC system using a gradient of 32-52% acetonitrile/$H_2O$ (0.05% TFA) over 12 minutes on an Agilent Prep-$C_{18}$ column, 50×100 mm, 5 μm. The product eluted at ~ 6 minutes and the resulting fractions were collected, frozen and then lyophilized to obtain a 47.9% yield of a spectroscopically pure (96.2% AUC at 220 nm) colorless oil. MS (ESI) Calculated for $C_{233}H_{368}N_{24}O_{90}$ m/z 4942.5, found 1237.2 $(M/4+H)^+$.

Compound 23, (Mannose-$PEG_3$)-$PEG_{48}$-($N_3$-DBCO)-Ahx-$W_5$

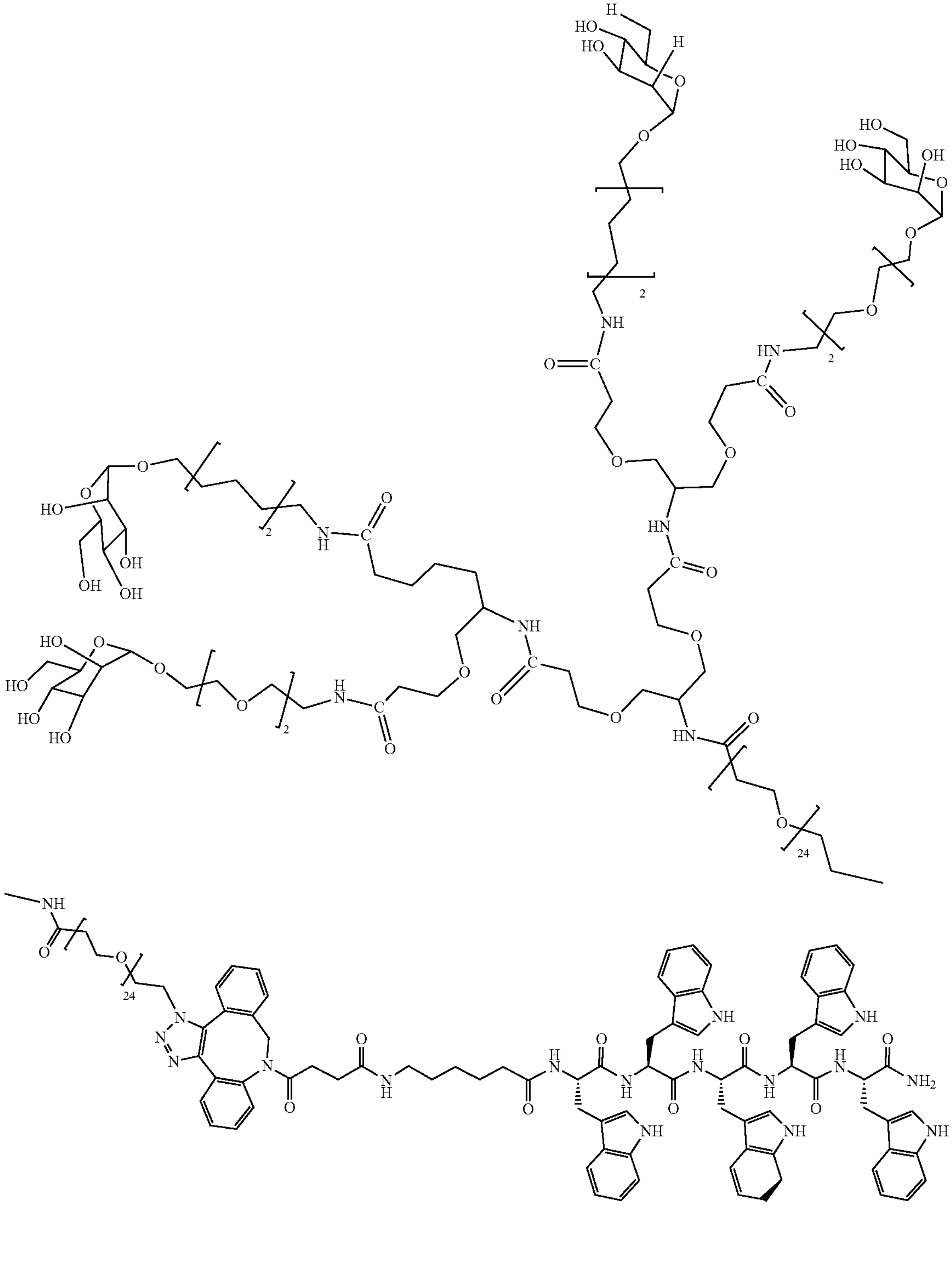

Compound 23, referred to as (Mannose-$PEG_3$)$_4$-$PEG_{24}$-$PEG_{24}$-Ahx-$W_5$, (Mannose-$PEG_3$)$_4$-$PEG_{48}$-Ahx-$W_5$, Tetra (Mannose-$PEG_3$)-$PEG_{48}$-Ahx-$W_5$ was synthesized following the same procedure at Compound 22, except that once Compound 9 was fully converted to (Mannose-$PEG_3$)-$PEG_{24}$-$NH_2$, Compound 21 was added instead of Compound 20. Compound 23 was purified on a preparative HPLC system using a gradient of 32-52% acetonitrile/$H_2O$ (0.05% TFA) over 12 minutes on an Agilent Prep-$C_{18}$ column, 30×100 mm, 5 μm. The product eluted at ~ 7 minutes and the resulting fractions were collected, frozen and then lyophilized to obtain a 40.9% yield of a spectroscopically pure (98.2% AUC at 220 nm) colorless oil. MS (ESI) Calculated for $C_{257}H_{416}N_{24}O_{102}$ m/z 5470.8, found 1095.9 $(M/5+H)^+$.

Example 1C: Lysine-Based Dendrons Via SPPS

Amphiphiles described herein were produced in solution phase, on-resin by solid-phase peptide synthesis (SPPS) or using a combination of on-resin and solution phase. For example, an amphiphile of Formula VI comprising mannose SG and a lysine-based dendron amplifier was prepared using both on-resin and solution phase synthesis.

Compound 24, (a-Mannose-PEG3)$_4$$K_2$K-$PEG_{24}$-Ahx-$W_5$

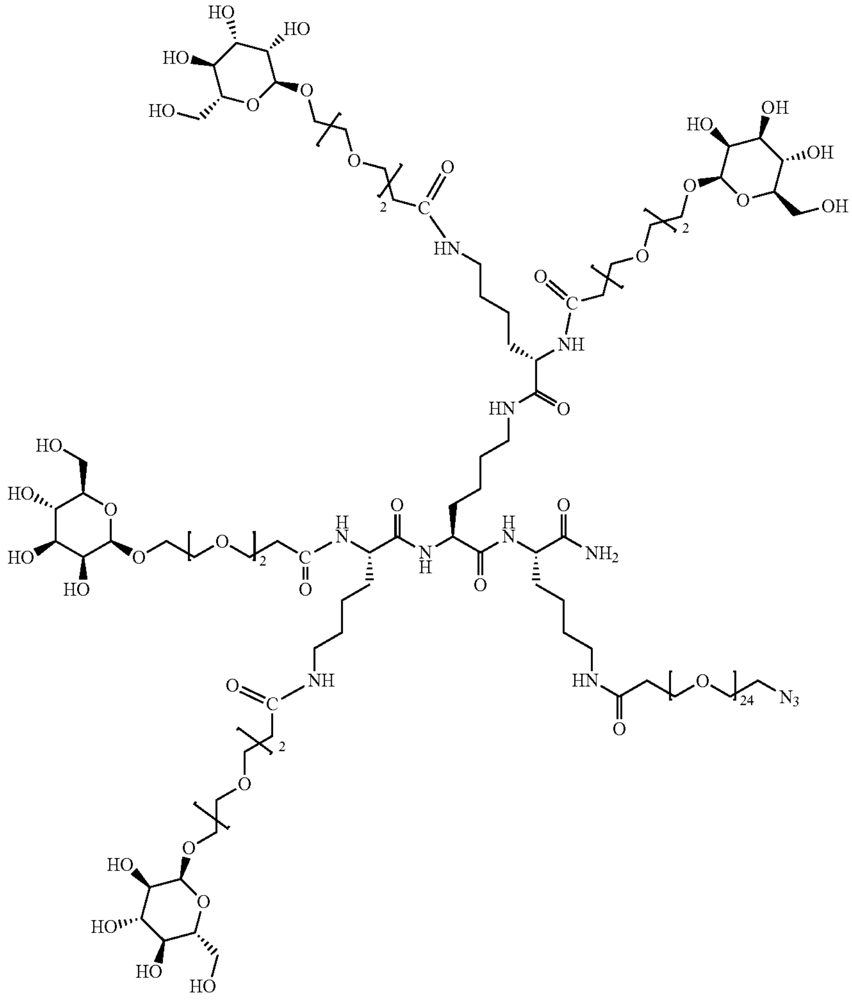

Compound 24, referred to as (a-Mannose-PEG3)$_4$K$_2$K-PEG$_{24}$-X or Tetra(Man-P3)K$_2$K-P24-X, where X=azidolysine, was synthesized using Fmoc based solid phase peptide synthesis, resulting in a spectroscopically pure (97.0% AUC at 220 nm) colorless oil. MS (ESI) calculated for $C_{127}H_{238}N_{12}O_{65}$ m/z 2971.6, found 1486.9 (M/2+H)$^+$.
Compound 25, (a-Mannose-PEG3)$_4$K$_2$K-PEG24-(X-DBCO)-Ahx-2B$_3$W$_2$
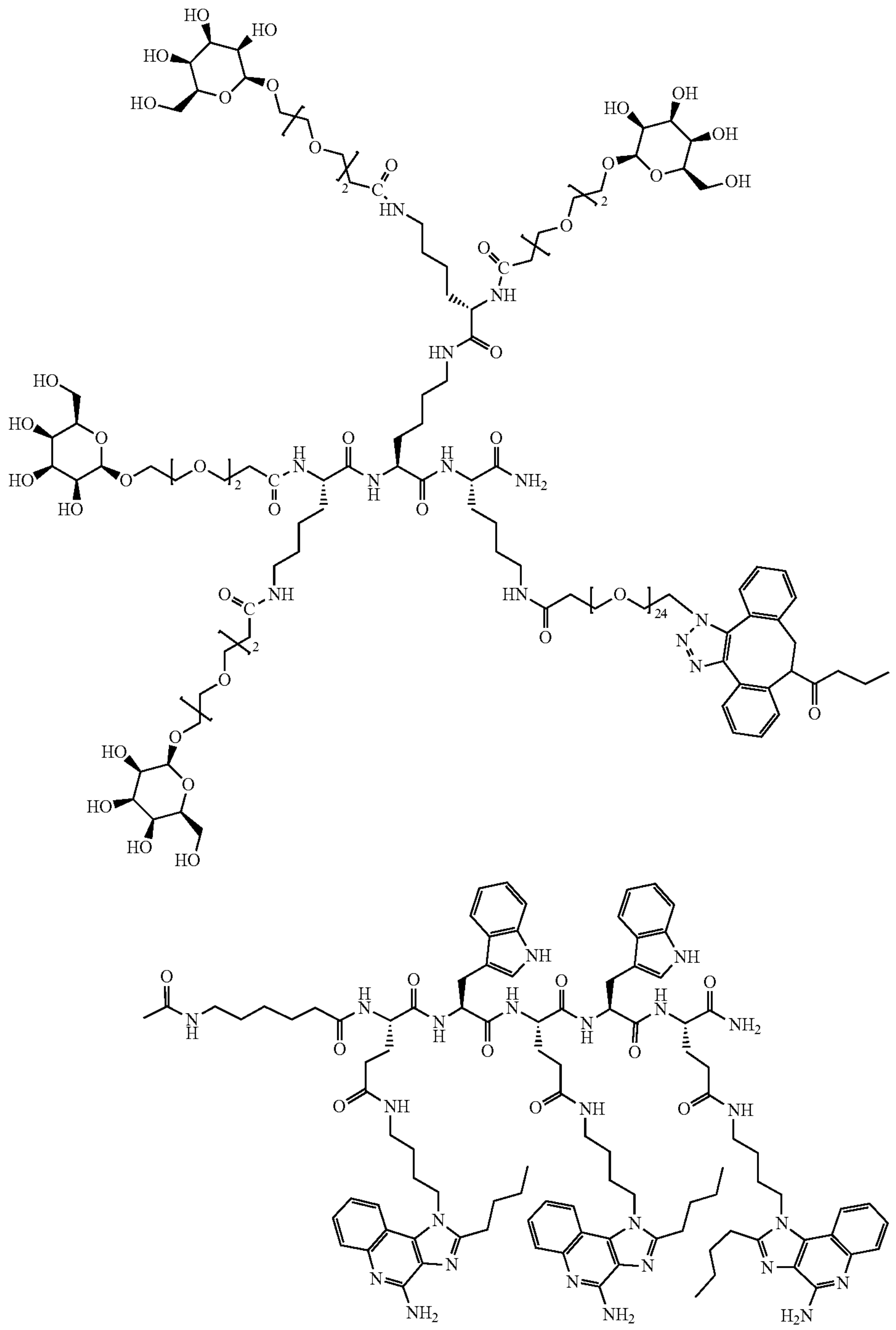

Compound 25, referred to as (a-Mannose-$PEG_3$)$_4$$K_2$K-$PEG_{24}$-(X-DBCO)-Ahx-2$B_3$$W_2$ or Tetra(Man-P3)$K_2$K-P24-(X-DBCO)-Ahx-2$B_3$$W_2$, was synthesized by reacting Compound 24 (0.001 mmol, 1.0 eq) with Compound 4 (0.001 mmol, 1.05 eq) in anhydrous DMSO for 16 hours at room temperature. HPLC was monitored to evaluate reaction progress and indicated complete conversion of Compound 24 to Compound 25, resulting in a spectroscopically pure (97.5% AUC at 220 nm) colorless solution. MS (ESI) calculated for $C_{243}H_{375}N_{37}O_{76}$ m/z 5027.7.4, found 1258.6 $(M/4+H)^+$.

Compound 26, (a-Mannose-PEG3)$_4$$K_2$K-PEG24-(X-DBCO)-Ahx-W5

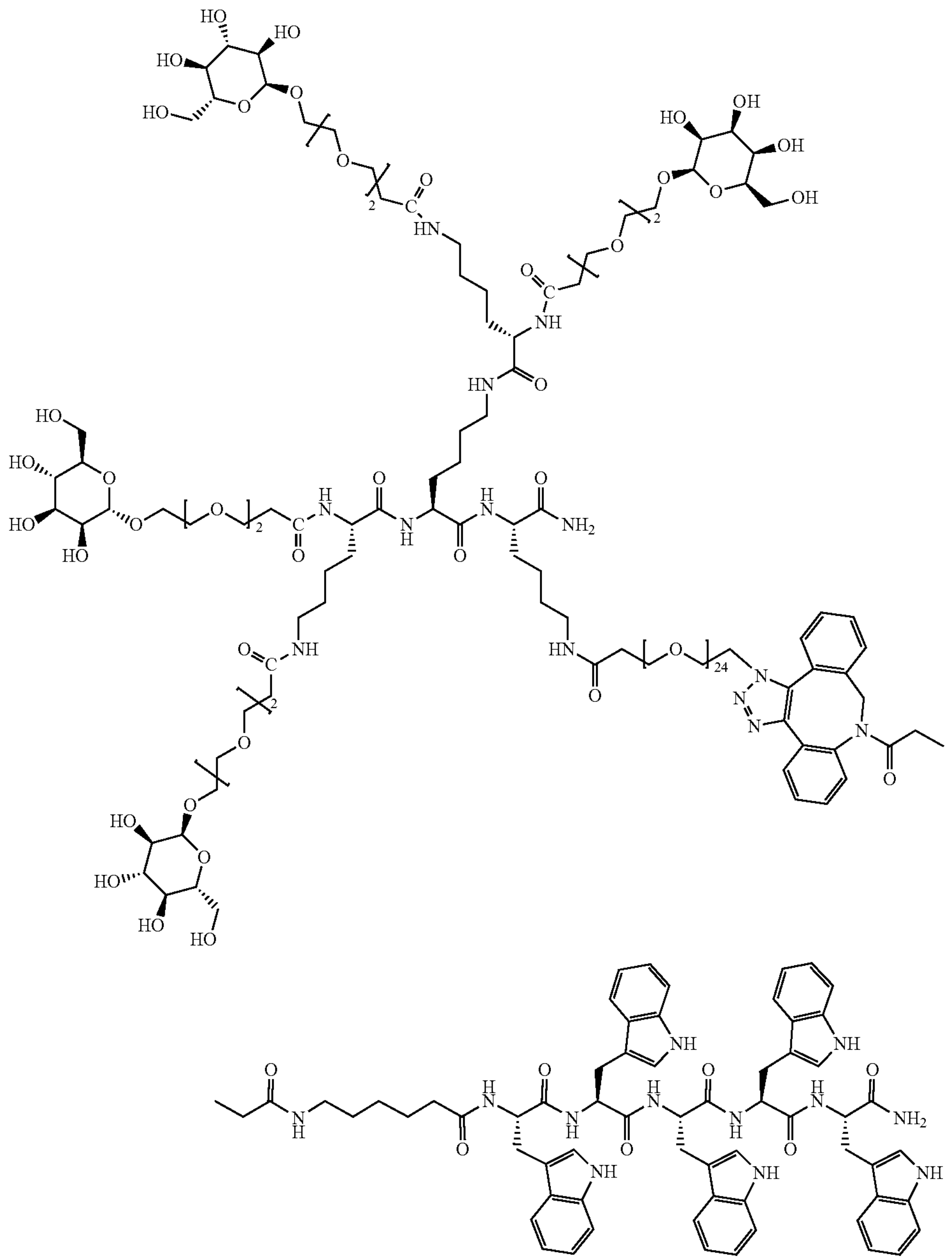

Compound 26, referred to as (a-Mannose-PEG3)$_4$K$_2$K-PEG$_{24}$-(X-DBCO)-Ahx-W5 or Tetra(Man-P3)K$_2$K-P24-(X-DBCO)-Ahx-W5, was synthesized following the same procedure as Compound 25, except that Compound 1 was used in place of Compound 4, resulting in a spectroscopically pure (94.7% AUC at 220 nm) colorless solution. MS (ESI) calculated for $C_{207}H_{315}$N25073 m/z. 4319.2, found 865.0 $(M/5+H)^+$.

Compound 27, (a-Mannose-PEG$_3$)$_4$K$_2$K-PEG$_{24}$-Ahx-W$_5$

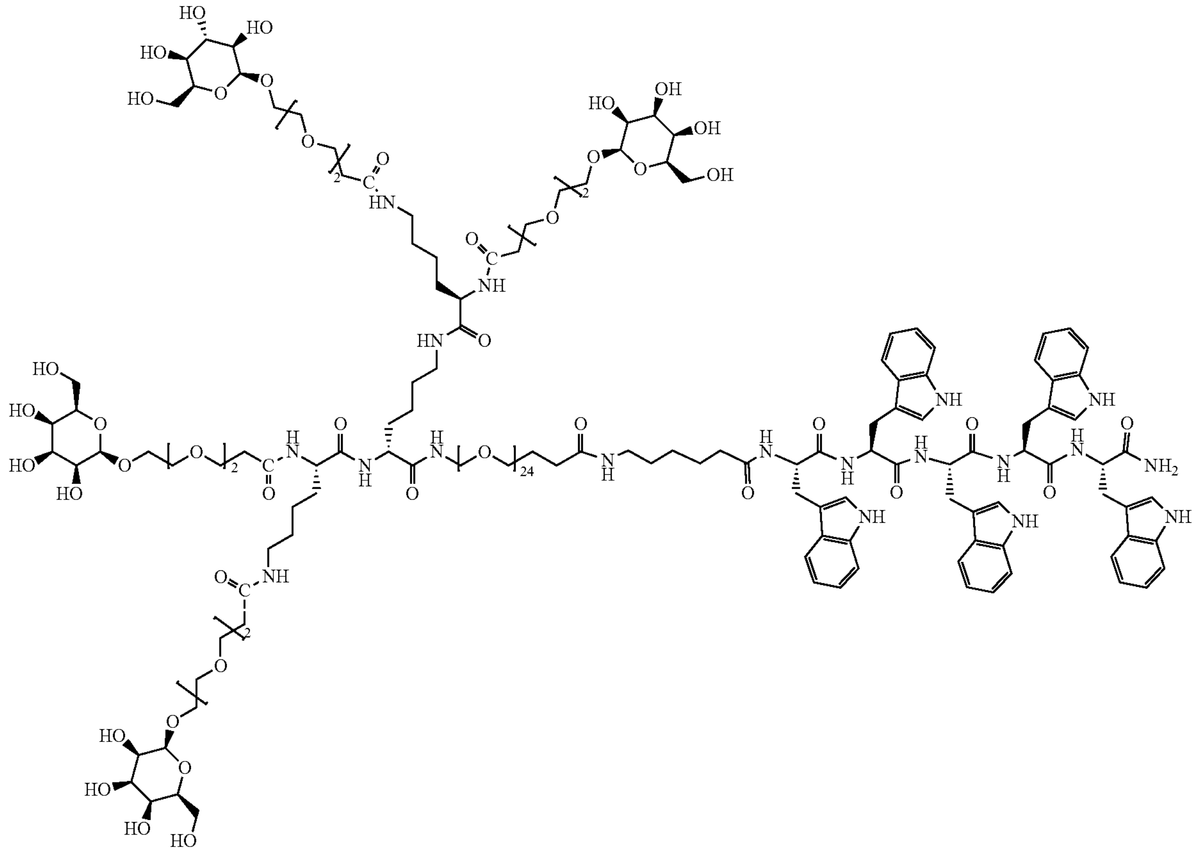

Compound 27, referred to as (a-Mannose-PEG$_3$)$_4$K$_2$K-PEG$_{24}$-Ahx-W$_5$ or Tetra(Man-P3)K$_2$K-P24-Ahx-W$_5$, was synthesized using Fmoc based solid phase peptide synthesis resulting in a spectroscopically pure (97.9% AUC at 220 nm) off-white solid. MS (ESI) calculated for 182$H_{289}N_{19}O_{70}$ m/z 3861.0, found 1288.4 $(M/3+H)^+$.

Example 1D: Synthesis of Peptide Antigen Conjugates of Formula PEG-[E1]-A-[E2]—U1 or U1-[E1]-A-[E2]-PEG Compound 28, OH-PEG-CPNE1-N3

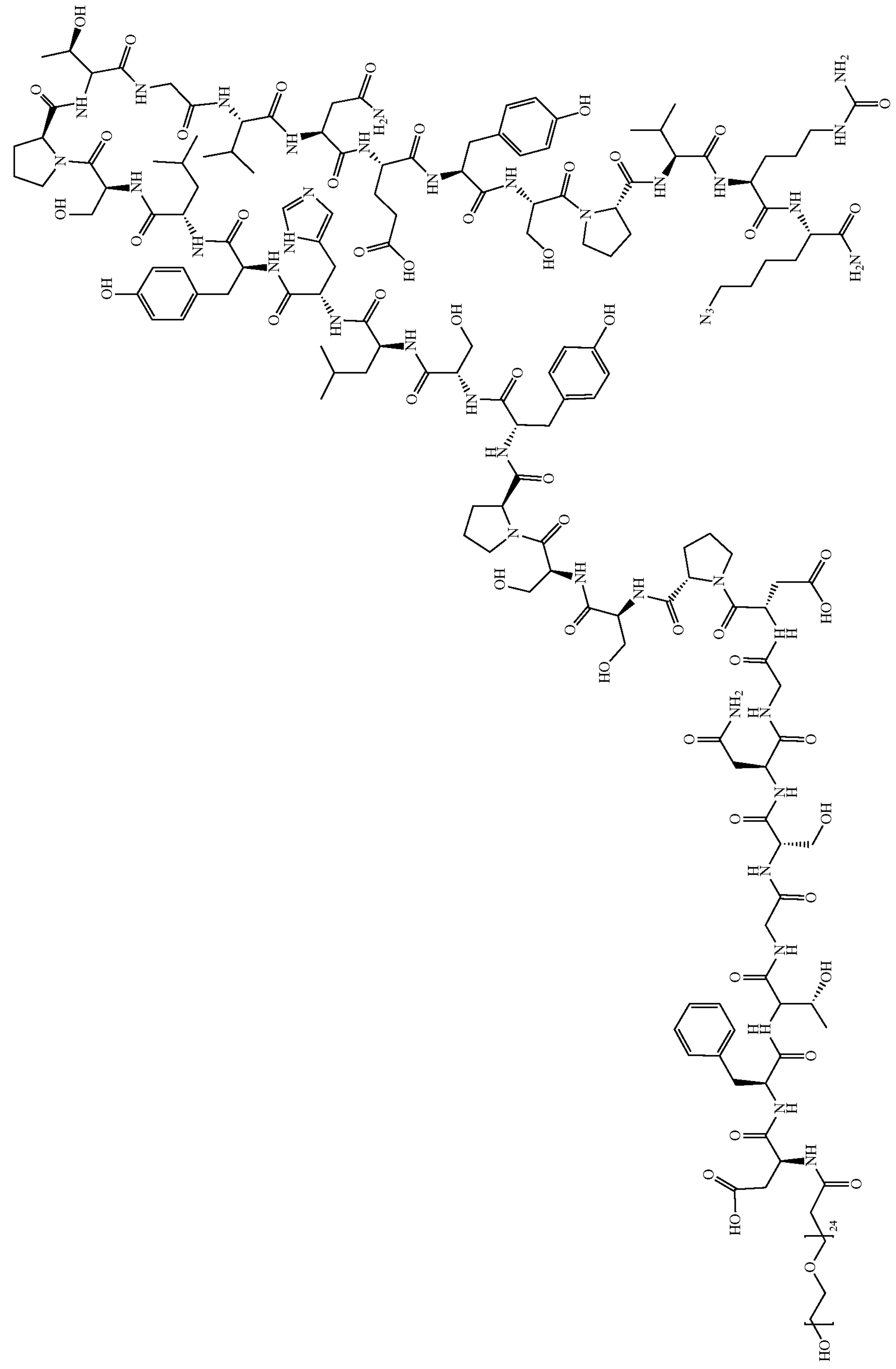

Compound 28, referred to as OH-PEG24-CPNE1-N3 was synthesized by reacting 50 mg DFTGSNGDPSSPYSLHYL-SPTGVNEYSPVZX (0.0147 mmol, 1 eq), which was prepared by solid phase peptide synthesis by Genscript (Piscataway, NJ), with 20.1 mg OH-PEG24-TFP (0.0162 mmol, 1.1 eq) and 7.2 mg triethylamine (4.8 eq). Compound 28 was purified on a preparative HPLC system using a gradient of 32-52% acetonitrile/$H_2O$ (0.05% TFA) over 10 minutes on an Agilent Prep-$C_{18}$ column, 30×100 mm, 5 μm. The product eluted at ~ 7 minutes and the resulting fractions were collected, frozen and then lyophilized to obtain a 78% yield of a spectroscopically pure (99.9% AUC at 220 nm) white powder. MS (ESI) Calculated for $C_{200}H_{317}N_{41}O_{77}$ m/z 4527.95, found 905.4 $(M/5+H)^+$.

Compounds 29-58 were produced following the same procedure as Compound 28, except that the equivalents of TEA added was determined by multiplying 1.2 by the sum of histidine, aspartic acid, and glutamic acid residues in the peptide sequence, and were purified using the solvent gradients listed in the below. Table 2A provides a summary of the synthesis and characterization of compounds 29-58.

TABLE 2A

Peptide antigen conjugates of formula PEG-[E1]-A-[E2]-U1 or U1-[E1]-A-[E2]-PEG

| Cmpd # | PEG | [E1]-A-[E2]-U1 or U1-[E1]-A-[E2] | Theo. MW | MS (ESI) m/n Found | Prep. HPLC gradient used |
|---|---|---|---|---|---|
| | Product | | | | |
| 29 | OH-PEG-24 | VRFSDEGGYTCFFRDHSYQEEAASPVZX (SEQ ID NO: 512) OH-PEG24-VRFSDEGGYTCFFRDHSYQEEAASPVZX | 4437.84 | 1110.1 $(M/4 + H)^+$ | 30-50%, 10 minutes |
| 30 | | SPVZGQAEPDRAHYNIVTFBBSPVZX (SEQ ID NO: 513) OH-PEG24-SPVZGQAEPDRAHYNIVTFBBSPVZX | 4051.62 | 1013.5 $(M/4 + H)^+$ | 32-52%, 10 minutes |
| 31 | | GIPVHLELASMTNMELMSSIVHQQVFPTSPVZX (SEQ ID NO: 514) OH-PEG24-GIPVHLELASMTNMELMSSIVHQQVFPTSPVZX | 4833.64 | 1209.2 $(M/4 + H)^+$ | 36-56% 10 minutes |
| 32 | | SPVZnEVGWYRSPFSRVVHLYRNGSPVZX(SEQ ID NO: 515) OH-PEG24-SPVZnEVGWYRSPFSRVVHLYRNGSPVZX | 4599.25 | 1149.3 $(M/4 + H)^+$ | 32-52% 10 minutes |
| 33 | | XaaSPVZnEVGWYRSPFSRVVHLYRNGSPVZX(SEQ ID NO: 516) OH-PEG24-XaaSPVZnEVGWYRSPFSRVVHLYRNGSPVZX | 4670.35 | 1168.0 $(M/4 + H)^+$ | 32-52% 10 minutes |
| 34 | | VZnEVGWYRSPFSRVVHLYRNGSPVZX (SEQ ID NO: 517) OH-PEG24-VZnEVGWYRSPFSRVVHLYRNGSPVZX | 4414.11 | 1104.4 $(M/4 + H)^+$ | 30-50% -12 min |
| 35 | | VZQLQPFPQPELPYPQPQLPYPQPQPFRSPVZX(SEQ ID NO: 498) OH-PEG24-VZQLQPFPQPELPYPQPQLPYPQPQPFRSPVZX | 5110.54 | 1278.4 $(M/4 + H)^+$ | 5-95% 10 minutes |
| 36 | | VZPQLPYPQPELPYPQPQPFRPEQPYPQPQPSPVZX (SEQ ID NO: 499) OH-PEG24-VZPQLPYPQPELPYPQPQPFRPEQPYPQPQPSPVZX | 5433.84 | 1359.3 $(M/4 + H)^+$ | 5-95% 10 minutes |
| 37 | | VZQGIIQPEQPAQLEVISPVZX (SEQ ID NO: 500) OH-PEG24-VZQGIIQPEQPAQLEVISPVZX | 3641.87 | 1214.8 $(M/3 + H)^+$ | 5-95% 10 minutes |
| 38 | | VZPQPQQPEQPFPQPEQEFPQPQQPQQSFPEQQPPLSPVZX(SEQ ID NO: 501) OH-PEG24-VZPQPQQPEQPFPQPEQEFPQPQQPQQSFPEQQPPLSPVZX | 5986.29 | 1497.4 $(M/4 + H)^+$ | 5-95% 10 minutes |
| 39 | | VZQQQPFPQPEQPFBQQPQSPVZX (SEQ ID NO: 502) OH-PEG24-VZQQQPFPQPEQPFBQQPQSPVZX | 3985.17 | 1329.2 $(M/3 + H)^+$ | 5-95% 10 minutes |
| 40 | | VZQQFLQPEQPFPQQPEQPYPQQPEQPFPQPQQSPVZX (SEQ ID NO: 503) OH-PEG24-VZQQFLQPEQPFPQQPEQPYPQQPEQPFPQPQQSPVZX | 5739.04 | 1435.7 $(M/4 + H)^+$ | 5-95% 10 minutes |
| 41 | | VZQQFSQPEQEFPQPQQPQQSFPEQQPPFSPVZX (SEQ ID NO: 504) OH-PEG24-VZQQFSQPEQEFPQPQQPQQSFPEQQPPFSPVZX | 5236.43 | 1310.2 $(M/4 + H)^+$ | 5-95% 10 minutes |
| 42 | | VZPTPLQPEQPFPQQPQQPQQPFPQPEQPFPWQPQSPVZX(SEQ ID NO: 505) OH-PEG24-VZPTPLQPEQPFPQQPQQPQQPFPQPEQPFPWQPQSPVZX | 5897.29 | 1475.3 $(M/4 + H)^+$ | 5-95% 10 minutes |

TABLE 2A-continued

Peptide antigen conjugates of formula PEG-[E1]-A-[E2]-U1 or U1-[E1]-A-[E2]-PEG

| Cmpd # | PEG | [E1]-A-[E2]-U1 or U1-[E1]-A-[E2] | Theo. MW | MS (ESI) m/n Found | Prep. HPLC gradient used |
|---|---|---|---|---|---|
| 43 | OH-PEG24-VZSSPLQPEQPFPQQPQQPFPEQPQQPQSPVZX | VZSSPLQPEQPFPQQPQQPFPEQPQQPQSPVZX (SEQ ID NO: 506) | 4992.23 | 1248.9 $(M/3 + H)^+$ | 5-95% 10 minutes |
| 44 | OH-PEG24-VZQSIPQPEQPFPQPEQPFPQSQESPVZX | VZQSIPQPEQPFPQPEQPFPQSQESPVZX (SEQ ID NO: 507) | 4542.72 | 1515.1 $(M/4 + H)^+$ | 5-95% 10 minutes |
| 45 | OH-PEG24-VZPQQPFPQQPQQIIPQSPVZX | VZPQQPFPQQPQQIIPQSPVZX (SEQ ID NO: 508) | 3752.98 | 1251.7 $(M/3 + H)^+$ | 5-95% 10 minutes |
| 46 | OH-PEG24-VZPQQPIPEQPQPYPEQPQPYPQQSPVZX | VZPQQPIPEQPQPYPEQPQPYPQQSPVZX (SEQ ID NO: 509) | 4593.81 | 1532.2 $(M/4 + H)^+$ | 5-95% 10 minutes |
| 47 | OH-PEG24-VZQQPPFSEQEQPVLPQSPVZX | VZQQPPFSEQEQPVLPQSPVZX (SEQ ID NO: 510) | 3730.88 | 1244.5 $(M/3 + H)^+$ | 5-95% 10 minutes |
| 48 | OH-PEG24-VZQPPFSQQQESPFSQQSPVZX | VZQPPFSQQQESPFSQQSPVZX (SEQ ID NO: 511) | 3741.82 | 1248.2 $(M/3 + H)^+$ | 5-95% 10 minutes |
| 49 | mPEG24-DFTGSNGDPSSPYSLHYLSPTGVNEYSPVZX | DFTGSNGDPSSPYSLHYLSPTGVNEYSPVZX(SEQ ID NO: 518) | 4497.98 | 1125.8 $(M/4 + H)^+$ | 32-52% 10 minutes |
| 50 | mPEG24-VRFSDEGGYTCFFRDHSYQEEAASPVZX | VRFSDEGGYTCFFRDHSYQEEAASPVZX(SEQ ID NO: 512) | 4407.92 | 1102.3 $(M/4 + H)^+$ | 33-53% 10 minutes |
| 51 | mPEG24-SPVZGQAEPDRAHYNIVTFBBSPVZX | SPVZGQAEPDRAHYNIVTFBBSPVZX(SEQ ID NO: 513) | 4021.63 | 1006.1 $(M/4 + H)^+$ | 32-52% 10 minutes |
| 52 | mPEG24-GIPVHLELASMTNMELMSSIVHQQVFPTSPVZX | GIPVHLELASMTNMELMSSIVHQQVFPTSPVZX(SEQ ID NO: 514) | 4803.72 | 1200.5 $(M/4 + H)^+$ | 36-56% 10 minutes |
| 53 | mPEG24-SPVZnEVGWYRSPFSRVVHLYRNGSPVZX | SPVZnEVGWYRSPFSRVVHLYRNGSPVZX (SEQ ID NO: 515) | 4569.33 | 1143.5 $(M/4 + H)^+$ | 30-50% 10 minutes |
| 54 | OH-PEG(1000)-DFTGSNGDPSSPYSLHYLSPTGVNEYSPVZX | DFTGSNGDPSSPYSLHYLSPTGVNEYSPVZX (SEQ ID NO: 518) | 4456.6 | NA | NA |
| 55 | OH-PEG(1000)-VRFSDEGGYTCFFRDHSYQEEAASPVZX | VRFSDEGGYTCFFRDHSYQEEAASPVZX (SEQ ID NO: 512) | 4366.5 | NA | NA |
| 56 | OH-PEG(1000)-SPVZGQAEPDRAHYNIVTFBBSPVZX | SPVZGQAEPDRAHYNIVTFBBSPVZX (SEQ ID NO: 513) | 3980.2 | NA | NA |
| 57 | OH-PEG(1000)-GIPVHLELASMTNMELMSSIVHQQVFPTSPVZX | GIPVHLELASMTNMELMSSIVHQQVFPTSPVZX (SEQ ID NO: 514) | 4762.3 | NA | NA |
| 58 | OH-PEG(1000)-SPVZnEVGWYRSPFSRVVHLYRNGSPVZX | SPVZnEVGWYRSPFSRVVHLYRNGSPVZX (SEQ ID NO: 515) | 4469.93 | NA | NA |

Single letter abbreviations are used for amino acid sequences in the above table; X=azidolysine, Z=citrulline, n=norleucine and Xaa=Beta-alanine. Peptide-based starting materials were manufactured by solid-phase peptide synthesis by Genscript (Piscataway, NJ). Sequences for peptide-based starting materials are written from N- to C-terminus, and C-terminal $NH_2$ indicates that the peptide is terminated with an Amide. Unless otherwise specified, any C-terminal X, azidolysine, is terminated with an amide and is implicit in the sequences (i.e., not shown). OH-PEG24-TFP was purchased from Peptide Solutions (Tuscan, AZ). mPEG24-NHS and OH-PEG (1000)-NHS, where 1000 indicates the average molecular weight, was purchased from Broadpharm (San Diego, CA).

Example 1E: Synthesis of Peptide Antigen Conjugates of Formula PEG-[E1]-A-[E2]-U-H-[D] and [D]-H-[U]-[E1]-A-[E2]-PEG Compounds 59-97 were produced in a similar manner as that described for Compound 13, except that excess of Compound 1 was removed using an agarose resin modified with azide. Accordingly, the general procedure consisted of the following steps: The peptide antigen fragment PEG-[E1]-[E2]—U1 in DMSO was suspended in DMSO at a concentration >10 mM, typically about 25 mM. The U2-fragment was suspended in DMSO at a concentration >10 mM, typically about 50 mM. To one equivalent of peptide antigen fragment was added at least 1.05 molar equivalents of U2-H, e.g., DBCO-Ahx-W5 in a polypropylene reaction vessel. The reaction mixtures were placed at room temperature for at least 16 hours, or up to 40° C. for 4 hours, after which the reaction was monitored by HPLC at 280 nm. If peptide antigen fragment remained, additional equivalents of U2-H were added. And the reaction was permitted to proceed for at least 16 hours at room temperature, or for 4 hours at 40° C., after which the reaction was again monitored by HPLC at 280 nm. If HPLC showed that the peptide antigen fragment had been fully consumed by the reaction then any excess of U2-H was removed using a resin reactive for the U2-H, such as an agarose azide resin. The agarose asize resin was added up to 0.25 molar equivalents (relative to the starting molar amount of peptide antigen fragment) in a minimum volume of DMSO and then incubated for at least 16 hours at room temperature and then monitored by HPLC at 280 nm to determine if any remaining U2-H had been removed. After confirming that the U2-H had been adequately removed, the resin was removed from the peptide antigen conjugate of formula PEG-E1-A-E2-U-H in DMSO by filtration. The resulting DMSO solution of peptide antigen conjugate was then assessed for peptide antigen conjugate concentration by UV-Vis and then optionally additional DMSO was added to achieve a target concentration. The resulting peptide antigen conjugate in DMSO was then sterile-filtered through a 0.2 micron filter with either a nylon or PTFE filter membrane.

Table 3A provides a summary of the synthesis and characterization of compounds 59-97.

TABLE 3A

Peptide antigen conjugates of formula PEG-[E1]-A-[E2]-U-H-[D] and [D]-H-[U]-[E1]-A-[E2]-PEG.

| Cmpd # | PEG-[E1]-A-[E2]-U1 or U1-[E1]-A-[E2]-PEG | U2-H | Theo. MW | Found MW |
|---|---|---|---|---|
| | Product | | | |
| 59 | Compound 28<br>OH-PEG24-DFTGSNGDPSSPYSLHYLSPTGVNEYSPVZ(X-DBCO)-Ahx-W5 | Compound 1 | 4527.95 | 1175.5 $(M/5 + H)^+$ |
| 60 | Compound 29<br>OH-PEG24-VRFSDEGGYTCFFRDHSYQEEAASPVZ(X-DBCO)-Ahx-W5 | Compound 1 | 5787.04 | 1158.2 $(M/5 + H)^+$ |
| 61 | Compound 30<br>OH-PEG24-SPVZGQAEPDRAHYNIVTFBBSPVZ(X-DBCO)-Ahx-W5 | Compound 1 | 5400.82 | 1080.5 $(M/5 + H)^+$ |
| 62 | Compound 31<br>OH-PEG24-GIPVHLELASMTNMELMSSIVHQQVFPTSPVZ(X-DBCO)-Ahx-W5 | Compound 1 | 6182.84 | 1237.6 $(M/5 + H)^+$ |
| 63 | Compound 32<br>OH-PEG24-SPVZnEVGWYRSPFSRVVHLYRNGSPVZ(X-DBCO)-Ahx-W5 | Compound 1 | 5948.45 | 1189.9 $(M/5 + H)^+$ |
| 64 | Compound 33<br>OH-PEG24-XaaSPVZnEVGWYRSPFSRVVHLYRNGSPVZ(X-DBCO)-Ahx-W5 | Compound 1 | 6019.55 | 1204.2 $(M/5 + H)^+$ |
| 65 | Compound 34<br>OH-PEG24-VZnEVGWYRSPFSRVVHLYRNGSPVZ(X-DBCO)-Ahx-W5 | Compound 1 | 5763.31 | 1153.4 $(M/5 + H)^+$ |
| 66 | Compound 35<br>OH-PEG24-VZQLQPFPQPELPYPQPQLPYPQPQPFRSPVZ(X-DBCO)-Ahx-W5 | Compound 1 | 6459.66 | 1291.9 $(M/5 + H)^+$ |
| 67 | Compound 36<br>OH-PEG24-VZPQLPYPQPELPYPQPQPFRPEQPYPQPQPSPVZ(X-DBCO)-Ahx-W5 | Compound 1 | 6782.96 | 1356.6 $(M/5 + H)^+$ |

TABLE 3A-continued

Peptide antigen conjugates of formula PEG-[E1]-A-[E2]-U-H-[D] and [D]-H-[U]-[E1]-A-[E2]-PEG.

| Cmpd # | PEG-[E1]-A-[E2]-U1 or U1-[E1]-A-[E2]-PEG | U2-H | Theo. MW | Found MW |
|---|---|---|---|---|
| 68 | Compound 37 OH-PEG24-VZQGIIQPEQPAQLEVISPVZ(X-DBCO)-Ahx-W5 | Compound 1 | 4990.99 | 998.2 (M/5 + H)+ |
| 69 | Compound 38 OH-PEG24-VZPQPQQPEQPFPQPEQEFPQPQQPQQSFPEQQPPLSPVZ(X-DBCO)-Ahx-W5 | Compound 1 | 7335.41 | 1467.1 (M/5 + H)+ |
| 70 | Compound 39 OH-PEG24-VZQQQPFPQPEQPFBQQPQSPVZ(X-DBCO)-Ahx-W5 | Compound 1 | 5365.30 | 1073.1 (M/5 + H)+ |
| 71 | Compound 40 OH-PEG24-VZQQFLQPEQPFPQQPEQPYPQQPEQPFPQPQQSPVZ(X-DBCO)-Ahx-W5 | Compound 1 | 7088.16 | 1417.6 (M/5 + H)+ |
| 72 | Compound 41 OH-PEG24-VZQQFSQPEQEFPQPQQPQQSFPEQQPPFSPVZ(X-DBCO)-Ahx-W5 | Compound 1 | 6585.55 | 1317.1 (M/5 + H)+ |
| 73 | Compound 42 OH-PEG24-VZPTPLQPEQPFPQQPQQPQQPFPQPEQPFPWQPQSPVZ(X-DBCO)-Ahx-W5 | Compound 1 | 7246.41 | 1449.3 (M/5 + H)+ |
| 74 | Compound 43 OH-PEG24-VZSSPLQPEQPFPQQPQQPFPEQPQQPQSPVZ(X-DBCO)-Ahx-W5 | Compound 1 | 6341.35 | 1268.3 (M/5 + H)+ |
| 75 | Compound 44 OH-PEG24-VZQSIPQPEQPFPQPEQPFPQSQESPVZ(X-DBCO)-Ahx-W5 | Compound 1 | 5889.72 | 1177.9 (M/5 + H)+ |
| 76 | Compound 45 OH-PEG24-VZPQQPFPQQPQQIIPQSPVZ(X-DBCO)-Ahx-W5 | Compound 1 | 5942.93 | 1188.6 (M/5 + H)+ |
| 77 | Compound 46 OH-PEG24-VZPQQPIPEQPQPYPEQPQPYPQQSPVZ(X-DBCO)-Ahx-W5 | Compound 1 | 5102.1 | 1020.4 (M/5 + H)+ |
| 78 | Compound 47 OH-PEG24-VZQQPPFSEQEQPVLPQSPVZX(N3-DBCO)-Ahx-W5 | Compound 1 | 5080.0 | 1016.0 (M/5 + H)+ |
| 79 | Compound 48 OH-PEG24-VZQPPFSQQQESPFSQQSPVZ(X-DBCO)-Ahx-W5 | Compound 1 | 5090.94 | 1018.2 (M/5 + H)+ |
| 80 | Compound 49 mPEG24-DFTGSNGDPSSPYSLHYLSPTGVNEYSPVZ(X-DBCO)-Ahx-W5 | Compound 1 | 5847.18 | 1170.9 (M/5 + H)+ |
| 81 | Compound 50 mPEG24-VRFSDEGGYTCFFRDHSYQEEAASPVZ(X-DBCO)-Ahx-W5 | Compound 1 | 5757.12 | 1151.8 (M/5 + H)+ |
| 82 | Compound 51 mPEG24-SPVZGQAEPDRAHYNIVTFBBSPVZ(X-DBCO)-Ahx-W5 | Compound 1 | 5370.83 | 1074.2 (M/5 + H)+ |
| 83 | Compound 52 mPEG24-GIPVHLELASMTNMELMSSIVHQQVFPTSPVZ(X-DBCO)-Ahx-W5 | Compound 1 | 6152.92 | 1230.9 (M/5 + H)+ |
| 84 | Compound 53 mPEG24-SPVZnEVGWYRSPFSRVVHLYRNGSPVZ(X-DBCO)-Ahx-W5 | Compound 1 | 5918.53 | 1184.1 (M/5 + H)+ |
| 85 | Compound 54 OH-PEG(1000)-DFTGSNGDPSSPYSLHYLSPTGVNEYSPVZ(X-DBCO)-Ahx-W5 | Compound 1 | 5805.8 | NA |
| 86 | Compound 55 OH-PEG(1000)-VRFSDEGGYTCFFRDHSYQEEAASPVZ(X-DBCO)-Ahx-W5 | Compound 1 | 5717.50 | NA |
| 87 | Compound 56 OH-PEG(1000)-SPVZGQAEPDRAHYNIVTFBBSPVZ(X-DBCO)-Ahx-W5 | Compound 1 | 5329.40 | NA |

TABLE 3A-continued

| Peptide antigen conjugates of formula PEG-[E1]-A-[E2]-U-H-[D] and [D]-H-[U]-[E1]-A-[E2]-PEG. | | | | |
|---|---|---|---|---|
| Cmpd # | PEG-[E1]-A-[E2]-U1 or U1-[E1]-A-[E2]-PEG | U2-H | Theo. MW | Found MW |
| 88 | Compound 57<br>OH-PEG(1000)-GIPVHLELASMTNMELMSSIVHQQVFPTSPVZ(X-DBCO)-Ahx-W5 | Compound 1 | 6111.52 | NA |
| 89 | Compound 58<br>OH-PEG(1000)-SPVZnEVGWYRSPFSRVVHLYRNGSPVZ(X-DBCO)-Ahx-W5 | Compound 1 | 5877.10 | |
| 90 | KKKKVRDFTGSNGDPSSPYSLHYLSPTGVNEYSPV ZX (SEQ ID NO: 519)<br>KKKKVRDFTGSNGDPSSPYSLHYLSPTGVNEYSPVZ(X-DBCO)-Ahx-W5 | Compound 1 | 5515.79 | 1104.2 (M/5 + H)$^+$ |
| 91 | KKKKKVRFSDEGGYTCFFRDHSYQEEAASPVZX (SEQ ID NO: 520)<br>KKKKKVRFSDEGGYTCFFRDHSYQEEAASPVZ(X-DBCO)-Ahx-W5 | Compound 1 | 5298.59 | 1059.9 (M/5 + H)$^+$ |
| 92 | KKKVRGIPVHLELASMTNMELMSSIVHQQVFPTSP VZX (SEQ ID NO: 521)<br>KKKVRGIPVHLELASMTNMELMSSIVHQQVFPTSPVZ(X-DBCO)-Ahx-W5 | Compound 1 | 5693.36 | 1138.4 (M/5 + H)$^+$ |
| 93 | KKVRGQAEPDRAHYNIVTFBBKBDSPVZX (SEQ ID NO: 522)<br>KKVRGQAEPDRAHYNIVTFBBKBDSPVZ(X-DBCO)-Ahx-W5 | Compound 1 | 4670.96 | 934.8 (M/5 + H)$^+$ |
| 94 | KKKVRnEVGWYRSPFSRVVHLYRNGSPVZX (SEQ ID NO: 523)<br>KKKVRnEVGWYRSPFSRVVHLYRNGSPVZ(X-DBCO)-Ahx-W5 | Compound 1 | 5146.64 | 1029.5 (M/5 + H)$^+$ |
| 95 | KKVRnEVGWYRSPFSRVVHLYRNGKSPVZX (SEQ ID NO: 524)<br>KKVRnEVGWYRSPFSRVVHLYRNGKSPVZ(X-DBCO)-Ahx-W5 | Compound 1 | 5019.41 | 1004.1 (M/5 + H)$^+$ |
| 96 | KKKVRnEVGWYRSPFSRVVHLYRNGKSPVZX (SEQ ID NO: 525)<br>KKKVRnEVGWYRSPFSRVVHLYRNGKSPVZ(X-DBCO)-Ahx-W5 | Compound 1 | 5147.59 | 1029.4 (M/5 + H)$^+$ |
| 97 | {OH}{PEG24} SPVZnEVGWYRSPFSRVVHLYRNGK SPVZX (SEQ ID NO: 526)<br>{OH}{PEG24}SPVZnEVGWYRSPFSRVVHLYRNGKSPVZ(X-DBCO)-Ahx-W5 | Compound 1 | 6075.54 | 1216.2 (M/5 + H)$^+$ |

Single letter abbreviations are used for amino acid sequences in the above table; X = azidolysine, Z = citrulline, Xaa = Beta-alanine, n = norleucine, B = alpha-aminobutyric acid. {OH}{PEG24}, sometimes abbreviated OH-PEG24, is OH—$(CH_2—CH_2—O)_{24}$-$CH_2—CH_2—C(O)—$; Peptide-based starting materials were manufactured by solid-phase peptide synthesis by Genscript (Piscataway, NJ). Sequences for peptide-based starting materials are written from N- to C-terminus, and C-terminal $NH_2$ indicates that the peptide is terminated with an Amide. Unless otherwise specified, any C-terminal X, azidolysine, is terminated with an amide and is implicit in the sequences (i.e., not shown).

Compounds 114-121 were produced in a similar manner as that described for Compound 59.

Table 9 provides a summary of the synthesis and characterization of compounds 114-121.

TABLE 9

| Peptide antigen conjugates of Formula PEG-E1-A-E2-U-H | | | | |
|---|---|---|---|---|
| # | PEG-[E1]-A-[E2]-U1 or U1-[E1]-A-[E2]-PEG | U2-H | Theo. MW | Found MW |
| | Product | | | |
| 114 | VZnEVGWYRSPFSRVVHLYRNGSPVZX (SEQ ID NO: 517)<br>VZnEVGWYRSPFSRVVHLYRNGSPVZ(X-DBCO)-Ahx-W5 | Compound 1 | 4633.99 | 1159.2 (M/4 + H)$^+$ |
| 115 | OH-PEG24-VZ-DFTGSNGDPSSPYSLHYLSPTGVNEY-SPVZX (SEQ ID NO: 528)<br>OH-PEG24-VZ-DFTGSNGDPSSPYSLHYLSPTGVNEY-SPVZ(X-DBCO)-Ahx-W5 | Compound 1 | 6133.40 | 1533.8 (M/4 + H)$^+$ |

TABLE 9-continued

| Peptide antigen conjugates of Formula PEG-E1-A-E2-U-H | | | | |
|---|---|---|---|---|
| # | PEG-[E1]-A-[E2]-U1 or U1-[E1]-A-[E2]-PEG | U2-H | Theo. MW | Found MW |
| 116 | OH-PEG24-VZARDETAALLNSAVLGAAPLFVPPADSPVZX (SEQ ID NO: 529) OH-PEG24-VZARDETAALLNSAVLGAAPLFVPPADSPVZ(X-DBCO)-Ahx-W5 | Compound 1 | 5808.30 | 1162.4 $(M/5 + H)^+$ |
| 117 | OH-PEG24-VZLSREWYVRPLWVRMEQLAKELTAEKSPVZX(SEQ ID NO: 530) OH-PEG24-VZLSREWYVRPLWVRMEQLAKELTAEKSPVZ(X-DBCO)-Ahx-W5 | Compound 1 | 6460.75 | 1293.1 $(M/5 + H)^+$ |
| 118 | OH-PEG24-VZKYNKANVFLSPVZX (SEQ ID NO: 531) OH-PEG24-VZKYNKANVFLSPVZ(X-DBCO)-Ahx-W5 | Compound 1 | 4424.38 | 1106.9 $(M/4 + H)^+$ |
| 119 | OH-PEG24-VZ-GVHMASLSKYNKANVFLFLFALGFY-SPVZX(SEQ ID NO: 532) OH-PEG24-VZ-GVHMASLSKYNKANVFLFLFALGFY-SPVZ(X-DBCO)-Ahx-W5 | Compound 1 | 6166.87 | 1234.2 $(M/5 + H)^+$ |
| 120 | OH-PEG24-VZ-YVRPLWVRME-SPVZX (SEQ ID NO: 533) OH-PEG24-VZ-YVRPLWVRME-SPVZ(X-DBCO)-Ahx-W5 | Compound 1 | 4677.10 | 1170.1 $(M/4 + H)^+$ |
| 121 | VZ-QLQPFPQPELPYPQPQLPYPQPQPFR-SPVZX(SEQ ID NO: 498) VZ-QLQPFPQPELPYPQPQLPYPQPQPFR-SPVZ(X-DBCO)-Ahx-W5 | Compound 1 | 5330.74 | 1067.2 $(M/5 + H)^+$ |

Note:
Single letter abbreviations are used for amino acid sequences in the above table; X = azidolysine, Z = citrulline, and n = norleucine. Peptide-based starting materials were manufactured by solid-phase peptide synthesis by Genscript (Piscataway, NJ). Sequences for peptide-based starting materials are written from N-to C-terminus, and C-terminal $NH_2$ indicates that the peptide is terminated with an Amide. Unless otherwise specified, any C-terminal X, azidolysine, is terminated with an amide and is implicit in the sequences (i.e., not shown).

Compound 98, Torin-1-piperazine

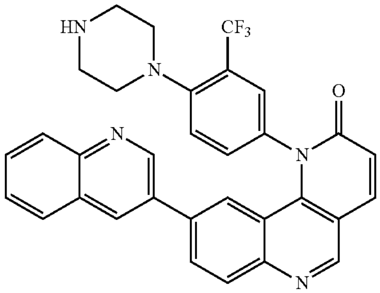 [SMILES: O=c1ccc2cnc3ccc(-c4cnc5ccccc5c4)cc3c2n1-c1ccc(N2CCNCC2)c(C(F)(F)F)c1]

Compound 98, also referred to as Torin-1-piperazine, was synthesized from Torin-1 (Toronto Research Chemicals, Toronto, CA). 200 mg of Torin1 was dissolved in 5 mL of 5M HCl. The solution was transferred to a sealed tube and the reaction mixture was heated to 70° C. for 16 h. HPLC (AUC @ 254 nm) confirmed that the reaction was complete. The reaction mixture was diluted with 20 mL DI water and cooled in an ice bath. This was followed by neutralization with 1M NaOH till the pH of the solution was ~7. White precipitate was formed which was isolated via filtration, washed with 3×50 mL DI water, air-dried, then dried under vacuum to give Torin-1-pip (160 g, 88%) as a light orange powder. MS (ESI) calculated for C32H24F3N50, m/z 551.6, found 552.6 (M+H)+.

Compound 99 Torin-1-dipiperazine

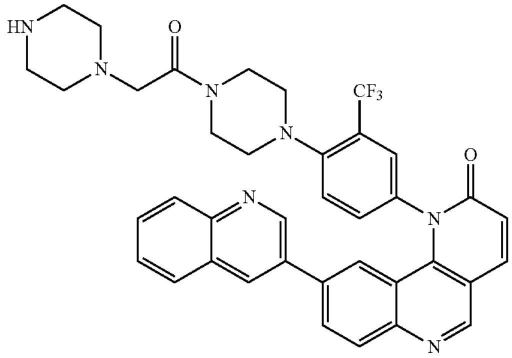 [SMILES: O=C(CN1CCNCC1)N1CCN(c2ccc(-n3c(=O)ccc4cnc5ccc(-c6cnc7ccccc7c6)cc5c43)cc2C(F)(F)F)CC1]

Compound 99, also referred to as Torin-1-dipiperazine, was synthesized from Torin-1-piperazine. 21 mg of [4-(tert-butoxycarbonyl) piperazin-1-yl]acetic acid (0.09 mmol, 1.25 eq), 34 mg of HATU (0.09 mmol, 1.25 eq) and 13 µL of TEA (0.09 mmol, 1.25 eq) were dissolved in 2 mL of DMF and the mixture was stirred for 5 mins. 40 mg of Torin-1-pip (0.07 mmol, 1 eq) was added to the mixture and the stirring was continued at room temperature for 1 h. The reaction was monitored using HPLC (AUC @ 254 nm) which indicated completion of reaction. 1 mL of 1M HCl was added to the mixture and reaction was allowed to go for 1 h at room temperature. HPLC indicated complete deprotection of Boc group (AUC @ 254 nm). The mixture was neutralized with 1 mL of 1M NaOH. The product was isolated via Prep-HPLC using a gradient of 5-65% acetonitrile/$H_2O$ (0.05% TFA) over 10 mins on an Agilent Preparatory C-18 column, 30×100 mm, 5 μm. The product eluted at 5 mins and the resulting fractions were combined, frozen and lyophilized to give 50 mg (90% yield) of a spectroscopically pure light orange powder (>95% AUC at 254 nm). MS (ESI) calculated for C38H34F3N702 m/z 677.7, found 678.8 (M+H).

Compound 100, Torin-1-Piperazine-Glycine

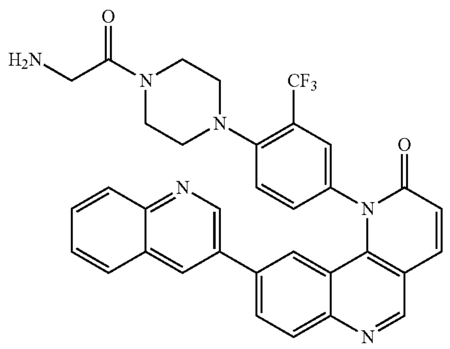 [SMILES: NCC(=O)N1CCN(c2ccc(-n3c(=O)ccc4cnc5ccc(-c6cnc7ccccc7c6)cc5c43)cc2C(F)(F)F)CC1]

Compound 100, referred to as Torin-1-Piperazine-Glycine was synthesized by reacting 20 mg (0.036 mmol, 1 eq) of Compound 98, with 14.7 mg of Fmoc-Gly-OH (0.047 mmol, 1.3 eq) using 15.2 mg of HATU (0.04 mmol, 1.1 eq) as the coupling reagent and 20.2 uL of triethylamine (0.145 mmol, 4 eq) as the base in 0.4 mL of DMF. The reaction was run for 1 hr at room temperature at which point HPLC indicated that the reaction was complete. The intermediate, Torin-1-Piperazine-Glycine-Fmoc was precipitated out by adding the reaction solution to 8 mL of 0.2M HCL. The solid was pelleted by centrifugation and the 0.2M HCL supernatant was decanted. To the pellet was added 8 mL of DI water and the pellet was broken up with a spatula. The solid was again pelleted by centrifugation and the DI water was decanted. The pelleted solid was frozen at −80C and dried by lyophilization. The intermediate, Torin-1-Piperazine-Glycine-Fmoc, was dissolved in 0.4 mL of 20% piperidine in DMF and incubated for 1 hr at room temperature at which point HPLC indicated that the deprotection was complete. The product was then precipitated in 8 mL of diethyl ether and pelleted by centrifugation. The diethyl ether supernatant was discarded, and the product was air dried. The product, Torin-1-Piperazine-Glycine, was purified on a preparative HPLC system using a gradient of 18-48% acetonitrile/$H_2O$ (0.05% TFA) over 12 minutes on an Agilent Prep C-18 column, 30×100 mm, 5 μm. The resulting fractions were combined, frozen and lyophilized to give 15.2 mg (69.4% yield) of a spectroscopically pure yellow powder. MS (ESI) calculated for $C_{34}H_{27}F_3N_6O_2$ m/z 608.3, found 609.2 $(M+H)^+$.

Compound 101, Torin-2-glycine

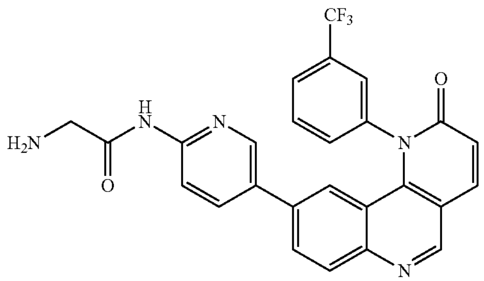 [SMILES: NCC(=O)Nc1ccc(-c2ccc3ncc4ccc(=O)n(-c5cccc(C(F)(F)F)c5)c4c3c2)cn1]

Compound 101, referred to as Torin 2-Glycine was synthesized by reacting 26.8 mg of Torin-2 (0.062 mmol, 1 eq) with 58.7 mg of Fmoc-Gly-Cl (0.186 mmol, 3 eq) in 500 μL of 1:1 DMF-Pyridine (anhydrous). The reaction was mixed at room temperature for 16 hours, until HPLC indicated the reaction was complete. Solvent from the reaction mixture was reduced by rotary evaporator. The reaction mixture was treated with 2:1 DCM-Diethylamine for 30 minutes. Analysis by HPLC indicated complete removal of Fmoc group. The resulting product was purified on a preparative HPLC system using a gradient of 10-30% acetonitrile/$H_2O$ (0.05% TFA) over 10 minutes on an Agilent Prep C-18 column, 30×100 mm, 5 μm. The product eluted at ~ 25% acetonitrile and the resulting fractions were combined, and lyophilized to give 21.0 mg (56% yield) of a spectroscopically pure white powder as TFA salt (>95% AUC at 220 nm). ESI-MS $[M+H]^+$ calculated for $C_{26}H_{19}F_3N_5O_2$ m/z 490.1, Found 490.0.

Compound 102, referred to as Torin-2-piperazine, was procured from WuXi AppTec, (Shanghai, China).

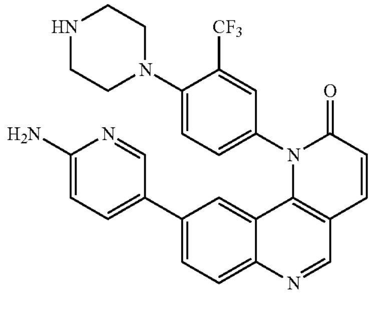 [SMILES: Nc1ccc(-c2ccc3ncc4ccc(=O)n(-c5ccc(N6CCNCC6)c(C(F)(F)F)c5)c4c3c2)cn1]

Compound 103, Torin-2-piperazine-glycine

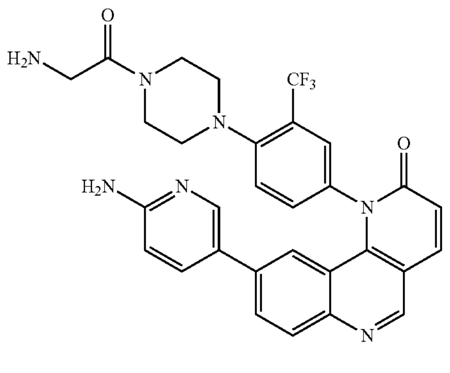 [SMILES: NCC(=O)N1CCN(c2ccc(-n3c(=O)ccc4cnc5ccc(-c6ccc(N)nc6)cc5c43)cc2C(F)(F)F)CC1]

Compound 103, referred to as Torin2-piperazine-glycine was synthesized by reacting Compound 102 (Torin 2-piperazine, 51.6 mg, 0.1 mmole, 1 eq) and Boc-Gly-OH (Sigma Aldrich), 27.2 mg, 0.155 mmole, 1.55 eq.) in the presence of HATU. To a solution of Boc-Gly-OH in DMF (0.4 mL), HATU (55.6 mg, 0.15 mmole, 1.5 eq.) and HOAt (13.3 mg, 0.098 mmole, 1 eq.) were added. Mixture was stirred for 10 minutes at RT. To this, DIPEA (51.2 uL, 0.294 mmole, 2.9 eq) was added followed by Torin2-piperazine (51.6 mg, 0.1 mmole, 1 eq.). Reaction was stirred for 1 h at RT and the reaction progress was monitored by HPLC (AUC 254 nm). Reaction was found to be complete. Reaction mixture was partitioned between water (20 mL) and DCM (20 mL). Aqueous phase was extracted with DCM (2×15 mL). All DCM phases were combined, dried with $Na_2SO_4$, and concentrated. Resulting crude syrup was re-dissolved in DCM (5 mL). To this, anisole (50 uL) was added followed by 1.5 mL TFA. Reaction was stirred for 1 h at RT. DCM from reaction mixture was removed by rotary evaporation. The resulting product was purified on a preparative HPLC system using a gradient of 10-30% acetonitrile/$H_2O$ (0.05% TFA) over 10 minutes on an Agilent Prep C-18 column, 30×100 mm, 5 μm. The product eluted at ~ 25% acetonitrile and the resulting fractions were combined and lyophilized to give 52.6 mg (77% yield) of a spectroscopically pure white powder as TFA salt (>95% AUC at 220 nm). ESI-MS $[M+H]^+$ Calculated for $C_{30}H_{27}F_3N_7O_2$ m/z 574.2, found 574.1.

Compound 104, also referred to as Torin-1-PAB-ZV, was procured from WuXi AppTec, (Shanghai, China).

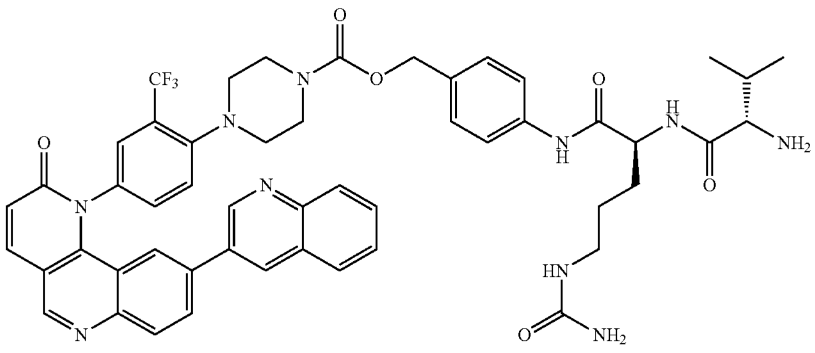 [SMILES: CC(C)[C@H](N)C(=O)N[C@@H](CCCNC(N)=O)C(=O)Nc1ccc(COC(=O)N2CCN(c3ccc(-n4c(=O)ccc5cnc6ccc(-c7cnc8ccccc8c7)cc6c54)cc3C(F)(F)F)CC2)cc1]

Compound 105, also referred to as Torin-1-ZV, was procured from WuXi AppTec, (Shanghai, China).
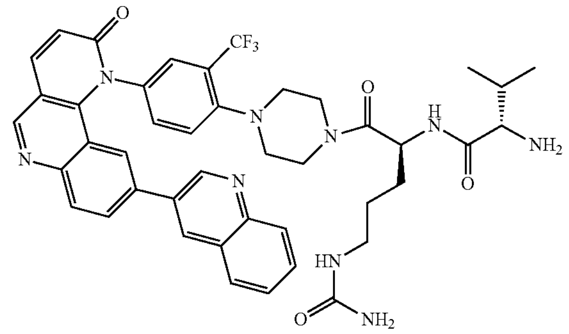 [SMILES: CC(C)[C@H](N)C(=O)N[C@@H](CCCNC(N)=O)C(=O)N1CCN(c2ccc(-n3c(=O)ccc4cnc5ccc(-c6cnc7ccccc7c6)cc5c43)cc2C(F)(F)F)CC1]
Compound 106, also referred to as Torin-2-piperazine-ZV, was procured from WuXi AppTec, (Shanghai, China).
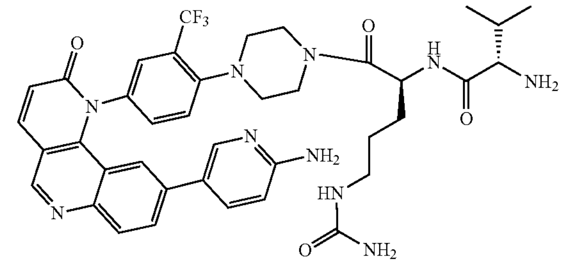 [SMILES: CC(C)[C@H](N)C(=O)N[C@@H](CCCNC(N)=O)C(=O)N1CCN(c2ccc(-n3c(=O)ccc4cnc5ccc(-c6ccc(N)nc6)cc5c43)cc2C(F)(F)F)CC1]
Compound 107, also referred to as Torin-2-piperazine-PAB-ZV, was procured from WuXi AppTec, (Shanghai, China).
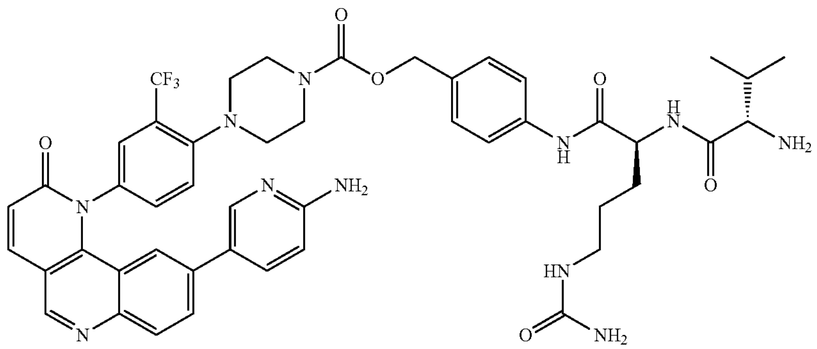 [SMILES: CC(C)[C@H](N)C(=O)N[C@@H](CCCNC(N)=O)C(=O)Nc1ccc(COC(=O)N2CCN(c3ccc(-n4c(=O)ccc5cnc6ccc(-c7ccc(N)nc7)cc6c54)cc3C(F)(F)F)CC2)cc1]

Compound 108, also referred to as Everolimus-amine, was procured from WuXi AppTec, (Shanghai, China).

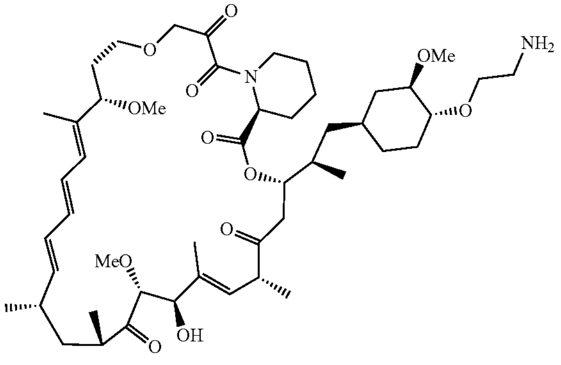

Compound 109, also referred to as Everolimus-azide, Everolimus-N3 was procured from WuXi AppTec, (Shanghai, China).

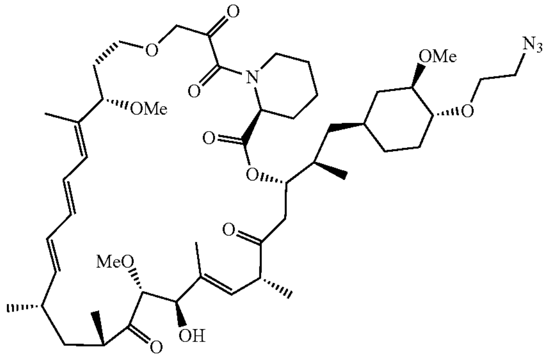

Compound 110, also referred to as Everolimus-acid, Everolimus-COOH was procured from WuXi AppTec, (Shanghai, China).

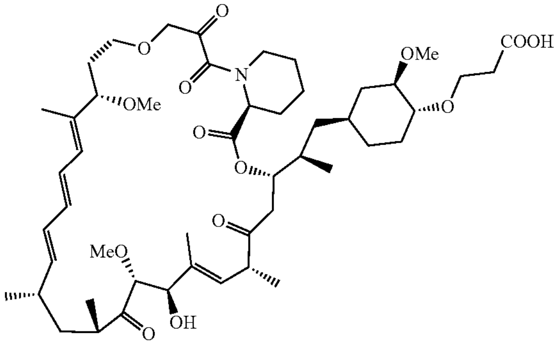

Compound 111, also referred to as Everolimus-PAB-ZV-azide, was procured from WuXi AppTec, (Shanghai, China).

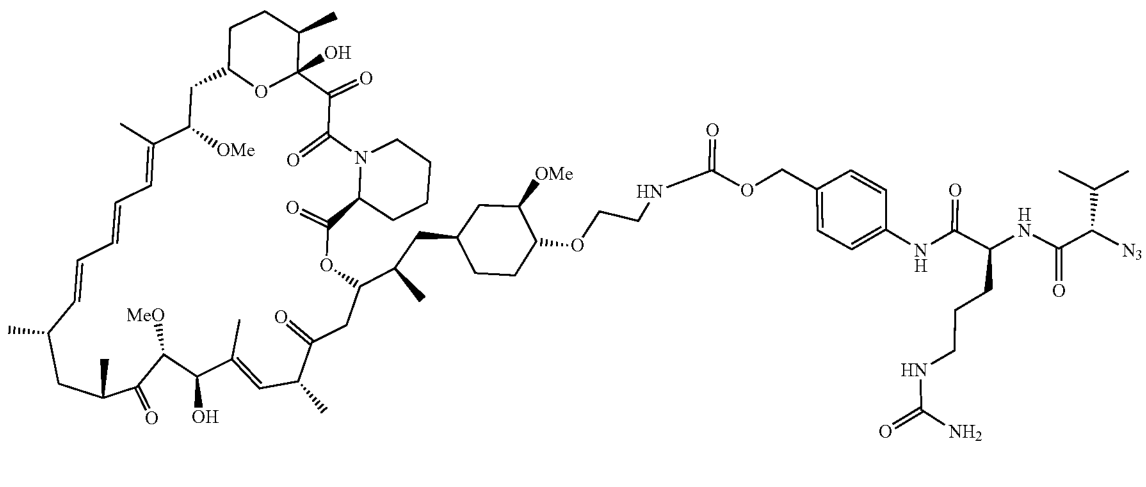

Compound 112, also referred to as Everolimus-PAB-ZV-amine, was procured from WuXi AppTec, (Shanghai, China).

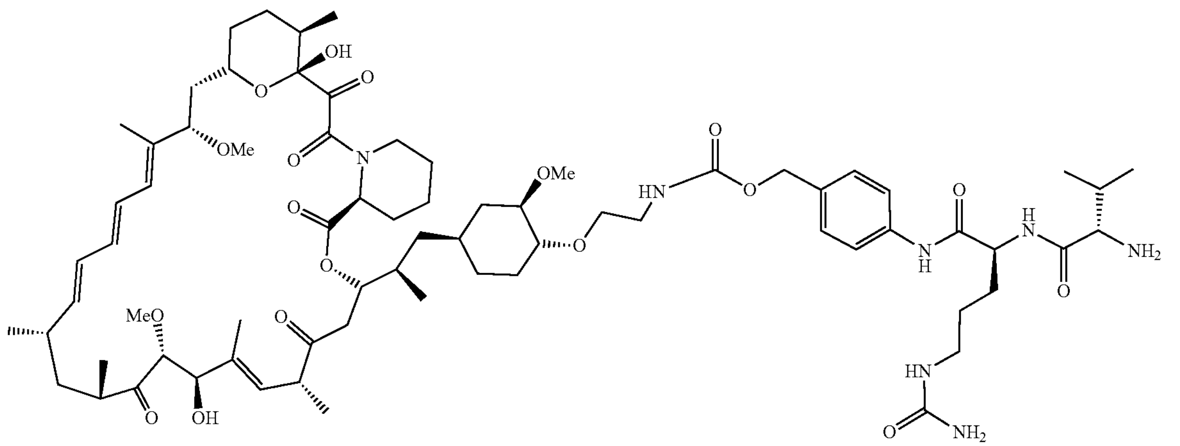

Compound 113, also referred to as Everolimus-piperazine, was procured from WuXi AppTec, (Shanghai, China).

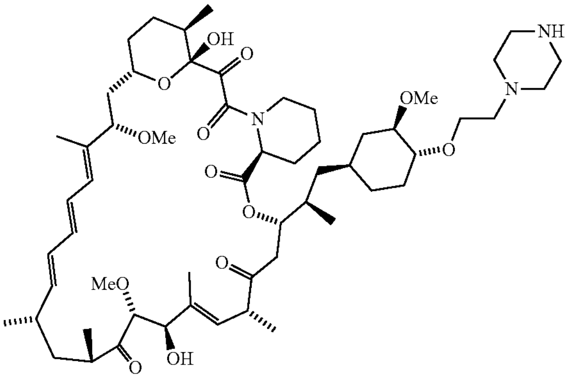 [SMILES: CO[C@H]1C[C@@H]2CC[C@@H](C)[C@@](O)(O2)C(=O)C(=O)N2CCCC[C@H]2C(=O)O[C@H]([C@H](C)C[C@@H]2CC[C@@H](OCCN3CCNCC3)[C@H](OC)C2)CC(=O)[C@H](C)/C=C(\C)[C@@H](O)[C@@H](OC)C(=O)[C@@H](C)C[C@H](C)/C=C/C=C/C=C/1C]

Compound 122, Torin-1-C1-COOH

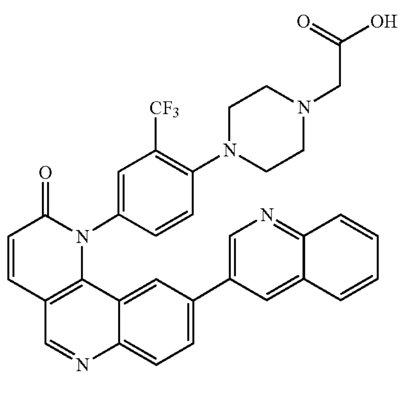 [SMILES: O=C(O)CN1CCN(c2ccc(-n3c(=O)ccc4cnc5ccc(-c6cnc7ccccc7c6)cc5c43)cc2C(F)(F)F)CC1]

Compound 122, also referred to as Torin-1-C1-COOH was synthesized by reacting 100 mg (1 eq) of Torin-1-piperazine (Compound 98) and 30 mg of methylbromoacetate (1.1 eq) in 10 mL of DMF in the presence of 108 mg of $K_2CO_3$ (4 eq) and 30 mg of KI (1 eq). The reaction mixture was stirred at 60° C. for 24 hours to allow the reaction to proceed. After the completion of the reaction, the filtrate was collected. Following this, 500 μL of 1 M NaOH was added to the collected filtrate and stirred for 1 hour until the methyl ester was completely hydrolyzed. After the hydrolysis step and neutralization with 1 M HCl (500 uL) to reach a neutral pH, the product was isolated via PREP HPLC using a gradient of 30-90% acetonitrile/water (0.05% TFA) over a 10-minute period on an Agilent Preparatory C-18 column, 30×100 mm, 5 μm. The desired fractions were combined to give 50 mg of Torin-1-$C_1$—COOH with a yield of 45%. MS (ESI) calculated for $C_{34}H_{26}F_3N_5O_3$ m/z 609.20, found 610.2 $(M+H)^+$.

Compound 123, Torin-1-C3-COOH

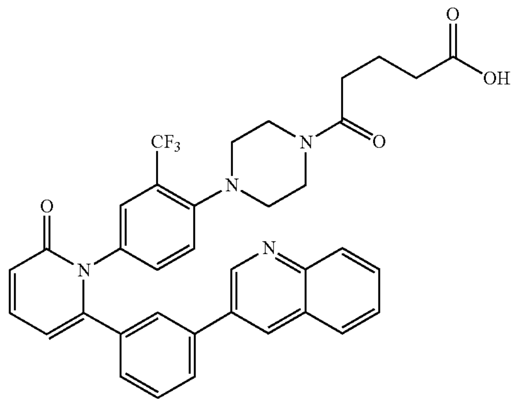 [SMILES: O=C(O)CCCC(=O)N1CCN(c2ccc(-n3c(-c4cccc(-c5cnc6ccccc6c5)c4)cccc3=O)cc2C(F)(F)F)CC1]

Compound 123, also referred to as Torin-1-C3-COOH was synthesized by reacting 100 mg (1 eq) of Torin-1-peperazine (Compound 98) and 23 mg of glutaric anhydride (1.1 eq) in 10 mL of DMF. The reaction mixture was stirred at 60° C. for 24 hours to allow the reaction to proceed. The product was isolated via PREP HPLC using a gradient of 30-90% acetonitrile/water (0.05% TFA) over a 10-minute period on an Agilent Preparatory C-18 column, 30×100 mm, 5 μm. The desired fractions were combined to give 50 mg of TORIN1-$C_3$—COOH with a yield of 42%. MS (ESI) calculated for $C_{37}H_{30}F3N_5O_4$ m/z 665.2, found 666.3 $(M+H)^+$.

Compound 124, Val-Cit-DBCO

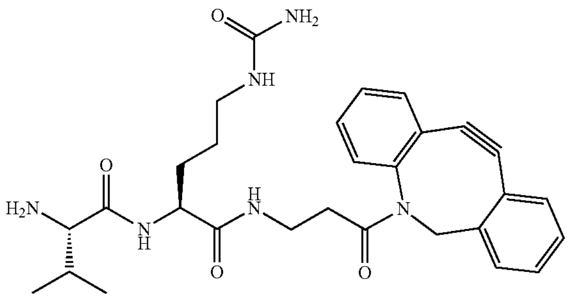 [SMILES: CC(C)[C@H](N)C(=O)N[C@@H](CCCNC(N)=O)C(=O)NCCC(=O)N1Cc2ccccc2C#Cc2ccccc21]

Compound 124, also referred to as Val-Cit-DBCO was synthesized through the reaction of Fmoc-Val-Cit-OH and DBCO-Amine. A solution comprising Fmoc-Val-Cit-COOH (50 mg, 0.1 mmol, 1 eq), DBCO-Amine (30 mg, 0.1 mmol, 1 eq), and DIPEA (13 mg, 0.1 mmol, 1 eq) was prepared in 4 mL of DMF and stirred at room temperature (RT). Subsequently, a solution of HATU (38 mg, 0.1 mmol, 1 eq) in 1 mL of DMF was added to this mixture over 30 minutes at RT. The resulting mixture was then stirred at RT for an additional 30 minutes. The progression of the reaction was tracked using high-performance liquid chromatography (HPLC). Upon achieving complete conversion of the Fmoc-VZ-COOH, diethylamine (100 uL) was introduced to the mixture and stirred for an additional 30 minutes. The mixture was concentrated under vacuum, yielding a residue that was redissolved in DMF. Purification was accomplished through C8 reversed-phase preparative HPLC(RP-PREP-HPLC) employing a gradient of 20% to 95% acetonitrile (CAN) (containing 0.05% TFA) over 10 minutes, with maintenance at 95% for an additional 5 minutes. The fractions containing the desired compound were collected, resulting in the isolation of 45 mg of the compound with an 85% yield. MS (ESI) calculated for $C_{29}H_{36}N_6O_4$ m/z 532.3, found 533.3 (M+H)+.

Compound 125, Ahx-DBCO

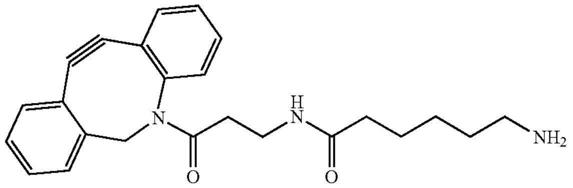 [SMILES: NCCCCCC(=O)NCCC(=O)N1Cc2ccccc2C#Cc2ccccc21]

Compound 125, also referred to as Ahx-DBCO was synthesized by reacting DBCO-amine (CAS: 1255942-06-3) and Fmoc-Ahx-COOH (CAS: 88574-06-5). To initiate the reaction, a solution was prepared by combining Fmoc-Ahx-COOH (50 mg, 0.14 mmol, 1 eq), DBCO-Amine (42 mg, 0.17 mmol, 1.2 eq), and DIPEA (18 mg, 0.14 mmol, 1 eq) in 4 mL of DMF, followed by stirring at room temperature (RT). Over a 30-minute period at RT, a solution of HATU (55 mg, 0.14 mmol, 1 eq) in 1 mL of DMF was added to this mixture. Subsequently, the mixture underwent an additional 30 minutes of stirring at RT, with the progress of the reaction closely monitored through high-performance liquid chromatography (HPLC). After achieving complete conversion of the Fmoc-Ahx-COOH, diethylamine (100 uL) was introduced to the mixture and stirred for an additional 30 minutes. The mixture was then concentrated under vacuum, yielding a residue that was redissolved in DMF. Purification was performed using C8 reversed-phase preparative HPLC (RP-PREP-HPLC), employing a gradient elution method from 20% to 95% acetonitrile (ACN) (containing 0.05% TFA) over 10 minutes, with a further 5 minutes at 95%. The desired compound was obtained in a yield of 74%. The isolation process was considered complete after freeze-drying. MS (ESI) calculated for $C_{24}H_{27}N_3O_2$ m/z 389.2, found 390.2 $(M+H)^+$ Compound 126, Val-Cit-Ahx-DBCO

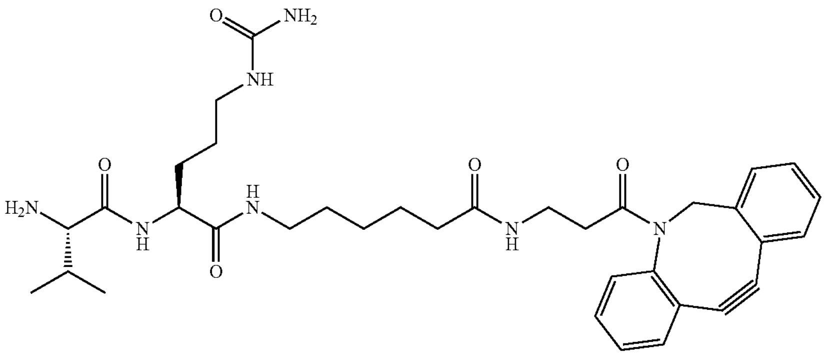 [SMILES: CC(C)[C@H](N)C(=O)N[C@@H](CCCNC(N)=O)C(=O)NCCCCCC(=O)NCCC(=O)N1Cc2ccccc2C#Cc2ccccc21]

Compound 126, also referred to as Val-Cit-Ahx-DBCO was synthesized from Ahx-DBCO and Fmoc-Val-Cit-OH. A solution of Fmoc-VZ-COOH (52 mg, 0.10 mmol, 1 eq), Ahx-DBCO (43 mg, 0.11 mmol, 1.1 eq), and DIPEA (13 mg, 0.10 mmol, 1 eq) in 4 mL of DMF was stirred at room temperature (RT). A solution of HATU (40 mg, 0.10 mmol, 1 eq) in 1 mL of DMF was added to this mixture over 30 minutes at RT. Subsequently, the mixture was stirred at RT for an additional 30 minutes, with the reaction progress monitored using high-performance liquid chromatography (HPLC). After achieving complete conversion of the Fmoc-VZ-COOH, diethylamine (100 uL) was introduced to the mixture and stirred for 30 minutes. The mixture was concentrated under vacuum, yielding a residue that was redissolved in DMF. Purification was carried out using C8 reversed-phase preparative HPLC(RP-PREP-HPLC), with a gradient elution method from 20% to 95% acetonitrile (ACN) (containing 0.05% TFA) over 10 minutes, followed by maintaining the elution at 95% for an additional 5 minutes. The mobile phase's aqueous component contained 0.05% TFA in water. The fractions containing the desired compound were collected and freeze dried to obtain the compound (45 mg, 70% yield). MS (ESI) calculated for $C_{35}H_{47}N_7O_5$ m/z 645.4, found 646.4 $(M+H)^+$.

Compound 127, Everolimus-Val-Cit-DBCO

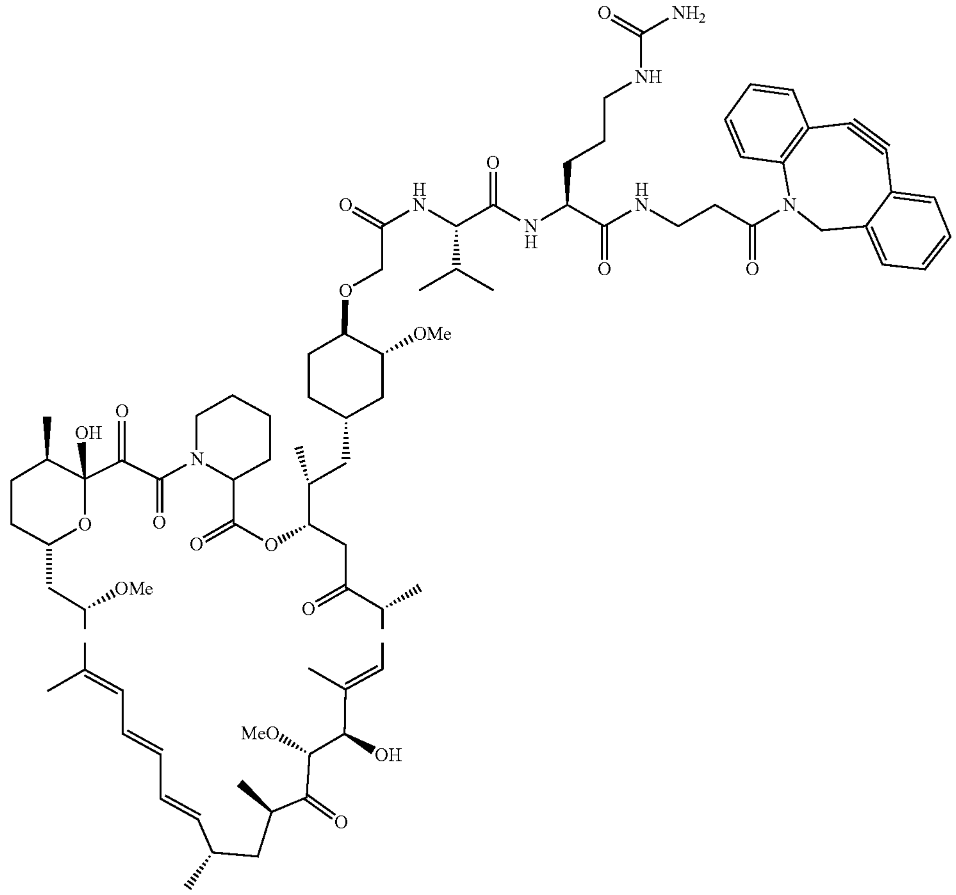 [SMILES: CO[C@H]1C[C@@H]2CC[C@@H](C)[C@@](O)(O2)C(=O)C(=O)N2CCCCC2C(=O)O[C@H]([C@H](C)C[C@@H]2CC[C@@H](OCC(=O)N[C@H](C(=O)N[C@@H](CCCNC(N)=O)C(=O)NCCC(=O)N3Cc4ccccc4C#Cc4ccccc43)C(C)C)[C@H](OC)C2)CC(=O)[C@H](C)/C=C(\C)[C@@H](O)[C@@H](OC)C(=O)[C@H](C)C[C@H](C)/C=C/C=C/C=C/1C]

Compound 127, also referred to as Everolimus-Val-Cit-DBCO was synthesized by reacting Everolimus-COOH (Compound 110) and Val-Cit-DBCO (Compound 124). Everolimus-COOH (20 mg, 0.02 mmol, 1 eq) with Val-Cit-DBCO (12 mg, 0.022 mmol, 1.1 eq) and DIPEA (5 mg, 0.04 mmol, 2 eq) were dissolved in 4 mL of DMF within an appropriate reaction vessel, ensuring complete dissolution for a homogeneous mixture. HATU (9 mg, 0.02 mmol, 1 eq), previously dissolved in 1 mL of DMF, was gradually added to the reaction mixture over 30 minutes at room temperature while stirring continuously. Following HATU addition, the mixture was stirred for an additional 30 minutes. The progress of the reaction was routinely monitored using Liquid Chromatography-Mass Spectrometry (LC-MS) to confirm the desired transformation. After the reaction's completion, as indicated by LC-MS analysis, the entire reaction mixture underwent preparative high-performance liquid chromatography (PREP HPLC) for product isolation, employing a reverse-phase C8 column. Purification involved an elution gradient ranging from 30% to 90% acetonitrile (ACN) in water, with both phases containing 0.05% acetic acid (AcOH) to aid in purification. Compound monitoring occurred at 280 nm, and the fractions containing the desired product were collected. Subsequently, these fractions underwent lyophilization (freeze-drying) to yield the purified Everolimus-Val-Cit-DBCO (5 mg, 17% yield) in solid form. MS (ESI) calculated for $C_{82}H_{115}N_7O_{18}$ m/z 1485.8, found 1509.1 $(M+Na)^+$.

Compound 128, Everolimus-Val-Cit-Ahx-DBCO

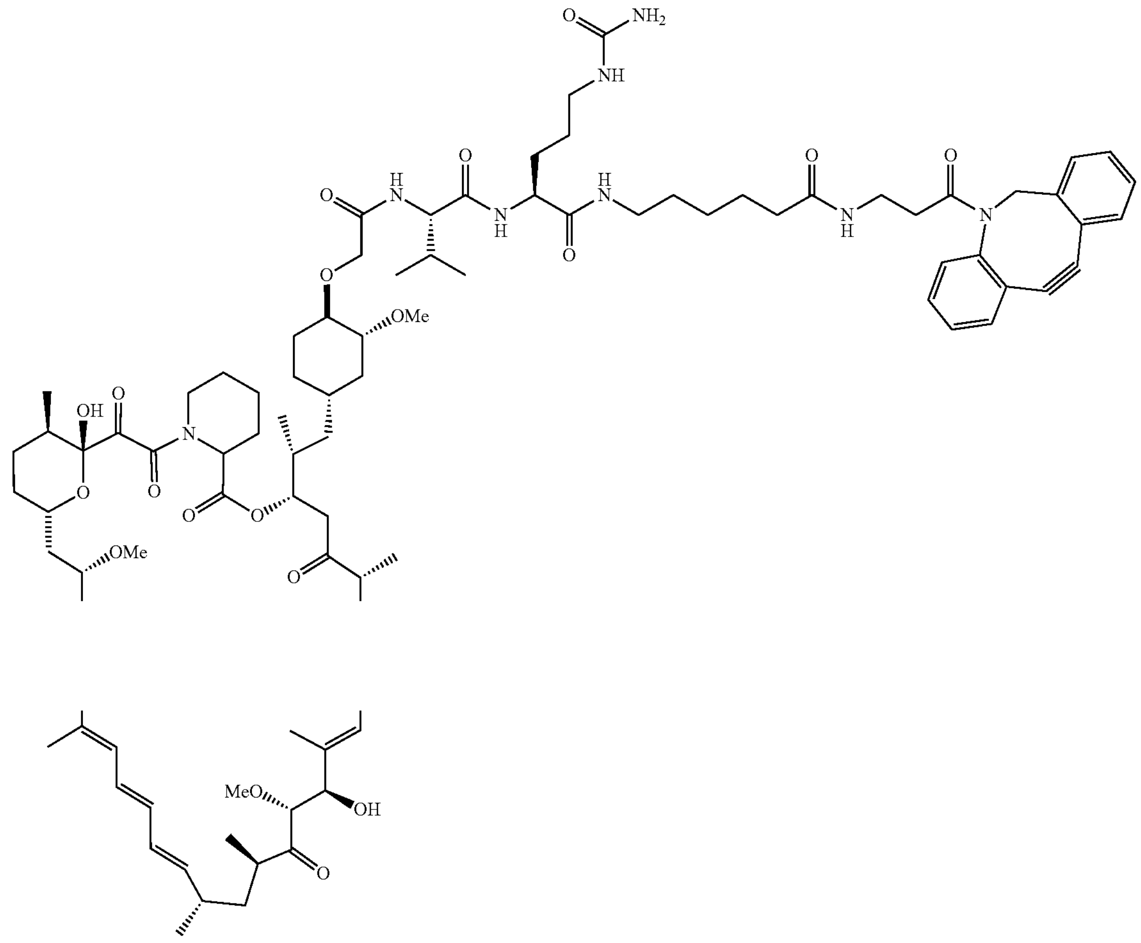

Compound 128, also referred to as Everolimus-Val-Cit-Ahx-DBCO was synthesized by reacting Everolimus-COOH (Compound 110) and Val-Cit-Ahx-DBCO (Compound 126). Everolimus-COOH (20 mg, 0.02 mmol, 1 eq) with Val-Cit-Ahx-DBCO (14 mg, 0.022 mmol, 1.1 eq) and DIPEA (5 mg, 0.04 mmol, 2 eq) were dissolved in 4 mL of DMF within an appropriate reaction vessel, ensuring complete dissolution for a homogeneous mixture. HATU (9 mg, 0.02 mmol, 1 eq), previously dissolved in 1 mL of DMF, was gradually added to the reaction mixture over 30 minutes at room temperature while stirring continuously. Following HATU addition, the mixture was stirred for an additional 30 minutes. The progress of the reaction was routinely monitored using Liquid Chromatography-Mass Spectrometry (LC-MS) to confirm the desired transformation. After the reaction's completion, as indicated by LC-MS analysis, the entire reaction mixture underwent preparative high-performance liquid chromatography (PREP HPLC) for product isolation, employing a reverse-phase C8 column. Purification involved an elution gradient ranging from 30% to 90% acetonitrile (ACN) in water, with both phases containing 0.05% acetic acid (AcOH) to aid in purification. Compound monitoring occurred at 280 nm, and the fractions containing the desired product were collected. Subsequently, these fractions underwent lyophilization (freeze-drying) to yield the purified Everolimus-Val-Cit-DBCO (6 mg, 32% yield) in solid form. MS (ESI) calculated for $C_{88}H_{126}N_8O_{19}$ m/z 1599.0, found 1622.1 $(M+Na)^+$.

Compound 129, Torin-1-C1-Val-Cit-DBCO

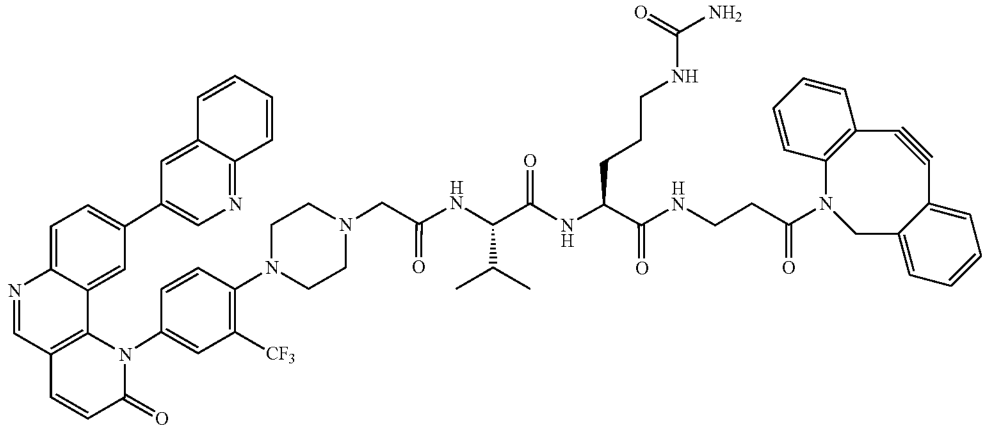 [SMILES: CC(C)[C@H](NC(=O)CN1CCN(c2ccc(-n3c(=O)ccc4cnc5ccc(-c6cnc7ccccc7c6)cc5c43)cc2C(F)(F)F)CC1)C(=O)N[C@@H](CCCNC(N)=O)C(=O)NCCC(=O)N1Cc2ccccc2C#Cc2ccccc21]

Compound 129, also referred to as Torin-1-C1-Val-Cit-DBCO was synthesized by reacting Torin-1-C1-COOH (Compound 122) and Val-Cit-DBCO (Compound 124). Torin-1-C1-COOH (6 mg, 0.010 mmol, 1 eq) with Val-Cit-DBCO (6 mg, 0.011 mmol, 1.1 eq) and DIPEA (5 mg, 0.04 mmol, 4 eq) were dissolved in 4 mL of DMF within an appropriate reaction vessel, ensuring complete dissolution for a homogeneous mixture. HATU (5 mg, 0.013 mmol, 1.3 eq), previously dissolved in 1 mL of DMF, was gradually added to the reaction mixture over 30 minutes at room temperature while stirring continuously. Following HATU addition, the mixture was stirred for an additional 30 minutes. The progress of the reaction was routinely monitored using Liquid Chromatography-Mass Spectrometry (LC-MS) to confirm the desired transformation. After the reaction's completion, as indicated by LC-MS analysis, the entire reaction mixture underwent preparative high-performance liquid chromatography (PREP HPLC) for product isolation, employing a reverse-phase C8 column. Purification involved an elution gradient ranging from 30% to 90% acetonitrile (ACN) in water, with both phases containing 0.05% acetic acid (AcOH) to aid in purification. Compound monitoring occurred at 325 nm, and the fractions containing the desired product were collected. Subsequently, these fractions underwent lyophilization (freeze-drying) to yield the purified Torin-1-C1-Val-Cit-DBCO (4 mg, 36% yield) in solid form. MS (ESI) calculated for $C_{63}H_{60}F3N_{11}O_6$ m/z 1123.5, found 1124.5 $(M+H)^+$.

Compound 130, Torin-1-C1-Val-Cit-Ahx-DBCO

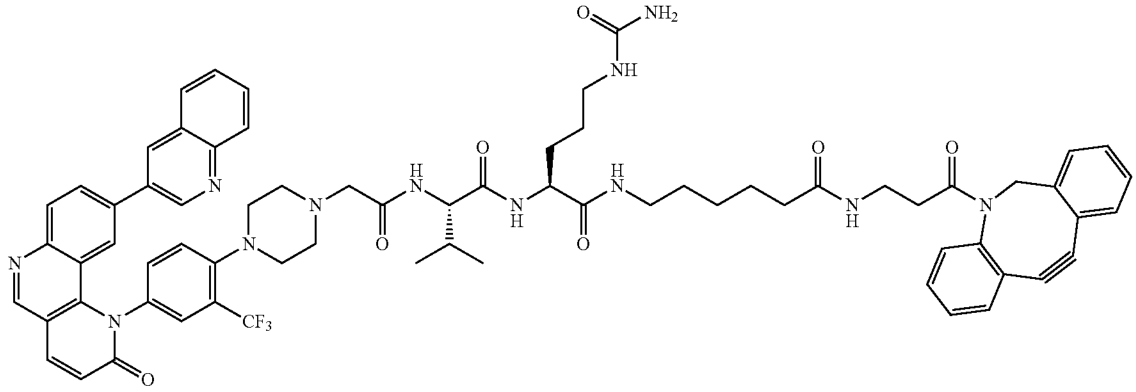 [SMILES: CC(C)[C@H](NC(=O)CN1CCN(c2ccc(-n3c(=O)ccc4cnc5ccc(-c6cnc7ccccc7c6)cc5c43)cc2C(F)(F)F)CC1)C(=O)N[C@@H](CCCNC(N)=O)C(=O)NCCCCCC(=O)NCCC(=O)N1Cc2ccccc2C#Cc2ccccc21]

Compound 130, also referred to as Torin-1-C1-Val-Cit-Ahx-DBCO was synthesized by reacting Torin-1-C1-COOH (Compound 122) and Val-Cit-Ahx-DBCO (Compound 126). Torin-1-C1-COOH (5 mg, 0.008 mmol, 1 eq) with Val-Cit-Ahx-DBCO (6 mg, 0.009 mmol, 1.1 eq) and DIPEA (5 mg, 0.04 mmol, 5 eq) were dissolved in 4 mL of DMF within an appropriate reaction vessel, ensuring complete dissolution for a homogeneous mixture. HATU (4 mg, 0.01 mmol, 1.3 eq), previously dissolved in 1 mL of DMF, was gradually added to the reaction mixture over 30 minutes at room temperature while stirring continuously. Following HATU addition, the mixture was stirred for an additional 30 minutes. The progress of the reaction was routinely monitored using Liquid Chromatography-Mass Spectrometry (LC-MS) to confirm the desired transformation. After the reaction's completion, as indicated by LC-MS analysis, the entire reaction mixture underwent preparative high-performance liquid chromatography (PREP HPLC) for product isolation, employing a reverse-phase C8 column. Purification involved an elution gradient ranging from 30% to 90% acetonitrile (CAN) in water, with both phases containing 0.05% acetic acid (AcOH) to aid in purification. Compound monitoring occurred at 325 nm, and the fractions containing the desired product were collected. Subsequently, these fractions underwent lyophilization (freeze-drying) to yield the purified TORIN1-C1-Val-Cit-Ahx-DBCO (5 mg, 50% yield) in solid form. MS (ESI) calculated for $C_{69}H_{71}F3N_{12}O_7$ for m/z 1236.5, found 1237.4 (M+H)+.

Compound 131, Torin-1-C3-Val-Cit-DBCO

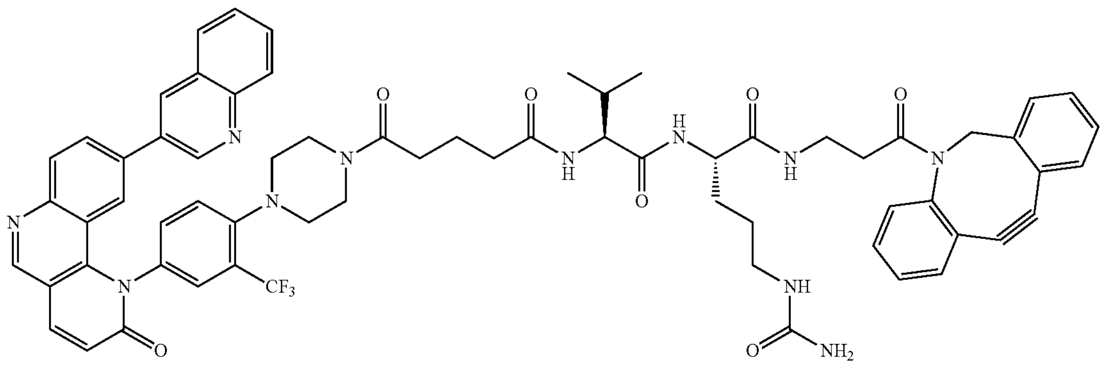 [SMILES: CC(C)[C@H](NC(=O)CCCC(=O)N1CCN(c2ccc(-n3c(=O)ccc4cnc5ccc(-c6cnc7ccccc7c6)cc5c43)cc2C(F)(F)F)CC1)C(=O)N[C@@H](CCCNC(N)=O)C(=O)NCCC(=O)N1Cc2ccccc2C#Cc2ccccc21]

Compound 131, also referred to as Torin-1-C3-Val-Cit-DBCO was synthesized by reacting Torin-1-C1-COOH (Compound 122) and Val-Cit-DBCO (Compound 124). Torin1-C3-COOH (6.5 mg, 0.010 mmol, 1 eq) with Val-Cit-DBCO (6 mg, 0.011 mmol, 1.1 eq) and DIPEA (5 mg, 0.04 mmol, 4 eq) were dissolved in 4 mL of DMF within an appropriate reaction vessel, ensuring complete dissolution for a homogeneous mixture. HATU (5 mg, 0.013 mmol, 1.3 eq), previously dissolved in 1 mL of DMF, was gradually added to the reaction mixture over 30 minutes at room temperature while stirring continuously. Following HATU addition, the mixture was stirred for an additional 30 minutes. The progress of the reaction was routinely monitored using Liquid Chromatography-Mass Spectrometry (LC-MS) to confirm the desired transformation. After the reaction's completion, as indicated by LC-MS analysis, the entire reaction mixture underwent preparative high-performance liquid chromatography (PREP HPLC) for product isolation, employing a reverse-phase C8 column. Purification involved an elution gradient ranging from 30% to 90% acetonitrile (ACN) in water, with both phases containing 0.05% acetic acid (AcOH) to aid in purification. Compound monitoring occurred at 325 nm, and the fractions containing the desired product were collected. Subsequently, these fractions underwent lyophilization (freeze-drying) to yield the purified TORIN1-C3-Val-Cit-DBCO (4 mg, 35% yield) in solid form. MS (ESI) calculated for $C_{66}H_{64}F3N_{11}O_7$ m/z 1179.5, found 1180.4 $(M+H)^+$ Compound 132, Torin-1-C3-Val-Cit-Ahx-DBCO

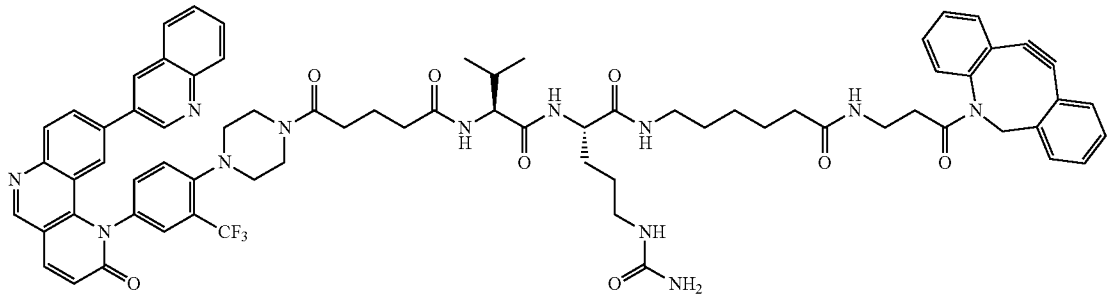 [SMILES: CC(C)[C@H](NC(=O)CCCC(=O)N1CCN(c2ccc(-n3c(=O)ccc4cnc5ccc(-c6cnc7ccccc7c6)cc5c43)cc2C(F)(F)F)CC1)C(=O)N[C@@H](CCCNC(N)=O)C(=O)NCCCCCC(=O)NCCC(=O)N1Cc2ccccc2C#Cc2ccccc21]

Compound 132, also referred to as Torin-1-C3-Val-Cit-Ahx-DBCO was synthesized by reacting Torin-1-C3-COOH (Compound 123) and Val-Cit-Ahx-DBCO (Compound 126). Torin-1-C3-COOH (5.5 mg, 0.008 mmol, 1 eq) with Val-Cit-Ahx-DBCO (6 mg, 0.009 mmol, 1.1 eq) and DIPEA (5 mg, 0.04 mmol, 5 eq) were dissolved in 4 mL of DMF within an appropriate reaction vessel, ensuring complete dissolution for a homogeneous mixture. HATU (5 mg, 0.01 mmol, 1.5 eq), previously dissolved in 1 mL of DMF, was gradually added to the reaction mixture over 30 minutes at room temperature while stirring continuously. Following HATU addition, the mixture was stirred for an additional 30 minutes. The progress of the reaction was routinely monitored using Liquid Chromatography-Mass Spectrometry (LC-MS) to confirm the desired transformation. After the reaction's completion, as indicated by LC-MS analysis, the entire reaction mixture underwent preparative high-performance liquid chromatography (PREP HPLC) for product isolation, employing a reverse-phase C8 column. Purification involved an elution gradient ranging from 30% to 90% acetonitrile (ACN) in water, with both phases containing 0.05% acetic acid (AcOH) to aid in purification. Compound monitoring occurred at 325 nm, and the fractions containing the desired product were collected. Subsequently, these fractions underwent lyophilization (freeze-drying) to yield the purified Torin-1-C3-Val-Cit-Ahx-DBCO (4 mg, 39% yield) in solid form. MS (ESI) calculated for $C_{72}H_{75}F3N_{12}O_8$ m/z 1292.6, found 1293.5 $(M+H)^+$.

Compound 133, Fmoc-Ahx-WWK(ZV)WW

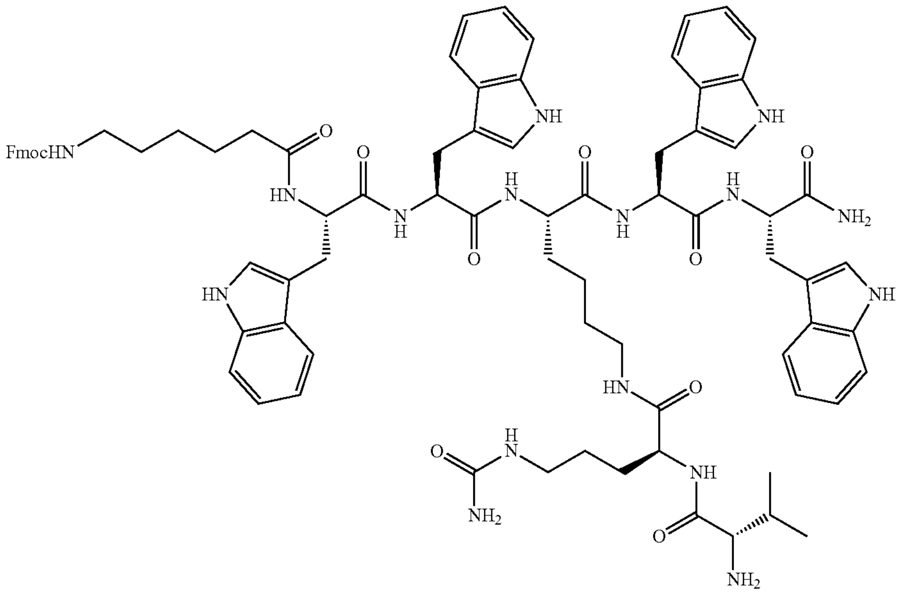

Compound 133, also referred to as Fmoc-Ahx-WWK(ZV)WW was synthesized by reacting Fmoc-Ahx-WWKWW (synthesized by Genscript) and Boc-Val-Cit-OH (CAS: 870487-08-4). A solution of Fmoc-Ahx-WWKWW (100 mg, 0.082 mmol, 1 eq), Boc-Val-Cit-COOH (46, 0.123 mmol, 1.5 eq) and DIPEA (11 mg, 0.085 mmol, 1 eq) was prepared in 4 mL of DMF and maintained at room temperature (RT). HATU (46 mg, 0.123 mmol, 1.5 eq), previously dissolved in 1 mL of DMF, was gradually added to the reaction mixture over 30 minutes at room temperature while stirring continuously. The mixture was stirred for an additional 30 minutes. The progress of the reaction was monitored through Liquid Chromatography-Mass Spectrometry (LC-MS). Upon the complete conversion of the Fmoc-Ahx-WWKWW, the DMF was removed under vacuum. To facilitate Boc deprotection, a solution of DCM and TFA (50:50 v/v, 5 mL) was added, and the mixture was stirred for 1 hour. The progress of the reaction was routinely monitored using Liquid Chromatography-Mass Spectrometry (LC-MS). After confirming the completion of Boc removal, the mixture was concentrated under reduced pressure. The resulting residue was redissolved in DMF and subjected to purification using C8 reversed-phase preparative HPLC(RP-PREP-HPLC). Purification involved a gradient elution method from 20% to 95% acetonitrile/water (CAN) (containing 0.05% TFA) over 10 minutes, followed by maintaining the elution at 95% for an additional 5 minutes. The fractions containing the desired compound were collected and subsequently freeze-dried to obtain the final compound (71 mg, 58% yield). MS (ESI) calculated for $C_{82}H_{96}N_{16}O_{11}$ m/z 1480.7, found 1481.7 $(M+H)^+$.

Compound 134, DBCO-Ahx-WWK(ZV-Everolimus)WW
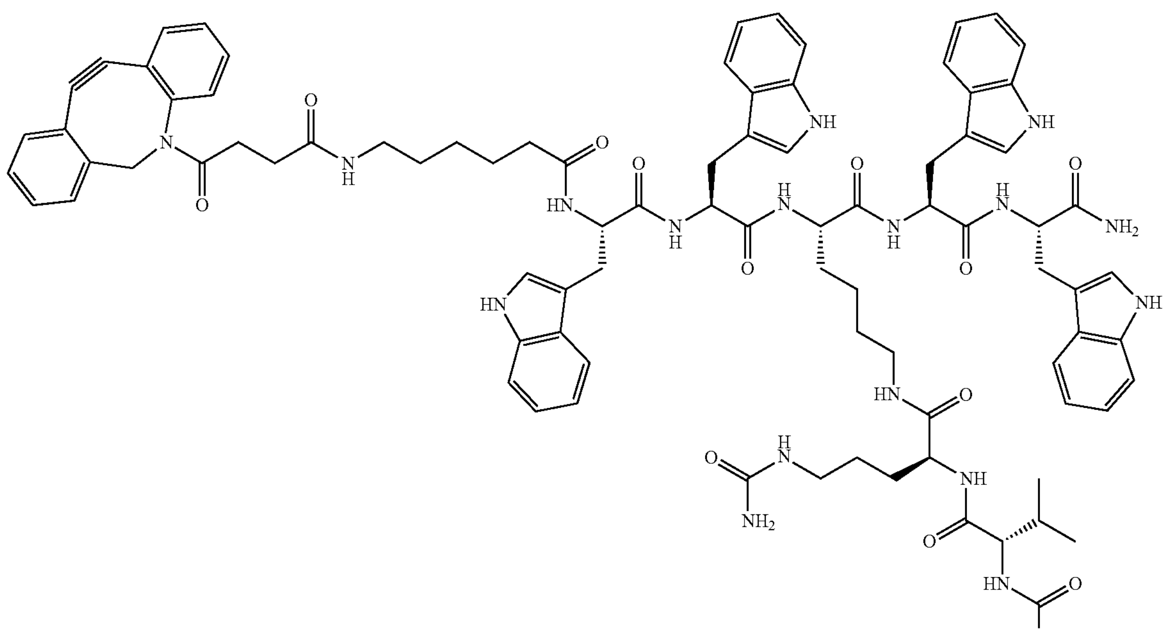
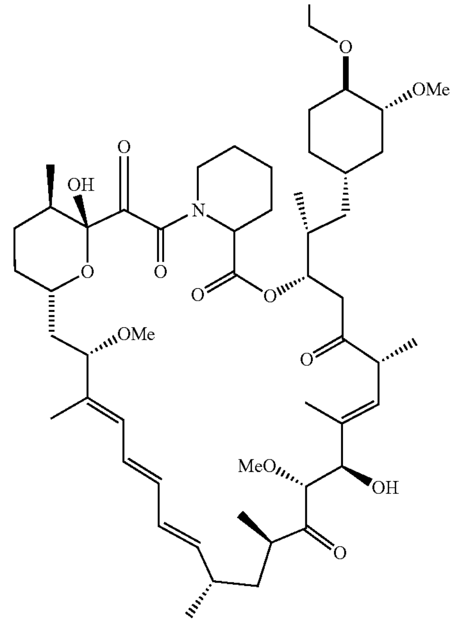

Compound 134, also referred to as DBCO-Ahx-WWK(ZV-Everolimus)WW was synthesized by reacting Fmoc-Ahx-WWK(ZV)WW and Everolimus-COOH (Compound 110). Fmoc-Ahx-WWK(ZV)WW (10 mg, 0.0067 mmol, 1 eq) was dissolved in an appropriate volume of DMF (4 mL). To this solution, Everolimus-COOH (7 mg, 0.0072, 1.1 eq) and DIPEA (5 mg, 0.039 mmol, 6 eq) were added. A DMF solution of HATU (3 mg, 0.0079, 1.2 eq in 1 mL DMF) was gradually introduced to the reaction mixture over a 30-minute period while maintaining the system at room temperature (RT). The mixture was stirred at RT for an additional 30 minutes, and the progress of the reaction was monitored through high-performance liquid chromatography (HPLC) to determine the conversion rate of the Fmoc compound. Upon the complete conversion of Everolimus-COOH, diethylamine (100 uL) was incorporated into the mixture and stirred for another 30 minutes. The mixture was then concentrated under vacuum. The concentrated residue was redissolved in 5 DMF, and DIPEA (5 mg, 0.039 mmol, 6 eq), was subsequently added. DBCO-NHS ester (3 mg, 0.0074 mmol, 1.1 eq) was introduced to the solution and stirred for 1 hour at room temperature. The progress of the reaction was routinely monitored using Liquid Chromatography-Mass Spectrometry (LC-MS). The resultant compound was purified using a C8 reversed-phase preparative HPLC(RP-PREP-HPLC). A purification gradient ranging from 20% to 95% acetonitrile in water (incorporating 0.05% AcOH) over 10 minutes was implemented, and it was maintained at 95% for an additional 5 minutes. The fractions containing the target compound were collected, and the purified, conjugated compound was obtained in solid form (5 mg, 29% yield) through freeze-drying. MS (ESI) calculated for $C_{139}H_{178}N_{18}O_{25}$ m/z 2499.3, found 2522.1 $(M+Na)^+$.

Compound 135, DBCO-Ahx-WWK(ZV-Torin-1-C1)WW

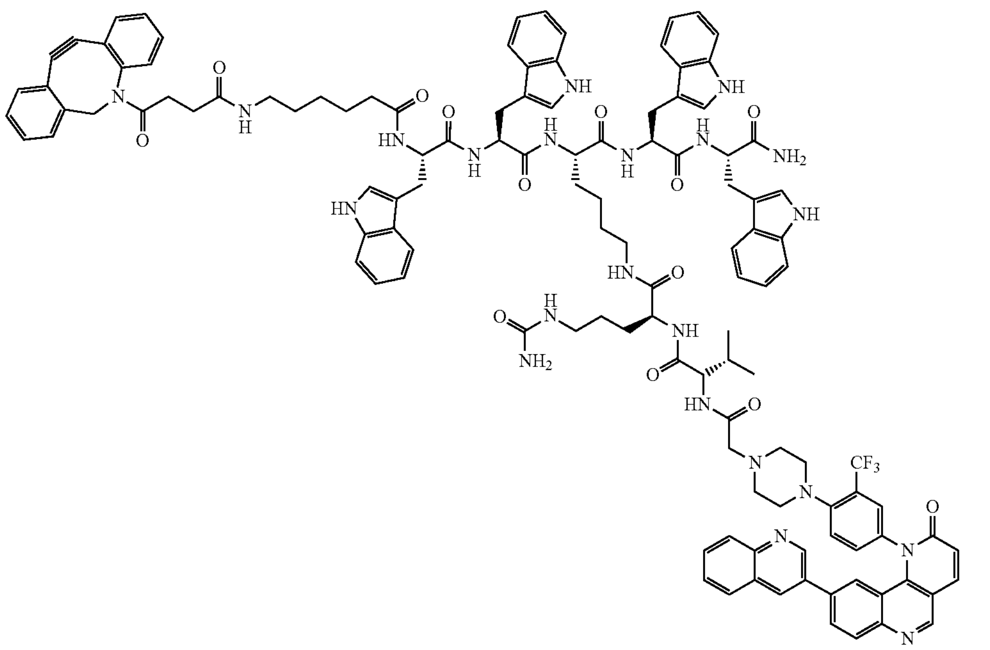

Compound 135, also referred to as DBCO-Ahx-WWK(ZV-Torin-1-C1)WW was synthesized by reacting Fmoc-Ahx-WWK(ZV)WW and Torin-1-C1-COOH. Fmoc-Ahx-WWK(ZV)WW (10 mg, 0.0067 mmol, 1 eq) was dissolved in an appropriate volume of DMF (4 mL). To this solution, Torin-1-C1-COOH (5 mg, 0.008, 1.2 eq) and DIPEA (5 mg, 0.039 mmol, 6 eq) were added. A DMF solution of HATU (3 mg, 0.0079, 1.2 eq in 1 mL DMF) was gradually introduced to the reaction mixture over a 30-minute period while maintaining the system at room temperature (RT). The mixture was stirred at RT for an additional 30 minutes, and the progress of the reaction was monitored through high-performance liquid chromatography (HPLC) to determine the conversion rate of the Fmoc compound. Upon the complete conversion of Torin-1-C1-COOH, diethylamine (100 uL) was incorporated into the mixture and stirred for another 30 minutes. The mixture was then concentrated under vacuum. The concentrated residue was redissolved in DMF, and DIPEA (5 mg, 0.039 mmol, 6 eq), was subsequently added. DBCO-NHS ester (3 mg, 0.0074 mmol, 1.1 eq) was introduced to the solution and stirred for 1 hour at room temperature. The progress of the reaction was routinely monitored using Liquid Chromatography-Mass Spectrometry (LC-MS). The resultant compound was purified using a C8 reversed-phase preparative HPLC(RP-PREP-HPLC). A purification gradient ranging from 20% to 95% acetonitrile in water (incorporating 0.05% AcOH) over 10 minutes was implemented, and it was maintained at 95% for an additional 5 minutes. The fractions containing the target compound were collected, and the purified, conjugated compound was obtained in solid form (3 mg, 21% yield) through freeze-drying. MS (ESI) calculated for $C_{120}H_{123}F_3N_{22}O_{13}$ m/z 2137.1, found 2138.1 (M+H)+.

Compound 136, DBCO-Ahx-WWK(ZV-Torin-1-C3)WW

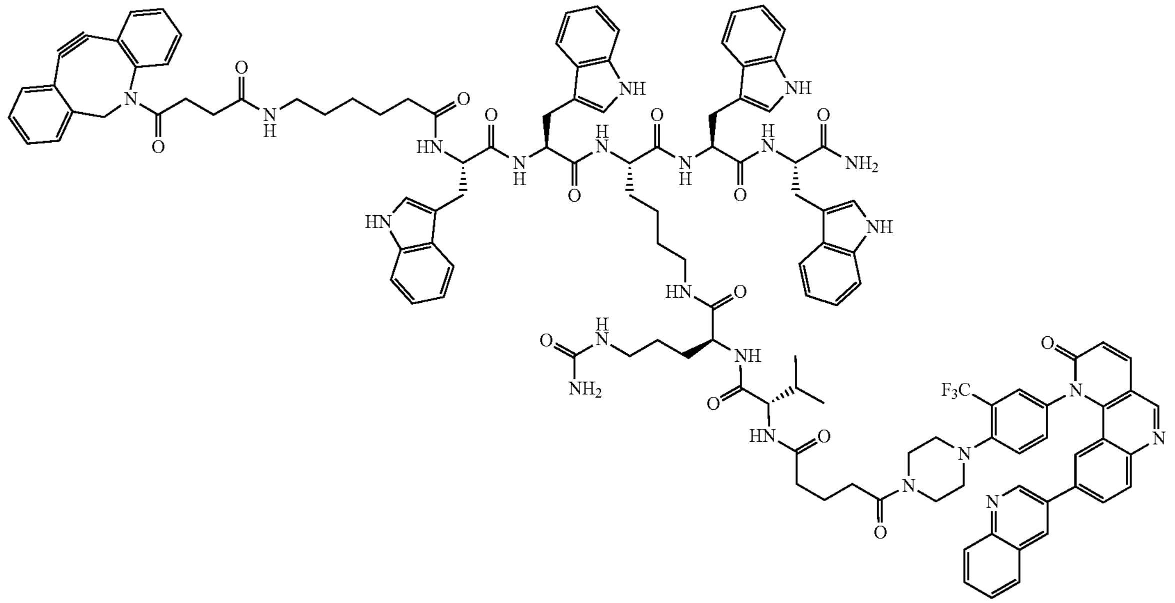 [SMILES: CC(C)[C@H](NC(=O)CCCC(=O)N1CCN(c2ccc(-n3c(=O)ccc4cnc5ccc(-c6cnc7ccccc7c6)cc5c43)cc2C(F)(F)F)CC1)C(=O)N[C@@H](CCCNC(N)=O)C(=O)NCCCC[C@H](NC(=O)[C@H](Cc1c[nH]c2ccccc12)NC(=O)[C@H](Cc1c[nH]c2ccccc12)NC(=O)CCCCCNC(=O)CCC(=O)N1Cc2ccccc2C#Cc2ccccc21)C(=O)N[C@@H](Cc1c[nH]c2ccccc12)C(=O)N[C@@H](Cc1c[nH]c2ccccc12)C(N)=O]

Compound 136, also referred to as DBCO-Ahx-WWK (ZV-TORIN1-C3)WW was synthesized by reacting Fmoc-Ahx-WWK(ZV)WW and Torin-1-C3-COOH. Fmoc-Ahx-WWK(ZV)WW (10 mg, 0.0067 mmol, 1 eq) was dissolved in an appropriate volume of DMF (4 mL). To this solution, TORIN1-C3-COOH (5 mg, 0.0075, 1.12 eq) and DIPEA (5 mg, 0.039 mmol, 6 eq) were added. A DMF solution of HATU (3 mg, 0.0079, 1.2 eq in 1 mL DMF) was gradually introduced to the reaction mixture over a 30-minute period while maintaining the system at room temperature (RT). The mixture was stirred at RT for an additional 30 minutes, and the progress of the reaction was monitored through high-performance liquid chromatography (HPLC) to determine the conversion rate of the Fmoc compound. Upon the complete conversion of Torin-1-C3-COOH, diethylamine (100 uL) was incorporated into the mixture and stirred for another 30 minutes. The mixture was then concentrated under vacuum. The concentrated residue was redissolved in DMF, and DIPEA (5 mg, 0.039 mmol, 6 eq), was subsequently added. DBCO-NHS ester (3 mg, 0.0074 mmol, 1.1 eq) was introduced to the solution and stirred for 1 hour at room temperature. The progress of the reaction was routinely monitored using Liquid Chromatography-Mass Spectrometry (LC-MS). The resultant compound was purified using a C8 reversed-phase preparative HPLC(RP-PREP-HPLC). A purification gradient ranging from 20% to 95% acetonitrile in water (incorporating 0.05% AcOH) over 10 minutes was implemented, and it was maintained at 95% for an additional 5 minutes. The fractions containing the target compound were collected, and the purified, conjugated compound was obtained in solid form (3 mg, 20% yield) through freeze-drying. MS (ESI) calculated for $C_{123}H_{127}F_3N_{22}O_{14}$ m/z 2193.0, found 2194.1 $(M+H)^+$.

Compound 137, DBCO-Ahx-WWK(Everolimus)WW

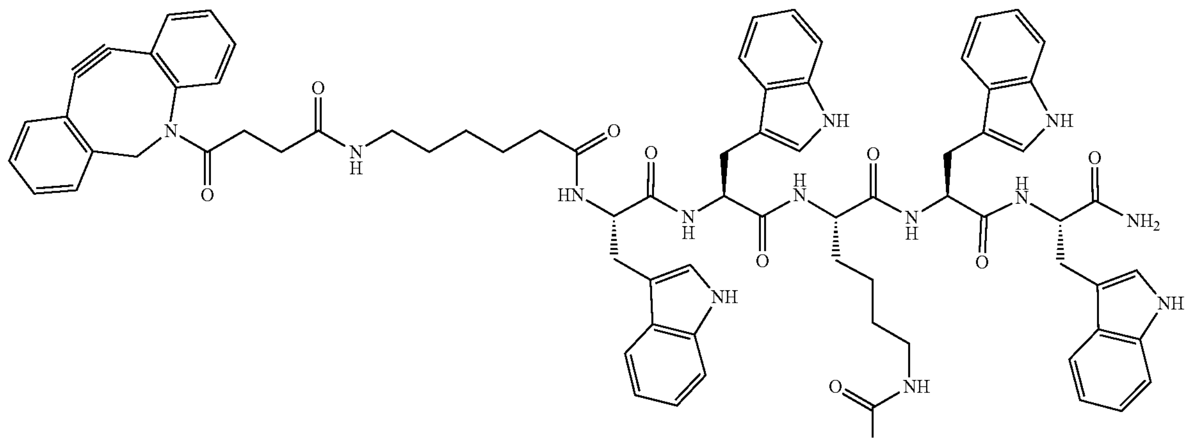

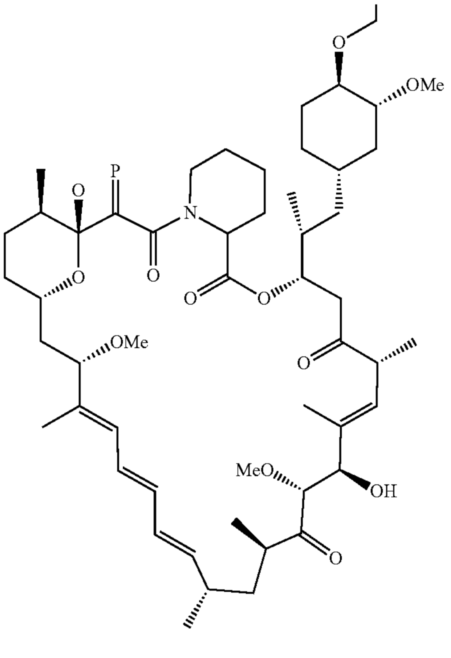

Compound 137, also referred to as DBCO-Ahx-WWK (Everolimus)WW was synthesized by reacting Fmoc-Ahx-WWKWW (Compound 133) and Everolimus —COOH (Compound 110). Fmoc-Ahx-WWKWW (9 mg, 0.0073 mmol, 1 eq) was dissolved in an appropriate volume of DMF (4 mL). To this solution, Everolimus —COOH (8 mg, 0.0082, 1.12 eq) and DIPEA (5 mg, 0.039 mmol, 6 eq) were added. A DMF solution of HATU (3 mg, 0.0079, 1.1 eq in 1 mL DMF) was gradually introduced to the reaction mixture over a 30-minute period while maintaining the system at room temperature (RT). The mixture was stirred at RT for an additional 30 minutes, and the progress of the reaction was monitored through high-performance liquid chromatography (HPLC) to determine the conversion rate of the Fmoc compound. Upon the complete conversion of Everolimus-COOH, diethylamine (100 uL) was incorporated into the mixture and stirred for another 30 minutes. The mixture was then concentrated under vacuum. The concentrated residue was redissolved in 5 DMF, and DIPEA (5 mg, 0.039 mmol, 6 eq), was subsequently added. DBCO-NHS ester (3 mg, 0.0074 mmol, 1.1 eq) was introduced to the solution and stirred for 1 hour at room temperature. The progress of the reaction was routinely monitored using Liquid Chromatography-Mass Spectrometry (LC-MS). The resultant compound was purified using a C8 reversed-phase preparative HPLC (RP-PREP-HPLC). A purification gradient ranging from 20% to 95% acetonitrile in water (incorporating 0.05% AcOH) over 10 minutes was implemented, and it was maintained at 95% for an additional 5 minutes. The fractions containing the target compound were collected, and the purified, conjugated compound was obtained in solid form (5 mg, 31% yield) through freeze-drying. MS (ESI) calculated for $C_{128}H_{158}N_{14}O_{22}$ m/z 2243.2, found 2266.3 $(M+Na)^+$.

Compound 138, DBCO-Ahx-WWE(Torin-1-Piperazine) WW

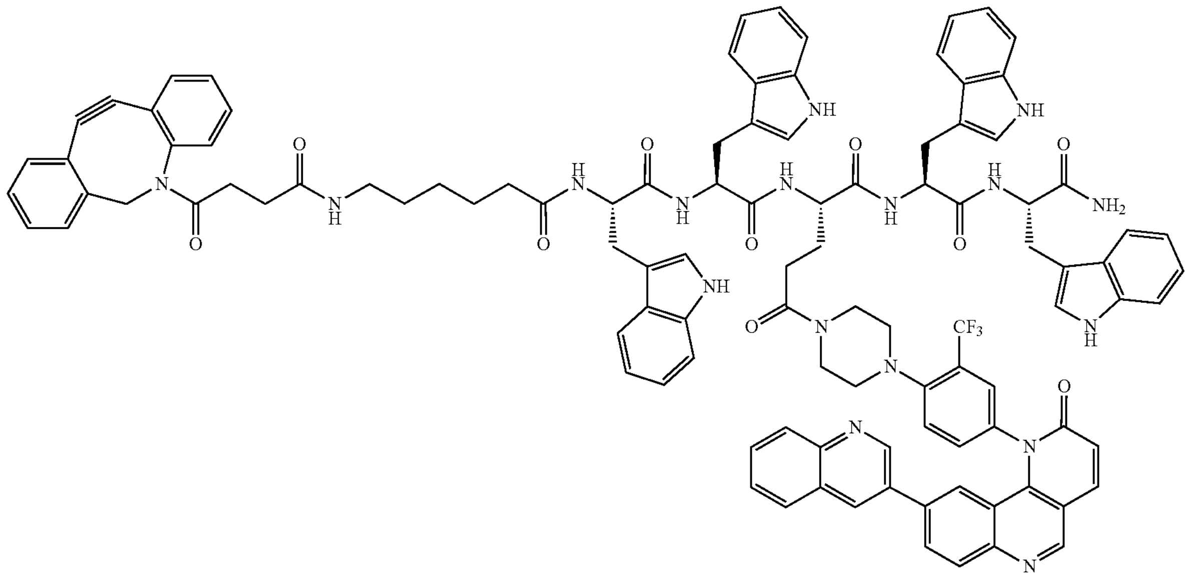 [SMILES: NC(=O)[C@H](Cc1c[nH]c2ccccc12)NC(=O)[C@H](Cc1c[nH]c2ccccc12)NC(=O)[C@H](CCC(=O)N1CCN(c2ccc(-n3c(=O)ccc4cnc5ccc(-c6cnc7ccccc7c6)cc5c43)cc2C(F)(F)F)CC1)NC(=O)[C@H](Cc1c[nH]c2ccccc12)NC(=O)[C@H](Cc1c[nH]c2ccccc12)NC(=O)CCCCCNC(=O)CCC(=O)N1Cc2ccccc2C#Cc2ccccc21]

Compound 138, also referred to as DBCO-Ahx-WWE (Torin-1-Piperazine)WW, was synthesized by reacting DBCO-Ahx-WWEWW (Compound 148) with Torin-1-Piperazine (Compound 98). Fmoc-Ahx-WWEWW (9 mg, 0.0069 mmol, 1 eq) was dissolved in an appropriate volume of DMF (4 mL). To this solution, TORIN1-PIP (5 mg, 0.009 mmol, 1.3 eq) and DIPEA (5 mg, 0.039 mmol, 5.5 eq) were added. A DMF solution of HATU (3 mg, 0.0079 mmol, 1.1 eq in 1 mL DMF) was gradually introduced to the reaction mixture over a 30-minute period while maintaining the system at room temperature (RT). The mixture was stirred at RT for an additional 30 minutes, and the progress of the reaction was monitored through high-performance liquid chromatography (HPLC) to determine the reaction's progress. The resultant compound was purified using C8 reversed-phase preparative HPLC(RP-PREP-HPLC). A purification gradient ranging from 20% to 95% acetonitrile in water (incorporating 0.05% AcOH) over 10 minutes was implemented, and it was maintained at 95% for an additional 5 minutes. The fractions containing the target compound were collected, and the purified, conjugated compound was obtained in solid form (5 mg, 40% yield) through freeze-drying. MS (ESI) calculated for $C_{106}H_{96}F_3N_{17}O_{10}$ m/z 1823.7, found 1825.0 $(M+H)^+$.

Compound 139, DBCO-Ahx-WWE(VZ-Torin-1)WW

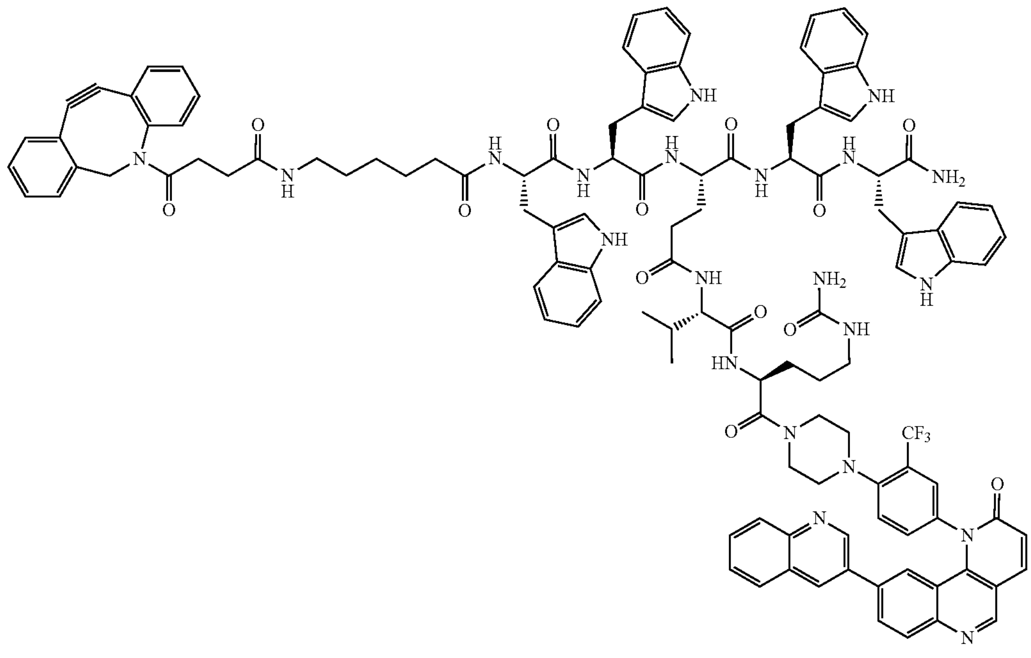 [SMILES: CC(C)[C@H](NC(=O)CC[C@H](NC(=O)[C@H](Cc1c[nH]c2ccccc12)NC(=O)[C@H](Cc1c[nH]c2ccccc12)NC(=O)CCCCCNC(=O)CCC(=O)N1Cc2ccccc2C#Cc2ccccc21)C(=O)N[C@@H](Cc1c[nH]c2ccccc12)C(=O)N[C@@H](Cc1c[nH]c2ccccc12)C(N)=O)C(=O)N[C@@H](CCCNC(N)=O)C(=O)N1CCN(c2ccc(-n3c(=O)ccc4cnc5ccc(-c6cnc7ccccc7c6)cc5c43)cc2C(F)(F)F)CC1]

Compound 139, also referred to as DBCO-Ahx-WWE (ZV-Torin-1)WW, was synthesized by reacting DBCO-Ahx-WWEWW (Compound 148) with Torin-1-ZV (Compound 105). Fmoc-Ahx-WWEWW (9 mg, 0.0069 mmol, 1 eq) was dissolved in an appropriate volume of DMF (4 mL). To this solution, Torin-1-ZV (6 mg, 0.074 mmol, 1.1 eq) and DIPEA (5 mg, 0.039 mmol, 5.5 eq) were added. A DMF solution of HATU (3 mg, 0.0079 mmol, 1.1 eq in 1 mL DMF) was gradually introduced to the reaction mixture over a 30-minute period while maintaining the system at room temperature (RT). The mixture was stirred at RT for an additional 30 minutes, and the progress of the reaction was monitored through high-performance liquid chromatography (HPLC) to determine the reaction's progress. The resultant compound was purified using C8 reversed-phase preparative HPLC(RP-PREP-HPLC). A purification gradient ranging from 20% to 95% acetonitrile in water (incorporating 0.05% AcOH) over 10 minutes was implemented, and it was maintained at 95% for an additional 5 minutes. The fractions containing the target compound were collected, and the purified, conjugated compound was obtained in solid form (5 mg, 35% yield) through freeze-drying. MS (ESI) calculated for $C_{117}H_{116}F_3N_{21}O_{13}$ m/z 2079.9, found 2081.0 $(M+H)^+$.

Compound 140, DBCO-Ahx-WWE(VZ-PAB-Torin-1)WW

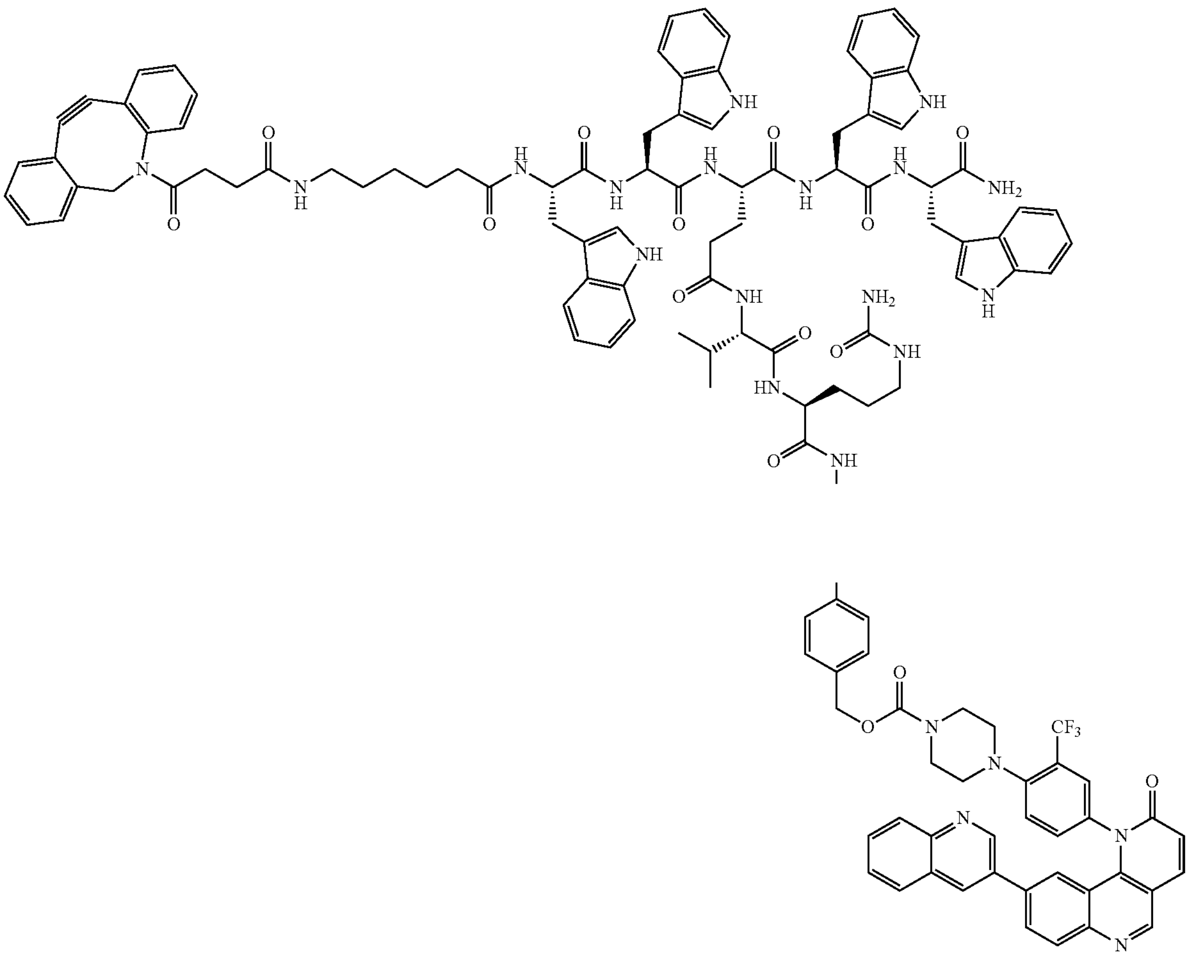

Compound 140, also referred to as DBCO-Ahx-WWE (ZV-PAB-Torin-1)WW, was synthesized by reacting DBCO-Ahx-WWEWW (Compound 148) with Torin-1-PAB-ZV (Compound 104). Fmoc-Ahx-WWEWW (9 mg, 0.0069 mmol, 1 eq) was dissolved in an appropriate volume of DMF (4 mL). To this solution, Torin-1-PAB-ZV (7 mg, 0.073 mmol, 1.1 eq) and DIPEA (5 mg, 0.039 mmol, 5.5 eq) were added. A DMF solution of HATU (3 mg, 0.0079 mmol, 1.1 eq in 1 mL DMF) was gradually introduced to the reaction mixture over a 30-minute period while maintaining the system at room temperature (RT). The mixture was stirred at RT for an additional 30 minutes, and the progress of the reaction was monitored through high-performance liquid chromatography (HPLC) to determine the reaction's progress. The resultant compound was purified using C8 reversed-phase preparative HPLC(RP-PREP-HPLC). A purification gradient ranging from 20% to 95% acetonitrile in water (incorporating 0.05% AcOH) over 10 minutes was implemented, and it was maintained at 95% for an additional 5 minutes. The fractions containing the target compound were collected, and the purified, conjugated compound was obtained in solid form (5 mg, 33% yield) through freeze-drying. MS (ESI) calculated for $C_{125}H_{123}F_3N_{22}O_{15}$ m/z 2229.1 found 2230.0 (M+H)+.

Compound 141, Everolimus -Val-Cit-nBu

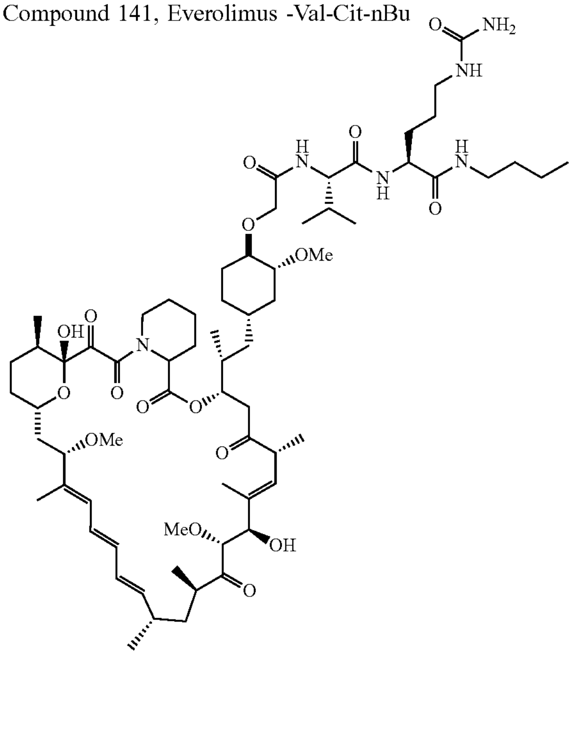

Compound 141, also referred to as Everolimus -Val-Cit-nBu was synthesized by reacting Everolimus-COOH (Compound 110) and Val-Cit-nBu (Compound 147). Everolimus-COOH (20 mg, 0.02 mmol, 1 eq) with Val-Cit-nBu (8 mg, 0.024 mmol, 1.2 eq) and DIPEA (5 mg, 0.04 mmol, 2 eq) were dissolved in 4 mL of DMF within an appropriate reaction vessel, ensuring complete dissolution for a homogeneous mixture. HATU (9 mg, 0.023 mmol, 1.1 eq), previously dissolved in 1 mL of DMF, was gradually added to the reaction mixture over 30 minutes at room temperature while stirring continuously. Following HATU addition, the mixture was stirred for an additional 30 minutes. The progress of the reaction was routinely monitored using Liquid Chromatography-Mass Spectrometry (LC-MS) to confirm the desired transformation. After the reaction's completion, as indicated by LC-MS analysis, the entire reaction mixture underwent preparative high-performance liquid chromatography (PREP HPLC) for product isolation, employing a reverse-phase C8 column (30×100 mm, 5 μm). Purification involved an elution gradient ranging from 30% to 90% acetonitrile (ACN) in water, with both phases containing 0.05% trifluoroacetic acid (TFA) to aid in purification. Compound monitoring occurred at 280 nm, and the fractions containing the desired product were collected. Subsequently, these fractions were freeze-dried to yield the purified compound (3 mg, 11% yield) in solid form. MS (ESI) calculated for $C_{68}H_{110}N_6O_{17}$ m/z 1282.8, found 1305.9 $(M+Na)^+$.

Compound 142, Everolimus -N3-DBCO-COOH

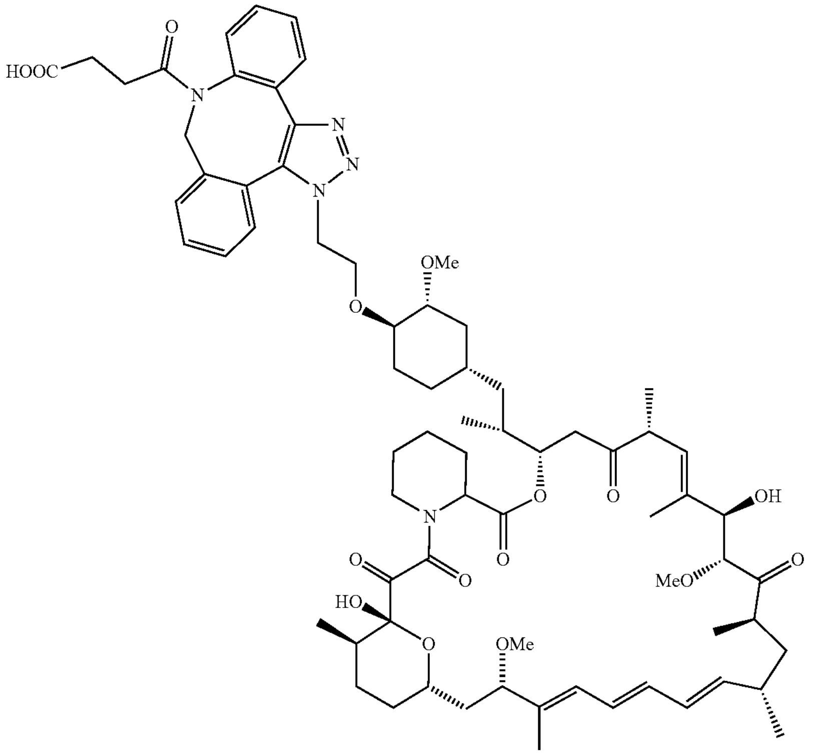

Compound 142 also referred to as Everolimus-N3-DBCO-COOH, was synthesized by reacting Everolimus-N3 (Compound 109) and DBCO-COOH. A solution of 20 mg of Everolimus-N3 (0.022 mmol, 1 eq) and 8 mg of DBCO-COOH (0.026 mmol, 1.2 eq) in 2 mL of DMF was stirred at room temperature for 1 hour. The reaction was monitored using High-Performance Liquid Chromatography (HPLC). Excess DBCO-COOH was removed using azide resin (azide-agarose purchased from Click Chemistry). The reaction mixture was filtered and concentrated under vacuum, resulting in 20 mg of the compound (71% yield). The compound was utilized without any chromatography purification. MS (ESI) calculated for $C_{72}H_{97}N_5O_{16}$ m/z 1287.7, found 1310.7 $(M+Na)^+$.

Compound 147, Val-Cit-nBu

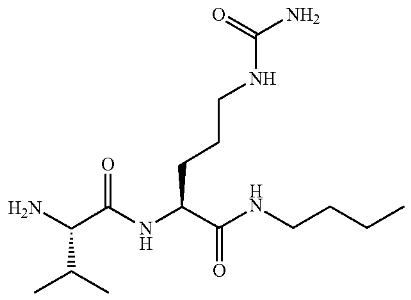 [SMILES: CCCCNC(=O)[C@H](CCCNC(N)=O)NC(=O)[C@@H](N)C(C)C]

Compound 147, also referred to as Val-Cit-nBu was synthesized through the reaction of Fmoc-Val-Cit-OH and butylamine. A solution comprising Fmoc-Val-Cit-COOH (50 mg, 0.1 mmol, 1 eq), Butylamine (8 mg, 0.11 mmol, 1.1 eq), and DIPEA (13 mg, 0.1 mmol, 1 eq) was prepared in 4 mL of DMF and stirred at room temperature (RT). Subsequently, a solution of HATU (38 mg, 0.1 mmol, 1 eq) in 1 mL of DMF was added to this mixture over 30 minutes at RT. The resulting mixture was then stirred at RT for an additional 30 minutes. The progression of the reaction was tracked using high-performance liquid chromatography (HPLC). Upon achieving complete conversion of the Boc-Val-Cit-OH, the DMF was removed under vacuum. To facilitate Boc deprotection, a solution of DCM and TFA (50:50 v/v, 5 mL) was added, and the mixture was stirred for 1 hour. After confirming the completion of Boc removal, the mixture was concentrated under reduced pressure. The resulting residue was redissolved in DMF. Purification was accomplished through C18 reversed-phase preparative HPLC (30×100 mm, 5 μm) employing a gradient of 5% to 95% acetonitrile (ACN) (containing 0.05% TFA) over 10 minutes. The fractions containing the desired compound were collected, resulting in the isolation of 20 mg of the compound with a 45% yield. MS (ESI) calculated for $C_{15}H_{31}N_5O_3$ m/z 329.2, found 330.1 $(M+H)^+$.

Compound 148, DBCO-Ahx-WWEWW

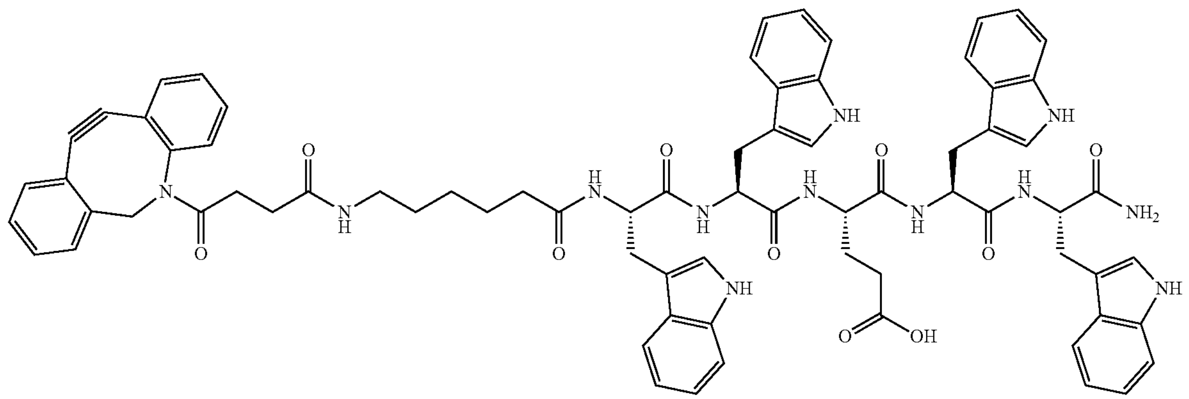 [SMILES: NC(=O)[C@H](Cc1c[nH]c2ccccc12)NC(=O)[C@H](Cc1c[nH]c2ccccc12)NC(=O)[C@H](CCC(=O)O)NC(=O)[C@H](Cc1c[nH]c2ccccc12)NC(=O)[C@H](Cc1c[nH]c2ccccc12)NC(=O)CCCCCNC(=O)CCC(=O)N1Cc2ccccc2C#Cc2ccccc21]

Compound 148, also known as DBCO-Ahx-WWEWW, was synthesized by reacting Ahx-WWEWW (synthesized by Genscript) and DBCO-NHS ester. A mixture of Ahx-WWEWW (100 mg, 0.1 mmol, 1 eq), DBCO-NHS ester (44 mg, 0.11 mmol, 1.1 eq), and triethylamine (12 mg, 0.12 mmol, 1.2 eq) was dissolved in 5 mL of DMSO and stirred at room temperature for 90 minutes. The reaction progress was monitored using High-Performance Liquid Chromatography (HPLC). The product was isolated via PREP HPLC using a gradient of 40-85% acetonitrile/water (0.05% TFA) over a 12-minute period on an Agilent Preparatory C-18 column, 30×100 mm, 5 μm. The desired fractions were combined, resulting in the production of 50 mg of DBCO-Ahx-WWEWW with a yield of 46%. MS (ESI) calculated for $C_{74}H_{74}$N12010 m/z 1290.6, found 1291.5 (M+H)+.

Compound 149, OH-PEG24-VZQLQPFPQPELPYPQPQLPYPQPQPFRSPVZK (DBCO), OH-PEG24-VZQLQPFPQPELPYPQPQLPYPQPQPFRSPVZK (DBCO) was synthesized from the peptide precursor OH-PEG24-VZQLQPFPQPELPYPQPQLPYPQPQPFR-SPVZK prepared by solid-phase peptide synthesis (wherein Z denotes citrulline). 10.8 mg of peptide OH-PEG24-VZQLQPFPQPELPYPQPQLPYPQPQPFRSPVZK (2.1 μmol, 1 eq) and 0.42 uL triethylamine (TEA) (2.52 umol, 2.4 eq) were added to 70 uL anhydrous DMSO and stirred at room temperature under ambient air for 5 minutes. 1.71 mg of DBCO-NHS ester (Scottsdale, Arizona, USA) (4.2 μmol, 2 eq) was then added while stirring vigorously and reacted for 1 hour. The reaction progress was monitored by HPLC (AUC 310 nm). Compound 149 was then purified on a preparatory HPLC system using a gradient of 20-50% acetonitrile/$H_2O$ (0.05% TFA) over 10 minutes on an Agilent Prep-$C_{18}$ column, 30×100 mm, 5 μm. Eluted fractions were checked for purity by HPLC, frozen and then lyophilized to obtain a 63% yield of a spectroscopically pure (97.8% AUC at 220 nm) white solid. MS (ESI) Calculated for $C_{126}H_{238}N_{10}O_{69}$ m/z 5372.3, found 1075.4 $(M/5)^+$.

Example IF: Peptide Antigen Conjugate with mTOR Inhibitor Conjugated H-Block

Peptide antigen conjugates (Compound 143 &144) were prepared containing Everolimus conjugated to a stable amide linker (DBCO-Ahx-WWK(Everolimus)WW, Compound 137) or tryptophan based H-block via a VZ cleavable linker (DBCO-Ahx-WWK(ZV-Everolimus)WW, compound 134). Peptide antigen conjugates (Compound 145 &146) were further prepared directly using Everolimus as a H-block (Compound 109) to yield Compound 145 or Everolimus via VZ cleavable linker (Everolimus-Val-Cit-Ahx-DBCO, Compound 128) to yield compound 146.

Peptide antigen conjugates (143-148) with mTOR inhibitor containing H-block are described in Table 24.

TABLE 24

Peptide antigen conjugates with mTOR inhibitor conjugated H-block

| Comp # | PEG-[E1]-A-[E2]-U1 or U1-[E1]-A-[E2]-PEG<br>Product | U2-H | Theo. MW | Found MW |
|---|---|---|---|---|
| 143 | OH-PEG24-VZQLQPFPQPELPYPQPQLPYPQPQPFR-SPVZX (compound 35)<br>OH-PEG24-VZQLQPFPQPELPYPQPQLPYPQPQPFR-SPVZ-(X DBCO)-Ahx-WWK(Everolimus)WW | Compound 137 | 7307.36 | 1218.3 $(M/6 + H)^+$ |
| 144 | OH-PEG24-VZQLQPFPQPELPYPQPQLPYPQPQPFR-SPVZX (compound 35)<br>OH-PEG24-VZQLQPFPQPELPYPQPQLPYPQPQPFR-SPVZ(X-DBCO)-Ahx-WWK(ZV-Everolimus)WW | Compound 134 | 7611.91 | 1088.3 $(M/7 + H)^+$ |
| 145 | OH-PEG24-VZQLQPFPQPELPYPQPQLPYPQPQPFRSPVZK(DBCO) (compound 149, SEQ ID NO: 527)<br>OH-PEG24-VZQLQPFPQPELPYPQPQLPYPQPQPFR-SPVZK(DBCO-N3)-Everolimus | Compound 109 | 6285.42 | 1048.4 $(M/6 + H)^+$ |
| 146 | OH-PEG24-VZQLQPFPQPELPYPQPQLPYPQPQPFR-SPVZX (Compound 35)<br>OH-PEG24-VZQLQPFPQPELPYPQPQLPYPQPQPFR-SPVZX(DBCO-Ahx-ZV-Everolimus) | Compound 128 | 6760.97 | 966.6 $(M/7 + H)^+$ |

Note:

Single letter abbreviations are used for amino acid sequences in the above table; X = azidolysine, Z = citrulline. Peptide-based starting materials were manufactured by solid-phase peptide synthesis by Genscript (Piscataway, NJ). Sequences for peptide-based starting materials are written from N- to C-terminus, and C-terminal $NH_2$ indicates that the peptide is terminated with an Amide. Unless otherwise specified, any C-terminal X, azidolysine, is terminated with an amide and is implicit in the sequences (i.e., not shown).

Example 2: General Method for Preparing and Characterizing Vaccine Formulations Comprising Nanoparticles Further Comprising Peptide Antigen Conjugates of Formula PEG-E1-A-E2-[U]-H or C-E1-A-E2-[U]-H and Amphiphiles of Formula S-B-[U]-H The general procedure for formulating and characterizing vaccines comprising peptide antigen conjugates was described previously by Lynn and colleagues (see: Lynn et al., *Nature Biotechnology.* 2020; and international patent application number WO 2022/177993). Briefly, peptide antigen conjugates of formula PEG-E1-A-E2-[U]-H and C-E1-A-E2-[U]-H and amphiphiles of formula S-B-[U]-H were suspended in DMSO at concentrations between 10-20 mM to create DMSO stocks. The DMSO stocks were then combined at specific molar ratios (e.g., 1:1 moles of peptide antigen conjugate to moles of amphiphile) to produce a peptide antigen conjugate mixture in DMSO. To generate a formulation suitable for vaccination, the peptide antigen conjugate mixture in DMSO was then diluted with aqueous buffer (or an aqueous solution), referred to as a formulation buffer, to produce a peptide conjugate mixture in formulation buffer.

The peptide antigen conjugate mixture in formulation buffer was optionally sterile-filtered and then characterized using various analytical methods to assess key material attributes, including UV-Vis to assess content; LC-MS to assess identity and purity; and dynamic light scattering (DLS) and turbidity measurements to assess the size of particles and presence of aggregates.

The method for assessing particle size by DLS comprised the following steps: at least one hour after addition of the formulation buffer, the peptide conjugate mixture in formulation buffer was assessed on a Malvern Zetasizer (Malvern Pananalytical, Malvern, UK) to determine hydrodynamic radius and size distribution. Results are reported as the number mean radius.

The method for assessing particle size by turbidity comprised the following steps: at least one hour after addition of the formulation buffer, the peptide conjugate mixture in formulation buffer was evaluated for absorbance at 490 nm to assess turbidity using a plate reader (Biotek, Winooski, VT) Briefly, 90 μL of the peptide conjugate mixture in formulation buffer was added to 96 well, flat bottom polystyrene plate and then reading the absorbance at 490 nm. Alternatively, the 3 μL of the peptide conjugate mixture in formulation buffer was added to a microplate reader (e.g., Take 3 Plate, Agilent) or added to a cuvette and assessed for absorbance at 490 nm. Results are reported as optical density (OD) at 490 nm.

Example 3: Impact of Ethylene Oxide (PEG) Modification of Peptide Antigen Conjugates on Hydrodynamic Stability and Hemolytic Activity In Vitro Prior studies evaluating the impact of the charge-modifying group, or charged block, C, on hydrodynamic behavior of peptide antigen conjugates of formula C-[E1]-A-[E2]-[U]-H [(D)] showed that net charge of the peptide antigen conjugate was an important factor impacting hydrodynamic size and stability. Accordingly, whereas peptide antigen conjugates of formula C-[E1]-A-[E2]-[U]-H [(D)] with near neutral net charge in aqueous buffer tended to aggregate those with net charge ≥+3 or ≤−3 tended to form stable nanoparticle micelles with increasing magnitude of net charge associated with increasing nanoparticle micelle stability (WO 2018/187515 and Lynn et al., Nature Biotechnology. 2020).

However, a potential challenge is that peptide antigen conjugates of formula C-[E1]-A-[E2]—[U]—H[(D)] with C selected from cationic groups, e.g., primary, secondary, tertiary or quaternary amine or ammonium groups, which were found to be most favorable for manufacturability and particle hydrodynamic behavior were found to cause dose-dependent red blood cell hemolysis (WO2022/177993). As a means for reducing hemolytic activity of vaccine formulations comprising peptide antigen conjugates of formula C-[E1]-A-[E2]-[U]-H[(D)] with C selected from cationic groups, an amphiphilic carrier for formula S-[B]—[U]—H [(D)] was introduced to promote solubilization of peptide antigen conjugates with reduced net charge and reduced cationic group density contributing to hemolytic activity. While reducing the number of charged residues (and therefore net charge) of peptide antigen conjugates of formula C-[E1]-A-[E2]-[U]-H[(D)] in vaccine formulations additionally comprising amphiphiles of formula S-[B]-[U]-H [(D)] was found to reduce dose-dependent hemolysis, there was also an associated decrease in hydrodynamic stability, i.e., reducing net charge of the peptide antigen conjugates of formula C-[E1]-A-[E2]-[U]-H[(D)] resulted in increased propensity for aggregation despite the presence of the amphiphile.

Therefore, there is currently a need for improved peptide antigen conjugate compositions that have reduced hemolytic activity while maintaining hydrodynamic stability. Toward this end, poly(ethylene glycol) (PEG) was evaluated as an alternative to use of a charged block (C) at the N-terminal position of peptide antigen conjugates and evaluated for its impact on hydrodynamic stability and hemolytic activity of peptide antigen conjugates admixed with amphiphile.

To evaluate the impact of N-terminal PEGylation, peptide antigen conjugates of formula PEG-E1-A-E2-U-H were prepared with either a hydroxy terminated PEG of about 24 units in length (OH-PEG (1000)) (Compounds 85, 86 and 88) or a methoxy terminated PEG of 24 units in length (m-o-PEG24) (Compounds 80, 81 and 83) and formulated with an amphiphile of formula S-B-U-H (Compound 13 at a molar ratio of 1:1 total moles of peptide antigen conjugate to moles of amphiphile to generate peptide antigen conjugate mixtures in formulation buffer as described above (see Table 1C). Formulations comprising peptide antigen conjugates of formula C-E1-A-E2-U-H (Compounds 90, 91 and 92) and S-B-H (Compound 13) were formulated at a molar ratio of 1:1 total moles of peptide antigen conjugate to moles of amphiphile to generate peptide antigen conjugate mixtures in formulation buffer in a similar manner described above and used for benchmarking purposes (see Table 1C).

TABLE 1C

Compositions of vaccines comprising peptide antigen conjugates with N-terminal PEG or C block and an amphiphile of formula S-B-U-H.

| Group # | PAC formula | PAC Compound # | PEG or C block |
|---|---|---|---|
| 1 | PEG-E1-A-E2-U-H | Compound 85<br>Compound 86<br>Compound 88 | HO-PEG(1000) |
| 2 | PEG-E1-A-E2-U-H | Compound 80<br>Compound 81<br>Compound 83 | m-o-PEG24 |

TABLE 1C-continued

| Compositions of vaccines comprising peptide antigen conjugates with N-terminal PEG or C block and an amphiphile of formula S-B-U-H. | | | |
|---|---|---|---|
| Group # | PAC formula | PAC Compound # | PEG or C block |
| 3 | C-E1-A-E2-U-H | Compound 90<br>Compound 91<br>Compound 92 | (K)c |

Note:

each set of peptide antigen conjugates was admixed with amphiphile of formula S-B-U-H (compound 13) at a 1:1 ratio of total peptide antigen conjugate to amphiphile in formulation buffer comprising PBS, pH 7.4 to a final concentration of either 1 mM total peptide antigen conjugate and 10% DMSO or 0.2 mM total peptide antigen conjugate and 2% DMSO.

PAC = peptide antigen conjugate.

Figure 1B:
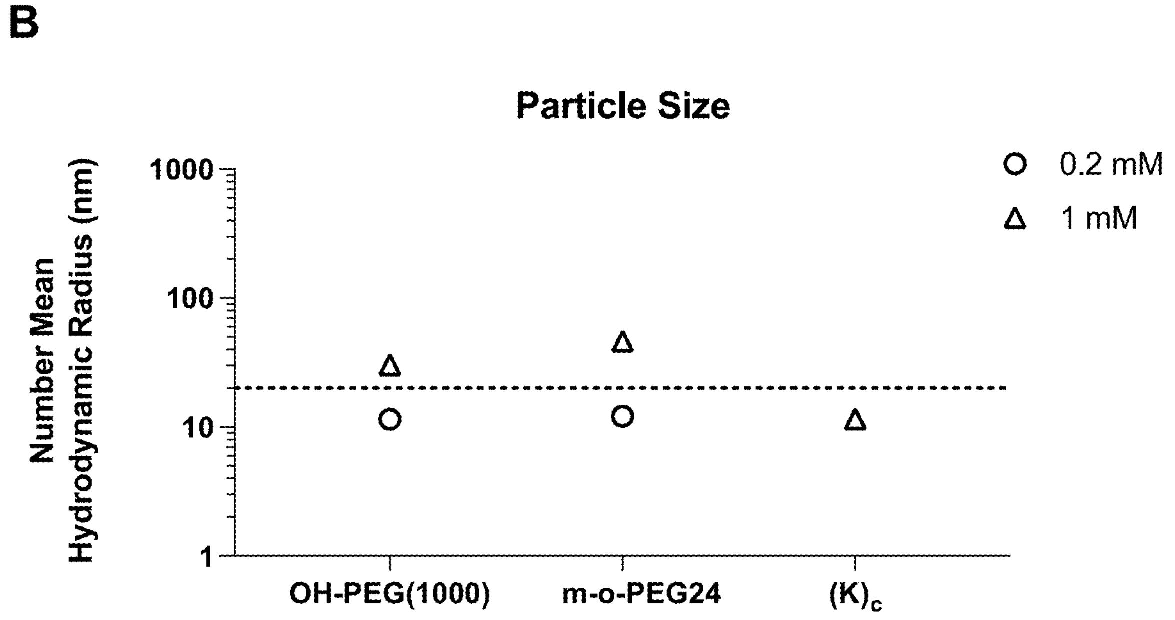

Notably, all the formulations showed uniformly sized nanoparticle micelles at 0.2 mM as indicated by the by the DLS and turbidity results (FIG. 1); however, Group 2 comprising methoxy-terminated PEG formulations exhibited an increased propensity to aggregate at the higher concentration assessed (1 mM) as compared with the Group 1 formulations comprising the hydroxy terminated PEG. These data suggest that the N-terminal PEG group may impact hydrodynamic stability and that peptide antigen conjugates comprising hydroxy terminated PEG may be preferred over those terminated with methoxy-terminal groups.

Example 4: Impact of Ethylene Oxide (PEG) Modification of Peptide Antigen Conjugates on Hydrodynamic Stability and Hemolytic Activity In Vitro We next assessed the hemolytic activity of different representative vaccine compositions comprising peptide antigen conjugates with either an N-terminal charged block or PEG group as compared with branched polyethyleneimine (bPEI), which is well known in the art to have hemolytic activity.

As representative compositions, peptide antigen conjugates of formula C-E1-A-E2-U-H and PEG-E1-A-E2-U-H summarized in Table 2B were assessed for hemolytic activity as compared with controls using substantially similar methods as described in WO2022/177993.

Briefly, the general process for assessing hemolytic activity is as follows: mouse RBCs were washed twice with PBS buffer pH 7.4 and then then suspended to 13.33% RBC on a volume by volume (v/v) basis in PBS. 30 uL/well of the 13.33% RBCs were transferred to a 96-well round bottom plate. Experimental formulations (e.g., vaccines comprising peptide antigen conjugates) and controls were then added to the RBCs to a final volume of 50 uL at the concentrations specified in the corresponding figures ensuring % DMSO was no more than 1% and then the plates were placed in an incubator at 37 C for 3 hours. After 3 hours, 150 μL of PBS was added to each well, then centrifuged for 5 min at 1000 g. Care was taken not to agitate the cell pellet and 100 μL of the cell-free supernatant was then transferred to a new 96-well flat bottom, and absorbance was measured at 540 nm to detect free heme. 1×PBS, bPEI, DMSO, and Triton-x were used as controls for the hemolysis assay and hemolysis.

TABLE 2B

| Peptide antigen conjugates assessed for hemolytic activity. | | | |
|---|---|---|---|
| Group # | PAC formula | PAC Compound # | PEG or C block |
| 1 | C-E1-A-E2-U-H | Compound 92 | $(K)_c$ |
| 2 | PEG-E1-A-E2-U-H | Compound 88 | HO-PEG(1000) |
| 3 | PEG-E1-A-E2-U-H | Compound 83 | m-o-PEG24 |
| 4 | DMSO control | — | — |
| 5 | Branched polyethyleneimine (bPEI) control | — | — |

Note:

each peptide antigen conjugate was admixed with amphiphile of formula S-B-U-H, compound 13, at a 1:1 ratio of total peptide antigen conjugate to amphiphile in formulation buffer comprising PBS, pH 7.4.

PAC = peptide antigen conjugate.

Figure 2:
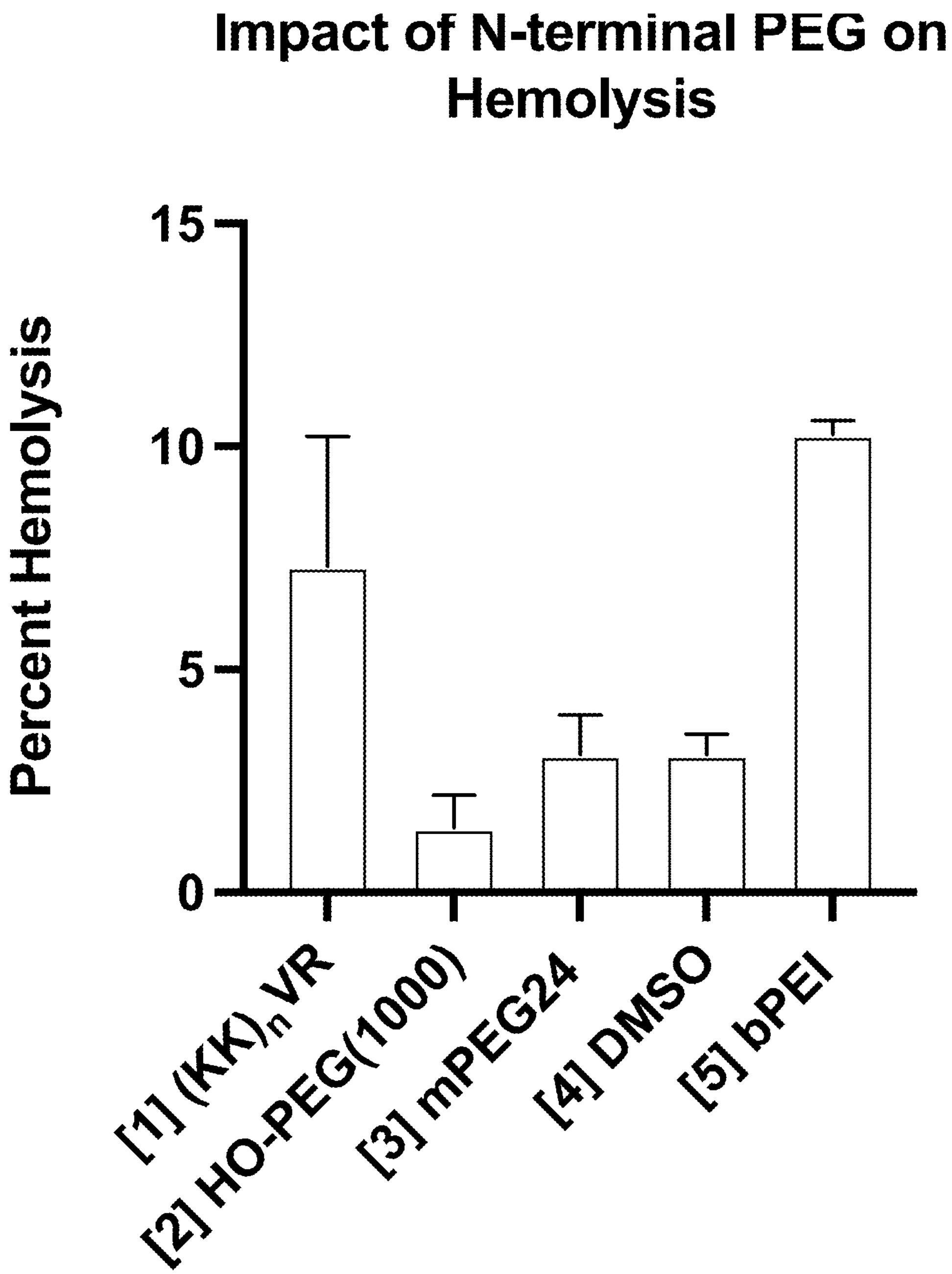
FIG. 2 shows that replacement of the positively charged block (C) of peptide antigen conjugates of formula C-E1-A-E2-U-H with a PEG group to produce conjugates of formula PEG-E1-A-E2-U-H abrogates dose-dependent hemolytic activity associated with the charged block. See Table 2B and experimental section for a description of the materials and methods.

Whereas group 1 comprising the peptide antigen conjugate having a N-terminal C block causes greater than 5% hemolysis at 40 uM comparable with bPEI, a known hemolytic material, groups 2 and 3 comprising the peptide antigen conjugates having N-terminal PEG groups (compounds 88 and 83) did not induce hemolysis above background, group 4 (FIG. 2).

Importantly, these data show that N-terminal PEGylation of peptide antigen conjugates can abrogate the hemolytic activity due to the N-terminal C block while maintaining favorable particle hydrodynamic behavior for use in vaccine compositions.

Example 5: Tolerability of Vaccines Comprising Peptide Antigen Conjugates of Formula PEG-E1-A-E2-[U]-H or C-E1-A-E2-[U]-H and Amphiphiles of Formula S-B-[U]-H by the Intravenous Route of Administration To extend the above findings, we next assessed the impact that the N-terminal group of peptide antigen conjugates (PEG and C block) has on gross tolerability following intravenous administration to mice.

Figure 3A:
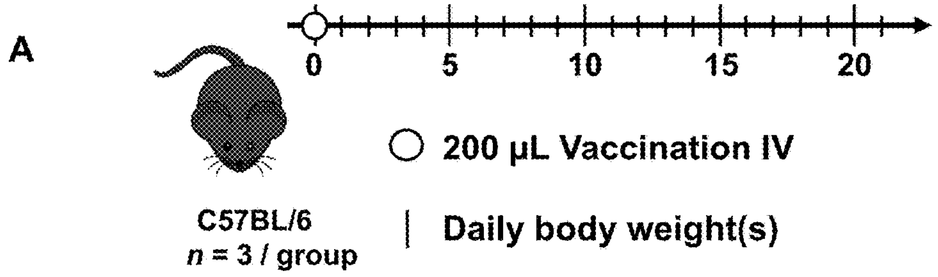
FIG. 3A-3C shows the impact that the N-terminal group of peptide antigen conjugates has on tolerability following intravenous administration. The data show that vaccine formulations comprising peptide antigen conjugates of formula PEG-E1-A-E2-U-H were more well tolerated following intravenous administration than peptide antigen conjugates of formula C-E1-A-E2-U-H.
Figure 3B:
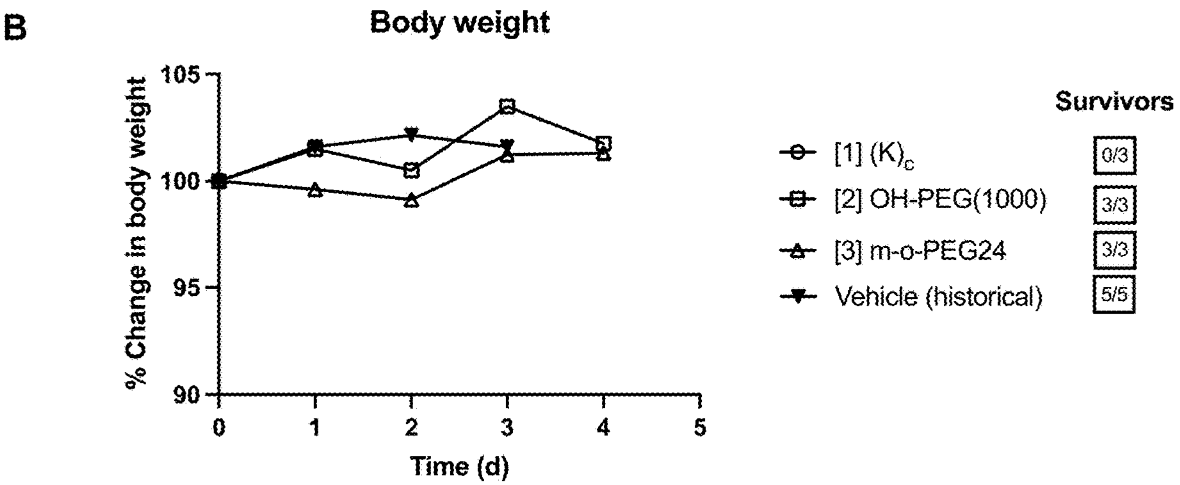
Figure 3C:
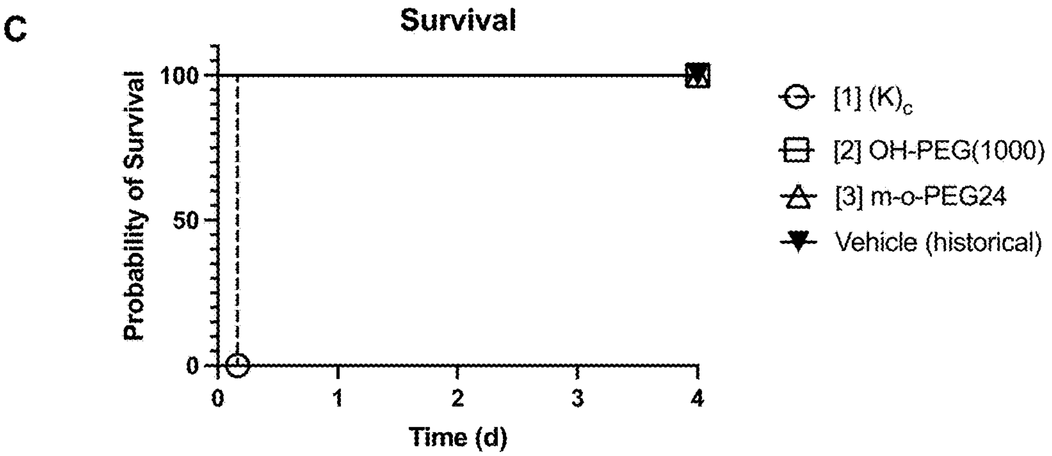

Representative vaccine compositions with either N-terminal PEG or C block were prepared as described above and summarized in Table 3. To assess the impact that the N-terminal block has on tolerability, the vaccine formulations summarized in Table 3 were formulated to a final concentration of 1 mM in 10% DMSO/PBS and injected in a volume of 200 uL (200 nmol of total peptide antigen conjugate) to the tail vein of C57BL/6 mice. Mice were then observed for signs of overt toxicity (e.g., hunched over, piloerection, decreased activity or sociability, etc.) and body weight was assessed at serial timepoints thereafter as a proxy for morbidity (FIG. 3).

A striking finding was that group 1 comprising the peptide antigen conjugates with a C block was uniformly fatal within 4 hours of injection at the assessed dose, whereas groups 2 and 3 comprising peptide antigen conjugates with N-terminal PEG groups were well tolerated (see FIG. 3; note that group 1 is not shown on the line plot) showing that N-terminal PEGylation of peptide antigen conjugates provides a significant advantage in terms of tolerability as compared with vaccine compositions comprising peptide antigen conjugates comprising charged blocks further comprising cationic groups.

TABLE 3B

| Compositions of vaccines assessed for tolerability. | | | | |
|---|---|---|---|---|
| Group | PAC Formula | PAC Compound # | PEG or C block | Survival (%) |
| 1 | C-E1-A-E2-U-H | Compound 92<br>Compound 93<br>Compound 94 | $(K)_c$ | 0 |
| 2 | PEG-E1-A-E2-U-H | Compound 88<br>Compound 87<br>Compound 89 | HO-PEG(1000) | 100 |
| 3 | PEG-E1-A-E2-U-H | Compound 83<br>Compound 82<br>Compound 84 | m-o-PEG24 | 100 |

Note:
each peptide antigen conjugate was admixed with amphiphile of formula S-B-U-H, compound 13, at a 1:1 ratio of total peptide antigen conjugate to amphiphile in formulation buffer comprising PBS, pH 7.4. PAC = peptide antigen conjugate. All vaccine compositions were prepared as 1 mM total peptide antigen conjugate administered by the IV route in 200 uL formulation buffer providing a total of 200 nmol peptide antigen conjugate per treatment.
Note:
HO-PEG(1000), sometimes abbreviated OH-PEG(1000) has on average 24 monomeric units.

In vivo efficacy of vaccine compositions comprising peptide antigen conjugates of formula PEG-E1-A-E2-[U]-H or C-E1-A-E2-[U]-H and amphiphiles of formula S-B-[U]-H for treating experimental autoimmune encephalomyelitis (EAE).

The above data show that replacement of the charged block (C) of peptide antigen conjugates of formula C-E1-A-E2-[U]-H with PEG leads to reduced hemolytic activity and improved tolerability by the IV route.

However, prior studies have shown that PEGylation reduces protein and peptide immunogenicity. Indeed, PEGylation has been widely deployed as a means for shielding molecules from the immune system and numerous PEGylated recombinant proteins (Ramos-de-la-Peña, A M, et al. International Journal of Peptide Research and Therapeutics, 2020) have been approved by the FDA on the basis of improved pharmacokinetics, which has been attributed to improved ability to evade the immune system. PEGylated liposomal carriers, including DOXIL have also been developed based on a similar principle that PEGylation reduces immune recognition, and prior results with PEGylated peptide antigen conjugates indicated that such PEGylation was likely deleterious to immune responses generated with peptide antigens (e.g., see FIG. 23 in patent application WO 2018/187515). Therefore, based on prior data and general teaching in the literature, N-terminal PEGylation of peptide antigen conjugates would be anticipated to be deleterious to immune responses.

To assess the impact that N-terminal PEGylation has on vaccines for inducing regulatory T cells for treating autoimmunity, vaccine compositions comprising peptide antigens conjugates of formula PEG-E1-A-E2-[U]-H or C-E1-A-E2-[U]-H, amphiphiles of formula S-B-[U]-H and optionally a drug molecule, D, wherein the peptide antigen (A) is a fragment of MOG protein and D is Torin-1 (See Table 4), were evaluated in a murine EAE model for the capacity to induce a regulatory CD4 T cell response and reverse disease. Of note: disease in the EAE model is mediated by autoreactive T cells that cause demyelination, which is comparable to the mechanism of disease in multiple sclerosis and related demyelinating diseases. EAE is therefore considered a model of T cell mediated demyelinating diseases.

TABLE 4

| Compositions of tolerance vaccines comprising peptide antigen conjugates with N-terminal PEG or C block and amphiphile of formula S-B-U-H assessed for efficacy in the treatment of Experimental Autoimmune Encephalomyelitis (EAE). | | | | | | |
|---|---|---|---|---|---|---|
| Group | Route | PAC formula | PAC Compound # | S-B-U-H Compound # | PEG or C block | Total PAC dose (nmol) |
| 1 | IV | — | — | — | — | — |
| 2 | IV | C-E1-A-E2-U-H | Compound 95 | Compound 13 | $(K)_c$ | 40 |
| 3 | IV | PEG-E1-A-E2-U-H | Compound 97 | Compound 13 | OH-PEG24 | 40 |
| 4 | IV | PEG-E1-A-E2-U-H | Compound 97 | Compound 13 | OH-PEG24 | 100 |
| 5 | SC | C-E1-A-E2-U-H | Compound 96 | — | $(K)_c$ | 40 |
| 6 | SC | PEG-E1-A-E2-U-H | Compound 97 | Compound 13 | OH-PEG24 | 40 |

Note:
The peptide antigen conjugate was admixed with amphiphile of formula S-B-U-H, compound 13, at a 1:1 ratio of total peptide antigen conjugate to amphiphile in formulation buffer comprising PBS, pH 7.4, unless otherwise stated in the table. Torin-1 was formulated at 1:1 ratio to total peptide antigen conjugate in all groups. PAC = peptide antigen conjugate. Vaccine compositions were prepared as 1 mM for group 4, and 0.4 mM for the remaining groups. Total peptide antigen conjugate administered by either the IV or IM route in 100 uL formulation buffer providing a total of 40 nmol or 100 nmol peptide antigen conjugate per treatment.

Figure 4A:
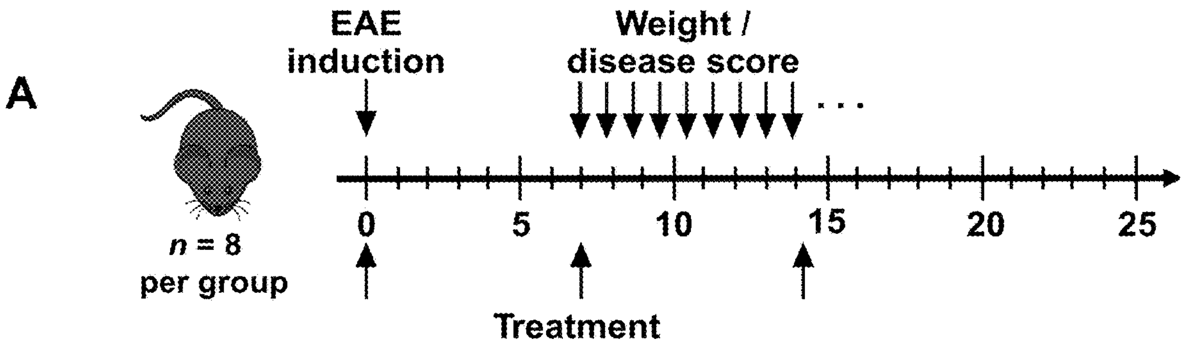
FIG. 4A-4C shows the disability score kinetics for mice with experimental autoimmune encephalomyelitis (EAE) receiving different treatments (Table 4) following EAE disease induction at time 0. The data show that treatments with vaccine compositions comprising peptide antigen conjugates of formula PEG-E1-A-E2-U-H or C-E1-A-E2-U-H reverse disease but that peptide antigen conjugates of formula PEG-E1-A-E2-U-H provided superior efficacy compared with C-E1-A-E2-U-H when administered by the SC route.
Figure 4B:
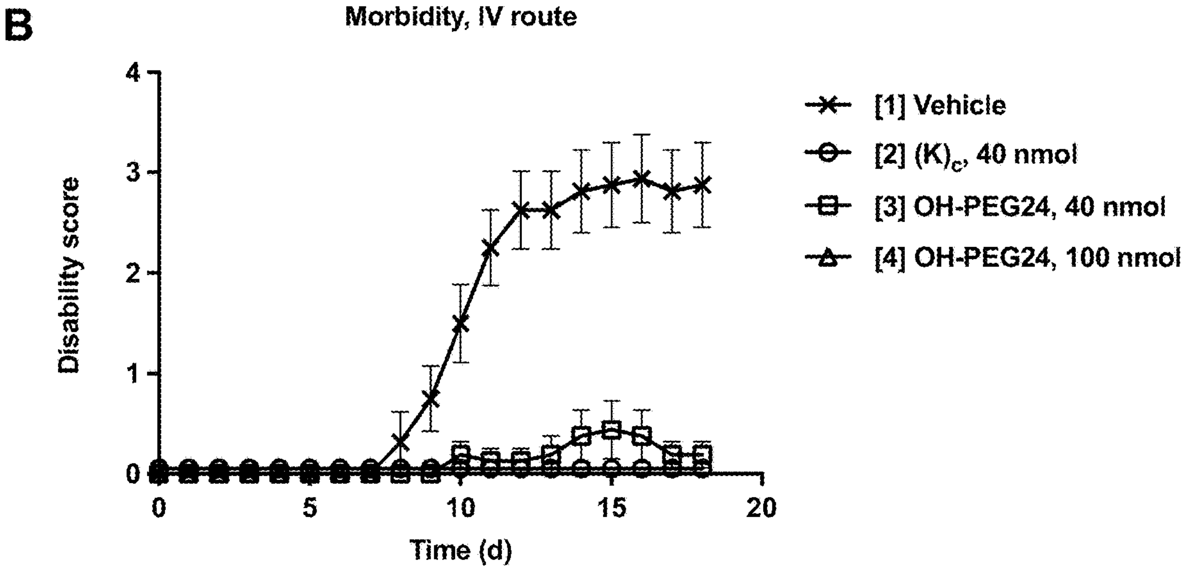
Figure 4C:
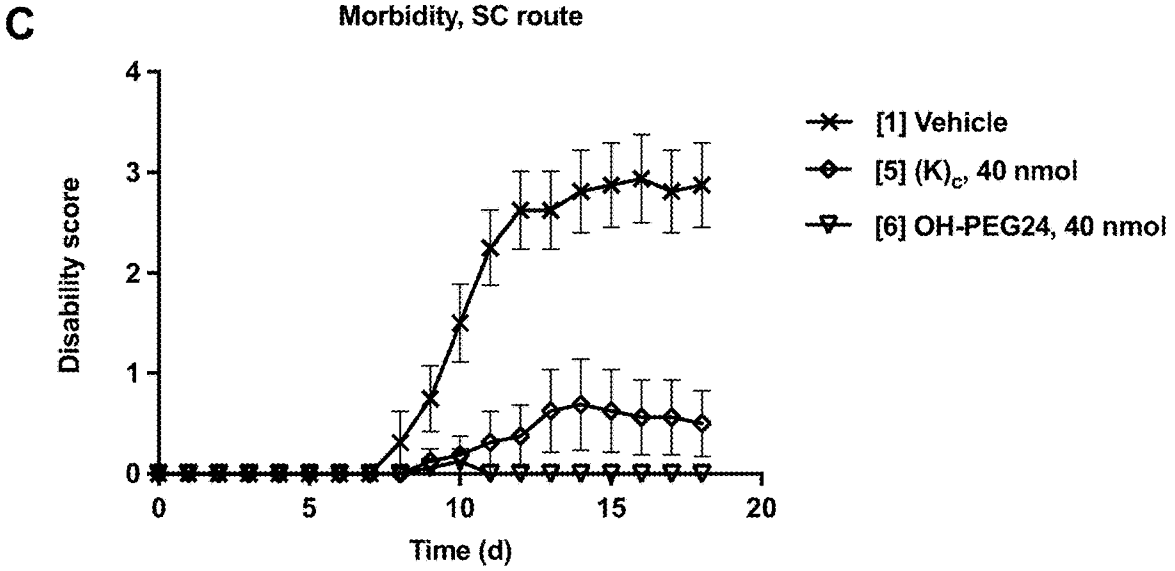

EAE was induced as previously described (Jewell, C M, et al. Cell Reports, 2016). Briefly, a MOG-derived peptide fragment, $MOG_{35-55}$, formulated in complete Freund's adjuvant was administered at two subcutaneous sites at day 0 and then pertussis toxin was administered at day 0 and once at day 1 by the intraperitoneal (IP) route to induce disease. Mice were then treated starting on day 0 with the treatments summarized in Table 4 according to the scheme shown in FIG. 4A. Disability scores were assessed daily according to a scoring rubric from Hooke Laboratories (St. Lawrence, MA).

An unexpected finding was that vaccine compositions comprising the PEGylated peptide antigen conjugates (groups 3, 4 and 6) led to a significant reduction in disease scores of treated animals comparable to that provided by treatments with peptide antigen conjugates comprising the C block. An additional unexpected finding was that the vaccine compositions comprising N-terminal PEGylated peptide antigen conjugates (group 6) provided complete protection when administered by the subcutaneous route, superior to that afforded by dose-matched peptide antigen conjugates of formula C-E1-A-E2-U-H.

To further investigate the mechanism of action accounting for disease reversal by the vaccine compositions comprising peptide antigen conjugates, we assessed functional and phenotypic markers of MOG specific CD4 T cells (FIG. 5) using flow cytometry as previously described in Lynn et al., *Nature Biotechnology*. 2020. Briefly, splenocytes were isolated from mice at day 18 and then resuspended in complete RPMI media (unstimulated) or complete RPMI+$MOG_{35-55}$ peptide antigen (stimulated) and incubated at 37 C for 6 hours. The splenocytes were then stained with CD4 T cell phenotypic and functional markers and assessed by flow cytometry.

Figure 5A:
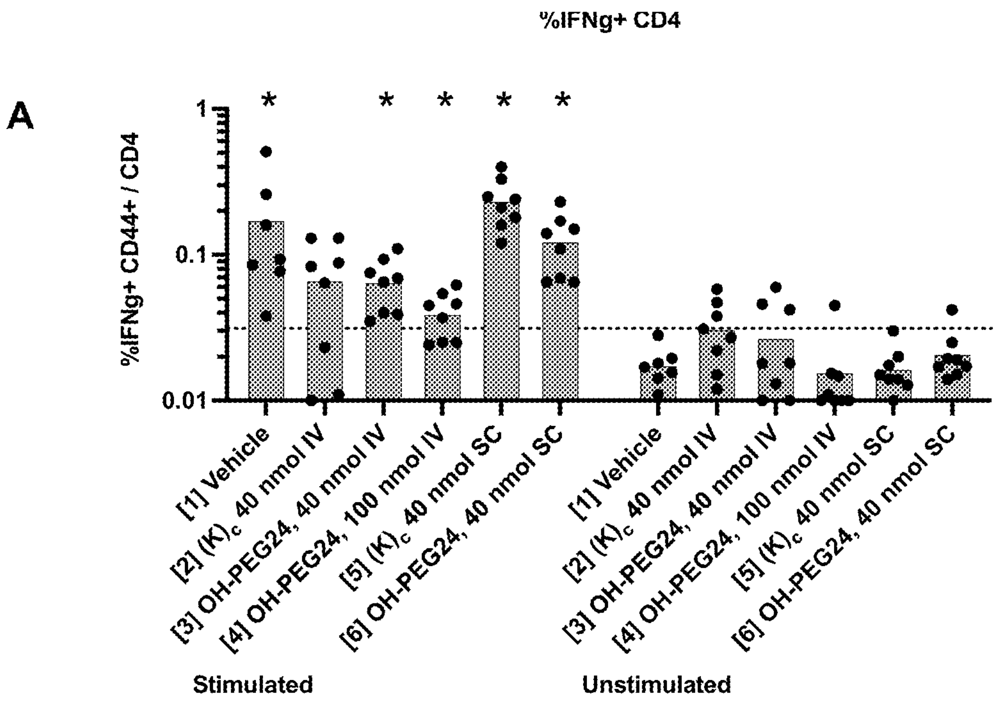
FIG. 5A-5B shows the impact that different treatments (Table 4) have on T cell phenotype of mice with experimental autoimmune encephalomyelitis (EAE). The data show that vaccines comprising peptide antigen conjugates of formula PEG-E1-A-E2-[U]-H and C-E1-A-E2-[U]-H reduced the proportion of CD4 T cells expressing IFN-gamma (Th1 CD4 T cells, FIG. 5A) and IL-17 (Th17 CD4 T cells, FIG. 5B) compared with untreated animals (group 1), but that but that peptide antigen conjugates of formula PEG-E1-A-E2-U-H provide a greater reduction in IFN-gamma producing cells as compared with C-E1-A-E2-U-H. Asterisks (*) indicate $p<0.05$ for student's T-test comparing stimulated and unstimulated samples.
Figure 5B:
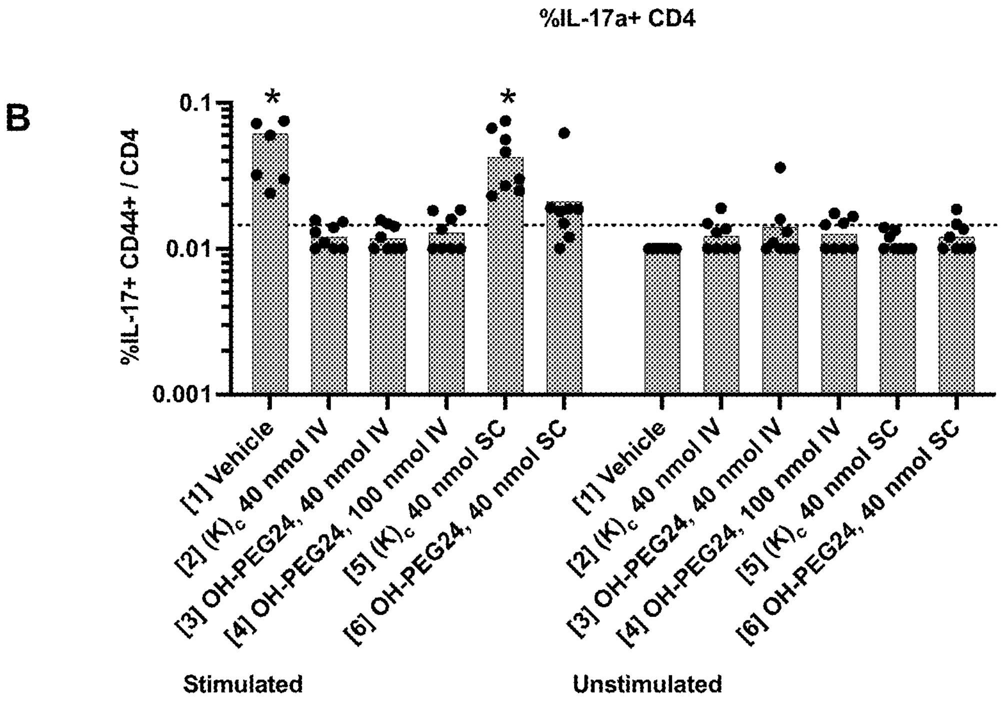

The data in FIG. 5 show that vaccine compositions comprising peptide antigen conjugates (both PEG-E1-A-E2-[U]-H or C-E1-A-E2-[U]-H) reduced the proportion of CD4 T cells expressing IFN-gamma (IFNg) (Th1 CD4 T cells) and IL-17 (Th17 CD4 T cells) compared with untreated animals (group 1).

Importantly, these data show that vaccine compositions comprising peptide antigen conjugates (both PEG-E1-A-E2-[U]-H or C-E1-A-E2-[U]-H) can reverse autoimmunity in a mouse model of EAE through reduction of antigen specific Th1- and Th17-type CD4 T cells. Prior studies have shown that disease reversal in the mouse EAE model is mediated by either or induction of regulatory T cells (Tregs), transdifferentiation of Th1-, Th2- or Th17-type CD4 T cells to Tregs and/or clonal deletion. All these mechanisms require antigen presentation by antigen presenting cells (APCs) within an appropriate context, which in the case of Treg priming or transdifferentiation includes specific cytokines and stimulatory molecules. Given that the mechanism of action for disease reversal in the EAE model requires antigen (i.e., MOG) uptake and presentation by APCs, the data suggest that peptide antigen conjugates of formula PEG-E1-A-E2-U-H are taken up by APCs and the antigen (A) contained therein is processed and presented to CD4 T cells to prime Tregs, transdifferentiate Th1-, Th2- or Th17-type CD4 T cells to Tregs or cause clonal deletion. These data are highly unexpected since prior studies have suggested that PEGylation of the peptide antigen at the solvent exposed position (e.g., the N-terminal position in the case of PEG-E1-A-E2-U-H has been associated with immune system evasion in the art.

TABLE 5

Compositions of tolerance vaccines comprising peptide antigen conjugates with N-terminal PEG or C block, amphiphile of formula S-B-U-H and drug selected from mTOR inhibitors assessed for efficacy in the treatment of EAE.

| Group | Route | PAC formula | PAC Compound # | S-B-U-H | PEG or C block | D |
|---|---|---|---|---|---|---|
| 1 | IM | — | — | — | — | — |
| 2 | IM | PEG-E1-A-E2-U-H | Compound 63 | Compound 13 | OH-PEG24 | Rapamycin |
| 3 | IM | PEG-E1-A-E2-U-H | Compound 63 | Compound 13 | OH-PEG24 | Torin-1 |
| 4 | IM | PEG-E1-A-E2-U-H | Compound 63 | Compound 13 | OH-PEG24 | Torin-2 |
| 5 | IM | C-E1-A-E2-U-H | Compound 96 | — | $(K)_c$ | Torin-1 |
| 6 | IM | C-E1-A-E2-U-H | Compound 96 | — | $(K)_c$ | Torin-2 |
| 7 | IM | PEG-E1-A-E2-U-H | Compound 61 | Compound 13 | OH-PEG24 | Torin-1 |
| 8 | IV | PEG-E1-A-E2-U-H | Compound 63 | Compound 13 | OH-PEG24 | Torin-1 |
| 9 | IV | PEG-E1-A-E2-U-H | Compound 63 | Compound 13 | OH-PEG24 | Torin-2 |

Note:

The peptide antigen conjugate was admixed with amphiphile of formula S-B-U-H, and mTORi at a 1:1:1 ratio of total peptide antigen conjugate to amphiphile in formulation buffer comprising 5% DMSO v/v PBS, pH 7.4. Group 1 contained only 5% DMSO v/v PBS, pH 7.4. PAC = peptide antigen conjugate. All vaccine compositions were prepared as 0.1 mM total peptide antigen conjugate administered by either the IV or IM route in 100 uL formulation buffer providing a total of 10 nmol peptide antigen conjugate per treatment.

Figure 6A:
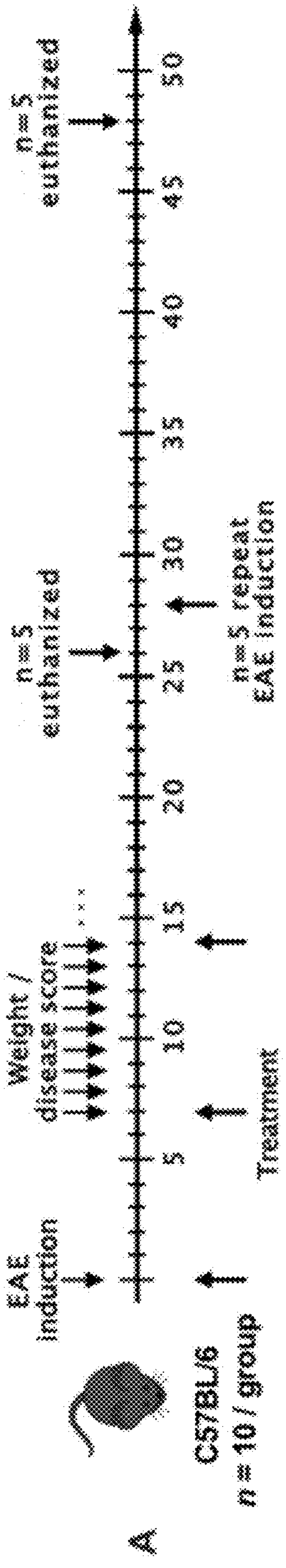
FIG. 6A-6D shows the disability score kinetics for mice with experimental autoimmune encephalomyelitis (EAE) receiving different treatments (Table 5) following EAE disease induction at day 0, and day 28.

We next investigated the interplay of peptide antigen conjugate composition, drug molecule and route on efficacy for treating EAE. EAE was induced as described in the preceding study and animals were randomly assigned to treatment groups (Table 5) and received treatment and sampling according to the scheme in FIG. 6A. At day 26, half the mice (n=5) were randomly euthanized by personnel blinded to the study design and assessed for functional and phenotypic markers of MOG specific Tregs, and the remaining mice (n=5) were re-induced with EAE on day 28 (using the same protocol as previously described) to assess the durability and functional memory of the MOG specific Tregs generated with the treatments.

Figure 6B:
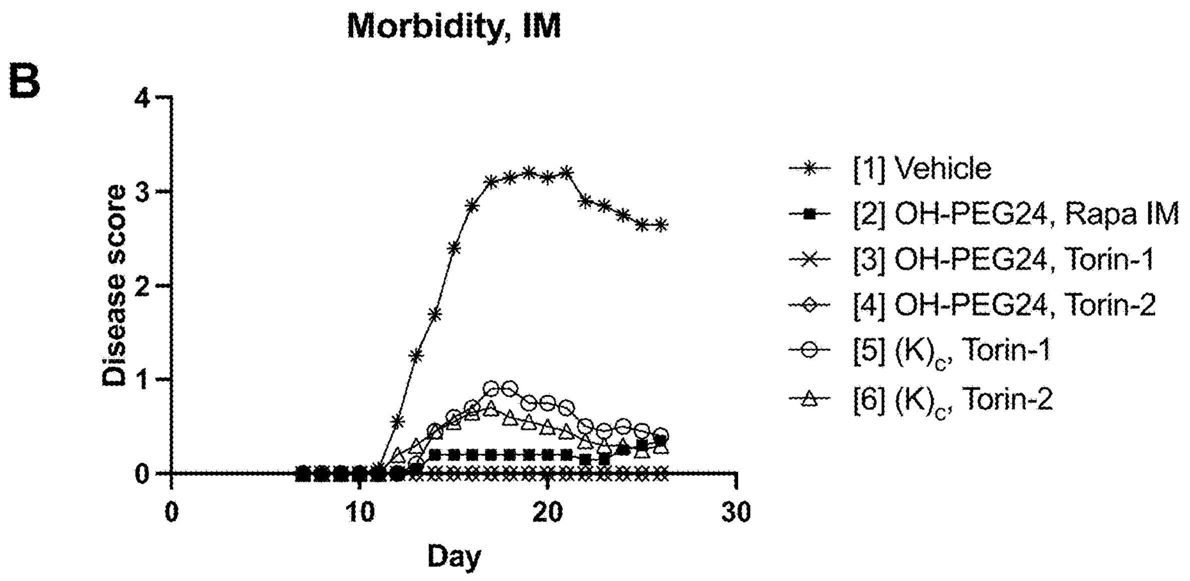
Figure 6C:
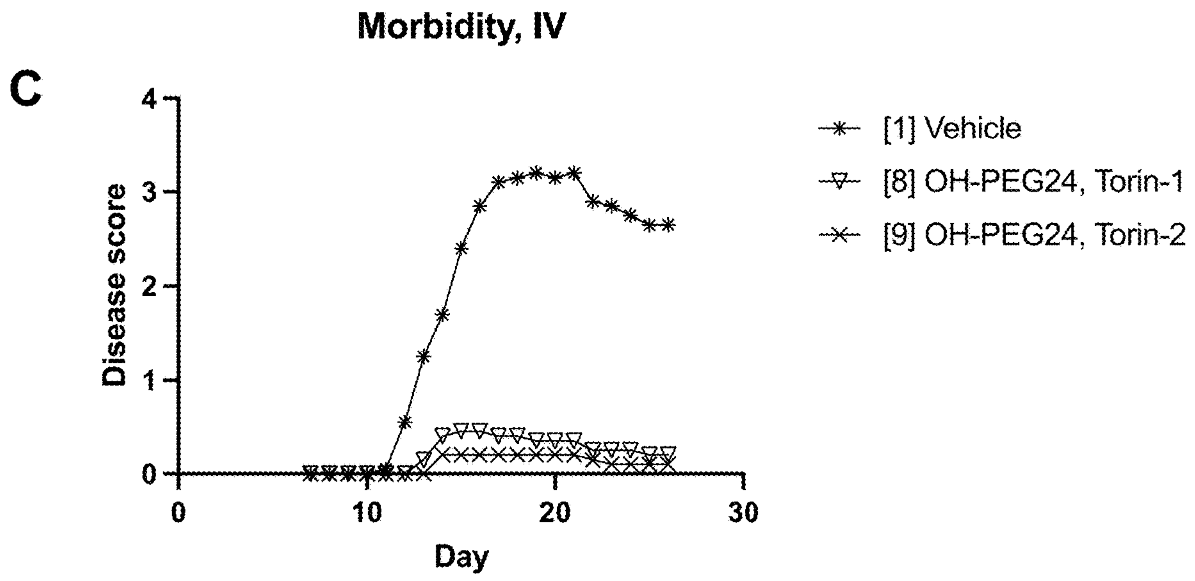
Figure 6D:
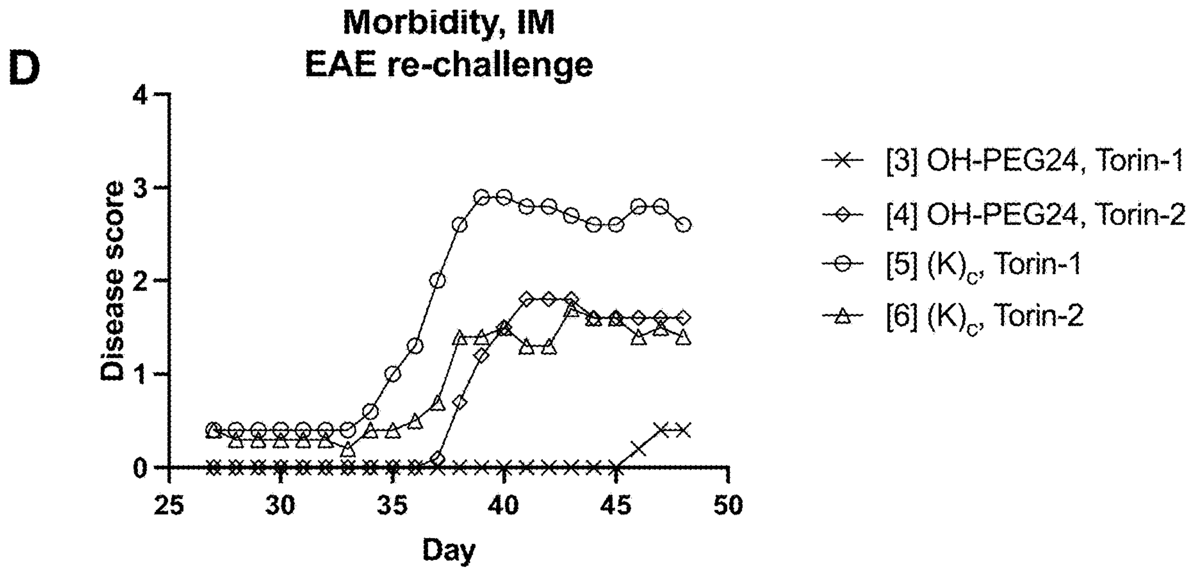

A notable finding was that vaccines comprising a peptide antigen conjugate of formula PEG-E1-A-E2-U-H and a combined mTORC1/2 inhibitor (Torin 1 or Torin 2) were completely protective by the intramuscular route providing improved efficacy after initial EAE induction and rechallenge as compared with vaccine compositions comprising peptide antigen conjugates of formula C-E1-A-E2-U-H and Torin 1 or Torin 2, as well as those comprising PEG-E1-A-E2-U-H and a mTORC1 inhibitor (rapamycin) (FIG. 6B-D), delivered by the same route. Notably, while vaccines comprising a peptide antigen conjugate of formula PEG-E1-A-E2-U-H and either Torin 1 or Torin 2 showed comparable efficacy following initial EAE induction, the composition comprising Torin1 showed improved efficacy following rechallenge (FIG. 6D). Finally, the route of administration was also found to have an impact on efficacy with the IM route leading to improved efficacy as compared with IV administration.

Figure 7A:
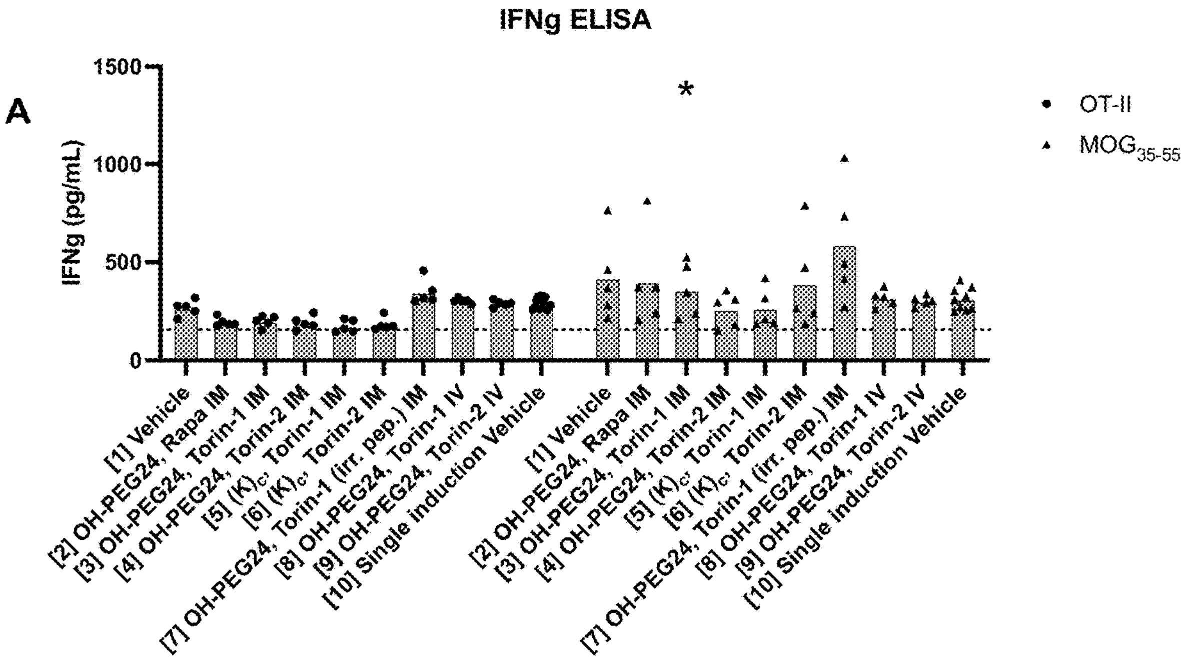
FIG. 7A-7B shows the impact that different treatments (Table 5) have on T cell phenotype of mice with experimental autoimmune encephalomyelitis. The data show that vaccines comprising peptide antigen conjugates of formula PEG-E1-A-E2-[U]-H and C-E1-A-E2-[U]-H reduced the proportion of CD4 T cells expressing IFN-gamma (Th1 CD4 T cells, FIG. 7A) and IL-17 (Th17 CD4 T cells, FIG. 7B) compared with untreated animals (group 1), and that vaccines comprising Torin lead to reduced proportion of CD4 T cells expressing IFN-gamma compared with animals treated with vaccines comprising Rapamycin (Group 7). Asterisks (*) indicate $p<0.05$ for student's T-test comparing stimulated and unstimulated samples.
Figure 7B:
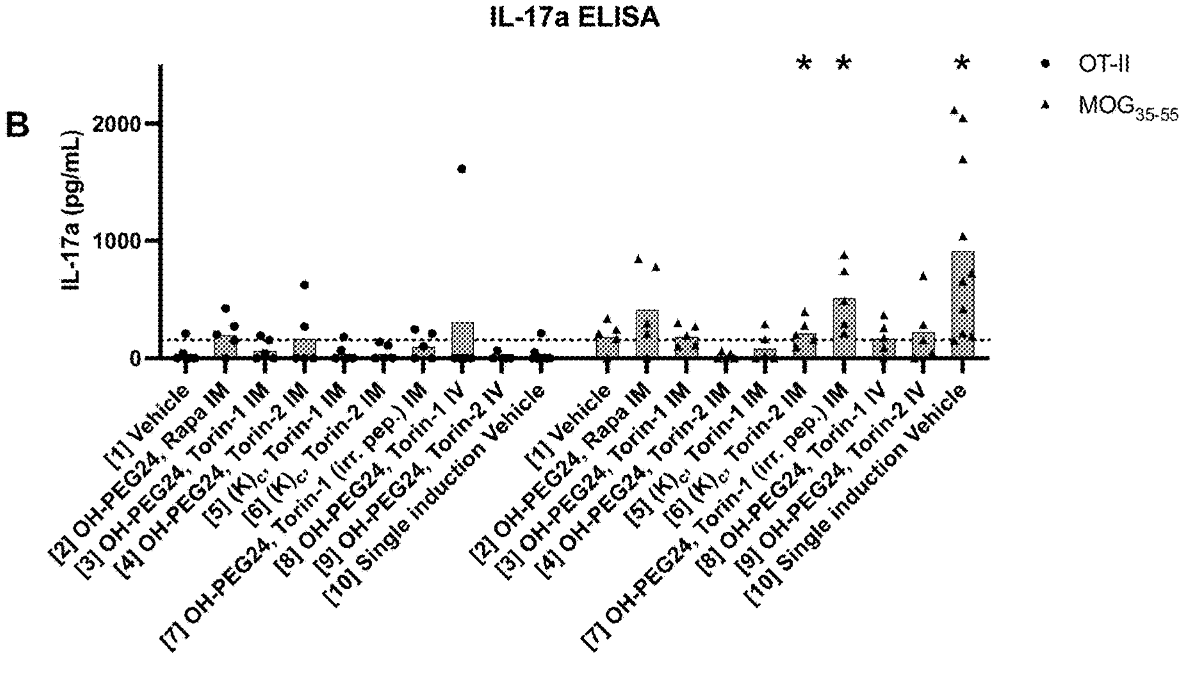

To gain additional mechanistic insight underlying the observed trends, we assessed functional and phenotypic markers on MOG-specific Tregs isolated from splenocytes of treated animals at day 26 after the first EAE induction. Notably, treatments with PEG-E1-A-E2-U-H and a combined mTORC1/2 inhibitor (Torin 1 or Torin 2) led to improved reduction in IFNg and IL-17-producing CD4 T cells as compared with treatments with rapamycin or C-E1-A-E2-U-H (FIG. 7A-B).

These results substantiate the importance of the peptide antigen conjugate and drug molecule composition for inducing tolerance and show that vaccines comprising peptide antigen conjugates with an N-terminal PEG and/or combined mTORC1/2 inhibitors are superior to compositions with charged block and/or mTORC1 inhibitors. Based on these observations, preferred vaccine compositions for inducing tolerance are those comprising peptide antigen conjugates of formula PEG-E1-A-E2-U-H and a combined mTORC1/2 inhibitor, most preferably Torin 1.

An additional notable finding was that IM administration with PEG-E1-A-E2-U-H and a combined mTORC1/2 inhibitor led to superior efficacy as compared with IV administration. Indeed, while IM vaccination is a typical route for vaccination for most licensed vaccines, the IV route has been described as the preferred for tolerance induction owing to APCs and microenvironment specialized for tolerance (Hunter Z, et. al ACS Nano, 2014), and prior publications on tolerance vaccines, including our prior work WO2022/177993, and clinically advanced tolerance vaccines have reported that IV route is the preferred route for tolerance vaccines based on superior tolerance induction. Therefore, the finding that vaccines comprising PEG-E1-A-E2-U-H and a combined mTORC1/2 inhibitor induce comparable efficacy by both IV and IM routes is an unexpected finding.

Example 6: Amphiphile with Linker (U) Comprising a Triazole

The linker U is an optional component of the amphiphiles of formula S-B-H. In some embodiments of amphiphiles of formula S-B-H, the amphiphile comprises a linker U further comprising a triazole formed by the reaction of a DBCO group with an azide.

It was hypothesized that vaccines comprising one or more peptide antigen conjugates of formula PEG-[E1]-A [E2]-[U]-H and/or [E1]-A [E2]-[U]-H and an amphiphile of formula S-B-U-H, wherein U is selected from a triazole would exhibit improved hydrodynamic properties (e.g., narrow size distribution particles) as compared with vaccines comprising an amphiphile without the linker U.

To assess the impact of the linker U on hydrodynamic properties, representative vaccines comprising a peptide antigen conjugate (Compound 97), the mTORi (Torin-1) and either an amphiphile of formula S-B-H (Compound 27) or S-B-U-H were (Compound 26) were admixed at a 1:1:1 ratio of peptide antigen conjugate to mTORi to amphiphile in DMSO, which was then diluted 1 to 10 with PBS buffer at pH 7.4 to yield a vaccine comprising 1 mM peptide antigen conjugate, 1 mM Torin-1 and 1 mM amphiphile in 10% DMSO (v/v) in PBS. The resulting vaccine compositions were then assessed for physical appearance (Table 6).

TABLE 6

Impact of amphiphile linker U on solution properties

| Group # | PAC of formula PEG-E1-A-E2-U-H | Amphiphile formula, Compound # | Solution properties |
|---|---|---|---|
| 1 | Compound 97 | S-B-H, Compound 27 | Gel |
| 2 | Compound 97 | S-B-U-H, Compound 26 | Liquid |

PAC = peptide antigen conjugate.
Solution properties were assessed by visual inspection.

Notably, whereas the vaccine comprising the amphiphile without the linker U formed a hydrogel not suitable for injection, the vaccine comprising the amphiphile with the linker U comprising a triazole formed a liquid suitable for injection (Table 6). A non-limiting explanation is that the triazole linker stabilizes the nanoparticles formed by the peptide antigen conjugates, amphiphile and mTOR inhibitor (Torin-1) through, e.g., pi-stacking.

Example 7: Vaccine Comprising Peptide Antigen Conjugates and Amphiphile Having a Propensity to Undergo Non-Covalent Cross-Linking and Hydrogel Formation Certain compositions of vaccines comprising peptide antigen conjugate(s) and amphiphile exhibited a propensity to undergo cross-linking that resulted in formation of hydrogel. For example, a vaccine comprising 4 unique peptide antigen conjugates, the mTORi Torin-1 and of formula S-B-U-H were (Compound 26) were admixed at a 1:1:1 ratio of peptide antigen conjugate to mTORi to amphiphile in DMSO, which was then diluted 1 to 10 with PBS buffer at pH 7.4 to yield a vaccine comprising 1 mM total peptide antigen conjugate, 1 mM Torin-1 and 1 mM amphiphile in 10% DMSO (v/v) in PBS (Table 7). The vaccine was stored at room temperature for 24 hours and then assessed for physical appearance, turbidity, and capacity to undergo sterile filtration through a 0.2 μm filter. The data showed that the vaccine was viscous, had increased turbidity and that >90% of material was lost post filtration as indicated by HPLC AUC (Table 7).

TABLE 7

Vaccine comprising peptide antigen conjugates and amphiphile having a propensity to undergo non-covalent cross-linking and hydrogel formation.

| PAC of formula PEG-E1-A-E2-U-H | Amphiphile of formula S-B-U-H | Solution properties | Turbidity | AUC pre filtration | AUC post filtration |
|---|---|---|---|---|---|
| Compound 64<br>Compound 61<br>Compound 59<br>Compound 62 | Compound 26 | Slightly viscous | 0.063 | 30409 | 843 |

PAC = peptide antigen conjugate.
Solution properties were assessed by visual inspection.
Turbidity is OD at 490 nm as determined by spectrophotometry.
AUC = area under the curve as assessed by HPLC at 220 nm.

We hypothesized that reducing solution temperature and/or peptide antigen conjugate concentration may be suitable means for preventing physical cross-linking and propensity to form hydrogels.

To evaluate the impact that concentration and temperature have on vaccine solution properties, peptide antigen conjugates (Compounds 59, 61, and 64) were admixed with amphiphile of formula S-B-U-H (Compound 26) and Torin-1 at the molar ratio specified in Table 8 and then diluted 1 to 10 with PBS buffer at pH 7.4 to yield a vaccine comprising 1 mM total peptide antigen conjugate, 1 mM Torin-1 and 1 mM amphiphile in 10% DMSO (v/v) in PBS.

TABLE 8

Representative vaccine compositions for assessing concentration and temperature.

| Group # | Total PAC concentration (mM) | PAC:SBH:mTORi molar ratio | Storage temp. (Celsius) |
|---|---|---|---|
| 1 | 0.2 | 1:1:1 | 23° |
| 2 | 0.5 | 1:1:1 | 23° |
| 3 | 0.75 | 1:1:1 | 23° |
| 4 | 1 | 1:1:1 | 23° |
| 5 | 1 | 1:2:1 | 23° |
| 6 | 1 | 1:4:1 | 23° |
| 7 | 0.75 | 1:1:1 | 4° |
| 8 | 1 | 1:1:1 | 4° |

The representative vaccines (Table 8) were stored at room temperature (~23° C.) or 4° C. for 24 hours and then filtered using a 0.2 μm spin column (UFC30LG25, Millipore Sigma).

Figure 8A:
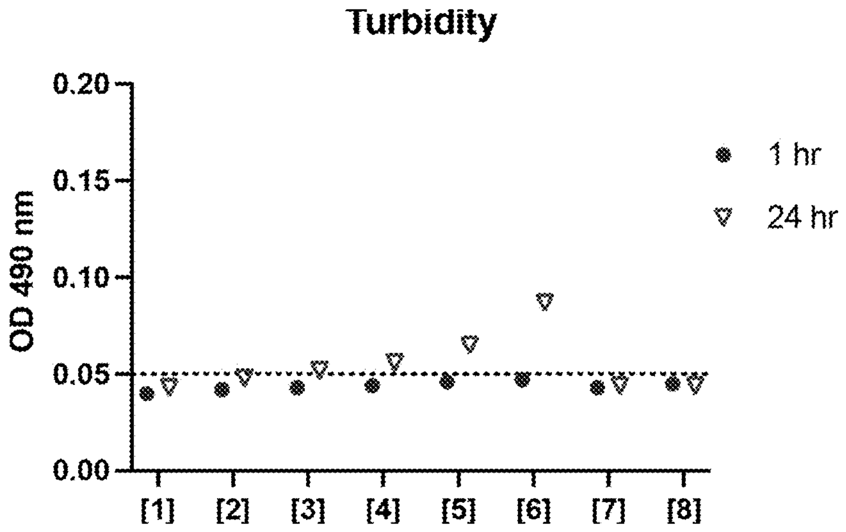
FIG. 8A-B shows turbidity at 1 hour (hr) and 24 hours (hr) for representative vaccines (Table 8) with varying storage temperature and concentration of peptide antigen conjugate.
Figure 8B:
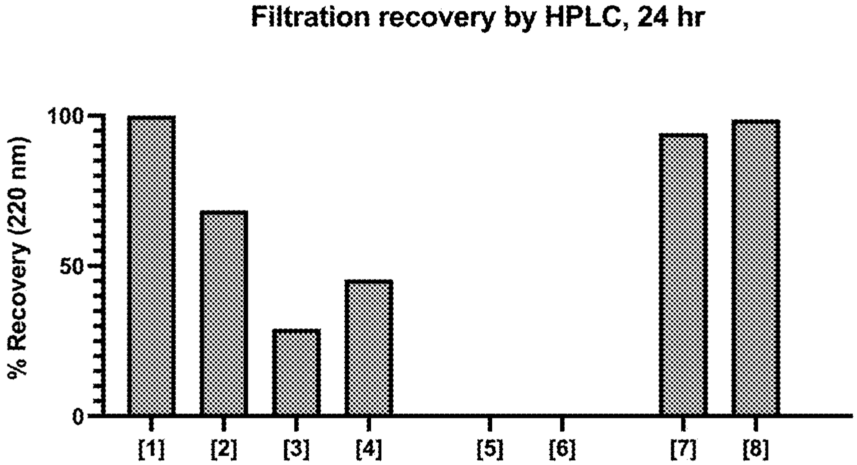

Key findings were that there was a direct correlation with increasing temperature and peptide antigen conjugate concentration and increased propensity for physical, non-covalent cross-linking/hydrogel formation to occur. Accordingly, whereas the vaccine compositions at 0.2 mM or 0.5 mM were relatively stable at 23° C., those at concentrations higher than 0.5 mM were not stable for 24 hours and exhibited extensive cross-linking as indicated by high turbidity and low filtration recovery (FIG. 8A-B). However, the concentration dependent effects could be mitigated by reducing storage temperature as vaccine compositions with up to 1 mM peptide antigen conjugate concentration did not exhibit cross-linking when stored at 4° C. for 24 hours.

These data show that physical cross-linking and propensity to form hydrogels for vaccines comprising peptide antigen conjugates can be mitigated by reducing concentration to at or below 1 mM of peptide antigen conjugate and/or storing at temperatures less than room temperature, e.g., 4° C.

Example 8: Impact of Amphiphile, Surfactant and Formulation Process on Hydrodynamic Behavior The earlier data showed that certain compositions of vaccines comprising peptide antigen conjugates of formula PEG-[E1]-A-[E2]-[U]-H and an amphiphile of formula S-B-[U]-H can undergo physical cross-linking leading to hydrogel formation. We hypothesized that this may be mitigated by (i) addition of a non-ionic or ionic surfactant; (ii) exclusion of the amphiphile or altering the amphiphile composition; and/or (iii) modifying the formulation procedure.

Compounds 66 and 121 were used as representative peptide antigen conjugates. Of note: these peptide conjugates comprise the same peptide antigen (A) that is hydrophilic and water soluble to at least 1 mg/mL. Given that the peptide antigens alone are water soluble, we also assessed an alternative vaccine composition that comprises peptide antigen conjugate but does not include an amphiphile as the peptide antigen conjugate alone may be sufficiently soluble and not require an amphiphile.

The representative vaccines were made using peptide antigen conjugates (Compounds 66 and 121) admixed with or without amphiphile of formula S-B-U-H (Compound 26), mTOR inhibitor (mTORi) Torin-1 at a 1:1:1 molar ratio of total peptide antigen conjugate to amphiphile to Torin-1 in DMSO at 10 mM total peptide antigen conjugate concentration. The formulations in aqueous buffer were then made according to either "Formulation method":

Version 1 (V1) consisting of diluting the DMSO solution 1 in 10 in PBS, pH 7.4 to yield 10% DMSO PBS solution with 1 mM total peptide antigen conjugate.

Version 2 (V2): consisting of diluting the DMSO solution 1 in 5 in PBS and then diluting 1 in 2 with PBS comprising a surfactant to yield 10% DMSO PBS solution with 1 mM total peptide antigen conjugate and surfactant at the specified weight/volume percent.

Version 3 (V3): consisting of diluting the DMSO solution 1 in 10 in PBS comprising an surfactant to yield 10% DMSO PBS solution with 1 mM peptide antigen conjugate and surfactant at the specified weight/volume percent.

Version 4 (V4): consisting of adding the surfactant to the DMSO solution and then diluting 1 in 10 in PBS to yield 10% DMSO PBS solution with 1 mM peptide antigen conjugate and surfactant at the specified weight/volume percent.

Version 5 (V5): consisting of lyophilizing the DMSO solution and then suspending in PBS comprising a surfactant to yield PBS solution (without DMSO) with 1 mM peptide antigen conjugate and surfactant at the specified weight/volume percent.

The resulting representative vaccines were then stored at room temperature for 24 hours and then assessed by turbidity and filtration recovery as previously described.

TABLE 10

Representative vaccines comprising peptide antigen conjugates, mTOR inhibitor (mTORi) Torin-1, with or without amphiphile of formula S-B-U-H and with or without surfactant.

| Group # | PAC formula | PAC compound # | Amphiphile | Surfactant | Formulation method |
|---|---|---|---|---|---|
| 1 | PEG-E1-A-E2-U-H | Compound 66 | Compound 26 | None | V1 |
| 2 | PEG-E1-A-E2-U-H | Compound 66 | Compound 13 | None | V1 |
| 3 | PEG-E1-A-E2-U-H | Compound 66 | | None | V1 |
| 4 | PEG-E1-A-E2-U-H | Compound 66 | Compound 26 | 5% Polysorbate-20 | V2 |
| 5 | PEG-E1-A-E2-U-H | Compound 66 | Compound 26 | 5% Polysorbate-20 | V3 |
| 6 | PEG-E1-A-E2-U-H | Compound 66 | Compound 26 | 5% Polysorbate-20 | V4 |
| 7 | PEG-E1-A-E2-U-H | Compound 66 | Compound 26 | 5% Polysorbate-20 | V5 |
| 8 | PEG-E1-A-E2-U-H | Compound 66 | | 5% Polysorbate-20 | V2 |
| 9 | PEG-E1-A-E2-U-H | Compound 66 | | 5% Polysorbate-20 | V3 |
| 10 | PEG-E1-A-E2-U-H | Compound 66 | | 5% Polysorbate-20 | V4 |
| 11 | PEG-E1-A-E2-U-H | Compound 66 | | 5% Polysorbate-20 | V5 |
| 12 | PEG-E1-A-E2-U-H | Compound 66 | Compound 26 | 0.5% Polysorbate-20 | V3 |
| 13 | PEG-E1-A-E2-U-H | Compound 66 | | 0.5% Polysorbate-20 | V3 |
| 14 | PEG-E1-A-E2-U-H | Compound 66 | Compound 26 | 5% Sodium dodecyl sulfate | V3 |
| 15 | PEG-E1-A-E2-U-H | Compound 66 | | 5% Sodium dodecyl sulfate | V3 |
| 16 | E1-A-E2-U-H | Compound 121 | Compound 26 | 0.5% Polysorbate-20 | V3 |
| 17 | E1-A-E2-U-H | Compound 121 | Compound 26 | 5% Polysorbate-20 | V3 |
| 18 | E1-A-E2-U-H | Compound 121 | | 0.5% Polysorbate-20 | V3 |
| 19 | E1-A-E2-U-H | Compound 121 | | 5% Polysorbate-20 | V3 |
| 20 | E1-A-E2-U-H | Compound 121 | Compound 26 | None | V3 |
| 21 | E1-A-E2-U-H | Compound 121 | | None | V3 |

Key findings were that the either (a) removing the amphiphile, (b) removing the PEG group of the peptide antigen conjugate (i.e., using peptide antigen conjugates of formula [E1]-A-[E2]-[U]-H instead of PEG-[E1]-A-[E2]-[U]-H) but keeping the amphiphile in the formulation, (c) and/or adding a surfactant generally led to decreased propensity of the vaccine compositions to undergo physical cross-linking and improved filtration recovery.

It was notable that the amphiphile or PEG group could be removed and suggests that vaccines comprising peptide antigen conjugates that comprise peptide antigens (A) that are water soluble may not require the amphiphile to achieve sufficient hydrodynamic stability of the nanoparticles formed by the peptide antigen conjugates in the formulation buffer (or aqueous solutions more generally). Based on these observations, preferred formulation of vaccines comprising peptide antigen conjugates of formula PEG-[E1]-A-[E2]-[U]-H that further comprise peptide antigens (A) that are water soluble up to at least 1 mg/mL do not include an amphiphile.

Example 9: Peptide Antigen Conjugates Comprising Gluten-Derived (GLU) Peptide Antigens Peptide antigen conjugates may be synthesized entirely on-resin by solid-phase peptide synthesis (SPPS), or by both solution phase and solid phase peptide synthesis. In a non-limiting example, 14 peptide antigen conjugates of formula PEG-E1-A-E2-U-H comprising GLU peptide antigens (Table 11), referred to as GLU peptide antigen conjugate Set 1, were synthesized in three distinct synthetic steps. The peptide antigen fragment of formula E1-A-E2-U1 was manufactured on resin, followed by addition of OH-PEG24 (PEG7240, Iris Biotech Gmbh, Germany) sometimes abbreviated "PEG," in solution to yield peptide antigen fragments of formula PEG-E1-A-E2-U. Finally, the H block was added as previously described for Compound 59 to generate PEG-E1-A-E2-U-H.

TABLE 11

GLU peptide antigen conjugate set 1.

| Compound # | Sequence |
|---|---|
| 66 | OH-PEG24-VZQLQPFPQPELPYPQPQLPYPQPQPFRSPVZ(X-DBCO)-Ahx-W5 |
| 67 | OH-PEG24-VZPQLPYPQPELPYPQPQPFRPEQPYPQPQPSPVZ(X-DBCO)-Ahx-W5 |
| 68 | OH-PEG24-VZQGIIQPEQPAQLEVISPVZ(X-DBCO)-Ahx-W5 |
| 69 | OH-PEG24-VZPQPQQPEQPFPQPEQEFPQPQQPQQSFPEQQPPLSPVZ(X-DBCO)-Ahx-W5 |
| 70 | OH-PEG24-VZQQQPFPQPEQPFBQQPQSPVZ(X-DBCO)-Ahx-W5 |
| 71 | OH-PEG24-VZQQFLQPEQPFPQQPEQPYPQQPEQPFPQPQQSPVZ(X-DBCO)-Ahx-W5 |
| 72 | OH-PEG24-VZQQFSQPEQEFPQPQQPQQSFPEQQPPFSPVZ(X-DBCO)-Ahx-W5 |
| 73 | OH-PEG24-VZPTPLQPEQPFPQQPQQPQQPFPQPEQPFPWQPQSPVZ(X-DBCO)-Ahx-W5 |
| 74 | OH-PEG24-VZSSPLQPEQPFPQQPQQPFPEQPQQPQSPVZ(X-DBCO)-Ahx-W5 |
| 75 | OH-PEG24-VZQSIPQPEQPFPQPEQPFPQSQESPVZ(X-DBCO)-Ahx-W5 |
| 76 | OH-PEG24-VZPQQPFPQQPQQIIPQSPVZ(X-DBCO)-Ahx-W5 |
| 77 | OH-PEG24-VZPQQPIPEQPQPYPEQPQPYPQQSPVZ(X-DBCO)-Ahx-W5 |
| 78 | OH-PEG24-VZQQPPFSEQEQPVLPQSPVZ(X-DBCO)-Ahx-W5 |

TABLE 11-continued

GLU peptide antigen conjugate set 1.

| Compound # | Sequence |
|---|---|
| 79 | OH-PEG24-VZQPPFSQQQESPFSQQSPVZ(X-DBCO)-Ahx-W5 |

Note:
OH-PEG24 is OH-(CH$_2$—CH$_2$—O)$_{24}$-CH$_2$—CH$_2$—C(O)—.

In a non-limiting example, 12 peptide antigen conjugates of formula PEG-E1-A-E2-U-H comprising GLU peptide antigens (Table 12), referred to as GLU peptide antigen conjugate Set 2, were synthesized in two distinct synthetic steps. The peptide antigen fragment PEG-E1-A-E2-U1 was synthesized on resin and the H block was added in solution to generate PEG-E1-A-E2-U-H.

TABLE 12

GLU peptide antigen conjugate set 2.

| Compound # | Sequence |
|---|---|
| 66 | OH-PEG24-VZQLQPFPQPELPYPQPQLPYPQPQPFRSPVZ(X-DBCO)-Ahx-W5 |
| 67 | OH-PEG24-VZPQLPYPQPELPYPQPQPFRPEQPYPQPQPSPVZ(X-DBCO)-Ahx-W5 |
| 69 | OH-PEG24-VZPQPQQPEQPFPQPEQEFPQPQQPQQSFPEQQPPLSPVZ(X-DBCO)-Ahx-W5 |
| 70 | OH-PEG24-VZQQQPFPQPEQPFBQQPQSPVZ(X-DBCO)-Ahx-W5 |
| 71 | OH-PEG24-VZQQFLQPEQPFPQQPEQPYPQQPEQPFPQPQQSPVZ(X-DBCO)-Ahx-W5 |
| 72 | OH-PEG24-VZQQFSQPEQEFPQPQQPQQSFPEQQPPFSPVZ(X-DBCO)-Ahx-W5 |
| 73 | OH-PEG24-VZPTPLQPEQPFPQQPQQPQQPFPQPEQPFPWQPQSPVZ(X-DBCO)-Ahx-W5 |
| 74 | OH-PEG24-VZSSPLQPEQPFPQQPQQPFPEQPQQPQSPVZ(X-DBCO)-Ahx-W5 |
| 75 | OH-PEG24-VZQSIPQPEQPFPQPEQPFPQSQESPVZ(X-DBCO)-Ahx-W5 |
| 76 | OH-PEG24-VZPQQPFPQQPQQIIPQSPVZ(X-DBCO)-Ahx-W5 |
| 77 | OH-PEG24-VZPQQPIPEQPQPYPEQPQPYPQQSPVZ(X-DBCO)-Ahx-W5 |
| 78 | OH-PEG24-VZQQPPFSEQEQPVLPQSPVZ(X-DBCO)-Ahx-W5 |

Figure 9A:
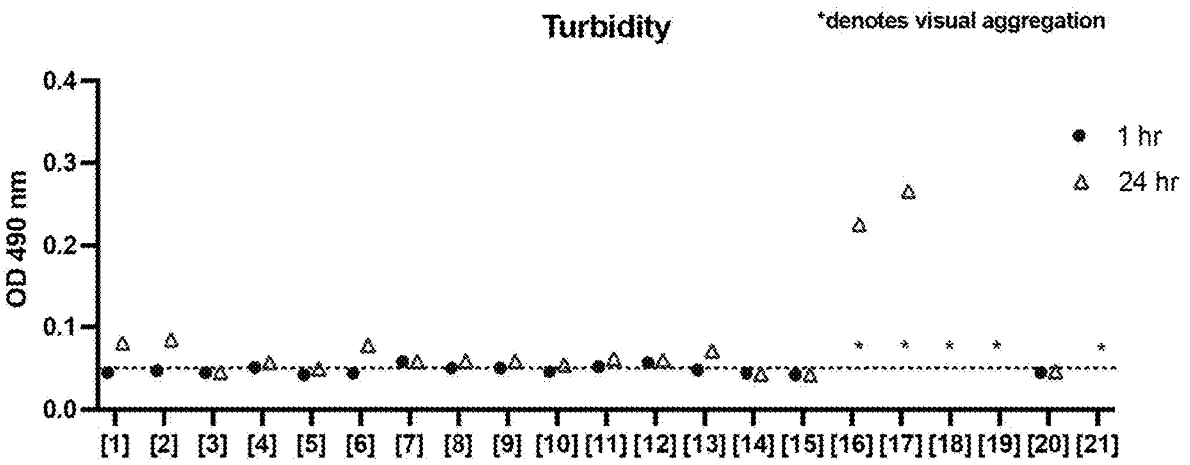
FIG. 9A shows turbidity at 1 hour (hr) and 24 hours (hr) for representative vaccines (Table 10) with varying peptide antigen conjugate (PAC) formula, surfactant identity and concentration, presence of amphiphile, and formulation method.
Figure 9B:
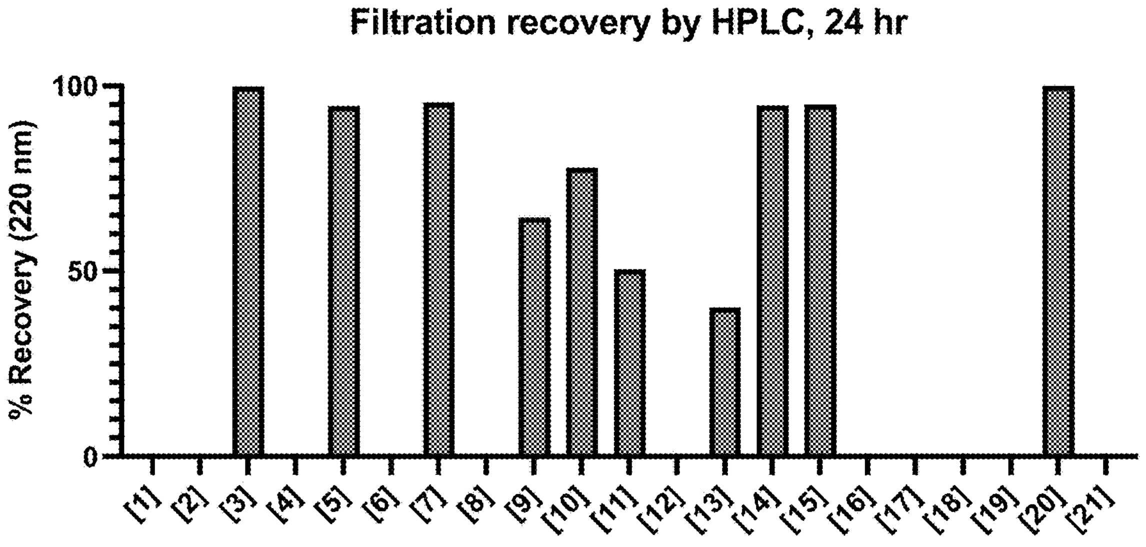
FIG. 9B shows filtration recovery at 24 hours (hr) for representative vaccines (Table 10) with varying PAC formula, surfactant identity and concentration, presence of amphiphile, and formulation method.

Example 10: Impact of Surfactant, Peptide Antigen Conjugate Formula, Amphiphile and Formulation Method on Vaccines Comprising Gluten-Derived Peptide Antigen Conjugates As an extension of the data shown in FIG. 9A-B we next assessed how (i) addition of a non-ionic surfactant; (ii) exclusion of the amphiphile; and/or (iii) formulation procedure impact properties of a vaccine comprising GLU peptide antigen conjugate Set 1.

GLU peptide antigen conjugate Set 1 (Compounds 66-79) were used as representative peptide antigen conjugates for a vaccine (sometimes referred to as immunotherapy) for treating celiac disease. Of note, these peptide conjugates (Compounds 66-79) comprise peptide antigens (A) that are hydrophilic and water soluble up to at least 1 mg/mL. Given that the peptide antigens alone are water soluble, we also assessed an alternative vaccine composition that comprises peptide antigen conjugates but does not include an amphiphile as the peptide antigen conjugate alone may be sufficiently soluble and not require an amphiphile.

The representative vaccines were made using the GLU peptide antigen conjugate Set 1 (as an equimolar mixture) admixed with or without amphiphile of formula S-B-U-H (Compound 26) and the mTORi Torin-1 at a 1:1:1 molar ratio at 10 mM total peptide antigen conjugate concentration. For clarity, the molar ratio 1:1:1 refers to the total peptide antigen conjugate to amphiphile (when present) to Torin-1. The formulations were then made according to the Formulation method V1, V3 or V5 to yield a final peptide antigen conjugate concentration of 1 mM in 10% DMSO v/v PBS, pH 7.4. The resulting vaccine compositions were stored at room temperature and then assessed for turbidity and filtration recovery after 24 and 48 hours.

TABLE 13

Representative vaccines comprising GLU peptide antigen conjugate Set 1.

| Group # | PAC formula | PAC composition | S-B-U-H | % w/v; Surfactant | Formulation method |
|---|---|---|---|---|---|
| 1 | PEG-E1-A-E2-U-H | GLU peptide antigen conjugate Set 1 | Compound 26 | | V1 |
| 2 | PEG-E1-A-E2-U-H | | Compound 26 | 5%; Polysorbate-20 | V3 |
| 3 | PEG-E1-A-E2-U-H | | | | V1 |
| 4 | E1-A-E2-U-H | GLU peptide antigen conjugate Set 1, except PEG is absent | Compound 26 | | V1 |
| 5 | PEG-E1-A-E2-U-H | GLU peptide antigen conjugate Set 1 | Compound 26 | | V5 |

% w/v = the percent weight per volume.

Figure 10A:
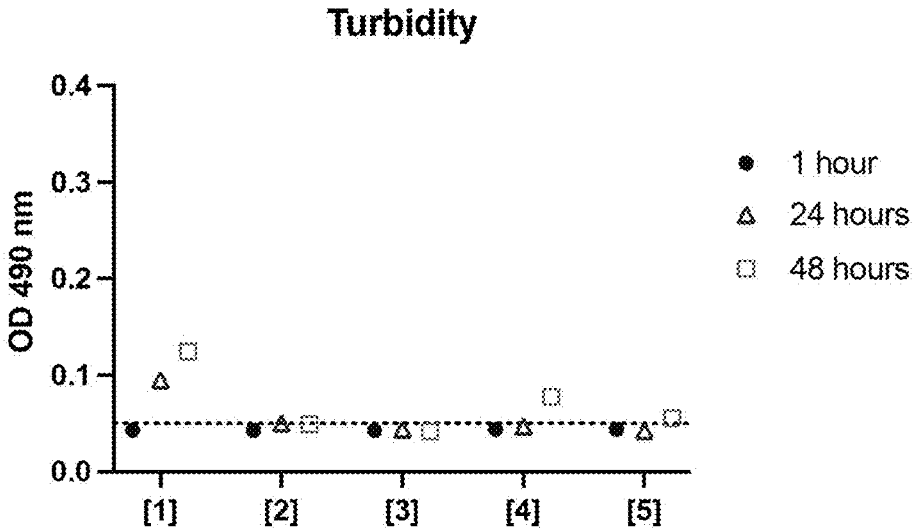
FIG. 10A shows turbidity at 1 hour, 24 hours, and 48 hours at room temperature (~23° C.) for representative vaccines (Table 13) with varying PAC formula, surfactant identity, presence of amphiphile, and formulation method.
Figure 10B:
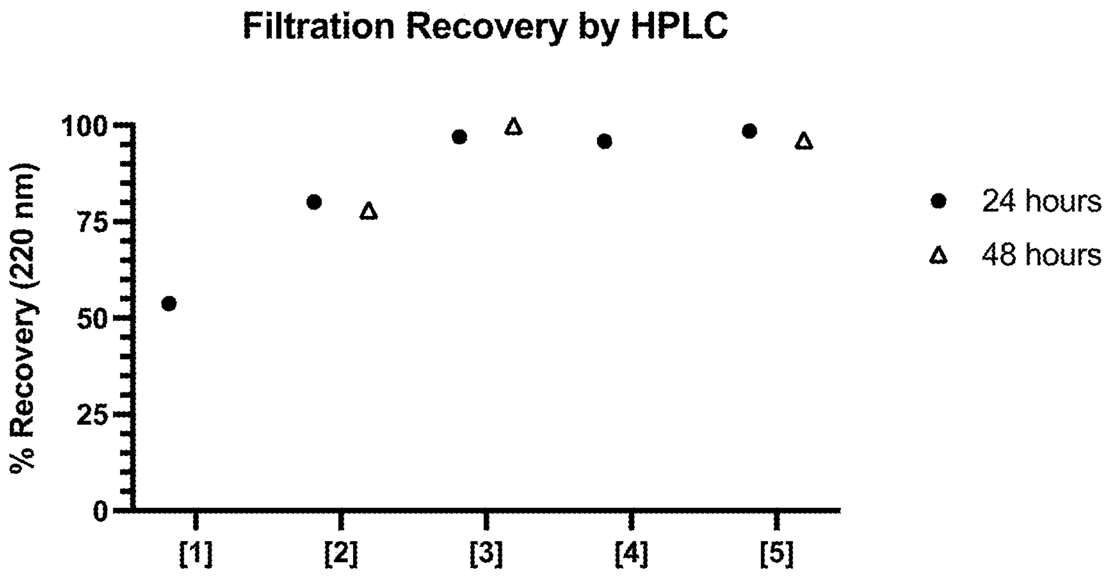
FIG. 10B shows filtration recovery at 24 hours and 48 hours at room temperature (~23° C.) for representative vaccines (Table 13) with varying PAC formula, emulsifier identity, presence of amphiphile, and formulation method.

Key findings were that the vaccine compositions based on both group 2 (comprising peptide antigen conjugate, amphiphile and surfactant) and group 3 (comprising peptide antigen conjugate only, Table 13) had low turbidity at all timepoints, but only group 3 had greater than 95% filtration recovery at all timepoints. These data confirm earlier findings that vaccines comprising peptide antigen conjugates of formula PEG-[E1]-A-[E2]-[U]-H further comprising peptide antigens (A) that are water soluble up to at least 1 mg/mL exhibit improved stability when the amphiphile is absent, and that excluding the amphiphile can prevent non-covalent cross-linking and/or particle aggregation that led to decreased filtration recovery for group 1 versus group 3 (FIG. 10A-B).

Example 11: Impact of mTORi, Tris, pH and Total Peptide Antigen Conjugate Concentration on Hydrodynamic Behavior of a Vaccine Comprising Gluten Derived Peptide Antigen Conjugates We next assessed how the mTORi composition and ratio of total peptide antigen conjugate to mTORi affects hydrodynamic behavior when formulated at different pH in normal saline buffered with Tris.

Representative vaccines were made using the GLU peptide antigen conjugate Set 1 (as an equimolar mixture, i.e., each conjugate was at the same concentration) and either the mTORi (Torin-1) or rapamycin at either a 1:1 or 4:1 molar ratio of total peptide antigen conjugate to mTORi ratio in DMSO at 10 mM and 20 mM total peptide antigen conjugate concentration. The formulation buffer specified in Table 14 was then added to the DMSO solution at a 10:1 volume to volume ratio of formulation buffer to DMSO solution. The resulting vaccine compositions were stored at room temperature and then assessed for turbidity after 24 and 48 hours.

TABLE 14

Vaccines comprising GLU peptide antigen conjugates of formula PEG-[E1]-A-[E2]-[U]-H with varying mTORi, total PAC concentration and pH.

| Group # | mTORi | PAC to mTORi molar ratio | Total PAC concentration | Formulation buffer | pH |
|---|---|---|---|---|---|
| 1 | Torin-1 | 4 | 1 mM | 0.9% saline, | 6.928 |
| 2 | | 1 | | 3 mM Tris | 6.941 |
| 3 | | 4 | 2 mM | 0.9% saline, | 6.931 |
| 4 | | 1 | | 6 mM Tris | 6.852 |
| 5 | | 4 | | 0.9% saline, | 8.484 |
| 6 | | 1 | | 16 mM Tris | 8.546 |
| 7 | Rapamycin | 4 | 1 mM | 0.9% saline, | 6.889 |
| 8 | | 1 | | 3 mM Tris | 6.817 |
| 9 | | 4 | 2 mM | 0.9% saline, | 6.771 |
| 10 | | 1 | | 6 mM Tris | 6.891 |
| 11 | | 4 | | 0.9% saline, | 8.465 |
| 12 | | 1 | | 16 mM Tris | 8.489 |

Figure 11A:
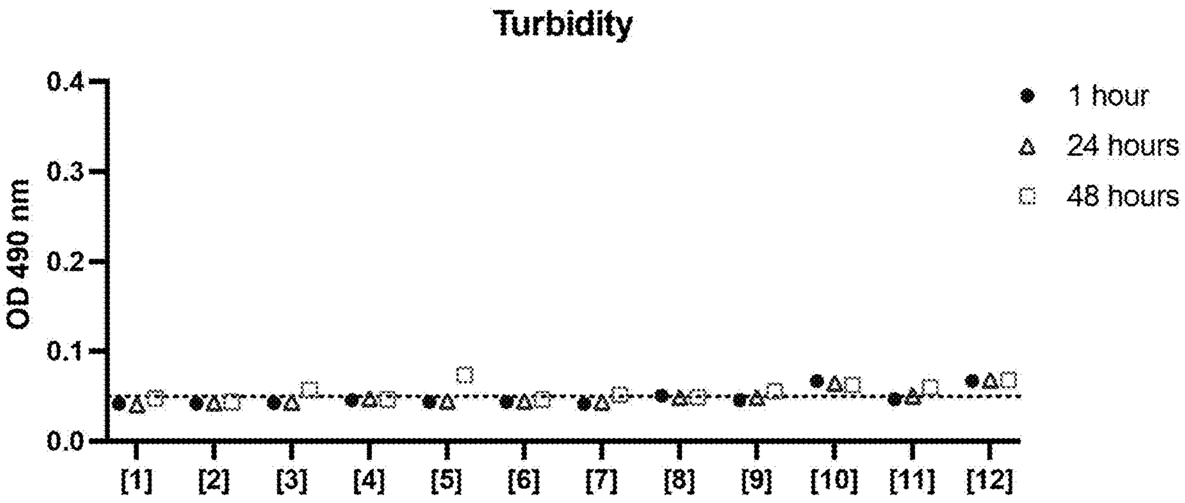
FIG. 11A shows turbidity at 24 hours and 48 hours at room temperature (~23° C.) for representative vaccines (Table 14) with varying mTORi identity, mTORi molar ratio, PAC concentration, and formulation buffer.
Figure 11B:
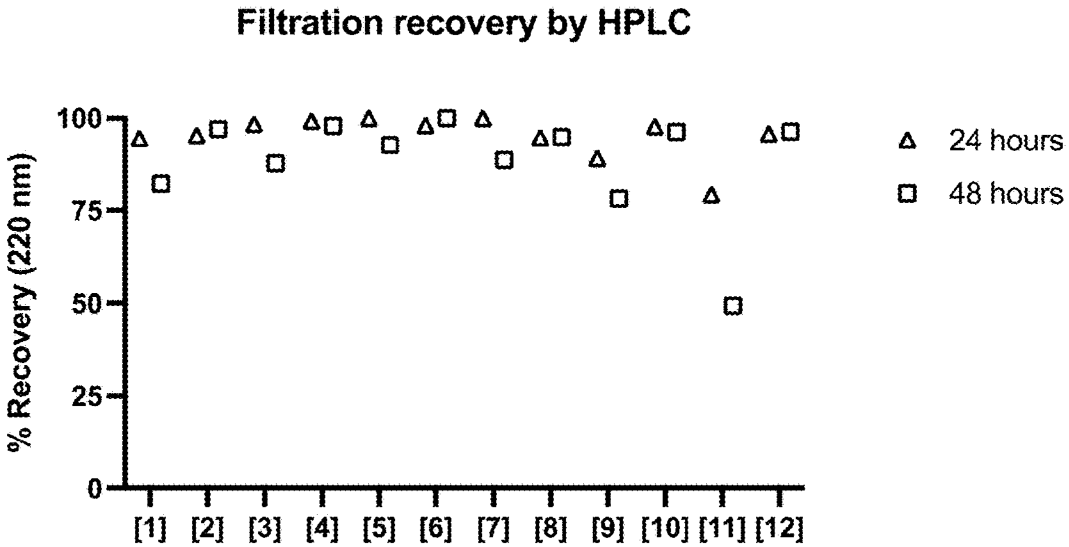
FIG. 11B shows filtration recovery at 1 hour, 24 hours, and 48 hours at room temperature (~23° C.) for representative vaccines (Table 14) with varying mTORi identity, mTORi molar ratio, PAC concentration, and formulation buffer.

A key finding was that the hydrodynamic behavior of the nanoparticles comprising the peptide antigen conjugates and mTORi had greater particle stability with 1:1 molar ratio total peptide antigen conjugate to mTORi as compared with the 4:1 molar ratio (FIG. 11A-B). Based on these results, the preferred ratio of mTORi to peptide antigen conjugate is about 1:1.

Example 12: Impact of Peptide Antigen Conjugate to mTORi Molar Ratio

To further assess the impact of mTORi composition and ratio of total peptide antigen conjugate to mTORi on hydrodynamic behavior, representative vaccines were made using the GLU peptide antigen conjugate Set 1 (as an equimolar mixture) and either no mTORi, the mTORi (Torin-1) or the mTORi rapamycin at either a 1:1 or 2:1 molar ratio of total peptide antigen conjugate to mTORi ratio in DMSO at 20 mM or 10 mM total peptide antigen conjugate concentration (Table 15). 3 mM Tris dissolved in 0.9% saline solution was then added to the DMSO solution at a 10:1 volume to volume ratio of formulation buffer to DMSO solution. The resulting vaccine compositions were stored at room temperature and then assessed for turbidity at 1, 24, and 48 hours and filtration recovery after 24 and 48 hours.

TABLE 15

Vaccines comprising GLU peptide antigen conjugates with varying mTORi, total PAC concentration and pH.

| Group # | mTORi | PAC to mTORi molar ratio | Total PAC concentration |
|---|---|---|---|
| 1 | None | 0 | 1 mM |
| 2 | | | 2 mM |
| 3 | Torin-1 | 1:1 | 1 mM |
| 4 | | | 2 mM |
| 5 | Rapamycin | | 1 mM |
| 6 | | | 2 mM |
| 7 | Torin-1 | 2:1 | 1 mM |
| 8 | | | 2 mM |
| 9 | Rapamycin | | 1 mM |
| 10 | | | 2 mM |

Figure 12A:
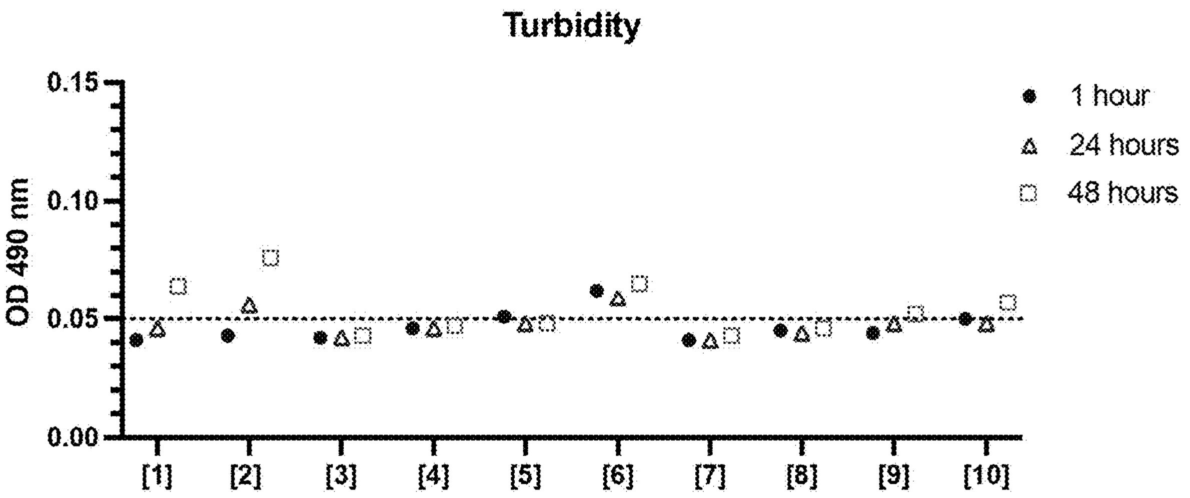
FIG. 12A shows turbidity at 24 hours and 48 hours at room temperature (~23° C.) for representative vaccines (Table 15) with varying mTORi identity, mTORi molar ratio, and PAC concentration.
Figure 12B:
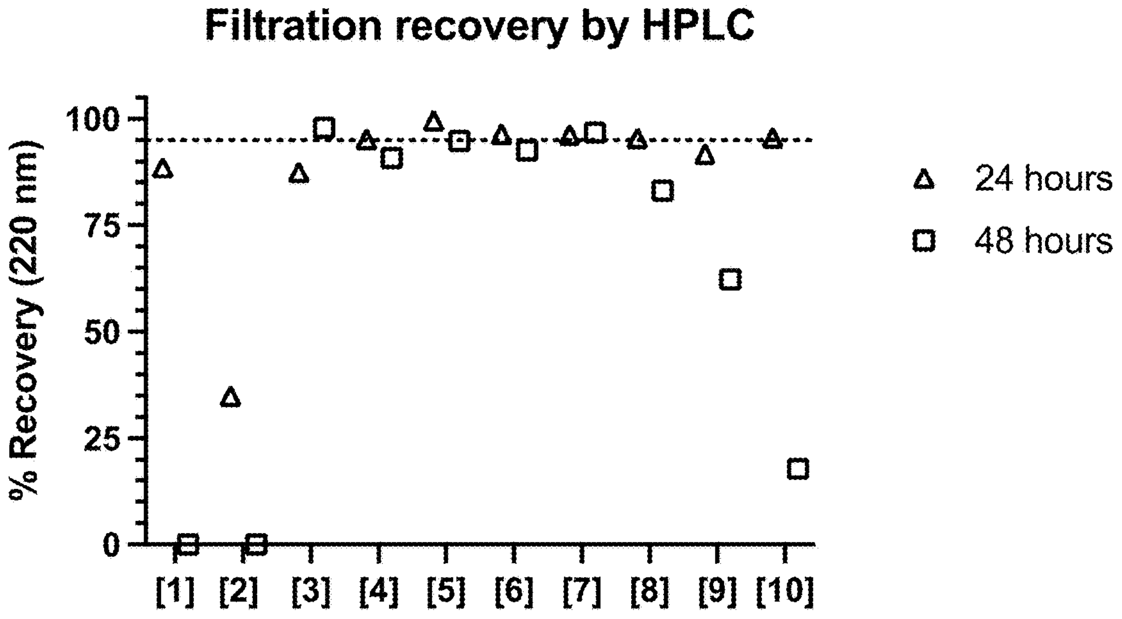
FIG. 12B shows filtration recovery at 1 hour, 24 hours, and 48 hours at room temperature (~23° C.) for representative vaccines (Table 15) with varying mTORi identity, mTORi molar ratio, and PAC concentration.

Consistent with the earlier data, hydrodynamic behavior was impacted by the both the total peptide antigen conjugate concentration and the molar ratio of peptide antigen conjugate to mTORi. Accordingly, the vaccines comprising peptide antigen conjugate and rapamycin at 1:1 molar ratio at 1 mM total peptide antigen conjugate concentration formed nanoparticles that were stable for up to 48 hours based on limited to no change in turbidity from 1 hour to 48 hours (see group [5], FIG. 12A), whereas the vaccine composition comprising peptide antigen conjugate to rapamycin at a 2:1 molar ratio at 1 mM total peptide antigen conjugate concentration exhibited a tendency to aggregate from 24 hours to 48 hours, suggesting that a ratio of around 1:1 is preferred. These data further substantiate that the preferred ratio of total peptide antigen conjugate to mTORi ratio is about 1:1.

Example 13: Additional Formulation Assessments

To further assess the impact of mTORi and buffer composition pH, representative vaccines were made using the GLU peptide antigen conjugate Set 1 (as an equimolar mixture) and either mTORi Torin-1 or the mTORi Rapamycin at a 1:1 molar ratio total peptide antigen conjugate to mTORi ratio in DMSO at 10 mM total peptide antigen conjugate concentration. The formulation buffer specified in Table 16 was then added to the DMSO solution at a 10:1 volume to volume ratio of formulation buffer to DMSO solution. The resulting vaccine compositions were stored at room temperature for 1 hour and then assessed for pH and inspected visually. The data showed that 50 mM tris in 0.9% saline adjusted to pH 7.5 with hydrochloric acid (HCl) had the greatest buffering capacity and that all of the formulations were stable, i.e., no aggregation was observed over the range of pH assessed between ~ pH 6.0 to pH 8.0.

TABLE 16

| Vaccines comprising GLU peptide antigen conjugates set 1 with varying formulation buffer and mTORi. | | | |
|---|---|---|---|
| Group # | mTORi | Formulation buffer | pH |
| 1 | Torin-1 | 3 mM Tris in 0.9% saline | 5.78 |
| 2 | | 4 mM Tris in 0.9% saline | 7.31 |
| 3 | | 5 mM Tris in 0.9% saline | 7.99 |
| 4 | | 25 mM Tris in 0.9% saline adjusted to pH 7.5 with HCl | 6.67 |
| 5 | | 50 mM Tris in 0.9% saline adjusted to pH 7.5 with HCl | 7.27 |
| 6 | Rapamycin | 3 mM Tris in 0.9% saline | 5.79 |
| 7 | | 4 mM Tris in 0.9% saline | 7.35 |
| 8 | | 5 mM Tris in 0.9% saline | 7.98 |
| 9 | | 25 mM Tris in 0.9% saline adjusted to pH 7.5 with HCl | 6.81 |
| 10 | | 50 mM Tris in 0.9% saline adjusted to pH 7.5 with HCl | 7.27 |
| 11 | Torin-1 | 25 mM Tris in 0.9% saline adjusted to pH 8 with HCl | 7.72 |
| 12 | Rapamycin | 25 mM Tris in 0.9% saline adjusted to pH 8 with HCl | 7.72 |

As an extension of this data, a representative vaccine comprising GLU peptide antigen conjugate set 1 and Rapamycin at a 1:1 molar ratio of total peptide antigen conjugate to Rapamycin was formulated with additional Tris buffered saline formulation buffers with 10% DMSO with total peptide antigen conjugate concentration at about 1 mM and pH between 6 and 7.5.

Example 14: Impact of mTORi to Peptide Antigen Conjugate Ratio and Irrelevant Antigen The impact of peptide antigen conjugate to mTORi molar ratio and effect of irrelevant antigen on the efficacy of a representative vaccine for inducing tolerance was assessed in the murine EAE model.

The different compositions of vaccine for inducing tolerance that were assessed are summarized in Table 17 and comprised the mTORi Torin-1 or the mTORi Rapamycin, a relevant peptide antigen conjugate of formula PEG-E1-A-E2-U-H (Compound 65) wherein A is a MOG-derived peptide antigen and optionally an irrelevant peptide antigen conjugate of formula PEG-E1-A-E2-U-H (Compound 115). The ratios of total peptide antigen conjugate to mTORi molar ratios assessed were 10:1, 2:1 and 1:1. Each of the vaccine compositions were formulated in formulation buffer consisting of 0.9% NaCl (normal saline) and 50 mM Tris at a pH between 6.5-8.5 with up to 10% DMSO by volume.

Figure 13A:
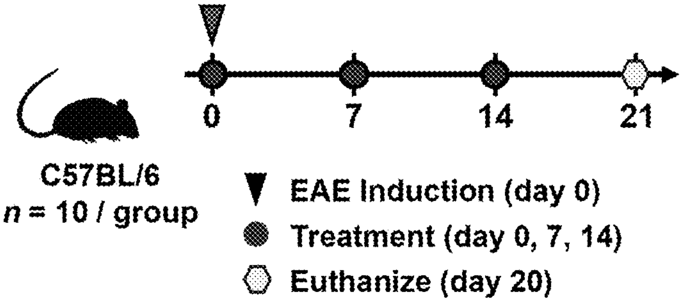
FIG. 13A-D shows disability score kinetics for mice with experimental autoimmune encephalomyelitis (EAE) receiving different treatments (Table 17) following EAE disease induction at day 0, treatment on days 0, 7 and 14.
Figure 13B:
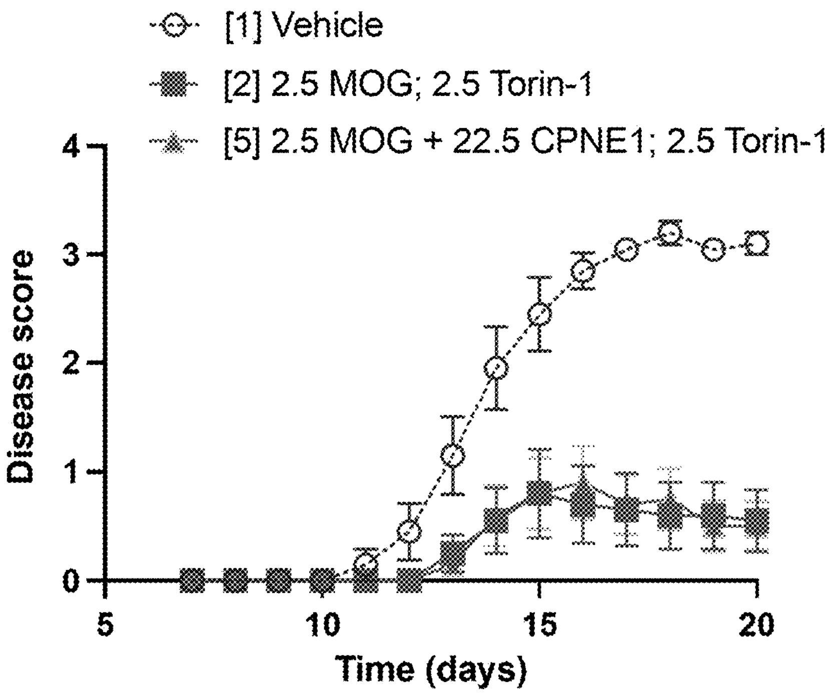
Figure 13C:
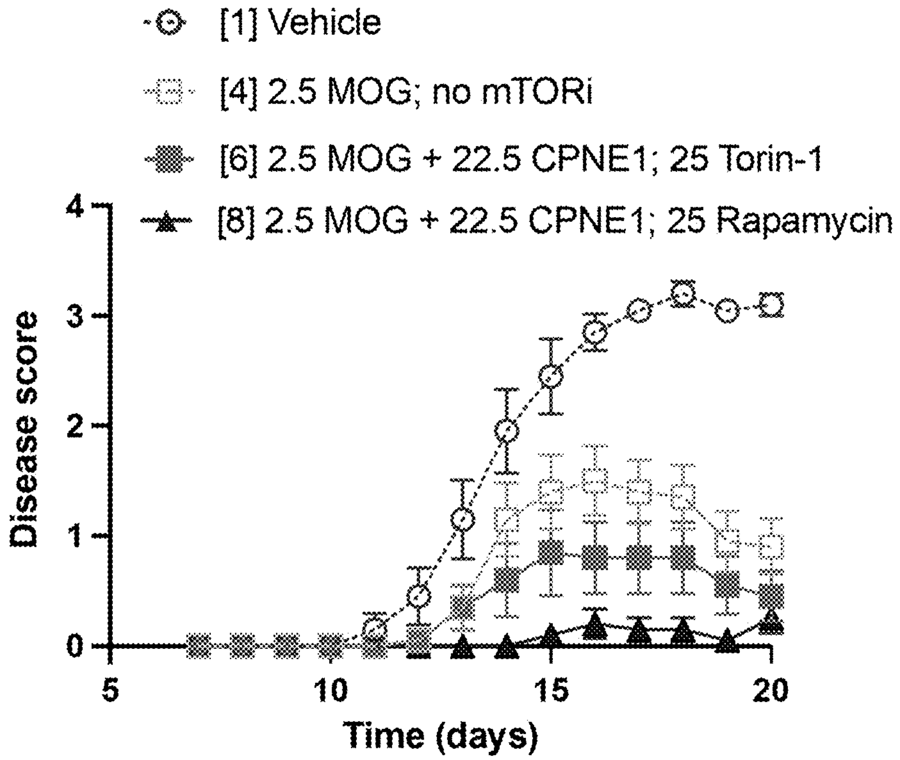

C57BL/6 mice (n=10/group) were induced with EAE on day 0 and then treated with the specified vaccine composition and doses (Table 17) at the timepoints specified in FIG. 13A. Disability scores, that account for disease severity (e.g., paralysis, weight loss, etc.) were assessed throughout the study and plotted in FIG. 13B-D.

Figure 13D:
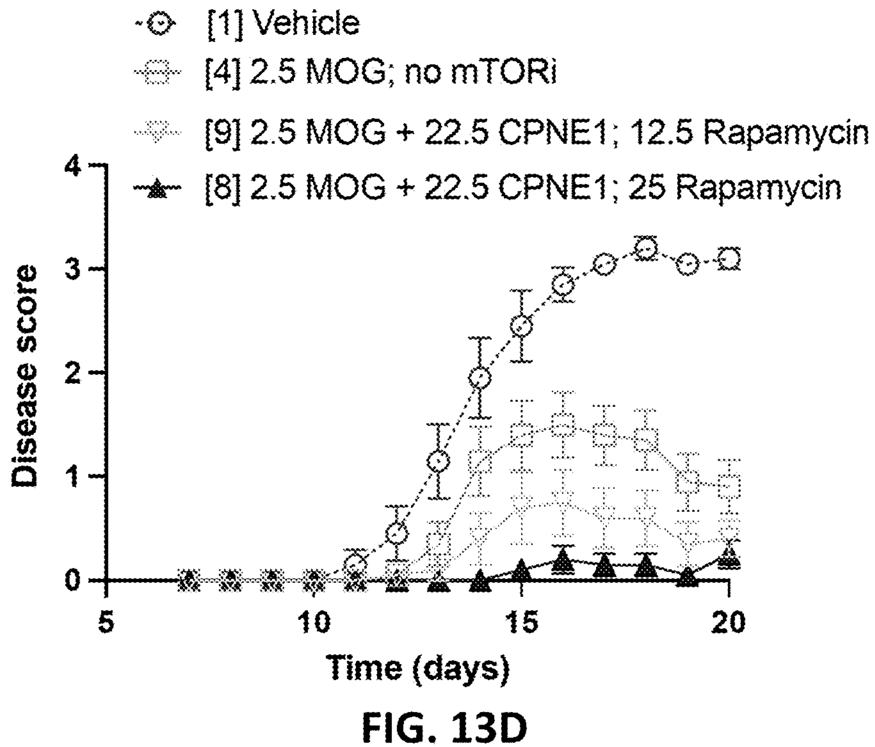

The data show that: (i) irrelevant peptide antigen conjugate comprising up to 90% of the total peptide antigen conjugate content on a molar basis does not effect efficacy; and (ii) molar ratios of total peptide antigen conjugate to mTORi down to 10:1 are efficacious but that highest efficacy is observed when the ratio is 1:1 (FIG. 13D).

Based on these findings, preferred embodiments of the vaccine for inducing tolerance that comprise an mTORi selected from Rapamycin or Torin have a total peptide antigen conjugate to mTORi molar ratio between about 2:1 to about 1:2, or about 1:1.

TABLE 17

| Compositions of tolerance vaccines assessed in the EAE model. | | | | | |
|---|---|---|---|---|---|
| Group | Route | PAC formula | Relevant PAC Compound # (dose) | Irrelevant PAC Compound # | Drug (D), mTORi (dose) |
| 1 | IM | — | — | — | — |
| 2 | IM | PEG-E1-A-E2-U-H | Compound 65 (2.5 nmol) | — | Torin-1 (2.5 nmol) |
| 3 | IM | PEG-E1-A-E2-U-H | Compound 65 (2.5 nmol) | — | Torin-1 (1.25 nmol) |
| 4 | IM | PEG-E1-A-E2-U-H | Compound 65 (2.5 nmol) | — | — |
| 5 | IM | PEG-E1-A-E2-U-H | Compound 65 (2.5 nmol) | Compound 115 (22.5 nmol) | Torin-1 (2.5 nmol) |
| 6 | IM | PEG-E1-A-E2-U-H | Compound 65 (2.5 nmol) | Compound 115 (22.5 nmol) | Torin-1 (25 nmol) |
| 7 | IM | PEG-E1-A-E2-U-H | Compound 65 (2.5 nmol) | Compound 115 (22.5 nmol) | Torin-1 (12.5 nmol) |
| 8 | IM | PEG-E1-A-E2-U-H | Compound 65 (2.5 nmol) | Compound 115 (22.5 nmol) | Rapamycin (25 nmol) |
| 9 | IM | PEG-E1-A-E2-U-H | Compound 65 (2.5 nmol) | Compound 115 (22.5 nmol) | Rapamycin (12.5 nmol) |

Example 15: Impact of PEG, Amphiphile and Surfactant on In Vivo Efficacy

Earlier data presented herein showed that vaccines comprising peptide antigen conjugates of formula PEG-[E1]-A-[E2]-[U]-H, wherein A is selected from peptide antigens that are water soluble up to at least 1 mg/mL had improved particle stability in aqueous buffer (e.g., formulation buffer comprising PBS or Tris buffered saline) when the amphiphile was not included in the formulation. However, it was unknown what impact the amphiphile, and other inactive components of the formulation, have on efficacy in vivo. Therefore, we assessed how different compositions of vaccines impact efficacy of vaccines for inducing tolerance in the murine EAE model, which is a mouse model of multiple sclerosis.

The different compositions assessed are summarized in Table 18 and comprised the mTORi (Torin-1) and either (i) a peptide antigen conjugate of formula E1-A-E2-U-H and an amphiphile of formula S-B-[U]-H; (ii) a peptide antigen conjugate of formula PEG-E1-A-E2-U-H, an amphiphile of formula S-B-[U]-H and a surfactant, polysorbate-20; or (iii) a peptide antigen conjugate of formula PEG-E1-A-E2-U-H and an amphiphile of formula S-B-[U]-H, wherein in each case A was selected from a MOG-derived peptide antigen and the molar ratio of each component was 1:1 (e.g., 1:1 molar ratio of peptide antigen conjugate to mTORi). Each of the vaccine compositions was formulated in formulation buffer consisting of 0.9% saline and 50 mM Tris at a pH between 6.5-8.5 with up to 10% DMSO by volume.

Figure 14A:
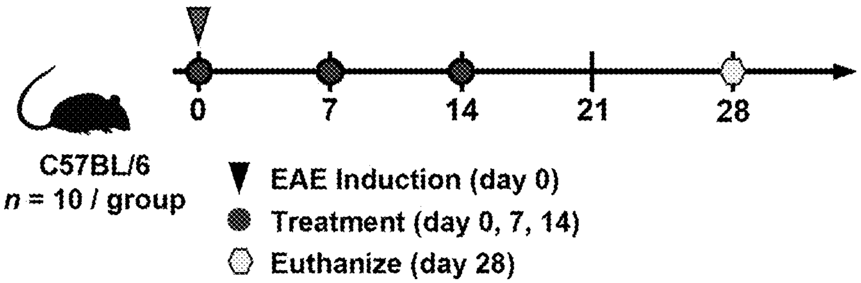
FIG. 14A-F shows disability score kinetics for mice with experimental autoimmune encephalomyelitis (EAE) receiving different treatments (Table 18) following EAE disease induction at day 0, treatment on days 0, 7 and 14.
Figure 14B:
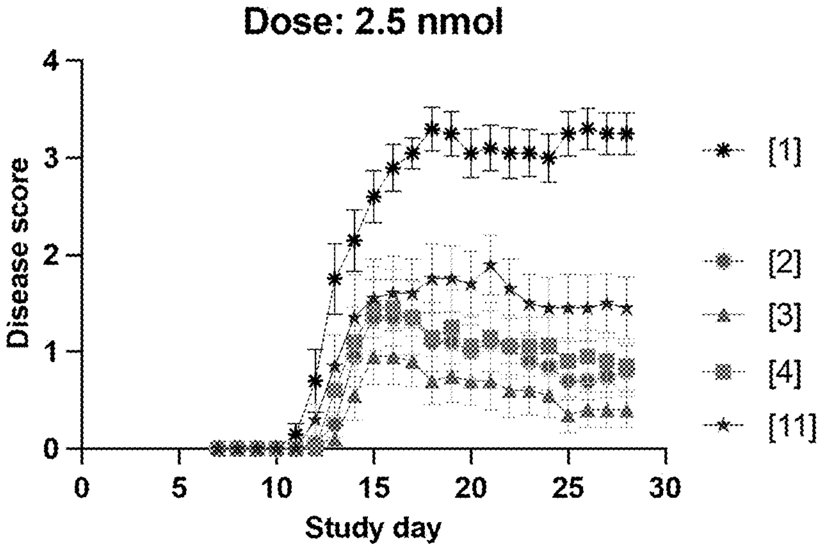
Figure 14C:
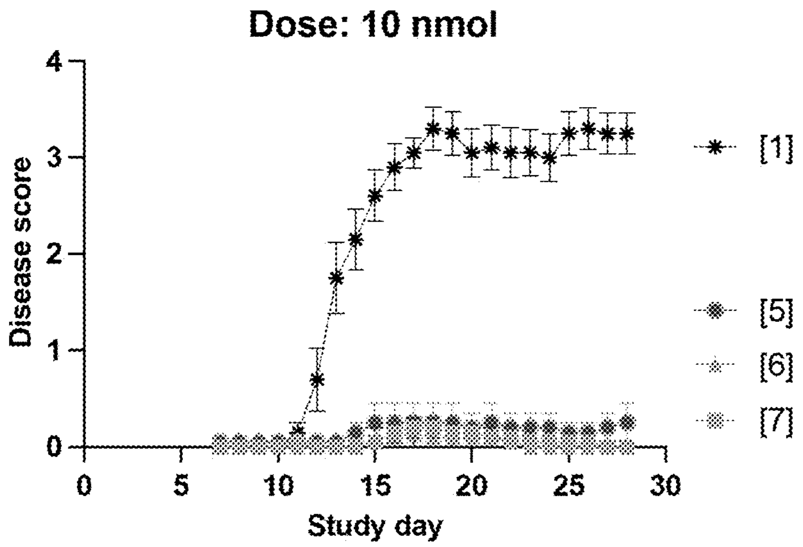
Figure 14D:
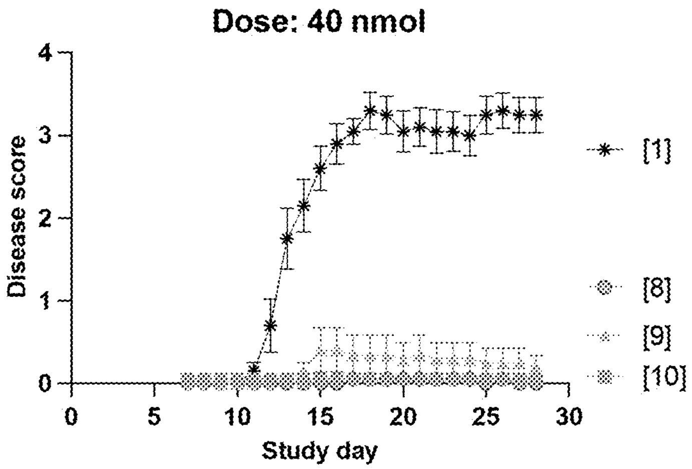
Figure 14E:
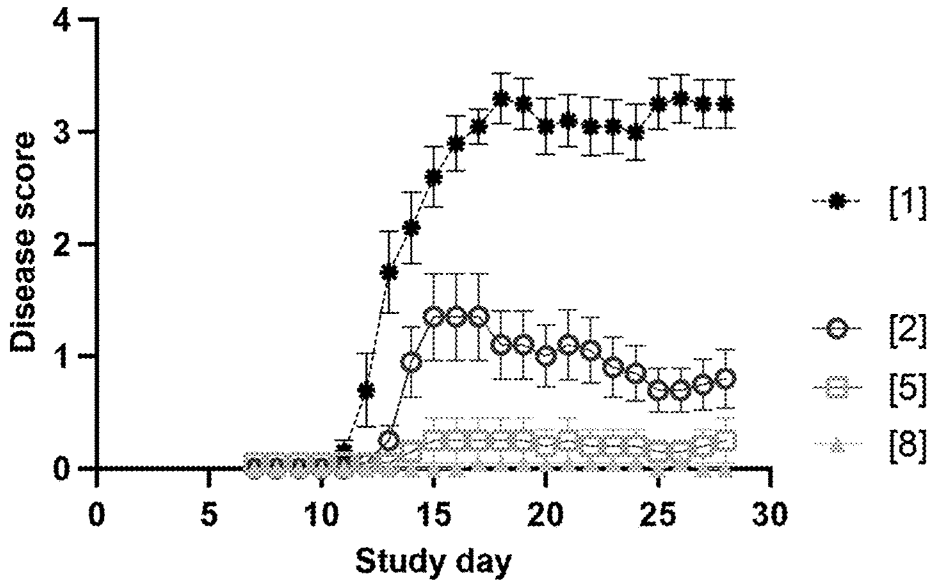
Figure 14F:
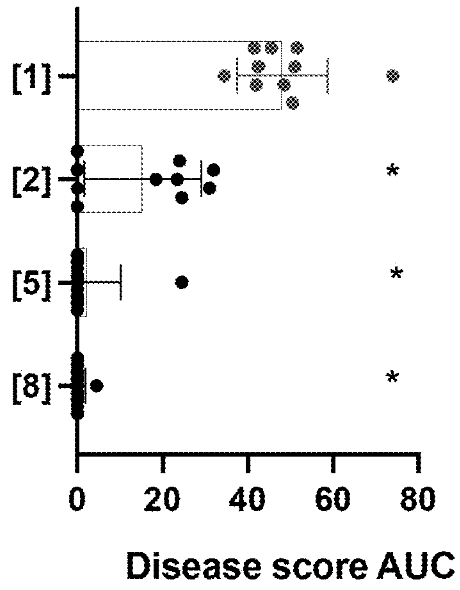

C57BL/6 mice (n=10/group) were induced with EAE on day 0 and then treated with the specified vaccine composition and dose (Table 18) at the timepoints specified in FIG. 14A. Disability scores, that account for disease severity (e.g., paralysis, weight loss, etc.) were assessed throughout the study and plotted in FIG. 14B-E.

TABLE 18

Compositions of tolerance vaccines assessed in the EAE model.

| Group | PAC formula | PAC Compound # (dose, nmol) | S-B-[U]-H Compound # | Surfactant | D (dose, nmol) |
|---|---|---|---|---|---|
| 1 | — | — | — | — | — |
| 2 | PEG-E1-A-E2-U-H | Compound 65 (2.5 nmol) | — | — | Torin-1 (2.5 nmol) |
| 3 | E1-A-E2-U-H | Compound 114 (2.5 nmol) | Compound 25 (2.5 nmol) | — | Torin-1 (2.5 nmol) |
| 4 | PEG-E1-A-E2-U-H | Compound 65 (2.5 nmol) | Compound 25 (2.5 nmol) | PS-20 (2.5 nmol) | Torin-1 (2.5 nmol) |
| 5 | PEG-E1-A-E2-U-H | Compound 65 (10 nmol) | — | — | Torin-1 (10 nmol) |
| 6 | E1-A-E2-U-H | Compound 114 (10 nmol) | Compound 25 (10 nmol) | — | Torin-1 (10 nmol) |
| 7 | PEG-E1-A-E2-U-H | Compound 65 (10 nmol) | Compound 25 (10 nmol) | PS-20 (2.5 nmol) | Torin-1 (10 nmol) |
| 8 | PEG-E1-A-E2-U-H | Compound 65 (40 nmol) | — | — | Torin-1 (40 nmol) |
| 9 | E1-A-E2-U-H | Compound 114 (40 nmol) | Compound 25 (40 nmol) | — | Torin-1 (40 nmol) |
| 10 | PEG-E1-A-E2-U-H | Compound 65 (40 nmol) | Compound 25 (40 nmol) | PS-20 (2.5 nmol) | Torin-1 (40 nmol) |
| 11 | PEG-E1-A-E2-U-H | Compound 65 (2.5 nmol) | Compound 25 (2.5 nmol) | — | Torin-1 (2.5 nmol) |

Importantly, the data show that the different peptide antigen conjugate compositions assessed have comparable dose-dependent efficacy (FIGS. 14A-F).

Based on these findings, preferred embodiments of the vaccine for inducing tolerance are selected based on the solubility of the peptide antigen A. For peptide antigens (A) that are soluble up to at least 1 mg/mL, the vaccine comprises a peptide antigen conjugate of formula PEG-E1-A-E2-U-H and mTORi at a 1:1 molar ratio in formulation buffer but does not include an amphiphile. Whereas, for peptide antigens (A) that are not soluble up to at least 1 mg/mL, the vaccine comprises a peptide antigen conjugate of formula PEG-E1-A-E2-U-H, mTORi and amphiphile of formula S-B-[U]-H at a 1:1:1 molar ratio in formulation buffer.

Example 16: Impact of the Number of Doses and Route of Administration

We next assessed the impact that the number of doses and route of administration (intramuscular (IM) versus subcutaneous (SC)) has on efficacy for a representative vaccine for inducing tolerance.

The representative vaccine composition assessed comprises a peptide antigen conjugate of formula PEG-E1-A-E2-U-H (Compound 65) and the mTORi Rapamycin at a 1:1 molar ratio in formulation buffer consisting of 0.9% saline and 50 mM Tris at a pH between 6.5-8.5 with up to 10% DMSO by volume.

Figure 15A:
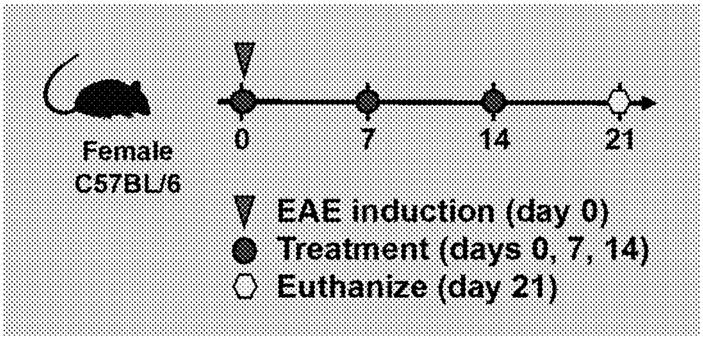
FIG. 15A-C shows disability score kinetics for mice with experimental autoimmune encephalomyelitis (EAE) and disease score area under the curve (AUC) of mice receiving different treatments (Table 19) following EAE disease induction at day 0, treatment on days 0, 7 and 14.

C57BL/6 mice (n=10/group) were induced with EAE on day 0 and then treated with the specified vaccine composition and doses (Table 19) at the timepoints specified in FIG. 15A. Disability scores, that account for disease severity (e.g., paralysis, weight loss, etc.) were assessed throughout the study and plotted in FIG. 15B-C.

TABLE 19

Compositions and treatment regimen of tolerance vaccines assessed in the EAE model.

| Group | PAC formula | PAC Compound # (dose, nmol) | mTORi | Route of administration | Treatment (days) |
|---|---|---|---|---|---|
| 1 | — | — | — | IM | 0, 7, 14 |
| 2 | — | — | — | SC | 0, 7, 14 |
| 5 | PEG-E1-A-E2-U-H | Compound 65 (8 nmol) | Rapamycin, 8 nmol | IM | 0, 7, 14 |
| 8 | PEG-E1-A-E2-U-H | Compound 65 (8 nmol) | Rapamycin, 8 nmol | SC | 0, 7, 14 |
| 12 | PEG-E1-A-E2-U-H | Compound 65 (8 nmol) | Rapamycin, 8 nmol | IM | 0 |
| 13 | PEG-E1-A-E2-U-H | Compound 65 (8 nmol) | Rapamycin, 8 nmol | SC | 0 |

Figure 15B:
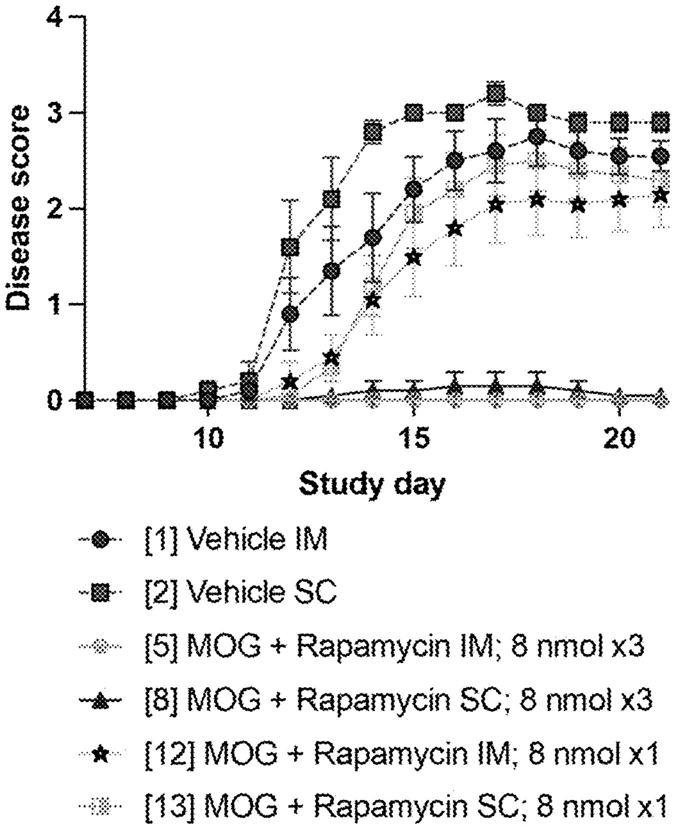
Figure 15C:
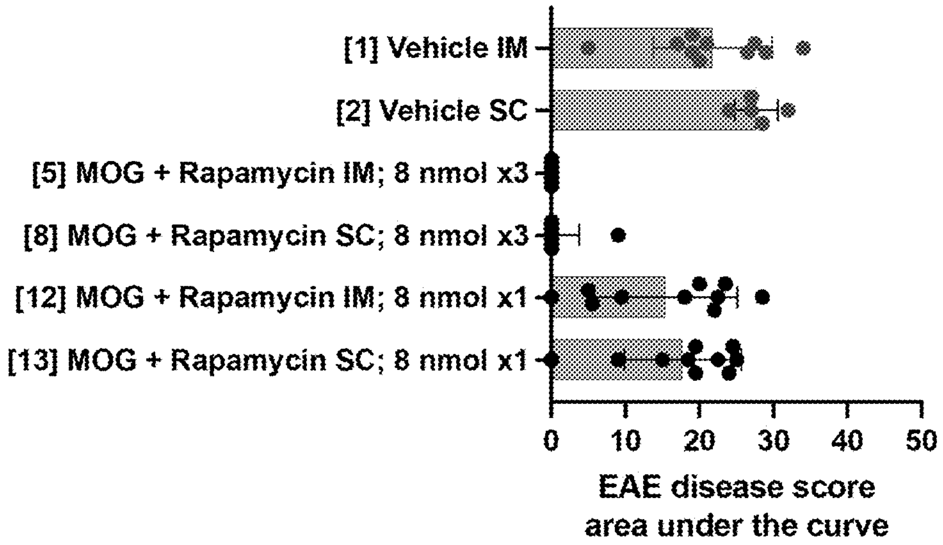

The data show that: (i) intramuscular and subcutaneous routes of administration have comparable efficacy but that (ii) three doses at least 1 week apart are superior to a single dose (FIG. 15B). Based on these findings, preferred methods for treating an allergy, autoimmunity or inflammatory disease process are to administer 1 or more treatments by either the IM or SC route of administration.

Example 17: Vaccine for Inducing Tolerance for the Treatment of Celiac Disease The vaccines for inducing tolerance described herein may be used for treating any autoimmune disease, allergy, transplant rejection, anti-drug antibodies or other unwanted immune responses.

As examples of vaccines for inducing tolerance for treating celiac disease, two different vaccine compositions each comprising 12 peptide antigen conjugates further comprising GLU peptide antigens (referred to as GLU peptide antigen conjugate set 2) and either Rapamycin or Torin-1 at a 1:1 mTORi to total peptide antigen conjugate molar ratio in formulation buffer comprising 50 mM Tris and normal saline (0.9% NaCl) at pH between about 6.5-8.5 was prepared as summarized in Table 20.

Figure 16A:
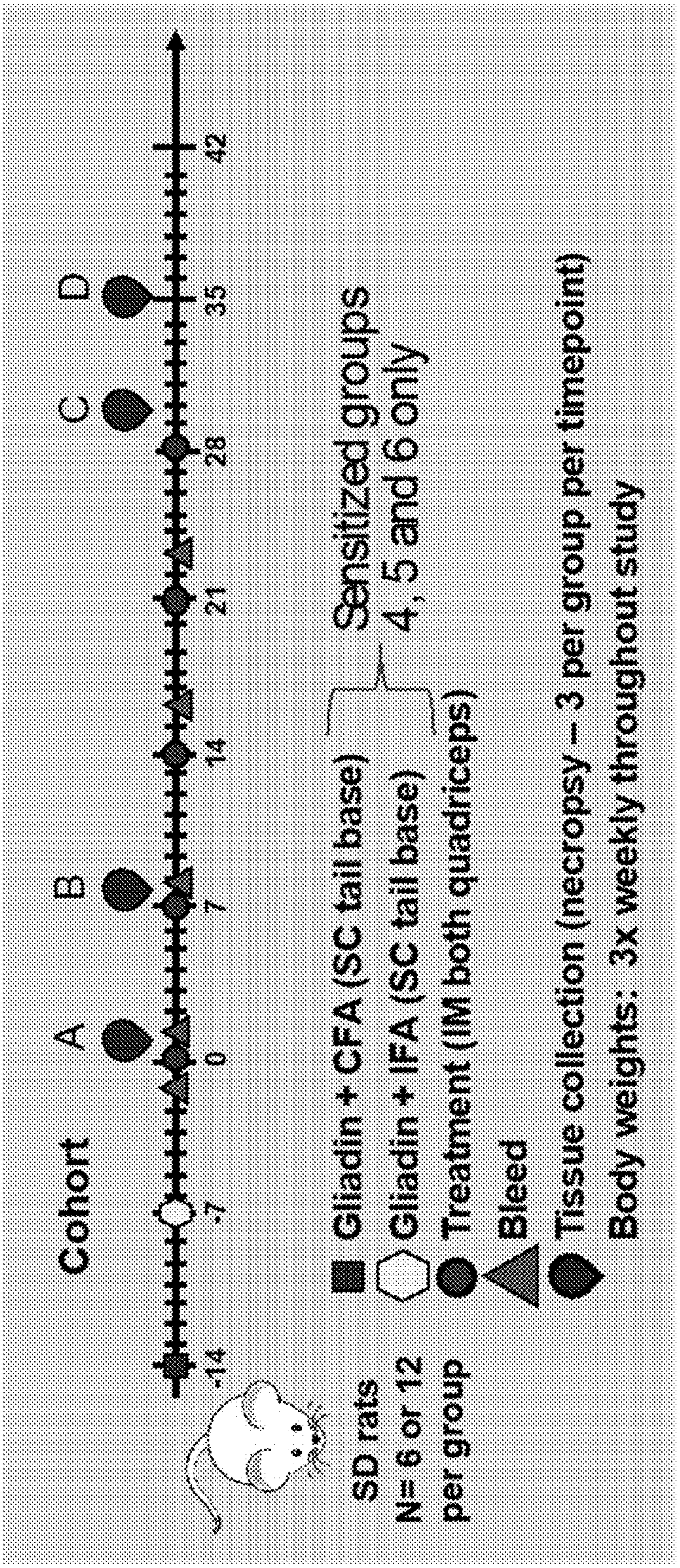
FIG. 16A-G shows experimental plan and immunological outcomes of testing GLU peptide antigen conjugate in Sprague Dawley rats using formulations (Table 21).

Sprague Dawley rats were divided into two cohorts with the second cohort (Groups [4], [5] and [6]) sensitized to gluten by subcutaneous administration of GLU peptides and deamidated gluten protein antigen administered in Complete Freund's adjuvant (CFA) at day-14, followed by re-administration of GLU peptides and deamidated gluten protein antigen in incomplete Freund's adjuvant (IFA) at day-7. Rats were treated with the specified vaccine composition and doses (Table 21) at the timepoints specified in FIG. 16A. Activity of the vaccine was assessed on the basis of mTORi activity as assessed by phosphor-S6 assay, anti-deamidated gluten peptide antibody titers and ratio of Treg to $T_{effector}$ cells, FIG. 16B-*G*.

Figure 16B:
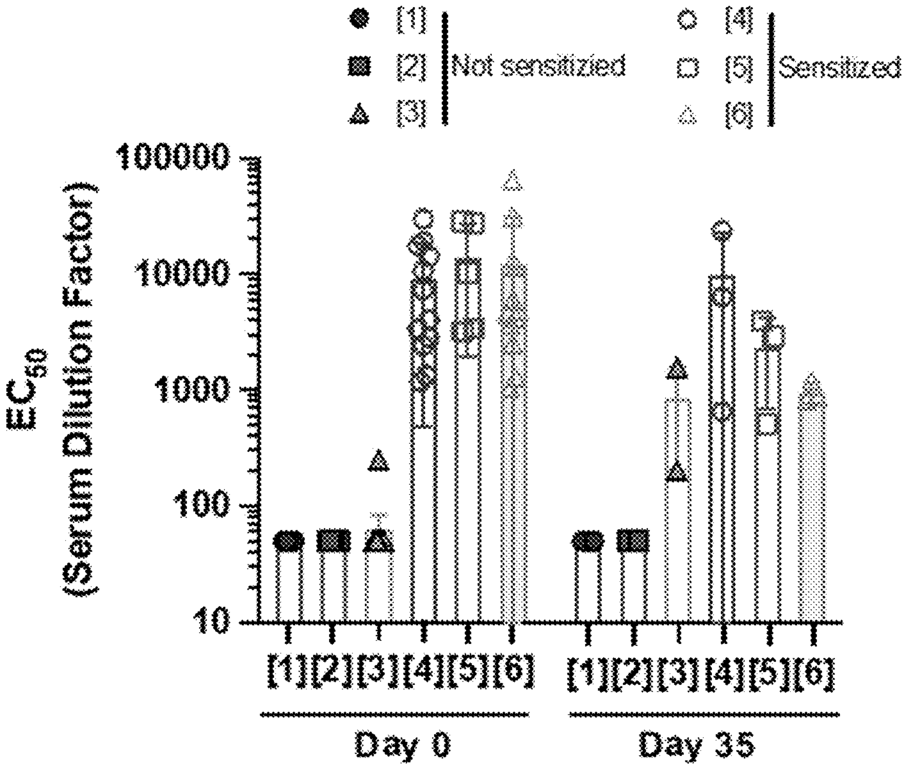
Figure 16C:
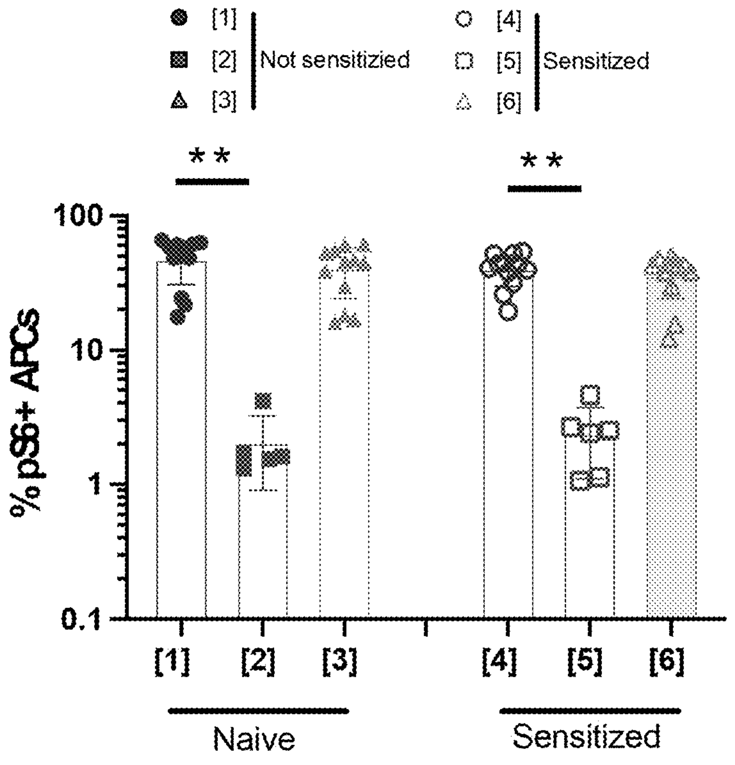
Figure 16D:
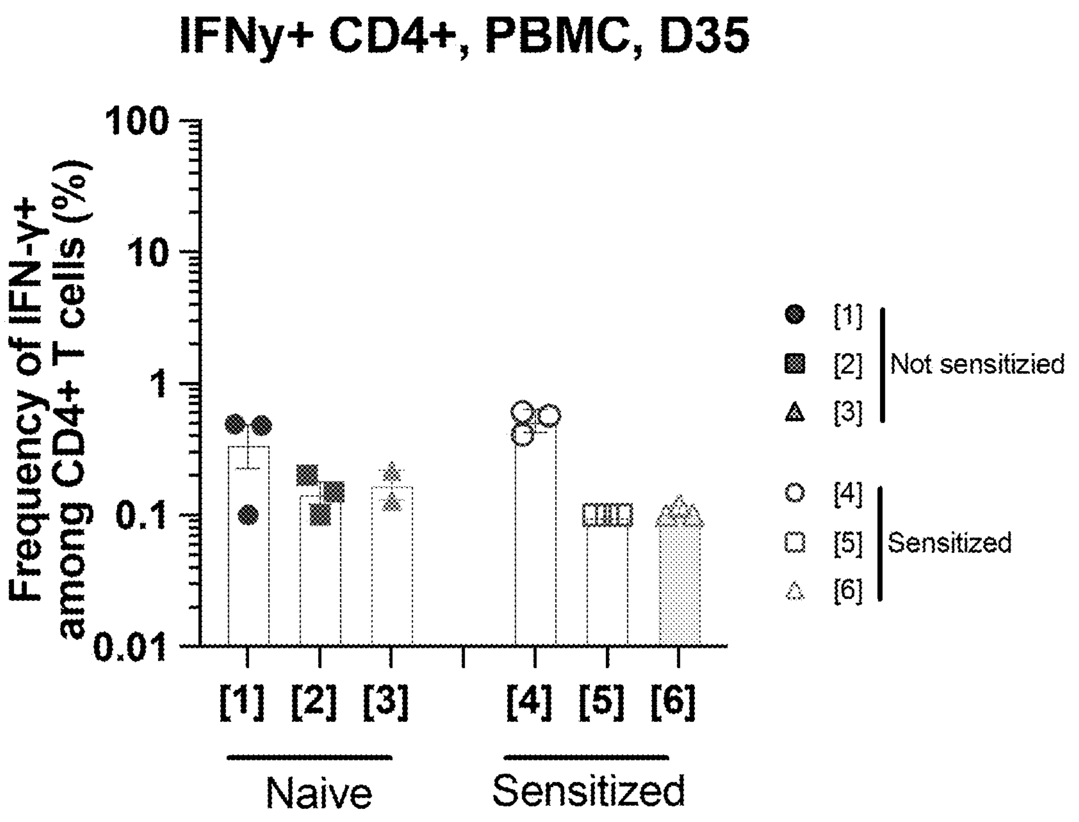
Figure 16E:
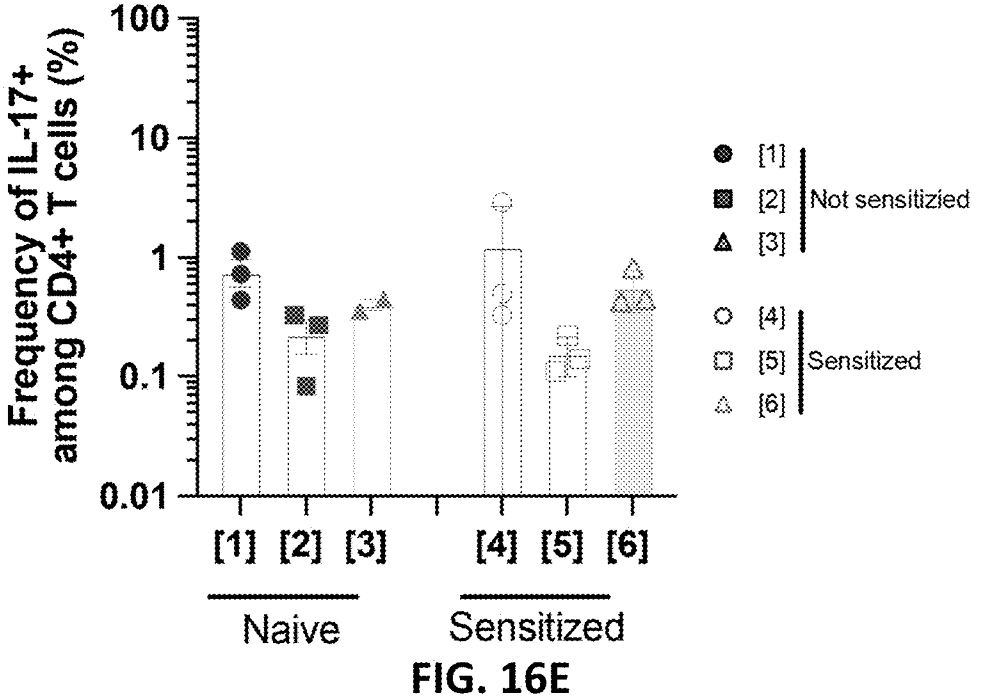
Figure 16F:
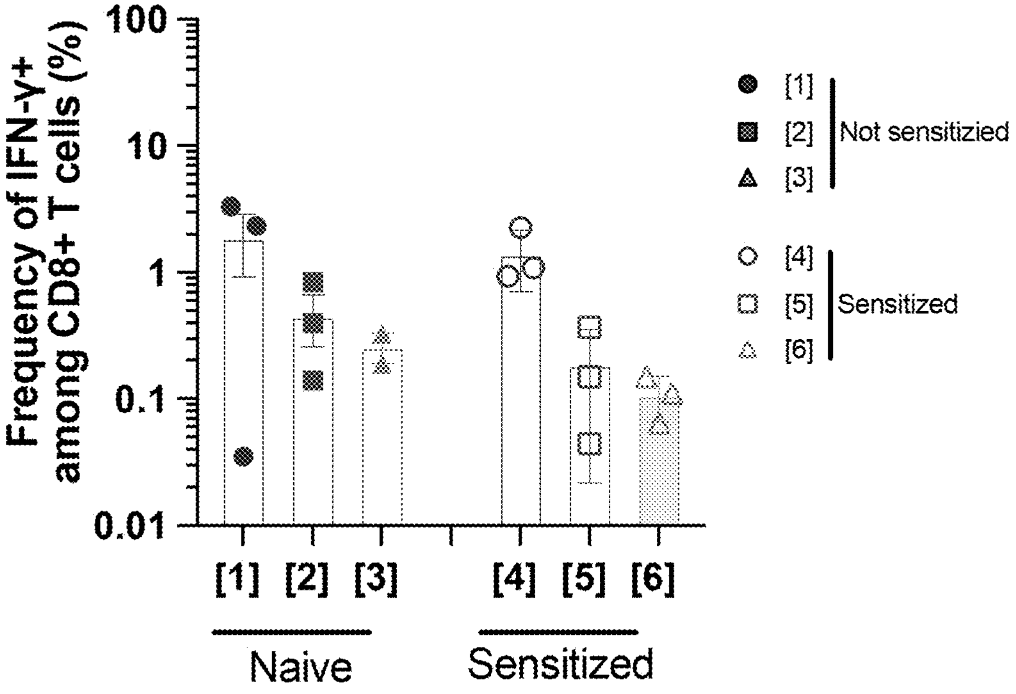
Figure 16G:
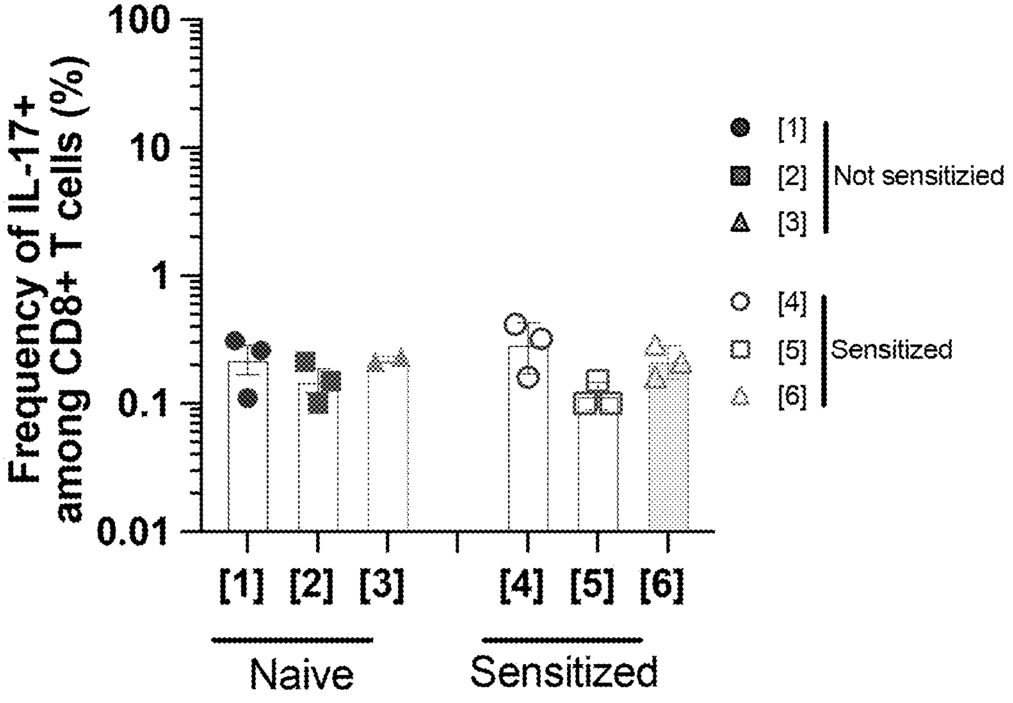
Figure 17A:
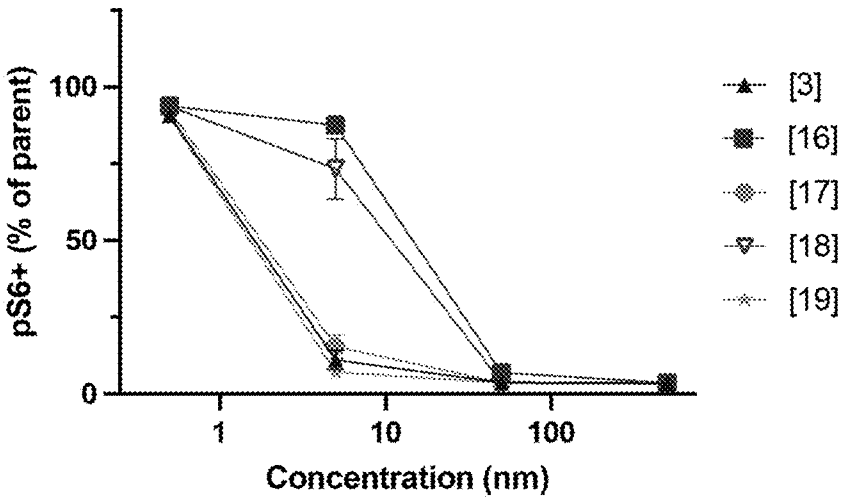
FIG. 17A-C shows in vitro mTOR inhibitor assay results in splenocyte populations following in vitro stimulation with LPS. Splenocytes from C57BL/6 mice were dissociated to single cell suspension and plated in vitro for stimulation. Test article compounds were added to cells at concentrations of 0.5, 5, 50 or 500 nM concentrations for one hour, after which lipopolysaccharide (LPS) was added to cells for two hours to stimulate mTOR activity and downstream S6 phosphorylation to phospho-S6 (pS6). Cells were then fixed and stained for flow cytometric analysis. Test article compounds (Table 24) were resuspended in PBS prior to adding to splenocyte culture.
Figure 17B:
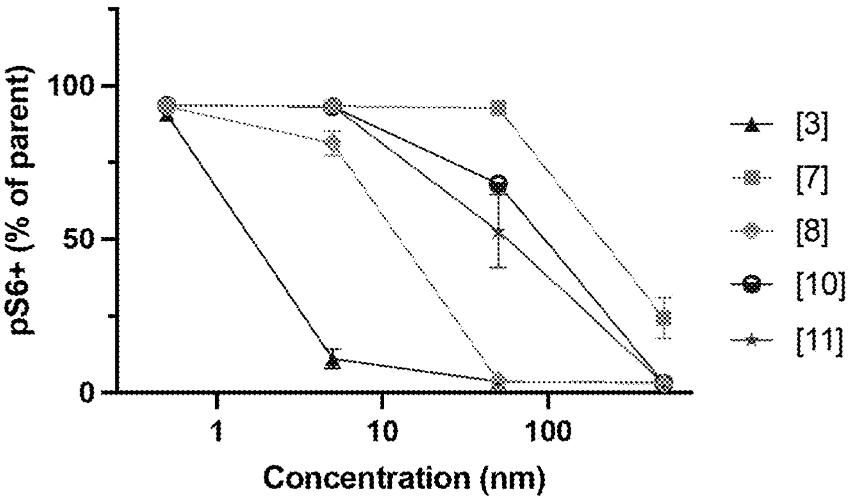
Figure 17C:
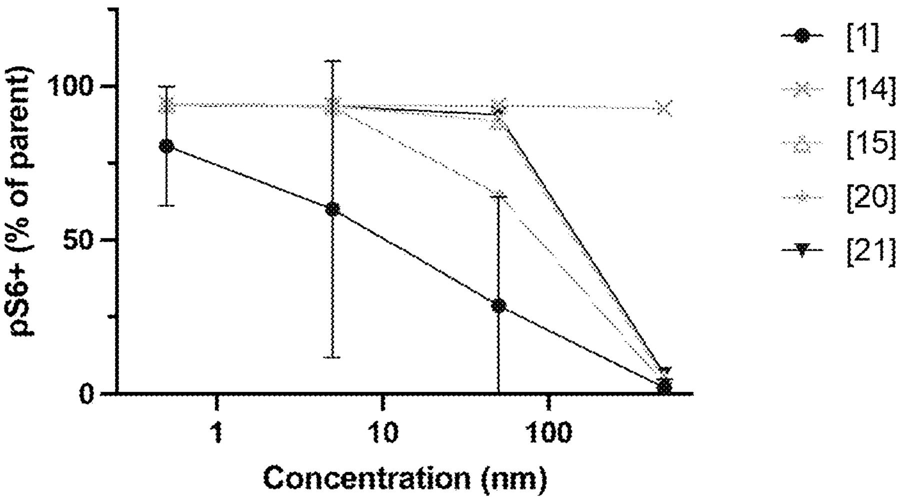

The data show that: (i) intramuscular administration of GLU peptide antigen conjugates in formulation including Rapamycin reduces anti-gliadin antibody titer (FIG. 16B); (ii) intramuscular administration of GLU peptide antigen conjugates in formulation buffer including Rapamycin inhibits pS6 in leukocytes isolated from blood four hours after treatment (FIG. 16C, pS6 is a protein that is phosphorylated by mTOR, thus measurement of pS6 inhibition demonstrates mTOR inhibition); (iii) intramuscular administration of GLU peptide antigen conjugates in formulation buffer including Rapamycin reduced the Teff cell populations in treated rats.

TABLE 20

Tolerance vaccines comprising GLU peptide antigen conjugate set 2 and mTOR inhibitors.

| PAC | GLU peptide antigen conjugate set 2 | |
| --- | --- | --- |
| mTORi | Rapamycin | Torin-1 |
| Molar ratio | 1:1 | 1:1 |
| Appearance | Clear solution, free from particulate matter | Clear solution, free from particulate matter |

TABLE 20-continued

Tolerance vaccines comprising GLU peptide antigen conjugate set 2 and mTOR inhibitors.

| PAC | GLU peptide antigen conjugate set 2 | |
| --- | --- | --- |
| mTORi | Rapamycin | Torin-1 |
| Purity | ≥80% AUC | ≥80% AUC |
| Identity | Conforms | Conforms |
| Peptide antigen conjugate (PAC) concentration | 1.01 mM | 0.99 mM |
| mTORi concentration | 1.04 mM | 1.01 mM |
| Particle size (Dh) | 17.5 nm | 15.6 nm |
| Buffer composition | 50 mM Tris, 10.3% DMSO in normal saline | 50 mM Tris, 10.2% DMSO in normal saline |
| Turbidity | 0.05 | 0.043 |
| pH | 7.37 | 7.57 |
| Vial Volume | 1.15 mL | 1.15 mL |

TABLE 21

Tolerance vaccines for treating celiac diseased assessed in Sprague Dawley rats.

| Group | PAC formula, or control | PAC (dose, nmol) | mTORi, dose (nmol) | Gliadin sensitiziation | Treatment (days) |
| --- | --- | --- | --- | --- | --- |
| 1 | Vehicle control | — | — | No | 0, 7, 14, 21, 28 |
| 2 | PEG-E1-A-E2-U-H | GLU peptide antigen conjugate set 2 | Rapamycin, 300 nmol | No | |
| 3 | PEG-E1-A-E2-U-H | (300 nmol) | Torin-1, 300 nmol | No | |
| 4 | Vehicle control | — | — | Yes | |
| 5 | PEG-E1-A-E2-U-H | GLU peptide antigen conjugate set 2 | Rapamycin, 300 nmol | Yes | |
| 6 | PEG-E1-A-E2-U-H | (300 nmol) | Torin-1, 300 nmol | Yes | |

Example 18: Vaccine for Inducing Tolerance for the Treatment of Type-1 Diabetes

The capacity of peptide antigen conjugate formulations to induce tolerance in a mouse model of Type 1 Diabetes (T1D) will be assessed.

As examples of vaccines for inducing tolerance for treating T1D, vaccine formulations comprised of peptide antigen conjugate and either Rapamycin or Torin-1 at a 1:1 mTORi to total peptide antigen conjugate molar ratio in formulation buffer comprising 50 mM Tris and normal saline (0.9% NaCl) at pH between about 6.5-8.5 will be prepared as summarized in Table 22. Combinations of peptide antigen conjugates for treatment of T1D included either CD4+ T cell epitope alone, a CD8+ cell epitope alone, the combination of both or an irrelevant peptide antigen epitope. Specific peptide antigens for T1D will be selected from P31 and NRP-V7.

Eight week old NOD/ShiLtJ mice (JAX: 001976) (n=10/group) will be treated with specified vaccine composition and doses (Table 22) on a weekly or bi-weekly basis from weeks 8-13. Glucose monitoring will be performed starting at week 10 and continued through week 30 and mice will be further monitored for survival. All remaining mice will be euthanized at an age of 30 weeks old.

TABLE 22

Compositions of tolerance vaccines assessed in a T1D model in NOD mice.

| | PAC formula, or control | PAC Compound # (dose, nmol) | mTORi (dose, nmol) | S-B-[U]-H Compound # | Treatment (weeks) |
|---|---|---|---|---|---|
| 1 | Vehicle control | — | — | — | 8, 9, 10, 11, 12, 13 |
| 2 | PEG-E1-A-E2-U-H | Compound 117 (5 nmol) Compound 119 (5 nmol) | Rapamycin (10 nmol) | Compound 26 (10 nmol) | 8, 9, 10, 11, 12, 13 |
| 3 | PEG-E1-A-E2-U-H | Compound 117 (5 nmol) Compound 119 (5 nmol) | — | Compound 26 (10 nmol) | 8, 9, 10, 11, 12, 13 |
| 4 | PEG-E1-A-E2-U-H | Compound 117 (10 nmol) | Rapamycin (10 nmol) | Compound 26 (10 nmol) | 8, 9, 10, 11, 12, 13 |
| 5 | PEG-E1-A-E2-U-H | Compound 119 (10 nmol) | Rapamycin (10 nmol) | Compound 26 (10 nmol) | 8, 9, 10, 11, 12, 13 |
| 6 | PEG-E1-A-E2-U-H | Compound 116 (10 nmol) | Rapamycin (10 nmol) | Compound 26 (10 nmol) | 8, 9, 10, 11, 12, 13 |
| 7 | PEG-E1-A-E2-U-H | Compound 118 (5 nmol) Compound 120 (5 nmol) | Rapamycin (10 nmol) | Compound 26 (10 nmol) | 8, 9, 10, 11, 12, 13 |
| 8 | PEG-E1-A-E2-U-H | Compound 117 (5 nmol) Compound 119 (5 nmol) | Rapamycin (10 nmol) | Compound 26 (10 nmol) | 8, 10, 12 |
| 9 | Anti-CD3 antibody; 5 μg administered IP daily, 5 times per week starting at week 10 | | | | |

Example 19: Conjugatable Treg Promoting Immunomodulators mTOR inhibitors (mTORi) were found to be effective Treg promoting immunomodulators for use in vaccines comprising peptide antigen conjugates. A potential challenge, however, is that many promising mTOR inhibitors for use in tolerance vaccines have poor aqueous solubility and/or have broad biodistribution that can lead to toxicity. In an effort to improve solubility of mTORi and restricting drug biodistribution, we evaluated approaches for covalently attaching mTORi directly to the hydrophobic blocks of peptide antigen conjugates and/or amphiphiles.

Our initial studies focused on assessing whether the Torin class of molecules can be modified to incorporate linkers that allow for covalent attachment to hydrophobic blocks of peptide antigen conjugates and/or amphiphiles. Several novel conjugatable Torin molecules were synthesized based on Torin-1 and Torin-2 with reactive handles introduced to allow for covalent attachment to hydrophobic blocks or for use as hydrophobic blocks (Table 23). The data show that modifications to both Torin-1 and Torin-2 could be made to facilitate conjugation without markedly reducing the potency for binding mTOR.

TABLE 23

Conjugatable mTOR inhibitors tested for mTOR binding affinity

| Group # | Compound # | Compound description | Dissociation constant (Kd) |
|---|---|---|---|
| 1 | 102 | Torin-2-piperazine | 0.029 |
| 2 | 103 | Torin-2-piperazine-glycine | 0.035 |
| 3 | N.A. | Torin-2 | 0.059 |
| 4 | 98 | Torin-1-piperazine | 0.059 |
| 5 | 100 | Torin-1-piperazine-glycine | 0.077 |
| 6 | N.A. | Torin-1 | 0.084 |
| 7 | 101 | Torin-2-glycine | 0.094 |
| 8 | 99 | Torin-1-dipiperazine | 0.12 |

As an additional chemical class, macrolides were also assessed for their potential use as conjugatable Treg promoting immunomodulators for use in vaccines for inducing tolerance. Accordingly, derivatives of Everolimus or Rapamycin with reactive handles were compared for potency of mTOR inhibition in vitro (FIG. 18A). Chemical modification of Everolimus to yield Everolimus-COOH (Compound 110), Everolimus-amine (Compound 108) and Everolimus-azide (Compound 109) were compared for inhibitory concentration 50 (IC50) efficacy of phospho-S6 (pS6), which is a down-stream marker of mTOR activity. Conversion of Everolimus to Everolimus-COOH (Compound 110) or Everolimus-azide (Compound 109) had no impact on IC50, whereas Everolimus-amine had a 10-fold reduction in IC50 potency (Table 25, FIG. 18A). Small molecule Everolimus derivatives with either the ZV dipeptide remaining attached (Compound 141, Everolimus-Val-Cit-nBu) or a DBCO/N3 (Compound 142, Everolimus-N3-DBCO-COOH) attached post cleavage were also investigated in vitro to assess the impact of linker fragments that could result from cleavage of the linker groups comprising peptides. The data showed that the Compound 141, ZV peptide and Compound 142, Everolimus derivatives with DBCO/N3 reduced the IC50 of Everolimus by 30- and 16-fold respectively.

Everolimus derivatives covalently attached to peptide antigen conjugates were investigated to evaluate their in vitro pS6 inhibition as well. Peptide antigen conjugates with mTOR inhibitor containing H-block are described in Table 24. Compounds 143, 144, 145 & 146 were tested for in vitro pS6 inhibition (Table 25, FIG. 18B), the results demonstrates that either amide linked (Group 7) or VZ cleavable linker-based conjugation of Everolimus-COOH to peptide antigen conjugates (Group 8) allows the mTORi to remain active. VZ cleavable linker based conjugation (Compound 144 and 146) resulted in a more potent IC50 compared to matched peptide antigen conjugates using an amide based linkage (Compound 143 and 145).

Torin-1-piperazine (Compound 98) was evaluated as a small molecule and as a conjugate compared to Torin-1 for efficacy of mTOR inhibition in vitro (FIG. 18C, Table 25). Torin-1-piperazine had a 6.3-fold reduction in IC50 potency compared to Torin-1. Torin-1-ZV (Compound 105) had an pS6 inhibition IC50 approximately equivalent to that of Torin-1-piperazine (Compound 98). Conjugated versions of Torin-1 demonstrated that the C3 linked was superior to the C1 linker for the two versions of conjugated Torin-1-piperazine tested.

TABLE 25

Compounds tested in splenocytes for mTOR inhibition by phospho-S6 assay. Analog drug molecule is listed for all compounds. Approximate half maximal inhibitory concentration (IC50) is listed in IA/IE+ cells as calculated from PBMC pS6 inhibition in nanomolar concentration.

| Group | Compound # or CAS number | Description | Drug molecule analog | Approximate IC50 |
|---|---|---|---|---|
| 1 | CAS: 1222998-36-8 | Torin-1 | Torin-1 | 23 nM |
| 2 | CAS: 53123-88-9 | Rapamycin | Rapamycin | 1 nM |
| 3 | CAS: 159351-69-6 | Everolimus | Everolimus | 1 nM |
| 7 | 143 | OH-PEG24-VZ-A-SPVZ(X-DBCO)-Ahx-WWK(Everolimus)WW | Everolimus | 150 nM |
| 8 | 144 | OH-PEG24-VZ-A-SPVZ(X-DBCO)-Ahx WWK(ZV-Everolimus) WW | Everolimus | 13 nM |
| 10 | 145 | OH-PEG24-VZ-A-SPVZK(DBCO-N3)-Everolimus | Everolimus | 185 nM |
| 11 | 146 | OH-PEG24-VZ-A-SPVZ(X-DBCO)-Ahx-VZ-Everolimus | Everolimus | 74 nM |
| 13 | 141 | nBu-ZV-Everolimus | Everolimus | 30 nM |
| 14 | 123 | DBCO-Ahx-ZV-Torin-1-C1 | Torin-1 | >500 nM |
| 15 | 124 | DBCO-Ahx-ZV-Torin-1-C3 | Torin-1 | 150 nM |
| 16 | 142 | Everolimus-N3-DBCO-acid | Everolimus | 16 nM |
| 17 | 110 | Everolimus-COOH | Everolimus | 1 nM |
| 18 | 108 | Everolimus-amine | Everolimus | 10 nM |
| 19 | 109 | Everolimus-N3 | Everolimus | 1 nM |
| 20 | 98 | Torin-1-piperazine | Torin-1 | 146 nM |
| 21 | 105 | VZ-Torin-1 | Torin-1 | 210 nM |

While the present disclosure has been described with reference to one or more embodiments, it will be understood by those skilled in the art that various changes may be made and equivalents may be substituted for elements thereof without departing from the scope of the disclosure. In addition, many modifications may be made to adapt a particular situation or material to the teachings of the disclosure without departing from the essential scope thereof. Therefore, it is intended that the disclosure not be limited to the particular embodiment disclosed as the best mode contemplated for carrying out this disclosure, but that the disclosure will include all embodiments falling within the scope of the appended claims. In addition, all numerical values identified in the detailed description shall be interpreted as though the precise and approximate values are both expressly identified.

SEQUENCE LISTING

```
Sequence total quantity: 542
SEQ ID NO: 1            moltype = AA  length = 4
FEATURE                 Location/Qualifiers
source                  1..4
                        mol_type = protein
                        organism = synthetic construct
SEQUENCE: 1
GFLG                                                                4

SEQ ID NO: 2            moltype = AA  length = 4
FEATURE                 Location/Qualifiers
source                  1..4
                        mol_type = protein
                        organism = synthetic construct
SEQUENCE: 2
KPLR                                                                4

SEQ ID NO: 3            moltype = AA  length = 4
FEATURE                 Location/Qualifiers
source                  1..4
                        mol_type = protein
                        organism = synthetic construct
SEQUENCE: 3
YLLL                                                                4

SEQ ID NO: 4            moltype = AA  length = 4
FEATURE                 Location/Qualifiers
source                  1..4
                        mol_type = protein
                        organism = synthetic construct
SEQUENCE: 4
SPLR                                                                4

SEQ ID NO: 5            moltype = AA  length = 5
FEATURE                 Location/Qualifiers
source                  1..5
                        mol_type = protein
                        organism = synthetic construct
SEQUENCE: 5
RYLLL                                                               5

SEQ ID NO: 6            moltype =   length =
SEQUENCE: 6
000

SEQ ID NO: 7            moltype = AA  length = 4
FEATURE                 Location/Qualifiers
source                  1..4
                        mol_type = protein
                        organism = synthetic construct
SEQUENCE: 7
SLVL                                                                4

SEQ ID NO: 8            moltype =   length =
SEQUENCE: 8
000

SEQ ID NO: 9            moltype = AA  length = 4
FEATURE                 Location/Qualifiers
source                  1..4
                        mol_type = protein
                        organism = synthetic construct
SEQUENCE: 9
ELVR                                                                4

SEQ ID NO: 10           moltype = AA  length = 4
FEATURE                 Location/Qualifiers
```

```
source                  1..4
                        mol_type = protein
                        organism = synthetic construct
SEQUENCE: 10
SPVR                                                                         4

SEQ ID NO: 11           moltype = AA  length = 4
FEATURE                 Location/Qualifiers
source                  1..4
                        mol_type = protein
                        organism = synthetic construct
SEQUENCE: 11
SLVR                                                                         4

SEQ ID NO: 12           moltype = AA  length = 4
FEATURE                 Location/Qualifiers
source                  1..4
                        mol_type = protein
                        organism = synthetic construct
SEQUENCE: 12
KPVR                                                                         4

SEQ ID NO: 13           moltype =   length =
SEQUENCE: 13
000

SEQ ID NO: 14           moltype = AA  length = 4
FEATURE                 Location/Qualifiers
source                  1..4
                        mol_type = protein
                        organism = synthetic construct
SEQUENCE: 14
ELVL                                                                         4

SEQ ID NO: 15           moltype =   length =
SEQUENCE: 15
000

SEQ ID NO: 16           moltype =   length =
SEQUENCE: 16
000

SEQ ID NO: 17           moltype = AA  length = 6
FEATURE                 Location/Qualifiers
source                  1..6
                        mol_type = protein
                        organism = synthetic construct
SEQUENCE: 17
GGKLVR                                                                       6

SEQ ID NO: 18           moltype = AA  length = 6
FEATURE                 Location/Qualifiers
source                  1..6
                        mol_type = protein
                        organism = synthetic construct
SEQUENCE: 18
GGKPLR                                                                       6

SEQ ID NO: 19           moltype = AA  length = 6
FEATURE                 Location/Qualifiers
source                  1..6
                        mol_type = protein
                        organism = synthetic construct
SEQUENCE: 19
GGSLVR                                                                       6

SEQ ID NO: 20           moltype = AA  length = 6
FEATURE                 Location/Qualifiers
SITE                    6
                        note = MISC_FEATURE - Xaa = Citrulline
source                  1..6
                        mol_type = protein
                        organism = synthetic construct
SEQUENCE: 20
GGSLVX                                                                       6

SEQ ID NO: 21           moltype = AA  length = 6
FEATURE                 Location/Qualifiers
SITE                    6
```

```
                        note = MISC_FEATURE - Xaa = Citrulline
source                  1..6
                        mol_type = protein
                        organism = synthetic construct
SEQUENCE: 21
GGSPVX                                                                    6

SEQ ID NO: 22           moltype = AA  length = 6
FEATURE                 Location/Qualifiers
source                  1..6
                        mol_type = protein
                        organism = synthetic construct
SEQUENCE: 22
GGSLVL                                                                    6

SEQ ID NO: 23           moltype = AA  length = 6
FEATURE                 Location/Qualifiers
source                  1..6
                        mol_type = protein
                        organism = synthetic construct
SEQUENCE: 23
GGELVR                                                                    6

SEQ ID NO: 24           moltype = AA  length = 6
FEATURE                 Location/Qualifiers
source                  1..6
                        mol_type = protein
                        organism = synthetic construct
SEQUENCE: 24
GGELVL                                                                    6

SEQ ID NO: 25           moltype = AA  length = 5
FEATURE                 Location/Qualifiers
source                  1..5
                        mol_type = protein
                        organism = synthetic construct
SEQUENCE: 25
GSLVR                                                                     5

SEQ ID NO: 26           moltype = AA  length = 5
FEATURE                 Location/Qualifiers
SITE                    5
                        note = MISC_FEATURE - Xaa = Citrulline
source                  1..5
                        mol_type = protein
                        organism = synthetic construct
SEQUENCE: 26
GSLVX                                                                     5

SEQ ID NO: 27           moltype = AA  length = 5
FEATURE                 Location/Qualifiers
SITE                    5
                        note = MISC_FEATURE - Xaa = Citrulline
source                  1..5
                        mol_type = protein
                        organism = synthetic construct
SEQUENCE: 27
GKPVX                                                                     5

SEQ ID NO: 28           moltype = AA  length = 5
FEATURE                 Location/Qualifiers
source                  1..5
                        mol_type = protein
                        organism = synthetic construct
SEQUENCE: 28
GKPVR                                                                     5

SEQ ID NO: 29           moltype = AA  length = 5
FEATURE                 Location/Qualifiers
source                  1..5
                        mol_type = protein
                        organism = synthetic construct
SEQUENCE: 29
GSLVL                                                                     5

SEQ ID NO: 30           moltype = AA  length = 5
FEATURE                 Location/Qualifiers
source                  1..5
                        mol_type = protein
```

-continued

```
                         organism = synthetic construct
SEQUENCE: 30
GELVL                                                        5

SEQ ID NO: 31            moltype =   length =
SEQUENCE: 31
000

SEQ ID NO: 32            moltype = AA  length = 12
FEATURE                  Location/Qualifiers
source                   1..12
                         mol_type = protein
                         organism = synthetic construct
SEQUENCE: 32
DDDDDDDDDD DD                                                12

SEQ ID NO: 33            moltype = AA  length = 11
FEATURE                  Location/Qualifiers
source                   1..11
                         mol_type = protein
                         organism = synthetic construct
SEQUENCE: 33
DDDDDDDDDD D                                                 11

SEQ ID NO: 34            moltype = AA  length = 10
FEATURE                  Location/Qualifiers
source                   1..10
                         mol_type = protein
                         organism = synthetic construct
SEQUENCE: 34
DDDDDDDDDD                                                   10

SEQ ID NO: 35            moltype = AA  length = 9
FEATURE                  Location/Qualifiers
source                   1..9
                         mol_type = protein
                         organism = synthetic construct
SEQUENCE: 35
DDDDDDDDD                                                    9

SEQ ID NO: 36            moltype = AA  length = 8
FEATURE                  Location/Qualifiers
source                   1..8
                         mol_type = protein
                         organism = synthetic construct
SEQUENCE: 36
DDDDDDDD                                                     8

SEQ ID NO: 37            moltype = AA  length = 7
FEATURE                  Location/Qualifiers
source                   1..7
                         mol_type = protein
                         organism = synthetic construct
SEQUENCE: 37
DDDDDDD                                                      7

SEQ ID NO: 38            moltype = AA  length = 6
FEATURE                  Location/Qualifiers
source                   1..6
                         mol_type = protein
                         organism = synthetic construct
SEQUENCE: 38
DDDDDD                                                       6

SEQ ID NO: 39            moltype = AA  length = 5
FEATURE                  Location/Qualifiers
source                   1..5
                         mol_type = protein
                         organism = synthetic construct
SEQUENCE: 39
DDDDD                                                        5

SEQ ID NO: 40            moltype = AA  length = 4
FEATURE                  Location/Qualifiers
source                   1..4
                         mol_type = protein
                         organism = synthetic construct
SEQUENCE: 40
DDDD                                                         4
```

```
SEQ ID NO: 41            moltype = AA  length = 12
FEATURE                  Location/Qualifiers
source                   1..12
                         mol_type = protein
                         organism = synthetic construct
SEQUENCE: 41
KKKKKKKKKK KK                                                            12

SEQ ID NO: 42            moltype = AA  length = 11
FEATURE                  Location/Qualifiers
source                   1..11
                         mol_type = protein
                         organism = synthetic construct
SEQUENCE: 42
KKKKKKKKKK K                                                             11

SEQ ID NO: 43            moltype = AA  length = 10
FEATURE                  Location/Qualifiers
source                   1..10
                         mol_type = protein
                         organism = synthetic construct
SEQUENCE: 43
KKKKKKKKKK                                                               10

SEQ ID NO: 44            moltype = AA  length = 9
FEATURE                  Location/Qualifiers
source                   1..9
                         mol_type = protein
                         organism = synthetic construct
SEQUENCE: 44
KKKKKKKKK                                                                9

SEQ ID NO: 45            moltype = AA  length = 8
FEATURE                  Location/Qualifiers
source                   1..8
                         mol_type = protein
                         organism = synthetic construct
SEQUENCE: 45
KKKKKKKK                                                                 8

SEQ ID NO: 46            moltype = AA  length = 7
FEATURE                  Location/Qualifiers
source                   1..7
                         mol_type = protein
                         organism = synthetic construct
SEQUENCE: 46
KKKKKKK                                                                  7

SEQ ID NO: 47            moltype = AA  length = 6
FEATURE                  Location/Qualifiers
source                   1..6
                         mol_type = protein
                         organism = synthetic construct
SEQUENCE: 47
KKKKKK                                                                   6

SEQ ID NO: 48            moltype = AA  length = 5
FEATURE                  Location/Qualifiers
source                   1..5
                         mol_type = protein
                         organism = synthetic construct
SEQUENCE: 48
KKKKK                                                                    5

SEQ ID NO: 49            moltype = AA  length = 4
FEATURE                  Location/Qualifiers
source                   1..4
                         mol_type = protein
                         organism = synthetic construct
SEQUENCE: 49
KKKK                                                                     4

SEQ ID NO: 50            moltype = AA  length = 4
FEATURE                  Location/Qualifiers
source                   1..4
                         mol_type = protein
                         organism = synthetic construct
SEQUENCE: 50
```

```
KDKD                                                                4

SEQ ID NO: 51           moltype = AA  length = 6
FEATURE                 Location/Qualifiers
source                  1..6
                        mol_type = protein
                        organism = synthetic construct
SEQUENCE: 51
KDKDKD                                                              6

SEQ ID NO: 52           moltype = AA  length = 28
FEATURE                 Location/Qualifiers
source                  1..28
                        mol_type = protein
                        organism = synthetic construct
SEQUENCE: 52
RGYLTKILHV FHGLLPGFLV KMSGDLLE                                      28

SEQ ID NO: 53           moltype = AA  length = 13
FEATURE                 Location/Qualifiers
source                  1..13
                        mol_type = protein
                        organism = synthetic construct
SEQUENCE: 53
PGFLVKMSGD LLE                                                      13

SEQ ID NO: 54           moltype = AA  length = 13
FEATURE                 Location/Qualifiers
SITE                    7
                        note = MISC_FEATURE - Xaa = Norleucine
source                  1..13
                        mol_type = protein
                        organism = synthetic construct
SEQUENCE: 54
PGFLVKXSGD LLE                                                      13

SEQ ID NO: 55           moltype = AA  length = 13
FEATURE                 Location/Qualifiers
source                  1..13
                        mol_type = protein
                        organism = synthetic construct
SEQUENCE: 55
PGFLVKMSSD LLG                                                      13

SEQ ID NO: 56           moltype = AA  length = 13
FEATURE                 Location/Qualifiers
SITE                    7
                        note = MISC_FEATURE - Xaa = Norleucine
source                  1..13
                        mol_type = protein
                        organism = synthetic construct
SEQUENCE: 56
PGFLVKXSSD LLG                                                      13

SEQ ID NO: 57           moltype = AA  length = 13
FEATURE                 Location/Qualifiers
source                  1..13
                        mol_type = protein
                        organism = synthetic construct
SEQUENCE: 57
SIPWNLERIT PPR                                                      13

SEQ ID NO: 58           moltype = AA  length = 13
FEATURE                 Location/Qualifiers
source                  1..13
                        mol_type = protein
                        organism = synthetic construct
SEQUENCE: 58
SIPWNLERIT PPR                                                      13

SEQ ID NO: 59           moltype = AA  length = 7
FEATURE                 Location/Qualifiers
source                  1..7
                        mol_type = protein
                        organism = synthetic construct
SEQUENCE: 59
SIPWNLE                                                             7

SEQ ID NO: 60           moltype = AA  length = 13
```

-continued

```
FEATURE                Location/Qualifiers
source                 1..13
                       mol_type = protein
                       organism = synthetic construct
SEQUENCE: 60
SIPWNLEKVT PPR                                              13

SEQ ID NO: 61          moltype = AA  length = 13
FEATURE                Location/Qualifiers
source                 1..13
                       mol_type = protein
                       organism = synthetic construct
SEQUENCE: 61
SIPWNLDRVT PPR                                              13

SEQ ID NO: 62          moltype = AA  length = 17
FEATURE                Location/Qualifiers
source                 1..17
                       mol_type = protein
                       organism = synthetic construct
SEQUENCE: 62
NVPEEDGTRF HRQASKC                                          17

SEQ ID NO: 63          moltype = AA  length = 16
FEATURE                Location/Qualifiers
source                 1..16
                       mol_type = protein
                       organism = synthetic construct
SEQUENCE: 63
NVPEEDGTRF HRQASK                                           16

SEQ ID NO: 64          moltype = AA  length = 7
FEATURE                Location/Qualifiers
source                 1..7
                       mol_type = protein
                       organism = synthetic construct
SEQUENCE: 64
PEEDGTR                                                     7

SEQ ID NO: 65          moltype = AA  length = 7
FEATURE                Location/Qualifiers
source                 1..7
                       mol_type = protein
                       organism = synthetic construct
SEQUENCE: 65
NVPEEDG                                                     7

SEQ ID NO: 66          moltype = AA  length = 16
FEATURE                Location/Qualifiers
source                 1..16
                       mol_type = protein
                       organism = synthetic construct
SEQUENCE: 66
NVPEEDATRF HRQGSK                                           16

SEQ ID NO: 67          moltype = AA  length = 30
FEATURE                Location/Qualifiers
source                 1..30
                       mol_type = protein
                       organism = synthetic construct
SEQUENCE: 67
LFAPGEDIIG ASSDCSTCFV SQSGTSQAAA                            30

SEQ ID NO: 68          moltype = AA  length = 16
FEATURE                Location/Qualifiers
source                 1..16
                       mol_type = protein
                       organism = synthetic construct
SEQUENCE: 68
CSTCFVSQSG TSQAAA                                           16

SEQ ID NO: 69          moltype = AA  length = 15
FEATURE                Location/Qualifiers
source                 1..15
                       mol_type = protein
                       organism = synthetic construct
SEQUENCE: 69
STCFVSQSGT SQAAA                                            15
```

```
SEQ ID NO: 70          moltype = AA  length = 15
FEATURE                Location/Qualifiers
SITE                   3
                       note = MISC_FEATURE - Xaa = beta Alanine
source                 1..15
                       mol_type = protein
                       organism = synthetic construct
SEQUENCE: 70
STXFVSQSGT SQAAA                                                   15

SEQ ID NO: 71          moltype = AA  length = 7
FEATURE                Location/Qualifiers
SITE                   3
                       note = MISC_FEATURE - Xaa = beta Alanine
source                 1..7
                       mol_type = protein
                       organism = synthetic construct
SEQUENCE: 71
STXFVSQ                                                            7

SEQ ID NO: 72          moltype = AA  length = 70
FEATURE                Location/Qualifiers
source                 1..70
                       mol_type = protein
                       organism = synthetic construct
SEQUENCE: 72
MFTIKLLLFI VPLVISSRID QDNSSFDSLS PEPKSRFAML DDVKILANGL LQLGHGLKDF  60
VHKTKGQIND                                                         70

SEQ ID NO: 73          moltype = AA  length = 39
FEATURE                Location/Qualifiers
source                 1..39
                       mol_type = protein
                       organism = synthetic construct
SEQUENCE: 73
EPKSRFAMLD DVKILANGLL QLGHGLKDFV HKTKGQIND                         39

SEQ ID NO: 74          moltype = AA  length = 14
FEATURE                Location/Qualifiers
source                 1..14
                       mol_type = protein
                       organism = synthetic construct
SEQUENCE: 74
EPKSRFAMLD DVKI                                                    14

SEQ ID NO: 75          moltype = AA  length = 14
FEATURE                Location/Qualifiers
source                 1..14
                       mol_type = protein
                       organism = synthetic construct
SEQUENCE: 75
MLDDVKILAN GLLQ                                                    14

SEQ ID NO: 76          moltype = AA  length = 14
FEATURE                Location/Qualifiers
source                 1..14
                       mol_type = protein
                       organism = synthetic construct
SEQUENCE: 76
LANGLLQLGH GLKD                                                    14

SEQ ID NO: 77          moltype = AA  length = 14
FEATURE                Location/Qualifiers
source                 1..14
                       mol_type = protein
                       organism = synthetic construct
SEQUENCE: 77
LGHGLKDFVH KTKG                                                    14

SEQ ID NO: 78          moltype = AA  length = 14
FEATURE                Location/Qualifiers
source                 1..14
                       mol_type = protein
                       organism = synthetic construct
SEQUENCE: 78
LKDFVHKTKG QIND                                                    14

SEQ ID NO: 79          moltype = AA  length = 20
FEATURE                Location/Qualifiers
```

```
source                  1..20
                        mol_type = protein
                        organism = synthetic construct
SEQUENCE: 79
RFAMLDDVKI LANGLLQLGH                                              20

SEQ ID NO: 80           moltype = AA  length = 20
FEATURE                 Location/Qualifiers
source                  1..20
                        mol_type = protein
                        organism = synthetic construct
SEQUENCE: 80
GLLQLGHGLK DFVHKTKGQI                                              20

SEQ ID NO: 81           moltype = AA  length = 69
FEATURE                 Location/Qualifiers
source                  1..69
                        mol_type = protein
                        organism = synthetic construct
SEQUENCE: 81
IFQKLNIFDQ SFYDLSLQTS EIKEEEKELR RTTYKLQVKN EEVKNMSLEL NSKLESLLEE  60
KILLQQKVK                                                          69

SEQ ID NO: 82           moltype = AA  length = 29
FEATURE                 Location/Qualifiers
source                  1..29
                        mol_type = protein
                        organism = Human papillomavirus
SEQUENCE: 82
MHQKRTAMFQ DPQERPRKLP QLCTELQTT                                    29

SEQ ID NO: 83           moltype = AA  length = 29
FEATURE                 Location/Qualifiers
source                  1..29
                        mol_type = protein
                        organism = Human papillomavirus
SEQUENCE: 83
PRKLPQLCTE LQTTIHDIIL ECVYCKQQL                                    29

SEQ ID NO: 84           moltype = AA  length = 29
FEATURE                 Location/Qualifiers
source                  1..29
                        mol_type = protein
                        organism = Human papillomavirus
SEQUENCE: 84
HDIILECVYC KQQLLRREVY DFAFRDLCI                                    29

SEQ ID NO: 85           moltype = AA  length = 29
FEATURE                 Location/Qualifiers
source                  1..29
                        mol_type = protein
                        organism = Human papillomavirus
SEQUENCE: 85
RREVYDFAFR DLCIVYRDGN PYAVCDKCL                                    29

SEQ ID NO: 86           moltype = AA  length = 29
FEATURE                 Location/Qualifiers
source                  1..29
                        mol_type = protein
                        organism = Human papillomavirus
SEQUENCE: 86
YRDGNPYAVC DKCLKFYSKI SEYRHYCYS                                    29

SEQ ID NO: 87           moltype = AA  length = 29
FEATURE                 Location/Qualifiers
source                  1..29
                        mol_type = protein
                        organism = Human papillomavirus
SEQUENCE: 87
FYSKISEYRH YCYSLYGTTL EQQYNKPLC                                    29

SEQ ID NO: 88           moltype = AA  length = 29
FEATURE                 Location/Qualifiers
source                  1..29
                        mol_type = protein
                        organism = Human papillomavirus
SEQUENCE: 88
YGTTLEQQYN KPLCDLLIRC INCQKPLCP                                    29
```

-continued

```
SEQ ID NO: 89          moltype = AA  length = 29
FEATURE                Location/Qualifiers
source                 1..29
                       mol_type = protein
                       organism = Human papillomavirus
SEQUENCE: 89
LLIRCINCQK PLCPEEKQRH LDKKQRFHN                                29

SEQ ID NO: 90          moltype = AA  length = 28
FEATURE                Location/Qualifiers
source                 1..28
                       mol_type = protein
                       organism = Human papillomavirus
SEQUENCE: 90
EKQRHLDKKQ RFHNIRGRWT GRCMSCCR                                 28

SEQ ID NO: 91          moltype = AA  length = 24
FEATURE                Location/Qualifiers
source                 1..24
                       mol_type = protein
                       organism = Human papillomavirus
SEQUENCE: 91
IRGRWTGRCM SCCRSSRTRR ETQL                                     24

SEQ ID NO: 92          moltype = AA  length = 27
FEATURE                Location/Qualifiers
source                 1..27
                       mol_type = protein
                       organism = Human papillomavirus
SEQUENCE: 92
MHGDTPTLHE YMLDLQPETT DLYCYEQ                                  27

SEQ ID NO: 93          moltype = AA  length = 25
FEATURE                Location/Qualifiers
source                 1..25
                       mol_type = protein
                       organism = Human papillomavirus
SEQUENCE: 93
DLQPETTDLY CYEQLNDSSE EEDEI                                    25

SEQ ID NO: 94          moltype = AA  length = 25
FEATURE                Location/Qualifiers
source                 1..25
                       mol_type = protein
                       organism = Human papillomavirus
SEQUENCE: 94
YEQLNDSSEE EDEIDGPAGQ AEPDR                                    25

SEQ ID NO: 95          moltype = AA  length = 27
FEATURE                Location/Qualifiers
source                 1..27
                       mol_type = protein
                       organism = Human papillomavirus
SEQUENCE: 95
DEIDGPAGQA EPDRAHYNIV TFCCKCD                                  27

SEQ ID NO: 96          moltype = AA  length = 32
FEATURE                Location/Qualifiers
source                 1..32
                       mol_type = protein
                       organism = Human papillomavirus
SEQUENCE: 96
RAHYNIVTFC CKCDSTLRLC VQSTHVDIRT LE                            32

SEQ ID NO: 97          moltype = AA  length = 32
FEATURE                Location/Qualifiers
source                 1..32
                       mol_type = protein
                       organism = Human papillomavirus
SEQUENCE: 97
LCVQSTHVDI RTLEDLLMGT LGIVCPICSQ KP                            32

SEQ ID NO: 98          moltype = AA  length = 20
FEATURE                Location/Qualifiers
source                 1..20
                       mol_type = protein
                       organism = Human papillomavirus
SEQUENCE: 98
QLYQTCKAAG TCPSDVIPKI                                          20
```

```
SEQ ID NO: 99          moltype = AA  length = 29
FEATURE                Location/Qualifiers
SITE                   8
                       note = MISC_FEATURE - Xaa = Norleucine
SITE                   1
                       note = MISC_FEATURE - Xaa = Norleucine
source                 1..29
                       mol_type = protein
                       organism = Human papillomavirus
SEQUENCE: 99
XHQKRTAXFQ DPQERPRKLP QLCTELQTT                                    29

SEQ ID NO: 100         moltype = AA  length = 29
FEATURE                Location/Qualifiers
SITE                   23
                       note = MISC_FEATURE - Xaa = beta Alanine
source                 1..29
                       mol_type = protein
                       organism = Human papillomavirus
SEQUENCE: 100
MHQKRTAMFQ DPQERPRKLP QLXTELQTT                                    29

SEQ ID NO: 101         moltype = AA  length = 29
FEATURE                Location/Qualifiers
SITE                   8
                       note = MISC_FEATURE - Xaa = beta Alanine
SITE                   22
                       note = MISC_FEATURE - Xaa = beta Alanine
SITE                   25
                       note = MISC_FEATURE - Xaa = beta Alanine
source                 1..29
                       mol_type = protein
                       organism = Human papillomavirus
SEQUENCE: 101
PRKLPQLXTE LQTTIHDIIL EXVYXKQQL                                    29

SEQ ID NO: 102         moltype = AA  length = 29
FEATURE                Location/Qualifiers
SITE                   7
                       note = MISC_FEATURE - Xaa = beta Alanine
SITE                   10
                       note = MISC_FEATURE - Xaa = beta Alanine
SITE                   28
                       note = MISC_FEATURE - Xaa = beta Alanine
source                 1..29
                       mol_type = protein
                       organism = Human papillomavirus
SEQUENCE: 102
HDIILEXVYX KQQLLRREVY DFAFRDLXI                                    29

SEQ ID NO: 103         moltype = AA  length = 29
FEATURE                Location/Qualifiers
SITE                   13
                       note = MISC_FEATURE - Xaa = beta Alanine
SITE                   25
                       note = MISC_FEATURE - Xaa = beta Alanine
SITE                   28
                       note = MISC_FEATURE - Xaa = beta Alanine
source                 1..29
                       mol_type = protein
                       organism = Human papillomavirus
SEQUENCE: 103
RREVYDFAFR DLXIVYRDGN PYAVXDKXL                                    29

SEQ ID NO: 104         moltype = AA  length = 29
FEATURE                Location/Qualifiers
SITE                   10
                       note = MISC_FEATURE - Xaa = beta Alanine
SITE                   13
                       note = MISC_FEATURE - Xaa = beta Alanine
SITE                   27
                       note = MISC_FEATURE - Xaa = beta Alanine
source                 1..29
                       mol_type = protein
                       organism = Human papillomavirus
SEQUENCE: 104
YRDGNPYAVX DKXLKFYSKI SEYRHYXYS                                    29
```

```
SEQ ID NO: 105          moltype = AA  length = 29
FEATURE                 Location/Qualifiers
SITE                    12
                        note = MISC_FEATURE - Xaa = beta Alanine
SITE                    29
                        note = MISC_FEATURE - Xaa = beta Alanine
source                  1..29
                        mol_type = protein
                        organism = Human papillomavirus
SEQUENCE: 105
FYSKISEYRH YXYSLYGTTL EQQYNKPLX                                     29

SEQ ID NO: 106          moltype = AA  length = 28
FEATURE                 Location/Qualifiers
SITE                    19
                        note = MISC_FEATURE - Xaa = beta Alanine
SITE                    22
                        note = MISC_FEATURE - Xaa = beta Alanine
SITE                    27
                        note = MISC_FEATURE - Xaa = beta Alanine
source                  1..28
                        mol_type = protein
                        organism = Human papillomavirus
SEQUENCE: 106
YGTTLEQQYN KPLDLLIRXI NXQKPLXP                                      28

SEQ ID NO: 107          moltype = AA  length = 29
FEATURE                 Location/Qualifiers
SITE                    5
                        note = MISC_FEATURE - Xaa = beta Alanine
SITE                    8
                        note = MISC_FEATURE - Xaa = beta Alanine
SITE                    13
                        note = MISC_FEATURE - Xaa = beta Alanine
source                  1..29
                        mol_type = protein
                        organism = Human papillomavirus
SEQUENCE: 107
LLIRXINXQK PLXPEEKQRH LDKKQRFHN                                     29

SEQ ID NO: 108          moltype = AA  length = 28
FEATURE                 Location/Qualifiers
SITE                    24
                        note = MISC_FEATURE - Xaa = Norleucine
source                  1..28
                        mol_type = protein
                        organism = Human papillomavirus
SEQUENCE: 108
EKQRHLDKKQ RFHNIRGRWT GRCXSCCR                                      28

SEQ ID NO: 109          moltype = AA  length = 28
FEATURE                 Location/Qualifiers
SITE                    23
                        note = MISC_FEATURE - Xaa = beta Alanine
SITE                    24
                        note = MISC_FEATURE - Xaa = Norleucine
SITE                    26
                        note = MISC_FEATURE - Xaa = beta Alanine
SITE                    27
                        note = MISC_FEATURE - Xaa = beta Alanine
source                  1..28
                        mol_type = protein
                        organism = Human papillomavirus
SEQUENCE: 109
EKQRHLDKKQ RFHNIRGRWT GRXXSXXR                                      28

SEQ ID NO: 110          moltype = AA  length = 28
FEATURE                 Location/Qualifiers
SITE                    23
                        note = MISC_FEATURE - Xaa = beta Alanine
SITE                    26
                        note = MISC_FEATURE - Xaa = beta Alanine
SITE                    27
                        note = MISC_FEATURE - Xaa = beta Alanine
source                  1..28
                        mol_type = protein
                        organism = Human papillomavirus
SEQUENCE: 110
EKQRHLDKKQ RFHNIRGRWT GRXMSXXR                                      28
```

```
SEQ ID NO: 111          moltype = AA  length = 24
FEATURE                 Location/Qualifiers
SITE                    10
                        note = MISC_FEATURE - Xaa = Norleucine
source                  1..24
                        mol_type = protein
                        organism = Human papillomavirus
SEQUENCE: 111
IRGRWTGRCX SCCRSSRTRR ETQL                                        24

SEQ ID NO: 112          moltype = AA  length = 24
FEATURE                 Location/Qualifiers
SITE                    9
                        note = MISC_FEATURE - Xaa = beta Alanine
SITE                    10
                        note = MISC_FEATURE - Xaa = Norleucine
SITE                    12
                        note = MISC_FEATURE - Xaa = beta Alanine
SITE                    13
                        note = MISC_FEATURE - Xaa = beta Alanine
source                  1..24
                        mol_type = protein
                        organism = Human papillomavirus
SEQUENCE: 112
IRGRWTGRXX SXXRSSRTRR ETQL                                        24

SEQ ID NO: 113          moltype = AA  length = 24
FEATURE                 Location/Qualifiers
SITE                    9
                        note = MISC_FEATURE - Xaa = beta Alanine
SITE                    12
                        note = MISC_FEATURE - Xaa = beta Alanine
SITE                    13
                        note = MISC_FEATURE - Xaa = beta Alanine
source                  1..24
                        mol_type = protein
                        organism = Human papillomavirus
SEQUENCE: 113
IRGRWTGRXM SXXRSSRTRR ETQL                                        24

SEQ ID NO: 114          moltype = AA  length = 27
FEATURE                 Location/Qualifiers
SITE                    1
                        note = MISC_FEATURE - Xaa = Norleucine
SITE                    12
                        note = MISC_FEATURE - Xaa = Norleucine
source                  1..27
                        mol_type = protein
                        organism = Human papillomavirus
SEQUENCE: 114
XHGDTPTLHE YXLDLQPETT DLYCYEQ                                     27

SEQ ID NO: 115          moltype = AA  length = 26
FEATURE                 Location/Qualifiers
SITE                    11
                        note = MISC_FEATURE - Xaa = Norleucine
SITE                    23
                        note = MISC_FEATURE - Xaa = beta Alanine
source                  1..26
                        mol_type = protein
                        organism = Human papillomavirus
SEQUENCE: 115
HGDTPTLHEY XLDLQPETTD LYXYEQ                                      26

SEQ ID NO: 116          moltype = AA  length = 27
FEATURE                 Location/Qualifiers
SITE                    1
                        note = MISC_FEATURE - Xaa = Norleucine
SITE                    12
                        note = MISC_FEATURE - Xaa = Norleucine
source                  1..27
                        mol_type = protein
                        organism = Human papillomavirus
SEQUENCE: 116
XHGDTPTLHE YXLDLQPETT DLYMYEQ                                     27

SEQ ID NO: 117          moltype = AA  length = 25
FEATURE                 Location/Qualifiers
```

```
SITE                    11
                        note = MISC_FEATURE - Xaa = beta Alanine
source                  1..25
                        mol_type = protein
                        organism = Human papillomavirus
SEQUENCE: 117
DLQPETTDLY XYEQLNDSSE EEDEI                                        25

SEQ ID NO: 118          moltype = AA  length = 25
FEATURE                 Location/Qualifiers
source                  1..25
                        mol_type = protein
                        organism = Human papillomavirus
SEQUENCE: 118
YEQLNDSSEE EDEIDGPAGQ AEPDR                                        25

SEQ ID NO: 119          moltype = AA  length = 27
FEATURE                 Location/Qualifiers
SITE                    23
                        note = MISC_FEATURE - Xaa = beta Alanine
SITE                    24
                        note = MISC_FEATURE - Xaa = beta Alanine
SITE                    26
                        note = MISC_FEATURE - Xaa = beta Alanine
source                  1..27
                        mol_type = protein
                        organism = Human papillomavirus
SEQUENCE: 119
DEIDGPAGQA EPDRAHYNIV TFXXKXD                                      27

SEQ ID NO: 120          moltype = AA  length = 32
FEATURE                 Location/Qualifiers
SITE                    10
                        note = MISC_FEATURE - Xaa = beta Alanine
SITE                    11
                        note = MISC_FEATURE - Xaa = beta Alanine
SITE                    13
                        note = MISC_FEATURE - Xaa = beta Alanine
SITE                    20
                        note = MISC_FEATURE - Xaa = beta Alanine
source                  1..32
                        mol_type = protein
                        organism = Human papillomavirus
SEQUENCE: 120
RAHYNIVTFX XKXDSTLRLX VQSTHVDIRT LE                                32

SEQ ID NO: 121          moltype = AA  length = 32
FEATURE                 Location/Qualifiers
SITE                    18
                        note = MISC_FEATURE - Xaa = Norleucine
source                  1..32
                        mol_type = protein
                        organism = Human papillomavirus
SEQUENCE: 121
LCVQSTHVDI RTLEDLLXGT LGIVCPICSQ KP                                32

SEQ ID NO: 122          moltype = AA  length = 32
FEATURE                 Location/Qualifiers
SITE                    2
                        note = MISC_FEATURE - Xaa = beta Alanine
SITE                    18
                        note = MISC_FEATURE - Xaa = Norleucine
SITE                    25
                        note = MISC_FEATURE - Xaa = beta Alanine
SITE                    28
                        note = MISC_FEATURE - Xaa = beta Alanine
source                  1..32
                        mol_type = protein
                        organism = Human papillomavirus
SEQUENCE: 122
LXVQSTHVDI RTLEDLLXGT LGIVXPIXSQ KP                                32

SEQ ID NO: 123          moltype = AA  length = 32
FEATURE                 Location/Qualifiers
SITE                    2
                        note = MISC_FEATURE - Xaa = beta Alanine
SITE                    25
                        note = MISC_FEATURE - Xaa = beta Alanine
SITE                    28
```

```
                         note = MISC_FEATURE - Xaa = beta Alanine
source                   1..32
                         mol_type = protein
                         organism = Human papillomavirus
SEQUENCE: 123
LXVQSTHVDI RTLEDLLMGT LGIVXPIXSQ KP                                32

SEQ ID NO: 124           moltype = AA  length = 20
FEATURE                  Location/Qualifiers
SITE                     6
                         note = MISC_FEATURE - Xaa = beta Alanine
SITE                     12
                         note = MISC_FEATURE - Xaa = beta Alanine
source                   1..20
                         mol_type = protein
                         organism = Human papillomavirus
SEQUENCE: 124
QLYQTXKAAG TXPSDVIPKI                                              20

SEQ ID NO: 125           moltype = AA  length = 29
FEATURE                  Location/Qualifiers
source                   1..29
                         mol_type = protein
                         organism = Human papillomavirus
SEQUENCE: 125
ALQAIELQLT LETIYNSQYS NEKWTLQDV                                    29

SEQ ID NO: 126           moltype = AA  length = 29
FEATURE                  Location/Qualifiers
source                   1..29
                         mol_type = protein
                         organism = Human papillomavirus
SEQUENCE: 126
NSQYSNEKWT LQDVSLEVYL TAPTGCIKK                                    29

SEQ ID NO: 127           moltype = AA  length = 29
FEATURE                  Location/Qualifiers
source                   1..29
                         mol_type = protein
                         organism = Human papillomavirus
SEQUENCE: 127
SVTVVEGQVD YYGLYYVHEG IRTYFVQFK                                    29

SEQ ID NO: 128           moltype = AA  length = 32
FEATURE                  Location/Qualifiers
source                   1..32
                         mol_type = protein
                         organism = Human papillomavirus
SEQUENCE: 128
LKGDANTLKC LRYRFKKHCT LYTAVSSTWH WT                                32

SEQ ID NO: 129           moltype = AA  length = 29
FEATURE                  Location/Qualifiers
source                   1..29
                         mol_type = protein
                         organism = Human papillomavirus
SEQUENCE: 129
KHKSAIVTLT YDSEWQRDQF LSQVKIPKT                                    29

SEQ ID NO: 130           moltype = AA  length = 29
FEATURE                  Location/Qualifiers
source                   1..29
                         mol_type = protein
                         organism = Human papillomavirus
SEQUENCE: 130
MHQKRTAMFQ DPQERPRKLP QLCTELQTT                                    29

SEQ ID NO: 131           moltype = AA  length = 29
FEATURE                  Location/Qualifiers
source                   1..29
                         mol_type = protein
                         organism = Human papillomavirus
SEQUENCE: 131
PRKLPQLCTE LQTTIHDIIL ECVYCKQQL                                    29

SEQ ID NO: 132           moltype = AA  length = 29
FEATURE                  Location/Qualifiers
source                   1..29
                         mol_type = protein
```

```
                         organism = Human papillomavirus
SEQUENCE: 132
HDIILECVYC KQQLLRREVY DFAFRDLCI                                         29

SEQ ID NO: 133           moltype = AA  length = 29
FEATURE                  Location/Qualifiers
source                   1..29
                         mol_type = protein
                         organism = Human papillomavirus
SEQUENCE: 133
RREVYDFAFR DLCIVYRDGN PYAVCDKCL                                         29

SEQ ID NO: 134           moltype = AA  length = 29
FEATURE                  Location/Qualifiers
source                   1..29
                         mol_type = protein
                         organism = Human papillomavirus
SEQUENCE: 134
YRDGNPYAVC DKCLKFYSKI SEYRHYCYS                                         29

SEQ ID NO: 135           moltype = AA  length = 29
FEATURE                  Location/Qualifiers
source                   1..29
                         mol_type = protein
                         organism = Human papillomavirus
SEQUENCE: 135
FYSKISEYRH YCYSLYGTTL EQQYNKPLC                                         29

SEQ ID NO: 136           moltype = AA  length = 29
FEATURE                  Location/Qualifiers
source                   1..29
                         mol_type = protein
                         organism = Human papillomavirus
SEQUENCE: 136
YGTTLEQQYN KPLCDLLIRC INCQKPLCP                                         29

SEQ ID NO: 137           moltype = AA  length = 31
FEATURE                  Location/Qualifiers
source                   1..31
                         mol_type = protein
                         organism = Human papillomavirus
SEQUENCE: 137
CPEEKQRHLD KKQRFHNIRG RWTGRCMSCC R                                      31

SEQ ID NO: 138           moltype = AA  length = 27
FEATURE                  Location/Qualifiers
source                   1..27
                         mol_type = protein
                         organism = Human papillomavirus
SEQUENCE: 138
MHGDTPTLHE YMLDLQPETT DLYCYEQ                                           27

SEQ ID NO: 139           moltype = AA  length = 29
FEATURE                  Location/Qualifiers
source                   1..29
                         mol_type = protein
                         organism = Human papillomavirus
SEQUENCE: 139
AGQAEPDRAH YNIVTFCCKC DSTLRLCVQ                                         29

SEQ ID NO: 140           moltype = AA  length = 32
FEATURE                  Location/Qualifiers
source                   1..32
                         mol_type = protein
                         organism = Human papillomavirus
SEQUENCE: 140
LCVQSTHVDI RTLEDLLMGT LGIVCPICSQ KP                                     32

SEQ ID NO: 141           moltype = AA  length = 29
FEATURE                  Location/Qualifiers
SITE                     26
                         note = MISC_FEATURE - Xaa = beta Alanine
source                   1..29
                         mol_type = protein
                         organism = Human papillomavirus
SEQUENCE: 141
NSQYSNEKWT LQDVSLEVYL TAPTGXIKK                                         29

SEQ ID NO: 142           moltype = AA  length = 32
```

-continued

```
FEATURE                 Location/Qualifiers
SITE                    10
                        note = MISC_FEATURE - Xaa = beta Alanine
SITE                    19
                        note = MISC_FEATURE - Xaa = beta Alanine
source                  1..32
                        mol_type = protein
                        organism = Human papillomavirus
SEQUENCE: 142
LKGDANTLKX LRYRFKKHXT LYTAVSSTWH WT                                 32

SEQ ID NO: 143          moltype = AA  length = 29
FEATURE                 Location/Qualifiers
SITE                    1
                        note = MISC_FEATURE - Xaa = Norleucine
SITE                    8
                        note = MISC_FEATURE - Xaa = Norleucine
SITE                    23
                        note = MISC_FEATURE - Xaa = beta Alanine
source                  1..29
                        mol_type = protein
                        organism = Human papillomavirus
SEQUENCE: 143
XHQKRTAXFQ DPQERPRKLP QLXTELQTT                                     29

SEQ ID NO: 144          moltype = AA  length = 29
FEATURE                 Location/Qualifiers
SITE                    8
                        note = MISC_FEATURE - Xaa = beta Alanine
SITE                    22
                        note = MISC_FEATURE - Xaa = beta Alanine
SITE                    25
                        note = MISC_FEATURE - Xaa = beta Alanine
source                  1..29
                        mol_type = protein
                        organism = Human papillomavirus
SEQUENCE: 144
PRKLPQLXTE LQTTIHDIIL EXVYXKQQL                                     29

SEQ ID NO: 145          moltype = AA  length = 29
FEATURE                 Location/Qualifiers
SITE                    7
                        note = MISC_FEATURE - Xaa = beta Alanine
SITE                    10
                        note = MISC_FEATURE - Xaa = beta Alanine
SITE                    28
                        note = MISC_FEATURE - Xaa = beta Alanine
source                  1..29
                        mol_type = protein
                        organism = Human papillomavirus
SEQUENCE: 145
HDIILEXVYX KQQLLRREVY DFAFRDLXI                                     29

SEQ ID NO: 146          moltype = AA  length = 29
FEATURE                 Location/Qualifiers
SITE                    13
                        note = MISC_FEATURE - Xaa = beta Alanine
SITE                    25
                        note = MISC_FEATURE - Xaa = beta Alanine
SITE                    28
                        note = MISC_FEATURE - Xaa = beta Alanine
source                  1..29
                        mol_type = protein
                        organism = Human papillomavirus
SEQUENCE: 146
RREVYDFAFR DLXIVYRDGN PYAVXDKXL                                     29

SEQ ID NO: 147          moltype = AA  length = 29
FEATURE                 Location/Qualifiers
SITE                    10
                        note = MISC_FEATURE - Xaa = beta Alanine
SITE                    13
                        note = MISC_FEATURE - Xaa = beta Alanine
SITE                    27
                        note = MISC_FEATURE - Xaa = beta Alanine
source                  1..29
                        mol_type = protein
                        organism = Human papillomavirus
SEQUENCE: 147
```

```
YRDGNPYAVX DKXLKFYSKI SEYRHYXYS                                  29

SEQ ID NO: 148          moltype = AA  length = 29
FEATURE                 Location/Qualifiers
SITE                    12
                        note = MISC_FEATURE - Xaa = beta Alanine
SITE                    29
                        note = MISC_FEATURE - Xaa = beta Alanine
source                  1..29
                        mol_type = protein
                        organism = Human papillomavirus
SEQUENCE: 148
FYSKISEYRH YXYSLYGTTL EQQYNKPLX                                  29

SEQ ID NO: 149          moltype = AA  length = 29
FEATURE                 Location/Qualifiers
SITE                    14
                        note = MISC_FEATURE - Xaa = beta Alanine
SITE                    20
                        note = MISC_FEATURE - Xaa = beta Alanine
SITE                    23
                        note = MISC_FEATURE - Xaa = beta Alanine
SITE                    28
                        note = MISC_FEATURE - Xaa = beta Alanine
source                  1..29
                        mol_type = protein
                        organism = Human papillomavirus
SEQUENCE: 149
YGTTLEQQYN KPLXDLLIRX INXQKPLXP                                  29

SEQ ID NO: 150          moltype = AA  length = 31
FEATURE                 Location/Qualifiers
SITE                    1
                        note = MISC_FEATURE - Xaa = beta Alanine
SITE                    26
                        note = MISC_FEATURE - Xaa = beta Alanine
SITE                    27
                        note = MISC_FEATURE - Xaa = Norleucine
SITE                    29
                        note = MISC_FEATURE - Xaa = beta Alanine
SITE                    30
                        note = MISC_FEATURE - Xaa = beta Alanine
source                  1..31
                        mol_type = protein
                        organism = Human papillomavirus
SEQUENCE: 150
XPEEKQRHLD KKQRFHNIRG RWTGRXXSXX R                               31

SEQ ID NO: 151          moltype = AA  length = 27
FEATURE                 Location/Qualifiers
SITE                    1
                        note = MISC_FEATURE - Xaa = Norleucine
SITE                    24
                        note = MISC_FEATURE - Xaa = beta Alanine
source                  1..27
                        mol_type = protein
                        organism = Human papillomavirus
SEQUENCE: 151
XHGDTPTLHE YNLDLQPETT DLYXYEQ                                    27

SEQ ID NO: 152          moltype = AA  length = 29
FEATURE                 Location/Qualifiers
SITE                    17
                        note = MISC_FEATURE - Xaa = beta Alanine
SITE                    18
                        note = MISC_FEATURE - Xaa = beta Alanine
SITE                    20
                        note = MISC_FEATURE - Xaa = beta Alanine
SITE                    27
                        note = MISC_FEATURE - Xaa = beta Alanine
source                  1..29
                        mol_type = protein
                        organism = Human papillomavirus
SEQUENCE: 152
AGQAEPDRAH YNIVTFXXKX DSTLRLXVQ                                  29

SEQ ID NO: 153          moltype = AA  length = 32
FEATURE                 Location/Qualifiers
SITE                    2
```

```
                         note = MISC_FEATURE - Xaa = beta Alanine
SITE                     18
                         note = MISC_FEATURE - Xaa = Norleucine
SITE                     25
                         note = MISC_FEATURE - Xaa = beta Alanine
SITE                     28
                         note = MISC_FEATURE - Xaa = beta Alanine
source                   1..32
                         mol_type = protein
                         organism = Human papillomavirus
SEQUENCE: 153
LXVQSTHVDI RTLEDLLXGT LGIVXPIXSQ KP                             32

SEQ ID NO: 154           moltype = AA  length = 244
FEATURE                  Location/Qualifiers
source                   1..244
                         mol_type = protein
                         organism = Homo sapiens
SEQUENCE: 154
APLILSRIVG GWECEKHSQP WQVLVASRGR AVCGGVLVHP QWVLTAAHCI RNKSVILLGR  60
HSLFHPEDTG QVFQVSHSFP HPLYDMSLLK NRFLRPGDDS SHDLMLLRLS EPAELTDAVK  120
VMDLPTQEPA LGTTCYASGW GSIEPEEFLT PKKLQCVDLH VISNDVCAQV HPQKVTKFML  180
CAGRWTGGKS TCSGDSGGPL VCNGVLQGIT SWGSEPCALP ERPSLYTKVV HYRKWIKDTI  240
VANP                                                            244

SEQ ID NO: 155           moltype = AA  length = 35
FEATURE                  Location/Qualifiers
source                   1..35
                         mol_type = protein
                         organism = Homo sapiens
SEQUENCE: 155
CGGVLVHPQW VLTAAHCIRN KSVILLGRHS LFHPE                          35

SEQ ID NO: 156           moltype = AA  length = 35
FEATURE                  Location/Qualifiers
source                   1..35
                         mol_type = protein
                         organism = Homo sapiens
SEQUENCE: 156
SLFHPEDTGQ VFQVSHSFPH PLYDMSLLKN RFLRP                          35

SEQ ID NO: 157           moltype = AA  length = 29
FEATURE                  Location/Qualifiers
source                   1..29
                         mol_type = protein
                         organism = Homo sapiens
SEQUENCE: 157
PCALPERPSL YTKVVHYRKW IKDTIVANP                                 29

SEQ ID NO: 158           moltype = AA  length = 364
FEATURE                  Location/Qualifiers
source                   1..364
                         mol_type = protein
                         organism = Homo sapiens
SEQUENCE: 158
FFWLDRSVLA KELKFVTLVF RHGDRSPIDT FPTDPIKESS WPQGFGQLTQ LGMEQHYELG  60
EYIRKRYRKF LNESYKHEQV YIRSTDVDRT LMSAMTNLAA LFPPEGVSIW NPILLWQPIP  120
VHTVPLSEDQ LLYLPFRNCP RFQELESETL KSEEFQKRLH PYKDFIATLG KLSGLHGQDL  180
FGIWSKVYDP LYCESVHNFT LPSWATEDTM TKLRELSELS LLSLYGIHKQ KEKSRLQGGV  240
LVNEILNHMK RATQIPSYKK LIMYSAHDTT VSGLQMALDV YNGLLPPYAS CHLTELYFEK  300
GEYFVEMYYR NETQHEPYPL MLPGCSPSCP LERFAELVGP VIPQDWSTEC MTTNSHQGTE  360
DSTD                                                            364

SEQ ID NO: 159           moltype = AA  length = 35
FEATURE                  Location/Qualifiers
source                   1..35
                         mol_type = protein
                         organism = Homo sapiens
SEQUENCE: 159
RTLMSAMTNL AALFPPEGVS IWNPILLWQP IPVHT                          35

SEQ ID NO: 160           moltype = AA  length = 35
FEATURE                  Location/Qualifiers
source                   1..35
                         mol_type = protein
                         organism = Homo sapiens
SEQUENCE: 160
PILLWQPIPV HTVPLSEDQL LYLPFRNCPR FQELE                          35
```

-continued

```
SEQ ID NO: 161         moltype = AA  length = 35
FEATURE                Location/Qualifiers
source                 1..35
                       mol_type = protein
                       organism = Homo sapiens
SEQUENCE: 161
ATEDTMTKLR ELSELSLLSL YGIHKQKEKS RLQGG                            35

SEQ ID NO: 162         moltype = AA  length = 35
FEATURE                Location/Qualifiers
source                 1..35
                       mol_type = protein
                       organism = Homo sapiens
SEQUENCE: 162
LQGGVLVNEI LNHMKRATQI PSYKKLIMYS AHDTT                            35

SEQ ID NO: 163         moltype = AA  length = 35
FEATURE                Location/Qualifiers
source                 1..35
                       mol_type = protein
                       organism = Homo sapiens
SEQUENCE: 163
MALDVYNGLL PPYASCHLTE LYFEKGEYFV EMYYR                            35

SEQ ID NO: 164         moltype = AA  length = 35
FEATURE                Location/Qualifiers
source                 1..35
                       mol_type = protein
                       organism = Homo sapiens
SEQUENCE: 164
YFEKGEYFVE MYYRNETQHE PYPLMLPGCS PSCPL                            35

SEQ ID NO: 165         moltype = AA  length = 338
FEATURE                Location/Qualifiers
source                 1..338
                       mol_type = protein
                       organism = Homo sapiens
SEQUENCE: 165
MESRKDITNQ EELWKMKPRR NLEEDDYLHK DTGETSMLKR PVLLHLHQTA HADEFDCPSE  60
LQHTQELFPQ WHLPIKIAAI IASLTFLYTL LREVIHPLAT SHQQYFYKIP ILVINKVLPM  120
VSITLLALVY LPGVIAAIVQ LHNGTKYKKF PHWLDKWMLT RKQFGLLSFF FAVLHAIYSL  180
SYPMRRSYRY KLLNWAYQQV QQNKEDAWIE HDVWRMEIYV SLGIVGLAIL ALLAVTSIPS  240
VSDSLTWREF HYIQSKLGIV SLLLGTIHAL IFAWNKWIDI KQFVWYTPPT FMIAVFLPIV  300
LIFKSILFLP CLRKKILKIR HGWEDVTKIN KTEICSQL                         338

SEQ ID NO: 166         moltype = AA  length = 35
FEATURE                Location/Qualifiers
source                 1..35
                       mol_type = protein
                       organism = Homo sapiens
SEQUENCE: 166
LFPQWHLPIK IAAIIASLTF LYTLLREVIH PLATS                            35

SEQ ID NO: 167         moltype = AA  length = 35
FEATURE                Location/Qualifiers
source                 1..35
                       mol_type = protein
                       organism = Homo sapiens
SEQUENCE: 167
YTLLREVIHP LATSHQQYFY KIPILVINKV LPMVS                            35

SEQ ID NO: 168         moltype = AA  length = 38
FEATURE                Location/Qualifiers
source                 1..38
                       mol_type = protein
                       organism = Homo sapiens
SEQUENCE: 168
RKQFGLLSFF FAVLHAIYSL SYPMRRSYRY KLLNWAYQ                         38

SEQ ID NO: 169         moltype = AA  length = 35
FEATURE                Location/Qualifiers
source                 1..35
                       mol_type = protein
                       organism = Homo sapiens
SEQUENCE: 169
EDAWIEHDVW RMEIYVSLGI VGLAILALLA VTSIP                            35

SEQ ID NO: 170         moltype = AA  length = 35
FEATURE                Location/Qualifiers
```

-continued

```
source                  1..35
                        mol_type = protein
                        organism = Homo sapiens
SEQUENCE: 170
LAVTSIPSVS DSLTWREFHY IQSKLGIVSL LLGTI                         35

SEQ ID NO: 171          moltype = AA  length = 35
FEATURE                 Location/Qualifiers
source                  1..35
                        mol_type = protein
                        organism = Homo sapiens
SEQUENCE: 171
DIKQFVWYTP PTFMIAVFLP IVLIFKSILF LPCLR                         35

SEQ ID NO: 172          moltype = AA  length = 389
FEATURE                 Location/Qualifiers
source                  1..389
                        mol_type = protein
                        organism = Homo sapiens
SEQUENCE: 172
SSPTSSASSF SSSAPFLASA VSAQPPLPDQ CPALCECSEA ARTVKCVNRN LTEVPTDLPA  60
YVRNLFLTGN QLAVLPAGAF ARRPPLAELA ALNLSGSRLD EVRAGAFEHL PSLRQLDLSH  120
NPLADLSPFA FSGSNASVSA PSPLVELILN HIVPPEDERQ NRSFEGMVVA ALLAGRALQG  180
LRRLELASNH FLYLPRDVLA QLPSLRHLDL SNNSLVSLTY VSFRNLTHLE SLHLEDNALK  240
VLHNGTLAEL QGLPHIRVFL DNNPWVCDCH MADMVTWLKE TEVVQGKDRL TCAYPEKMRN  300
RVLLELNSAD LDCDPILPPS LQTSYVFLGI VLALIGAIFL LVLYLNRKGI KKWMHNIRDA  360
CRDHMEGYHY RYEINADPRL TNLSSNSDV                                389

SEQ ID NO: 173          moltype = AA  length = 35
FEATURE                 Location/Qualifiers
source                  1..35
                        mol_type = protein
                        organism = Homo sapiens
SEQUENCE: 173
SPTSSASSFS SSAPFLASAV SAQPPLPDQC PALCE                         35

SEQ ID NO: 174          moltype = AA  length = 35
FEATURE                 Location/Qualifiers
source                  1..35
                        mol_type = protein
                        organism = Homo sapiens
SEQUENCE: 174
RNLTEVPTDL PAYVRNLFLT GNQLAVLPAG AFARR                         35

SEQ ID NO: 175          moltype = AA  length = 35
FEATURE                 Location/Qualifiers
source                  1..35
                        mol_type = protein
                        organism = Homo sapiens
SEQUENCE: 175
ALQGLRRLEL ASNHFLYLPR DVLAQLPSLR HLDLS                         35

SEQ ID NO: 176          moltype = AA  length = 35
FEATURE                 Location/Qualifiers
source                  1..35
                        mol_type = protein
                        organism = Homo sapiens
SEQUENCE: 176
LSNNSLVSLT YVSFRNLTHL ESLHLEDNAL KVLHN                         35

SEQ ID NO: 177          moltype = AA  length = 35
FEATURE                 Location/Qualifiers
source                  1..35
                        mol_type = protein
                        organism = Homo sapiens
SEQUENCE: 177
DCDPILPPSL QTSYVFLGIV LALIGAIFLL VLYLN                         35

SEQ ID NO: 178          moltype = AA  length = 11
FEATURE                 Location/Qualifiers
source                  1..11
                        mol_type = protein
                        organism = Alphainfluenzavirus influenzae
SEQUENCE: 178
RNNILRTQES E                                                   11

SEQ ID NO: 179          moltype = AA  length = 17
FEATURE                 Location/Qualifiers
source                  1..17
```

```
                        mol_type = protein
                        organism = Alphainfluenzavirus influenzae
SEQUENCE: 179
LNDKHSNGTI KDRSPYR                                              17

SEQ ID NO: 180          moltype = AA  length = 12
FEATURE                 Location/Qualifiers
source                  1..12
                        mol_type = protein
                        organism = Alphainfluenzavirus influenzae
SEQUENCE: 180
SWRNNILRTQ ES                                                   12

SEQ ID NO: 181          moltype = AA  length = 9
FEATURE                 Location/Qualifiers
source                  1..9
                        mol_type = protein
                        organism = Alphainfluenzavirus influenzae
SEQUENCE: 181
DNWHGSNRP                                                       9

SEQ ID NO: 182          moltype = AA  length = 11
FEATURE                 Location/Qualifiers
source                  1..11
                        mol_type = protein
                        organism = Alphainfluenzavirus influenzae
SEQUENCE: 182
DNPRPNDKTG S                                                    11

SEQ ID NO: 183          moltype = AA  length = 14
FEATURE                 Location/Qualifiers
source                  1..14
                        mol_type = protein
                        organism = Alphainfluenzavirus influenzae
SEQUENCE: 183
DPNGWTGTDN NFSI                                                 14

SEQ ID NO: 184          moltype = AA  length = 9
FEATURE                 Location/Qualifiers
source                  1..9
                        mol_type = protein
                        organism = Hepatitis B virus
SEQUENCE: 184
QLDPAFRAG                                                       9

SEQ ID NO: 185          moltype = AA  length = 9
FEATURE                 Location/Qualifiers
source                  1..9
                        mol_type = protein
                        organism = Hepatitis B virus
SEQUENCE: 185
RGLYFPAGL                                                       9

SEQ ID NO: 186          moltype = AA  length = 11
FEATURE                 Location/Qualifiers
source                  1..11
                        mol_type = protein
                        organism = Hepatitis B virus
SEQUENCE: 186
STGPCRTCMT K                                                    11

SEQ ID NO: 187          moltype = AA  length = 9
FEATURE                 Location/Qualifiers
source                  1..9
                        mol_type = protein
                        organism = Human immunodeficiency virus 1
SEQUENCE: 187
AVGIGAVFL                                                       9

SEQ ID NO: 188          moltype = AA  length = 30
FEATURE                 Location/Qualifiers
source                  1..30
                        mol_type = protein
                        organism = Human immunodeficiency virus 1
SEQUENCE: 188
EINCTRPNNN TRPGEIIGDI RQAHCNISRA                                30

SEQ ID NO: 189          moltype = AA  length = 23
FEATURE                 Location/Qualifiers
```

```
source                1..23
                      mol_type = protein
                      organism = Human immunodeficiency virus 1
SEQUENCE: 189
YNKRKRIHIG PGRAFYTTKN IIG                                          23

SEQ ID NO: 190        moltype = AA  length = 15
FEATURE               Location/Qualifiers
source                1..15
                      mol_type = protein
                      organism = PLASMODIUM falciparum
SEQUENCE: 190
PADGNPDPNA NPNVD                                                   15

SEQ ID NO: 191        moltype = AA  length = 15
FEATURE               Location/Qualifiers
source                1..15
                      mol_type = protein
                      organism = PLASMODIUM falciparum
SEQUENCE: 191
NPDPNANPNV DPNAN                                                   15

SEQ ID NO: 192        moltype = AA  length = 15
FEATURE               Location/Qualifiers
source                1..15
                      mol_type = protein
                      organism = PLASMODIUM falciparum
SEQUENCE: 192
NANPNVDPNA NPNVD                                                   15

SEQ ID NO: 193        moltype = AA  length = 15
FEATURE               Location/Qualifiers
source                1..15
                      mol_type = protein
                      organism = PLASMODIUM falciparum
SEQUENCE: 193
NANPNANPNA NPNAN                                                   15

SEQ ID NO: 194        moltype = AA  length = 12
FEATURE               Location/Qualifiers
source                1..12
                      mol_type = protein
                      organism = PLASMODIUM falciparum
SEQUENCE: 194
DPNANPNVDP NA                                                      12

SEQ ID NO: 195        moltype = AA  length = 16
FEATURE               Location/Qualifiers
source                1..16
                      mol_type = protein
                      organism = PLASMODIUM falciparum
SEQUENCE: 195
KQPADGNPDP NANPNV                                                  16

SEQ ID NO: 196        moltype = AA  length = 35
FEATURE               Location/Qualifiers
source                1..35
                      mol_type = protein
                      organism = PLASMODIUM falciparum
SEQUENCE: 196
EDNEKLRKPK HKKLKQPADG NPDPNANPNV DPNAN                             35

SEQ ID NO: 197        moltype = AA  length = 20
FEATURE               Location/Qualifiers
source                1..20
                      mol_type = protein
                      organism = PLASMODIUM falciparum
SEQUENCE: 197
KLRKPKHKKL KQPADGNPDP                                              20

SEQ ID NO: 198        moltype = AA  length = 18
FEATURE               Location/Qualifiers
source                1..18
                      mol_type = protein
                      organism = Human betacoronavirus SARS-CoV-2
SEQUENCE: 198
TESNKKFLPF QQFGRDIA                                                18

SEQ ID NO: 199        moltype = AA  length = 31
```

-continued

```
FEATURE                Location/Qualifiers
source                 1..31
                       mol_type = protein
                       organism = Human betacoronavirus SARS-CoV-2
SEQUENCE: 199
SQILPDPSKP SKRSFIEDLL FNKVTLADAG F                                31

SEQ ID NO: 200         moltype = AA  length = 25
FEATURE                Location/Qualifiers
source                 1..25
                       mol_type = protein
                       organism = Human betacoronavirus SARS-CoV-2
SEQUENCE: 200
SQILPDPSKP SKRSFIEDLL FNKVT                                       25

SEQ ID NO: 201         moltype = AA  length = 25
FEATURE                Location/Qualifiers
source                 1..25
                       mol_type = protein
                       organism = Human betacoronavirus SARS-CoV-2
SEQUENCE: 201
PSKPSKRSFI EDLLFNKVTL ADAGF                                       25

SEQ ID NO: 202         moltype = AA  length = 31
FEATURE                Location/Qualifiers
source                 1..31
                       mol_type = protein
                       organism = Human betacoronavirus SARS-CoV-2
SEQUENCE: 202
DYSVLYNSAS FSTFKCYGVS PTKLNDLCFT N                                31

SEQ ID NO: 203         moltype = AA  length = 20
FEATURE                Location/Qualifiers
source                 1..20
                       mol_type = protein
                       organism = Human betacoronavirus SARS-CoV-2
SEQUENCE: 203
LYNSASFSTF KCYGVSPTKL                                             20

SEQ ID NO: 204         moltype = AA  length = 25
FEATURE                Location/Qualifiers
source                 1..25
                       mol_type = protein
                       organism = Human betacoronavirus SARS-CoV-2
SEQUENCE: 204
SNNLDSKVGG NYNYLYRLFR KSNLK                                       25

SEQ ID NO: 205         moltype = AA  length = 25
FEATURE                Location/Qualifiers
source                 1..25
                       mol_type = protein
                       organism = Human betacoronavirus SARS-CoV-2
SEQUENCE: 205
YRLFRKSNLK PFERDISTEI YQAGS                                       25

SEQ ID NO: 206         moltype = AA  length = 25
FEATURE                Location/Qualifiers
source                 1..25
                       mol_type = protein
                       organism = Human betacoronavirus SARS-CoV-2
SEQUENCE: 206
ISTEIYQAGS TPCNGVEGFN CYFPL                                       25

SEQ ID NO: 207         moltype = AA  length = 24
FEATURE                Location/Qualifiers
source                 1..24
                       mol_type = protein
                       organism = Human betacoronavirus SARS-CoV-2
SEQUENCE: 207
VEGFNCYFPL QSYGFQPTNG VGYQ                                        24

SEQ ID NO: 208         moltype = AA  length = 58
FEATURE                Location/Qualifiers
source                 1..58
                       mol_type = protein
                       organism = Human betacoronavirus SARS-CoV-2
SEQUENCE: 208
SNNLDSKVGG NYNYLYRLFR GSGIYQAGST PCNGVEGFNC YFPLQSYGFQ PTNGVGYQ    58
```

-continued

```
SEQ ID NO: 209         moltype = AA  length = 247
FEATURE                Location/Qualifiers
source                 1..247
                       mol_type = protein
                       organism = Homo sapiens
SEQUENCE: 209
MASLSRPSLP SCLCSFLLLL LLQVSSSYAG QFRVIGPRHP IRALVGDEVE LPCRISPGKN  60
ATGMEVGWYR PPFSRVVHLY RNGKDQDGDQ APEYRGRTEL LKDAIGEGKV TLRIRNVRFS  120
DEGGFTCFFR DHSYQEEAAM ELKVEDPFYW VSPGVLVLLA VLPVLLLQIT VGLIFLCLQY  180
RLRGKLRAEI ENLHRTFDPH FLRVPCWKIT LFVIVPVLGP LVALIICYNW LHRRLAGQFL  240
EELRNPF                                                            247

SEQ ID NO: 210         moltype = AA  length = 192
FEATURE                Location/Qualifiers
source                 1..192
                       mol_type = protein
                       organism = Homo sapiens
SEQUENCE: 210
MGNHAGKREL NAEKASTNSE TNRGESEKKR NLGELSRTTS EDNEVFGEAD ANQNNGTSSQ  60
DTAVTDSKRT ADPKNAWQDA HPADPGSRPH LIRLFSRDAP GREDNTFKDR PSESDELQTI  120
QEDSAATSES LDVMASQKRP SQRHGSKYLA TASTMDHARH GFLPRHRDTG ILDSIGRFFG  180
GDRGAPKRGS GK                                                      192

SEQ ID NO: 211         moltype = AA  length = 277
FEATURE                Location/Qualifiers
source                 1..277
                       mol_type = protein
                       organism = Homo sapiens
SEQUENCE: 211
MGLLECCARC LVGAPFASLV ATGLCFFGVA LFCGCGHEAL TGTEKLIETY FSKNYQDYEY  60
LINVIHAFQY VIYGTASFFF LYGALLLAEG FYTTGAVRQI FGDYKTTICG KGLSATVTGG  120
QKGRGSRGQH QAHSLERVCH CLGKWLGHPD KFVGITYALT VVWLLVFACS AVPVYIYFNT  180
WTTCQSIAFP SKTSASIGSL CADARMYGVL PWNAFPGKVC GSNLLSICKT AEFQMTFHLF  240
IAAFVGAAAT LVSLLTFMIA ATYNFAVLKL MGRGTKF                            277

SEQ ID NO: 212         moltype = AA  length = 35
FEATURE                Location/Qualifiers
source                 1..35
                       mol_type = protein
                       organism = Homo sapiens
SEQUENCE: 212
SLPSCLCSFL LLLLLQVSSS YAGQFRVIGP RHPIR                              35

SEQ ID NO: 213         moltype = AA  length = 35
FEATURE                Location/Qualifiers
source                 1..35
                       mol_type = protein
                       organism = Homo sapiens
SEQUENCE: 213
VSSSYAGQFR VIGPRHPIRA LVGDEVELPC RISPG                              35

SEQ ID NO: 214         moltype = AA  length = 35
FEATURE                Location/Qualifiers
source                 1..35
                       mol_type = protein
                       organism = Homo sapiens
SEQUENCE: 214
EEAAMELKVE DPFYWVSPGV LVLLAVLPVL LLQIT                              35

SEQ ID NO: 215         moltype = AA  length = 35
FEATURE                Location/Qualifiers
source                 1..35
                       mol_type = protein
                       organism = Homo sapiens
SEQUENCE: 215
SPGVLVLLAV LPVLLLQITV GLIFLCLQYR LRGKL                              35

SEQ ID NO: 216         moltype = AA  length = 35
FEATURE                Location/Qualifiers
source                 1..35
                       mol_type = protein
                       organism = Homo sapiens
SEQUENCE: 216
QITVGLIFLC LQYRLRGKLR AEIENLHRTF DPHFL                              35

SEQ ID NO: 217         moltype = AA  length = 35
FEATURE                Location/Qualifiers
source                 1..35
                       mol_type = protein
```

```
                          organism = Homo sapiens
SEQUENCE: 217
GKLRAEIENL HRTFDPHFLR VPCWKITLFV IVPVL                              35

SEQ ID NO: 218            moltype = AA  length = 35
FEATURE                   Location/Qualifiers
source                    1..35
                          mol_type = protein
                          organism = Homo sapiens
SEQUENCE: 218
HFLRVPCWKI TLFVIVPVLG PLVALIICYN WLHRR                              35

SEQ ID NO: 219            moltype = AA  length = 32
FEATURE                   Location/Qualifiers
source                    1..32
                          mol_type = protein
                          organism = Homo sapiens
SEQUENCE: 219
PVLGPLVALI ICYNWLHRRL AGQFLEELRN PF                                 32

SEQ ID NO: 220            moltype = AA  length = 35
FEATURE                   Location/Qualifiers
source                    1..35
                          mol_type = protein
                          organism = Homo sapiens
SEQUENCE: 220
DPGSRPHLIR LFSRDAPGRE DNTFKDRPSE SDELQ                              35

SEQ ID NO: 221            moltype = AA  length = 35
FEATURE                   Location/Qualifiers
source                    1..35
                          mol_type = protein
                          organism = Homo sapiens
SEQUENCE: 221
GRTQDENPVV HFFKNIVTPR TPPPSQGKGR GLSLS                              35

SEQ ID NO: 222            moltype = AA  length = 35
FEATURE                   Location/Qualifiers
source                    1..35
                          mol_type = protein
                          organism = Homo sapiens
SEQUENCE: 222
GGRASDYKSA HKGFKGVDAQ GTLSKIFKLG GRDSR                              35

SEQ ID NO: 223            moltype = AA  length = 35
FEATURE                   Location/Qualifiers
source                    1..35
                          mol_type = protein
                          organism = Homo sapiens
SEQUENCE: 223
FSKNYQDYEY LINVIHAFQY VIYGTASFFF LYGAL                              35

SEQ ID NO: 224            moltype = AA  length = 35
FEATURE                   Location/Qualifiers
source                    1..35
                          mol_type = protein
                          organism = Homo sapiens
SEQUENCE: 224
AFQYVIYGTA SFFFLYGALL LAEGFYTTGA VRQIF                              35

SEQ ID NO: 225            moltype = AA  length = 35
FEATURE                   Location/Qualifiers
source                    1..35
                          mol_type = protein
                          organism = Homo sapiens
SEQUENCE: 225
GALLLAEGFY TTGAVRQIFG DYKTTICGKG LSATV                              35

SEQ ID NO: 226            moltype = AA  length = 35
FEATURE                   Location/Qualifiers
source                    1..35
                          mol_type = protein
                          organism = Homo sapiens
SEQUENCE: 226
HPDKFVGITY ALTVVWLLVF ACSAVPVYIY FNTWT                              35

SEQ ID NO: 227            moltype = AA  length = 35
FEATURE                   Location/Qualifiers
source                    1..35
```

mol_type = protein
organism = Homo sapiens
SEQUENCE: 227
LLVFACSAVP VYIYFNTWTT CQSIAFPSKT SASIG 35

SEQ ID NO: 228 moltype = AA length = 35
FEATURE Location/Qualifiers
source 1..35
mol_type = protein
organism = Homo sapiens
SEQUENCE: 228
TWTTCQSIAF PSKTSASIGS LCADARMYGV LPWNA 35

SEQ ID NO: 229 moltype = AA length = 35
FEATURE Location/Qualifiers
source 1..35
mol_type = protein
organism = Homo sapiens
SEQUENCE: 229
SICKTAEFQM TFHLFIAAFV GAAATLVSLL TFMIA 35

SEQ ID NO: 230 moltype = AA length = 35
FEATURE Location/Qualifiers
source 1..35
mol_type = protein
organism = Homo sapiens
SEQUENCE: 230
AAFVGAAATL VSLLTFMIAA TYNFAVLKLM GRGTK 35

SEQ ID NO: 231 moltype = AA length = 20
FEATURE Location/Qualifiers
source 1..20
mol_type = protein
organism = Homo sapiens
SEQUENCE: 231
MIAATYNFAV LKLMGRGTKF 20

SEQ ID NO: 232 moltype = AA length = 283
FEATURE Location/Qualifiers
source 1..283
mol_type = protein
organism = Secale cereale
SEQUENCE: 232
MKTFLILALL AIVATTATIA VRVPVPQLQP QNTSQQQPQE QVPLVQQQQF PGQQQPFPPQ 60
QPYPQPQPFP SQQPYLQLQP FPQPQLPYPQ PQPFRPQQPY PQPQPQYSQP QQPISQQQQQ 120
QQQQQQQQQQ QQQILQQILQ QQLIPCRDVV LQQHNIAHGS SQILQQSTYQ LVQQLCCQQL 180
WQIPEQSRCQ AIHNVVHAII LHQQQQQPLS QVSFQQPQQQ YPSGQGSFQP SQQNPQAQGS 240
VQPQQLPQFE EIRNLALETL PAMCNVYIPP YCTIAPVGIF GTN 283

SEQ ID NO: 233 moltype = AA length = 292
FEATURE Location/Qualifiers
source 1..292
mol_type = protein
organism = Secale cereale
SEQUENCE: 233
MKTFLILALL AIVATTATIA VRVPVPQLQP QNPSQQQPQE QVPLVQQQQF PGQQQPFPPQ 60
QPYPQPQPFP SQQPYLQLQP FPQPQLPYPQ PQLPYPQPQP FRPQQPYPQP QPQYSQPQQP 120
ISQQQQQQQQ QQQQQQILQQ ILQQQLIPCR DVVLQQHSIA HGSSQVLQQS TYQLVQQLCC 180
QQLWQIPEQS RCQAIHNVVH AIILHQQQQQ QQQQQQPLSQ VSFQQPQQQY PSGQGSFQPS 240
QQNPQAQGSV QPQQLPQFEE IRNLALETLP AMCNVYIPPY CTIAPVGIFG TN 292

SEQ ID NO: 234 moltype = AA length = 310
FEATURE Location/Qualifiers
source 1..310
mol_type = protein
organism = Triticum aestivum
SEQUENCE: 234
MKTFLILALL AIVATTATIA VRVPVPQLQP QNPSQQQPQE QVPLVQQQQF PGQQQPFPPQ 60
QPYPQPQPFP SQQPYLQLQP FPQPQLPYPQ PQLPYPQPQL PYPQPQPFRP QQPYPQSQPQ 120
YSQPQQPISQ QQQQQQQQQQ QKQQQQQQQQ ILQQILQQQL IPCRDVVLQQ HSIAYGSSQV 180
LQQSTYQLVQ QLCCQQLWQI PEQSRCQAIH NVVHAIILHQ QQQQQQQQQQ QQPLSQVSFQ 240
QPQQQYPSGQ GSFQPSQQNP QAQGSVQPQQ LPQFEEIRNL ALETLPAMCN VYIPPYCTIA 300
PVGIFGTNYR 310

SEQ ID NO: 235 moltype = AA length = 294
FEATURE Location/Qualifiers
source 1..294
mol_type = protein
organism = Triticum aestivum

```
SEQUENCE: 235
MKTFLILALL AIVATTATIA VRVPVPQLQP QNPSQQQPQE QVPLVQQQQF PGQQQPFPPQ  60
QPYPQLQPFP SQQPYMQLQP FPQPQLPYPQ PQLPYPQPQP FRPQQSYPQP QPQYSQPQQP  120
ISQQQQQQQQ QQQQQQILQQ ILQQQLIPCR DVVLQQHSIA HGSSQVLQQS TYQLVQQLCC  180
QQLWQIPEQS RCQAIHNVVH AIILHQQQQQ QQQQQQPLSQ VCFQQPQQQY PSGQGSFQPS  240
QQNPQAQGSV QPQQLPQFEE IRNLALETLP AMCNVYIPPY CTIAPVGIFG TNYR        294

SEQ ID NO: 236         moltype = AA  length = 305
FEATURE                Location/Qualifiers
SITE                   304
                       note = misc_feature - Xaa can be any naturally occurring
                        amino acid
source                 1..305
                       mol_type = protein
                       organism = Triticum aestivum
SEQUENCE: 236
MKTFLILALL AIVATTATTA VRVPVPQLQP QNPSQQQPQE QVPLVQQQQF PGQQQQFPPQ  60
QPYPQPQPFP SQQPYLQLQP FPQPQPFPPQ LPYPQPQSFP PQQPYPQQQP QYLQPQQPIS  120
QQQAQQQQQQ QQQQQQQQQI LQQILQQQLI PCRDVVLQQH NIAHASSQVL QQSTYQLLQQ  180
LCCQQLWQIP EQSRCQAIHN VVHAIILHQQ QQQQQQQQQQ QQQQQPSSQV SFQQPQQQYP  240
SGQGSFQPSQ QNPQAQGSVQ PQQLPQFEEI RNLALQTLPA MCNVYIPPYC STTIAPFGIF  300
GTNXR                                                             305

SEQ ID NO: 237         moltype = AA  length = 285
FEATURE                Location/Qualifiers
source                 1..285
                       mol_type = protein
                       organism = Triticum aestivum
SEQUENCE: 237
MKTFLILALL AIVATTATSA VRVPVPQLQP QNPSQQQPQE QVPLMQQQQQ FPGQQEQFPP  60
QQPYPHQQPF PSQQPYPQPQ PFPPQLPYPQ TQPFPPQQPY PQPQPQYPQP QQPISQQQAQ  120
QQQQQQQILQ QILQQQLIPC RDVVLQQHNI AHASSQVLQQ SSYQQLQQLC CQQLFQIPEQ  180
SRCQAIHNVV HAIILHHHQQ QQQQQPSSQV SYQQPQEQYP SGQGSFQSSQ QNPQAQGSVQ  240
PQQLPQFQEI RNLALQTLPA MCNVYIPPYC STTIAPFGIF GTNYR                 285

SEQ ID NO: 238         moltype = AA  length = 288
FEATURE                Location/Qualifiers
source                 1..288
                       mol_type = protein
                       organism = Triticum aestivum
SEQUENCE: 238
MKTFLILALL AIVATTATTA VRVPVPQLQP QNPSQQQPQE QVPLVQQQQF LGQQQPFPPQ  60
QPYPQPQPFP SQQPYLQLQP FPQPQLPYSQ PQPFRPQQPY PQPQPQYSQP QQPISQQQQQ  120
QQQQQQQQQQ QQQILQQILQ QQLIPCMDVV LQQHNIAHGR SQVLQQSTYQ LLQELCCQHL  180
WQIPEQSQCQ AIHNVVHAII LHQQQKQQQQ PSSQVSFQQP LQQYPLGQGS FRPSQQNPQA  240
QGSVQPQQLP QFEEIRNLAL QTLPAMCNVY IPPYCTIAPF GIFGTNYR              288

SEQ ID NO: 239         moltype = AA  length = 292
FEATURE                Location/Qualifiers
source                 1..292
                       mol_type = protein
                       organism = Triticum aestivum
SEQUENCE: 239
MKTFLILALL AIVATTTTTA VRVPVPQLQP QNPSQQQPQE QVPLVQQQQF LGQQQQQFPG  60
QQQPFPPQQP YPQPQPFLPQ LPYPQPQPFP PQQSYPQPQP QYPQPQQPIS QQQAQLQQQQ  120
QQQQQQQQQI LQQILQQQLI PCRDVVLQQP NIAHASSQVS QQSYQLLQQL CCQQLWQTPE  180
QSRCQAIHNV IHAIILHQQQ QQQQQQQQQQ QQQQPSSQVS YQQPQQQYPS GQGFFQPSQQ  240
NPQAQGFVQP QQLPQFEEIR NLALQTLPAM CNVYIPPYCS TTIAPFGIMS TN         292

SEQ ID NO: 240         moltype = AA  length = 307
FEATURE                Location/Qualifiers
source                 1..307
                       mol_type = protein
                       organism = Triticum spelta
SEQUENCE: 240
MKTFLILALL AIVATTATIA VRVPVPQLQP QNPSQQQPQE QVPLVQQQQF PGQQQPFPPQ  60
QPYPQPQPFP SQQPYLQLQP FPQPQLPYPQ PQLPYPQPQL PYPQPQPFRP QQPYPQSQPQ  120
YSQPQQPISQ QQQQQQQQQQ QQQQQQQQQI LQQILQQQLI PCRDVVLQQH SIAYGSSQVL  180
QQSTYQLVQQ LCCQQLWQIP EQSRCQAIHN VVHAIILHQQ QQQQQQQQQQ QPLSQVSFQQ  240
PQQQYPSGQG SFQPSQQNPQ AQGSVQPQQL PQFEEIRNLA LETLPAMCNV YIPPYCTIAP  300
VGIFGTN                                                           307

SEQ ID NO: 241         moltype = AA  length = 291
FEATURE                Location/Qualifiers
SITE                   66
                       note = misc_feature - Xaa can be any naturally occurring
                        amino acid
source                 1..291
                       mol_type = protein
```

```
                          organism = Triticum spelta
SEQUENCE: 241
MKTFLILALL AIVATTATIA VRVPVPQLQP QNPSQQQPQE QVPLVQQQQF PGQQQPFPPQ  60
QPYPQXQPFP SQQPYMQLQP FPQPQLPYPQ PQLPYPQPQP FRPQQSYPQP QPQYSQPQQP  120
ISQQQQQQQQ QQQQQILQQI LQQQLIPCRD VVLQQHSIAH GSSQVLQQST YQLVQQLCCQ  180
QLWQIPEQSR CQAIHNVVHA IILHQQQQQQ QQQQQPLSQV SFQQPQQQYP SGQGSFQPSQ  240
QNPQAQGSVQ PQQLPQFEEI RNLALETLPA MCNVYIPPYC TIAPVGIFGT N           291

SEQ ID NO: 242            moltype = AA  length = 287
FEATURE                   Location/Qualifiers
source                    1..287
                          mol_type = protein
                          organism = Triticum spelta
SEQUENCE: 242
MKTFLILALL AIVATTATTA VRVPVPQLQP QNPSQQQPQE QVPLVQQQQF PGQQQQFPPQ  60
QPYPQPQPFP SQQPYLQLQP FPQPQPFPPQ LPYPQPQSFP PQQPYPQQQP QYLQPQQPIS  120
QQQAQQQQQQ QQILQQILQQ QLIPCRDVVL QQHNIAHASS QVLQQSSYQQ LQQLCCQQLF  180
QIPEQSRCQA IHNVVHAIIL HHHQQQQQQP SSQVSYQQPQ EQYPSGQGSF QSSQQNPQAQ  240
GSVQPQQLPQ FQEIRNLALQ TLPAMCNVYI PPYCSTTIAP FGIFGTN                287

SEQ ID NO: 243            moltype = AA  length = 313
FEATURE                   Location/Qualifiers
source                    1..313
                          mol_type = protein
                          organism = Triticum spelta
SEQUENCE: 243
MKTFLILALL AIVATTATTA VRVPVPQLQP QNPSQQQPQE QVPLVQQQQF PGQQQQFPPQ  60
QPYPQPQPFP SQQPYLQLQP FPQPQPFPPQ LPYPQPQSFP PQQPYPQQQP QYLQPQQPIS  120
QQQAQQQQQQ QQQQQQQQQI LQQILQQQLI PCRDVVLQQH NIAHASSQVL QQSTYQLLQQ  180
LCCQQLLQIP EQSRCQAIHN VAHAIIMHQQ QQQQQEQQQQ LQQQQQQQLH QQRQQPSSQV  240
SFQQPQQQYP SSQVSFQPSQ LNPQAQGSVQ PQQLPQFAEI RNLALQTLPA MCNVYIPPHC  300
STTIAPFGIF GTN                                                     313

SEQ ID NO: 244            moltype = AA  length = 284
FEATURE                   Location/Qualifiers
source                    1..284
                          mol_type = protein
                          organism = Triticum spelta
SEQUENCE: 244
MKTFLILALL AIVATTATSA VRVPVPQLQP QNPSQQQPQE QVPLMQQQQQ FPGQQEQFPP  60
QQPYPHQQPF PSQQPYPQPQ PFPPQLPYPQ TQPFPPQQPY PQPQPQYPQP QQPISQQQAQ  120
QQQQQQQILQ QILQQQLIPC RDVVLQQHNI AHASSQVLQQ SSYQQLQQLC CQQLFQIPEQ  180
SRCQAIHNVV HAIILHHHQQ QQQQPSSQVS YQQPQEQYPS GQGSFQSSQQ NPQAQGSVQP  240
QQLPQFQEIR NLALQTLPAM CNVYIPPYCS TTIAPFGIFG TNYR                   284

SEQ ID NO: 245            moltype = AA  length = 287
FEATURE                   Location/Qualifiers
source                    1..287
                          mol_type = protein
                          organism = Triticum spelta
SEQUENCE: 245
MKTFLILALL AIVATTATTA VRVPVPQLQP QNPSQQQPQE QVPLVQQQQF LGQQQPFPPQ  60
QPYPQPQPFP SQQPYLQLQP FPQPQLPYSQ PQPFRPQQPY PQPQPQYSQP QQPISQQQQQ  120
QQQQQQQQQQ QQQQILQQIL QQQLIPCMDV VLQQHNIAHG RSQVLQQSTY QLLQELCCQH  180
LWQIPEQSQC QAIHNVVHAI ILHQQQKQQQ QPSSQVSFQQ PQQQYPLGQG SFRPSQQNPQ  240
AQGSVQPQQL PQFEEIRNLA LQTLPAMCNV YIPPYCTIAP FGIFGTN                287

SEQ ID NO: 246            moltype = AA  length = 313
FEATURE                   Location/Qualifiers
SITE                      221
                          note = misc_feature - Xaa can be any naturally occurring
                           amino acid
source                    1..313
                          mol_type = protein
                          organism = Triticum turgidum
SEQUENCE: 246
MKTFLILALL AIVATTATTA VRVPVPQLQP QNPSQQQPQE QVPLVQQQQF PGQQQQFPPQ  60
QPYPQPQPFP SQQPYLQLQP FPQPQPFPPQ LPYPQPQSFP PQQPYPQQQP QYLQPQQPIS  120
QQQAQQQQQQ QQQQQQQQQI LQQILQQQLI PCRDVVLQQH NIAHASSQVL QQSTYQLLQQ  180
LCCQQLLQIP EQSRCQAIHN VVHAIIMHQQ QQQQQEQQQQ XQQQQQQQLH QQRQQPSSQV  240
SFQQPQQQYP SSQVSFQPSQ LNPQAQGSVQ PQQLPQFAEI RNLALQTLPA MCNVYIPPHC  300
STTIAPFGIF GTN                                                     313

SEQ ID NO: 247            moltype = AA  length = 286
FEATURE                   Location/Qualifiers
source                    1..286
                          mol_type = protein
                          organism = Triticum turgidum
SEQUENCE: 247
```

```
MKTFLILALL AIVATTATTA VRVPVPQLQP QNPSQQQPQE QVPLVQQQQF LGQQQPFPPQ  60
QPYPQPQPFP SQQPYLQLQP FPQPQLPYSQ PQPFRPQQPY PQPQPQYSQP QQPISQQQQQ  120
QQQQQQQQQQ EQQILQQILQ QQLIPCMDVV LQQHNIAHGR SQVLQQSTYQ LLQELCCQHL  180
WQIPEQSQCQ AIHNVVHAII LHQQQKQQQQ PSSQVSFQQP LQQYPLGQGS FRPSQQNPQA  240
QGSVQPQQLP QFEEIRNLAL QTLPAMCNVY IPPYCTIAPF GIFGTN                286

SEQ ID NO: 248          moltype = AA  length = 216
FEATURE                 Location/Qualifiers
source                  1..216
                        mol_type = protein
                        organism = Hordeum vulgare
SEQUENCE: 248
METFLILSLI AIVATTATTA VRVPVPQLQL QNPSMQQPQE QVPLVQQQQF LGQQQTFPPQ  60
QPYPQPQPFP TQQPYPQPQP FPQPQPFPPQ LPYPQPQPFP PQQPYPQPQT QHLQPQQPIS  120
QQQAQQQQQQ QQQQQQQQQQ QLQQQILQQI LQQYPLGQGS FRPSQQNPQA QGSVQPQQQP  180
QFEEIRNLAL QTLPAMCNAY IPPYCTIAPF GIFGTN                           216

SEQ ID NO: 249          moltype = AA  length = 244
FEATURE                 Location/Qualifiers
source                  1..244
                        mol_type = protein
                        organism = Triticum aestivum
SEQUENCE: 249
PQQPFPLQPQ QSFLWQSQQP FLQQPQQPSP QPQQVVQIIS PATPTTIPSA GKPTSAPFPQ  60
QQQQHQQLAQ QQIPVVQPSI LQQLNPCKVF LQQQCSPVAM PQRLARSQML QQSSCHVMQQ  120
QCCQQLPQIP QQSRYQAIRA IIYSIILQEQ QQVQGSIQSQ QQQPQQLGQC VSQPQQQSQQ  180
QLGQQPQQQQ LAQGTFLQPH QIAQLEVMTS IALRILPTMC SVNVPLYRTT TSVPFGVGTG  240
VGAY                                                              244

SEQ ID NO: 250          moltype = AA  length = 329
FEATURE                 Location/Qualifiers
source                  1..329
                        mol_type = protein
                        organism = Triticum aestivum
SEQUENCE: 250
MKTLLILTIL AMAITIGTAN IQVDPSGQVQ WLQQQLVPQL QQPLSQQPQQ TFPQPQQTFP  60
HQPQQQVPQP QQPQQPFLQP QQPFPQQPQQ PFPQTQQPQQ PFPQQPQQPF PQTQQPQQPF  120
PQQPQQPFPQ TQQPQQPFPQ LQQPQQPFPQ PQQQLPQPQQ PQQSFPQQQR SFIQPSLQQQ  180
LNPCKNILLQ QCKPASLVSS LWSIIWPQSD CQVMRQQCCQ QLAQIPQQLQ CAAIHSVVHS  240
IIMQQQQQQQ QQQGMHIFLP LSQQQQVGQG SLVQGQGIIQ PQQPAQLEAI RSLVLQTLPS  300
MCNVYVPPEC SIMRAPFASI VAGIGGQYR                                   329

SEQ ID NO: 251          moltype = AA  length = 300
FEATURE                 Location/Qualifiers
source                  1..300
                        mol_type = protein
                        organism = Triticum aestivum
SEQUENCE: 251
MKTLLIQTIL VMAITIATAN MQVDPSGQVP WPQQQPFPQP HQPFSQQPQQ TFPQPQQTFP  60
HQPQQQFSQP QQPQQQFIQP QQPFPQQPQQ TYPQRPQQPF PQTQQPQQPF PQSQQPQQPF  120
PQPQQQFPQP QQPQQSFPQQ QPSLIQQSLQ QQLNPCKNFL LQQCKPVSLV SSLWSMILPR  180
SDCQVMRQQC CQQLAQIPQQ LQCAAIHSIV HSIIMQQEQQ EQRQGVQILV PLSQQQQVGQ  240
GTLVQGQGII QPQQPAQLEV IRSLVLQTLA TMCNVYVPPE CSIIKAPFSS VVAGIGGQYR  300

SEQ ID NO: 252          moltype = AA  length = 368
FEATURE                 Location/Qualifiers
SITE                    132
                        note = misc_feature - Xaa can be any naturally occurring
                         amino acid
SITE                    269
                        note = misc_feature - Xaa can be any naturally occurring
                         amino acid
source                  1..368
                        mol_type = protein
                        organism = Triticum aestivum
SEQUENCE: 252
MKTLLILTIL AMAITISTAN MQVDPSGQVQ WPQQQLVPQP QQPLSQQPQQ AFPQPQQTFP  60
HQPQQQVPQP QQPQQPFLQP QQAFPQQPQQ PFPQTQQPQQ PFPQQPQQPF PQTQQPQQPF  120
PQQPQQPFPQ QXQQPFPQTQ QPQQPFPQQP QQPFPQTQQP QQPFPQFQQP HQPFPQPQQQ  180
FPQPQQPQQS FPQQQRPFIQ PSLQQRLNPC KNILLQQCKP ASLVSSLWSI IWPQSDCQVM  240
QQQCCQELAQ IPQQLQCAAI HSVVHSIIXQ QQQQQQQQQQ QQQGMHILLP LSQQQQLGQG  300
TLVQGQGIIQ PQQLAQLEAI RSLVLQTLPT MCNVYVPPEC SIIRAPFASI RASSGHHLPA  360
LVAGIGGQ                                                          368

SEQ ID NO: 253          moltype = AA  length = 329
FEATURE                 Location/Qualifiers
SITE                    258
                        note = misc_feature - Xaa can be any naturally occurring
                         amino acid
```

```
source                 1..329
                       mol_type = protein
                       organism = Triticum aestivum
SEQUENCE: 253
MKTLLILTII AVALTTTTAN IQVDPSGQVQ WPQQQPFPQ PQQPQQIFPQ PQQTFPHQPQ  60
QAFPQPQQTF PHQPQQQFPQ PQQPQQPFPQ QPQQQFPQPQ QPQQPFPQQP QQQFPQPQQP  120
QQPFPQPQQP QLPFPQQPQQ PFPQPQQPQQ PFPQLQQPQQ PLPQPQQPQQ PFPQQQQPLI  180
QPYLQQQMNP CKNYLLQQCN PVSLVSSLVS MILPRSDCKV MRQQCCQQLA QIPQQLQCAA  240
IHGVVHSIIM QQEQQQQXQQ QQQGIQIMRP LFQLVQGQGI IQPQQPAQLE VIRSLVLGTL  300
PTMCNVFVPP ECSTTKAPFA SIVADIGGQ                                  329

SEQ ID NO: 254         moltype = AA  length = 285
FEATURE                Location/Qualifiers
source                 1..285
                       mol_type = protein
                       organism = Triticum aestivum
SEQUENCE: 254
MKTLFILTIL AMATTIATAN MQVDPSGQVQ WPQQQPFRQP QQPFYQQPQQ TFPQPQQTFP  60
HQPQQQFPQP QQPQQQFPQP QQPQQPFPQP QQAQLPFPQQ PQQPFPQPQQ PQQPFPQSQQ  120
PQQPFPQPQQ PQQSFPQQQQ PLIQPYLQQQ MNPCKNYLLQ QCNPVSLVSS LVSMILPRSD  180
CQVMQQQCCQ QLAQIPRQLQ CAAIHSVVHS IVMQQEQQQG IQILRPLFQL VQGQGIIQPQ  240
QPAQYEVIRS LVLRTLPNMC NVYVRPDCST INAPFASIVA GISGQ                285

SEQ ID NO: 255         moltype = AA  length = 285
FEATURE                Location/Qualifiers
source                 1..285
                       mol_type = protein
                       organism = Triticum aestivum
SEQUENCE: 255
MKTLFILTIL AMATTIATAN MQVDPSGQVQ WPQQQPFRQP QQPFYQQPQQ TFPQPQQAFP  60
HQPQQQFPQP QQPQQQFPQP QQPQQPFPQP QQAQLPFPQQ PQQPFPQPQQ PQQPFPQSQQ  120
PQQPFPQPQQ PQQSFPQQQQ PLIQPYLQQQ MNPCKNYLLQ QCNPVSLVSS LVSMILPRSD  180
CQVMQQQCCQ QLAQIPRQLQ CAAIHSVVHS IVMQQEQQQG IQILRPLFQL VQGQGIIQPQ  240
QPAQYEVIRS LVLRTLPNMC NVYVRPDCST INAPFASIVA GISGQ                285

SEQ ID NO: 256         moltype = AA  length = 292
FEATURE                Location/Qualifiers
source                 1..292
                       mol_type = protein
                       organism = Triticum aestivum
SEQUENCE: 256
MKTLLILTIF AAALTIATAN IQVDPSGQVQ WPQQQPFPQP QPFSQQPQQA FLQPQHTFPL  60
QPQQVFPQPQ QPQQQFPQPQ QPQQPFPQPQ QPQLPFPQQP QQPFPQPQQP QQPFPQSQQP  120
QQPFPQPQQQ FPQPQQPQQS FPQQQPPLIQ PYLQQQMNPC KNYLLQQCNP VSLVSSLVSM  180
ILPRNDCQVM QQQCCQQLAQ IPRQLQCTAI HSVVHAIIMQ QEQQGIQILR PLFQLVQGQG  240
IIQPQQPAQY EVIRSLVLRT LPNMCNVYVR PDCSTINAPF ASIVAGIGGQ YR        292

SEQ ID NO: 257         moltype = AA  length = 302
FEATURE                Location/Qualifiers
source                 1..302
                       mol_type = protein
                       organism = Triticum aestivum
SEQUENCE: 257
MKTLLILTIL AMATTIATAN MQVDPSGQVQ WPQQQPFPQP QQPFCQQPQR TIPQPHQTFH  60
HQPQQTFPQP EQTYPHQPQQ QFPQTQQPQQ PFPQPQQTFP QQPQLPFPQQ PQQPFPQPQQ  120
PQQPFPQSQQ PQQPFPQPQQ QFPQPQQPQQ SFPQQQQPAI QSFLQQQMNP CKNFLLQQCN  180
HVSLVSSLVS IILPRSDCQV MQQQCCQQLA QIPQQLQCAA IHSVAHSIIM QQEQQQGVPI  240
LRPLFQLAQG LGIIQPQQPA QLEGIRSLVL KTLPTMCNVY VPPDCSTINV PYANIDAGIG  300
GQ                                                               302

SEQ ID NO: 258         moltype = AA  length = 302
FEATURE                Location/Qualifiers
SITE                   290
                       note = misc_feature - Xaa can be any naturally occurring
                        amino acid
source                 1..302
                       mol_type = protein
                       organism = Triticum aestivum
SEQUENCE: 258
MKTLLILTIL AMATTIATAN MQVDPSGQVQ WPQQQPFPQP QQPFCQQPQR TIPQPHQTFH  60
HQPQQTFPQP QQTYPHQPQQ QFPQTQQPQQ PFPQPQQTFP QQPQLPFPQQ PQQPFPQPQQ  120
PQQPFPQSQQ PQQPFPQPQQ QFPQPQQPQQ SFPQQQQPAI QSFLQQQMNP CKNFLLQQCN  180
HVSLVSSLVS IILPRSDCQV MQQQCCQQLA QIPQQLQCAA IHSVAHSIIM QQEQQQGVPI  240
LRPLFQLAQG LGIIQPQQPA QLEGIRSLVL KTLPTMCNVY VPPDCSTINX PYANIDAGIG  300
GQ                                                               302

SEQ ID NO: 259         moltype = AA  length = 300
FEATURE                Location/Qualifiers
source                 1..300
```

-continued

```
                         mol_type = protein
                         organism = Triticum aestivum
SEQUENCE: 259
MKTLLILTIL VMAITIATAN MQVDPSGQVP WPQQQPFPQP HQPFSQQPQQ TFPQPQQTFP  60
HQPQQQFSQP QQPQQQFIQP QQPFPQQPQQ TYPQRPQQPF PQTQQPQQPF PQSQQPQQPF  120
PQPQQQFPQP QQPQQSFPQQ QPSLIQQSLQ QQLNPCKNFL LQQCKPVSLV SSLWSMILPR  180
SDCQVMRQQC CQQLAQIPQQ LQCAAIHSIV HSIIMQQEQQ EQRQGVQILV PLSQQQQVGQ  240
GTLVQGQGII QPQQPAQLEV IRSLVLQTLA TMCNVYVPPY CSTIRAPFAS IVAGIGGQYR  300

SEQ ID NO: 260           moltype = AA  length = 277
FEATURE                  Location/Qualifiers
SITE                     251
                         note = misc_feature - Xaa can be any naturally occurring
                          amino acid
source                   1..277
                         mol_type = protein
                         organism = Triticum aestivum
SEQUENCE: 260
MKTFIILTIL AMATTIATAN MQVGSSGQVE WPQHQQLPQP QQPLYHQPQQ IFPQPRQTFP  60
HLPQQTFPQP QQTIPHQPQQ QFPQTQQPLQ PFPQPQQTFP QQPQQPLPQP QQPQQPFPQS  120
QQPQPQQPFP QPQQQFPQPQ QPQQSIPQQQ QPLIQSSLQQ QMNPCKNFLL QQCNPVSLVS  180
SLVSLIFPRS DCQVMQLQCC QQLAQIPQQL QCAAIHSVVH SIMMQQEQQQ PQQLAHLEVI  240
RSLVLKTLQT XCNVYVRPDC STIRTPFAST VAGIGGQ                         277

SEQ ID NO: 261           moltype = AA  length = 292
FEATURE                  Location/Qualifiers
source                   1..292
                         mol_type = protein
                         organism = Triticum aestivum
SEQUENCE: 261
MKTLLILTIL AMAITIATAN MQVDPSGQVQ WPQQQPFLQP HQPFSQQPQQ IFPQPQQTFP  60
HQPQQQFPQP QQPQQQFLQP RQPFPQQPQQ PYPQQPQQPF PQTQQPQQPF PQSKQPQQPF  120
PQPQQPQQSF PQQQPSLIQQ SLQQQLNPCK NFLLQQCKPV SLVSSLWSII LPPSDCQVMR  180
QQCCQQLAQI PQQLQCAAIH SVVHSIIMQQ EQQEQLQGVQ ILVPLSQQQQ VGQGILVQGQ  240
GIIQPQQPAQ LEVIRSLVLQ TLPTMCNVYV PPYCSTIRAP FASIVASIGG QE          292

SEQ ID NO: 262           moltype = AA  length = 285
FEATURE                  Location/Qualifiers
source                   1..285
                         mol_type = protein
                         organism = Triticum aestivum
SEQUENCE: 262
MKTLFILTIL AMATTIATAN MQVDPSGQVQ WPQQQPFRQP QQPFYQQPQH TFPQPQQTFP  60
HQPQQQFPQP QQPQQQFPQP QQPQQPFPQP QQAQLPFPQQ PQQPFPQPQQ PQQPFPQSQQ  120
PQQPFPQPQQ PQQSFPQQQQ PLIQPYLQQQ MNPCKNYLLQ QCNPVSLVSS LVSMILPRSD  180
CQVMQQQCCQ QLAQIPRQLQ CAAIHSVVHS IVMQQEQQQG IQILRPLFQL VQGQGIIQPQ  240
QPAQYEVIRS LVLRTLPNMC NVYVRPDCST INAPFASIVA GISGQ                285

SEQ ID NO: 263           moltype = AA  length = 276
FEATURE                  Location/Qualifiers
source                   1..276
                         mol_type = protein
                         organism = Triticum aestivum
SEQUENCE: 263
MKTLLILTIL AMATTIATAN MQVDPSSRVQ WPQEQPPPQS QQPFSQQPQQ IFPQPQQTFP  60
HQPQQAFLQP QQTFPRRPQQ QFPQPQQPQQ PFPQPQQPQL PFPQQPQQPF PQPQQPQQPF  120
PQSQQPQQPF PQPQQQFPQP QQPQQSFPQQ QQWMIQSFLQ QQMNPCKNFL LQQCNPVSLV  180
SSLVSIILPR SDCQLMQQQC CQQLAQIPQQ LQCAAIHNVA HSIIMQQEQQ RGVQILRPLF  240
QLAQGLGIIQ PQQPAQLEGI RSLVLKTLPT MCNVYV                          276

SEQ ID NO: 264           moltype = AA  length = 320
FEATURE                  Location/Qualifiers
source                   1..320
                         mol_type = protein
                         organism = Triticum aestivum
SEQUENCE: 264
MKTLLILTIL AMAITIGTAN MQVDPSSQVQ WPQQQPVPQP HQPFSQQPQR TIPQPHQTFH  60
HQPQQTFPQP QQTFPHQPQQ QFPQPQQPQQ QFLQPQQPFP QQPQQPYPQQ PQQPFPQTQQ  120
PQQLFPQSQQ PQQQFSQPQQ QFPQPQQPQQ SFPQQQPPFI QPSLQQQVNP CKNFLLQQCK  180
PVSLVSSLWS MIWPQSDCQV MRQQCCQQLA QIPQQLQCAA IHTVIHSIIM QQQQQQQEQQ  240
EQQQGMHILL PLYQQQQVGQ GTLVQGQGII QPQQPAQLEA IRSLVLQTLP TMCNVYVPPE  300
CSIIKAPFSS VVAGIGGQYR                                            320

SEQ ID NO: 265           moltype = AA  length = 302
FEATURE                  Location/Qualifiers
source                   1..302
                         mol_type = protein
                         organism = Triticum aestivum
SEQUENCE: 265
```

-continued

```
MKTLLILTIL AMATTIATAN MQVDPSGQVQ WPQQQPFPQP QQPFCEQPQR TIPQPHQTFH  60
HQPQQTFPQP EQTYPHQPQQ QFPQTQQPQQ PFPQPQQTFP QQPQLPFPQQ PQQPFPQPQQ  120
PQQPFPQSQQ PQQPFPQPQQ QFPQPQQPQQ SFPQQQQPAI QSFLQQQMNP CKNFLLQQCN  180
HVSLVSSLVS IILPRSDCQV MQQQCCQQLA QIPQQLQCAA IHSVAHSIIM QQEQQQGVPI  240
LRPLFQLAQG LGIIQPQQPA QLEGIRSLVL KTLPTMCNVY VPPDCSTINV PYANIDAGIG  300
GQ                                                                302

SEQ ID NO: 266          moltype = AA  length = 471
FEATURE                 Location/Qualifiers
SITE                    143
                        note = misc_feature - Xaa can be any naturally occurring
                         amino acid
source                  1..471
                        mol_type = protein
                        organism = Secale cereale
SEQUENCE: 266
MKTLLMLAIL AMATTIATAN MQVNPSGQVQ CPQQQPFPQP QQSSPQQPQQ PFPQQSQQPF  60
PQQPQQSSPQ PQQPYPQQPF PQQPQQPYPQ QPQQPFPQQP QQPYPQQPQQ PFPQQPQQPV  120
PQQPQQQFPQ QPQQPVPQQP LQXFPQQPQQ PVPQQPLQQF PQQPQQPFPQ QPQQPVPQQS  180
QQPFPQTQQP QQPFPQPQQP QQLFPQTQQS SPQQPQQVTS QPQQPFPQAQ PPQQSSPQSQ  240
QPYPQEPQQL FPQSQQPQQP FPQPQQPQQP FPQPQPQTQQ SIPQPQQPFP QPQQPFPQSQ  300
EPFPQVHQPQ QPSPQQQQPS IQLSLQQQLN PCKNVLLQQC SPVALVSSLR SKIFPQSECQ  360
VMQQQCCQQL AQIPQQLQCA AIHSVVHAII MQQEQREGVQ ILLPQSHKQH VGQGALAQVQ  420
GIIQPQQLSQ LEVVRSLVLQ NLPTMCNVYV PRQCSTIQAP FASIVTGIVG H           471

SEQ ID NO: 267          moltype = AA  length = 479
FEATURE                 Location/Qualifiers
REGION                  103..174
                        note = misc_feature - Xaa can be any naturally occurring
                         amino acid
REGION                  283..284
                        note = misc_feature - Xaa can be any naturally occurring
                         amino acid
source                  1..479
                        mol_type = protein
                        organism = Secale cereale
SEQUENCE: 267
MKTLLMLAIL AMATTIATAN MQVNPSGQVQ CPQQQPFPQP QQSSPQQPQQ PFPQQSQQPF  60
PQQPQQSSPQ PQQPYPQQPF PQQPQQPYPQ QPQQPFPQQP QQXXXXXXXX XXXXXXXXXX  120
XXXXXXXXXX XXXXXXXXXX XXXXXXXXXX XXXXXXXXXX XXXXXXXXXX XXXXPFPQQP  180
QQPVPQQSQQ PFPQTQQPQQ PFPQPQQPQQ LFPQTQQSSP QQPQQVTSQP QQPFPQAQPP  240
QQSSPQSQQP YPQEPQQLFP QSQQPQQPFP QPQQPQQPFP QPXXQTQQSI PQPQQPFPQP  300
QQPFPQSQEQ FPQVHQPQQP SPQQQQPSIQ LSLQQQLNPC KNVLLQQCSP VALVSSLRSK  360
IFPQSECQVM QQQCCQQLAQ IPQQLQCAAI HSVVHAIIMQ QEQREGVQIL LPQSHQQHVG  420
QGALAQVQGI IQPQQLSQLE VVRSLVLQNL PTMCNVYVPR QCSTIQAPFA SIVTGIVGH   479

SEQ ID NO: 268          moltype = AA  length = 458
FEATURE                 Location/Qualifiers
SITE                    269
                        note = misc_feature - Xaa can be any naturally occurring
                         amino acid
source                  1..458
                        mol_type = protein
                        organism = Triticum aestivum
SEQUENCE: 268
MKTLLMLAIL AMVTTIATAN MQVNPSGQVQ CPQQQPFPQP QQSSPLQPQQ PFPQQSQQPF  60
PHQPQQSSPQ PQQPYPQQPF PQQPQQPYPQ QPQQPFPQQP QQPYPQQPQQ PFPQQPQQPV  120
PQQPQQQFPQ QPQQPVPQQP LQQFPQQPQQ PFPQQPQQPV PQQPLQQFPQ QPQQPFPQQP  180
QQLVPQQSQQ PFPQTQQPQQ PFPQPQQPQQ LFPQTQQSSP QQPQQVTSQP QQPFPQAQPP  240
QQSSPQSQQP YPQEPQQLFP QSQQPQQPXP QPQQPFPQPQ QPFPQSQEQF PQVHQPQQPS  300
PQQQQPSIQL SLQQQLNPCK NVLLQQCSPV ALVSSLRSKI FPQSECQVMQ QQCCQQLAQI  360
PQQLQCAAIH SVVHAIIMQQ EQREGVQILL PQSHQQHVGQ GALAQVQGII QPQQLSQLEV  420
VRSLVLQNLP TMCNVYVPRQ CSTIQAPFAS IVTGIVGH                         458

SEQ ID NO: 269          moltype = AA  length = 458
FEATURE                 Location/Qualifiers
source                  1..458
                        mol_type = protein
                        organism = Triticum aestivum
SEQUENCE: 269
MKTLLMLAIL AMVTTIATAN MQVNPSGQVQ CPQQQPFPQP QQSSPLQPQQ PFPQQSQQPF  60
PHQPQQSSPQ PQQPYPQQPF PQQPQQPYPQ QPQQPFPQQP QQPYPQQPQQ PFPQQPQQPV  120
PQQPQQQFPQ QPQQPVPQQP LQQFPQQPQQ PFPQQPQQPV PQQPLQQFPQ QPQQPFPQQP  180
QQLVPQQSQQ PFPQTQQPQQ PFPQPQQPQQ LFPQTQQSSP QQPQQVTSQP QQPFPQAQPP  240
QQSSPQSQQP YPQEPQQLFP QSQQPQQPFP QPQQPFPQPQ QPFPQSQEQF PQVHQPQQPS  300
PQQQQPSIQL SLQQQLNPCK NVLLQQCSPV ALVSSLRSKI FPQSECQVMQ QQCCQQLAQI  360
PQQLQCAAIH SVVHAIIMQQ EQREGVQILL PQSHQQHVGQ GALAQVQGII QPQQLSQLEV  420
VRSLVLQNLP TMCNVYVPRQ CSTIQAPFAS IVTGIVGH                         458
```

-continued

```
SEQ ID NO: 270         moltype = AA  length = 397
FEATURE                Location/Qualifiers
source                 1..397
                       mol_type = protein
                       organism = Triticum aestivum
SEQUENCE: 270
MKTLLMLAIL AMVTTIATAN MQVNPSGQVQ CPQQQPFPQP QQSSPLQPQQ PFPQQSQQPF  60
PHQPQQSSPQ PQQPYPQQPF PQQPQQPYPQ QPQQPQQPQQ LVPQQSQQPF PQTQQPQQPF  120
PQPQQPQQLF PQTQQSSPQQ PQQVTSQPQQ PFPQAQPPQQ SSPQSQQPYP QEPQQLFPQS  180
QQPQQPFPQP QQPQQPFPQP QPQTQQSIPQ PQQPFPQPQQ PFPQSQEQFP QVHQPQQPSP  240
QQQQPSIQLS LQQQLNPCKN VLLQQCSPVA LVSSLRSKIF PQSECQVMQQ QCCQQLAQIP  300
QQLQCAAIHS VVHAIIMQQE QREGVQILLP QSHQQHVGQG ALAQVQGIIQ PQQLSQLEVV  360
RSLVLQNLPT MCNVYVPRQC STIQAPFASI VTGIVGH                          397

SEQ ID NO: 271         moltype = AA  length = 294
FEATURE                Location/Qualifiers
source                 1..294
                       mol_type = protein
                       organism = Triticum aestivum
SEQUENCE: 271
MKTLLMLAIL AMVTTIATAN MQVNPSGQVQ CPQQQPFPQP QQSSPLQPQQ PFPQQSQQPF  60
PQQPQQSSPQ PQQPYPQQPF PQQPQQQPQQ QQPFPQPQPQ TQQSIPQPQQ PFPQPQQPFP  120
QSQEPFPQVH QPQQPSPQQQ QPSIQLSLQQ QLNPCKNVLL QQCSPVALVS SLRSKIFPQS  180
ECQVMQQQCC QQLAQIPQQL QCAAIHSVVH AIIMQQEQRE GVQILLPQSH QQHVGQGALA  240
QVQGIIQPQQ LSQLEVVRSL VLQNLPTMCN VYVPRQCSTI QAPFASIVTG IVGH        294

SEQ ID NO: 272         moltype = AA  length = 387
FEATURE                Location/Qualifiers
source                 1..387
                       mol_type = protein
                       organism = Triticum aestivum
SEQUENCE: 272
ARELNPSEQE LQSPQPRFQK GQQPVPKEQS YPQQPYPSHQ PFPTPQQYSP YQPQQPFPQP  60
QQPTPIQPQQ PFPQQPQQPQ QPFPQPQQQL PLQPQQPFPQ PQQPIPQQPQ QSFPQQPFPQ  120
PLQRPEQQFP QQPQQIIPQQ TQQPFPLQPQ QPFPQQPQRP FAQQPEQIIS QQPFPLQPQQ  180
PFSQPQQPFP QQPGQIIPQQ PQQPSPLQPQ QPFSQPQRP QQPFPQQPQQ IIPQQPQQPF  240
PLQPQQPVPQ QPQRPFGQQP EQIISQRPQQ PFPLQPQQPF SQPQQPFPQQ PGQIIPQQPQ  300
QPFPLQPQQP FPQQPEQIIP QQPQQPFPLQ PQQPFPQQPE QIISQQPQQP FPLQPQQPSP  360
QQPPHQQLPF PQPQQPFVVV ETSIGGQ                                     387

SEQ ID NO: 273         moltype = AA  length = 754
FEATURE                Location/Qualifiers
SITE                   594
                       note = misc_feature - Xaa can be any naturally occurring
                        amino acid
source                 1..754
                       mol_type = protein
                       organism = Secale cereale
SEQUENCE: 273
MAKQLVLFAA VVVALVALTV AEGEASGQLQ CERELQEREL EACRQIVDQQ LRDTSPGCRP  60
VAVSPGTGQH EQQTVVPLKG GSFYPDETSP PQQLEQRILW GIPTLLKRYY PSVTSPHQGS  120
YYPGQTSLQQ PGQAQQPGQG QQPGQAQQPG QGQQPGQGQQ PKKGQQGYYP TTPQQPGQEQ  180
QPGQGQQPGQ GQPGYYLTSS QQPGQGQQPG QGQPGYYPTS PQQSGQGQQL GQGQQGQQPG  240
QGQPGYYPTS PQQPGQGQQP GQGQRPGQGQ QGQQPGQGQQ GQQSGQGQQP GEGQQGYYPT  300
FPQQPGQVQQ PGEGQQPGQG QPGYYPTSPQ QPGQGQQPGQ RQQPGQGKPG YYPTSPQQSG  360
QGQQPGQGQS GYYPTSPQQP GQEQQPGQGQ QVQQPGQGQQ PGQGQQGYYP TSPQQSGQAQ  420
QPGQWQQPGQ GQSGYYPTSQ QQPGQGQQPG QGQQGQQQGQ GQQPGQGQQG YYPTSPQQPG  480
QGQQPGQGQQ PGQGQPGYYP TSPQQPGQGQ QTGQGQQPGQ GQQPGQGQQG QQPGQGQQGQ  540
QPGQGQQPGQ GQQGYYPTSP QQPGQGQLEY YPTSPQQPGQ GQPGYYPTSP QLPXQLQQPA  600
QGQQGYYSTS PRQPGQGQQE YYPTSPQQPG QWQQPGQGQQ GYYITSPQQS GQGQQPGQGQ  660
QPGQWLQPEQ GQEGYYPTSG QQPGQWLQIG QGQQGYYLTS PQQPGQGQQG YDSPYHVSAE  720
HQAASLKVAK AQQLAAQLPA MCRLEGGDAL SASQ                             754

SEQ ID NO: 274         moltype = AA  length = 713
FEATURE                Location/Qualifiers
source                 1..713
                       mol_type = protein
                       organism = Secale cereale
SEQUENCE: 274
MAKRLVLFGI VVIALVALTA AEGEASRQLQ CERELQESSL EACRQVVDQQ LAGRLPWSTG  60
LQMRCCQQLR DVSAKCRHVA VSQVARQYEQ TAVPPKGGSI YPGETTPLQQ LQQGIFWGTS  120
SQTVQGYYPS VTSPQQGSYY PGQASPQQPG QGQQQGKWQE PGQGQQGYYP TSQQQPGQGQ  180
QGHYPASQQQ PGQGQQGHYP ASLQQPGQGQ QGHYPASLQQ PGQGQQTEQP GQMQQPGQGQ  240
QIGQGQQPGQ GQQIGQGQQI RQGQQPGQGQ QGYYQTHPQQ PGQGQQPGQG QQGYYPTSPQ  300
QPGQGQQGHY PGSLQQPGQG QPGQRQQPGQ GQQTGQGQQP EQEQQPGQGQ QGYYPTSPQQ  360
PGQGQQPGQG QQGYYPTSLQ QPGQGQQPHY PASQQQPGQG QQGHYPTSLL QPGQGQQGHY  420
PASSLQPGQG QQGHYPASLQ QPGQGQQTEQ PGQGQQPAQE QQSGQGQQGH YPTSLQQPGQ  480
GQPGQRQQPG QGQQIGQGQQ PEQEQQPGQG QPGHYPASVQ QPGQGQQTEQ TGQGQQPGQG  540
QQPEQEQQPG QGQQGYYITS LQQPGQGKQL GQWQQPGQGQ EGYYPTSPQQ PGQGQQGHCP  600
```

-continued

```
TSRQQPGQAQ QPGQGQQIGQ AQKPGQGQQG YYPTSLQQPG QGQQSGQGNQ PGQGHQPGQG  660
QQSGQDQQGY DSPCHVSAEQ KATSPKVAKA QQPVAQLPTM CQMEGGDTLS ASQ         713

SEQ ID NO: 275         moltype = AA  length = 402
FEATURE                Location/Qualifiers
REGION                 287..315
                       note = misc_feature - Xaa can be any naturally occurring
                        amino acid
source                 1..402
                       mol_type = protein
                       organism = Triticum aestivum
SEQUENCE: 275
MAKRLVLFAT VVIGLVSLTV AEGEASKQLQ CERELQESSL EACRLVVDQQ LAGRLPWSTG  60
LQMRCCQQLR DISAKCRPVA LSQVARQYGQ TAVPPKGGSF YHRETTQLQQ LQQGIFGGTS  120
SQTVQGYYPS VISPQQGSYY PGQASPQQPG KWQELGQGQQ WYYPTSLQQP GQGQQGYYRT  180
SLQQPGQRQQ GYYRTSRQQP GQGQQIGQWQ QGYYPTSPQH PGQGQQPGQV QKIGQGQQPE  240
KGQQLGQEQQ IGQGQQPEQG QQPGQGQQGY YPTSPQQPGQ GQQPGQXXXX XXXXXXXXXX  300
XXXXXXXXXX XXXXXGQQGY YPTSLQQPGQ EQQSGQGQQL GQGHQPGQGQ QSGQEQQGYG  360
TPYHVSVEQQ AASPKVAKAH HPVAQLPTMC QMEGGDALSA SQ                    402

SEQ ID NO: 276         moltype = AA  length = 830
FEATURE                Location/Qualifiers
source                 1..830
                       mol_type = protein
                       organism = Triticum aestivum
SEQUENCE: 276
MTKRLVLFAA VVVALVALTA AEGEASGQLQ CERELQEHSL KACRQVVDQQ LRDVSPECQP  60
VGGGPVARQY EQQVVVPPKG GSFYPGETTP PQQLQQSILW GIPALLRRYY LSVTSPQQVS  120
YYPGQASSQR PGQGQQPGQG QQEYYLTSPQ QSGQWQQPGQ GQSGYYPTSP QQSGQEQPGY  180
YPTSPWQPEQ LQQPTQGQQR QQPGQGQQLR QGQQGQQSGQ GQPRYYPTSS QQPGQLQQLA  240
QGQQGQQPER GQQGQQSGQG QQLGQGQQGQ QPGQKQQSGQ GQQGYYPISP QQLGQGQQSG  300
QGQLGYYPTS PQQSGQGQSG YYPTSAQQPG QLQQSTQEQQ LGQEQQDQQS GQGRQGQQSG  360
QRQQDQQSGQ GQQPGQRQPG YYSTSPQQLG QGQPRYYPTS PQQPGQEQQP RQLQQPEQGQ  420
QGQQPEQGQQ GQQPGQGEQG QQPGQGQQGQ QPGQGQPGYY PTSPQQSGQG QPGYYPTSPQ  480
QSGQLQQPAQ GQQPGQEQQG QQPGQGQQGQ QPGQGQQPGQ GQPGYYPTSP QQSGQEQQLE  540
QWQQSGQGQP GHYPTSPLQP GQGQPGYYPT SPQQIGQGQQ PGQLQQPTQG QQGQQPGQGQ  600
QGQQPGQGQQ GQQPGQGQQP GQGQPGYYPT SLQQSGQGQQ PGQWQQPGQG QPGYYPTSSL  660
QPEQGQQGYY PTSQQQPGQG PQPGQWQQSG QGQQGYYPTS PQQSGQGQQP GQWLQPGQWL  720
QSGYYLTSPQ QLGQGQQPRQ WLQPRQGQQG YYPTSPQQSG QGQQLGQGQQ GYYPTSPQQS  780
GQGQQGYDSP YHVSAEHQAA SLKVAKAQQL AAQLPAMCRL EGGDALLASQ            830

SEQ ID NO: 277         moltype = AA  length = 831
FEATURE                Location/Qualifiers
SITE                   677
                       note = misc_feature - Xaa can be any naturally occurring
                        amino acid
SITE                   685
                       note = misc_feature - Xaa can be any naturally occurring
                        amino acid
SITE                   691
                       note = misc_feature - Xaa can be any naturally occurring
                        amino acid
SITE                   718
                       note = misc_feature - Xaa can be any naturally occurring
                        amino acid
SITE                   721
                       note = misc_feature - Xaa can be any naturally occurring
                        amino acid
SITE                   745
                       note = misc_feature - Xaa can be any naturally occurring
                        amino acid
SITE                   748
                       note = misc_feature - Xaa can be any naturally occurring
                        amino acid
SITE                   754
                       note = misc_feature - Xaa can be any naturally occurring
                        amino acid
SITE                   760
                       note = misc_feature - Xaa can be any naturally occurring
                        amino acid
SITE                   769
                       note = misc_feature - Xaa can be any naturally occurring
                        amino acid
SITE                   772
                       note = misc_feature - Xaa can be any naturally occurring
                        amino acid
source                 1..831
                       mol_type = protein
                       organism = Triticum aestivum
```

-continued

```
SEQUENCE: 277
MAKRLVLFVA VVVALVALTV AEGEASEQLQ CERELKACQQ VMDQQLRDIS PECHPVVVSP  60
VAGQYEQQIV VPPKGGSFYP GETTPPQQLQ QRIFWGIPAL LKRYYPSVTS PQQVSYYPGQ  120
ASPQRPGQGQ QPGQGQQSGQ GQQGYYPTSP QQPGQWQQPE QGQPGYYPTS PQQPGQLQQP  180
AQGQQPGQGQ QGRQPGQGQP GYYPTSSQLQ PGQLQQPAQG QQGQQPGQGQ QGQQPGQGQQ  240
PGQGQQGQQP GQGQQPGQGQ QGQQLGQGQQ GYYPTSLQQS GQGQPGYYPT SLQQLGQGQS  300
GYYPTSPQQP GQGQQPGQLQ QPAQGQQPEQ GQQGQQPGQG QQGQQPGQGQ QPGQGQPGYY  360
PTSPQQSGQG QPGYYPTSSQ QPTQSQQPGQ GQQGQQVGQG QQAQQPGQGQ QPGQGQPGYY  420
PTSPLQSGQG QPGYYLTSPQ QSGQGQQPGQ LQQSAQGQKG QQPGQGQQPG QGQQGQQPGQ  480
GQQGQQPGQG QPGYYPTSPQ QSGQGQQPGQ WQQPGQGQPG YYPTSPLQPG QGQPGYDPTS  540
PQQPGQGQQP GQLQQPAQGQ QGQQLAQGQQ GQQPAQVQQG QQPAQGQQGQ QLGQGQQGQQ  600
PGQGQQPAQG QQGQQPGQGQ QGQQPGQGQQ PGQGQPWYYP TSPQESGQGQ QPGQWQQPGQ  660
WQQPGQGQPG YYLTSPXQPG QGQQXYYPTS XQQPGQWQQP GQGQQGYYPT SPQQSGQXQQ  720
XGQGQQPGQW LQPGQGQQGY YPTSXQQXGQ GQQXGQWLQX GQGQQGYYXT SXQQPGQGQQ  780
SGQGQQGYDS PYHVSAEHQA ASLKVAKAQQ LAAQLPAMCR LEGGDALSAS Q           831

SEQ ID NO: 278         moltype = AA  length = 839
FEATURE                Location/Qualifiers
source                 1..839
                       mol_type = protein
                       organism = Triticum aestivum
SEQUENCE: 278
MAKRLVLFVA VVVALVALTV AEGEASEQLQ CERELQELQE RELKACQQVM DQQLRDISPE  60
CHPVVVSPVA GQYEQQIVVP PKGGSFYPGE TTPPQQLQQR IFWGIPALLK RYYPSVTSPQ  120
QVSYYPGQAS PQRPGQGQQP GQGQQSGQGQ QGYYPTSPQQ PGQWQQPEQG QPGYYPTSPQ  180
QPGQLQQPAQ GQQPGQGQQG RQPGQGQPGY YPTSSQLQPG QLQQPAQGQQ GQQPGQGQQG  240
QQPGQGQQPG QGQQGQQPGQ GQQPGQGQQG QQLGQGQQGY YPTSLQQSGQ GQPGYYPTSL  300
QQLGQGQSGY YPTSPQQPGQ GQQPGQLQQP AQGQQPEQGQ QGQQPGQGQQ GQQPGQGQQP  360
GQGQPGYYPT SPQQSGQGQP GYYPTSSQQP TQSQQPGQGQ QGQQVGQGQQ AQQPGQGQQP  420
GQGQPGYYPT SPLQSGQGQP GYYLTSPQQS GQGQQPGQLQ QSAQGQKGQQ PGQGQQPGQG  480
QQGQQPGQGQ QGQQPGQGQP GYYPTSPQQS GQGQQPGQWQ QPGQGQPGYY PTSPLQPGQG  540
QPGYDPTSPQ QPGQGQQPGQ LQQPAQGQQG QQLAQGQQGQ QPAQVQQGQQ PAQGQQGQQL  600
GQGQQGQQPG QGQQPAQGQQ GQQPGQGQQG QQPGQGQQPG QGQPWYYPTS PQESGQGQQP  660
GQWQQPGQWQ QPGQGQPGYY LTSPLQLGQG QQGYYPTSLQ QPGQGQQPGQ WQQSGQGQHG  720
YYPTSPQLSG QGQRPGQWLQ PGQGQQGYYP TSPQQSGQGQ QLGQWLQPGQ GQQGYYPTSL  780
QQTGQGQQSG QGQQGYYSSY HVSVEHQAAS LKVAKAQQLA AQLPAMCRLE GGDALSASQ   839

SEQ ID NO: 279         moltype = AA  length = 720
FEATURE                Location/Qualifiers
REGION                 454..467
                       note = misc_feature - Xaa can be any naturally occurring
                        amino acid
source                 1..720
                       mol_type = protein
                       organism = Triticum aestivum
SEQUENCE: 279
MAKRLVLFAT VVITLVALTA AEGEASRQLQ CERELQESSL EACRQVVDQQ LAGRLPWSTG  60
LQMRCCQQLR DVSAKCRPVA VSQVVRQYEQ TVVPPKGGSF YPGETTPLQQ LQQVIFWGTS  120
SQTVQGYYPS VSSPQQGPYY PGQASPQQPG QGQQPGKWQE LGQGQQGYYP TSLHQSGQGQ  180
QGYYPSSLQQ PGQGQQIGQG QQGYYPTSLQ QPGQGQQIGQ GQQGYYPTSP QHPGQRQQPG  240
QGQQIGQGQQ LGQGRQIGQG QQSGQGQQGY YPTSPQQLGQ GQQPGQWQQS GQGQQGYYPT  300
SQQQPGQGQQ GQYPASQQQP GQGQQGQYPA SQQQPGQGQQ GQYPASQQQP AQGQQGQYPA  360
SQQQPGQGQQ GHYLASQQQP GQGQQRHYPA SLQQPGQGQQ GHYTASLQQP GQGQQGHYPA  420
SLQQVGQGQQ IGQLGQRQQP GQGQQTRQGQ QLEXXXXXXX XXXXXXXQQL EQGQQPGQGQ  480
QGYYPTSPQQ SGQGQQPGQS QQPGQGQQGY YSSSLQQPGQ GLQGHYPASL QQPGQGHPGQ  540
RQQPGQGQQP EQGQQPGQGQ QGYYPTSPQQ PGQGKQLGQG QQGYYPTSPQ QPGQGQQPGQ  600
GQQGHCPTSP QQTGQAQQPG QGQQIGQVQQ PGQGQQGYYP ISLQQSGQGQ QSGQGQQSGQ  660
GHQLGQGQQS GQEQQGYDNP YHVNTEQQTA SPKVAKVQQP ATQLPIMCRM EGGDALSASQ  720

SEQ ID NO: 280         moltype = AA  length = 672
FEATURE                Location/Qualifiers
REGION                 331..333
                       note = misc_feature - Xaa can be any naturally occurring
                        amino acid
source                 1..672
                       mol_type = protein
                       organism = Triticum aestivum
SEQUENCE: 280
MAKRLVLFAA VVIALVALTT AEGEASRQLQ CERELQESSL EACRQVVDQQ LAGRLPWSTG  60
LQMRCCQQLR DVSAKCRSVA VSQVARQYEQ TVVPPKGGSF YPGETTPLQQ LQQGIFWGTS  120
SQTVQGYYPS VTSPRQGSYY PGQASPQQPG QGQQPGKWQE PGQGQQWYYP TSLQQPGQGQ  180
QIGKGKQGYY PTSLQQPGQG QQIGQGQQGY YPTSPQHTGQ RQQPVQGQQI GQGQQPEQGQ  240
QPGQWQQGYY PTSPQQLGQG QQPGQWQQSG QGQQGHYPTS LQQPGQGQQG HYLASQQQPA  300
QGQQGHYPAS QQQPGQGQQG HYPASQQQPG XXXGHYPASQ QQPGQGQQGH YPASQQEPGQ  360
GQQGQIPASQ QQPGQGQQGH YPASLQQPGQ QGHYPTSLQQ LGQGQQIGQP GQKQQPGQGQ  420
QTGQGQQPEQ EQQPGQGQQG YYPTSLQQPG QGQQQGQGQQ GYYPTSLQQP GQGQQGHYPA  480
SLQQPGQGQP GQRQQPGQGQ HPEQGQQPGQ GQQGYYPTSP QQPGQGQQLG QGQQGYYPTS  540
PQQPGQGQQP GQGQQGHCPM SPQQTGQAQQ LGQGQQIGQV QQPGQGQQGY YPTSLQQPGQ  600
GQQSGQGQQS GQGHQPGQGQ QSGQEKQGYD SPYHVSAEQQ AASPMVAKAQ QPATQLPTVC  660
```

-continued

```
RMEGGDALSA SQ                                                   672

SEQ ID NO: 281         moltype = AA  length = 488
FEATURE                Location/Qualifiers
SITE                   317
                       note = misc_feature - Xaa can be any naturally occurring
                        amino acid
source                 1..488
                       mol_type = protein
                       organism = Triticum aestivum
SEQUENCE: 281
MAKRLVLFAA VVVALLALTA AEGEASGQLQ CERELQESSL EACRRVVDQQ LAGQLPWSTG  60
LQMRCCQQLR DVSPECRPIA VSQVARQYEQ QIVVPPKGGS FYPGETTPPQ QLQQRIFWGR  120
SSQTVQGYYP SVTSPQQGSY YPGQASPQQP GQGQQPGQWQ EPGQGIQGYG LTSPQQPGQG  180
QQLGQRQQPE QGQQGYCPIS PQQPGQWQQS GQGQQGYYQT SPQQPAQGQQ GYDLTSPQQS  240
GQGQQLGQRQ QPGQGQQGYY PISPQQPGQW QQPGQGQQGY YPTSPQQPGQ GQQGYYPTSP  300
QQSGQGQQPG QGYYPTXPQS PQQPGQWQQP GQGQQGYYPT SPQQPGQGQQ GYYPTSPQQP  360
GQWQQLGQGY YPTFPQQSGQ GQQPGQGYYP TFPQQPGQGQ QGYYPTSPQQ SGQWQQSGQW  420
QQGYYPTFPQ QPGQGQQLGQ EPQGYNSPYH VSAEQQAASL MVAKAQQLAA QLPAMCRLEG  480
SGALSASQ                                                        488

SEQ ID NO: 282         moltype = AA  length = 648
FEATURE                Location/Qualifiers
source                 1..648
                       mol_type = protein
                       organism = Triticum aestivum
SEQUENCE: 282
MAKRLVLFAA VVIALVALTT AEGEASRQLQ CERELQESSL EACRQVVDQQ LAGRLPWSTG  60
LQMRCCQQLR DVSAKCRSVA VSQVARQYEQ TVVPPKGGSF YPGETTPLQQ LQQGIFWGTS  120
SQTVQGYYPG VTSPRQGSYY PGQASPQQPG QGQQPGKWQE PGQGQQWYYP TSLQQPGQGQ  180
QIGKGQQGYY PTSLQQPGQG QQGYYPTSLQ HTGQRQQPVQ GQQPEQGQQP GQWQQGYYPT  240
SPQQLGQGQQ PRQWQQSGQG QQGHYPTSLQ QPGQGQQGHY LASQQQPGQG QQGHYPASQQ  300
QPGQGQQGHY PASQQQPGQG QQGHYPASQQ EPGQGQQGQI PASQQQPGQG QQGHYPASLQ  360
QPGQGQQGHY PTSLQQLGQG QQTGQPGQKQ QPGQGQQTGQ GQQPEQEQQP GQGQQGYYPT  420
SLQQPGQGQQ QGQGQQGYYP TSLQQPGQGQ QGHYPASLQQ PGQGQPGQRQ QPGQGQHPEQ  480
GKQPGQGQQG YYPTSPQQPG QGQQLGQGQQ GYYPTSPQQP GQGQQPGQGQ QGHCPTSPQQ  540
SGQAQQPGQG QQIGQVQQPG QGQQGYYPTS VQQPGQGQQS GQGQQSGQGH QPGQGQQSGQ  600
EQQGYDSPYH VSAEQQAASP MVAKAQQPAT QLPTVCRMEG GDALSASQ            648

SEQ ID NO: 283         moltype = AA  length = 608
FEATURE                Location/Qualifiers
SITE                   32
                       note = misc_feature - Xaa can be any naturally occurring
                        amino acid
SITE                   36
                       note = misc_feature - Xaa can be any naturally occurring
                        amino acid
SITE                   599
                       note = misc_feature - Xaa can be any naturally occurring
                        amino acid
source                 1..608
                       mol_type = protein
                       organism = Triticum aestivum
SEQUENCE: 283
MAKRLVLFAT VVIGLVSLTV AEGEASRQLQ CXRELXESSL EACRLVVDQQ LAGRLPWSTG  60
LQMRCCQQLR DISAKCRPVA VSQVARQYGQ TAVPPKGGSF YPRETTPLQQ LQQEIFGGTS  120
SQTVQGYYPS VISPQQGSYY PGQASPQQPG KWQELGQEQQ GYYPTSLQQP GQGQQGYYRT  180
SLQQSGQGQQ GYYRTSLQQP GQGQQIGQWQ QGYYPTSPQH PGQGQQPGQV QKIGQGQQPE  240
KGQQLGQEQQ IGQGQQPEQG QQPGQGQQPG QGQQGYYPTS LQQPGQGQQP GQWQQPGQGQ  300
QGYYPTSLQQ PGQGQQGHYP ASQHQPGQGQ QGHHPASLQQ SGQGQQGHHP ASLQQPGQGK  360
QTGQREQRQQ PGQGQQTGQG QQPEQEQQPG QGQQGYYPTY MQQPGQGQQP EQWQQPGQGQ  420
QGHYPASLQQ SGQGQQGHYP ASLQQPGQGQ PGQTQQPGQG QQPEQEEQSG QGQQGYYPTS  480
PQQPGQGQQP GQGQQGHFPT SGQAQQPGQG QQIGQAQQLG QGQQGYYPTS LQQPGQEQQS  540
RQGQQLGQGH QPGQGQQSGQ EQQGYDSPYH VSVEQQAASP KVAKAHHPVA QLPTMCQMXG  600
GDALSASQ                                                        608

SEQ ID NO: 284         moltype = AA  length = 786
FEATURE                Location/Qualifiers
REGION                 178..181
                       note = misc_feature - Xaa can be any naturally occurring
                        amino acid
SITE                   222
                       note = misc_feature - Xaa can be any naturally occurring
                        amino acid
SITE                   381
                       note = misc_feature - Xaa can be any naturally occurring
                        amino acid
SITE                   469
                       note = misc_feature - Xaa can be any naturally occurring
```

```
                          amino acid
SITE                     474
                         note = misc_feature - Xaa can be any naturally occurring
                          amino acid
SITE                     489
                         note = misc_feature - Xaa can be any naturally occurring
                          amino acid
SITE                     498
                         note = misc_feature - Xaa can be any naturally occurring
                          amino acid
SITE                     527
                         note = misc_feature - Xaa can be any naturally occurring
                          amino acid
REGION                   530..531
                         note = misc_feature - Xaa can be any naturally occurring
                          amino acid
SITE                     540
                         note = misc_feature - Xaa can be any naturally occurring
                          amino acid
SITE                     574
                         note = misc_feature - Xaa can be any naturally occurring
                          amino acid
SITE                     605
                         note = misc_feature - Xaa can be any naturally occurring
                          amino acid
SITE                     624
                         note = misc_feature - Xaa can be any naturally occurring
                          amino acid
SITE                     628
                         note = misc_feature - Xaa can be any naturally occurring
                          amino acid
SITE                     636
                         note = misc_feature - Xaa can be any naturally occurring
                          amino acid
SITE                     714
                         note = misc_feature - Xaa can be any naturally occurring
                          amino acid
SITE                     724
                         note = misc_feature - Xaa can be any naturally occurring
                          amino acid
SITE                     734
                         note = misc_feature - Xaa can be any naturally occurring
                          amino acid
source                   1..786
                         mol_type = protein
                         organism = Triticum aestivum
SEQUENCE: 284
MAKRLVLFAA VVVALVALTV AEGEASGQLQ CERELQEREL EACRQIVDQQ LRDTSPGCRP  60
VAVSPGTGQQ EQQTVVPLKG GSFYPDETSP PQQLEQRILW GIPTLLKRYY PSVTSPHQGS  120
YYPGQTSLQQ PGQAQQPGQG QQPGQAQQPG HGQQSGQGQQ PEKGQQGYYP TTPQQPGXXX  180
XQGQQPGQGQ PGYYLTSSQQ PGQGQQPGQG QPGYYPTSSQ QXGQGQQLGQ GQQGQQPGQG  240
QPGYYPTSPQ QPGQGQQPGQ GQQPGQGQQG QQPGQGQQGQ QPGQGQQPGE GQQGYYPTFP  300
QQPGQVQQPG QGQQPGQGQP GYYPTSPQQP GQGQQPGQEQ QPGQRQQPGQ GKPGYYPTSP  360
QQSGQGQSGY YPTSPQQPGQ XQQPGQGQQV QQPGQGQQPG QGQQGYYPTS PQQSGQAQQP  420
GQWQQPGQGQ SGYYPTSQQQ PGQGQQPGQG QQPGQGQQPG QGQQGQQPXQ GQQXGQGQQG  480
YYPTSPQQXG QGQQPGQXQQ PGQGQPGYYP TSPQQSGQGQ QPGQGQXGYX XTSPQQPGQX  540
QQPGQGQQGQ QPGQGQQPGQ GQQGYYPTSP QQPXQGQQPG QGQLEYYPTS PQQPGQGQPG  600
YYPTXPQLPG QLQQPAQGQQ GYYXTSPXQP GQGQQXYYPT SPQQPGQWQQ PGQGQQGYYI  660
TSPQQSGQGQ QPGQGQQPGQ WLQPGQGQEG YYPTSGQQPG QWLQIGQGQQ GYYXTSPQQQ  720
GYYXTSPQQP GQGXQPGQGQ QGYDSPYHVS AEHQAASLKV AKAQQLAAQL PAMCRLEGGD  780
ALSASQ                                                            786

SEQ ID NO: 285           moltype = AA  length = 795
FEATURE                  Location/Qualifiers
SITE                     273
                         note = misc_feature - Xaa can be any naturally occurring
                          amino acid
SITE                     593
                         note = misc_feature - Xaa can be any naturally occurring
                          amino acid
SITE                     745
                         note = misc_feature - Xaa can be any naturally occurring
                          amino acid
source                   1..795
                         mol_type = protein
                         organism = Triticum aestivum
SEQUENCE: 285
MAKRLVLFAA VVVALVALTA AEGEASGQLQ CEHELEACQQ VVDQQLRDVS PGCRPITVSP  60
GTRQYEQQPV VPSKAGSFYP SETTPSQQLQ QMIFWGIPAL LRRYYPSVTS SQQGSYYPGQ  120
```

-continued

```
ASPQQSGQGQ QPGQEQQPGQ GQQDQQPGQR QQGYYPTSPQ QPGQGQQLGQ GQPGYYPTSQ  180
QPGQKQQAGQ GQQSGQGQQG YYPTSPQQSG QGQQPGQGQP GYYPTSPQQS GQWQQPGQGQ  240
QPGQGQQSGQ GQQGQQPGQG QRPGQGQQGY YPXSPQQPGQ GQQSGQGQPG YYPTSLRQPG  300
QWQQPGQGQQ PGQGQQGQQP GQGQQSGQGQ QGYYPTSLQQ PGQGQQLGQG QPGYYPTSQQ  360
SEQGQQPGQG KQPGQGQQGY YPTSPQQSGQ GQQLGQGQPG YYPTSPQQSG QGQQSGQGQQ  420
GYYPTSPQQS GQGQQPGQGQ SGYFPTSRQQ SGQGQQPGQG QQSGQGQQGQ QPGQGQQAYY  480
PTSSQQSRQR QQAGQWQRPG QGQPGYYPTS PQQPGQEQQS GQAQQSGQWQ LVYYPTSPQQ  540
PGQLQQPAQG QQPAQGQQSA QEQQPGQAQQ SGQWQLVYYP TSPQQPGQLQ QPXQGQQGYY  600
PTSPQQSGQG QQGYYPTSPQ QSGQGQQGYY PTSPQQSGQG QQPGQGQQPR QGQQGYYPIS  660
PQQSGQGQQP GQGQQGYYPT SPQQSGQGQQ PGHEQQPGQW LQPGQGQQGY YPTSSQQSGQ  720
GQQSGQGQQG YYPTSLWQPG QGQQXGQGQQ GYDSPYHVSA EYQAARLKVA KAQQLAAQLP  780
AMCRLEGSDA LSARQ                                                   795

SEQ ID NO: 286          moltype = AA  length = 848
FEATURE                 Location/Qualifiers
source                  1..848
                        mol_type = protein
                        organism = Triticum spelta
SEQUENCE: 286
MAKRLVLFVA VVVALVALTV AEGEASEQLQ CERELQELQE RELKACQQVM DQQLRDISPE  60
CHPVVVSPVA GQYEQQIVVP PKGGSFYPGE TTPPQQLQQR IFWGIPALLK RYYPSVTCPQ  120
QVSYYPGQAS PQRPGQGQQP GQGQQGYYPT SPQQPGQWQQ PEQGQPRYYP TSPQQSGQLQ  180
QPAQGQQPGQ GQQGQQPGQG QPGYYPTSSQ LQPGQLQQPA QGQQGQQPGQ GQQGQQPGQG  240
QQPGQGQQGQ QPGQGQQPGQ GQQGQQLGQG QQGYYPTSLQ QSGQGQPGYY PTSLQQLGQG  300
QSGYYPTSPQ QPGQGQQPGQ LQQPAQGQQP GQGQQGQQPG QGQQGQQPGQ GQQPGQGQPG  360
YYPTSPQQSG QGQPGYYPTS SQQPTQSQQP GQGQQGQQVG QGQQAQQPGQ GQQPGQGQPG  420
YYPTSPQQSG QGQPGYYLTS PQQSGQGQQP GQLQQSAQGQ KGQQPGQGQQ PGQGQQGQQP  480
GQGQQGQQPG QGQPGYYPTS PQQSGQGQQP GQWQQPGQGQ PGYYPTSPLQ PGQGQPGYDP  540
TSPQQPGQGQ QPGQLQQPAQ GQQGQQLAQG QQGQQPAQVQ QGQRPAQGQQ GQQPGQGQQG  600
QQLGQGQQGQ QPGQGQQGQQ PAQGQQGQQP GQGQQGQQPG QGQQGQQPGQ GQQPGQGQPW  660
YYPTSPQESG QGQQPGQWQQ PGQGQPGYYL TSPLQLGQGQ QGYYPTSLQQ PGQGQQPGQW  720
QQSGQGQHWY YPTSPQLSGQ GQRPGQWLQP GQGQQGYYPT SPQQPGQGQQ LGQWLQPGQG  780
QQGYYPTSLQ QTGQGQQSGQ GQQGYYSSYH VSVEHQAASL KVAKAQQLAA QLPAMCRLEG  840
GDALSASQ                                                           848

SEQ ID NO: 287          moltype = AA  length = 119
FEATURE                 Location/Qualifiers
source                  1..119
                        mol_type = protein
                        organism = Triticum spelta
SEQUENCE: 287
MAKRLVLFAA VVVALVALTA AEGEASGQLQ CERELRKREL EACQQVVDQQ LRDVSPGCRP  60
ITVSPGTRQY EQQPVVPSKA GSFYPSETTP SQQLQQMIFW GIPALLRRYY PSVTSSQQG   119

SEQ ID NO: 288          moltype = AA  length = 274
FEATURE                 Location/Qualifiers
SITE                    96
                        note = misc_feature - Xaa can be any naturally occurring
                         amino acid
source                  1..274
                        mol_type = protein
                        organism = Hordeum vulgare
SEQUENCE: 288
MKTFLIFALL AIAATNTIAQ QQPFPQQPQP YPQQPQPYPQ QPFPPQQPFP QQPPFWWQQP  60
VQSQQQPCQQ QQTPLPQGQQ YQPLLQQQIP FVHPSXLQQL NPCKVFLQQQ CSPVPMPQRI  120
ARSQMLQQSS CHVLQQQCCQ QLPQIPEQFR HEAIRAIIYS IILQEQQQVQ DFVQPQQQQP  180
QQSVQGVSQS QQQSQQPQLG QCSFQQPQLQ QLGQQPQQQQ VPLWAFLQPQ QMAQLEVMTS  240
VALRTLPTMC NVNVPLYGIT TSVPLSVGTG VGPY                              274

SEQ ID NO: 289          moltype = AA  length = 308
FEATURE                 Location/Qualifiers
REGION                  39..58
                        note = misc_feature - Xaa can be any naturally occurring
                         amino acid
SITE                    140
                        note = misc_feature - Xaa can be any naturally occurring
                         amino acid
SITE                    264
                        note = misc_feature - Xaa can be any naturally occurring
                         amino acid
source                  1..308
                        mol_type = protein
                        organism = Hordeum vulgare
SEQUENCE: 289
MKTFLIFALL AIVATSTIAQ QQPYPQQPQP FPQQPIPQXX XXXXXXXXXX XXXXXXXXPI  60
PQQPQPYPQQ PQPFPQQPIP QQPQPYPQQP QPFPLQPFPS QQPFPQQPPF WQQQPVLSQQ  120
QPCTQEQTPL LQEQQDQMLX QVQIPFVHPS ILQQLNPCKV FLQQQCSPVA MSQRIARSQM  180
LQQSSCHVLQ QQCCQQLPQI PEQLRHEAVR AIVYSIVLQE QSLQLVQGVS QPQQQSQQQQ  240
VGQCSFQQPQ PQQGQQQQVP QSVXLQPHQI AQLEATTSIA LRTLPTMCSV NVPLYRIVPL  300
```

-continued

```
AIDTRVGV                                                    308

SEQ ID NO: 290          moltype = AA  length = 265
FEATURE                 Location/Qualifiers
source                  1..265
                        mol_type = protein
                        organism = Hordeum vulgare
SEQUENCE: 290
MKTFLIFALL AIVATSTIAQ QQPYPQQPQP FPQQPIPQQP QPFPQQPQPF PQQPFPSRQP  60
FPQQPPFWQQ QPVLSQQQPC TQDQTPLLQE QQDQMLLQVQ IPFVHPSILQ QLNPCKVFLQ  120
QQCSPVAMSQ RIARSQMLQQ SSCHVLQQQC CQQLPQIPEQ IRHEAVRAIV YSIVLQEQPL  180
QLVQGVSQPQ QQSQQQQVGQ CSFQQPQPQQ GQQQQVPQSV FLQPHQIAQL EATASIALRT  240
LPTMCSVNVP LYRIVPLAID TRVGV                                  265

SEQ ID NO: 291          moltype = AA  length = 301
FEATURE                 Location/Qualifiers
source                  1..301
                        mol_type = protein
                        organism = Hordeum vulgare
SEQUENCE: 291
MKTFLIFALL AIAATSTIAQ QQPFPQQPIP QQPQPYPQQP QPYPQQPFQP QQPFPQQTIP  60
QQPQPYPQQP QPYPQQPFPP QQAFPQQPPF WPQQPFPQQP PFGLQQPILS QQQPCTPQQT  120
PLPQGQLYQT LLQLQIPNVQ PSILQQLNPC KVFLQQQCSP VRMQQLIARS QMLQQSSCHV  180
LQQQCCQQLP QIPEQFRHEA IRAIVYSIFL QEQPQQSVQG VSQPQQQLQQ EQVGQCYFQQ  240
PQPQQLGQPQ QVPQSVFLQP HQIAQLEATT SIALRTLPTM CNVNVPLYDI MPFGVGTRVG  300
V                                                           301

SEQ ID NO: 292          moltype = AA  length = 294
FEATURE                 Location/Qualifiers
SITE                    291
                        note = misc_feature - Xaa can be any naturally occurring
                         amino acid
SITE                    293
                        note = misc_feature - Xaa can be any naturally occurring
                         amino acid
source                  1..294
                        mol_type = protein
                        organism = Hordeum vulgare
SEQUENCE: 292
MKTFLIFALL VIAATSTIAQ QQPFPQQPFP QQPQPYPQQP QPYPQQPFQP QQPFPQQTIP  60
QQPQPYPQQP FPPQQEFPQQ PPFWPQQPFP QQPPFGLQQP ILSQQQPCTP QQTPLPQGQL  120
YQTLLQLQIP YVHPSILQQL NPCKVFLQQQ CSPVRMPQLI ARLQMLQQSS CHVLQQQCCQ  180
QLPQISEQFR HEAIRAIVYS IFLQEQPQQS VQGVSQTQQQ LQQEQVGQCS FQQPQPQQLG  240
QAQQVPQSVF LQPHQIAQLE ATTSIALRTL PRMCNVNVPL YDIMPPDFWH XVXV        294

SEQ ID NO: 293          moltype = AA  length = 273
FEATURE                 Location/Qualifiers
source                  1..273
                        mol_type = protein
                        organism = Hordeum vulgare
SEQUENCE: 293
MKTFLIFALL AIAATSTIAQ QQPFPQQPQQ IPQQPQPYPQ QPQPYPQQPF PPQQEFPQQP  60
PFWPQQPFPQ QPPFGLQQPI LSQQQPCTPQ QTPLPQGQLY QTLLQLQIPY VHPSILQQLN  120
PCKVFLQQQC SPVRMPQLIA RLQMLQQSSC HVLQQQCCQQ LPQISEQFRH EAIRAIVYSI  180
FLQEQPQQSV QGVSQTQQQL QQEQVGQCSF QQPQPQQLGQ PQQVPQSVFL QPHQIAQLEA  240
TTSIALRTLP RMCNVNVPLY DIMPPDFWHR VGV                          273

SEQ ID NO: 294          moltype = AA  length = 328
FEATURE                 Location/Qualifiers
SITE                    27
                        note = misc_feature - Xaa can be any naturally occurring
                         amino acid
REGION                  36..41
                        note = misc_feature - Xaa can be any naturally occurring
                         amino acid
SITE                    51
                        note = misc_feature - Xaa can be any naturally occurring
                         amino acid
SITE                    97
                        note = misc_feature - Xaa can be any naturally occurring
                         amino acid
REGION                  99..100
                        note = misc_feature - Xaa can be any naturally occurring
                         amino acid
SITE                    105
                        note = misc_feature - Xaa can be any naturally occurring
                         amino acid
SITE                    119
                        note = misc_feature - Xaa can be any naturally occurring
```

-continued

```
                         amino acid
REGION                  128..129
                        note = misc_feature - Xaa can be any naturally occurring
                         amino acid
REGION                  135..136
                        note = misc_feature - Xaa can be any naturally occurring
                         amino acid
SITE                    159
                        note = misc_feature - Xaa can be any naturally occurring
                         amino acid
SITE                    167
                        note = misc_feature - Xaa can be any naturally occurring
                         amino acid
SITE                    170
                        note = misc_feature - Xaa can be any naturally occurring
                         amino acid
SITE                    172
                        note = misc_feature - Xaa can be any naturally occurring
                         amino acid
source                  1..328
                        mol_type = protein
                        organism = Hordeum vulgare
SEQUENCE: 294
MKTFLTFVLL AMAMSIVTTA RQLNPSXQEL QSPQQXXXXX XSYLQQPYPQ XPYLPQQPFP  60
TPQQFFPYLP QQTFPQSQQP TPLQPQQPFP LQPQQPXPXX QQPFXWQPQQ PFPQPQQPXP  120
QQPQQPFXXQ PQQIXXQQPQ QPFPQQPQQP FPQPQQPFXW QPQQPFXQPX QXFPLQPQQP  180
FPWQPQQPFP QPQQPIAHQP QQPFSFSQQP QQPFPLQPQQ PFPQQPQQPF PQQPQQIIFQ  240
QPQQSYPVQP QQPFPQPQQP FPQIPQQPFP LQPQPFPQQP QQPLPQPQQP FRQQAELIIP  300
QQPQQPFPLQ PHQPYTQQTI WSMVALLG                                    328

SEQ ID NO: 295          moltype = AA  length = 747
FEATURE                 Location/Qualifiers
source                  1..747
                        mol_type = protein
                        organism = Hordeum vulgare
SEQUENCE: 295
MAKRLVLFVA VIVALVALTT AEREINGNNI FLDSRSRQLQ CERELQESSL EACRRVVDQQ  60
LVGQLPWSTG LQMQCCQQLR DVSPECRPVA LSQVVRQYEQ QTEVPSKGGS FYPGGTAPPL  120
QQGGWWGTSV KWYYPDQTSS QQSWQGQQGY HQSVTSSQQP GQGQQGSYPG STFPQQPGQG  180
QQPGQRQPWS YPSATFPQQP GQGQGQQGYY PGATSLLQPG QGQQGPYQSA TSPQQPGQGQ  240
GQQETYPIAT SPHQPGQWQQ PGQGQQGYYP SVTSPQQSGQ GQQGYPSTTS PQQSGQGQQL  300
GQGQQPGQGQ QGYPSATFPQ QPGQWQQGSY PSTTSPQQSG QGQQGYNPSG TSTQQPGQVQ  360
QLGQGQQGYY PIATSPQQPG QGQQLGQGQQ PGHGQQLVQG QQQGQGQQGH YPSMTSPHQT  420
GQGQKGYYPS AISPQQSGQG QQGYQPSGAS SQGSVQGACQ HSTSSPQQQA QGCQASSPKQ  480
GLGSLYYPSG AYTQQKPGQG YNPGGTSPLH QQGGGFGGGL TTEQPQGGKQ PFHCQQTTVS  540
PHQGQQTTVS PHQGQQTTVS PHQGQQTTVS PHQGQQTTVS PHQGQQTTVS PHQGQQTTVS  600
PHPGQQTTVS PHQGQQTTVS PHPGQQTTVS PHQGQQTTVS PHQGQQTTVS PHQGQQTTVS  660
PHQGQQTTVS PHQGQQPGEQ PCGFPGQQTT VSLHHGQQSN ELYYGSPYHV SVEQPSASLK  720
VAKAQQLAAQ LPAMCRLEGG GGLLASQ                                     747

SEQ ID NO: 296          moltype = AA  length = 305
FEATURE                 Location/Qualifiers
source                  1..305
                        mol_type = protein
                        organism = Hordeum vulgare
SEQUENCE: 296
MKILIILTIL AMATTFATSE MQVNPSVQVQ PTQQQPYPES QQPFISQSQQ QFPQPQQPFP  60
QQPQQPFPQS QQQCLQQPQH QFPQPTQQFP QRPLLPFTHP FLTFPDQLLP QPPHQSFPQP  120
PQSYPQPPLQ PFPQPPQQKY PEQPQQPFPW QQPTIQLYLQ QQLNPCKEFL LQQCRPVSLL  180
SYLWSKIVQQ SSCRVMQQQC CLQLAQIPEQ YKCTAIDSIV HAIFMQQGQR QGVQIVQQQP  240
QPQQVGQCVL VQGQGVVQPQ QLAQMEAIRT LVLQSVPSMC NFNVPPNCST IKAPFVGVVT  300
GVGGQ                                                             305

SEQ ID NO: 297          moltype = AA  length = 304
FEATURE                 Location/Qualifiers
source                  1..304
                        mol_type = protein
                        organism = Hordeum vulgare
SEQUENCE: 297
MKIFLLFSLL GVATAITTTT MQFNPSGLEL ERPQQLFPQW QPLPQQPPFL QQEPEQPYPQ  60
QQPLPQQQPF PQQPQLPHQH QFPQQLPQQQ FPQQMPLQPQ QQFPQQMPLQ PQQQPQFPQQ  120
KPFGQYQQPL TQQPYPQQQP LAQQQPSIEE QHQLNLCKEF LLQQCTLDEK VPLLQSVISF  180
LRPHISQQNS CQLKRQQCCQ QLANINEQSR CPAIQTIVHA IVMQQQVQQQ VGHGFVQSQL  240
QQLGQGMPIQ LQQQPGQAFV LPQQQAQFKV VGSLVIQTLP MLCNVHVPPY CSPFGSMATG  300
SGGQ                                                              304

SEQ ID NO: 298          moltype = AA  length = 274
FEATURE                 Location/Qualifiers
SITE                    96
```

```
                       note = misc_feature - Xaa can be any naturally occurring
                        amino acid
source                 1..274
                       mol_type = protein
                       organism = Hordeum vulgare
SEQUENCE: 298
MKTFLIFALL AIAATNTIAQ QQPFPQQPQP YPQQPQPYPQ QPFPPQQPFP QQPPFWWQQP  60
VQSQQQPCQQ QQTPLPQGQQ YQPLLQQQIP FVHPSXLQQL NPCKVFLQQQ CSPVPMPQRI  120
ARSQMLQQSS CHVLQQQCCQ QLPQIPEQFR HEAIRAIIYS IILQEQQQVQ DFVQPQQQQP  180
QQSVQGVSQS QQQSQQPQLG QCSFQQPQLQ QLGQQPQQQQ VPLWAFLQPQ QMAQLEVMTS  240
VALRTLPTMC NVNVPLYGIT TSVPLSVGTG VGPY                              274

SEQ ID NO: 299         moltype = AA  length = 308
FEATURE                Location/Qualifiers
REGION                 39..58
                       note = misc_feature - Xaa can be any naturally occurring
                        amino acid
SITE                   140
                       note = misc_feature - Xaa can be any naturally occurring
                        amino acid
SITE                   264
                       note = misc_feature - Xaa can be any naturally occurring
                        amino acid
source                 1..308
                       mol_type = protein
                       organism = Hordeum vulgare
SEQUENCE: 299
MKTFLIFALL AIVATSTIAQ QQPYPQQPQP FPQQPIPQXX XXXXXXXXXX XXXXXXXXPI  60
PQQPQPYPQQ PQPFPQQPIP QQPQPYPQQP QPFPLPQPFPS QQPFPQQPPF WQQQPVLSQQ  120
QPCTQEQTPL LQEQQDQMLX QVQIPFVHPS ILQQLNPCKV FLQQQCSPVA MSQRIARSQM  180
LQQSSCHVLQ QQCCQQLPQI PEQLRHEAVR AIVYSIVLQE QSLQLVQGVS QPQQQSQQQQ  240
VGQCSFQQPQ PQQGQQQQVP QSVXLQPHQI AQLEATTSIA LRTLPTMCSV NVPLYRIVPL  300
AIDTRVGV                                                           308

SEQ ID NO: 300         moltype = AA  length = 265
FEATURE                Location/Qualifiers
source                 1..265
                       mol_type = protein
                       organism = Hordeum vulgare
SEQUENCE: 300
MKTFLIFALL AIVATSTIAQ QQPYPQQPQP FPQQPIPQQP QPFPQQPQPF PQQPFPSRQP  60
FPQQPPFWQQ QPVLSQQQPC TQDQTPLLQE QQDQMLLQVQ IPFVHPSILQ QLNPCKVFLQ  120
QQCSPVAMSQ RIARSQMLQQ SSCHVLQQQC CQQLPQIPEQ IRHEAVRAIV YSIVLQEQPL  180
QLVQGVSQPQ QQSQQQQVGQ CSFQQPQPQQ GQQQQVPQSV FLQPHQIAQL EATASIALRT  240
LPTMCSVNVP LYRIVPLAID TRVGV                                        265

SEQ ID NO: 301         moltype = AA  length = 301
FEATURE                Location/Qualifiers
source                 1..301
                       mol_type = protein
                       organism = Hordeum vulgare
SEQUENCE: 301
MKTFLIFALL AIAATSTIAQ QQPFPQQPIP QQPQPYPQQP QPYPQQPFQP QQPFPQQTIP  60
QQPQPYPQQP QPYPQQPFPP QQAFPQQPPF WPQQPFPQQP PFGLQQPILS QQQPCTPQQT  120
PLPQGQLYQT LLQLQIPNVQ PSILQQLNPC KVFLQQQCSP VRMQQLIARS QMLQQSSCHV  180
LQQQCCQQLP QIPEQFRHEA IRAIVYSIFL QEQPQQSVQG VSQPQQQLQQ EQVGQCYFQQ  240
PQPQQLGQPQ QVPQSVFLQP HQIAQLEATT SIALRTLPTM CNVNVPLYDI MPFGVGTRVG  300
V                                                                  301

SEQ ID NO: 302         moltype = AA  length = 294
FEATURE                Location/Qualifiers
SITE                   291
                       note = misc_feature - Xaa can be any naturally occurring
                        amino acid
SITE                   293
                       note = misc_feature - Xaa can be any naturally occurring
                        amino acid
source                 1..294
                       mol_type = protein
                       organism = Hordeum vulgare
SEQUENCE: 302
MKTFLIFALL VIAATSTIAQ QQPFPQQPFP QQPQPYPQQP QPYPQQPFQP QQPFPQQTIP  60
QQPQPYPQQP FPPQQEFPQQ PPFWPQQPFP QQPPFGLQQP ILSQQQPCTP QQTPLPQGQL  120
YQTLLQLQIP YVHPSILQQL NPCKVFLQQQ CSPVRMPQLI ARLQMLQQSS CHVLQQQCCQ  180
QLPQISEQFR HEAIRAIVYS IFLQEQPQQS VQGVSQTQQQ LQQEQVGQCS FQQPQPQQLG  240
QAQQVPQSVF LQPHQIAQLE ATTSIALRTL PRMCNVNVPL YDIMPPDFWH XVXV        294

SEQ ID NO: 303         moltype = AA  length = 273
FEATURE                Location/Qualifiers
```

-continued

```
source                  1..273
                        mol_type = protein
                        organism = Hordeum vulgare
SEQUENCE: 303
MKTFLIFALL AIAATSTIAQ QQPFPQQPQQ IPQQPQPYPQ QPQPYPQQPF PPQQEFPQQP  60
PFWPQQPFPQ QPPFGLQQPI LSQQQPCTPQ QTPLPQGQLY QTLLQLQIPY VHPSILQQLN  120
PCKVFLQQQC SPVRMPQLIA RLQMLQQSSC HVLQQQCCQQ LPQISEQFRH EAIRAIVYSI  180
FLQEQPQQSV QGVSQTQQQL QQEQVGQCSF QQPQPQQLGQ PQQVPQSVFL QPHQIAQLEA  240
TTSIALRTLP RMCNVNVPLY DIMPPDFWHR VGV                               273

SEQ ID NO: 304          moltype = AA  length = 328
FEATURE                 Location/Qualifiers
SITE                    27
                        note = misc_feature - Xaa can be any naturally occurring
                         amino acid
REGION                  36..41
                        note = misc_feature - Xaa can be any naturally occurring
                         amino acid
SITE                    51
                        note = misc_feature - Xaa can be any naturally occurring
                         amino acid
SITE                    97
                        note = misc_feature - Xaa can be any naturally occurring
                         amino acid
REGION                  99..100
                        note = misc_feature - Xaa can be any naturally occurring
                         amino acid
SITE                    105
                        note = misc_feature - Xaa can be any naturally occurring
                         amino acid
SITE                    119
                        note = misc_feature - Xaa can be any naturally occurring
                         amino acid
REGION                  128..129
                        note = misc_feature - Xaa can be any naturally occurring
                         amino acid
REGION                  135..136
                        note = misc_feature - Xaa can be any naturally occurring
                         amino acid
SITE                    159
                        note = misc_feature - Xaa can be any naturally occurring
                         amino acid
SITE                    167
                        note = misc_feature - Xaa can be any naturally occurring
                         amino acid
SITE                    170
                        note = misc_feature - Xaa can be any naturally occurring
                         amino acid
SITE                    172
                        note = misc_feature - Xaa can be any naturally occurring
                         amino acid
source                  1..328
                        mol_type = protein
                        organism = Hordeum vulgare
SEQUENCE: 304
MKTFLTFVLL AMAMSIVTTA RQLNPSXQEL QSPQQXXXXX XSYLQQPYPQ XPYLPQQPFP  60
TPQQFFPYLP QQTFPQSQQP TPLQPQQPFP LQPQQPXPXX QQPFXWQPQQ PFPQPQQPXP  120
QQPQQPFXXQ PQQIXXQQPQ QPFPQQPQQP FPQPQQPFXW QPQQPFXQPX QXFPLQPQQP  180
FPWQPQQPFP QPQQPIAHQP QQPFSFSQQP QQPFPLQPQQ PFPQQPQQPF PQQPQQIIFQ  240
QPQQSYPVQP QQPFPQPQQP FPQIPQQPFP LQPQPFPQQP QQPLPQPQQP FRQQAELIIP  300
QQPQQPFPLQ PHQPYTQQTI WSMVALLG                                     328

SEQ ID NO: 305          moltype = AA  length = 747
FEATURE                 Location/Qualifiers
source                  1..747
                        mol_type = protein
                        organism = Hordeum vulgare
SEQUENCE: 305
MAKRLVLFVA VIVALVALTT AEREINGNNI FLDSRSRQLQ CERELQESSL EACRRVVDQQ  60
LVGQLPWSTG LQMQCCQQLR DVSPECRPVA LSQVVRQYEQ QTEVPSKGGS FYPGGTAPPL  120
QQGGWWGTSV KWYYPDQTSS QQSWQGQQGY HQSVTSSQQP GQGQQGSYPG STFPQQPGQG  180
QQPGQRQPWS YPSATFPQQP GQGQGQQGYY PGATSLLQPG QGQQGPYQSA TSPQQPGQGQ  240
GQQETYPIAT SPHQPGQWQQ PGQGQQGYYP SVTSPQQSGQ GQQGYPSTTS PQQSGQGQQL  300
GQGQQPGQGQ QGYPSATFPQ QPGQWQQGSY PSTTSPQQSG QGQQGYNPSG TSTQQPGQVQ  360
QLGQGQQGYY PIATSPQQPG QGQQLGQGQQ PGHGQQLVQG QQQGQGQQGH YPSMTSPHQT  420
GQGQKGYYPS AISPQQSGQG QQGYQPSGAS SQGSVQGACQ HSTSSPQQQA QGCQASSPKQ  480
GLGSLYYPSG AYTQQKPGQG YNPGGTSPLH QQGGGFGGGL TTEQPQGGKQ PFHCQQTTVS  540
PHQGQQTTVS PHQGQQTTVS PHQGQQTTVS PHQGQQTTVS PHQGQQTTVS PHQGQQTTVS  600
PHPGQQTTVS PHQGQQTTVS PHPGQQTTVS PHQGQQTTVS PHQGQQTTVS PHQGQQTTVS  660
```

-continued

```
PHQGQQTTVS PHQGQQPGEQ PCGFPGQQTT VSLHHGQQSN ELYYGSPYHV SVEQPSASLK  720
VAKAQQLAAQ LPAMCRLEGG GGLLASQ                                      747

SEQ ID NO: 306          moltype = AA  length = 305
FEATURE                 Location/Qualifiers
source                  1..305
                        mol_type = protein
                        organism = Hordeum vulgare
SEQUENCE: 306
MKILIILTIL AMATTFATSE MQVNPSVQVQ PTQQQPYPES QQPFISQSQQ QFPQPQQPFP  60
QQPQQPFPQS QQQCLQQPQH QFPQPTQQFP QRPLLPFTHP FLTFPDQLLP QPPHQSFPQP  120
PQSYPQPPLQ PFPQPPQQKY PEQPQQPFPW QQPTIQLYLQ QQLNPCKEFL LQQCRPVSLL  180
SYLWSKIVQQ SSCRVMQQQC CLQLAQIPEQ YKCTAIDSIV HAIFMQQGQR QGVQIVQQQP  240
QPQQVGQCVL VQGQGVVQPQ QLAQMEAIRT LVLQSVPSMC NFNVPPNCST IKAPFVGVVT  300
GVGGQ                                                              305

SEQ ID NO: 307          moltype = AA  length = 304
FEATURE                 Location/Qualifiers
source                  1..304
                        mol_type = protein
                        organism = Hordeum vulgare
SEQUENCE: 307
MKIFLLFSLL GVATAITTTT MQFNPSGLEL ERPQQLFPQW QPLPQQPPFL QQEPEQPYPQ  60
QQPLPQQQPF PQQPQLPHQH QFPQQLPQQQ FPQQMPLQPQ QQFPQQMPLQ PQQQPQFPQQ  120
KPFGQYQQPL TQQPYPQQQP LAQQQPSIEE QHQLNLCKEF LLQQCTLDEK VPLLQSVISF  180
LRPHISQQNS CQLKRQQCCQ QLANINEQSR CPAIQTIVHA IVMQQQVQQQ VGHGFVQSQL  240
QQLGQGMPIQ LQQQPGQAFV LPQQQAQFKV VGSLVIQTLP MLCNVHVPPY CSPFGSMATG  300
SGGQ                                                               304

SEQ ID NO: 308          moltype = AA  length = 361
FEATURE                 Location/Qualifiers
REGION                  259..260
                        note = misc_feature - Xaa can be any naturally occurring
                         amino acid
REGION                  301..305
                        note = misc_feature - Xaa can be any naturally occurring
                         amino acid
source                  1..361
                        mol_type = protein
                        organism = Triticum aestivum
SEQUENCE: 308
MKTFLIFVLL AMAMKIATAA RELNPSNKEL QSPQQSFSHQ QQPFPQQPYP QQPYPSQQPY  60
PSQQPFPTPQ QQFPQQSQQP FTQPQQPTPL QPQQPFPQQP QQPQQPFPQP QQPFPWQPQQ  120
PFPQTQQSFP LQPQQPFPQQ PQQPFPQPQL PFPQQSEQII PQQPQQPFPL QPQQPFPQQP  180
QQPFPQQIPQ PQQFPQQSQQ SQQPFPQQLF PELQQPIPQQ PQQPFPLQPQ QPFPQQPQQP  240
FPQQPQQPFP QQPQQPFPXX QQPFPLRPQQ PFPQQPQQSQ QSFPQPQPQQ PQQPSILQPQ  300
XXXXXQPQQP FQQPQQQLSQ QPEQTISQQP QQPFPQQPHQ PQQPYPQQQP YGSSLTSIGG  360
Q                                                                  361

SEQ ID NO: 309          moltype = AA  length = 355
FEATURE                 Location/Qualifiers
SITE                    3
                        note = MISC_FEATURE - Xaa = Citrulline
REGION                  69..71
                        note = MISC_FEATURE - Xaa is any naturally occurring amino
                         acid
SITE                    114
                        note = MISC_FEATURE - Xaa = Citrulline
REGION                  301..305
                        note = MISC_FEATURE - Xaa is any naturally occurring amino
                         acid
SITE                    312
                        note = MISC_FEATURE - Xaa is any naturally occurring amino
                         acid
REGION                  332..334
                        note = MISC_FEATURE - Xaa is any naturally occurring amino
                         acid
REGION                  347..349
                        note = MISC_FEATURE - Xaa is any naturally occurring amino
                         acid
SITE                    351
                        note = MISC_FEATURE - Xaa is any naturally occurring amino
                         acid
source                  1..355
                        mol_type = protein
                        organism = Triticum aestivum
SEQUENCE: 309
ARXLNPSEQE LQSPQQAVPK EQSYPQQPYP SHQPFPTPQQ YSPYQPQQPF PQPQQPTPIQ  60
PQQPFPQQXX XPQQPFPQPQ QQLPLQPQQP FPQPQQPIPQ QPQQSFPQQP QRPXQQFPQQ  120
```

-continued

```
PQQIIPQQTQ QPFPLQPQQP FPQQPQRPFA QQPEQIISQQ PFPLQPQQPF SQPQQPFPQQ  180
PGQIIPQQPQ QPSPLQPQQP FSQQPQRPQQ PFPQQPQQII PQQPQQPFPL QPQQPVPQQP  240
QRPFGQQPEQ IISQRPQQPF PLQPQQPFSQ PQQPFPQQPG QIIPQQPQQP FPLQPQQPFP  300
XXXXXQPEQI IXQQPQQPFP LQPQQPSPQQ PXXXQLPFPQ PQQPFVXXXT XIGGQ       355

SEQ ID NO: 310         moltype = AA  length = 285
FEATURE                Location/Qualifiers
source                 1..285
                       mol_type = protein
                       organism = Triticum aestivum
SEQUENCE: 310
MKTLFILTIL AMATTIATAN MQVDPSGQVQ WPQQQPFRQP QQPFYQQPQH TFPQPQQTFP  60
HQPQQQFPQP QQPQQQFPQP QQPQQPFPQP QQAQLPFPQQ PQQPFPQPQQ PQQPFPQSQQ  120
PQQPFPQPQQ PQQSFPQQQQ PLIQPYLQQQ MNPCKNYLLQ QCNPVSLVSS LVSMILPRSD  180
CQVMQQQCCQ QLAQIPRQLQ CAAIHSVVHS IVMQQEQQQG IQILRPLFQL VQGQGIIQPQ  240
QPAQYEVIRS LVLRTLPNMC NVYVRPDCST INAPFASIVA GISGQ                  285

SEQ ID NO: 311         moltype = AA  length = 117
FEATURE                Location/Qualifiers
REGION                 44..46
                       note = misc_feature - Xaa can be any naturally occurring
                        amino acid
source                 1..117
                       mol_type = protein
                       organism = Triticum aestivum
SEQUENCE: 311
MKTFIIFVLL AMAMNIASAS RLLSPRGKEL HTPQEQFPQQ QQFXXXQLTQ QQFPQPQQSP  60
EQQQFPQQQF PQQPPQQFPQ QQFPIPYPPQ QSQEPSPYQQ YPQQQPSGSD VISISGL     117

SEQ ID NO: 312         moltype = AA  length = 155
FEATURE                Location/Qualifiers
REGION                 77..83
                       note = misc_feature - Xaa can be any naturally occurring
                        amino acid
REGION                 86..87
                       note = misc_feature - Xaa can be any naturally occurring
                        amino acid
source                 1..155
                       mol_type = protein
                       organism = Triticum aestivum
SEQUENCE: 312
MKTFIIFVLL AMAMNIASAS RLLSPRGKEL HTPQEQFPQQ QQFPQPQQFP QQQIPQQHQI  60
PQQPQQFPQQ QQFQQQXXXX XXXQFXXQQQ FPRPQQSPEQ QQFPQQQFPQ QPPQQFPQQQ  120
FPIPYPPQQS QEPSPYQQYP QQQPSGSDVI SISGL                             155

SEQ ID NO: 313         moltype = AA  length = 356
FEATURE                Location/Qualifiers
SITE                   201
                       note = misc_feature - Xaa can be any naturally occurring
                        amino acid
source                 1..356
                       mol_type = protein
                       organism = Secale cereale
SEQUENCE: 313
MKTFLIFVLA MTMSIITTAR QLNPSEQELQ SPQQPVPKEQ SYPQQPYPSH QPFPTPQQYS  60
PYQPQQPFPQ PQQPTPIQPQ QPFPQQPQQP FPQPQQQLPL QPQQPFPQPQ QPIPQQPQQS  120
FPQQPQRPEQ QFPQQPQQII PQQTQQPFPL QPQQPFPQQP QRPFAQQPEQ ISQQPFPLQP  180
QQPFSQPQQP FPQQPGQIIP XQPQQPSPLQ PQQPFSQQPQ RPQQPFPQQP QQIIPQQPQQ  240
PFPLQPQQPV PQQPQRPFGQ QPEQIISQRP QQPFPLQPQQ PFSQPQQPFP QQPGQIIPQQ  300
PQQPFPLQPQ QPFPQQPEQI ISQQPQQPFP LQPQQPSPQQ PQLPFPQPQQ PFVVVV      356

SEQ ID NO: 314         moltype = AA  length = 277
FEATURE                Location/Qualifiers
SITE                   120
                       note = misc_feature - Xaa can be any naturally occurring
                        amino acid
SITE                   129
                       note = misc_feature - Xaa can be any naturally occurring
                        amino acid
SITE                   133
                       note = misc_feature - Xaa can be any naturally occurring
                        amino acid
SITE                   136
                       note = misc_feature - Xaa can be any naturally occurring
                        amino acid
source                 1..277
                       mol_type = protein
                       organism = Triticum aestivum
SEQUENCE: 314
```

-continued

```
MKTFLIFVLA MTMSIITTAR QLNPSEQELQ SPQQPVPKEQ SYPQQPYPSH QPFPTPQQYS  60
PYQPQQPFPQ PQQPTPIQPQ QPFPQQPQQP FPQPQQQLPL QPQQPFPQPQ QPIPQQPQQX  120
FPQQQRPSXL QPXQPXSQQP QRPQQPFPQQ PQQIIPQQPQ QPFPLQPQQP VPQQPQRPFG  180
QQPEQIISQR PQQPFPLQPQ QPFSQPQQPF PQQPGQIIPQ QPQQPFPLQP QQPFPQQPEQ  240
IIPQQPQQPF PLQPQQPSPQ QPQLPFPQPQ QPFVVVV                           277

SEQ ID NO: 315          moltype = AA  length = 44
FEATURE                 Location/Qualifiers
source                  1..44
                        mol_type = protein
                        organism = Secale cereale
SEQUENCE: 315
PYLQLQPFPQ PQLPYPQPQP FRPQQPYPQP QPQYSQPQQP ISQQ                    44

SEQ ID NO: 316          moltype = AA  length = 30
FEATURE                 Location/Qualifiers
source                  1..30
                        mol_type = protein
                        organism = Secale cereale
SEQUENCE: 316
YPSGQGSFQP SQQNPQAQGS VQPQQLPQFE                                    30

SEQ ID NO: 317          moltype = AA  length = 51
FEATURE                 Location/Qualifiers
source                  1..51
                        mol_type = protein
                        organism = Secale cereale
SEQUENCE: 317
PYLQLQPFPQ PQLPYPQPQL PYPQPQPFRP QQPYPQPQPQ YSQPQQPISQ Q            51

SEQ ID NO: 318          moltype = AA  length = 29
FEATURE                 Location/Qualifiers
source                  1..29
                        mol_type = protein
                        organism = Secale cereale
SEQUENCE: 318
YPSGQGSFQP SQQNPQAQGS VQPQQLPQF                                     29

SEQ ID NO: 319          moltype = AA  length = 58
FEATURE                 Location/Qualifiers
source                  1..58
                        mol_type = protein
                        organism = Triticum aestivum
SEQUENCE: 319
PYLQLQPFPQ PQLPYPQPQL PYPQPQLPYP QPQPFRPQQP YPQSQPQYSQ PQQPISQQ    58

SEQ ID NO: 320          moltype = AA  length = 29
FEATURE                 Location/Qualifiers
source                  1..29
                        mol_type = protein
                        organism = Triticum aestivum
SEQUENCE: 320
YPSGQGSFQP SQQNPQAQGS VQPQQLPQF                                     29

SEQ ID NO: 321          moltype = AA  length = 51
FEATURE                 Location/Qualifiers
source                  1..51
                        mol_type = protein
                        organism = Triticum aestivum
SEQUENCE: 321
PYMQLQPFPQ PQLPYPQPQL PYPQPQPFRP QQSYPQPQPQ YSQPQQPISQ Q            51

SEQ ID NO: 322          moltype = AA  length = 30
FEATURE                 Location/Qualifiers
source                  1..30
                        mol_type = protein
                        organism = Triticum aestivum
SEQUENCE: 322
QYPSGQGSFQ PSQQNPQAQG SVQPQQLPQF                                    30

SEQ ID NO: 323          moltype = AA  length = 30
FEATURE                 Location/Qualifiers
source                  1..30
                        mol_type = protein
                        organism = Triticum aestivum
SEQUENCE: 323
QYPSGQGSFQ SSQQNPQAQG SVQPQQLPQF                                    30

SEQ ID NO: 324          moltype = AA  length = 44
```

-continued

```
FEATURE                Location/Qualifiers
source                 1..44
                       mol_type = protein
                       organism = Triticum aestivum
SEQUENCE: 324
PYLQLQPFPQ PQLPYSQPQP FRPQQPYPQP QPQYSQPQQP ISQQ                  44

SEQ ID NO: 325         moltype = AA  length = 30
FEATURE                Location/Qualifiers
source                 1..30
                       mol_type = protein
                       organism = Triticum aestivum
SEQUENCE: 325
QYPLGQGSFR PSQQNPQAQG SVQPQQLPQF                                  30

SEQ ID NO: 326         moltype = AA  length = 30
FEATURE                Location/Qualifiers
source                 1..30
                       mol_type = protein
                       organism = Triticum spelta
SEQUENCE: 326
QYPSSQVSFQ PSQLNPQAQG SVQPQQLPQF                                  30

SEQ ID NO: 327         moltype = AA  length = 116
FEATURE                Location/Qualifiers
source                 1..116
                       mol_type = protein
                       organism = Triticum aestivum
SEQUENCE: 327
PWPQQQPFPQ PHQPFSQQPQ QTFPQPQQTF PHQPQQQFSQ PQQPQQQFIQ PQQPFPQQPQ  60
QTYPQRPQQP FPQTQQPQQP FPQSQQPQQP FPQPQQQFPQ PQQPQQSFPQ QQPSLI      116

SEQ ID NO: 328         moltype = AA  length = 30
FEATURE                Location/Qualifiers
source                 1..30
                       mol_type = protein
                       organism = Triticum aestivum
SEQUENCE: 328
GQGTLVQGQG IIQPQQPAQL EVIRSLVLQT                                  30

SEQ ID NO: 329         moltype = AA  length = 77
FEATURE                Location/Qualifiers
source                 1..77
                       mol_type = protein
                       organism = Triticum aestivum
SEQUENCE: 329
FPQPQQPQQQ FPQPQQPQQP FPQPQQAQLP FPQQPQQPFP QPQQPQQPFP QSQQPQQPFP  60
QPQQPQQSFP QQQQPLI                                                77

SEQ ID NO: 330         moltype = AA  length = 84
FEATURE                Location/Qualifiers
source                 1..84
                       mol_type = protein
                       organism = Triticum aestivum
SEQUENCE: 330
FPQPQQPQQQ FPQPQQPQQP FPQPQQPQLP FPQQPQQPFP QPQQPQQPFP QSQQPQQPFP  60
QPQQQFPQPQ QPQQSFPQQQ PPLI                                        84

SEQ ID NO: 331         moltype = AA  length = 30
FEATURE                Location/Qualifiers
source                 1..30
                       mol_type = protein
                       organism = Triticum aestivum
SEQUENCE: 331
GQVQWPQQQP FPQPQQPFCQ QPQRTIPQPH                                  30

SEQ ID NO: 332         moltype = AA  length = 84
FEATURE                Location/Qualifiers
source                 1..84
                       mol_type = protein
                       organism = Triticum aestivum
SEQUENCE: 332
QPQQQFPQTQ QPQQPFPQPQ QTFPQQPQLP FPQQPQQPFP QPQQPQQPFP QSQQPQQPFP  60
QPQQQFPQPQ QPQQSFPQQQ QPAI                                        84

SEQ ID NO: 333         moltype = AA  length = 36
FEATURE                Location/Qualifiers
source                 1..36
                       mol_type = protein
```

```
                        organism = Triticum aestivum
SEQUENCE: 333
GVPILRPLFQ LAQGLGIIQP QQPAQLEGIR SLVLKT                           36

SEQ ID NO: 334          moltype = AA  length = 27
FEATURE                 Location/Qualifiers
source                  1..27
                        mol_type = protein
                        organism = Triticum aestivum
SEQUENCE: 334
GQVPWPQQQP FPQPHQPFSQ QPQQTFP                                     27

SEQ ID NO: 335          moltype = AA  length = 79
FEATURE                 Location/Qualifiers
source                  1..79
                        mol_type = protein
                        organism = Triticum aestivum
SEQUENCE: 335
FSQPQQPQQQ FIQPQQPFPQ QPQQTYPQRP QQPFPQTQQP QQPFPQSQQP QQPFPQPQQQ  60
FPQPQQPQQS FPQQQPSLI                                              79

SEQ ID NO: 336          moltype = AA  length = 29
FEATURE                 Location/Qualifiers
source                  1..29
                        mol_type = protein
                        organism = Triticum aestivum
SEQUENCE: 336
GQGTLVQGQG IIQPQQPAQL EVIRSLVLQ                                   29

SEQ ID NO: 337          moltype = AA  length = 49
FEATURE                 Location/Qualifiers
source                  1..49
                        mol_type = protein
                        organism = Triticum aestivum
SEQUENCE: 337
FPQQPQQPLP QPQQPQQPFP QSQQPQPQQP FPQPQQQFPQ PQQPQQSIP             49

SEQ ID NO: 338          moltype = AA  length = 72
FEATURE                 Location/Qualifiers
source                  1..72
                        mol_type = protein
                        organism = Triticum aestivum
SEQUENCE: 338
FPQPQQPQQQ FLQPRQPFPQ QPQQPYPQQP QQPFPQTQQP QQPFPQSKQP QQPFPQPQQP  60
QQSFPQQQPS LI                                                     72

SEQ ID NO: 339          moltype = AA  length = 29
FEATURE                 Location/Qualifiers
source                  1..29
                        mol_type = protein
                        organism = Triticum aestivum
SEQUENCE: 339
GQGILVQGQG IIQPQQPAQL EVIRSLVLQ                                   29

SEQ ID NO: 340          moltype = AA  length = 82
FEATURE                 Location/Qualifiers
source                  1..82
                        mol_type = protein
                        organism = Triticum aestivum
SEQUENCE: 340
FPRRPQQQFP QPQQPQQPFP QPQQPQLPFP QQPQQPFPQP QQPQQPFPQS QQPQQPFPQP  60
QQQFPQPQQP QQSFPQQQQW MI                                          82

SEQ ID NO: 341          moltype = AA  length = 35
FEATURE                 Location/Qualifiers
source                  1..35
                        mol_type = protein
                        organism = Triticum aestivum
SEQUENCE: 341
GVQILRPLFQ LAQGLGIIQP QQPAQLEGIR SLVLK                            35

SEQ ID NO: 342          moltype = AA  length = 32
FEATURE                 Location/Qualifiers
source                  1..32
                        mol_type = protein
                        organism = Triticum aestivum
SEQUENCE: 342
DPSGQVQWPQ QQPFPQPQQP FCEQPQRTIP QP                               32
```

```
SEQ ID NO: 343          moltype = AA  length = 87
FEATURE                 Location/Qualifiers
source                  1..87
                        mol_type = protein
                        organism = Triticum aestivum
SEQUENCE: 343
YPHQPQQQFP QTQQPQQPFP QPQQTFPQQP QLPFPQQPQQ PFPQPQQPQQ PFPQSQQPQQ  60
PFPQPQQQFP QPQQPQQSFP QQQQPAI                                      87

SEQ ID NO: 344          moltype = AA  length = 18
FEATURE                 Location/Qualifiers
source                  1..18
                        mol_type = protein
                        organism = Hordeum vulgare
SEQUENCE: 344
PQQPFPQPQQ PFPWQPQQ                                                18

SEQ ID NO: 345          moltype = AA  length = 67
FEATURE                 Location/Qualifiers
source                  1..67
                        mol_type = protein
                        organism = Hordeum vulgare
SEQUENCE: 345
FPQPQQPQQP FPQPQQAQLP FPQQPQQPFP QPQQPQQPFP QSQQPQQPFP QPQQPQQSFP  60
QQQQPLI                                                            67

SEQ ID NO: 346          moltype = AA  length = 36
FEATURE                 Location/Qualifiers
source                  1..36
                        mol_type = protein
                        organism = Triticum aestivum
SEQUENCE: 346
QQPFISQSQQ QFPQPQQPFP QQPQQPFPQS QQQCLQ                            36

SEQ ID NO: 347          moltype = AA  length = 30
FEATURE                 Location/Qualifiers
source                  1..30
                        mol_type = protein
                        organism = Triticum aestivum
SEQUENCE: 347
PFPQPPQQKY PEQPQQPFPW QQPTIQLYLQ                                   30

SEQ ID NO: 348          moltype = AA  length = 22
FEATURE                 Location/Qualifiers
source                  1..22
                        mol_type = protein
                        organism = Triticum aestivum
SEQUENCE: 348
PQPQQPFPQP QQPFPQSQEQ FP                                           22

SEQ ID NO: 349          moltype = AA  length = 36
FEATURE                 Location/Qualifiers
source                  1..36
                        mol_type = protein
                        organism = Triticum aestivum
SEQUENCE: 349
LFPQSQQPQQ PFPQPQQPFP QPQQPFPQSQ EQFPQV                            36

SEQ ID NO: 350          moltype = AA  length = 25
FEATURE                 Location/Qualifiers
source                  1..25
                        mol_type = protein
                        organism = Triticum aestivum
SEQUENCE: 350
FPQPQQSSPL QPQQPFPQQS QQPFP                                        25

SEQ ID NO: 351          moltype = AA  length = 30
FEATURE                 Location/Qualifiers
source                  1..30
                        mol_type = protein
                        organism = Triticum aestivum
SEQUENCE: 351
QSIPQPQQPF PQPQQPFPQS QEQFPQVHQP                                   30

SEQ ID NO: 352          moltype = AA  length = 53
FEATURE                 Location/Qualifiers
source                  1..53
                        mol_type = protein
                        organism = Secale cereale
```

```
SEQUENCE: 352
PQPQQSSPLQ PQQPFPQQSQ QPFPQQPQQS SPQPQQPYPQ QPFPQQPQQQ PQQ         53

SEQ ID NO: 353         moltype = AA  length = 25
FEATURE                Location/Qualifiers
source                 1..25
                       mol_type = protein
                       organism = Secale cereale
SEQUENCE: 353
QSIPQPQQPF PQPQQPFPQS QEPFP                                         25

SEQ ID NO: 354         moltype = AA  length = 54
FEATURE                Location/Qualifiers
source                 1..54
                       mol_type = protein
                       organism = Secale cereale
SEQUENCE: 354
GQGQQPGQGQ PGYYPTSPQQ SGQGQQLGQG QQGQQPGQGQ PGYYPTSPQQ PGQG        54

SEQ ID NO: 355         moltype = AA  length = 100
FEATURE                Location/Qualifiers
source                 1..100
                       mol_type = protein
                       organism = Secale cereale
SEQUENCE: 355
GQGQPGYYPT SPQQPGQGQQ PGQRQQPGQG KPGYYPTSPQ QSGQGQQPGQ GQSGYYPTSP  60
QQPGQEQQPG QGQQVQQPGQ GQQPGQGQQG YYPTSPQQSG                         100

SEQ ID NO: 356         moltype = AA  length = 45
FEATURE                Location/Qualifiers
source                 1..45
                       mol_type = protein
                       organism = Secale cereale
SEQUENCE: 356
GQGQQGYYPT SPQQPGQGQQ PGQGQQPGQG QPGYYPTSPQ QPGQG                  45

SEQ ID NO: 357         moltype = AA  length = 45
FEATURE                Location/Qualifiers
source                 1..45
                       mol_type = protein
                       organism = Secale cereale
SEQUENCE: 357
GQGQQGYYPT SPQQPGQGQL EYYPTSPQQP GQGQPGYYPT SPQLP                  45

SEQ ID NO: 358         moltype = AA  length = 77
FEATURE                Location/Qualifiers
source                 1..77
                       mol_type = protein
                       organism = Triticum aestivum
SEQUENCE: 358
GQGQQGYYPT SPQQPGQGQQ GHYPGSLQQP GQGQPGQRQQ PGQGQQTGQG QQPEQEQQPG  60
QGQQGYYPTS PQQPGQG                                                  77

SEQ ID NO: 359         moltype = AA  length = 18
FEATURE                Location/Qualifiers
source                 1..18
                       mol_type = protein
                       organism = Triticum aestivum
SEQUENCE: 359
GQGQEGYYPT SPQQPGQG                                                 18

SEQ ID NO: 360         moltype = AA  length = 77
FEATURE                Location/Qualifiers
source                 1..77
                       mol_type = protein
                       organism = Triticum aestivum
SEQUENCE: 360
QIGQWQQGYY PTSPQHPGQG QQPGQVQKIG QGQQPEKGQQ LGQEQQIGQG QQPEQGQQPG  60
QGQQGYYPTS PQQPGQG                                                  77

SEQ ID NO: 361         moltype = AA  length = 18
FEATURE                Location/Qualifiers
source                 1..18
                       mol_type = protein
                       organism = Triticum aestivum
SEQUENCE: 361
GQGQSGYYPT SPQQSGQE                                                 18

SEQ ID NO: 362         moltype = AA  length = 18
```

```
FEATURE                Location/Qualifiers
source                 1..18
                       mol_type = protein
                       organism = Triticum aestivum
SEQUENCE: 362
GQGQLGYYPT SPQQSGQG                                             18

SEQ ID NO: 363         moltype = AA  length = 126
FEATURE                Location/Qualifiers
source                 1..126
                       mol_type = protein
                       organism = Triticum aestivum
SEQUENCE: 363
GQGQPGYYPT SPQQSGQGQP GYYPTSPQQS GQLQQPAQGQ QPGQEQQGQQ PGQGQQGQQP  60
GQGQQPGQGQ PGYYPTSPQQ SGQEQQLEQW QQSGQGQPGH YPTSPLQPGQ GQPGYYPTSP  120
QQIGQG                                                          126

SEQ ID NO: 364         moltype = AA  length = 92
FEATURE                Location/Qualifiers
source                 1..92
                       mol_type = protein
                       organism = Triticum aestivum
SEQUENCE: 364
GQGQQGYYPT SPQQSGQGQQ PGQWLQPGQW LQSGYYLTSP QQLGQGQQPR QWLQPRQGQQ  60
GYYPTSPQQS GQGQQLGQGQ QGYYPTSPQQ SG                             92

SEQ ID NO: 365         moltype = AA  length = 38
FEATURE                Location/Qualifiers
source                 1..38
                       mol_type = protein
                       organism = Triticum aestivum
SEQUENCE: 365
GQGQQGYYPT SPQQPGQWQQ PEQGQPGYYP TSPQQPGQ                       38

SEQ ID NO: 366         moltype = AA  length = 73
FEATURE                Location/Qualifiers
source                 1..73
                       mol_type = protein
                       organism = Triticum aestivum
SEQUENCE: 366
GQGQSGYYPT SPQQPGQGQQ PGQLQQPAQG QQPEQGQQGQ QPGQGQQGQQ PGQGQQPGQG  60
QPGYYPTSPQ QSG                                                  73

SEQ ID NO: 367         moltype = AA  length = 39
FEATURE                Location/Qualifiers
source                 1..39
                       mol_type = protein
                       organism = Triticum aestivum
SEQUENCE: 367
GQGQQGYYPT SPQQPGQWQQ PEQGQPGYYP TSPQQPGQL                      39

SEQ ID NO: 368         moltype = AA  length = 75
FEATURE                Location/Qualifiers
source                 1..75
                       mol_type = protein
                       organism = Triticum aestivum
SEQUENCE: 368
GQGQSGYYPT SPQQPGQGQQ PGQLQQPAQG QQPEQGQQGQ QPGQGQQGQQ PGQGQQPGQG  60
QPGYYPTSPQ QSGQG                                                75

SEQ ID NO: 369         moltype = AA  length = 45
FEATURE                Location/Qualifiers
source                 1..45
                       mol_type = protein
                       organism = Triticum aestivum
SEQUENCE: 369
GQGQHGYYPT SPQLSGQGQR PGQWLQPGQG QQGYYPTSPQ QSGQG               45

SEQ ID NO: 370         moltype = AA  length = 63
FEATURE                Location/Qualifiers
source                 1..63
                       mol_type = protein
                       organism = Triticum aestivum
SEQUENCE: 370
GQGQQGYYPT SPQHPGQRQQ PGQGQQIGQG QQLGQGRQIG QGQQSGQGQQ GYYPTSPQQL  60
GQG                                                             63

SEQ ID NO: 371         moltype = AA  length = 39
FEATURE                Location/Qualifiers
```

```
source                  1..39
                        mol_type = protein
                        organism = Triticum aestivum
SEQUENCE: 371
GQGQQGYYPT SPQQPGQGKQ LGQGQQGYYP TSPQQPGQG                         39

SEQ ID NO: 372          moltype = AA  length = 57
FEATURE                 Location/Qualifiers
source                  1..57
                        mol_type = protein
                        organism = Triticum aestivum
SEQUENCE: 372
GQGQQGYYPT SPQHTGQRQQ PVQGQQIGQG QQPEQGQQPG QWQQGYYPTS PQQLGQG     57

SEQ ID NO: 373          moltype = AA  length = 37
FEATURE                 Location/Qualifiers
source                  1..37
                        mol_type = protein
                        organism = Triticum aestivum
SEQUENCE: 373
GQGQQGYYPT SPQQPGQGQQ LGQGQQGYYP TSPQQPG                           37

SEQ ID NO: 374          moltype = AA  length = 160
FEATURE                 Location/Qualifiers
SITE                    65
                        note = misc_feature - Xaa can be any naturally occurring
                         amino acid
source                  1..160
                        mol_type = protein
                        organism = Triticum aestivum
SEQUENCE: 374
GQGQQGYYPI SPQQPGQWQQ PGQGQQGYYP TSPQQPGQGQ QGYYPTSPQQ SGQGQQPGQG  60
YYPTXPQSPQ QPGQWQQPGQ GQQGYYPTSP QQPGQGQQGY YPTSPQQPGQ WQQLGQGYYP  120
TFPQQSGQGQ QPGQGYYPTF PQQPGQGQQG YYPTSPQQSG                        160

SEQ ID NO: 375          moltype = AA  length = 39
FEATURE                 Location/Qualifiers
source                  1..39
                        mol_type = protein
                        organism = Triticum aestivum
SEQUENCE: 375
GQGQQGYYPT SPQQPGQGQQ LGQGQQGYYP TSPQQPGQG                         39

SEQ ID NO: 376          moltype = AA  length = 18
FEATURE                 Location/Qualifiers
source                  1..18
                        mol_type = protein
                        organism = Triticum aestivum
SEQUENCE: 376
GQWQQGYYPT SPQHPGQG                                                18

SEQ ID NO: 377          moltype = AA  length = 16
FEATURE                 Location/Qualifiers
source                  1..16
                        mol_type = protein
                        organism = Triticum aestivum
SEQUENCE: 377
EKGQQGYYPT TPQQPG                                                  16

SEQ ID NO: 378          moltype = AA  length = 100
FEATURE                 Location/Qualifiers
SITE                    66
                        note = misc_feature - Xaa can be any naturally occurring
                         amino acid
source                  1..100
                        mol_type = protein
                        organism = Triticum aestivum
SEQUENCE: 378
GQGQPGYYPT SPQQPGQGQQ PGQEQQPGQR QQPGQGKPGY YPTSPQQSGQ GQSGYYPTSP  60
QQPGQXQQPG QGQQVQQPGQ GQQPGQGQQG YYPTSPQQSG                        100

SEQ ID NO: 379          moltype = AA  length = 18
FEATURE                 Location/Qualifiers
source                  1..18
                        mol_type = protein
                        organism = Triticum aestivum
SEQUENCE: 379
GQRQQGYYPT SPQQPGQG                                                18
```

```
SEQ ID NO: 380          moltype = AA  length = 38
FEATURE                 Location/Qualifiers
source                  1..38
                        mol_type = protein
                        organism = Triticum aestivum
SEQUENCE: 380
GQGQQGYYPT SPQQSGQGQQ PGQGQPGYYP TSPQQSGQ                          38

SEQ ID NO: 381          moltype = AA  length = 60
FEATURE                 Location/Qualifiers
source                  1..60
                        mol_type = protein
                        organism = Hordeum vulgare
SEQUENCE: 381
GQGQQGYYPT SPQQSGQGQQ LGQGQPGYYP TSPQQSGQGQ QSGQGQQGYY PTSPQQSGQG  60

SEQ ID NO: 382          moltype = AA  length = 95
FEATURE                 Location/Qualifiers
source                  1..95
                        mol_type = protein
                        organism = Hordeum vulgare
SEQUENCE: 382
QGQQGYYPTS PQQSGQGQQG YYPTSPQQSG QGQQGYYPTS PQQSGQGQQP GQGQQPRQGQ  60
QGYYPISPQQ SGQGQQPGQG QQGYYPTSPQ QSGQG                             95

SEQ ID NO: 383          moltype = AA  length = 34
FEATURE                 Location/Qualifiers
source                  1..34
                        mol_type = protein
                        organism = Hordeum vulgare
SEQUENCE: 383
QQQPYPQQPQ PFPQQPIPQQ PQPFPQQPQP FPQQ                              34

SEQ ID NO: 384          moltype = AA  length = 52
FEATURE                 Location/Qualifiers
source                  1..52
                        mol_type = protein
                        organism = Hordeum vulgare
SEQUENCE: 384
PQQPIPQQPQ PYPQQPQPYP QQPFQPQQPF PQQTIPQQPQ PYPQQPQPYP QQ          52

SEQ ID NO: 385          moltype = AA  length = 26
FEATURE                 Location/Qualifiers
source                  1..26
                        mol_type = protein
                        organism = Hordeum vulgare
SEQUENCE: 385
QPFPQQPFPQ QPQPYPQQPQ PYPQQP                                       26

SEQ ID NO: 386          moltype = AA  length = 33
FEATURE                 Location/Qualifiers
source                  1..33
                        mol_type = protein
                        organism = Hordeum vulgare
SEQUENCE: 386
TIAQQQPFPQ QPQQIPQQPQ PYPQQPQPYP QQP                               33

SEQ ID NO: 387          moltype = AA  length = 38
FEATURE                 Location/Qualifiers
source                  1..38
                        mol_type = protein
                        organism = Hordeum vulgare
SEQUENCE: 387
PIPQQPQPYP QQPQPFPQQP IPQQPQPYPQ QPQPFPLQ                          38

SEQ ID NO: 388          moltype = AA  length = 24
FEATURE                 Location/Qualifiers
source                  1..24
                        mol_type = protein
                        organism = Hordeum vulgare
SEQUENCE: 388
IAQQQPFPQQ PQPYPQQPQP YPQQ                                         24

SEQ ID NO: 389          moltype = AA  length = 25
FEATURE                 Location/Qualifiers
source                  1..25
                        mol_type = protein
                        organism = Triticum aestivum
SEQUENCE: 389
```

-continued

```
SQQQFPQPQQ PFPQQPQQPF PQSQQ                                    25

SEQ ID NO: 390          moltype = AA  length = 17
FEATURE                 Location/Qualifiers
source                  1..17
                        mol_type = protein
                        organism = Triticum aestivum
SEQUENCE: 390
PLPQQQPFPQ QPQLPHQ                                             17

SEQ ID NO: 391          moltype = AA  length = 18
FEATURE                 Location/Qualifiers
source                  1..18
                        mol_type = protein
                        organism = Triticum aestivum
SEQUENCE: 391
PQQPQLPFPQ PQQPFVVV                                            18

SEQ ID NO: 392          moltype = AA  length = 22
FEATURE                 Location/Qualifiers
source                  1..22
                        mol_type = protein
                        organism = Triticum aestivum
SEQUENCE: 392
PILSQQPPFS QQQQPVLPQQ SP                                       22

SEQ ID NO: 393          moltype = AA  length = 16
FEATURE                 Location/Qualifiers
source                  1..16
                        mol_type = protein
                        organism = Triticum aestivum
SEQUENCE: 393
QQPPFSQQQQ SPFSQQ                                              16

SEQ ID NO: 394          moltype = AA  length = 17
FEATURE                 Location/Qualifiers
source                  1..17
                        mol_type = protein
                        organism = Triticum aestivum
SEQUENCE: 394
PQQPPFSQQQ QPVLPPQ                                             17

SEQ ID NO: 395          moltype = AA  length = 67
FEATURE                 Location/Qualifiers
source                  1..67
                        mol_type = protein
                        organism = Triticum aestivum
SEQUENCE: 395
LQQSPFSQQQ QPVLPQQQPV IILQQPPFSQ QQQPVLPQQP PFSQQQQQQQ QQQPPFSQQQ  60
QPVLPQQ                                                        67

SEQ ID NO: 396          moltype = AA  length = 65
FEATURE                 Location/Qualifiers
source                  1..65
                        mol_type = protein
                        organism = Triticum aestivum
SEQUENCE: 396
QQSPFSQQQQ PVLPQQQPVI ILQQPPFSQQ QQPVLPQQPP FSQQQQQQQQ QQPPFSQQQQ  60
PVLPQ                                                         65

SEQ ID NO: 397          moltype = AA  length = 59
FEATURE                 Location/Qualifiers
source                  1..59
                        mol_type = protein
                        organism = Triticum aestivum
SEQUENCE: 397
QQPPFSQQQQ PVLPQQPSFS QQQLPPFSQQ QPPFSQQQQP VLPQQPPFSQ QQQPILPQQ   59

SEQ ID NO: 398          moltype = AA  length = 132
FEATURE                 Location/Qualifiers
source                  1..132
                        mol_type = protein
                        organism = Triticum aestivum
SEQUENCE: 398
QQPPFSQQQQ PVLPQQPSFS QQQLPPFSQQ QQPPFSQQQQ PVLPQQPSFS QQQLPPFSQQ  60
LPPFSQQQQP VLPQQPPFSQ QQLPPFSQQL PPFSQQQQPV LPQQPPFSQQ QQQPILPQQP  120
PFSQQQQPVL LQ                                                  132

SEQ ID NO: 399          moltype = AA  length = 66
```

-continued

```
FEATURE                 Location/Qualifiers
source                  1..66
                        mol_type = protein
                        organism = Triticum aestivum
SEQUENCE: 399
QQSPFSQQQQ PVLPQQQPVI ILQQPPFSQQ QQPVLPQQPP FSQQQQQQQQ QQPPFSQQQQ  60
PVLPQQ                                                             66

SEQ ID NO: 400          moltype = AA  length = 45
FEATURE                 Location/Qualifiers
source                  1..45
                        mol_type = protein
                        organism = Triticum aestivum
SEQUENCE: 400
QQPPFSQQQQ PVLPQQPSFS QQQLPPFSQQ QPPFSQQQQP VLPQQ                  45

SEQ ID NO: 401          moltype = AA  length = 9
FEATURE                 Location/Qualifiers
source                  1..9
                        mol_type = protein
                        organism = Secale cereale
SEQUENCE: 401
PFPQPQLPY                                                          9

SEQ ID NO: 402          moltype = AA  length = 9
FEATURE                 Location/Qualifiers
source                  1..9
                        mol_type = protein
                        organism = Secale cereale
SEQUENCE: 402
PYPQPQLPY                                                          9

SEQ ID NO: 403          moltype = AA  length = 9
FEATURE                 Location/Qualifiers
source                  1..9
                        mol_type = protein
                        organism = Secale cereale
SEQUENCE: 403
PQPQLPYPQ                                                          9

SEQ ID NO: 404          moltype = AA  length = 9
FEATURE                 Location/Qualifiers
source                  1..9
                        mol_type = protein
                        organism = Secale cereale
SEQUENCE: 404
FRPQQPYPQ                                                          9

SEQ ID NO: 405          moltype = AA  length = 9
FEATURE                 Location/Qualifiers
source                  1..9
                        mol_type = protein
                        organism = Triticum aestivum
SEQUENCE: 405
PQQSFPQQQ                                                          9

SEQ ID NO: 406          moltype = AA  length = 9
FEATURE                 Location/Qualifiers
source                  1..9
                        mol_type = protein
                        organism = Triticum aestivum
SEQUENCE: 406
IQPQQPAQL                                                          9

SEQ ID NO: 407          moltype = AA  length = 9
FEATURE                 Location/Qualifiers
source                  1..9
                        mol_type = protein
                        organism = Triticum aestivum
SEQUENCE: 407
QQPQQPYPQ                                                          9

SEQ ID NO: 408          moltype = AA  length = 9
FEATURE                 Location/Qualifiers
source                  1..9
                        mol_type = protein
                        organism = Triticum aestivum
SEQUENCE: 408
SQPQQQFPQ                                                          9
```

SEQ ID NO: 409 moltype = AA length = 9
FEATURE Location/Qualifiers
source 1..9
mol_type = protein
organism = Triticum aestivum
SEQUENCE: 409
PQPQQQFPQ 9

SEQ ID NO: 410 moltype = AA length = 9
FEATURE Location/Qualifiers
source 1..9
mol_type = protein
organism = Triticum aestivum
SEQUENCE: 410
QQPQQPFPQ 9

SEQ ID NO: 411 moltype = AA length = 9
FEATURE Location/Qualifiers
source 1..9
mol_type = protein
organism = Triticum aestivum
SEQUENCE: 411
PQPQQPFCQ 9

SEQ ID NO: 412 moltype = AA length = 9
FEATURE Location/Qualifiers
source 1..9
mol_type = protein
organism = Triticum aestivum
SEQUENCE: 412
LQPQQPFPQ 9

SEQ ID NO: 413 moltype = AA length = 9
FEATURE Location/Qualifiers
source 1..9
mol_type = protein
organism = Triticum aestivum
SEQUENCE: 413
QQPFPQQPQ 9

SEQ ID NO: 414 moltype = AA length = 9
FEATURE Location/Qualifiers
source 1..9
mol_type = protein
organism = Triticum aestivum
SEQUENCE: 414
PFPQPQQPF 9

SEQ ID NO: 415 moltype = AA length = 9
FEATURE Location/Qualifiers
source 1..9
mol_type = protein
organism = Triticum aestivum
SEQUENCE: 415
PQPQQPFPW 9

SEQ ID NO: 416 moltype = AA length = 9
FEATURE Location/Qualifiers
source 1..9
mol_type = protein
organism = Triticum aestivum
SEQUENCE: 416
PFSQQQQPV 9

SEQ ID NO: 417 moltype = AA length = 9
FEATURE Location/Qualifiers
source 1..9
mol_type = protein
organism = Triticum aestivum
SEQUENCE: 417
FSQQQQSPF 9

SEQ ID NO: 418 moltype = AA length = 9
FEATURE Location/Qualifiers
source 1..9
mol_type = protein
organism = Hordeum vulgare
SEQUENCE: 418

-continued

```
PQPQQPFPQ                                                        9

SEQ ID NO: 419          moltype = AA  length = 9
FEATURE                 Location/Qualifiers
source                  1..9
                        mol_type = protein
                        organism = Hordeum vulgare
SEQUENCE: 419
PIPQQPQPY                                                        9

SEQ ID NO: 420          moltype = AA  length = 9
FEATURE                 Location/Qualifiers
source                  1..9
                        mol_type = protein
                        organism = Hordeum vulgare
SEQUENCE: 420
PYPQQPQPY                                                        9

SEQ ID NO: 421          moltype = AA  length = 9
FEATURE                 Location/Qualifiers
source                  1..9
                        mol_type = protein
                        organism = Triticum aestivum
SEQUENCE: 421
PFPQQPQQI                                                        9

SEQ ID NO: 422          moltype = AA  length = 9
FEATURE                 Location/Qualifiers
source                  1..9
                        mol_type = protein
                        organism = Avena sativa
SEQUENCE: 422
PYPQQQQPF                                                        9

SEQ ID NO: 423          moltype = AA  length = 9
FEATURE                 Location/Qualifiers
source                  1..9
                        mol_type = protein
                        organism = Secale cereale
SEQUENCE: 423
QGSVQPQQL                                                        9

SEQ ID NO: 424          moltype = AA  length = 9
FEATURE                 Location/Qualifiers
source                  1..9
                        mol_type = protein
                        organism = Secale cereale
SEQUENCE: 424
QYSQPQQPI                                                        9

SEQ ID NO: 425          moltype = AA  length = 9
FEATURE                 Location/Qualifiers
source                  1..9
                        mol_type = protein
                        organism = Secale cereale
SEQUENCE: 425
QGSFQPSQQ                                                        9

SEQ ID NO: 426          moltype = AA  length = 9
FEATURE                 Location/Qualifiers
source                  1..9
                        mol_type = protein
                        organism = Triticum aestivum
SEQUENCE: 426
QGYYPTSPQ                                                        9

SEQ ID NO: 427          moltype = AA  length = 9
FEATURE                 Location/Qualifiers
source                  1..9
                        mol_type = protein
                        organism = Secale cereale
SEQUENCE: 427
PFPQPELPY                                                        9

SEQ ID NO: 428          moltype = AA  length = 9
FEATURE                 Location/Qualifiers
source                  1..9
                        mol_type = protein
                        organism = Secale cereale
```

-continued

```
SEQUENCE: 428
PYPQPELPY                                                            9

SEQ ID NO: 429          moltype = AA  length = 9
FEATURE                 Location/Qualifiers
source                  1..9
                        mol_type = protein
                        organism = Secale cereale
SEQUENCE: 429
PQPELPYPQ                                                            9

SEQ ID NO: 430          moltype = AA  length = 9
FEATURE                 Location/Qualifiers
source                  1..9
                        mol_type = protein
                        organism = Secale cereale
SEQUENCE: 430
FRPEQPYPQ                                                            9

SEQ ID NO: 431          moltype = AA  length = 9
FEATURE                 Location/Qualifiers
source                  1..9
                        mol_type = protein
                        organism = Triticum aestivum
SEQUENCE: 431
PQQSFPEQQ                                                            9

SEQ ID NO: 432          moltype = AA  length = 9
FEATURE                 Location/Qualifiers
source                  1..9
                        mol_type = protein
                        organism = Triticum aestivum
SEQUENCE: 432
IQPEQPAQL                                                            9

SEQ ID NO: 433          moltype = AA  length = 9
FEATURE                 Location/Qualifiers
source                  1..9
                        mol_type = protein
                        organism = Triticum aestivum
SEQUENCE: 433
QQPEQPYPQ                                                            9

SEQ ID NO: 434          moltype = AA  length = 9
FEATURE                 Location/Qualifiers
source                  1..9
                        mol_type = protein
                        organism = Triticum aestivum
SEQUENCE: 434
SQPEQEFPQ                                                            9

SEQ ID NO: 435          moltype = AA  length = 9
FEATURE                 Location/Qualifiers
source                  1..9
                        mol_type = protein
                        organism = Triticum aestivum
SEQUENCE: 435
PQPEQEFPQ                                                            9

SEQ ID NO: 436          moltype = AA  length = 9
FEATURE                 Location/Qualifiers
source                  1..9
                        mol_type = protein
                        organism = Triticum aestivum
SEQUENCE: 436
QQPEQPFPQ                                                            9

SEQ ID NO: 437          moltype = AA  length = 9
FEATURE                 Location/Qualifiers
source                  1..9
                        mol_type = protein
                        organism = Triticum aestivum
SEQUENCE: 437
PQPEQPFCQ                                                            9

SEQ ID NO: 438          moltype = AA  length = 9
FEATURE                 Location/Qualifiers
source                  1..9
                        mol_type = protein
```

```
                         organism = Triticum aestivum
SEQUENCE: 438
LQPEQPFPQ                                                                   9

SEQ ID NO: 439           moltype = AA  length = 9
FEATURE                  Location/Qualifiers
source                   1..9
                         mol_type = protein
                         organism = Triticum aestivum
SEQUENCE: 439
QQPFPEQPQ                                                                   9

SEQ ID NO: 440           moltype = AA  length = 9
FEATURE                  Location/Qualifiers
source                   1..9
                         mol_type = protein
                         organism = Triticum aestivum
SEQUENCE: 440
PFPQPEQPF                                                                   9

SEQ ID NO: 441           moltype = AA  length = 9
FEATURE                  Location/Qualifiers
source                   1..9
                         mol_type = protein
                         organism = Triticum aestivum
SEQUENCE: 441
PQPEQPFPW                                                                   9

SEQ ID NO: 442           moltype = AA  length = 9
FEATURE                  Location/Qualifiers
source                   1..9
                         mol_type = protein
                         organism = Triticum aestivum
SEQUENCE: 442
PFSEQEQPV                                                                   9

SEQ ID NO: 443           moltype = AA  length = 9
FEATURE                  Location/Qualifiers
source                   1..9
                         mol_type = protein
                         organism = Triticum aestivum
SEQUENCE: 443
FSQQQESPF                                                                   9

SEQ ID NO: 444           moltype = AA  length = 9
FEATURE                  Location/Qualifiers
source                   1..9
                         mol_type = protein
                         organism = Hordeum vulgare
SEQUENCE: 444
PQPEQPFPQ                                                                   9

SEQ ID NO: 445           moltype = AA  length = 9
FEATURE                  Location/Qualifiers
source                   1..9
                         mol_type = protein
                         organism = Hordeum vulgare
SEQUENCE: 445
PIPEQPQPY                                                                   9

SEQ ID NO: 446           moltype = AA  length = 9
FEATURE                  Location/Qualifiers
source                   1..9
                         mol_type = protein
                         organism = Hordeum vulgare
SEQUENCE: 446
PYPEQPQPY                                                                   9

SEQ ID NO: 447           moltype = AA  length = 9
FEATURE                  Location/Qualifiers
source                   1..9
                         mol_type = protein
                         organism = Triticum aestivum
SEQUENCE: 447
PFPEQPEQI                                                                   9

SEQ ID NO: 448           moltype = AA  length = 9
FEATURE                  Location/Qualifiers
source                   1..9
```

```
                        mol_type = protein
                        organism = Avena sativa
SEQUENCE: 448
PYPEQEEPF                                                                9

SEQ ID NO: 449          moltype = AA  length = 9
FEATURE                 Location/Qualifiers
source                  1..9
                        mol_type = protein
                        organism = Avena sativa
SEQUENCE: 449
PYPEQEQPF                                                                9

SEQ ID NO: 450          moltype = AA  length = 9
FEATURE                 Location/Qualifiers
source                  1..9
                        mol_type = protein
                        organism = Avena sativa
SEQUENCE: 450
PYPEQEQPI                                                                9

SEQ ID NO: 451          moltype = AA  length = 9
FEATURE                 Location/Qualifiers
source                  1..9
                        mol_type = protein
                        organism = Secale cereale
SEQUENCE: 451
QGSVQPQQL                                                                9

SEQ ID NO: 452          moltype = AA  length = 9
FEATURE                 Location/Qualifiers
source                  1..9
                        mol_type = protein
                        organism = Secale cereale
SEQUENCE: 452
QYSQPEQPI                                                                9

SEQ ID NO: 453          moltype = AA  length = 9
FEATURE                 Location/Qualifiers
source                  1..9
                        mol_type = protein
                        organism = Secale cereale
SEQUENCE: 453
EGSFQPSQE                                                                9

SEQ ID NO: 454          moltype = AA  length = 9
FEATURE                 Location/Qualifiers
source                  1..9
                        mol_type = protein
                        organism = Triticum aestivum
SEQUENCE: 454
EQPQQPFPQ                                                                9

SEQ ID NO: 455          moltype = AA  length = 9
FEATURE                 Location/Qualifiers
source                  1..9
                        mol_type = protein
                        organism = Triticum aestivum
SEQUENCE: 455
EQPQQPYPE                                                                9

SEQ ID NO: 456          moltype = AA  length = 9
FEATURE                 Location/Qualifiers
source                  1..9
                        mol_type = protein
                        organism = Triticum aestivum
SEQUENCE: 456
PQQSFPEQE                                                                9

SEQ ID NO: 457          moltype = AA  length = 15
FEATURE                 Location/Qualifiers
source                  1..15
                        mol_type = protein
                        organism = Secale cereale
SEQUENCE: 457
QLQPFPQPEL PYPQP                                                         15

SEQ ID NO: 458          moltype = AA  length = 15
FEATURE                 Location/Qualifiers
```

```
source                  1..15
                        mol_type = protein
                        organism = Secale cereale
SEQUENCE: 458
PQLPYPQPEL PYPQP                                                    15

SEQ ID NO: 459          moltype = AA  length = 15
FEATURE                 Location/Qualifiers
source                  1..15
                        mol_type = protein
                        organism = Secale cereale
SEQUENCE: 459
QPFPQPELPY PQPQL                                                    15

SEQ ID NO: 460          moltype = AA  length = 15
FEATURE                 Location/Qualifiers
source                  1..15
                        mol_type = protein
                        organism = Secale cereale
SEQUENCE: 460
LPYPQPELPY PQPQP                                                    15

SEQ ID NO: 461          moltype = AA  length = 15
FEATURE                 Location/Qualifiers
source                  1..15
                        mol_type = protein
                        organism = Secale cereale
SEQUENCE: 461
PQPFRPEQPY PQPQP                                                    15

SEQ ID NO: 462          moltype = AA  length = 15
FEATURE                 Location/Qualifiers
source                  1..15
                        mol_type = protein
                        organism = Triticum aestivum
SEQUENCE: 462
PQQPQQSFPE QQPPL                                                    15

SEQ ID NO: 463          moltype = AA  length = 15
FEATURE                 Location/Qualifiers
source                  1..15
                        mol_type = protein
                        organism = Triticum aestivum
SEQUENCE: 463
PQQPQQSFPE QQPPF                                                    15

SEQ ID NO: 464          moltype = AA  length = 15
FEATURE                 Location/Qualifiers
source                  1..15
                        mol_type = protein
                        organism = Triticum aestivum
SEQUENCE: 464
QGIIQPEQPA QLEVI                                                    15

SEQ ID NO: 465          moltype = AA  length = 15
FEATURE                 Location/Qualifiers
source                  1..15
                        mol_type = protein
                        organism = Triticum aestivum
SEQUENCE: 465
PFPQQPEQPY PQQPE                                                    15

SEQ ID NO: 466          moltype = AA  length = 15
FEATURE                 Location/Qualifiers
source                  1..15
                        mol_type = protein
                        organism = Triticum aestivum
SEQUENCE: 466
QQFSQPEQEF PQPQQ                                                    15

SEQ ID NO: 467          moltype = AA  length = 15
FEATURE                 Location/Qualifiers
source                  1..15
                        mol_type = protein
                        organism = Triticum aestivum
SEQUENCE: 467
QPFPQPEQEF PQPQQ                                                    15

SEQ ID NO: 468          moltype = AA  length = 15
```

-continued

```
FEATURE                Location/Qualifiers
source                 1..15
                       mol_type = protein
                       organism = Triticum aestivum
SEQUENCE: 468
PQPQQPEQPF PQPEQ                                                    15

SEQ ID NO: 469         moltype = AA  length = 15
FEATURE                Location/Qualifiers
source                 1..15
                       mol_type = protein
                       organism = Triticum aestivum
SEQUENCE: 469
PYPQQPEQPF PQPQQ                                                    15

SEQ ID NO: 470         moltype = AA  length = 15
FEATURE                Location/Qualifiers
source                 1..15
                       mol_type = protein
                       organism = Triticum aestivum
SEQUENCE: 470
QPFPQPEQPF CQQPQ                                                    15

SEQ ID NO: 471         moltype = AA  length = 15
FEATURE                Location/Qualifiers
source                 1..15
                       mol_type = protein
                       organism = Triticum aestivum
SEQUENCE: 471
QPFLQPEQPF PQQPQ                                                    15

SEQ ID NO: 472         moltype = AA  length = 15
FEATURE                Location/Qualifiers
source                 1..15
                       mol_type = protein
                       organism = Triticum aestivum
SEQUENCE: 472
SSPLQPEQPF PQQPE                                                    15

SEQ ID NO: 473         moltype = AA  length = 15
FEATURE                Location/Qualifiers
source                 1..15
                       mol_type = protein
                       organism = Triticum aestivum
SEQUENCE: 473
PTPLQPEQPF PQQPQ                                                    15

SEQ ID NO: 474         moltype = AA  length = 15
FEATURE                Location/Qualifiers
source                 1..15
                       mol_type = protein
                       organism = Triticum aestivum
SEQUENCE: 474
QQPQQPFPEQ PQQPF                                                    15

SEQ ID NO: 475         moltype = AA  length = 15
FEATURE                Location/Qualifiers
source                 1..15
                       mol_type = protein
                       organism = Triticum aestivum
SEQUENCE: 475
PEQPFPQPEQ PFPQS                                                    15

SEQ ID NO: 476         moltype = AA  length = 15
FEATURE                Location/Qualifiers
source                 1..15
                       mol_type = protein
                       organism = Triticum aestivum
SEQUENCE: 476
PQQPFPQPEQ PFPWQ                                                    15

SEQ ID NO: 477         moltype = AA  length = 15
FEATURE                Location/Qualifiers
source                 1..15
                       mol_type = protein
                       organism = Triticum aestivum
SEQUENCE: 477
PQQPFPQPEQ PFCQQ                                                    15
```

```
SEQ ID NO: 478          moltype = AA  length = 15
FEATURE                 Location/Qualifiers
source                  1..15
                        mol_type = protein
                        organism = Triticum aestivum
SEQUENCE: 478
QPFPQPEQPF PWQPQ                                                    15

SEQ ID NO: 479          moltype = AA  length = 15
FEATURE                 Location/Qualifiers
source                  1..15
                        mol_type = protein
                        organism = Hordeum vulgare
SEQUENCE: 479
QSIPQPEQPF PQPEQ                                                    15

SEQ ID NO: 480          moltype = AA  length = 15
FEATURE                 Location/Qualifiers
source                  1..15
                        mol_type = protein
                        organism = Hordeum vulgare
SEQUENCE: 480
QPFPQPEQPF PQSQE                                                    15

SEQ ID NO: 481          moltype = AA  length = 15
FEATURE                 Location/Qualifiers
source                  1..15
                        mol_type = protein
                        organism = Hordeum vulgare
SEQUENCE: 481
PQQPIPEQPQ PYPEQ                                                    15

SEQ ID NO: 482          moltype = AA  length = 15
FEATURE                 Location/Qualifiers
source                  1..15
                        mol_type = protein
                        organism = Hordeum vulgare
SEQUENCE: 482
QPQPYPEQPQ PYPQQ                                                    15

SEQ ID NO: 483          moltype = AA  length = 15
FEATURE                 Location/Qualifiers
source                  1..15
                        mol_type = protein
                        organism = Triticum aestivum
SEQUENCE: 483
PQQPFPEQPE QIIPQ                                                    15

SEQ ID NO: 484          moltype = AA  length = 15
FEATURE                 Location/Qualifiers
source                  1..15
                        mol_type = protein
                        organism = Triticum aestivum
SEQUENCE: 484
QQPPFSEQEQ PVLPQ                                                    15

SEQ ID NO: 485          moltype = AA  length = 15
FEATURE                 Location/Qualifiers
source                  1..15
                        mol_type = protein
                        organism = Triticum aestivum
SEQUENCE: 485
QPPFSQQQES PFSQQ                                                    15

SEQ ID NO: 486          moltype = AA  length = 26
FEATURE                 Location/Qualifiers
source                  1..26
                        mol_type = protein
                        organism = Secale cereale
SEQUENCE: 486
QLQPFPQPEL PYPQPQLPYP QPQPFR                                        26

SEQ ID NO: 487          moltype = AA  length = 29
FEATURE                 Location/Qualifiers
source                  1..29
                        mol_type = protein
                        organism = Secale cereale
SEQUENCE: 487
PQLPYPQPEL PYPQPQPFRP EQPYPQPQP                                     29
```

```
SEQ ID NO: 488          moltype = AA  length = 34
FEATURE                 Location/Qualifiers
source                  1..34
                        mol_type = protein
                        organism = Triticum aestivum
SEQUENCE: 488
PQPQQPEQPF PQPEQEFPQP QQPQQSFPEQ QPPL                          34

SEQ ID NO: 489          moltype = AA  length = 17
FEATURE                 Location/Qualifiers
source                  1..17
                        mol_type = protein
                        organism = Triticum aestivum
SEQUENCE: 489
PQQPFPQPEQ PFCQQPQ                                             17

SEQ ID NO: 490          moltype = AA  length = 31
FEATURE                 Location/Qualifiers
source                  1..31
                        mol_type = protein
                        organism = Triticum aestivum
SEQUENCE: 490
QQFLQPEQPF PQQPEQPYPQ QPEQPFPQPQ Q                             31

SEQ ID NO: 491          moltype = AA  length = 27
FEATURE                 Location/Qualifiers
source                  1..27
                        mol_type = protein
                        organism = Triticum aestivum
SEQUENCE: 491
QQFSQPEQEF PQPQQPQQSF PEQQPPF                                  27

SEQ ID NO: 492          moltype = AA  length = 33
FEATURE                 Location/Qualifiers
source                  1..33
                        mol_type = protein
                        organism = Triticum aestivum
SEQUENCE: 492
PTPLQPEQPF PQQPQQPQQP FPQPEQPFPW QPQ                           33

SEQ ID NO: 493          moltype = AA  length = 26
FEATURE                 Location/Qualifiers
source                  1..26
                        mol_type = protein
                        organism = Triticum aestivum
SEQUENCE: 493
SSPLQPEQPF PQQPQQPFPE QPQQPQ                                   26

SEQ ID NO: 494          moltype = AA  length = 22
FEATURE                 Location/Qualifiers
source                  1..22
                        mol_type = protein
                        organism = Triticum aestivum
SEQUENCE: 494
QSIPQPEQPF PQPEQPFPQS QE                                       22

SEQ ID NO: 495          moltype = AA  length = 15
FEATURE                 Location/Qualifiers
source                  1..15
                        mol_type = protein
                        organism = Triticum aestivum
SEQUENCE: 495
PQQPFPQQPQ QIIPQ                                               15

SEQ ID NO: 496          moltype = AA  length = 22
FEATURE                 Location/Qualifiers
source                  1..22
                        mol_type = protein
                        organism = Hordeum vulgare
SEQUENCE: 496
PQQPIPEQPQ PYPEQPQPYP QQ                                       22

SEQ ID NO: 497          moltype = AA  length = 15
FEATURE                 Location/Qualifiers
source                  1..15
                        mol_type = protein
                        organism = Triticum aestivum
SEQUENCE: 497
```

-continued

```
QPPFSQQQES PFSQQ                                          15

SEQ ID NO: 498          moltype = AA  length = 33
FEATURE                 Location/Qualifiers
SITE                    2
                        note = MISC_FEATURE - Xaa = Citrulline
SITE                    32
                        note = MISC_FEATURE - Xaa = Citrulline
SITE                    33
                        note = MISC_FEATURE - Xaa = Azidoleucine
source                  1..33
                        mol_type = protein
                        organism = synthetic construct
SEQUENCE: 498
VXQLQPFPQP ELPYPQPQLP YPQPQPFRSP VXX                      33

SEQ ID NO: 499          moltype = AA  length = 36
FEATURE                 Location/Qualifiers
SITE                    2
                        note = MISC_FEATURE - Xaa = Citrulline
SITE                    35
                        note = MISC_FEATURE - Xaa = Citrulline
SITE                    36
                        note = MISC_FEATURE - Xaa = Azidoleucine
source                  1..36
                        mol_type = protein
                        organism = synthetic construct
SEQUENCE: 499
VXPQLPYPQP ELPYPQPQPF RPEQPYPQPQ PSPVXX                   36

SEQ ID NO: 500          moltype = AA  length = 22
FEATURE                 Location/Qualifiers
SITE                    2
                        note = MISC_FEATURE - Xaa = Citrulline
SITE                    21
                        note = MISC_FEATURE - Xaa = Citrulline
SITE                    22
                        note = MISC_FEATURE - Xaa = Azidoleucine
source                  1..22
                        mol_type = protein
                        organism = synthetic construct
SEQUENCE: 500
VXQGIIQPEQ PAQLEVISPV XX                                  22

SEQ ID NO: 501          moltype = AA  length = 41
FEATURE                 Location/Qualifiers
SITE                    2
                        note = MISC_FEATURE - Xaa = Citrulline
SITE                    40
                        note = MISC_FEATURE - Xaa = Citrulline
SITE                    41
                        note = MISC_FEATURE - Xaa = Azidoleucine
source                  1..41
                        mol_type = protein
                        organism = synthetic construct
SEQUENCE: 501
VXPQPQQPEQ PFPQPEQEFP QPQQPQQSFP EQQPPLSPVX X             41

SEQ ID NO: 502          moltype = AA  length = 24
FEATURE                 Location/Qualifiers
SITE                    2
                        note = MISC_FEATURE - Xaa = Citrulline
SITE                    15
                        note = MISC_FEATURE - Xaa = beta Alanine
SITE                    23
                        note = MISC_FEATURE - Xaa = Citrulline
SITE                    24
                        note = MISC_FEATURE - Xaa = Azidoleucine
source                  1..24
                        mol_type = protein
                        organism = synthetic construct
SEQUENCE: 502
VXPQQPFPQP EQPFXQQPQS PVXX                                24

SEQ ID NO: 503          moltype = AA  length = 38
FEATURE                 Location/Qualifiers
SITE                    2
                        note = MISC_FEATURE - Xaa = Citrulline
SITE                    37
```

-continued

```
                        note = MISC_FEATURE - Xaa = Citrulline
SITE                    38
                        note = MISC_FEATURE - Xaa = Azidoleucine
source                  1..38
                        mol_type = protein
                        organism = synthetic construct
SEQUENCE: 503
VXQQFLQPEQ PFPQQPEQPY PQQPEQPFPQ PQQSPVXX                         38

SEQ ID NO: 504          moltype = AA  length = 34
FEATURE                 Location/Qualifiers
SITE                    2
                        note = MISC_FEATURE - Xaa = Citrulline
SITE                    33
                        note = MISC_FEATURE - Xaa = Citrulline
SITE                    34
                        note = MISC_FEATURE - Xaa = Azidoleucine
source                  1..34
                        mol_type = protein
                        organism = synthetic construct
SEQUENCE: 504
VXQQFSQPEQ EFPQPQQPQQ SFPEQQPPFS PVXX                             34

SEQ ID NO: 505          moltype = AA  length = 40
FEATURE                 Location/Qualifiers
SITE                    2
                        note = MISC_FEATURE - Xaa = Citrulline
SITE                    39
                        note = MISC_FEATURE - Xaa = Citrulline
SITE                    40
                        note = MISC_FEATURE - Xaa = Azidoleucine
source                  1..40
                        mol_type = protein
                        organism = synthetic construct
SEQUENCE: 505
VXPTPLQPEQ PFPQQPQQPQ QPFPQPEQPF PWQPQSPVXX                       40

SEQ ID NO: 506          moltype = AA  length = 33
FEATURE                 Location/Qualifiers
SITE                    2
                        note = MISC_FEATURE - Xaa = Citrulline
SITE                    32
                        note = MISC_FEATURE - Xaa = Citrulline
SITE                    33
                        note = MISC_FEATURE - Xaa = Azidoleucine
source                  1..33
                        mol_type = protein
                        organism = synthetic construct
SEQUENCE: 506
VXSSPLQPEQ PFPQQPQQPF PEQPQQPQSP VXX                              33

SEQ ID NO: 507          moltype = AA  length = 29
FEATURE                 Location/Qualifiers
SITE                    2
                        note = MISC_FEATURE - Xaa = Citrulline
SITE                    28
                        note = MISC_FEATURE - Xaa = Citrulline
SITE                    29
                        note = MISC_FEATURE - Xaa = Azidoleucine
source                  1..29
                        mol_type = protein
                        organism = synthetic construct
SEQUENCE: 507
VXQSIPQPEQ PFPQPEQPFP QSQESPVXX                                   29

SEQ ID NO: 508          moltype = AA  length = 22
FEATURE                 Location/Qualifiers
SITE                    2
                        note = MISC_FEATURE - Xaa = Citrulline
SITE                    21
                        note = MISC_FEATURE - Xaa = Citrulline
SITE                    22
                        note = MISC_FEATURE - Xaa = Azidoleucine
source                  1..22
                        mol_type = protein
                        organism = synthetic construct
SEQUENCE: 508
VXPQQPFPQQ PQQIIPQSPV XX                                          22
```

-continued

```
SEQ ID NO: 509          moltype = AA  length = 29
FEATURE                 Location/Qualifiers
SITE                    2
                        note = MISC_FEATURE - Xaa = Citrulline
SITE                    28
                        note = MISC_FEATURE - Xaa = Citrulline
SITE                    29
                        note = MISC_FEATURE - Xaa = Azidoleucine
source                  1..29
                        mol_type = protein
                        organism = synthetic construct
SEQUENCE: 509
VXPQQPIPEQ PQPYPEQPQP YPQQSPVXX                                           29

SEQ ID NO: 510          moltype = AA  length = 22
FEATURE                 Location/Qualifiers
SITE                    2
                        note = MISC_FEATURE - Xaa = Citrulline
SITE                    21
                        note = MISC_FEATURE - Xaa = Citrulline
SITE                    22
                        note = MISC_FEATURE - Xaa = Azidoleucine
source                  1..22
                        mol_type = protein
                        organism = synthetic construct
SEQUENCE: 510
VXQQPPFSEQ EQPVLPQSPV XX                                                  22

SEQ ID NO: 511          moltype = AA  length = 22
FEATURE                 Location/Qualifiers
SITE                    2
                        note = MISC_FEATURE - Xaa = Citrulline
SITE                    21
                        note = MISC_FEATURE - Xaa = Citrulline
SITE                    22
                        note = MISC_FEATURE - Xaa = Azidoleucine
source                  1..22
                        mol_type = protein
                        organism = synthetic construct
SEQUENCE: 511
VXQPPFSQQQ ESPFSQQSPV XX                                                  22

SEQ ID NO: 512          moltype = AA  length = 28
FEATURE                 Location/Qualifiers
SITE                    27
                        note = MISC_FEATURE - Xaa = Citrulline
SITE                    28
                        note = MISC_FEATURE - Xaa = Azidoleucine
source                  1..28
                        mol_type = protein
                        organism = synthetic construct
SEQUENCE: 512
VRFSDEGGYT CFFRDHSYQE EAASPVXX                                            28

SEQ ID NO: 513          moltype = AA  length = 26
FEATURE                 Location/Qualifiers
SITE                    4
                        note = MISC_FEATURE - Xaa = Citrulline
SITE                    20
                        note = MISC_FEATURE - Xaa = beta Alanine
SITE                    21
                        note = MISC_FEATURE - Xaa = beta Alanine
SITE                    25
                        note = MISC_FEATURE - Xaa = Citrulline
SITE                    26
                        note = MISC_FEATURE - Xaa = Azidoleucine
source                  1..26
                        mol_type = protein
                        organism = synthetic construct
SEQUENCE: 513
SPVXGQAEPD RAHYNIVTFX XSPVXX                                              26

SEQ ID NO: 514          moltype = AA  length = 33
FEATURE                 Location/Qualifiers
SITE                    32
                        note = MISC_FEATURE - Xaa = Citrulline
SITE                    33
                        note = MISC_FEATURE - Xaa = Azidoleucine
source                  1..33
```

```
                        mol_type = protein
                        organism = synthetic construct
SEQUENCE: 514
GIPVHLELAS MTNMELMSSI VHQQVFPTSP VXX                                33

SEQ ID NO: 515          moltype = AA  length = 29
FEATURE                 Location/Qualifiers
SITE                    4
                        note = MISC_FEATURE - Xaa = Citrulline
SITE                    5
                        note = MISC_FEATURE - Xaa = Norleucine
SITE                    28
                        note = MISC_FEATURE - Xaa = Citrulline
SITE                    29
                        note = MISC_FEATURE - Xaa = Azidoleucine
source                  1..29
                        mol_type = protein
                        organism = synthetic construct
SEQUENCE: 515
SPVXXEVGWY RSPFSRVVHL YRNGSPVXX                                     29

SEQ ID NO: 516          moltype = AA  length = 30
FEATURE                 Location/Qualifiers
SITE                    1
                        note = MISC_FEATURE - Xaa = beta Alanine
SITE                    5
                        note = MISC_FEATURE - Xaa = Citrulline
SITE                    6
                        note = MISC_FEATURE - Xaa = Norleucine
SITE                    29
                        note = MISC_FEATURE - Xaa = Citrulline
SITE                    30
                        note = MISC_FEATURE - Xaa = Azidoleucine
source                  1..30
                        mol_type = protein
                        organism = synthetic construct
SEQUENCE: 516
XSPVXXEVGW YRSPFSRVVH LYRNGSPVXX                                    30

SEQ ID NO: 517          moltype = AA  length = 27
FEATURE                 Location/Qualifiers
SITE                    2
                        note = MISC_FEATURE - Xaa = Citrulline
SITE                    3
                        note = MISC_FEATURE - Xaa = Norleucine
SITE                    26
                        note = MISC_FEATURE - Xaa = Citrulline
SITE                    27
                        note = MISC_FEATURE - Xaa = Azidoleucine
source                  1..27
                        mol_type = protein
                        organism = synthetic construct
SEQUENCE: 517
VXXEVGWYRS PFSRVVHLYR NGSPVXX                                       27

SEQ ID NO: 518          moltype = AA  length = 31
FEATURE                 Location/Qualifiers
SITE                    30
                        note = MISC_FEATURE - Xaa = Citrulline
SITE                    31
                        note = MISC_FEATURE - Xaa = Azidoleucine
source                  1..31
                        mol_type = protein
                        organism = synthetic construct
SEQUENCE: 518
DFTGSNGDPS SPYSLHYLSP TGVNEYSPVX X                                  31

SEQ ID NO: 519          moltype = AA  length = 37
FEATURE                 Location/Qualifiers
SITE                    36
                        note = MISC_FEATURE - Xaa = Citrulline
SITE                    37
                        note = MISC_FEATURE - Xaa = Azidoleucine
source                  1..37
                        mol_type = protein
                        organism = synthetic construct
SEQUENCE: 519
KKKKVRDFTG SNGDPSSPYS LHYLSPTGVN EYSPVXX                            37
```

-continued

```
SEQ ID NO: 520         moltype = AA  length = 33
FEATURE                Location/Qualifiers
SITE                   32
                       note = MISC_FEATURE - Xaa = Citrulline
SITE                   33
                       note = MISC_FEATURE - Xaa = Azidoleucine
source                 1..33
                       mol_type = protein
                       organism = synthetic construct
SEQUENCE: 520
KKKKKVRFSD EGGYTCFFRD HSYQEEAASP VXX                                  33

SEQ ID NO: 521         moltype = AA  length = 38
FEATURE                Location/Qualifiers
SITE                   37
                       note = MISC_FEATURE - Xaa = Citrulline
SITE                   38
                       note = MISC_FEATURE - Xaa = Azidoleucine
source                 1..38
                       mol_type = protein
                       organism = synthetic construct
SEQUENCE: 521
KKKVRGIPVH LELASMTNME LMSSIVHQQV FPTSPVXX                             38

SEQ ID NO: 522         moltype = AA  length = 29
FEATURE                Location/Qualifiers
SITE                   20
                       note = MISC_FEATURE - Xaa = beta Alanine
SITE                   21
                       note = MISC_FEATURE - Xaa = beta Alanine
SITE                   23
                       note = MISC_FEATURE - Xaa = beta Alanine
SITE                   28
                       note = MISC_FEATURE - Xaa = Citrulline
SITE                   29
                       note = MISC_FEATURE - Xaa = Azidoleucine
source                 1..29
                       mol_type = protein
                       organism = synthetic construct
SEQUENCE: 522
KKVRGQAEPD RAHYNIVTFX XKXDSPVXX                                       29

SEQ ID NO: 523         moltype = AA  length = 31
FEATURE                Location/Qualifiers
SITE                   7
                       note = MISC_FEATURE - Xaa = Norleucine
SITE                   30
                       note = MISC_FEATURE - Xaa = Citrulline
SITE                   31
                       note = MISC_FEATURE - Xaa = Azidoleucine
source                 1..31
                       mol_type = protein
                       organism = synthetic construct
SEQUENCE: 523
KKKKVRXEVG WYRSPFSRVV HLYRNGSPVX X                                    31

SEQ ID NO: 524         moltype = AA  length = 30
FEATURE                Location/Qualifiers
SITE                   5
                       note = MISC_FEATURE - Xaa = Norleucine
SITE                   29
                       note = MISC_FEATURE - Xaa = Citrulline
SITE                   30
                       note = MISC_FEATURE - Xaa = Azidoleucine
source                 1..30
                       mol_type = protein
                       organism = synthetic construct
SEQUENCE: 524
KKVRXEVGWY RSPFSRVVHL YRNGKSPVXX                                      30

SEQ ID NO: 525         moltype = AA  length = 31
FEATURE                Location/Qualifiers
SITE                   6
                       note = MISC_FEATURE - Xaa = Norleucine
SITE                   30
                       note = MISC_FEATURE - Xaa = Citrulline
SITE                   31
                       note = MISC_FEATURE - Xaa = Azidoleucine
source                 1..31
```

-continued

```
                        mol_type = protein
                        organism = synthetic construct
SEQUENCE: 525
KKKVRXEVGW YRSPFSRVVH LYRNGKSPVX X                                 31

SEQ ID NO: 526          moltype = AA  length = 30
FEATURE                 Location/Qualifiers
SITE                    4
                        note = MISC_FEATURE - Xaa = Citrulline
SITE                    5
                        note = MISC_FEATURE - Xaa = Norleucine
SITE                    29
                        note = MISC_FEATURE - Xaa = Citrulline
SITE                    30
                        note = MISC_FEATURE - Xaa = Azidoleucine
source                  1..30
                        mol_type = protein
                        organism = synthetic construct
SEQUENCE: 526
SPVXXEVGWY RSPFSRVVHL YRNGKSPVXX                                   30

SEQ ID NO: 527          moltype = AA  length = 33
FEATURE                 Location/Qualifiers
source                  1..33
                        mol_type = protein
                        organism = synthetic construct
MOD_RES                 2
                        note = Citrulline
MOD_RES                 32
                        note = Citrulline
SEQUENCE: 527
VXQLQPFPQP ELPYPQPQLP YPQPQPFRSP VXK                               33

SEQ ID NO: 528          moltype = AA  length = 33
FEATURE                 Location/Qualifiers
source                  1..33
                        mol_type = protein
                        organism = synthetic construct
MOD_RES                 2
                        note = Citrulline
MOD_RES                 32
                        note = Citrulline
MOD_RES                 33
                        note = Azidolysine
SEQUENCE: 528
VXDFTGSNGD PSSPYSLHYL SPTGVNEYSP VXX                               33

SEQ ID NO: 529          moltype = AA  length = 32
FEATURE                 Location/Qualifiers
source                  1..32
                        mol_type = protein
                        organism = synthetic construct
MOD_RES                 2
                        note = Citrulline
MOD_RES                 31
                        note = Citrulline
MOD_RES                 32
                        note = Azidolysine
SEQUENCE: 529
VXARDETAAL LNSAVLGAAP LFVPPADSPV XX                                32

SEQ ID NO: 530          moltype = AA  length = 32
FEATURE                 Location/Qualifiers
source                  1..32
                        mol_type = protein
                        organism = synthetic construct
MOD_RES                 2
                        note = Citrulline
MOD_RES                 31
                        note = Citrulline
MOD_RES                 32
                        note = Azidolysine
SEQUENCE: 530
VXLSREWYVR PLWVRMEQLA KELTAEKSPV XX                                32

SEQ ID NO: 531          moltype = AA  length = 16
FEATURE                 Location/Qualifiers
source                  1..16
                        mol_type = protein
```

```
                       organism = synthetic construct
MOD_RES                2
                       note = Citrulline
MOD_RES                15
                       note = Citrulline
MOD_RES                16
                       note = Azidolysine
SEQUENCE: 531
VXKYNKANVF LSPVXX                                                16

SEQ ID NO: 532         moltype = AA  length = 32
FEATURE                Location/Qualifiers
source                 1..32
                       mol_type = protein
                       organism = synthetic construct
MOD_RES                2
                       note = Citrulline
MOD_RES                31
                       note = Citrulline
MOD_RES                32
                       note = Azidolysine
SEQUENCE: 532
VXGVHMASLS KYNKANVFLF LFALGFYSPV XX                              32

SEQ ID NO: 533         moltype = AA  length = 17
FEATURE                Location/Qualifiers
source                 1..17
                       mol_type = protein
                       organism = synthetic construct
MOD_RES                2
                       note = Citrulline
MOD_RES                16
                       note = Citrulline
MOD_RES                17
                       note = Azidolysine
SEQUENCE: 533
VXYVRPLWVR MESPVXX                                               17

SEQ ID NO: 534         moltype = AA  length = 20
FEATURE                Location/Qualifiers
source                 1..20
                       mol_type = protein
                       organism = synthetic construct
SEQUENCE: 534
HGVTSAPDTR PAPGSTAPPA                                            20

SEQ ID NO: 535         moltype = AA  length = 20
FEATURE                Location/Qualifiers
source                 1..20
                       mol_type = protein
                       organism = synthetic construct
SEQUENCE: 535
DTRPAPGSTA PPAHGVTSAP                                            20

SEQ ID NO: 536         moltype = AA  length = 27
FEATURE                Location/Qualifiers
source                 1..27
                       mol_type = protein
                       organism = synthetic construct
SEQUENCE: 536
GSTAPPAHGV TSAPDTRPAP GSTAPPA                                    27

SEQ ID NO: 537         moltype = AA  length = 12
FEATURE                Location/Qualifiers
source                 1..12
                       mol_type = protein
                       organism = synthetic construct
SEQUENCE: 537
GVTSAPDTRP AP                                                    12

SEQ ID NO: 538         moltype = AA  length = 12
FEATURE                Location/Qualifiers
source                 1..12
                       mol_type = protein
                       organism = synthetic construct
SEQUENCE: 538
APDTRPAPGS TA                                                    12

SEQ ID NO: 539         moltype = AA  length = 14
```

-continued

```
FEATURE                 Location/Qualifiers
source                  1..14
                        mol_type = protein
                        organism = synthetic construct
SEQUENCE: 539
GSTAPPAHGV TSAP                                            14

SEQ ID NO: 540          moltype = AA  length = 5
FEATURE                 Location/Qualifiers
source                  1..5
                        mol_type = protein
                        organism = synthetic construct
SEQUENCE: 540
VTSAP                                                      5

SEQ ID NO: 541          moltype = AA  length = 6
FEATURE                 Location/Qualifiers
source                  1..6
                        mol_type = protein
                        organism = synthetic construct
SEQUENCE: 541
DTRPAP                                                     6

SEQ ID NO: 542          moltype = AA  length = 5
FEATURE                 Location/Qualifiers
source                  1..5
                        mol_type = protein
                        organism = synthetic construct
SEQUENCE: 542
GSTAP                                                      5
```

What is claimed is:

1. A compound of Formula (1):

Formula (1)

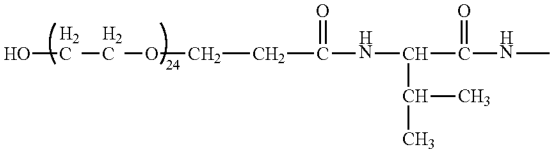

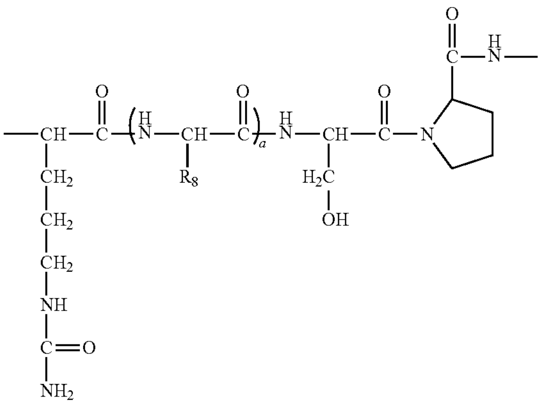

-continued

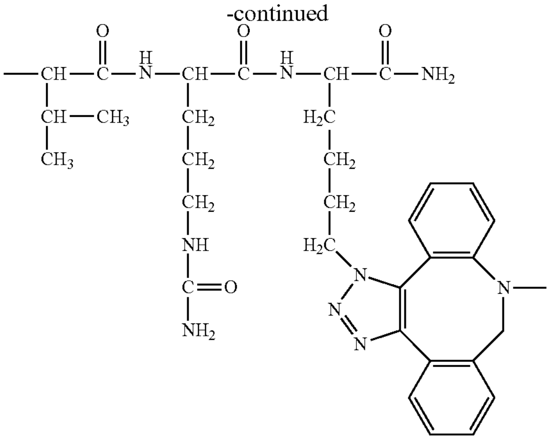

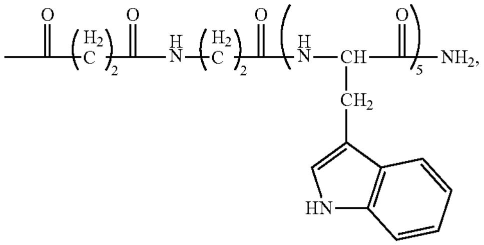

wherein

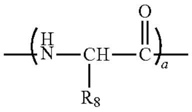

is an antigen (A), wherein each $R_8$ is independently an amino acid side chain, and a is an integer number of amino acids, and wherein A comprises an amino acid sequence selected from the group consisting of:

(SEQ ID NO: 464)
QGIIQPEQPAQLEVI, (SEQ ID NO: 486)
QLQPFPQPELPYPQPQLPYPQPQPFR, (SEQ ID NO: 487)
PQLPYPQPELPYPQPQPFRPEQPYPQPQP, (SEQ ID NO: 488)
PQPQQPEQPFPQPEQEFPQPQQPQQSFPEQQPPL, (SEQ ID NO: 489)
PQQPFPQPEQPFCQQPQ, (SEQ ID NO: 490)
QQFLQPEQPFPQQPEQPYPQQPEQPFPQPQQ, (SEQ ID NO: 491)
QQFSQPEQEFPQPQQPQQSFPEQQPPF, (SEQ ID NO: 492)
PTPLQPEQPFPQQPQQPQQPFPQPEQPFPWQPQ, (SEQ ID NO: 493)
SSPLQPEQPFPQQPQQPFPEQPQQPQ, (SEQ ID NO: 494)
QSIPQPEQPFPQPEQPFPQSQE, (SEQ ID NO: 495)
PQQPFPQQPQQIIPQ, (SEQ ID NO: 496)
PQQPIPEQPQPYPEQPQPYPQQ,
and (SEQ ID NO: 497)
PQQPFPQPEQPFBQQPQ, wherein B represents alpha-aminobutyric acid, 2. The compound of claim 1, wherein A comprises an amino acid sequence selected from the group consisting of:

(SEQ ID NO: 486)
QLQPFPQPELPYPQPQLPYPQPQPFR, (SEQ ID NO: 487)
PQLPYPQPELPYPQPQPFRPEQPYPQPQP, (SEQ ID NO: 488)
PQPQQPEQPFPQPEQEFPQPQQPQQSFPEQQPPL, (SEQ ID NO: 490)
QQFLQPEQPFPQQPEQPYPQQPEQPFPQPQQ, (SEQ ID NO: 491)
QQFSQPEQEFPQPQQPQQSFPEQQPPF, (SEQ ID NO: 492)
PTPLQPEQPFPQQPQQPQQPFPQPEQPFPWQPQ,

-continued (SEQ ID NO: 493)
SSPLQPEQPFPQQPQQPFPEQPQQPQ, (SEQ ID NO: 494)
QSIPQPEQPFPQPEQPFPQSQE, (SEQ ID NO: 495)
PQQPFPQQPQQIIPQ, (SEQ ID NO: 496)
PQQPIPEQPQPYPEQPQPYPQQ,
and (SEQ ID NO: 497)
PQQPFPQPEQPFBQQPQ,
wherein B represents alpha-aminobutyric acid.

3. The compound of claim 2, wherein A comprises an amino acid sequence selected from the group consisting of:

(SEQ ID NO: 486)
QLQPFPQPELPYPQPQLPYPQPQPFR, (SEQ ID NO: 487)
PQLPYPQPELPYPQPQPFRPEQPYPQPQP, (SEQ ID NO: 488)
PQPQQPEQPFPQPEQEFPQPQQPQQSFPEQQPPL, (SEQ ID NO: 490)
QQFLQPEQPFPQQPEQPYPQQPEQPFPQPQQ, (SEQ ID NO: 491)
QQFSQPEQEFPQPQQPQQSFPEQQPPF, (SEQ ID NO: 493)
SSPLQPEQPFPQQPQQPFPEQPQQPQ, (SEQ ID NO: 494)
QSIPQPEQPFPQPEQPFPQSQE, (SEQ ID NO: 495)
PQQPFPQQPQQIIPQ, (SEQ ID NO: 496)
PQQPIPEQPQPYPEQPQPYPQQ,
and (SEQ ID NO: 497)
PQQPFPQPEQPFBQQPQ,
wherein B represents alpha-aminobutyric acid.

4. A composition comprising a compound of claim 1, and optionally further comprising a compound of Formula (1) wherein A comprises an amino acid sequence selected from QQPPFSEQEQPVLPQ (SEQ ID NO:484) or QPPFSQQQESPFSQQ (SEQ ID NO: 485).

5. A composition comprising a compound of Formula (1):

Formula (1)

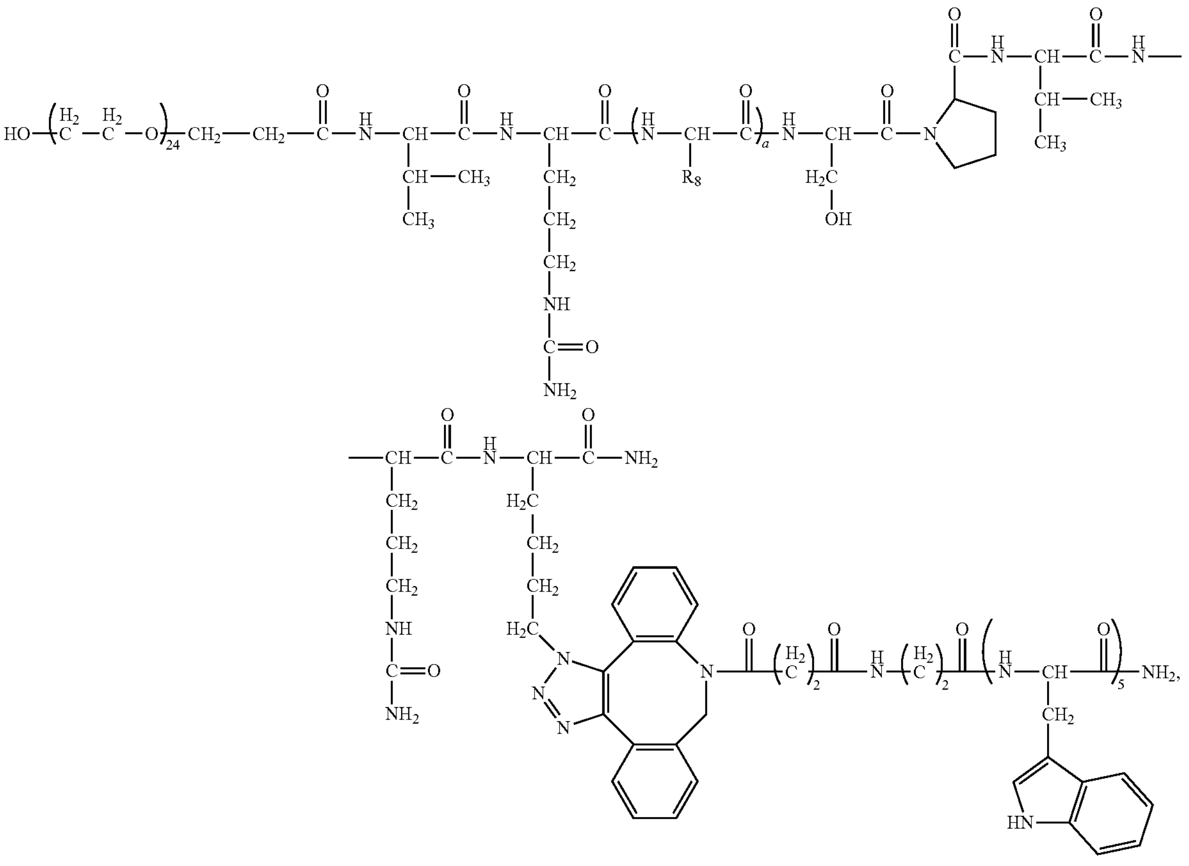

wherein

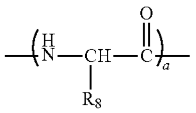

is an antigen (A), wherein each $R_8$ is independently an amino acid side chain, and a is an integer number of amino acids, wherein A comprises an amino acid sequence selected from the group consisting of:

(SEQ ID NO: 464)
QGIIQPEQPAQLEVI, (SEQ ID NO: 484)
QQPPFSEQEQPVLPQ, (SEQ ID NO: 486)
QLQPFPQPELPYPQPQLPYPQPQPFR, (SEQ ID NO: 487)
PQLPYPQPELPYPQPQPFRPEQPYPQPQP, (SEQ ID NO: 488)
PQPQQPEQPFPQPEQEFPQPQQPQQSFPEQQPPL,

-continued (SEQ ID NO: 489)
PQQPFPQPEQPFCQQPQ, (SEQ ID NO: 490)
QQFLQPEQPFPQQPEQPYPQQPEQPFPQPQQ, (SEQ ID NO: 491)
QQFSQPEQEFPQPQQPQQSFPEQQPPF, (SEQ ID NO: 492)
PTPLQPEQPFPQQPQQPQQPFPQPEQPFPWQPQ, (SEQ ID NO: 493)
SSPLQPEQPFPQQPQQPFPEQPQQPQ, (SEQ ID NO: 494)
QSIPQPEQPFPQPEQPFPQSQE, (SEQ ID NO: 495)
PQQPFPQQPQQIIPQ, (SEQ ID NO: 496)
PQQPIPEQPQPYPEQPQPYPQQ,
and (SEQ ID NO: 497)
PQQPFPQPEQPFBQQPQ,
wherein B represents alpha-aminobutyric acid, and wherein the composition comprises two or more unique compounds of Formula (1).

6. The composition of claim 5, wherein A comprises an amino acid sequence selected from the group consisting of:

(SEQ ID NO: 484)
QQPPFSEQEQPVLPQ, (SEQ ID NO: 486)
QLQPFPQPELPYPQPQLPYPQPQPFR, (SEQ ID NO: 487)
PQLPYPQPELPYPQPQPFRPEQPYPQPQP, (SEQ ID NO: 488)
PQPQQPEQPFPQPEQEFPQPQQPQQSFPEQQPPL, (SEQ ID NO: 490)
QQFLQPEQPFPQQPEQPYPQQPEQPFPQPQQ, (SEQ ID NO: 491)
QQFSQPEQEFPQPQQPQQSFPEQQPPF, (SEQ ID NO: 492)
PTPLQPEQPFPQQPQQPQQPFPQPEQPFPWQPQ, (SEQ ID NO: 493)
SSPLQPEQPFPQQPQQPFPEQPQQPQ, (SEQ ID NO: 494)
QSIPQPEQPFPQPEQPFPQSQE, (SEQ ID NO: 495)
PQQPFPQQPQQIIPQ, (SEQ ID NO: 496)
PQQPIPEQPQPYPEQPQPYPQQ,
and (SEQ ID NO: 497)
PQQPFPQPEQPFBQQPQ,
wherein B represents alpha-aminobutyric acid.

7. The composition of claim 6, wherein A comprises an amino acid sequence selected from the group consisting of:

(SEQ ID NO: 486)
QLQPFPQPELPYPQPQLPYPQPQPFR, (SEQ ID NO: 487)
PQLPYPQPELPYPQPQPFRPEQPYPQPQP, (SEQ ID NO: 488)
PQPQQPEQPFPQPEQEFPQPQQPQQSFPEQQPPL, (SEQ ID NO: 490)
QQFLQPEQPFPQQPEQPYPQQPEQPFPQPQQ, (SEQ ID NO: 491)
QQFSQPEQEFPQPQQPQQSFPEQQPPF, (SEQ ID NO: 493)
SSPLQPEQPFPQQPQQPFPEQPQQPQ, (SEQ ID NO: 494)
QSIPQPEQPFPQPEQPFPQSQE, (SEQ ID NO: 495)
PQQPFPQQPQQIIPQ, (SEQ ID NO: 496)
PQQPIPEQPQPYPEQPQPYPQQ,
and (SEQ ID NO: 497)
PQQPFPQPEQPFBQQPQ,
wherein B represents alpha-aminobutyric acid.

8. The composition of claim 6, wherein the composition comprises twelve unique compounds of Formula (1).

9. The composition of claim 5, wherein the composition comprises three or more unique compounds of Formula (1).

10. The composition of claim 9, wherein the composition comprises four or more unique compounds of Formula (I).

11. The composition of claim 10, wherein the composition comprises five or more unique compounds of Formula (1).

12. The composition of claim 11, wherein the composition comprises six or more unique compounds of Formula (1).

13. The composition of claim 12, wherein the composition comprises seven or more unique compounds of Formula (1).

14. The composition of claim 13, wherein the composition comprises eight or more unique compounds of Formula (1).

15. The composition of claim 14, wherein the composition comprises nine or more unique compounds of Formula (1).

16. The composition of claim 15, wherein the composition comprises ten or more unique compounds of Formula (1).

17. The composition of claim 16, wherein the composition comprises eleven or more unique compounds of Formula (1).

18. The composition of claim 17, wherein the composition comprises twelve or more unique compounds of Formula (1).

19. The composition of claim 5, wherein the composition comprises:

i) a compound of Formula (1), wherein A is QQPPFSEQEQPVLPQ (SEQ ID NO: 484), ii) a compound of Formula (1), wherein A is QLQPFPQPELPYPQPQLPYPQPQPFR (SEQ ID NO:486), iii) a compound of Formula (1), wherein A is PQLPYPQPELPYPQPQPFRPEQPYPQPQP (SEQ ID NO:487), iv) a compound of Formula (1), wherein A is PQPQQPEQPFPQPEQEFPQPQQPQQSFPEQQPPL (SEQ ID NO:488), v) a compound of Formula (1), wherein A is QQFLQPEQPFPQQPEQPYPQQPEQPFPQPQQ (SEQ ID NO:490), vi) a compound of Formula (1), wherein A is QQFSQPEQEFPQPQQPQQSFPEQQPPF (SEQ ID NO:491), vii) a compound of Formula (1), wherein A is PTPLQPEQPFPQQPQQPQQPFPQPEQPFPWQPQ (SEQ ID NO:492), viii) a compound of Formula (1), wherein A is SSPLQPEQPFPQQPQQPFPEQPQQPQ (SEQ ID NO:493), ix) a compound of Formula (1), wherein A is QSIPQPEQPFPQPEQPFPQSQE (SEQ ID NO:494), x) a compound of Formula (1), wherein A is PQQPFPQQPQQIIPQ (SEQ ID NO: 495), xi) a compound of Formula (1), wherein A is PQQPIPEQPQPYPEQPQPYPQQ (SEQ ID NO: 496), and xii) a compound of Formula (1), wherein A is PQQPFPQPEQPFBQQPQ, wherein B represents alpha-aminobutyric acid (SEQ ID NO: 497).

20. The composition of claim 19, wherein the composition further comprises rapamycin.

21. A pharmaceutical composition comprising a composition of claim 5 and a pharmaceutically acceptable carrier.

22. A composition comprising twelve or more peptides selected from:

i) a peptide having the amino acid sequence of QGIIQPEQPAQLEVI (SEQ ID NO: 464), ii) a peptide having the amino acid sequence of QQPPFSEQEQPVLPQ (SEQ ID NO: 484), iii) a peptide having the amino acid sequence of QPPFSQQQESPESQQ (SEQ ID NO: 485), iv) a peptide having the amino acid sequence of QLQPFPQPELPYPQPQLPYPQPQPFR (SEQ ID NO:486), v) a peptide having the amino acid sequence of PQLPYPQPELPYPQPQPFRPEQPYPQPQP (SEQ ID NO:487), vi) a peptide having the amino acid sequence of PQPQQPEQPFPQPEQEFPQPQQPQQSFPEQQPPL (SEQ ID NO:488), vii) a peptide having the amino acid sequence of PQQPFPQPEQPFCQQPQ (SEQ ID NO:489), viii) a peptide having the amino acid sequence of QQFLQPEQPFPQQPEQPYPQQPEQPFPQPQQ (SEQ ID NO:490), ix) a peptide having the amino acid sequence of QQFSQPEQEFPQPQQPQQSFPEQQPPF (SEQ ID NO:491), x) a peptide having the amino acid sequence of PTPLQPEQPFPQQPQQPQQPFPQPEQPFPWQPQ (SEQ ID NO:492), xi) a peptide having the amino acid sequence of SSPLQPEQPFPQQPQQPFPEQPQQPQ (SEQ ID NO:493), xii) a peptide having the amino acid sequence of QSIPQPEQPFPQPEQPFPQSQE (SEQ ID NO:494), xiii) a peptide having the amino acid sequence of PQQPFPQQPQQIIPQ (SEQ ID NO: 495), xiv) a peptide having the amino acid sequence of PQQPIPEQPQPYPEQPQPYPQQ (SEQ ID NO: 496), and xv) a peptide having the amino acid sequence of PQQPFPQPEQPFBQQPQ, wherein B represents alpha-aminobutyric acid (SEQ ID NO: 497).

23. The composition of claim 22, comprising each of the following:

i) a peptide having the amino acid sequence of QQPPFSEQEQPVLPQ (SEQ ID NO: 484), ii) a peptide having the amino acid sequence of QLQPFPQPELPYPQPQLPYPQPQPFR (SEQ ID NO:486), iii) a peptide having the amino acid sequence of PQLPYPQPELPYPQPQPFRPEQPYPQPQP (SEQ ID NO:487), iv) a peptide having the amino acid sequence of PQPQQPEQPFPQPEQEFPQPQQPQQSFPEQQPPL (SEQ ID NO:488), v) a peptide having the amino acid sequence of QQFLQPEQPFPQQPEQPYPQQPEQPFPQPQQ (SEQ ID NO:490), vi) a peptide having the amino acid sequence of QQFSQPEQEFPQPQQPQQSFPEQQPPF (SEQ ID NO:491), vii) a peptide having the amino acid sequence of PTPLQPEQPFPQQPQQPQQPFPQPEQPFPWQPQ (SEQ ID NO:492), viii) a peptide having the amino acid sequence of SSPLQPEQPFPQQPQQPFPEQPQQPQ (SEQ ID NO:493), ix) a peptide having the amino acid sequence of QSIPQPEQPFPQPEQPFPQSQE (SEQ ID NO:494), x) a peptide having the amino acid sequence of PQQPFPQQPQQIIPQ (SEQ ID NO: 495), xi) a peptide having the amino acid sequence of PQQPIPEQPQPYPEQPQPYPQQ (SEQ ID NO: 496), and xii) a peptide having the amino acid sequence of PQQPFPQPEQPFBQQPQ, wherein B represents alpha-aminobutyric acid (SEQ ID NO: 497).

24. The composition of claim 23, wherein the composition further comprises rapamycin.

25. A pharmaceutical composition comprising a composition of claim 22 and a pharmaceutically acceptable carrier.

* * * * *